(12) United States Patent
Schwartz et al.

(10) Patent No.: US 12,396,991 B2
(45) Date of Patent: Aug. 26, 2025

(54) BIOMARKERS FOR THE DIAGNOSIS AND TREATMENT OF FIBROTIC LUNG DISEASE

(71) Applicant: The Regents of the University of Colorado, Denver, CO (US)

(72) Inventors: David A. Schwartz, Aurora, CO (US); Ivana V. Yang, Englewood, CO (US); Joyce S. Lee, Cherry Hills Village, CO (US); Christopher M. Evans, Denver, CO (US); Marvin I. Schwarz, Denver, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 0 days.

(21) Appl. No.: 17/930,488

(22) Filed: Sep. 8, 2022

(65) Prior Publication Data
US 2023/0390280 A1    Dec. 7, 2023

Related U.S. Application Data

(63) Continuation of application No. 16/624,500, filed as application No. PCT/US2018/039573 on Jun. 26, 2018, now abandoned.

(60) Provisional application No. 62/525,088, filed on Jun. 26, 2017, provisional application No. 62/525,087, filed on Jun. 26, 2017.

(51) Int. Cl.
| | | |
|---|---|---|
| *C12Q 1/68* | (2018.01) | |
| *A61K 9/00* | (2006.01) | |
| *A61K 31/197* | (2006.01) | |
| *A61K 31/4412* | (2006.01) | |
| *A61K 31/496* | (2006.01) | |
| *A61P 11/00* | (2006.01) | |
| *C12P 19/34* | (2006.01) | |
| *C12Q 1/6883* | (2018.01) | |
| *A61K 31/198* | (2006.01) | |
| *A61K 31/4418* | (2006.01) | |

(52) U.S. Cl.
CPC .......... *A61K 31/496* (2013.01); *A61K 9/0056* (2013.01); *A61K 31/197* (2013.01); *A61K 31/4412* (2013.01); *A61P 11/00* (2018.01); *C12Q 1/6883* (2013.01); *A61K 31/198* (2013.01); *A61K 31/4418* (2013.01); *C12Q 2600/106* (2013.01); *C12Q 2600/156* (2013.01)

(58) Field of Classification Search
CPC ........ C12Q 2600/106; C12Q 2600/156; C12Q 1/6883
See application file for complete search history.

(56) References Cited

U.S. PATENT DOCUMENTS

| | | |
|---|---|---|
| 5,582,981 A | 12/1996 | Toole et al. |
| 5,595,877 A | 1/1997 | Gold et al. |
| 5,637,459 A | 6/1997 | Burke et al. |
| 8,673,565 B2 | 3/2014 | Schwartz et al. |
| 2011/0280457 A1 | 11/2011 | Nielsen et al. |
| 2015/0150862 A1 | 6/2015 | Hood et al. |
| 2016/0060701 A1 | 3/2016 | Schwartz et al. |
| 2020/0171024 A1 | 6/2020 | Schwartz et al. |

FOREIGN PATENT DOCUMENTS

| | | |
|---|---|---|
| WO | WO-2014127290 A2 | 8/2014 |
| WO | WO-2016172150 A1 | 10/2016 |
| WO | WO-2017053952 A1 | 3/2017 |
| WO | WO-2019005847 A1 | 1/2019 |

OTHER PUBLICATIONS

Rosas I. O., et al. "Automated quantification of high-resolution CT scan findings in individuals at risk for pulmonary fibrosis" Chest. Dec. 2011;140(6):1590-1597. (Year: 2011).*
Anthimopoulos M, "Lung Pattern Classification for Interstitial Lung Diseases Using a Deep Convolutional Neural Network". IEEE Trans Med Imaging. May 2016;35(5):1207-1216. Epub Feb. 29, 2016 (Year: 2016).*
Juge et al., "MUC5B promoter variant rs35705950 and rheumatoid arthritis associated interstitial lung disease survival and progression". InSeminars in Arthritis and Rheumatism Oct. 1, 2021 (vol. 51, No. 5, pp. 996-1004).
Mathai et al., "MUC5B variant is associated with visually and quantitatively detected preclinical pulmonary fibrosis", Thorax, Dec. 2019, vol. 74(12), pp. 1131-1139.
Bonella et al., "Idiopathic pulmonary fibrosis: current treatment options and critical appraisal of nintedanib", Drug Design, Development and Therapy, 2015, vol. 2015, No. 9, 2015, pp. 6407-6419.
Chen et al., "Asymptomatic Preclinical Rheumatoid Arthritis-Associated Interstitial Lung Disease" Clinical and Developmental Immunology vol. 2013, Article ID 406927, 5 pages. (Year: 2013).
Cordier "Idiopathic pulmonary fibrosis: advances in etiology, diagnosis and treatment", Database Medline US National Library of Medicine (NLM), 2014, Database accession No. NLM27120908, Bulletin De L'Academie Nationale De Medecine, 2014, vol. 198, No. 7, pp. 1353-1364. Bethesda, MD, US, 2014, Cordier Jean-Francois, Database accession No. NLM27120908, Bulletin De L'Academie Nationale De Medecine, 2014, vol. 198, No. 7, pp. 1353-1364.
DbSNP short genetic variations—SNP linked to Gene (geneID:727897) Via Contig Annotation, SNPs in the MUC5B gene region, printed from ncbi.nlm.nih.gov, Mar. 3, 2022, pp. 1-30 provided (Year: 2022).

(Continued)

*Primary Examiner* — Stephen T Kapushoc
(74) *Attorney, Agent, or Firm* — Cooley LLP

(57) ABSTRACT

The present disclosure provides a method of treating a fibrotic lung disease in a subject comprising administering to the subject an effective amount of a therapeutic agent, wherein the subject is asymptomatic and wherein the subject is at risk of developing the fibrotic lung disease.

7 Claims, 33 Drawing Sheets

Specification includes a Sequence Listing.

(56) References Cited

OTHER PUBLICATIONS

Hambly et al., "Molecular classification of idiopathic pulmonary fibrosis: Personalized medicine, genetics and biomarkers : Molecular classification of IPF", Respirology, 2015, vol. 20, No. 7, pp. 1010-1022.
Hegele "SNP Judgments and Freedom of Association" Arterioscler Thromb Vasc Biol. Jul. 1, 2002; 22(7): 1058-61.
Juppner "Functional Properties of the PTH/PTHrP Receptor" Bone. Aug. 1, 1995; 17(2): S39-42.
Lucentini "Gene Association Studies Typically Wrong.", The Scientist. Dec. 20, 2004; 18(24): 20-1.
Magnini et al., "Idiopathic Pulmonary Fibrosis: Molecular Endotypes of Fibrosis Stratifying Existing and Emerging Therapies.", Respiration. May 23, 2017; 93(6): 379-95.
Mathai et al., "Desmoplakin Variants Are Associated with Idiopathic Pulmonary Fibrosis" Am J Respir Crit Care Med vol. 193, Iss 10, pp. 1151-1160, 2016.
Mathai et al., "Incorporating genetics into the identification and treatment of Idiopathic Pulmonary Fibrosis" BMC medicine. Dec. 2015; 13(1): 1-6.
Mathai et al., "MUC5B Promoter Polymorphism rs35705950 Enhances the Risk of Asymptomatic Fibrotic Interstitial Lung Disease" American Journal of Respiratory and Critical Care Medicine 2016;193:A4550; American Thoracic Society International Conference, Poster Discussion Session on Monday, May 16, 2016, pp. 1-10.
Mazzei et al., "Nintedanib in the treatment of idiopathic pulmonary fibrosis" Ther Adv Respir Dis. Jun. 2015; 9(3): 121-9.
Pennisi "A closer look at SN Ps suggests difficulties", Science; Sep. 18, 1998; 281, 5384.
Pepe et al., "Phases of biomarker development for early detection of cancer". Journal of the National Cancer Institute. Jul. 18, 2001; 93(14): 1054-61.
Seibold et al., "A Common MUC5B Promoter Polymorphism and Pulmonary Fibrosis." New Eng. J. Med. Apr. 21, 2011; 364(16): 1503-12.
Ariani A. et al. "Quantitative chest computed tomography is associated with two prediction models of mortality in interstitial lung disease related to systemic sclerosis" Rheumatology (2017); 56(6):922-927.
Chung J.H. et al.: "CT imaging phenotypes of pulmonary fibrosis in the MUC5B promoter site polymorphism" Chest (2016); 149(5):1215-1222.

* cited by examiner

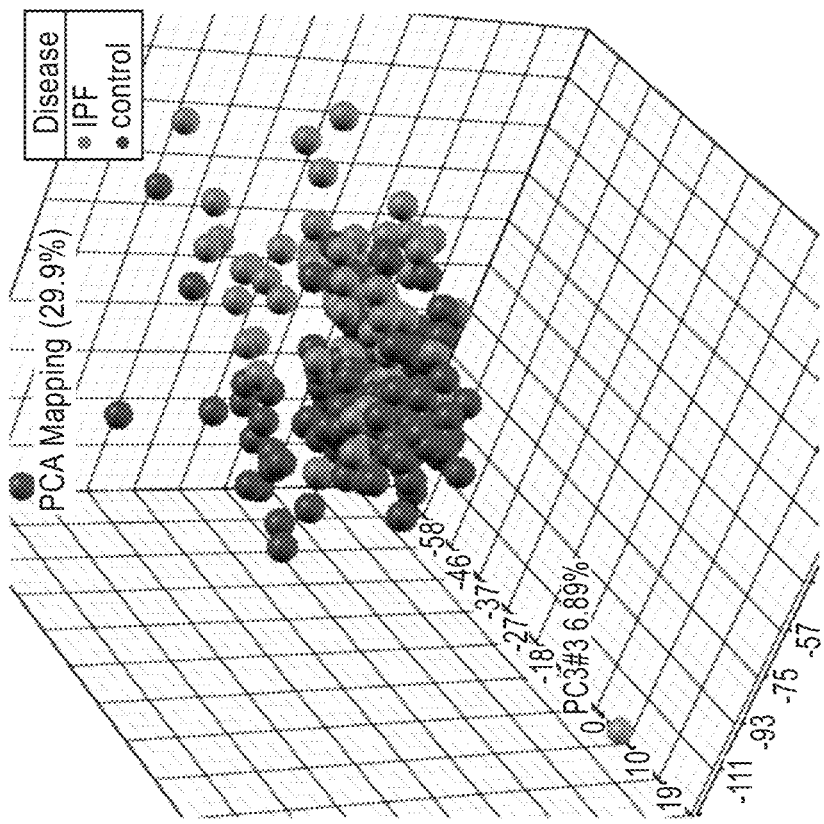
FIG. 2A  Before outlier exclusion
FIG. 2B  After outlier exclusion

FIG. 13

| Characteristic | RA-ILD (N=620) | RA-noILD (N=614) | Crude P Value | Adjusted P Value* |
|---|---|---|---|---|
| Female-no. (%) | 345/565 (61.1) | 446/540 (82.6) | 1.5x10-3 | 3.7x10-12 |
| Age at inclusion | 69.0±10.8 | 60.4±12.6 | 1.20x10-24 | 1.3x10-21 |
| Age at RA onset-yr | 55.7±14.6 | 45.7±13.5 | 7.0x10-23 | 5.6x10-14 |
| RA duration-yr | 13.3±11.5 | 14.8±10.2 | 0.034 | 0.38 |
| Age at ILD onset-yr | 62.7±11.8 | | | |
| ILD duration-yr | 4.3±4.0 | | | |
| Ever smoker-no. (%) | 282/516 (54.7) | 168/465 (36.1) | 4.6x10-4 | 0.53 |
| Methotrexate use ever-no. (%) | 260/318 (81.8) | 142/153 (92.8) | 0.42 | 0.69 |
| RA manifestations | | | | |
| ACPA and/or RF-positive-no. (%) | 449/506 (88.7) | 446/468 (95.3) | 0.47 | 0.72 |
| Erosive disease-no. (%) | 224/482 (46.5) | 274/469 (58.4) | 0.045 | 0.30 |
| Chest CT scan pattern | | | | |
| UIP and possible UIP-no. (%) | 207/505 (41.0) | | | |
| Inconsistent UIP-no. (%) | 298/505 (59.0) | | | |
| Pulmonary function testing | | | | |
| FVC% of predicted value | 78.2±25.0 | | | |
| DLco% of predicted value | 57.6±23.4 | | | |
| TLC% of predicted value | 81.3±20.3 | | | |

RA: rheumatoid arthritis, ILD: interstitial lung disease, ACPA: anti-citrullinated protein antibody, RF: rheumatoid factor, CT: computed tomography, UIP: usual interstitial pneumonia, FVC: forced vital capacity, DLco: diffusion capacity of carbon monoxide, TLC: total lung capacity

* Adjusted P value for sex and cohort.

FIG. 14

| Cohorts | N of individuals | | | MUC5B rs35705950 Minor Allele Frequency Percent | | | | Genotypic Association Test RA-ILD vs Controls | | | | | Genotypic Association Test RA-noILD vs Controls | | | | | Genotypic Association Test RA-ILD vs RA-noILD | | |
|---|---|---|---|---|---|---|---|---|---|---|---|---|---|---|---|---|---|---|---|---|
| | RA-ILD | RA-noILD | Controls | RA-ILD | RA-noILD | Controls | P value | Crude Odds Ratio for RA-ILD (95% CI) | P value | Adjusted* Odds Ratio for RA-ILD (95% CI) | P value | | Crude Odds Ratio for RA-ILD (95% CI) | P value | Adjusted* Odds Ratio for RA-ILD (95% CI) | P value | | Crude Odds Ratio for RA-ILD (95% CI) | P value | Adjusted** Odds Ratio for RA-ILD (95% CI) |
| France (Discovery) | 118 | 105 | 1229 | 32.6 | 12.9 | 10.9 | 3.8x10⁻¹⁷ | 3.8(2.8-5.2) | 9.7x10⁻¹⁷ | 3.8(2.8-5.2) | 0.40 | | 1.2(0.8-1.9) | 0.28 | 1.3(0.8-1.9) | 5.9x10⁻⁶ | | 3.8(2.2-6.8) | 9.4x10⁻⁴ | 3.1(1.6-6.3) |
| Greece | 56 | - | 1795 | 26.8 | - | 3.8 | 2.2x10⁻²⁰ | 13.2(7.6-22.9) | 6.2x10⁻²⁰ | 13.2(7.6-23.0) | - | | - | - | - | - | | - | - | - |
| The Netherlands | 40 | - | 249 | 30.0 | - | 9.0 | 5.0x10⁻⁷ | 5.6(2.9-11.2) | 1.2x10⁻⁴ | 4.9(2.2-11.5) | - | | - | - | - | - | | - | - | - |
| USA-1 | 99 | 68 | 500 | 28.8 | 11.0 | 10.7 | 5.8x10⁻¹¹ | 4.1(2.7-6.3) | 5.6x10⁻¹¹ | 4.1(2.7-6.3) | 0.91 | | 1.0(0.6-1.8) | 0.99 | 1.0(0.5-1.7) | 7.9x10⁻⁶ | | 5.4(2.6-11.7) | NA | NA |
| USA-2 | 48 | - | 75 | 13.5 | - | 12.5 | - | - | - | - | - | | - | - | - | 0.80 | | 1.1(0.5-2.5) | NA | NA |
| Mexico | 55 | 69 | 347 | 16.4 | 3.6 | 5.3 | 1.1x10⁻⁴ | 3.4(1.8-6.2) | 2.2x10⁻⁴ | 3.6(1.8-7.3) | 0.42 | | 0.7(0.2-1.6) | 0.42 | 0.7(0.2-1.7) | 1.5x10⁻³ | | 5.7(2.1-18.6) | 0.03 | 3.8(1.2-13.3) |
| Japan | 182 | 300 | 315 | 1.1 | 0.5 | 0.2 | 0.08 | 7.4(1.0-138.6) | 0.16 | 5.5(0.6-119.1) | 0.26 | | 3.2(0.4-64.3) | 0.32 | 3.7(0.5-75.1) | 0.30 | | 2.2(0.5-11.4) | 0.30 | 3.1(0.3-28.0) |
| China | 22 | - | 1013 | 2.3 | - | 0.8 | 0.30 | 3.0(0.2-15.6) | 0.14 | 4.9(0.3-27.5) | - | | - | - | - | - | | - | - | - |
| Multi Ethnic Replication Sample | 454 | 437 | 4219 | - | - | - | 3.9x10⁻³⁵ | 5.5(4.2-7.2) | 4.7x10⁻³⁵ | 5.5(4.2-7.3) | 0.90 | | 1.0(0.6-1.5) | 0.83 | 1.0(0.6-1.5) | 5.3x10⁻⁷ | | 3.1(2.0-5.0) | 0.04 | 2.9(1.1-8.4) |
| Combined Analysis | 572 | 542 | 5448 | - | - | - | 1.3x10⁻⁴⁹ | 4.7(3.8-5.8) | 1.3x10⁻⁴⁹ | 4.7(3.9-5.8) | 0.60 | | 1.1(0.8-1.5) | 0.54 | 1.1(0.8-1.5) | 1.6x10⁻¹¹ | | 3.4(2.4-4.8) | 7.4x10⁻⁵ | 3.1(1.8-5.4) |

RA: rheumatoid arthritis, ILD: interstitial lung disease, RA-ILD: patients with rheumatoid arthritis associated interstitial lung disease, RA-noILD: rheumatoid arthritis patients without interstitial lung disease.
*P values and odds ratios in the category were adjusted for sex and cohort.
** P values and odds ratios in this category were adjusted for sex, age at inclusion, ever smoking status and cohort.
NA: All above-cited covariates not available for adjusting

FIG. 15

| Cohorts | RA-ILD Cases | | MUC5B rs35705950 Minor Allele Frequency | | | Genotypic Association Test | | | |
|---|---|---|---|---|---|---|---|---|---|
| | RA-UIP | RA-nonUIP | RA-UIP | RA-nonUIP | P value | Crude Odds Ratio for RA-UIP (95%CI) | P value | Adjusted* Odds Ratio for RA-UIP (95%CI) | |
| | N of individuals | | percent | | | | | | |
| France (Discovery) | 50 | 31 | 34.0 | 12.9 | 3.9x10⁻⁴ | 6.1(2.3-17.5) | 2.7x10⁻³ | 4.9(1.8-14.6) | |
| Greece | 18 | 38 | 36.1 | 21.1 | 0.04 | 3.6(1.1-13.1) | 0.12 | 2.9(0.8-12.1) | |
| The Netherlands | 18 | 22 | 33.3 | 25.0 | 0.29 | 2.0(0.6-7.6) | 0.51 | 1.6(0.4-6.7) | |
| USA-1 | 34 | 42 | 33.8 | 23.8 | 0.08 | 2.3(0.9-6.0) | 0.18 | 2.1(0.7-6.3) | |
| Mexico | 19 | 36 | 28.9 | 8.3 | 2.8x10⁻³ | 6.9(2.0-26.0) | 0.07 | 3.8(0.9-16.8) | |
| Japan | 60 | 122 | 1.7 | 0.8 | 0.47 | 2.1(0.2-17.6) | 0.99 | NA† | |
| China | 8 | 7 | 0 | 7.1 | 1.0 | NA† | 1.0 | NA† | |
| Multi-Ethnic Replication Sample | 157 | 267 | - | - | 1.5x10⁻⁴ | 2.9(1.7-5.0) | 6.3x10⁻³ | 2.3(1.3-4.1) | |
| Combined Analysis | 207 | 298 | - | - | 3.6x10⁻⁷ | 3.5(2.2-5.6) | 5.1x10⁻⁵ | 2.9(1.7-4.8) | |

RA: rheumatoid arthritis, UIP: usual interstitial pneumonia, ILD: interstitial lung disease
The RA-UIP subset includes RA-ILD patients with the following HRCT scan patterns: usual interstitial pneumonia and possible usual interstitial pneumonia.

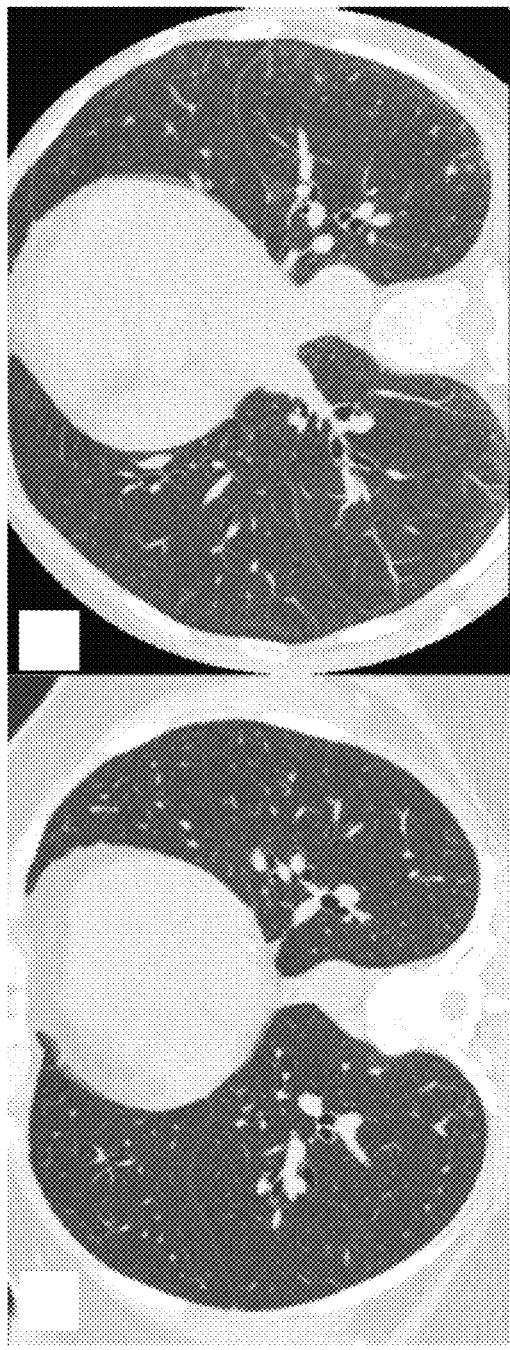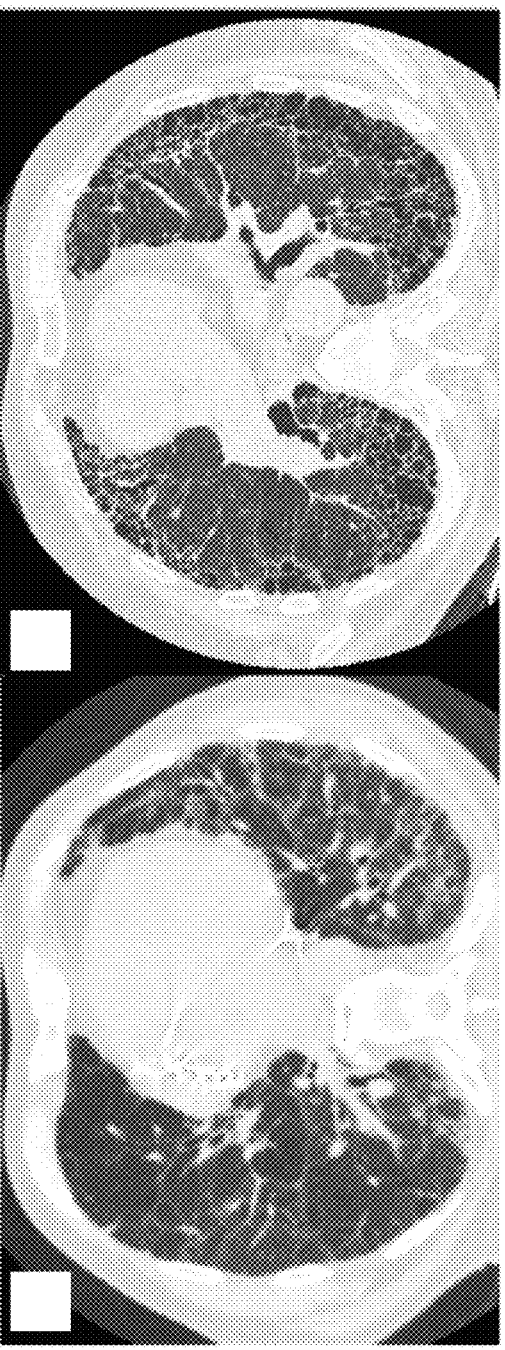
FIG. 19A  FIG. 19B  FIG. 19C  FIG. 19D

FIG. 20

|  | COPDGene Nonsmoking Controls (n=100) | FIP Relative in Dataset (n=402) |
|---|---|---|
| Age, mean (95%CI) | 57.2 (55.3-59.0) | 57.4 (56.5-58.3) |
| Male, n (%) | 47 (47%) | 153 (38%) |
| rs35705950 minor allele frequency* | NA | 0-22 |

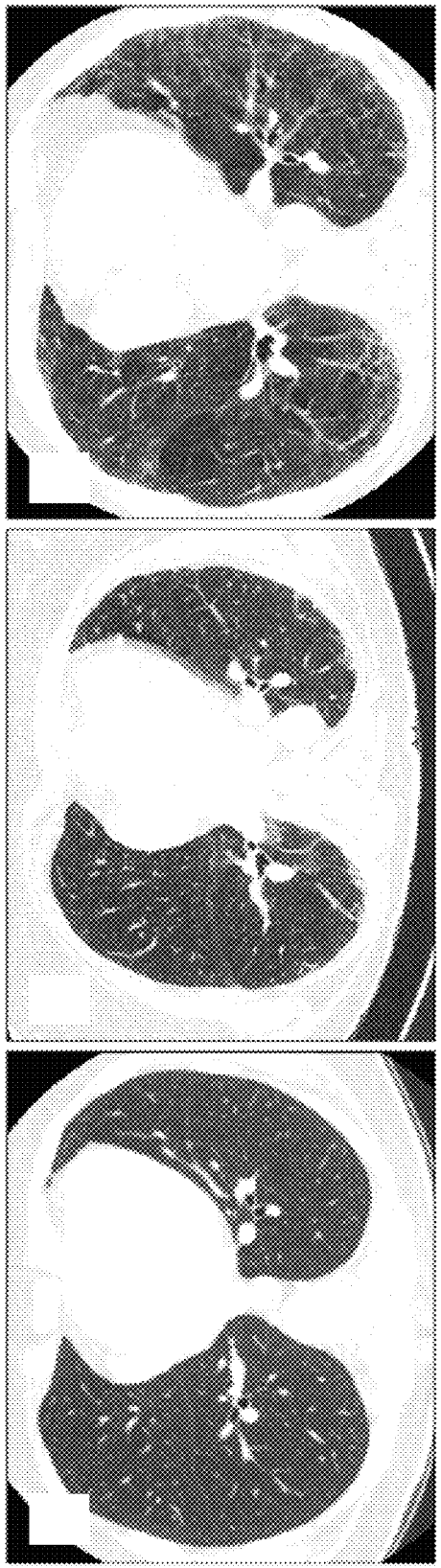
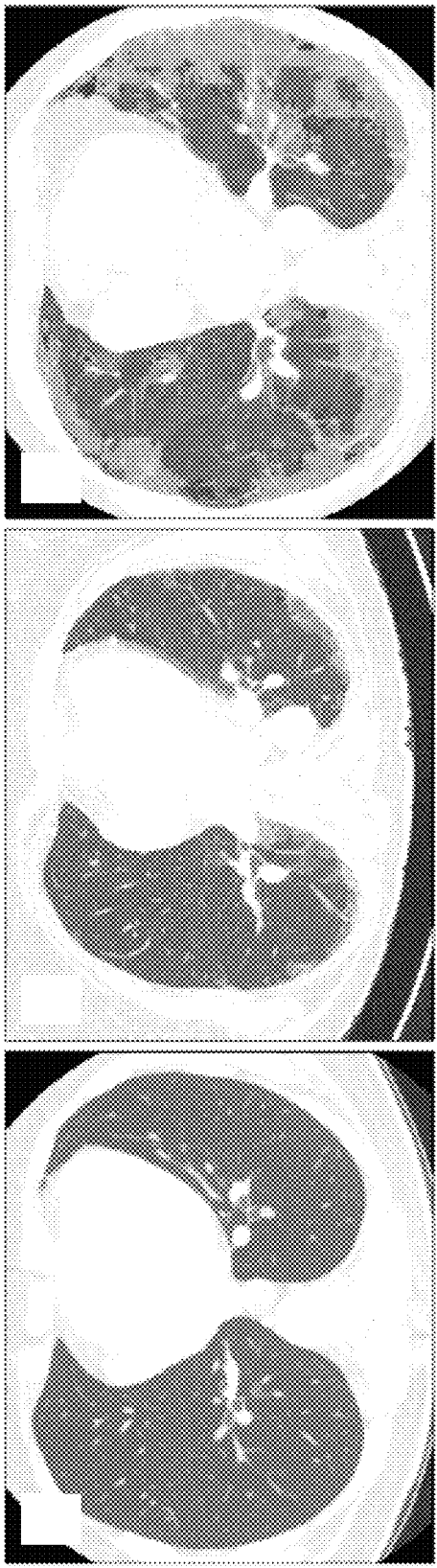

FIG. 22

| | No Fibrosis (n=419) | PrePF (n=77) | p-value | OR (95% CI) controlling for family** | Mixed effects logistic regression p-value |
|---|---|---|---|---|---|
| Age, mean (95%CI) | 55.8 (54.9-56.6) | 65.8 (63.5-68.1) | $6.36 \times 10^{-13}$ | 1.15 (1.09-1.22) | $7.34 \times 10^{-7}$ |
| Male, % | 36% | 48% | 0.05 | 1.80 (0.88-3.68) | 0.11 |
| Ever smoker, % | 27% | 48% | 0.007 | 1.46 (0.70-3.06) | 0.31 |
| MUC5B Promoter Variant (rs35705950), MAF (% subjects with variant)* | 0.21 (40%) | 0.29 (53%) | 0.03 | 2.18 (1.00-4.73) | 0.05*** |
| TERT Common Variant (rs2736100), MAF (%subjects with variant)* | 0.45 (68%) | 0.45 (67%) | 0.88 | NA | NA |

FIG. 23

| | |
|---|---|
| Total with Fibrotic ILD | 77 |
| Cranio-caudal distribution | |
| Upper | 11 (14%) |
| Middle | 5 (7%) |
| Lower | 54 (70%) |
| Diffuse | 4 (5%) |
| Not noted | 3 (4%) |
| Axial distribution | |
| Subpleural | 67 (87%) |
| Diffuse | 5 (6·5%) |
| Peribronchovasular | 2 (2.5%) |
| Not noted | 3 (4%) |
| Honeycombing? | 12 (15·6%) |
| | |
| CT pattern* | |
| UIP | 59 (77·7%) |
| Possible | 41 (70%) |
| Probable | 9 (15%) |
| Definite | 9 (15%) |
| NSIP | 45 (58·4%) |
| Possible | 41 (91%) |
| Probable | 2 (4%) |
| Definite | 2 (4%) |
| Sarcoidosis | 3 (3·9%) |
| Hypersensitivity Pneumonitis | 14 - Possible (18·2%) |

FIG. 26

A. Breathlessness Responses for Cohort:

| | Yes | No | No answer |
|---|---|---|---|
| Are you troubled by shortness of breath when hurrying on the level or walking up a slight hill? | 121 | 344 | 31 |
| Do you have to walk slower than people of your age on the level because of breathlessness? | 46 | 422 | 28 |
| Do you ever have to stop for breath when walking at your own pace on the level? | 32 | 442 | 22 |
| Do you ever have to stop for breath after walking about 100 yards (or after a few minutes)? | 36 | 439 | 21 |
| Are you too breathless to leave the house or breathless dressing or undressing? | 7 | 470 | 19 |

B. Breathlessness Responses by Visual CT Diagnosis:

| | PrePF (n=77) | No Fibrosis (n=419) |
|---|---|---|
| Are you troubled by shortness of breath when hurrying on the level or walking up a slight hill? | 43 no<br>26 yes (37%)<br>8 no answer | 301 no<br>95 yes (24%)<br>23 no answer |
| Do you have to walk slower than people of your age on the level because of breathlessness? | 60 no<br>9 yes (13%)<br>8 no answer | 362 no<br>37 yes (9.3%)<br>20 no answer |
| Do you ever have to stop for breath when walking at your own pace on the level? | 64 no<br>6 yes (8.6%)<br>7 no answer | 378 no<br>26 yes (6.4%)<br>15 no answer |
| Do you ever have to stop for breath after walking about 100 yards (or after a few minutes)? | 66 no<br>6 yes (8.3%)<br>5 no answer | 373 no<br>30 yes (7.4%)<br>16 no answer |
| Are you to breathless to leave the house or breathless dressing or undressing? | 71 no<br>1 yes (1.4%)<br>5 no answer | 399 no<br>6 yes (1.4%)<br>14 no answer |

FIG. 28

| | Fibrosis score negative (n=295) | Fibrosis score positive (n=107) | p-value* | Linear regression, p-value |
|---|---|---|---|---|
| Age, mean (95%CI) | 55.4 (54.5-56.3) | 62.9 (60.8-64.9) | $7.05 \times 10^{-10}$ | $2.17 \times 10^{-9}$ |
| Male, n (%) | 112 (38%) | 41 (38%) | 0.95 | 0.63 |
| Ever smoker, n (%) | 87 (29.8%) | 32 (29.9%) | 0.98 | 0.94 |
| MUC5B Promotor Variant (rs35705950), MAF (% subjects with variant) | 0.21 (39.4%) | 0.26 (48.6%) | 0.12 | 0.03** |

FIG. 29

| SNP | Position* | Minor allele | Locus | Nearest gene | Minor allele frequency (%) | | | | | | Genotypic association test | | | |
|---|---|---|---|---|---|---|---|---|---|---|---|---|---|---|
| | | | | | France | | USA | | Mexico | | Crude | | Adjusted** | |
| | | | | | RA-ILD n=118 | RA-noILD n=105 | RA-ILD n=99 | RA-noILD n=68 | RA-ILD n=55 | RA-noILD n=69 | Odds Ratio (95%CI) | P value | Odds Ratio (95%CI) | P value |
| rs6793295 | 169518455 | C | 3q26 | LRRC34 | 21.9 | 21.2 | 29.7 | 32.1 | 60.8 | 60.9 | 0.89(0.68-1.15) | 0.36 | 0.84(0.56-1.25) | 0.39 |
| rs2609255 | 89811195 | G | 4q22 | FAM13A | 28.6 | 28.7 | 25.3 | 25.4 | 29.4 | 37.5 | 0.89(0.67-1.16) | 0.38 | 0.89(0.62-1.29) | 0.54 |
| rs2736100 | 1286516 | A | 5p15 | TERT | 46.5 | 42.2 | 48.1 | 47.8 | 71.6 | 71.7 | 1.00(0.79-1.27) | 0.99 | 1.18(0.84-1.67) | 0.35 |
| rs7887 | 31864547 | T | 6p21.3 | EHMT2 | 42.3 | 38.6 | 36.7 | 42.5 | 58.8 | 72.5 | 0.82(0.64-1.04) | 0.10 | 0.91(0.64-1.29) | 0.59 |
| rs2076295 | 7563232 | G | 6p24 | DSP | 50.0 | 50.0 | 44.3 | 46.3 | 31.0 | 34.0 | 1.01(0.80-1.28) | 0.94 | 1.03(0.73-1.46) | 0.85 |
| rs4727443 | 99593346 | A | 7q22 | Intergenic | 35.2 | 46.0 | 41.8 | 35.8 | 50.0 | 53.7 | 0.83(0.65-1.07) | 0.15 | 0.76(0.53-1.07) | 0.11 |
| rs11191865 | 105672842 | G | 10q24 | OBFC1 | 49.5 | 46.8 | 38.0 | 55.4 | 37.3 | 43.4 | 0.81(0.62-1.05) | 0.11 | 1.13(0.78-1.65) | 0.52 |
| rs35705950 | 1241221 | T | 11p15.5 | MUCSB | 32.6 | 12.9 | 28.8 | 11.0 | 16.4 | 3.6 | 3.63(2.54-5.31) | 7.31x10⁻¹² | 3.00(1.6-4.99) | 1.15Ex10⁻⁰⁵ |
| rs5743890 | 1325829 | C | 11p15.5 | TOLLIP | 21.5 | 14.2 | 16.7 | 15.1 | 10.0 | 4.5 | 1.61(1.06-2.48) | 0.03 | 2.13(1.13-4.10) | 0.02 |
| rs111521887 | 1312706 | G | 11p15.5 | TOLLIP | 16.7 | 18.0 | 19.2 | 12.3 | 6.9 | 4.4 | 1.33(0.89-1.98) | 0.16 | 0.96(0.55-1.69) | 0.89 |
| rs1278769 | 113536627 | A | 13q34 | ATP11A | 19.6 | 26.1 | 23.4 | 23.8 | 12.7 | 18.1 | 0.83(0.61-1.12) | 0.22 | 0.64(0.41-0.99) | 0.05 |
| rs2034650 | 40717302 | G | 15q14-15 | IVD | 43.3 | 53.7 | 41.0 | 48.4 | 27.5 | 38.1 | 0.71(0.54-0.95) | 0.02 | 0.59(0.38-0.89) | 0.01 |
| rs12610495 | 4717672 | G | 19p13 | DPP | 31.4 | 33.0 | 32.9 | 31.1 | 19.6 | 12.5 | 1.14(0.87-1.50) | 0.33 | 1.19(0.82-1.75) | 0.37 |

*Based on GRCh 37/hg19 database

**P values and odds ratios in this category were adjusted for sex, age at inclusion, ever smoking status and case-series origin.

SEQUENCE LISTING

```
Sequence total quantity: 61
SEQ ID NO: 1            moltype = DNA  length = 1001
FEATURE                 Location/Qualifiers
source                  1..1001
                        mol_type = genomic DNA
                        organism = Homo sapiens
SEQUENCE: 1
agaaagaagt catgaaagta ggaaccacat ttttactcat ctttctgtct ccagcaagca  60
gcttactgct tttcatacac attttgcttt tattactcat gatttcaaag gtgtaatggt  120
tcagccacat caatgtaaca aacagttcac actgggctct tatagtctgg cctttaaaac  180
```

-continued

```
cttcactatt tatgctttca tcttaactac tttgaccctc acaggtttac tcactaagaa    240
cttgagtttc aagagaaaag atgacatgtt tgctgcttaa acaagcaata tctaaaagca    300
tatttagtta taaacgtctt accaagaatt gatataattt tcatttaaac atttttataa    360
atagtagttt acaagatata gtaagtacat ctctaaaaat acagtgtatt catgtaccct    420
gacataaact tgtagtagta ccttagttt attcatgttg ttatattaac taccatcact    480
ttgaatacat acctgttcac bgtacagtat aggtcggttt aggtttattg ccttaattgc    540
ttggttttga gttagtactg tagcaaatgc tatcacactt tgcattccct aaaaacaggt    600
aaattcatta aggaaacaga caaagtatat aataatctcg ctacataaat atttcaagat    660
cagctatctg cattctgata aaattgtttt taaaatttaa gcattccttg gactttgaat    720
tgtaagttga tcaaattcaa aaatgaattg ttactgtatt cttctctcct ggccctaaaa    780
tctatctaaa acatggcatg gggagtttct taatgtttca gtgtccattt cctgggtgtt    840
tccctctagg ttttttttcc tcacccctca agcttctatg tggatcccag ctagagctca    900
tactacttat ccaacacaca tcattgtgca agcactcttt tatattcata ctagtacttt    960
taagtgtgtg tgcggtggga aaaggttacc aatcacattt t                       1001

SEQ ID NO: 2             moltype = DNA  length = 1001
FEATURE                  Location/Qualifiers
source                   1..1001
                         mol_type = genomic DNA
                         organism = Homo sapiens
SEQUENCE: 2
gtattcatca actcctattt cattccctct tcctgtgctc actgaagat gacatttccc    60
agacttccaa gaatgttact gagttctgga atgtaagtag aagggataag tatcacttct    120
gtgctgtggc ggtatggac ctgtgaactt tgcacacgcc ttctatcttc tttttcagtg    180
tccatttcag agggcatgtt ttcagatgaa accagtagaa gatggaagca gcctgtgact    240
agaatcactg cttagggtct tgctgcctag gaatcccact ctacctgcaa cagactgtga    300
aagaaccgag aaatacactg attttgaaca tagcccatac tataatgggg atgtttgtta    360
cagcagttag cattaaaaac cttggctagg cattggtcat aattgtagaa cacagcaaat    420
gaagggaaac tggaacatag aggccagtga gaactttagg gttaatgaaa aatgagggca    480
accaggataa tttggttctt kgccaaatag gaaggtgaaa ccaaaggtag actggaggtc    540
agaaaatcag tccagcacat gtgatgtttt catttagttg cctgtatgtc tgtctggtct    600
ccagctcagc ctggctcctt gaggtaagag gcagtggctg ttcacctttg catcccagca    660
cctggcatac aatagatggg atgaaatgtt caaactgagc ctaagcttca gggtgcttat    720
caaagcaggg aagatacaca agaggagatg attcaggtcc agggcaggtc aggtatctaa    780
acccagtgtc ttaggaagct ggatcctccg aaccagggag aacaagctgg atatgcactg    840
gatttcccag cagtactgat ctagagactc tcatagagtc cctttattc cttggcctag    900
ggttacaact gctttatagca tctggaaaga ctcaacacct caaagagac tttcagtaga    960
tacagcaaat acactcatgg aattgataat taagcttcaa t                        1001

SEQ ID NO: 3             moltype = DNA  length = 1001
FEATURE                  Location/Qualifiers
source                   1..1001
                         mol_type = genomic DNA
                         organism = Homo sapiens
SEQUENCE: 3
attgtcgttg tttgcttttg tttattgaga cagtctcact ctgtcaccca ggctggagtg    60
taatggcaca atctcggctc actgcaacct ctgcctcctc ggttcaagca gttctcattc    120
ctcaacctca tgagtagctg ggattacagg cgcccaccac cacgcctggc taatttttgt    180
attttagta gagataggct ttcaccatgt tggccaggct ggtctcaaac tcctgacctc    240
aagtgatctg cccgccttgg cctcccacag tgctgggatt acaggtgcaa gccaccgtgc    300
ccggcatacc ttgatctttt aaaatgaagt ctgaaacatt gctaccctg tcctgagcaa    360
taagaccctt agtgtatttt agctctggcc accccccagc ctgtgtgctg ttttccctgc    420
tgacttagtt ctatctcagg catcttgaca ccccacaag ctaagcatta ttaatattgt    480
tttccgtgtt gagtgtttct ktagctttgc ccccgccctg cttttcctcc tttgttcccc    540
gtctgcttc tgtctcaggc ccgccgtctg gggtccctt ccttgtcctt tgcgtggttc    600
ttctgtcttg ttattgctgg taaacccag ctttacctgt gctggcctcc atggcatcta    660
gcgacgtccg ggaccctctg cttatgatgc acagatgaag atgtgaggac tcacgaggag    720
ggcggtcatc ttggccgtg agtgtctgga gcaccacgtg gccagcgttc cttagccagt    780
gagtgacagc aacgtccgct cggcctggggt tcagcctgga aaaccccagg catgtcgggg    840
tctgtggct ccgcggtgtc gagtttgaaa tcgcgcaaac ctgcggtgtg gcgccagctc    900
tgacggtgct gcctgcggg ggagtgtctg cttcctcct tctgcttggg aaccaggaca    960
aaggatgagg ctccgagccg ttgtcgccca acaggagcat g                        1001

SEQ ID NO: 4             moltype = DNA  length = 1001
FEATURE                  Location/Qualifiers
source                   1..1001
                         mol_type = genomic DNA
                         organism = Homo sapiens
SEQUENCE: 4
atttgggaac ctttaaaaaa tattctggct tcaaaaatac tccatatta catctttggt    60
tctatctgaa gtaaagccgt gatggtgtgc gtaagtgaaa caggtgcaaa ggggcaacaa    120
caaagggcgc ctctctttgt ctttgtgtcg caggcggaga tggacatggt ggcctgggt    180
gtggacctgg cctcagtgga gcagcacatt aacagccacc ggggcatcca caactccatc    240
ggcgactatc gctggcagct ggacaaaatc aagccgacc tggtacttgt ctgtgttttca    300
ttttagagtc ttcaaaatat ctaccgaagg atcgtgtaat tactcaatcc cagggagttt    360
cttctgaaac attgctatta tttctttccc agaagactgg aaatgtttag aaatcccact    420
tcttaaatgg ggaagtggaa tcagtagccc tattagagat tatgttaaca cttgaagagg    480
agttaaacca gaggctgagg ktgtgcaaac actcatttgc agtttgtgaa taagtctctt    540
taggggtggc agtttgtttc tgcggtaagc agaacatctt tttgaatagg ggaaatgcaa    600
```

```
cagtcttata cagtagtttg tgtcattggt gaatccttc ctaggtggta attaaaacat    660
tatttctact gagcaaagcc atatgtcatc ccgacacccg ctcccatgct gaaaaaagtc    720
agacttgaaa ctgggttgag aattacagca taaaatcata actgatctta agtgcttagt    780
ttcccgcagg tctctacact tgtaaatcac taaacttttt ttttttttt ttacctgaga    840
ccatagcttc tcatcctcat ttcttcttct ggctttttgg cttacttt tgtccacctg     900
agccctgac caacttttct cttcatttct ctaagaccta gggaatccta aatgatgtct    960
ttaaactta agacaatttt ctaacacgtg agtctttaag t                      1001

SEQ ID NO: 5            moltype = DNA   length = 941
FEATURE                 Location/Qualifiers
source                  1..941
                        mol_type = genomic DNA
                        organism = Homo sapiens
SEQUENCE: 5
ttctctgtga gtcttaggga aatgaggagc atgatcttct agcagtaaaa cacctgtaga     60
gaattgcctt atgttttttg tttgtttatt tgtttgtgtg ctttggtttg gtttgctttt    120
tttttttttt ttttttttt tttgagatgg agtctcgccc tgttgcccag gctggagtgt    180
agtggcgaaa tctcggctca ctgcaacctc cacctccctg gttcaagcaa ttcccctgtc    240
tcagcctccc gagtagctga gattacaggt gcacaccacc acgcccggct aattttttgg    300
tatttttagt agagatgggg tttcaccatg ttggccagac tggtctcgaa cttctgacct    360
caggcaatcc gcctgcctca gcctcccaaa gcgctgggat tacaggcatg agccactgcg    420
cccgccctc atgttaatca mtcttttctga tttcaaataa ctcattatcc ccatgaccctt   480
atggatttgt ttttcctctt catccacaaa attctccaga gaagtctccc ttgttatctc    540
ttggctgtgc tttctatctc accagttatc ttttctcaaa gagcttcctc tgcaaagaag    600
ctttgtatat gaagaccatg tgggggctga atcaagacca agtttcacaa cctaaaagta    660
gttcacaaag cttccttgcc tctattctct gcaaatctgt aaactcttca gctgaccaa     720
tttctctctt tagccttcag agattatttt attttatttt attcattc atttcatttc    780
attttgacag aatctagctc tgtcgcccag gctggagtgc agtggcacca tctttgctca    840
ctgcaacctc ccctcacag gttcaagcaa ctgtcctgcc tcagcctccc gagtagctgg    900
gattacaggc gtgagccacc acgcccagct gattttttt t                       941

SEQ ID NO: 6            moltype = DNA   length = 1001
FEATURE                 Location/Qualifiers
source                  1..1001
                        mol_type = genomic DNA
                        organism = Homo sapiens
SEQUENCE: 6
cctctactgc cgtacacccc accactcagc cttggagtgc ctgtgtgcag agcagggctg     60
aggcaggtg ctgctttggt ggtctaggtt tgctgcaggg ccaggtggcc tgagctccaa    120
gcaggatctc tggctgcact cagccccttc tgcctcccca aatgctctat atcactattt    180
gtacactgag cagagtaaag ttagagaaa ctgttttata gaatagggct ggccccgct     240
cccctggcct acgtgatggt ccttcctggc tgccaggtac ttgtttgtat tagagacaga    300
cactccacag ggtctgttgt ggcccacagc acataggcaa tcagaggcag aaagcagagc    360
tgtttggacc cacagagggc cggctgtctg ccactgaaat gtctttccag ttggttgaga    420
agcagcagga tgctctgctg gtgatgtctg aaagtcccag gattcttttgg gtctccaagg    480
agatcctagc atataccact rtcgtggttt taataaaag caaaaacact ttcagatggg    540
gagaagagtg gaacaaaagg tattcttcct gggttgaagt ctgggggaaa ggcattgaga    600
agactgggct aatggcacaa accaatgaag tactcaagtc acctgtgatg gaggccagtc    660
atccaatggt atcaactttg tatgtggcaa cacttaataa aaatctgaac aggtcttcac    720
ttgtggacac agtagacttt cttgaaaaag gacagaaaag tgagccctgt gaattttcat    780
ctcacggact gacaacaatg acttgccttt aaggacagtc actcaagatg aagatgcaac    840
aaaaccccttc cagttccaag tggctgatga aaaaaaaaaa atcttaaaag catcacagaa    900
caacggagaa agagatcaga agactataac agatagtttg aattttaaaa ctcagagaaa    960
agcaactgag gaggaaatac actgcttaga aagaagaaac t                      1001

SEQ ID NO: 7            moltype = DNA   length = 601
FEATURE                 Location/Qualifiers
source                  1..601
                        mol_type = genomic DNA
                        organism = Homo sapiens
SEQUENCE: 7
tggacggcct ctgaaggggt ctgtggggtc ctggacgggt ccccattcat ggcaggatta     60
accccctcg ggttctgtgt ggtccaggcc gccccttttgt ctccactgcc ccctggccag    120
aatgagggac agtgacccac ccagggctgg gcctggctca gactccgtca gagccgcagg    180
gcaagttcct ggcacgtccg aggtgggagg ctcctctgcg ctccaggagg ctgtgcctgc    240
cccccttcc cggcaggaac cggctgtgtc cctttccttc ctttatcttc tgttttcagc    300
dccttcaact gtgaagaggt gaactcttca aacacgctga gcaaacaggc ccgactccca    360
gggccgcatc cgggatgtct caatagctgt ggccttgacg tccacctcgg accccctgcc    420
cggaccccagc ccagttccca atgggccctc tgcccggggga ggtgcctagt gggagggacg    480
agggcaaagt cggggccccc acttgttttgg tgtcactgtg tgccagcggc cactgggtgg    540
cgaggctgtt ccaggggtgga ggcggggagg gttggaccac aggcactgag cggggacaga    600
g                                                                   601

SEQ ID NO: 8            moltype = DNA   length = 732
FEATURE                 Location/Qualifiers
source                  1..732
                        mol_type = genomic DNA
                        organism = Homo sapiens
SEQUENCE: 8
```

```
gtcattggtc aaatgtggcc tgtatctaaa ttccaactgt tagaatcata gacatctaga    60
gcttacgtca gttttagata tttcttatga attctcagaa ttcatagatt ctcatttta    120
ttcttagact tctcagatat tccgttttg atagtatacc cttctgagtc taatatgtcc    180
taaagtgcga acttgtacaa tttttttttt ttttttttt ttttttttt tktgataagg    240
agtttactc tgtcacccag gctggagtgc agtgaccga tctcggctca ctgcaacctc    300
tgcctcccgg gttcaagtga ttgtgatgtc tcagtctccc aagtagctgg gattacaggc    360
tcctgccacc acatgcctag ctaattgtta tactttagta gaaatggggc ttcgccgtgt    420
tagtcaggct ggtcttgtac tcctgacctc agttgatctg cctaccttgg cccccaaggt    480
gctgggatta caggcatgag ccaccgcgcc tgacccagct tcttaaatta ttctgggcca    540
ccagtaatgt gaatcatgta aattaaaata tataattaaa caaaatcata tagcgattag    600
agataatagt tgtgaaatgc ttgaaaaatc ataggcattt aataaataga agccattcca    660
attaggattc ttcttgattt tttttcaaga ccaaaaaaat actctttaa atatttatta    720
taatactcca tg                                                        732

SEQ ID NO: 9          moltype = DNA  length = 1320
FEATURE               Location/Qualifiers
source                1..1320
                      mol_type = genomic DNA
                      organism = Homo sapiens
SEQUENCE: 9
aggctgcagt tagtcatgac tgcgcgctgc actccagcct gggtgacaaa gtgaggccct    60
gtctcaaaaa caataaaaaa tttaaaagag ctgagcatgg ctgaccacttt gggaggctga    120
ggcaggcaga tctcttaagc ccaggagtct gagaccagcc tgggcgacat gatgaagccc    180
catctctaca aaaatacaa aaaaattagc tgagctttat ggcaaatccc tgtaatccca    240
gttacctagg aggcccaggc aggaagatgg cttgagccca aaaggttgag gctgtagtga    300
gctgtgatca tgaacagagt gagaccctgt ttcaaaacaa aatgaaaaac aaacaaacaa    360
aaaaaccaag aaaacaagaa aacaaaaact atacaatgat gagccaaaaa gcaagatatg    420
gaagaatata tatatatata tatatatata tatagtatga gtccagctat agaaagtttg    480
aaatcaggca acctaaacaa tattgttcag ggatctatac agaggcagga agccattgag    540
aaaggtaagg ggaggattat caccaaattc aggatggtgg ctcccctggg gagaatatgt    600
caaggagggg cacatgggct tggaatactg tcttcattga cctgcgtgtt gggtacacag    660
gagtttgtta tttttcacac tgcatatgtg catgtatata ctctcccata tataccatgc    720
atttcacaca agaacacaaa ggctgtgtgg ctctgctctg ccccttccc cttccagctc    780
ccattctcgt cytcagctag cagaggaggg tcagggtctt ttagcacagc ttccttctgt    840
ctctgagtgg gtcagaggag tacggggatg agggcctccc ttctgcggct gggctctgg    900
cactccaggg tgggaaggcc tggagaaaac agggccaggc aaagccggct ggccctgctg    960
tttctgccaa tgctgggatt aggccagggc tctggcccac ctgtcatttc actcattcag   1020
catgaacata gccactgagc acttactgtg agccccgggt gctattggga gagttcagat   1080
aagtgagaga gggtcttttga cctcaaagat cttacagaga ggaccgtata cacaaataac   1140
agtataccag caaaatgtga gctaagtgtc atgtgactac tcatctactc tttcaataaa   1200
tatttgttgt gcacctatta catgccagga actgtgctgg atggtgatca tgtaaagaca   1260
gtcaaatcac agtcctagct ctcagattca cagcctgcct aatgctgggg aaactggaat   1320

SEQ ID NO: 10         moltype = DNA  length = 1001
FEATURE               Location/Qualifiers
source                1..1001
                      mol_type = genomic DNA
                      organism = Homo sapiens
SEQUENCE: 10
ccagccagaa ggggcgcagt ttgttagttc agctcctcct gagacagaaa taaagacacg     60
aaccaaagga catcagcact tacagggctc tcaggtcaca cacaggatgt ccgcgcccac    120
tgcagagctg caggtcccct ccagggcagt ggggagccac aagcagcgtt aggcagcggc    180
tgggaccagg accgcctgag cactcaagaa ccccccactgc cccaagcact gctggcagca    240
agcccagaaa actgagcccg gggagctcct ctgagcggcc taagcacccc tctaagctgt    300
gctgcccaa ttcaagcctg gctcacggca gcaaagaaaa aatgtgactc tcggagctcc    360
caaaggggcc acccataagc tgagagcctg cccggaagca cttatagacc cgcgtggctt    420
gttttcattg caaagaacaa taaaaattat cttgcctctg atcaccactg atagcccaag    480
aagcaaaat tcgatcccgg dgatgagaaa tgaaatgaaa catcgcgaga aacttccagg    540
aatcttctgg atgtggctag actcttttagc ttgagcttcc agacaggccg aggcttggtg    600
ctggagcctg gccctcgct gacctctctt ctacccgggg gcacagcccg gattgcagag    660
aggctggcgc aagagtgagg gagcgagggc tagcctgtga tgggcttct ccacctagca    720
ccacccatg ctgtggctca ggggagtcaa gagtttacac agctgcagag atggattcca    780
ggccacttac tcaagtctac ctactccttc cttcggccaa tcagctgggt gcctctgcgg    840
cctgtgacac caccagcaaa cagctccaga cctcctaagc tgtctctgt caaggctggg    900
tggcagatct gtgatctcct ttttaaattt tcatttttt ttaagagatg gggtcttgct    960
atattgccca ggctggtctc aaactcctgg gctccagcg t                         1001

SEQ ID NO: 11         moltype = DNA  length = 17916
FEATURE               Location/Qualifiers
source                1..17916
                      mol_type = genomic DNA
                      organism = Homo sapiens
SEQUENCE: 11
cacccggcc ggctccctcc ctgcccgtcc ccgtccccc acccgtgcca gcccccagga     60
tgggtgccc gagcgcgtgc cggacgctgg tgttggctct ggcggccatg ctcgtggtgc    120
cgcaggcaga gacccagggc cctgtggagc cgagctggga gaatgcaggg cacaccatgg    180
atggcggtgc cccgacgtcc tcgcccaccc ggcgcgtgag ctttgttcca cccgtcactg    240
tcttcccag cctgagcccc ctgaacccgg cgcacaatgg gcgggtgtgc agcacctggg    300
gtgacttcca ctacaagacc ttcgacgcg acgtcttccg cttccctggc ctttgcaact    360
```

```
acgtgttctc tgagcactgc cgcgccgcct acgaggactt caacgtccag ctacgccgag    420
gcctagtggg ctccaggcct gtggtcaccc gtgttgtcat caaggcccag ggcctggtgc    480
tggaggcgtc caacggctcc gtcctcatca atgggcagcg ggaggagctg ccttacagcc    540
gcactggcct cctggtggag cagagcgggg actacatcaa ggtcagcatc cggctggtgc    600
tgacattcct gtgaaacgga gaggacagtg ccctgctgga gctggatccc aaatacgcca    660
accagacctg tggcctgtgt ggggacttca acggcctccc ggccttcaac gagttctatg    720
cccacaacgc caggctgacc ccgctccagt ttgggaacct gcagaagttg gatgggccca    780
cggagcagtg cccggaccccg ctgcccttgc cggccggcaa ctgcacggac gaggagggca    840
tctgccaccg caccctgctg gggccggcct ttgcggagtg ccacgcactg gtggacagca    900
ctgcgtacct ggccgcctgc gcccaggacc tgtgccgctg ccccacctgc ccgtgtgcca    960
cctttgtgga atactcacgc cagtgcgccc acgcggggg  ccagccgcgg aactggaggt   1020
gccctgagct ctgccccggg acctgccccc tcaacatgca gcaccaggag tgtggctcac   1080
cctgcacgga cacctgctcc aaccccagc  gcgcgcagct ctgcgaggac cactgtgtgg   1140
acggctgctt ctgccccca  ggcacggtgc tggatgacat cacgcactct ggctgcctgc   1200
ccctcgggca gtgcccctgc acccacggcg gccgcaccta cagcccgggc acctccttca   1260
acaccacctg cagctcctgc acctgctccg gggggctatg gcagtgccag gacctgccgt   1320
gccctggcac ctgctctgtg cagggcgggg cccacatctc cacctatgat gagaaactct   1380
acgacctgca tggtgactgc agctacgttc tgtccaagaa atgtgccgac agcagcttca   1440
ccgtgctggc tgagctgcgg aagtgcggcc tgacggacaa cgagaactgc ctgaaagcgg   1500
tgacgctcag cctggacggc ggggacacgg ccatccgggt ccaagcggac ggcggcgtgt   1560
tcctcaactc catctacacg cagctgcccc tgtcggcagc caacatcacc ctgttcacac   1620
cctcgagctt cttcatcgtg gtgcagacag gcctgggcct gcagctgtg  tgcagctgga   1680
tgccactcat gcaggtgttt gtcaggctgg accccgccca ccagggccag atgtgcggcc   1740
tgtgtgggaa cttcaaccag aaccaggctg acgacttcac ggccctcagc ggggtggtgg   1800
aggccacggg cgcagccttc gccaacacct ggaaggccca ggctgcctgt gccaatgcca   1860
ggaacagctt tgaggacccc tgctccctca gtgtggagga tgagaactac gcccggcact   1920
ggtgctcgcg cctgaccgat cccaacagtg ccttctcgcg ctgccactcc atcatcaacc   1980
ccaagccctt ccactcgaac tgcatgtttt acacctgcaa ctgtgagcgg agcgaggact   2040
gcctgtgcgc cgcgctgtcc tcctatgtgc acgcctgtgc cgccaaggc  gtacagctca   2100
gcgactggga ggacggcgtc tgcaccaagt acatgcagaa ctgccccaag tcccagcgct   2160
acgcctacgt ggtggatgcc tgccagccca cttgccgcgg cctgagtgag gccgacgtca   2220
cctgcagcgt ttccttcgtg cctgtggacg gctgcacctg ccccgcgggc accttcctca   2280
atgacgcggg cgcctgtgtg cccgcccagg agtgccctg  ctacgctcac ggcaccgtgc   2340
tggctcctgg agaggtggtg cacgcagagg cgccgtgtg  ttcatgtacg ggtgggaagc   2400
taagctgcct gggagcctct ctgcagaaaa gcacagggtg tgcagcccca atggtgtacc   2460
tggactgcag caacagctcg gcgggcaccc ctggggccga gtgcctccgg agctgccaca   2520
cgctggacgt gggctgtttc agcacacact gcgtgtccgg ctgtgtctgt cccccggggc   2580
tggtgtcgga tgggagtggg ggctgcattg ccgaggagga ctgcccctgt gtgcacaacg   2640
aggccaccta caagcctgga gagaccatca ggtcgactg  acctgc  cctgcagga     2700
accggaggtg ggagtgcagc caccggctct gcctgggcac ctgcgtgcc  tacggggatg   2760
gccacttcat caccttttga tggcgatcgct acagctttga aggcagctgc gagtacatct   2820
tggcccagga ctactgtggg acaaacacca cccacggac  cttccgcatc gtcaccgaga   2880
acatccctg  tgggaccacc ggcaccaccc gctccaagg  catcaagctc ttcgtggaga   2940
gctacgagct gatcctccaa gagggggacct ttaaggcggt ggcgagaggg ccgggtgggg   3000
acccacccta caagatacgc tacatgggga tcttcctggt catcgagacc acgggatgg    3060
ccgtgtcctg ggaccggaag accagcgtgt tcatccgact gcaccaggac tacaagggca   3120
gggtcgcgg  cctgtgcggg aacttcgacg acaatgccat caatgacttt gccacgcgta   3180
gccggtccgt ggtgggggac gcactggagt ttgggaacag ctggaagctc tcccctcct    3240
gcccggacgc cctggcaccc aaggacccct gcacggccaa ccccttccgc aagtcctggg   3300
cccagaagca gtgcagcatc ctccacgccc ccaccttcgc cgcctgccgc tcccaggttg   3360
actccaccaa gtactacgag gcctgcgtga acgacgcgtg tgcctgcgac tcgggtgcgg   3420
actgcgagtg tttctgcacg gctgtggctg cctacgccca ggcctgccac gacgcgggcc   3480
tgtgtgtgtc ctggcggact ccggacacct gccccttgtt ctgtgacttc tacaacccac   3540
atgggggctg tgagtggcac taccagccct gcgggcacc  ctgcctaaaa acctgccgga   3600
accccagtgg gcactgcctg gtggacctgc ctggcctgga aggctgctac ccgaagtgcc   3660
caccccagcca gcccttcttc aatgaggacc agatgaagtg cgtggcccag tgtggctgct   3720
acgacaagga cggaaactac tatgacgtcg gtgcaagggt cccacacgcg gagaactgcc   3780
agagctgtaa ctgcacaccc agtggcatcc agtgcgctca cagccttgag gcctgcacct   3840
gcacctatga ggacaggacc tacagctacc aggacgtcat ctacaacacc accgatggc    3900
ttggcgcctg cttgatcgcc atctgcggaa gcaacggcac catcatcagg aaggctgtgg   3960
catgtcctgg aactccagcc acaacgccat tcaccttcac caccgcctgg gtccccact    4020
ccacgacaag cccggccctc ccggtctcca ccgtgtgtgt ccgcgaggtc tgccgctggt   4080
ccagctggta caatgggcac cgcccagagc ccggcctggg aggcggagac tttgagacgt   4140
ttgaaaacct gaggcagaga gggtaccagg tatgccctgt gctggctgac atcagtgcg    4200
gggcggcgca gcttcccgac atgccgctgg aggagctggg ccagcaggtg gactgtgacc   4260
gcatgcgggg gctgatgtgc ccaacagcc aacagagtcc cccgctctgt cacgactacg    4320
agctgcgggt tctctgctgc gaatacgtgc cctgtggccc ctcccggcc  ccaggcacca   4380
gccctcagcc ctccctccagt gccagcacgg agctgctgt  gcctacccca acccagacca   4440
cagcaaccga aaagaccacc ctatgggtga ccccgagcat ccggtcgacg gcggccctca   4500
cctcgcagac tggtcccagc tcaggccccg tgacggtcac cccctcggcc ccaggtacca   4560
ccacctgcca gccccggtgt cagtggacag agtggtttga tgaggactac cccaagtctg   4620
aacaacttgg aggggacgtt gagtcctacg ataagatcag gccgctggaa gggccactat   4680
gccagcagcc taaggacata gagtgccagg ccgagagctt cccaactgg  accctggcac   4740
aggtgggga  aaggtgcac tgtgacgtcc acttcggct ggtgtgcagg aactggggac    4800
aggagggcgt cttcaagatg tgctacaact acaggatccg ggtcctctgc tgcagtgacg   4860
accactgcag gggacgtgcc acaacccgc  caccgaccac agagctggag acggccacca   4920
ccaccaccac ccaggccctg ttctcaacgc cgcagcctac gagtagcccg gggctgacca   4980
gggctccccc ggccagcacc acagcagtcc ccaccctctc agaaggactg acatccccca   5040
gatacacaag caccccttggt acagccacca cgggaggccc cacgacgcct gcaggctcca   5100
```

```
cagaacccac tgtcccaggg gtggccacat ccacccttcc aacacgctca gcccttccag  5160
ggacgacggg gagcttgggc acatggcgcc cctcacagcc acccacgctg gcccaacaa   5220
caatggcaac ctccagagct cgcccgacag gcacagccag caccgcttcc aaagagccgc  5280
tgaccacgag cctggcgcca acactcacga gcgagctgtc cacctctcag gccgagacca  5340
gcacgcccag gacagagacg acaatgagcc ccttgactaa caccaccacc agccagggca  5400
cgacccgctg tcaaccgaag tgtgagtgga cagagtggtt tgacgtggac ttcccaacct  5460
caggggttgc aggcgggac atggaaactt ttgaaaacat cagggctgct ggggcaaga   5520
tgtgctgggc accaaagagc atagagtgcc gggcggagaa ctaccccgag gtaagcatcg  5580
accaggtcgg gcaggtgctg acctgcagcc tggagacggg gctgacctgc aagaacgaag  5640
accagacagg caggttcaac atgtgcttca actacaacgt gcgtgtgctt tgctgtgacg  5700
actacagcca ctgccccagt accccagcca ccagctccac ggccacgccc tcctcaactc  5760
cggggacgac ctggatcctc acaaagccga ccacaacagc cactacgact gcgtccactg  5820
gatccacggc caccccgacc tcacccctga gaacagctcc ccctcccaaa gtgctgacca  5880
ccacggccac cacacccaca gtcaccagct ccaaagccac tccctcctcc agtccaggga  5940
ctgcaaccgc ccttccagca ctgagaagca cagccaccac acccacagct accagcgtta  6000
cacccatccc ctcttcctcc ctgggcacca cctggacccg cctatcacag accaccacac  6060
ccacggccac catgtccaca gccacaccct cctccactcc agagactgcc cacacctcca  6120
cagtgcttac cgccacggcc accaactg gggccaccgg ctctgtggcc accccctcct    6180
ccaccccagg aacagctcac actaccaaag tgccaactac cacaaccacg ggcttcacag  6240
ccacccccct ctccagccca gggacggcac tcacgcctcc agtgtggatc agcacaacca  6300
ccacacccac aaccagaggc tccacggtga cccctcctc catcccgggg accacccaca   6360
ccgccacagt gctgaccacc accaccacaa ctgtggccac tggttctatg gcaacacccct 6420
cctctagcac acagaccagt ggtactcccc catcactgac caccacgcc actacgatca   6480
cggccacccgg ctccaccacc aacccctcct caactcctgg gacaactccc atcccccag   6540
tgctgaccac caccgccacc acacctgcag ccaccagcaa cacagtgact ccctcctctg  6600
ccctagggac cacccacaca cccccagtgc cgaacaccat gccaccacca cacgggcgat  6660
ccctgccccc cagcagtccc cacacggtgc gcacagcctg gacttcggcc acctcgggca  6720
tcttgggcac cacccacatc acagagcctt ccacggtgac ttcccacacc ctagcagcaa  6780
ccaccggtac cacccagcac tcgactccag cccttccag cccctcaccct agcagcagaa  6840
ccaccgagtc accccccttct ccagggacga ccaccccggg ccacaccacg gccaactcca   6900
ggaccacagc cacggccaca cccagcaaga cccgcacctc gaccctgctg cccagcagcc  6960
ccacatcggc ccccataacc acggtggtga ccatgggctg tgagcccag tgtgcctggt    7020
cagagtggct ggactacagc tacccccatgc cggggccctc tggcggga cc tttgacacct  7080
actccaacat ccgtgcggcc ggaggggccg tctgtgagca gccccctgggc ctcgagtgcc  7140
gtgccagc ccagcctggt gtccccctgc gggagttggg ccaggtcgtg gaatgcagcc     7200
tggactttgg cctggtctgc aggaaccgtg agcaggtggg gaagttcaag atgtgcttca   7260
actatgaaat ccgtgtgttc tgctgcaact acggccactg ccccagcacc ccggccacca   7320
gctctacggc catgccctcc tccactccgg ggacgacctg gatcctcaca gagctgacca   7380
caacagcacc tacgactgag tccactggat ccacgggcac ccgtcctcc acccccaggga   7440
ccacctggat cctcacagag ccgagcacta cagccaccgt gacggtgccc accggatcca   7500
cggcaccgc ctcctccacc caggcaactg ctggcacccc acatgtgagc accacggcca   7560
cgacacccac agtcaccagc tccaaagcca ctcccttctc cagtcaggg actgcaaccg    7620
ccttccagc actgagaagc acagccacca caccacagc taccagcttt acagccatcc   7680
cctcctcctc cctgggcacc acctggaccc gcctatcaca gaccaccaca cccacggcca   7740
ccatgtccac agccacaccc tcctccactc cagagactgt ccacacctcc acagtgctta   7800
ccaccacggc caccacaacc ggggccaccg gctctgtggc caccccctcc tccacccag    7860
gaacagctca cactaccaaa gtgctgacta ccacaaccac gggcttcaca gccacccct   7920
cctccagccc agggacggca cgcacgcttc cagtgtggat cagcacaacc accacaccca   7980
caaccagagg ttccacggtg acccctcct ccatcccggg gaccacccac accccacag   8040
tgctgaccac caccaccaca actgtggcca ctggttctat ggcaacaccc tcctctagca   8100
cacagaccag tggtactccc ccatcactga caccacccgg cactacgatc acggccacg    8160
gctccaccac caacccctcc tcaactccag ggacaacacc tatcccccca gtgctgacca   8220
ccaccgccac cacacctgca gccaccagca gcacagtgac tccctcctct gcctagggaa   8280
ccacccacac accccagtg ccgaacacca cggccaccac acacgggcga tccctgtccc    8340
ccagcagtcc ccacacggtg cgcacagcct ggacttcggc cacctcaggc accttgggca   8400
ccacccacat cacagagcct tccacgggga cttcccacac cccagcagca accaccggta   8460
ccacccagca ctcgactcca gcccctgtcca gccctcaccc tagcagcagg accaccgagt   8520
cacccccttc tccagggacg accaccccgg ccacaccag gccacctcc aggaccacgg     8580
ccacgccccac acccagcaag accccagcct cgacccctgct gcccagcagc cccacatcgg  8640
ccccaataac acggtggtg accatgggct gtgagcccca gtgtgcctgg tcagagtgc     8700
tggactacag ctacccccatg ccggggccct ggcgggga ctttgacacc tactccaaca   8760
tccgtgcggc cggagggcc gtctgtgagc agccccctggg cctcgagtgc cgtgcccagg   8820
cccagcctgt tgtcccctg cgggagttgg ccaggtcgt ggaatgcagc ctggactttg      8880
gcctggtctg caggaaccgt gagcaggtgg ggaagttcaa gatgtgcttc aactatgaaa    8940
tccgtgtgtt ctgctgcaac tacgccactg ccccagcac ccggccacc agctctacgg    9000
ccacgccctc ctcactcca gggacgacct ggatcctcac agagcagacc acagcagcca   9060
ctacgaccgc aaccactgga tccacggcca tcccgtcctc caccccggga acagctcccc   9120
ctcccaaagt gctgaccagc acggccacca cccccacagc caccagttcc aaagccactt   9180
cctcctccag tccaaggact gcaaccaccc ttccagtgct gacaagcaca gccaccaaat   9240
ccacagctac cagcttaca cccatccct ccttcacccct tgggaccacc gggaccctcc    9300
cagaacagac caccacccc atggccacca tgtccacaat ccaccctccc tccactccgg   9360
agaccaccca cacctccaca gtgctgacca cgaaggccac cacgacaagg gccaccagtt   9420
ccatgtccac ccctcctcc actccgggga cgacctggat cctcacagag ctgaccacag   9480
cagccacaa aactgccca ccggcccca gtctccacc ccagggaacca                 9540
cctggatcct cacagagccc agcactacag ccacgtgac ggtgccacc ggatccaccg     9600
ccaccgcctc ctcacccgg gcaactgctg gcacctcaa gtgctgacc agcacggcca      9660
ccacccacc agtcatcagc tccagagcca ctcctcctc cagtcaggg actgcaaccg      9720
cccttccagc actgagaagc acagccaca cccacagc taccagcgtt acagccatcc       9780
cctcttcctc cctgggcacc gcctggaccc gcctatcaca gaccaccaca cccacggcca   9840
```

```
ccatgtccac agccacaccc tcctctactc cagagactgt ccacacctcc acagtgctta   9900
ccaccacgac cacccaaacc agggccaccg gctctgtggc cacccctcc tccaccccag   9960
gaacagctca cactaccaaa gtgccgacta ccacaaccac gggcttcaca gccacccct  10020
cctccagccc agggacggca ctcacgcctc cagtgtggat cagcacaacc accacaccca  10080
caaccagagg ctccacggtg accccctcct ccatcccggg gaccacccac accgccacag  10140
tgctgaccac caccaccaca actgtggcca ctggttctat ggcaacaccc tcctctagca  10200
cacagaccag tggtactccc ccatcactga ccaccacggc cactacgatc acagccaccg  10260
gctccaccac caacccctcc tcaactccag ggacaactcc catcccccca gtgctgacca  10320
ccaccgccac cacacctgca gccaccagca gcacagtgac tccctcctct gccctaggga  10380
ccacccacac accccagtg ccgaaccacca cggccaccac acacgggcgg tccctgcccc  10440
ccagcagtcc ccacacggtg cgcacagcct ggacttcggc cacctcgggc atcttgggca  10500
ccacccacat cacagagcct tccacggtga cttccacac cccagcagca accaccagta  10560
ccacccagca ctcgactcca gccctgtcca gccctcaccc tagcagcagg accaccgagt  10620
caccccctc tccagggacg accccccgg gccacacag gggcacctcc aggaccacag  10680
ccacagccac acccagcaag acccgcacct cgacccctgct gcccagcagc cccacatcgg  10740
cccccataac cacggtggtg accacgggct gtgagcccca gtgtgcctgg tcagagtggc  10800
tggactacag ctaccccatg ccggggccct ctggcgggga ctttgacacc tactccaaca  10860
tccgtgcggc cggagggca gtctgtgagc agccctggg cctcgagtgc cgtgcccagg  10920
cccagcctgg tgtcccctg cgggagttgg gccaggtcgt ggaatgcagc ctggacttg  10980
gcctggtctg caggaaccgt gagcaggtgg ggaagttcaa gatgtgcttc aactatgaaa  11040
tccgtgtgtt ctgctgcaac tacgccact gccccagcac cccggccacc agctctacgg  11100
ccacgccctc ctcaactccg gggacgacct ggatcctcac aaagctgacc acaacagcca  11160
ctacgactga gtccactgga tccacggcca ccccgtcctc caccccaggg accacctgga  11220
tcctcacaga gccgagcact acagccaccg tgacggtgcc caccggatcc acggccaccg  11280
cctcctccac ccaggcaact gctggcaccc cacatgtgag caccacggcc acgacaccca  11340
cagtcaccag ctccaaagcc actccctcct ccagtccagg gactgcaacc gcccttccag  11400
cactgagaag cacagccacc acacccacag ctaccagctt tacagccatc ccctcctcct  11460
ccctgggcac caccctggacc cgcctatcac agaccaccac acccacggcc accatgtcca  11520
cagccacacc ctcctccact ccagagactg cccacacctc cacagtgctt accaccacgg  11580
ccaccacaac cagggccacg ggctctgtgg ccaccccctc ttccacccca ggaacagctc  11640
acactaccaa agtgccgact accacaacca cgggcttcac agtcacccc tcctccagcc  11700
cagggacggc acgcacgcct ccagtgtgga tcagcacaac caccacaccc acaaccagtg  11760
gctccacggt gaccccctcc tccgtcccgg ggaccaccca cacccccaca gtgctgacca  11820
ccaccaccac aactgtggcc actggttcta tggcaacacc ctcctctagc acacagacca  11880
gtggtactcc cccatcactg atcaccacgg ccactacgat cacggccacc ggctccacca  11940
ccaacccctc ctcaactcca gggacaacac ctatccccc agtgctgacc accaccgcca  12000
ccacacctgc agccaccagc agcacagtga ctccctcctc tgccctaggg accacccaca  12060
caccccagt gccgaaacacc acggccacca cacgggcg atccctgtcc cccagcagtc  12120
cccacacggt gcgcacagcc tggacttcgg ccacctcggg cacccccaca  12180
tcacagagcc ttccacggg acttcccaca cccagcagc aaccaccggt accaccagc  12240
actcgactcc agccctgtcc agccctcacc ctagcagcag gaccaccgag tcacccctt  12300
ccccagggac gaccaccccg ggccacacca cggccacctc caggaccacg gccacggcca  12360
cacccagcaa ccccgcacc tcgaccctgc tgcccagcag cccccatcg gcccccataa  12420
ccacggtggt gaccacgggc tgtgagcccc agtgtgcctg gtcagagtgg ctggactaca  12480
gctaccccat gccgggggccc tctggcgggg actttgacac ctactccaac atccgtgcgg  12540
ccggagggggc cgtctgtgag cagccctgg gcctcgagtg ccgtgcccag gcccagcctg  12600
gtgtcccct ggggggagttg gccaggtcg tggaatgcag cctggactt ggcctggtct  12660
gcaggaaccg tgagcaggtg gggaagttca agatgtgctt caactatgaa atccgtgtgt  12720
tctgctgcaa ctacgccac tgccccagca cccggccac cagctctacg gccatgccct  12780
cctccactcc ggggacgacc tggatcctca cagagctgac cacaacagcc actacgactg  12840
catccactgg atccacgggcc acccccgtcct ccacccccggg aacagctccc cctcccaaag  12900
tgctgaccag cccggccacc acacccacag ccaccagttc caaagccact tcctcctcca  12960
gtccaaggac tgcaaccacc cttccagtgc tgacaagcac agccaccaaa tccacagcta  13020
ccagcgttac acccatcccc tcctccaccc ttgggaccac cgggaccctc ccagaacaga  13080
ccaccacacc cgtggcctcc atgtccacaa tccacccctc ctccactccg gagaccaccc  13140
acacctccac agtgctgacc acgaaggcca ccacgacaag ggccaccagt tccacgtcca  13200
cccctcctc cactccgggg acgacctgga tcctcacaga gctgaccaca gcagccacta  13260
caactgcagc cactggcccc acggccaccc cgtcctccac cccagggacc acctggatcc  13320
tcacagagct gaccacaaca gccactacga ctgcgtccac tggatccacg gccacccgt  13380
cctccacccc agggaccacc tggatcctca cagagccgag cactacagcc accgtgacgg  13440
tgcccaccgg atcacggcc accgcctcct ccacccagga aactgctggc acccacatg  13500
tgagcaccac ggccacgaca cccacagtca ccagctccaa agccactccc tcctccagtc  13560
cagggactgc aactgccctt ccagcactga gaagcacagc caccacccc acagctacca  13620
gctttacagc catcccctcc tcctccctgg gcaccaccct ggaccgccta tcacagacca  13680
ccacacccac ggccaccatg tccagcca caccctcctc cactccagag actgtccaca  13740
cctccacagt gcttaccgcc acggccacca aaccggggc caccggctct gtggccaccc  13800
cctcctccac cccaggaaca gctcacacta ccaaagtgcc gactaccaca accacggct  13860
tcacagccc ccctcctcc agcccaggga cggcacccc gcctcagtgg ggatcagca  13920
caaccaccac accaccacca caaccagtgg ctccacggtg accccctcct  13980
ccatcccggg gaccacccac accgccagag tgctgaccac caccaccaca actgtggcca  14040
ctggttctat ggcaacaccc tcctctagca cacagaccag tggtactccc ccatcactga  14100
ccaccacggc cactacgatc acggccaccg gctccaccac caacccctcc tcaactccag  14160
ggacaacacc catcccccca gtgctgacca gcacggccac cacacccgca gccaccagct  14220
ccaaagctcc ttcctcctcc agtccaagga ctgcaaccac ccttccagtg ctgacaagca  14280
cagccacaaa atccacagct accagcttta cacccatccc ctcctccacc ctgtggacca  14340
cgtggaccgt cccagcacag accaccacac ccatgtccac catgtccaca atccacacct  14400
cctctactcc agagaccacc cacacctcca cagtgctgac caccacagcc accatgacaa  14460
gggccaccaa ttccacggcc acaccctcct ccactctggg gacgacccgg atcctcactg  14520
agctgaccac aacagccact acaactgcag ccactggatc cacggccacc ctgtcctcca  14580
```

```
                                        -continued
ccccagggac cacctggatc ctcacagagc cgagcactat agccaccgtg atggtgccca    14640
ccggttccac ggccaccgcc tcctccactc tgggaacagc tcacacccc aaagtggtga     14700
ccaccatggc cactatgccc acagccactg cctccacggt tcccagctcg tccaccgtgg    14760
ggaccacccg caccccctgca gtgctcccca gcagcctgcc aaccttcagc gtgtccactg   14820
tgtcctcctc agtcctcacc accctgagac ccactgctcc ccccagctcc cacttctcta   14880
ctccctgctt ctgcagggca tttgacagt ttttctcgcc cggggaagtc atctacaata    14940
agaccgaccg agccggctgc catttctacg cagtgtgcaa tcagcactgt gacattgacc    15000
gcttccaggg cgcctgtccc acctcccac cgccagtgtc ctccgccccg ctgtcctcgc    15060
cctccctgc ccctggctgt gacaatgcca tccctctccg gcaggtgaat gagacctgga    15120
ccctggagaa ctgcacggtg gccaggtgcg tgggtgacaa ccgtgtcgtc ctgctgacaa   15180
caaagcctgt ggccaacgtc acctgcgtga caagcacct gcccatcaaa gtgtcggacc    15240
cgagccagcc ctgtgacttc cactatgagt gcgagtgcat ctgcagcatg tggggcgggct  15300
cccactattc caccttgac ggcacctctt acaccttccg gggcaactgc acctatgtcc    15360
tcatgagaga gatccatgca cgctttggga atctcagcct ctacctggac aaccactact   15420
gcacggcctc tgccactgcc gctgccgccc gctgccccg cgcctcagc atccactaca     15480
agtccatgga tatcgtcctc actgtcacca tggtgcatgg gaaggaggag ggcctgatcc   15540
tgtttgacca aattccggtg agcagcggtt tcagcaagaa cggcgtgctt gtgtctgtgc   15600
tggggaccac caccatgcgt ctggacattc ctgccctggg cgtgagcgtc accttcaatg   15660
gccaagtctt ccaggcccgg ctgccctaca gcctcttcca caacaacacc gagggccagt   15720
gcggcacctg caccaacaac cagagggacg actgtctcca gcgggacgga accactgccg   15780
ccagttgcaa ggacatggcc aagacgtggc tggtccccga cagcagaaag gatggctgct   15840
gggccccgac tggcacaccc ccactgcca gccccgcagc cccggtgtct agcacaccca    15900
ccccaccccc atgccacca cagccgctct gtgatctgat gctgagccag gtctttgctg    15960
agtgccacaa ccttgtgccc ccgggcccat tcttcaacgc ctgcatcagc gaccactgca   16020
ggggccgcct tgaggtgccc tgccagagcc tggaggctta cgcagagctc tgccgcgccc   16080
ggggagtgtg cagtgactgg cgaggtgcaa ccggtggcct gtgcgacctc acctgcccac   16140
ccaccaaagt gtacaagcca tgcggcccca tacagcctgc cacctgcaac tctaggaacc   16200
agagcccaca gctggagggg atgcggagg gctgcttctg ccctgaggac cagatcctct    16260
tcaacgcaca catgggcatc tgcgtgcagg cctgccctg cgtgggaccc gatgggtttc    16320
ctaaatttcc cggggcagtc tgggtcagca actgccagtc ctgcgtgtgt gacgagggtt   16380
cagtgtcggt gcagtgcaag cccctgccct gtgacgccca gggtcagccc ccgccgtgca   16440
accgtcccgg cttcgtaacc gtgaccaggc cccgggccga gaaccctgc tgccccgaga   16500
cggtgtgcgt gtgcaacaca accacctgcc ccagagcct gcctgtgc cgccagggc     16560
aggagtccat ctgcacccag gaggagggcg actgctgtcc caccttccgc tgcagacctc    16620
agctgtgttc gtacaatggc accttctacg gggttggtgc aaccttccca ggcgcccttc   16680
cctgccacat gtgtacctgc ctctctgggg acacccagga cccaacggtg caatgtcagg   16740
aggatgcctg caacaatact acctgtcccc agggctttga gtacaagaga gtggccgggc   16800
agtgctgtgg ggagtgcgtc cagaccgcct gcctcacgcc cgatgccag ccagtccagc    16860
tgaatgaaac ctgggtcaac agccatgtgg acaactgcac cgtgtacctc tgtgaggctg   16920
agggtggagt ccatttgctg accccacagc ctgcatcctg cccagatgtg tccagctgca  16980
gggggagcct caggaaaacc ggctgctgct actcctgtga ggaggactcc tgtcaagtcc   17040
gcatcaacac gaccatcctg tggcaccagg gctgcgagac cgaggtcaac atcacccttct  17100
gcgagggctc ctgccccga gcgtcaagt actcagcaga ggccaggcc atgcagcacc      17160
agtgcacctg ctgccaggag aggcgggtcc acgaggagac ggtgcccttg cactgtccta   17220
acggctcagc catcctgcac acctacaccc acgtggatga gtgtgctgc acgcccttct   17280
gtgtccctgc ccccatggct ccccacacac ccgtggcttt ccggcccag gaggccactg   17340
ctgtctgaga acgttctgcc tccatcccca tgctctgtcc acctggaagc aggatgtgca  17400
ttgtctgatc atgaaaacct tgggcctcct ctgcggagcc cccggcctg tgtgtggcac   17460
cccgcgctcc gtgctcctgc tgccccccc gtgggtgaaa ccggcccag aagggtgagg   17520
ggccagcagg acccctttcg ggagggcgcc actcaggagt cctaccctgg gagagcctgt   17580
ggcccacctt ggccttgccc ctccctgatg tcactgggac tcactggaac aaactaagca   17640
tgtgcgggcc tatgtgtccc tgccacggcc ggagcgcccg cgcagcacgg attccagctg   17700
gccacgtccg gccgctgggg cagacaggct ggtccaggca aggccagctg ctgccaggaa   17760
gctgcgacag gcaaggcggc cgcctgtcca tgcctgctgc agggtaactc agggctgagg   17820
tcgcaacggc caggtcagag aggggtcagc atcccaaagc cccctctgct caacccagcc   17880
cagttttgca aataaaccct gagcattgag tacgtt                             17916
```

SEQ ID NO: 12        moltype = AA   length = 5762
FEATURE              Location/Qualifiers
source               1..5762
                      mol_type = protein
                      organism = Homo sapiens
SEQUENCE: 12

```
MGAPSACRTL VLALAAMLVV PQAETQGPVE PSWENAGHTM DGGAPTSSPT RRVSFVPPVT    60
VFPSLSPLNP AHNGRVCSTW GDFHYKTFDG DVFRFPGLCN YVFSEHCRAA YEDFNVQLRR   120
GLVGSRPVVT RVVIKAQGLV LEASNGSVLI NGQREELPYS RTGLLVEQSG DYIKVSIRLV   180
LTFLWNGEDS ALLELDPKYA NQTCGLCGDF NGLPAFNEFY AHNARLTPLQ FGNLQKLDGP   240
TEQCPDPLPL PAGNCTDEEG ICHRTLLGPA FAECHALVDS TAYLAACAQD LCRCPTCPCA   300
TFVEYSRQCA HAGGQPRNWR CPELCPRTCP LNMQHQECGS PCTDTCSNPQ RAQLCEDHCV   360
DGCFCPPGTV LDDITHSGCL PLGQCPCTHG GRTYSPGTSF NTTCSSCTCS GGLWQCQDLP   420
CPGTCSVQGG AHISTYDEKL YDLHGDCSYV LSKKCADSSF TVLAELRKCG LTDNENCLKA   480
VTLSLDGGDT AIRVQADGGV FLNSIYTQLP LSAANITLFT PSSFFIVVQT GLGLQLLVQL   540
VPLMQVFVRL DPAHQGQMCG LCGNFNQNQA DDFTALSGVV EATGAAFANT WKAQAACANA   600
RNSFEDPCSL SVENENYARH WCSRLTDPNS AFSRCHSIIN PKPFHSNCMF DTCNCERSED   660
CLCAALSSYV HACAAKGVQL SDWRDGVCTK YMQNCPKSQR YAYVVDACQP TCRGLSEADV   720
TCSVSFVPVD GCTCPAGTPL NDAGACVPAQ ECPCYAHGTV LAPGEVVHDE GAVCSCTGGK   780
LSCLGASLQK STGCAAPMVY LDCSNSSAGT PGAECLRSCH TLDVGCFSTH CVSGCVCPPG   840
LVSDGSGGCI AEEDCPCVHN EATYKPGETI RVDCNTCTCR NRRWECSHRL CLGTCVAYGD   900
GHFITFDGDR YSFEGSCEYI LAQDYCGDNT THGTFRIVTE NIPCGTTGTT CSKAIKLFVE   960
```

```
SYELILQEGT FKAVARGPGG DPPYKIRYMG IFLVIETHGM AVSWDRKTSV FIRLHQDYKG   1020
RVCGLCGNFD DNAINDFATR SRSVVGDALE FGNSWKLSPS CPDALAPKDP CTANPFRKSW   1080
AQKQCSILHG PTFAACRSQV DSTKYYEACV NDACACDSGG DCECFCTAVA AYAQACHDAG   1140
LCVSWRTPDT CPLFCDFYNP HGGCEWHYQP CGAPCLKTCR NPSGHCLVDL PGLEGCYPKC   1200
PPSQPFFNED QMKCVAQCGC YDKDGNYYDV GARVPTAENC QSCNCTPSGI QCAHSLEACT   1260
CTYEDRTYSY QDVIYNTTDG LGACLIAICG SNGTIIRKAV ACPGTPATTP FTFTTAWVPH   1320
STTSPALPVS TVCVREVCRW SSWYNGHRPE PGLGGGDFET FENLRQRGYQ VCPVLADIEC   1380
RAAQLPDMPL EELGQQVDCD RMRGLMCANS QQSPPLCHDY ELRVLCCEYV PCGPSPAPGT   1440
SPQPSLSAST EPAVPTPTQT TATEKTTLWV TPSIRSTAAL TSQTGSSSGP VTVTPSAPGT   1500
TTCQPRCQWT EWFDEDYPKS EQLGGDVESY DKIRAAGGHL CQQPKDIECQ AESFPNWTLA   1560
QVGQKVHCDV HFGLVCRNWE QEGVFKMCYN YRIRVLCCSD DHCRGRATTP PPTTELETAT   1620
TTTTQALFST PQPTSSPGLT RAPPASSTAV PTLSEGLTSP RYTSTLGTAT TGGPTTPAGS   1680
TEPTVPGVAT STLPTRSALP GTTGSLGTWR PSQPPTLAPT TMATSRARPT GTASTASKEP   1740
LTTSLAPTLT SELSTSQAET STPRTETTMS PLTNTTTSQG TTRCQPKCEW TEWFDVDFPT   1800
SGVAGGDMET FENIRAAGGK MCWAPKSIEC RAENYPEVSI DQVGQVLTCS LETGLTCKNE   1860
DQTGRFNMCF NYNVRVLCCD DYSHCPSTPA TSSTATPSST PGTTWILTKP TTTATTTAST   1920
GSTATPTSTL RTAPPPKVLT TTATTPTVTS SKATPSSSPG TATALPALRS TATTPTATSV   1980
TPIPSSSLGT TWTRLSQTTT PTATMSTATP SSTPETAHTS TVLTATATTT GATGSVATPS   2040
STPGTAHTTK VPTTTTTGFT ATPSSSPGTA LTPPVWISTT TTPPTTRGSTV TPSSIPGTTH   2100
TATVLTTTTT TVATGSMATP SSSTQTSGTP PSLTTTATTI TATGSTTNPS STPGTTPIPP   2160
VLTTTATTPA ATSNTVTPSS ALGTTHTPPV PNTMATTHGR SLPPSSPHTV RTAWTSATSG   2220
ILGTTHITEP STVTSHTLAA TTGTTQHSTP ALSSPHPSSR TTESPPSPGT TTPGHTTATS   2280
RTTATATPSK TRTSTLLPSS PTSAPITTVV TMGCEPQCAW SEWLDYSYPM PGPSGGDFDT   2340
YSNIRAAGGA VCEQPLGLEC RAQAQPGVPL RELGQVVECS LDFGLVCRNR EQVGKFKMCF   2400
NYEIRVFCCN YGHCPSTPAT SSTAMPSSTP GTTWILTELT TTATTTESTG STATPSSTPG   2460
TTWILTEPST TATVTVPTGS TATASSTQAT AGTPHVSTTA TPFSSPGTAT ALPALRSTAT   2520
TPTATSFTAI PSSSLGTTWT RLSQTTTPTA TMSTATPSST PETVHTSTVL TTTATTTGAT   2580
GSVATPSSTP GTAHTTKVLT TTTTGFTATP SSSPGTARTL PVWISTTTTP   2640
TTRGSTVTPS SIPGTTHTPT VLTTTTTTVA TGSMATPSSS TQTSGTPPSL TTTATTITAT   2700
GSTTNPSSTP GTTPIPPVLT TTATTPAATS STVTPSSALG TTHTPPVPNT TATTHGRSLS   2760
PSSPHTVRTA WTSATSGTLG TTHITEPSTG TSHTPAATTG TTQHSTPALS SPHPSSRTTE   2820
SPPSPGTTTP GHTRATSRTT ATATPSKTRT STLLPSSPTS APITTVVTMG CEPQCAWSEW   2880
LDYSYPMPGP SGGDFDTYSN IRAAGGAVCE QPLGLECRAQ AQPGVPLREL GQVVECSLDF   2940
GLVCRNREQV GKFKMCFNYE IRVFCCNYGH CPSTPATSST ATPSSTPGTT WILTEQTTAA   3000
TTTATTGSTA IPSSTPGTAP PPKVLTSTAT TPTATSSKAT SSSSPRTATT LPVLTSTATK   3060
STATSFTPIP SFTLGTTGTL PEQTTTPMAT MSTIHPSSTP ETTHTSTVLT TKATTTRATS   3120
SMSTPSSTPG TTWILTELTT AATTTAATGP TATPSSTPGT TWILTEPSTT ATVTVPTGST   3180
ATASSTRATA GTLKVLTSTA TTPTVISSRA TPSSSPGTAT ALPALRSTAT TPTATSVTAI   3240
PSSSLGTAWT RLSQTTTPTA TMSTATPSST PETVHTSTVL TTTTTTTRAT GSVATPSSTP   3300
GTAHTTKVPT TTTTGFTATP SSSPGTALTP PVWISTTTTP TTRGSTVTPS SIPGTTHTAT   3360
VLTTTTTTVA TGSMATPSSS TQTSGTPPSL TTTATTITAT GSTTNPSSTP GTTPIPPVLT   3420
TTATTPAATS STVTPSSALG TTHTPPVPNT TATTHGRSLP PSSPHTVRTA WTSATSGILG   3480
TTHITEPSTV TSHTPAATTS TTQHSTPALS SPHPSSRTTE SPPSPGTTTP GHTRGTSRTT   3540
ATATPSKTRT STLLPSSPTS APITTVVTTG CEPQCAWSEW LDYSYPMPGP SGGDFDTYSN   3600
IRAAGGAVCE QPLGLECRAQ AQPGVPLREL GQVVECSLDF GLVCRNREQV GKFKMCFNYE   3660
IRVFCCNYGH CPSTPATSST ATPSSTPGTT WILTKLTTTA TTTESTGSTA TPSSTPGTTW   3720
ILTEPSTTAT VTVPTGSTAT ASSTQATAGT PHVSTTATLP TVTSSKATPF SSPGTATALP   3780
ALRSTATTPT ATSFTAIPSS SLGTTWTRLS QTTTPTATMS TATPSSTPET AHTSTVLTTT   3840
ATTTRATGSV ATPSSTPGTA HTTKVPTTTT TGFTVTPSSS PGTARTPPVW ISTTTTPTTS   3900
GSTVTPSSVP GTTHTPTVLT TTTTVATGS MATPSSSTQT SGTPPSLITT ATTITATGST   3960
TNPSSTPGTT PIPPVLTTTA TTPAATSSTV TPSSALGTTH TPPVPNTTAT THGRSLPSS   4020
PHTVRTAWTS ATSGTLGTTH ITEPSTGTSH TPAATTGTTQ HSTPALSSPH PSSRTTESPP   4080
SPGTTTPGHT TATSRTTATA TPSKTRTSTL LPSSPTSAPI TTVVTTGCEP QCAWSEWLDY   4140
SYPMPGPSGG DFDTYSNIRA AGGAVCEQPL GLECRAQAQP GVPLGELGQV VECSLDFGLV   4200
CRNREQVGKF KMCFNYEIRV FCCNYGHCPS TPATSSTAMP SSTPGTTWIL TELTTTATT   4260
ASTGSTATPS STPGTAPPPK VLTSPATTPT ATSSKATSSS SPRTATTLPV LTSTATKSTA   4320
TSVTPIPSST LGTTGTLPEQ TTTPVATMST IHPSSTPETT HTSVLTTKA TTTRATSSTS   4380
TPSSTPGTTW ILTELTTAAT TTAATGPTAT PSSTPGTTWI LTELTTTATT TASTGSTATP   4440
SSTPGTTWIL TEPSTTATVT VPTGSTATAS STQATAGTPH VSTTATPPTV TSSKATPSSS   4500
PGTATALPAL RSTATTPTAT SFTAIPSSSL GTTWTRLSQT TTPTATMSTA TPSSTPETVH   4560
TSTVLTATAT TTGATGSVAT PSSTPGTAHT TKVPTTTTTG FTATPSSSPG TALTPPVWIS   4620
TTTTPTTTTP TTSGSTVTPS SIPGTTHTAR VLTTTTTTVA TGSMATPSSS TQTSGTPPSL   4680
TTTATTITAT GSTTNPSSTP GTTPITPVLT STATTPAATS SKATSSSSPR TATTLPVLTS   4740
TATKSTATSF TPIPSSTLWT TWTVPAQTTT PMSTMSTIHT SSTPETTHTS TVLTTTATMT   4800
RATNSTATPS STLGTTRILT ELTTTATTTA ATGSTATLSS TPGTTWILTE PSTIATVMVP   4860
TGSTATASST LGTAHTPKVV TTMATMPTAT ASTVPSSSTV GTTRTPAVLP SSLPTFSVST   4920
VSSSVLTTLR PTGFPSSHFS TPCFCRAFGQ FFSPGEVIYN KTDRAGCHFY AVCNQHCDID   4980
RFQGACPTSP PPVSSAPLSS PSPAPGCDNA IPLRQVNETW TLENCTVARC VGDNRVVLLD   5040
PKPVANVTCV NKHLPIKVSD PSQPCDFHYE CECICSMWGG SHYSTFDGTS YTFRGNCTYV   5100
LMREIHARFG NLSLYLDNHY CTASATAAAA RCPRALSIHY KSMDIVLTVT MVHGKEEGLI   5160
LFDQIPVSSG FSKNGVLVSV LGTTTMRVDI PALGVSVTFN GQVFQARLPY SLFHNNTEGQ   5220
CGTCTNNQRD DCLQRDGTTA ASCKDMAKTW LVPDSRKDGC WAPTGPPTA SPAAPVSSTP   5280
TPTPCPPQPL CDLMLSQVFA ECHNLVPPGP FFNACISDHC RGRLEVPCQS LEAYAELCRA   5340
RGVCSDWRGA TGGLCDLTCP PTKVYKPCGP IQPATCNSRN QSPQLEGMAE GCFCPEDQIL   5400
FNAHMGICVQ ACPCVGPDGF PKFPGERWVS NCQSCVCDEG SVSVQCKPLP CDAQGQPPPC   5460
NRPGFVTVTR PRAENPCCPE TVCVCNTTTC PQSLPVCPPG QESICTQEEG DCCPTFRCRP   5520
QLCSYNGTFY GVGATFPGAL PCHMCTCLSG DTQDPTVQCQ EDACNNTTCP QGFEYKRVAG   5580
QCCGECVQTA CLTPDGQPVQ LNETWVNSHV DNCTVYLCEA EGGVHLLTPQ PASCPDVSSC   5640
RGSLRKTGCC YSCEEDSCQV RINTTILWHQ GCETEVNITF CEGSCPGASK YSAEAQAMQH   5700
```

QCTCCQERRV HEETVPLHCP NGSAILHTYT HVDECGCTPF CVPAPMAPPH TRGFPAQEAT    5760
AV                                                                  5762

SEQ ID NO: 13           moltype = DNA  length = 4018
FEATURE                 Location/Qualifiers
source                  1..4018
                        mol_type = genomic DNA
                        organism = Homo sapiens
SEQUENCE: 13
caggcagcgc tgcgtcctgc tgcgcacgtg ggaagccctg gccccggcca ccccgcgat    60
gccgcgcgct ccccgctgcc gagccgtgcg ctccctgctg cgcagccact accgcgaggt    120
gctgccgctg gccacgttcg tgcggcgcct ggggcccag ggctggcggc tggtgcagcg    180
cggggacccg gcggctttcc gcgcgctggt ggcccagtgc ctggtgtgcg tgccctggga    240
cgcacggccg cccccgccg ccccctcctt ccgcagggtg tcctgcctga aggagctggt    300
ggcccgagtg ctgcagaggc tgtgcgagcg cggcgcgaag aacgtgctgg ccttcggctt    360
cgcgctgctg gacggggccc gcgggggccc ccccgaggcc ttcaccacca gcgtgcgcag    420
ctacctgccc aacacggtga ccgacgcact gcggggagc ggggcgtggg ggctgctgct    480
gcgccgcgtg ggcgacgacg tgctggttca cctgctggca cgctgcgcgc tctttgtgct    540
ggtggctccc agctgcgcct accaggtgtg cgggccgccg ctgtaccagc tcggcgctgc    600
cactcaggcc cggcccccgc cacacgctag tggaccccga aggcgtctgg gatgcgaacg    660
ggcctggaac catagcgtca gggaggccgg ggtcccctg gcctgccag ccccgggtgc    720
gagggaggcc ggggcagtg ccagccgaag tctgccgttg cccaagaggc ccaggcgttg    780
cgctgcccct gagccggagc ggacgcccgt tgggcagggg tcctgggccc acccgggcag    840
gacgcgtgga ccgagtgacc gtggtttctg tgtggtgtca cctgccagac ccgccgaaga    900
agccacctct ttggagggtg cgctctctgg cacgcgccac tcccacccat ccgtgggccg    960
ccagcaccac gcgggccccc catccacatc gcggccacca cgtccctggg acacgccttg    1020
tccccggtg tacgccgaga ccaagcactt cctctactcc tcaggcgaca aggagcagct    1080
gcggccctcc ttcctactca gctctctgag gcccagcctg actggcgctc ggaggctcgt    1140
ggagaccatc tttctggggtt ccaggccctg gatgccaggg actcccgca ggttgccccg    1200
cctgccccag cgctactggc aaatgcggcc cctgtttctg gagctgcttg ggaaccacgc    1260
gcagtgcccc tacggggtgc tcctcaagac gcactgcccg ctgcgagctg cggtcacccc    1320
agcagccggt gtctgtgccc gggagaagcc ccagggctct gtggcggccc ccgaggagga    1380
ggacacagac ccccgtcgcc tggtgcagct gctccgccag cacagcagcc cctggcaggt    1440
gtacggcttc gtgcgggcct gcctgcgccg gctggtgccc ccaggcctct ggggctccag    1500
gcacaacgaa cgccgcttcc tcaggaacac caagaagttc atctccctgg ggaagcatgc    1560
caagctctcg ctgcaggagc tgacgtgaa gatgagcgtg cgggactgcg cttggctgcg    1620
caggagccca ggggttggct gtgttccggc cgcagagcac cgtctgcgtg aggagatcct    1680
ggccaagttc ctgcactggc tgatgagtgt gtacgtcgtc gagctgctca ggtctttctt    1740
ttatgtcacg gagaccacgt ttcaaaagaa caggctcttt ttctaccgga agagtgtctg    1800
gagcaagttg caaagcattg gaatcagaca gcacttgaag ggggtgcagc tgcgggagct    1860
gtcggaagca gaggtcaggc agcatcggga agccaggccc gccctgctga cgtccagact    1920
ccgcttcatc cccaagcctg acgggctgcg gccgattgtg aacatggact acgtcgtggg    1980
agccagaacg ttccgcagag aaaagagggc cgagcgtctc acctcgaggg tgaaggcact    2040
gttcagcgtg ctcaactacg agcgggcgcg gcgccccggc ctcctgggcg cctctgtgct    2100
gggcctggac gatatccaca gggcctggcc caccttcgtg ctgcgtgtgc gggcccagga    2160
cccgccgcct gagctgtact ttgtcaaggt ggatgtgacg ggcgcgtacg acaccatccc    2220
ccaggacagg tcacggagg tcatcgccag catcatcaaa cccccagaaca cgtactgcgt    2280
gcgtcggtat gccgtggtcc agaaggccgc ccatgggcac gtccgcaagg ccttcaagag    2340
ccacgtctct accttgacag acctccagcc gtacatgcga cagttcgtgg ctcacctgca    2400
ggagaccagc ccgctgaggg atgccgtcgt catcgagcag agctcctccc tgaatgaggc    2460
cagcagtggc ctcttcgacg tcttcctacg cttcatgtgc caccacgccg tgcgcatcag    2520
gggcaagtcc tacgtccagt gccagggggat cccgcagggc tccatcctct ccacgctgct    2580
ctgcagcctg tgctacggcg acatggagaa caagctgttt gcggggattc ggcgggacgg    2640
gctgctcctg cgtttggtgg atgatttctt gttggtgaca cctcacctca cccacgcgaa    2700
aaccttcctc aggaccctgg tccgaggtgt ccctgagtat ggctgcgtgg tgaacttgcg    2760
gaagacagtg gtgaacttcc ctgtagaaga cgaggccctg ggtggcacgg cttttgttca    2820
gatgccggcc cacggcctat tccctggtg cggcctgctg ctggatacccc ggaccctgga    2880
ggtgcagagc gactactcca gctatgcccg gacctccatc agagccagtc tcaccttcaa    2940
ccgcggcttc aaggctggga ggaacatgcg tcgcaaactc tttggggtct tgcggctgaa    3000
gtgtcacgc ctgttttctgg atttgcaggt gaacagcctc cagacggttg gcaccaacat    3060
ctacaagatc ctcctgctgc aggcgtacag gttcacgca tgtgtgctgc agctcccatt    3120
tcatcagcaa gtttggaaga ccccacatt tttcctgcgc gtcatctctg acacggcctc    3180
cctctgctac tccatcctga aagccaagaa cgcaggggatg tcgctggggg ccaagggcgc    3240
cgccggcccct ctgccctccg aggccgtgca gtggctgcga caccaagcat tcctgctcaa    3300
gctgactcga caccgtgtca cctacgtgcc actcctgggg tcactcagga cagcccgac    3360
gcagctgagt cggaagctcc cggggacgac gctgactgcc ctgaggccg agccaaccc    3420
ggcactgccc tcagacttca agaccatcct ggactgatgg ccaccgcccc acagccaggc    3480
cgagagcaga caccagcagc cctgtcacgc cgggctctac gtccaggga ggagggcg    3540
gcccacaccc aggccgcac gcctgggagt ctgaggcctg agtgagtgtt tggccgaggc    3600
ctgcatgtcc ggctgaaggc tgagtgtccg gctgaggcct gagcgagtgt ccagccaagg    3660
gctgagtgtc cagcacacct gccgtcttca cttccccaca ggctggcgct cggctccacc    3720
ccagggccca cttttcctca ccaggagccc ggcttccact ccccatatag gaatagtcca    3780
tccccagatt cgcattgtt caccccctcgc cctgccctcc tttgccttcc accccacca    3840
tccaggtgga gaccctgaga aatttggagt gaccaaaggt    3900
gtgccctgta cacaggcgag gaccctgcac ctgatgggg gtccctgtgg gtcaaattgg    3960
ggggaggtgc tgtgggagta aaatactgaa tatatgagtt tttcagtttt gaaaaaaa    4018

SEQ ID NO: 14           moltype = AA  length = 1132
FEATURE                 Location/Qualifiers

```
source                  1..1132
                        mol_type = protein
                        organism = Homo sapiens
SEQUENCE: 14
MPRAPRCRAV RSLLRSHYRE VLPLATFVRR LGPQGWRLVQ RGDPAAFRAL VAQCLVCVPW    60
DARPPPAAPS FRQVSCLKEL VARVLQRLCE RGAKNVLAFG FALLDGARGG PPEAFTTSVR   120
SYLPNTVTDA LRGSGAWGLL LRRVGDDVLV HLLARCALFV LVAPSCAYQV CGPPLYQLGA   180
ATQARPPPHA SGPRRRLGCE RAWNHSVREA GVPLGLPAPG ARRRGGSASR SLPLPKRPRR   240
GAAPEPERTP VGQGSWAHPG RTRGPSDRGF CVVSPARPAE EATSLEGALS GTRHSHPSVG   300
RQHHAGPPST SRPPRPWDTP CPPVYAETKH FLYSSGDKEQ LRPSFLLSSL RPSLTGARRL   360
VETIFLGSRP WMPGTPRRLP RLPQRYWQMR PLFLELLGNH AQCPYGVLLK THCPLRAAVT   420
PAAGVCAREK PQGSVAAPEE EDTDPRRLVQ LLRQHSSPWQ VYGFVRACLR RLVPPGLWGS   480
RHNERRFLRN TKKFISLGKH AKLSLQELTW KMSVRDCAWL RRSPGVGCVP AAEHRLREEI   540
LAKFLHWLMS VYVVELLRSF FYVTETTFQK NRLFFYRKSV WSKLQSIGIR QHLKRVQLRE   600
LSEAEVRQHR EARPALLTSR LRFIPKPDGL RPIVNMDYVV GARTFRREKR AERLTSRVKA   660
LFSVLNYERA RRPGLLGASV LGLDDIHRAW RTFVLRVRAQ DPPPELYFVK VDVTGAYDTI   720
PQDRLTEVIA SIIKPQNTYC VRRYAVVQKA AHGHVRKAFK SHVSTLTDLQ PYMRQFVAHL   780
QETSPLRDAV VIEQSSSLNE ASSGLFDVFL RFMCHHAVRI RGKSYVQCQG IPQGSILSTL   840
LCSLCYGDME NKLFAGIRRD GLLLRLVDDF LLVTPHLTHA KTFLRTLVRG VPEYGCVVNL   900
RKTVVNFPVE DEALGGTAFV QMPAHGLFPW CGLLLDTRTL EVQSDYSSYA RTSIRASLTF   960
NRGFKAGRNM RRKLFGVLRL KCHSLFLDLQ VNSLQTVCTN IYKILLLQAY RFHACVLQLP  1020
FHQQVWKNPT FFLRVISDTA SLCYSILKAK NAGMSLGAKG AAGPLPSEAV QWLCHQAFLL  1080
KLTRHRVTYV PLLGSLRTAQ TQLSRKLPGT TLTALEAAAN PALPSDFKTI LD          1132

SEQ ID NO: 15           moltype = DNA   length = 3829
FEATURE                 Location/Qualifiers
source                  1..3829
                        mol_type = genomic DNA
                        organism = Homo sapiens
SEQUENCE: 15
caggcagcgc tgcgtcctgc tgcgcacgtg ggaagccctg ccccggcca ccccgcgat      60
gccgcgcgct ccccgctgcc gagccgtgcg ctcctgctg cgcagccact accgcgaggt    120
gctgccgctg ccacgttcg tgcggcgcct ggggccccag ggctggcgg tggtgcagcg    180
cggggacccg gcggctttcc gcgcgctggt ggccagtgc ctggtgtgcg tgcccgtggga  240
cgcacggccg ccccccgcg cccctcctt ccgcaggtg tcctgcctga aggagctggt    300
ggcccgagtg ctgcagaggc tgtgcgagcg cggcgcgaag aacgtgctgg ccttcggctt   360
cgcgctgctg gacggggccc gcgggggccc cccgaggcc ttcaccacca gcgtgcgcag    420
ctacctgccc aacacggtga ccgacgcact gcggggagc gggcgtggg ggctgctgct    480
gcgccgcgtg ggcgacgacg tgctggttca cctgctggca cgctgcgcg tctttgtgct   540
ggtggctccc agctgcgcct accaggtgtg cgggccgccg ctgtaccagc tcggcgctgc  600
cactcaggcc cggccccgc cacacgctag tggaccccga aggcgtctgg gatgcgaacg   660
ggcctggaac catagcgtca ggaggccgg ggtccctg gcctgccag ccccgggtgc     720
gaggaggcgc gggggcagtg ccagccgaag tctgccgttg cccaagaggc ccaggcgtgg  780
cgctgcccct gagccggagc ggacgcccgt tgggcagggg tcctgggccc acccgggcag   840
gacgcgtgga ccgagtgacc gtggtttctg tgtggtgtca cctgccagac ccgccgaaga   900
agccacctct ttggagggtg cgctctctgg cacgcgccac tcccacccat ccgtgggccg   960
ccagcaccac gcgggccccc catccacatc gcggccacca cgtccctggg acacgccttg  1020
tccccggtg tacgccgaga ccaagcactt cctctactcc tcaggcgaca aggagcagct   1080
gcggccctcc ttcctactca gctctctgag gcccagcctg actggcgctc ggaggctcgt  1140
ggagaccatc tttctgggtt ccaggccctg gatgccaggg actccccgca ggttgccccg  1200
cctgcccag cgctactggc aaatgcggcc cctgtttctg gagctgcttg ggaaccacgc   1260
gcagtgcccc tacggggtgc tcctcaagac gcactgcccg ctgcgagctg cggtcacccc   1320
agcagcggt gtctgtgccc gggagaagcc ccagggctct gtggcggccc cgaggagga    1380
ggacacagac cccgtcgcc tggtgcagct gctccgccag cacagcagcc cctggcaggt   1440
gtacggcttc gtgcgggcct gcctgcgccg gctggtgccc ccaggcctct ggggctccag   1500
gcacaacgaa cgccgcttcc tcaggaacac caagaagttc atctccctgg ggaagcatgc   1560
caagctctcg ctgcaggagc tgacgtggaa gatgagcgtg cgggactgcg cttggctgcg   1620
caggagccca ggggttggct gtgttccggc cgcagagcac cgtctgcgtg aggagatcct   1680
ggccaagttc ctgcactggc tgatgagtgt gtacgtcgtc gagctgctca ggtcttcctt   1740
ttatgtcacg gagaccacgt ttcaaaagaa caggctcttt tcctaccgga agagtgtctg   1800
gagcaagttg caaagcattg gaatcagaca gcacttgaag agggtgcagc tgcgggagct   1860
gtcggaagca gaggtcaggc agcatcggga agccaggccc gccctgctga cgtccagact   1920
ccgcttcatc cccaagcctg acgggctgcg gccgattgtg aacatggact acgtcgtggg   1980
agccagaacg ttccgcagag aaaagagggc cgagcgtcc acctcgaggg tgaaggcact   2040
gttcagcgtg ctcaactacg agcgggcgcg gcgccccggc ctcctgggcg cctctgtgct   2100
gggcctggac gatatccaca gggcctggcg caccttcgtg ctgcgtgtgc gggcccagga   2160
cccgccgcct gagctgtact ttgtcaaggt ggatgtgacg ggcgcgtacg acaccatccc   2220
ccaggacagg ctcacggagg tcatcgccag catcatcaaa cccagaaca cgtactgcgt   2280
gcgtcggtat gccgtggtcc agaaggccgc ccatgggcac gtccgcaagg ccttcaagag   2340
ccacgtctct accttgacag acctccagcc gtacatgcga cagttcgtgg ctcacctgca   2400
ggagaccagc ccgctgaggg atgccgtcgt catcgagcag agtcctccc tgaatgaggc   2460
cagcagtggc ctcttcgacg tcttcctacg cttcatgtgc caccacgccg tgcgcatcag   2520
gggcaagtcc tacgtccagt gccaggggat ccgcagggc tccatcctct ccacgctgct   2580
ctgcagctgc tgctacgggg acatggagaa caagctgttt gcgggattc ggcggacg     2640
gctgctcctg cgtttggtgg atgatttctt gttggtgaca cctcacctca cccacgcgaa   2700
aaccttcctc agctatgccc ggaccttcca cagagccagt ctcacttca accgcggctt    2760
caaggctggg aggaacatgc gtcgcaaact ctttggggtc ttgcggctga agtgtcacag   2820
cctgtttctg gatttgcagg tgaacagcct ccagacggtg tgcaccaaca tctacaagat   2880
cctcctgctg caggcgtaca ggtttcacgc atgtgtgctg cagctcccat tcatcagca    2940
```

```
agtttggaag aaccccacat ttttcctgcg cgtcatctct gacacggcct ccctctgcta   3000
ctccatcctg aaagccaaga acgcaggaat gtcgctgggg gccaagggcg ccgccggccc   3060
tctgccctcc gaggccgtgc agtggctgtg ccaccaagca ttcctgctca agctgactcg   3120
acaccgtgtc acctacgtgc cactcctggg gtcactcagg acagcccaga cgcagctgag   3180
tcggaagctc ccgggggacga cgctgactgc cctggaggcc gcagccaacc cggcactgcc   3240
ctcagacttc aagaccatcc tggactgatg gccaccgcc cacagccagg ccgagagcag    3300
acaccagcag ccctgtcacg ccgggctcta cgtcccaggg agggaggggc ggcccacacc   3360
caggcccgca ccgctgggag tctgaggcct gagtgagtgt ttggccgagg cctgcatgtc   3420
cggctgaagg ctgagtgtcc ggctgaggcc tgagcgagtg tccagccaag ggctgagtgt   3480
ccagcacacc tgccgtcttc acttccccac aggctggcgc tcggctccac cccagggcca   3540
gcttttcctc accaggagcc cggcttccac tccccacata ggaatagtcc atccccagat   3600
tcgccattgt tcacccctcg ccctgccctc ctttgccttc cacccccacc atccaggtgg   3660
agaccctgag aaggaccctg ggagctctgg gaatttggag tgaccaaagg tgtgccctgt   3720
acacaggcag ggaccctgca cctggaatggg ggtccctgtg ggtcaaattg gggggaggtg   3780
ctgtgggagt aaaatactga atatatgagt ttttcagttt tgaaaaaaa              3829

SEQ ID NO: 16           moltype = AA   length = 1069
FEATURE                 Location/Qualifiers
source                  1..1069
                        mol_type = protein
                        organism = Homo sapiens
SEQUENCE: 16
MPRAPRCRAV RSLLRSHYRE VLPLATFVRR LGPQGWRLVQ RGDPAAFRAL VAQCLVCVPW   60
DARPPPAAPS FRQVSCLKEL VARVLQRLCE RGAKNVLAFG FALLDGARGG PPEAFTTSVR   120
SYLPNTVTDA LRGSGAWGLL LRRVGDDVLV HLLARCALFV LVAPSCAYQV CGPPLYQLGA   180
ATQARPPPHA SGPRRRLGCE RAWNHSVREA GVPLGLPAPG ARRRGGSASR SLPLPKRPRR   240
GAAPEPERTP VGQGSWAHPG RTRGPSDRGF CVVSPARPAE EATSLEGALS GTRHSHPSVG   300
RQHHAGPPST SRPPRPWDTP CPPVYAETKH FLYSSGDKEQ LRPSFLLSSL RPSLTGARRL   360
VETIFLGSRP WMPGTPRRLP RLPQRYWQMR PLFLELLGNH AQCPYGVLLK THCPLRAAVT   420
PAAGVCAREK PQGSVAAPEE EDTDPRRLVQ LLRQHSSPWQ VYGFVRACLR RLVPPGLWGS   480
RHNERRFLRN TKKFISLGKH AKLSLQELTW KMSVRDCAWL RRSPGVGCVP AAEHRLREEI   540
LAKFLHWLMS VYVVELLRSF FYVTETTFQK NRLFFYRKSV WSKLQSIGIR QHLKRVQLRE   600
LSEAEVRQHR EARPALLTSR LRFIPKPDGL RPIVNMDYVV GARTFRREKR AERLTSRVKA   660
LFSVLNYERA RRPGLLGASV LGLDDIHRAW RTFVLRVRAQ DPPPELYFVK VDVTGAYDTI   720
PQDRLTEVIA SIIKPQNTYC VRRYAVVQKA AHGHVRKAFK SHVSTLTDLQ PYMRQFVAHL   780
QETSPLRDAV VIEQSSSLNE ASSGLFDVFL RFMCHHAVRI RGKSYVQCQG IPQGSILSTL   840
LCSLCYGDME NKLFAGIRRD GLLLRLVDDF LLVTPHLTHA KTFLSYARTS IRASLTFNRG   900
FKAGRNMRRK LFGVLRLKCH SLFLDLQVNS LQTVCTNIYK ILLLQAYRFH ACVLQLPFHQ   960
QVWKNPTFFL RVISDTASLC YSILKAKNAG MSLGAKGAAG PLPSEAVQWL CHQAFLLKLT   1020
RHRVTYVPLL GSLRTAQTQL SRKLPGTTLT ALEAAANPAL PSDFKTILD              1069

SEQ ID NO: 17           moltype = DNA   length = 5030
FEATURE                 Location/Qualifiers
source                  1..5030
                        mol_type = genomic DNA
                        organism = Homo sapiens
SEQUENCE: 17
attgaggagc agaaggagta gggtgcgggg gaggaggagg agcgccttta gtgctgcagc   60
agctgctgct ctgattggcc cggtggttca gctgcttccc tggaacaaaa ggtcaaagtg   120
gactgcagtg taaatgtaga gaagcagccg ataaaatagc attgcctgaa gaagtttgga   180
ggctgagagc agcagtagac tggccaactg cagagcaagt tgtttctcca gccgtgcagt   240
gcagcctcat gccccaacc cagcttagcc actgtaagaa gacgttcact gtacagacga    300
ccaaacttgc cgtggaagag acagttgtga gattcccttg caaatttaca tacgagaatg   360
gcttgtgaaa tcatgcctct gcaaagttca caggaagatg aaagaccctct gtcacctttc   420
tatttgagtg ctcatgtacc ccaagtcagc aatgtgtctg caaccggaga actcttagaa   480
agaaccatcc gatcagctgt gaacaacat cttttttgatg ttaataactc tggaggtcaa    540
agttcagagg actcagaatc tggaaacacta tcagcatctt ctgccacatc tgccagacag   600
cgccgccgcc agtccaagga gcaggatgaa gttcgacatg ggagagacaa gggacttatc   660
aacaaagaaa atactccttc tgggttcaac caccttgatg attgtatttt gaatactcag   720
gaagtcgaaa aggtacacaa aaatactttt ggttgtgctg agaaaggag caagcctaaa    780
cgtcagaaat ccagtactaa actttctgag cttcatgaca atcaggacgg tcttgtgaat   840
atggaaagtc tcaattccac acgatctcat gagagaactg gacctgatga ttttgaatgg   900
atgtctgatg aaaggaaagg aaatgaaaaa gatggtggac acactcagca ttttgagagc   960
cccacaatga agatccagga gcatcccagc ctatctgaca ccaaacagca gagaaatcaa   1020
gatgccggtg accaggagga gagctttgtc tccgaagtgc cccagtcgga cctgactgca   1080
ttgtgtgatg aaaagaactg ggaagagcct atccctgctt ctcctcctg gcagcggag     1140
aacagtgact ctgatgaagc ccacctctcg ccgcaggctg ggcgcctgat ccgtcagctg   1200
ctggacgaag acagcgaccc catgctctct cctcggttct acgcttatgg gcagagcagg   1260
caatacctgg atgacagaa agtgcctcct tccccaccaa agtcctcct tttcatgagg    1320
cggcgaagct cctctctggg gtcctatgat gatgagcaag aggacctgac acctgcccag   1380
ctcacacgaa ggattcagag ccttaaaaag aagatccgga gtttgaaga tagattcgaa    1440
gaagagaaga agtacagacc ttcccacagt gacaaagcag ccaatccgga ggttctgaaa   1500
tggacaaatg accttgccaa attccggaga caactttaaag aatcaaaact aaagatatct   1560
gaagaggacc taactcccag gatgcggcag cagcacccaa cactcccaa gagttttggt    1620
tcccaacttg agaaagaaga tgagaagaag caagagctgg tggataaagc aataaagccc   1680
agtgttgaag ccacattgga atctattcag aggaagctcc aggagaagcg agcggaaagc   1740
agccgccctg aggacattaa ggatatgacc aagaccagga ttgctaatga gaaagtggct   1800
ctgcagaaag ctctgttata ttatgaaagc attcatggac ggccgtaac aaagaacgaa    1860
cggcaggtga tgaagccact atacgacagg taccggctgg tcaaacagat cctctcccga   1920
```

```
gctaacacca tacccatcat tggttccccc tccagcaagc ggagaagccc tttgctgcag  1980
ccaattatcg agggcgaaac tgcttccttc ttcaaggaga taaaggaaga agaggagggg  2040
tcagaagacg atagcaatgt gaagccagac ttcatggtca ctctgaaaac cgatttcagt  2100
gcacgatgct ttctggacca attcgaagat gacgctgatg gatttatttc cccaatggat  2160
gataaaatac catcaaaatg cagccaggac acagggcttt caaatctcca tgctgcctca  2220
atacctgaac tcctggaaca cctccaggaa atgagagaag aaaagaaaag gattcgaaag  2280
aaacttcggg atttttgaaga caactttttc agacagaatg gaagaaatgt ccagaaggaa  2340
gaccgcactc ctatggctga agaatacagt gaatataagc acataaaggc gaaactgagg  2400
ctcctggagg tgctcatcag caagagagac actgattcca agtccatgtg aggggcatgg  2460
ccaagcacag ggggctggca gctgcggtga gagtttactg tccccagaga aagtgcagct  2520
ctggaaggca gccttgggc tggccctgca aagcatgcag cccttctgcc tctagaccat  2580
ttggcatcgc ctcctgtttc cattgcctgc cttagaaact ggctggaaga agacaatgtg  2640
acctgactta ggcattttgt aattggaaag tcaagactgc agtatgtgca catgcgcacg  2700
cgcatgcacg cacacacaca cacagtagtg gagcttttcct aacactagca agattaatc  2760
actacattag acaacactca tctacagaga atatacactg ttcttccctg gataactgag  2820
aaacaagaga ccattctctg tctaactgtg ataaaaacaa gctcaggact ttattctata  2880
gagcaaactt gctgtggagg gccatgctct ccttggaccc agttaactgc aaacgtgcat  2940
tggagcccta tttgctgccg ctgccattct agtgacctt cccacagagct gcgccttcct  3000
cacgtgtgtg aaaggttttc cccttcagcc ctcaggtaga tggaagctgc atctgcccac  3060
gatggcagtg cagtcatcat cttcaggatg tttcttcagg acttcctcag ctgacaagga  3120
atttttggtcc ctgcctagga ccgggtcatc tgcagaggac agagagatgg taagcagctg  3180
tatgaatgct gattttaaaa ccaggtcatg ggagaagagc ctggagattc tttcctgaac  3240
actgactgca cttaccagtc tgattttatc gtcaaacacc aagccaggct agcatgctca  3300
tggcaatctg tttggggctg ttttgttgtg gcactagcca aacataaagg ggcttaagtc  3360
agcctgcata cagaggatcg gggagagaag gggcctgtgt tctcagcctc ctgagtactt  3420
accagagttt aatttttta aaaaaaatct gcactaaaat ccccaaactg acaggtaaat  3480
gtagccctca gagctcagcc caaggcagaa tctaaatcac actatttcg agatcatgta  3540
taaaaagaaa aaaagaagt catgctgtgt ggccaattat aatttttttc aaagactttg  3600
tcacaaaact gtctatatta gacatttttgg agggaccagg aaatgtaaga caccaaatcc  3660
tccatctctt cagtgtgcct gatgtcacct catgatttgc tgttacttt ttaactcctg  3720
cgccaaggac agtgggttct gtgtccacct ttgtgctttg cgaggccgag cccaggcatc  3780
tgctcgcctg ccacggctga ccagagaagg tgcttcagga gctctgcctt agacgacgtg  3840
ttacagtatg aacacacagc agaggcaccc tcgtatgttt tgaaagttgc cttctgaaag  3900
ggcacagttt taaggaaaag aaaaagaatg taaaactata ctgacccgtt ttcagttta  3960
aagggtcgtg agaaactggc tggtccaatg ggatttacag caacatttc cattgctgaa  4020
gtgaggtagc agctctcttc tgtcagctga atgttaagga tggggaaaaaa gaatgccttt  4080
aagtttgctc ttaatcgtat ggaagcttga gctatgtgtt ggaagtgccc tggttttaat  4140
ccatacacaa agacggtaca taatcctaca ggtttaaatg tacataaaaa tatagtttgg  4200
aattctttgc tctactgttt acattgcaga ttgctataat ttcaaggagt gagattataa  4260
ataaaatgat gcactttagg atgtttccta tttttgaaat ctgaactgaa atcattcaca  4320
tgaccaaaaa ttgtgttttt ttaaaaatac atgtctagtc tgtccttaa tagctctctt  4380
aaataagcta tgatattaat cagatcatta ccagttagct tttaaagcac atttgtttaa  4440
gactatgttt ttggaaaaat acgctacaga attttttttt aagctacaaa taaatgagat  4500
gctactaatt gttttggaat ctgttgtttc tgccaaggt aaattaacta aagattatt  4560
caggaatccc catttgaatt tgtatgattc aataaaagaa aacaccaagt aagttatata  4620
aaataaattg tgtatgagat gttgtgtttt cctttgtaat ttccactaac taactaacta  4680
acttatattc ttcatggaat ggagcccaga agaaatgaga ggaagccctt ttcacactag  4740
atcttatttg aagaaatgtt tgttagtcag tcagtcagtg gtttctggct ctgccgaggg  4800
agatgtgttc cccagcaacc atttctcag cccagaatct caaggcacta gaggcggtgt  4860
cttaattaat tggcttcaca aagacaaaat gctctggact gggattttc ctttgctgtg  4920
ttgggaatat gtgtttatta attagcacat gccaacaaaa taaatgtcaa gagttatttc  4980
ataagtgtaa gtaaacttaa gaattaaaga gtgcagactt ataattttca              5030
```

SEQ ID NO: 18        moltype = AA   length = 697
FEATURE              Location/Qualifiers
source               1..697
                     mol_type = protein
                     organism = Homo sapiens
SEQUENCE: 18
MACEIMPLQS SQEDERPLSP FYLSAHVPQV SNVSATGELL ERTIRSAVEQ HLFDVNNSGG    60
QSSEDSESGT LSASSATSAR QRRRQSKEQD EVRHGRDKGL INKENTPSGF NHLDDCILNT   120
QEVEKVHKNT FGCAGERSKP KRQKSSTKLS ELHDNQDGLV NMESLNSTRS HERTGPDDFE   180
WMSDERKGNE KDGGHTQHFE SPTMKIQEHP SLSDTKQQRN QDAGDQEESF VSEVPQSDLT   240
ALCDEKNWEE PIPAFSSWQR ENSDSDEAHL SPQAGRLIRQ LLDEDSDPML SPRFYAYGQS   300
RQYLDDTEVP PSPPNSHSFM RRRSSSLGSY DDEQEDLTPA QLTRRIQSLK KKIRKFEDRF   360
EEEKKYRPSH SDKAANPEVL KWTNDLAKFR RQLKESKLKI SEEDLTPRMR QRSNTLPKSF   420
GSQLEKEDEK KQELVDKAIK PSVEATLESI QRKLQEKRAE SSRPEDIKDM TKDQIANEKV   480
ALQKALLYYE SIHGRPVTKN ERQVMKPLYD RYRLVKQILS RANTIPIIGS PSSKRRSPLL   540
QPIIEGETAS FFKEIKEEEE GSEDDSNVKP DFMVTLKTDF SARCFLDQFE DDADGFISPM   600
DDKIPSKCSQ DTGLSNLHAA SIPELLEHLQ EMREEKKRIR KKLRDFEDNF FRQNGRNVQK   660
EDRTPMAEEY SEYKHIKAKL RLLEVLISKR DTDSKSM                            697

SEQ ID NO: 19        moltype = DNA   length = 8005
FEATURE              Location/Qualifiers
source               1..8005
                     mol_type = genomic DNA
                     organism = Homo sapiens
SEQUENCE: 19
aagaaaccgg ccaggtgtgg cctaggcgcc cagtgccagc ggggaggaga ctcgctccgc    60

```
cgccgaccaa caccaacacc cagctccgac gcagctcctc tgcgcccttg ccgccctccg    120
agccacagct ttcctcccgc tcctgccccc ggcccgtcgc cgtctccgcg ctcgcagcgg    180
cctcgggagg gcccaggtag cgagcagcga cctcgcgagc cttccgcact cccgccggt    240
tccccggccg tccgcctatc cttggccccc tccgctttct ccgcgccggc ccgcctcgct    300
tatgcctcgg cgctgagccg ctctcccgat tgcccgccga catgagctgc aacggaggct    360
cccaccgcg gatcaacact ctgggccgca tgatccgcgc cgagtctggc ccggacctgc    420
gctacgaggt gaccagcggc ggcgggggca ccagcaggat gtactattct cggcgcggcg    480
tgatcaccga ccagaactcg gacggctact gtcaaaccgg cacgatgtcc aggcaccaga    540
accagaacac catccaggag ctgctgcaga actgctccga ctgcttgatg cgagcagagc    600
tcatcgtgca gcctgaattg aagtatggag atggaataca actgactcgg agtcgagaat    660
tggatgagtg ttttgcccag gccaatgacc aaatggaaat cctcgacagc ttgatcagag    720
agatgcggca gatgggccag ccctgtgatg cttaccagaa aaggcttctt cagctccaag    780
agcaaatgcg agccctttat aaagccatca gtgtccctcg agtccgcagg gccagctcca    840
agggtggtgg aggctacact tgtcagagtg gctctggctg gatgagttc accaaacatg    900
tcaccagtga atgtttgggg tggatgaggc agcaaagggc ggagatggac atggtggcct    960
ggggtgtgga cctggcctca gtggagcagc acattaacag ccaccggggc atccacaact    1020
ccatcggcga ctatcgctgg cagctggaca aaatcaaagc cgacctgcgc gagaaatctg    1080
cgatctacca gttggaggag gagtatgaaa acctgctgaa agcgtccttt gagaggatga    1140
atcacctgcg acagctgcag aacatcattc aggccacgtc cagggagatc atgtggatca    1200
atgactgcga ggaggaggag ctgctgtacg actggagcga caagaacacc aacatcgctc    1260
agaaacagga ggccttctcc atacgcatga gtcaactgga agttaaagaa aaagagctca    1320
ataagctgaa acaagaaagt gaccaacttg tcctcaatca gcatccagct tcagacaaaa    1380
ttgaggccta tatggacact ctgcagacgc agtggagttg gattcttcag atcaccaagt    1440
gcattgatgt tcatctgaaa gaaaatgctc cctactttca gttttttgaa gaggcgcagt    1500
ctactgaagc ataccgaag gggctccagg actccatcag gaagaagtac ccctgcgaca    1560
agaacatgcc cctgcagcac ctgctggaac agatcaaggg gctggagaaa gaacgagaga    1620
aaatccttga atacaagcgt caggtgcaga acttggtaaa caagtctaag aagattgtac    1680
agctgaagcc tcgtaaccca gactacgaaa gcaataaacc cattattctc agagctctct    1740
gtgactacaa acaagatcag aaaatcgtgc ataaggggga tgagtgtatc ctgaaggaca    1800
acaacgagcg cagcaagtgg tacgtgacgg gcccgggagg cgttgacatg cttgttccct    1860
ctgtggggct gatcatccct cctccgaacc cactgccgt ggacctctct tgcaagattg    1920
agcagtacta cgaagccatc ttggctctgt ggaaccagct ctacatcaac atgaagagcc    1980
tggtgtcctg gcactactgc atgattgaca tagagaagat caggggccatg acaatcgcca    2040
agctgaaaac aatgcggcag gaagattaca tgaagacgat agccgaccct gagttacatt    2100
accaagagtt catcagaaat agccaaggct cagagatgtt tggagatgat gacaagcgga    2160
aaatacagtc tcagttcacc gatgcccaga agcattacca gacctggtc attcagctcc    2220
ctggctatcc ccagcaccag acagtgacca caactgaaat cactcatcat ggaacctgcc    2280
aagatgtcaa ccataaataa gtaattgaaa ccaacagaga aaatgacaag caagaaacat    2340
ggatgctgat ggagctgcaa aagattcgca ggcagataga gcactgcagg ggcaggatga    2400
ctctcaaaaa cctccctcta gcagaccagg gatcttctca ccacatcaca gtgaaaatta    2460
acgagcttaa gagtgtgcag aatgattcac aagcaattgc tgaggttctc aaccagctta    2520
aagatatgct tgccaacttc agaggttctg aaaagtactg ctatttacag aatgaagtat    2580
ttggactatt tcagaaactg gaaaaatatca atggtgttac agatggctac ttaaatagct    2640
tatgcacagt aagggcactg ctccaggcta ttctccaaac agaagacatg ttaaaggttt    2700
atgaagccag gctcactgag gaggaaactg tctgcctgga cctggataaa gtggaagctt    2760
accgctgtga actgaagaaa ataaaaatg acttgaactt gaagaagtcg ttgttggcca    2820
ctatgaagac agaactacag aaagcccagc agatccactc tcagacttca cagcagtatc    2880
cactttatga tctggacttg ggcaagttcg gtgaaaaagt cacacagctg acagaccgct    2940
ggcaaaggat agataaacag atcgacttta ggttatggga cctggagaaa caaatcaagc    3000
aattgaggaa ttatcgtgat aactatcagg ctttctgcaa gtggctctat gatgctaaac    3060
gccgccagga ttccttagaa tccatgaaat ttggagattc caacacagtc atgcggtttt    3120
tgaatgagca gaagaacttg cacagtgaaa tatctggcaa acgagacaaa tcagaggaag    3180
tacaaaaaat tgctgaactt tgcgccaatt caattaagga ttatgagctc cagctggcct    3240
catacacctc aggactggaa actctgctga acatacctat caagaggacc atgattcagt    3300
cccttctgg ggtgattctg caagaggctg cagatgttca tgctcggtac attgaactac    3360
ttacaagatc tggagactat tacaggttct taagtgagat gctgaagagt ttggaagatc    3420
tgaagctgaa aaataccaag atcgaagttt ggaagagga gctcagactg gcccgagatg    3480
ccaactcgga aaactgtaat aagaacaaat tcctggatca gaacctgcag aaataccagg    3540
cagagtgttc ccagttcaaa gcgaagcttg cgagcctgga ggagctgaag agacaggctg    3600
agctggatgg gaagtcggct aagcaaaatc tagacaagtg ctacggccaa ataaagaac    3660
tcaatgagaa gatcacccga ctgacttatg agattgaaga tgaaaagaga agaagaaat    3720
ctgtggaaga cagatttgac caacagaaga atgactatga ccaactgcag aaagcaaggc    3780
aatgtgaaaa ggagaacctt ggttggcaga aattagagtc tgagaaagcc atcaaggaga    3840
aggagtacga gattgaaagg ttgaggggttc tactgcagga agaaggcacc cggaagagga    3900
aatatgaaaa tgagctggca aaggcatcta ataggattca ggaatcaaag aatcagtgta    3960
ctcaggtggt acaggaaaga gagagccttc tggtgaaaat caaagtcctg gagcaagaca    4020
aggcaaggct gcagaggctg gaggatgagc tgaatcgtgc aaaatcaact ctagaggcag    4080
aaaccagggt gaaacagcgc ctggagtgtg agaaacagca aattcagaat gacctgaatc    4140
agtggaagac tcaatattcc cgcaaggagg aggctattag gaagatagaa tcggaaagag    4200
aaaagagtga gagagagaag aacagtctta ggagtgagat cgaaagactc caagcagaga    4260
tcaagagaat tgaagagagg tgcaggcgta agctggagga ttctaccagg agacacagt    4320
cacagttaga aacagaacgc tcccgatatc agagggagat tgataaactc agacagcgcc    4380
catatgggtc ccatcgagag acccagactg agtgtgagtg gaccgttgac acctccaagc    4440
tggtgtttga tgggctgagg aagaaggttga cagcaatgca gctctatgag tgtcagctga    4500
tcgacaaaac aaccttggac aaactattga aggggaagaa gtcagtggaa gaagttgctt    4560
ctgaaatcca gccattcctt cggggtgcag gatctatcgc tggagcatct gcttctccta    4620
aggaaaaata ctctttggta gaggccaaga gaaagaaatt aatcagccca gaatccacag    4680
tcatgcttct ggaggcccag gcagctacag gtggtataat tgatccccat cggaatgaga    4740
agctgactgt cgacagtgcc atagctcggg acctcattga cttcgatgac cgtcagcaga    4800
```

```
tatatgcagc agaaaaagct atcactggtt ttgatgatcc attttcaggc aagacagtat   4860
ctgtttcaga agccatcaag aaaaatttga ttgatagaga aaccggaatg cgcctgctgg   4920
aagcccagat tgcttcaggg ggtgtagtag accctgtgaa cagtgtcttt ttgccaaaag   4980
atgtcgcctt ggcccggggg ctgattgata gagatttgta tcgatccctg aatgatcccc   5040
gagatagtca gaaaaacttt gtggatccag tcaccaaaaa gaaggtcagt tacgtgcagc   5100
tgaaggaacg gtgcagaatc gaaccacata ctggtctgct cttgctttca gtacagaaga   5160
gaagcatgtc cttccaagga atcagacaac ctgtgaccgt cactgagcta gtagattctg   5220
gtatattgag accgtccact gtcaatgaac tggaatctgg tcagatttct tatgacgagg   5280
ttggtgagag aattaaggac ttcctccagg gttcaagctg catagcaggc atatacaatg   5340
agaccacaaa acagaagctt ggcatttatg aggccatgaa aattggctta gtccgacctg   5400
gtactgctct ggagttgctg gaagcccaag cagctactgg ctttatagtg atcctgttaa   5460
gcaacttgag gttaccagtg gaggaagcct acaagagagg tctggtgggc attgagttca   5520
aagagaagct cctgtctgca gaacgagctg tcactgggta taatgatcct gaaacaggaa   5580
acatcatctc tttgttccaa gccatgaata aggaactcat cgaaaagggc cacggtattc   5640
gcttattaga agcacagatc gcaaccgggg ggatcattga cccaaaggag agccatcgtt   5700
taccagttga catagcatat aagagggggct atttcaatga ggaactcagt gagattctct   5760
cagatccaag tgatgatacc aaaggatttt ttgaccccaa cactgaagaa aatcttacct   5820
atctgcaact aaaaagaaga tgcattaagg atgaggaaac agggctctgt cttctgcctc   5880
tgaaagaaaa aagaaacag gtgcagacat cacaaaagaa taccctcagg aagcgtagag   5940
tggtcatagt tgacccagaa accaataaag aaatgtctgt tcaggaggcc tacaagaagg   6000
gcctaattga ttatgaaacc ttcaaagaac tgtgtgagca ggaatgtgaa tgggaagaaa   6060
taaccatcac gggatcagat ggctccacca gggtggtcct ggtagataga aagacaggca   6120
gtcagtatga tattcaagat gctattgaca agggccttgt tgacaggaag ttctttgatc   6180
agtaccgatc cggcagcctc agcctcactc aatttgctga catgatctcc ttgaaaaatg   6240
gtgtcggcac cagcagcagc atgggcagtg tgtcagcga tgatgttttt agcagctccc   6300
gacatgaatc agtaagtaag atttccacca tatccagcgt caggaattta accataagga   6360
gcagctcttt ttcagacacc ctggaagaat cgagccccat tgcagccatc tttgacacag   6420
aaaacctgga gaaatctcc attacagaag gtatagagcg gggcatcgtt gacagcatca   6480
cgggtcagag gcttctggag gctcaggcct gcacaggtgg catcatccac ccaaccacgg   6540
gccagaagct gtcacttcag gacgcagtct cccagggtgt gattgaccaa gacatggcca   6600
ccaggctgaa gcctgctcag aaagccttca taggcttcga gggtgtgaag ggaaagaaga   6660
agatgtcagc agcagaggca gtgaagaaaa atggctccc gtatgaggct ggccagcgct   6720
tcctggagtt ccagtacctc acgggaggtc ttgttgaccc ggaagtgcat gggaggataa   6780
gcaccgaaga agccatccgg aaggggttca tagatgccgg cgccgcacag aggctgcaag   6840
acaccagcag ctatgccaaa atcctgacct gccccaaaac caaattaaaa atatcctata   6900
aggatgccat aaatcgctcc atggtagaag atatcactgg gctgcgcctt ctggaagccg   6960
cctccgtgtc gtccaagggc ttacccagcc cttacaacat gtcttcggct ccggggtccc   7020
gctccggctc ccgctcggga tctcgctccg gatctcgctc cgggtcccgc agtgggtccc   7080
ggagagaaga ctttgacgcc acagggaatt cttcctactc ttattcctac tcattttagca   7140
gtagttctat tgggcactag tagtcagttg ggagtggttg ctataccttg acttcatttta   7200
tatgaatttc cactttatta aataatagaa aagaaaatcc cggtgcttgc agtagagtga   7260
taggacattc tatgcttaca gaaaatatag ccatgattga aatcaaatag taaaggctgt   7320
tctggctttt tatcttctta gctcatctta aataagcagt acacttggat gcagtgcgtc   7380
tgaagtgcta atcagttgta acaatagcac aaatcgaact taggatttgt ttcttctctt   7440
ctgtgtttcg atttttgatc aattcttttaa ttttggaagc ctataataca gttttctatt   7500
cttggagata aaaattaaat ggatcactga tattttagtc attctgcttc tcatctaaat   7560
atttccatat tctgtattag gagaaaaatta ccctcccagc accagccccc ctctcaaacc   7620
cccaacccaa aaccaagcat tttgaatga gtcctcttta gtttcagagt gtggattgta   7680
taacccatat actcttcgat gtacttgttt ggtttggtat taatttgact gtgcatgaca   7740
gcggcaatct tttctttggt caaagttttc tgtttatttt gcttgtcata ttcgatgtac   7800
tttaaggtgt ctttatgaag tttgctattc tggcaataaa cttttagact tttgaagtgt   7860
ttgtgtttta atttaatatg tttataagca tgtataaaca tttagcatat ttttatcata   7920
ggtctaaaaa tatttgttta ctaaatacct gtgaagaaat accattaaaa aactatttgg   7980
ttctgaattc ttactagaaa aaaaa                                        8005

SEQ ID NO: 20          moltype = AA    length = 2272
FEATURE                Location/Qualifiers
source                 1..2272
                       mol_type = protein
                       organism = Homo sapiens
SEQUENCE: 20
MSCNGGSHPR INTLGRMIRA ESGPDLRYEV TSGGGGTSRM YYSRRGVITD QNSDGYCQTG     60
TMSRHQNQNT IQELLQNCSD CLMRAELIVQ PELKYGDGIQ LTRSRELDEC FAQANDQMEI    120
LDSLIREMRQ MGQPCDAYQK RLLQLQEQMR ALYKAISVPR VRRASSKGGG GYTCQSGSGW    180
DEFTKHVTSE CLGWMRQQRA EMDMVAWGVD LASVEQHINS HRGIHNSIGD YRWQLDKIKA    240
DLREKSAIYQ LEEEYENLLK ASFERMDHLR QLQNIIQATS REIMWINDCE EEELLYDWSD    300
KNTNIAQKQE AFSIRMSQLE VKEKELNKLK QESDQLVLNQ HPASDKIEAY MDTLQTWSW     360
ILQITKCIDV HLKENAAYFQ FFEEAQSTEA YLKGLQDSIR KKYPCDKNMP LQHLLEQIKE    420
LEKEREKILE YKRQVQNLVN KSKKIVQLKP RNPDYRSNKP IILRALCDYK QDQKIVHKGD    480
ECILKDNNER SKWYVTGPGG VDMLVPSVGL IIPPPNPLAV DLSCKIEQYY EAILALWNQL    540
YINMKSLVSW HYCMIDIEKI RAMTIAKLKT MRQEDYMKTI ADLELHYQEF IRNSQGSEMF    600
GDDDKRKIQS QFTDAQKHYQ TLVIQLPGYP QHTVTTTEI THHGTCQDVN HNKVIETNRE    660
NDKQETWMLM ELQKIRRQIE HCEGRMTLKN LPLADQGSSH HITVKINELK SVQNDSQAIA    720
EVLNQLKDML ANFRGSEKYC YLQNEVFGLF QKLENINGVT DGYLNSLCTV RALLQAILQT    780
EDMLKVYEAR LTEETVCLD LDKVEAYRCG LKKIKNDLNL KKSLLATMKT ELQKAQQIHS    840
QTSQQYPLYD LDLGKFGEKV TQLTDRWQRI DKQIDFRLWD LEKQIKQLRN YRDNYQAFCK    900
WLYDAKRRQD SLESMKFGDS NTVMRFLNEQ KNLHSEISGK RDKSEEVQKI AELCANSIKD    960
YELQLASYTS GLETLLNIPI KRTMIQSPSG VILQEAADVH ARYIELLTRS GDYYRFLSEM   1020
LKSLEDLKLK NTKIEVLEEE LRLARDANSE NCNKNKFLDQ NLQKYQAECS QFKAKLASLE   1080
```

-continued

```
ELKRQAELDG KSAKQNLDKC YGQIKELNEK ITRLTYEIED EKRRRKSVED RFDQQKNDYD    1140
QLQKARQCEK ENLGWQKLES EKAIKEKEYE IERLRVLLQE EGTRKREYEN ELAKASNRIQ    1200
ESKNQCTQVV QERESLLVKI KVLEQDKARL QRLEDELNRA KSTLEAETRV KQRLECEKQQ    1260
IQNDLNQWKT QYSRKEEAIR KIESEREKSE REKNSLRSEI ERLQAEIKRI EERCRRKLED    1320
STRETQSQLE TERSRYQREI DKLRQRPYGS HRETQTECEE TVDTSKLVFD GLRKKVTAMQ    1380
LYECQLIDKT TLDKLLKGKK SVEEVASEIQ PFLRGAGSIA GASASPKEKY SLVEAKRKKL    1440
ISPESTVMLL EAQAATGGII DPHRNEKLTV DSAIARDLID FDDRQQIYAA EKAITGFDDP    1500
FSGKTVSVSE AIKKNLIDRE TGMRLLEAQI ASGGVVDPVN SVFLPKDVAL ARGLIDRDLY    1560
RSLNDPRDSQ KNFVDPVTKK KVSYVQLKER CRIEPHTGLL LLSVQKRSMS FQGIRQPVTV    1620
TELVDSGILR PSTVNELESG QISYDEVGER IKDFLQGSSC IAGIYNETTK QKLGIYEAMK    1680
IGLVRPGTAL ELLEAQAATG FIVDPVSNLR LPVEEAYKRG LVGIEFKEKL LSAERAVTGY    1740
NDPETGNIIS LFQAMNKELI EKGHGIRLLE AQIATGGIID PKESHRLPVD IAYKRGYFNE    1800
ELSEILSDPS DDTKGFFDPN TEENLTYLQL KERCIKDEET GLCLLPLKEK KKQVQTSQKN    1860
TLRKRRVVIV DPETNKEMSV QEAYKKGLID YETFKELCEQ ECEWEEITIT GSDGSTRVVL    1920
VDRKTGSQYD IQDAIDKGLV DRKFFDQYRS GSLSLTQFAD MISLKNGVGT SSSMGSGVSD    1980
DVFSSSRHES VSKISTISSV RNLTIRSSSF SDTLEESSPI AAIFDTENLE KISITEGIER    2040
GIVDSITGQR LLEAQACTGG IIHPTTGQKL SLQDAVSQGV IDQDMATRLK PAQKAFIGFE    2100
GVKGKKKMSA AEAVKEKWLP YEAGQRFLEF QYLTGGLVDP EVHGRISTEE AIRKGFIDGR    2160
AAQRLQDTSS YAKILTCPKT KLKISYKDAI NRSMVEDITG LRLLEAASVS SKGLPSPYNM    2220
SSAPGSRSGS RSGSRSGSRS GSRSGSRRGS FDATGNSSYS YSYSFSSSSI GH            2272

SEQ ID NO: 21           moltype = DNA  length = 1278
FEATURE                 Location/Qualifiers
source                  1..1278
                        mol_type = genomic DNA
                        organism = Homo sapiens
SEQUENCE: 21
ccattggcct gtagattcac ctcccctggg cagggcccca ggacccagga taatatctgt      60
gcctcctgcc cagaaccctc caagcagaca caatggtaag aatggtgcct gtcctgctgt     120
ctctgctgct gcttctgggt cctgctgtcc cccaggagaa ccaagatgtg cgttactctc     180
tgacctatat ctacactggg ctgtccaagc atgttgaaga cgtccccgcg tttcaggccc     240
ttggctcact caatgacctc cagttcttta gatacaacag taaagacagg aagtctcagc     300
ccatgggact ctggagacag gtggaaggaa tggaggattg gaagcaggac agccaacttc     360
agaaggccag ggaggacatc tttatggaga ccctgtggag catcgtggag tattacaacg     420
acagtaacgg gtctcacgta ttgcagggaa ggtttggttg tgagtcgaga ataacagaa      480
gcagcggagc attctggaaa tattactatg atggaaagga ctacattgaa ttcaacaaag     540
aaatcccagc ctgggtcccc ttcgaccag cagcccagat aaccaagcag aagtgggagg      600
cagaaccagt ctacgtgcag cgggccaagg cttacctgga ggaggagtgc cctgcgactc     660
tgcggaaata cctgaaatac agcaaaaata tcctggaccg gcaagatcct ccctctgtgg     720
tggtcaccag ccaccaggcc ccaggagaaa agaagaaact gaagtgcctg gcctacgact     780
tctacccagg gaaaattgat gtgcactgga ctcgggccgg cgaggtgcag gagcctgagt     840
tacgggagata tgttcttcac aatggaaatg gcacttacca gtcctgggtg gtggtggcag     900
tgccccccgca ggacacagcc ccctactcct gccacgtgca gcagcctctg gcccagc       960
ccctcgtggt gcctgggag gccagctagg aagcaagggt tggaggcaat gtgggatctc     1020
agacccagta gctgccttc ctgcctgatg tgggagctga accacagaaa tcacagtcaa     1080
tggatccaca aggcctgagg agcagtgtgg gggacagac aggaggtgga tttggagacc     1140
gaagactggg atgcctgtct tgagtagact tggacccaaa aaatcatctc accttgagcc    1200
cacccccacc ccattgtcta atctgtagaa gctaataaat aatcatccct ccttgcctag    1260
cataaaaaaa aaaaaaaa                                                  1278

SEQ ID NO: 22           moltype = AA  length = 298
FEATURE                 Location/Qualifiers
source                  1..298
                        mol_type = protein
                        organism = Homo sapiens
SEQUENCE: 22
MVRMVPVLLS LLLLLGPAVP QENQDGRYSL TYIYTGLSKH VEDVPAFQAL GSLNDLQFFR      60
YNSKDRKSQP MGLWRQVEGM EDWKQDSQLQ KAREDIFMET LKDIVEYYND SNGSHVLQGR     120
FGCEIENNRS SGAFWKYYYD GKDYIEFNKE IPAWVPFDPA AQITKQKWEA EPVYVQRAKA     180
YLEEECPATL RKYLKYSKNI LDRQDPPSVV VTSHQAPGEK KKLKCLAYDF YPGKIDVHWT     240
RAGEVQEPEL RGDVLHNGNG TYQSWVVVAV PPQDTAPYSC HVQHSSLAQP LVVPWEAS       298

SEQ ID NO: 23           moltype = DNA  length = 6483
FEATURE                 Location/Qualifiers
source                  1..6483
                        mol_type = genomic DNA
                        organism = Homo sapiens
SEQUENCE: 23
aaatgcgctg gcggggagac cggggttggt ccctggcggg gcaggggcg ggctcaggcc       60
ggaactccag agacgacctc agccaactgc tcctgcgccg gcggggtcg tcgccgccag     120
cggctccgag cgccggaagg gccaggtctc agggctcctg gagctgcagg cggcgggagg     180
ggctacaaat gcttgactca gtgatgcaga acctttcaga gttagctgga agccacagcc     240
ctgcctcttg atgcagcctg atccagccg gtgtgaagag agacccctt ccctcttgtg      300
gggtttggat cctgtgtttc tagcctttgc aaaactctac atcagggata tcctggacat     360
gaaggagtcc cgccaggtgc caggtgtatt tttgtacaat ggacatccaa taaaacaggt     420
agatgtcttg ggaactgtca ttggagtgag agaaagagat gctttctaca gttatgggagt    480
ggatgacagc actggagtta taaactgcat ctgctggaaa aagttgaata ctgagtctgt     540
atcagctgct ccaagtgcag caagagagct cagcttaacc tcacaactta agaagctaca     600
agagaccatt gagcagaaaa caaagataga gatcgggac acgatccgag tcagaggcag     660
```

```
tatccgcaca tacagagaag agcgagagat tcatgccacc acttactata aagtggacga    720
cccagtgtgg aacattcaaa ttgcaaggat gcttgagctg cccactatct acaggaaagt    780
ttatgaccag cctttcaca gctcagccct agagaaagaa gaggcactaa gcaatccagg     840
cgccctggac ctcccagtc tcacgagttt gctgagtgaa aaagccaaag aattcctcat     900
ggagaacaga gtgcagagct tttaccagca ggagctggaa atggtggagt cttgtctgtc    960
ccttgccaat cagcctgtga ttcacagtgc ctcctccgac caagtgaatt ttaagaagga   1020
caccacttcc aaggcaattc atagtatat taagaatgct atacaactgc tgcaggaaaa    1080
aggacttgtt ttccagaaag atgatggttt tgataaccta tactatgtaa ccagagaaga   1140
caaagacctg cacagaaaga tccaccggat cattcagcag gactgccaga aaccaaatca   1200
catggagaag ggctgtcact tcctgcacat cttggcctgt gctcgcctga gcatccgccc   1260
gggcctgagc gaggctgtgc tgcagcaagt tctggagctc ctggaggacc agagtgacat   1320
tgtcagcaca atggagcact actacacagc gttctgagca gagacacgca gaccagctga   1380
ggaggacaaa gataaggtgg cattcacccc caggctctga ctttcagcat catgcagggg   1440
cttatctgtc tggaggcagt tacctcataa taaactataa aatatagtca tcttgggaat   1500
gggatttggc ataaatgttg ttggctccct tctgtccact atgtccttgg tgtacaatga   1560
ctttgatctc agccatgaca caacaagaaa accctccctg ttgagctcct ggctggactg   1620
tgcgttgttc gcagagcaga atggggagga acagtgttgt gcagcttaac tgatgtgtgt   1680
ggttggagtc tcttccatgg caaagggaca ccacagggta gtgaacattc aggaactgag   1740
gggcatatgg cctgatcaca cagttctaag cttttcaaaa cttcaggtta tcagagacct   1800
tcctgtgggc ctctcttgct ggctaagaac cggtttaggg gagtagttct ccctggatga   1860
gtgcttacag tttctgtggc tcagttacca gcagtgggt tgagacctgg gtcgatgctc     1920
tttacaggcc tgcccagaga tgggaataaa caggggatcca gcgtgact atgtgtttgt    1980
cattttcctt ttatttcctt gggaatcgaa aggtgtccca gtacatttcc ctgcacttac   2040
agaggtgcat gactaaatac attgtccctc gatgcccctg aagatcacgg aggcagtcag   2100
ccaattgcct ggcaggtggt agatgttatt ttcagggttg ccgctgagtg tgcaggatgt   2160
gctgacacca tccagacaaa gactcggtat gtgcccagac aggtgatgga gtcatgcttt   2220
tgctcagaat gacaaggtaa aggaaaaaca tctgaggtat gttgtaggcc tgttctgaca   2280
gcaaaatgac aaatccagcc agcaaaata aagtgtggag aaagatttgg agttaattac    2340
agtcatttca cagaaggcac tgccttcgtc tgctgcattt gctcttgatg tgataagctc   2400
ttcgtggctc agctggagat cctttaggcc tggagagttg ctcctctctc cgtggaaaca   2460
ggacagtctt tatacgcaga agtccgctgc agctcgatca gtcaggctga gagctagaac   2520
cagtagattg cctcctgtca tagacttttg taatgatgca aacctttgct gatttctaac   2580
agtgattatg tagtggctgc cctgcatctt ctctgtgtac agaagggtcc ctagcataga   2640
gtctgcctgg aatgatgtcc tgggcagttc ttccttgagg tcagcagctg ttccacgttg   2700
aatgcatctg attagtgggg ctgcccagga aggagttcag aatcagaagg taaaaagggc   2760
ataccccttgc ctatagcaac tctgctctta gggtttatc tcaaggagat ggctacacaa    2820
gtgtgaaagg atggttgcac aaggtgttca ttgctgtata atctagaatt ctatattggg   2880
gaaaatacct atagggaaaa agttaattac ggttcttggg cacaatgaaa tactatgcag   2940
ctatgaaaaa aatgatgaaa gcagacagac agtgttgcca tggcacactg tccctagtag   3000
atttagtggg aagtagatag agttatagat ctgtttctat agtataacac cattatctac   3060
agctccctgt gtgtatgtat atatccgtag agagagtgta tatttctgca tggaggtctt   3120
tataaatgta gcacatgtac atatatatat atatacacac acacagtcga ccactccctt   3180
ctcctggaag tacttccgc gtttggcttt caggacacca agctctctgg ttgctccttc    3240
tcaggttcct ttgttcagtg ctctgcctcc ctgaggactc agtcccagac ctcttttcta   3300
tctggcttgc tcactgggggt gtctccagca gccacatgga ttataccatc tacatgctgt   3360
ctaacacctc agtttaaacc cagaatgggc ctcttccctg aactgcagac ccctatattc   3420
agtttgctac tgacatctcc acttaggtct ctaatgaca tctcagattt cacaggccca    3480
aagccaggct cccaattact cctgacccca ggcttgctcc tgatagtgac atgaggcagc   3540
caaatgccta ggcagagagg ggagggtccc aaatgaaacc ccacgttcaa gcaaagatca   3600
gcctgaaggc taaagacca gattgctggt cctggatgaa acccaccacg cagagtggga    3660
acttcgttc ctgttgccc accctttccc aattgttctt tctgaataac gccttaacca    3720
atcgaatgtt gccttttcca gtaatacctta cagcctgccc ctcccccat tctgagccca   3780
taaaagacc cagactcccc catattaagg ggactttcct gcctttgggt aggggaccca   3840
cccccacgtc tcctctctgt tgaaaactgt ttcatcactc aataaaactc ccagctttgc   3900
tcactcttcc actgtcagca cattctcatt ctttctttggt gctgggcaag aactcaacca   3960
gtgtggaagc catacttggc ccaggcgggt gaagtgggcg ggccgtctcc tgcagcaggt   4020
agcatggtca agcgaggccc aggtgggcg tcaccagcca gaggtccctg gcttgcaaag   4080
tgaccgagaa aaaaatcctg tgccactcct ttggaaatg tccctgattc aggaagaggt    4140
agctccatcc agttgctcaa accaaatcca ttggcttctt tctttctatc ataccccaca  4200
tccaatctgt ctgcaagtct tttggctcta ccttcagaat atctccagaa tcttaactga   4260
ttcaccctcc tcccggcct cctcagtcct ctctgcttcc gccctggccc ctcttgggct    4320
gttcacagca cagcagctgt tgccaccctg ttaatgctcc cactctccta cagccttcgg   4380
tcttgcccca ggtaggagcc tgaggctgca cagaggtcag cacggcccg cttacccctgc  4440
cctcccagcc cagccgcacg ggccttgcac acatgcctgg gcatattcct gccttagggc   4500
tggtgctcct gctatttcct cttcccaggt aaccatgtga agtgcctccc tctgccctct  4560
ttccagcctt tacttgagtg tcaccttctc agtgaggcct gccctcattc ctcttttcgct   4620
gtttgcaacc catctcctgt cccccttccc agaactccct ttcctactc gttttcttc    4680
acagtacttg atactgccta acacactcca tggttcctta cttgccctgt ttattattt   4740
ccccaatag acagaatgtt ccatgatggc agaattctct gttttgtttc cttccatgtc    4800
cccagcacct agaacagtgc ctgacgcatc tcctaagcaa tacgaccaat aagtatgtgt   4860
ctggctgcct tccggctgcc agtgtctgcc tcttcctag gggcagtggt tgcgggggtg    4920
cttcctcaca tgtcttagta ggctgtgcag gctggaagtg ctcagaagtc acacccccag   4980
ggagcagcct cagccaacag cacctggct gtaaatgccc cagctccctc gccctcaggt    5040
aagcattgct gaggcacacg ttccatactc ttttccacag ggactgagca ccacccagcc   5100
acccacagga gcagctaacc tgataaccac cagcctcacc ctccctgcct               5160
tacttccccg ctcccctta ccacatgctg acctcccaga tgcatttctt gctttccggt    5220
ctctgtctca ggattggctc ctggatgaac acaaactaac actatgttca caaatatatt   5280
tgggaaatgc tggatgaata attatacaca tcagacagat tactagaaat tctcaccaaa   5340
gggatgcaca tgttacctct gcatggtgag atctcaggtg cttttacccc cacatagcta   5400
```

-continued

```
tcctttggca ttttttataat tagcaagtgc tcactcttcc actgtcagta cattctcatt    5460
cttcttgggc gctggacaag aattcaaccg gtgtgtaagc cagactcggc ccgggcagtc    5520
tcaaactcct gactccttat ataatttcta caaaaattat aaagctattt cccactcccc    5580
accccacatt catgtaacct gaagcatgag taaaccaaga atgaggtagg cctctgtctt    5640
ctaagcaaca tcagaactct aagaacatga gggactctta gaaaactctc tggagctaac    5700
cacagctggg tcactgctca tgtactgaag accagccaga gggttcccct gaaaaggagg    5760
gaaactgagc aaacattctc cagttctctt agtgtgcaca tgtttcagga ggtgtgaacc    5820
ccacatgtag cttgtgtagg caagaagaca aatagtgcta ctgtctggtc aaggatttgt    5880
ttgaagagcc atgatatgc ccatatggta agccaccagt gctccccatc cctgtaagac     5940
acttctttct cattattttc tcctctgatg gtgtgccagg atgctggcca agagaagcca    6000
agtggaaaga aggctgttca gtgacaagga acctaagact tagtgccaag gactgaaacc    6060
aagtaaactt gtaattttcc atgatggaaa catctacact ttctcattag tggcctctac    6120
agcagttgcc ccaaagaagc gtctcattgt ttttttacta catttatgtg aagcatacag    6180
gcaaactcag aaagactgtg ataaggctcg ccagagatgc ctgcacaggt gctggggaa    6240
aagcaggacc atcctgaagg gagatggtgt ctgtggacaa agaactgctc agtggttctt    6300
atttgcatga tttctgctgg tggaggctgt aaatgtgagc tcaaactccc acataagtga    6360
gttttcattg taatccagaa tgttttaaa tcaccctact tctattgaac ttgcactatc     6420
atctgttaac ctctactgta tttattaaat aaacctgaat aggtaaatca cagtacagca    6480
aaa                                                                   6483
```

SEQ ID NO: 24        moltype = AA  length = 368
FEATURE              Location/Qualifiers
source               1..368
                     mol_type = protein
                     organism = Homo sapiens
SEQUENCE: 24
MQPGSSRCEE ETPSLLWGLD PVFLAFAKLY IRDILDMKES RQVPGVFLYN GHPIKQVDVL     60
GTVIGVRERD AFYSYGVDDS TGVINCICWK KLNTESVSAA PSAARELSLT SQLKKLQETI    120
EQKTKIEIGD TIRVRGSIRT YREEREIHAT TYYKVDDPVW NIQIARMLEL PTIYRKVYDQ    180
PPFHSSALEKE EALSNPGALD LPSLTSLLSE KAKEFLMENR VQSFYQQELE MVESLLSLAN   240
QPVIHSASSD QVNFKKDTTS KAIHSIFKNA IQLLQEKGLV FQKDDGFDNL YYVTREDKDL    300
HRKIHRIIQQ DCQKPNHMEK GCHFLHILAC ARLSIRPGLS EAVLQQVLEL LEDQSDIVST    360
MEHYYTAF                                                            368

SEQ ID NO: 25        moltype = DNA  length = 8795
FEATURE              Location/Qualifiers
source               1..8795
                     mol_type = genomic DNA
                     organism = Homo sapiens
SEQUENCE: 25
gcggccgcac tagtacccg gagcccatgg gcgcgccgag ccgggcgcgg gggcgctgaa      60
cggcggagcg ggagcggccg gaggagccat ggactgcagc ctcgtgcgga cgctcgtgca    120
cagatactgt gcaggagaag agaattgggt ggacagcagc accatctacg tgggacacag    180
ggagccacct ccgggcgcag aggcctacat cccacagaga tacccagaca acaggatcgt    240
ctcgtccaag tacacatttt ggaactttat acccaagaat ttatttgaac aattcagaag    300
agtagccaac ttttatttcc ttatcatatt tctggtgcag ttgattattg atacacccac    360
aagtccagtg acaagcggac ttccactctt cttttgtcatt actgtgacgg ctatcaaaca    420
gggttatgaa gactggcttc gacataaagc agacaatgcc atgaaccagt gtcctgttca    480
tttcattcag cacggcaagc tcgttcggaa acaaagtcga aagctgcgag ttggggacat    540
tgtcatggtt aaggaggacg agacctttcc ctgcgacttg atcttccttt ccagcaaccg    600
gggagatggg acgtgccacg tcaccaccgc cagcttggat ggagaatcca gccataaaac    660
gcattacgcg gtccaggaca ccaaaggctt ccacacagag gaggatatcg gcggacttca    720
cgccaccatc gagtgtgagc agcccagcc cgacctctac aagttcgtgg gtcgcatcaa     780
cgtttacagt gacctgaatg accccgtggt gaggcccctta ggatcggaaa acctgctgct    840
tagaggagct acactgaaga acactgagaa atctttcgt gtggctattt acacgggaat    900
ggaaaccaag atggcattaa attatcaatc aaaatctcag aagcgatctg ccgtggaaaa    960
atcgatgaat gcgttcctca ttgtgtatct ctgcattctg atcagcaaag ccctgataaa    1020
cactgtgctg aaatacatgt ggcagagtga gcccttttcgg gatgagccgt ggtataatca    1080
gaaaacggag tcgaaaggc agaggaatct gttcctcaag gcattcacgg acttcctggc    1140
cttcatggtc ctcttttaact acatccccc tgtgtccatg tacgtcacgg tcgagatgca    1200
gaagttcctc ggctcttact tcatcacctg ggacgaagac atgttgacg aggagactgg    1260
cgaggggcct ctggtgaaca cgtcggacct caatgaagag ctgggacagg tggagtacat    1320
cttcacagac aagaccggca ccctcacgga aaacaacatg gagttcaagg agtgctgcat    1380
cgaaggccat gtctacgtgc cccacgtcat ctgcaacggg caggtcctcc cagagtcgtc    1440
aggaatcgac atgattgact cgtccccag cgtcaacggg agggagcgcg aggagctgtt    1500
tttccgggcc ctctgtctct gccacaccgt ccaggtgaaa gacgatgaca cgtagacgg    1560
cccaggaaa tcgccggacg gggggaaatc ctgtgtgtac atctcatcct cgcccgacga    1620
ggtggcgctg gtcgaaggtg tccagagact tggctttacc tacctaaggc tgaaggacaa    1680
ttacatggag atattaaaca gggagaacca catcgaaagg tttgaattgc tggaaatttt    1740
gagttttgac tcagtcagaa ggagaatgag tgtaattgta aaatctgcta caggagaaat    1800
ttatctgttt tgcaaaggag cagattcttc gatattcccc cgagtgatag aaggcaaagt    1860
tgaccagatc cgagccagag tggagcgtaa cgcagtggag gggctccgaa ctttgtgtgt    1920
tgcttataaa aggctgatcc aagaagaata tgaaggcatt tgtaagctgc tgcaggctgc    1980
caaagtgac cttcaagatc gagagaaaaa gttagcaa gcctatgac aaatagagaa        2040
agatcttact ctgcttggtg ctacagctgt tgaggaccgg ctgcaggaga aagctgcaga    2100
caccatcgag gccctgcaga aggcggat caaagtctgg gttctcacgg agacaagat      2160
ggagacggcc gcgccacgt gctacgcctg caagctcttc gcaggaaca cgcagctgct    2220
ggagctgacc accaagagga tcgaggagca gagcctgcac gacgtcctgt tcgagctgag    2280
caagacggtc ctgcgccaca gcgggagcct gaccagagac aacctgtccg gactttcagc    2340
```

```
agatatgcag gactacggtt taattatcga cggagctgca ctgtctctga taatgaagcc   2400
tcgagaagac gggagttccg gcaactacag ggagctcttc ctggaaatct gccggagctg   2460
cagcgcggtg ctctgctgcc gcatggcgcc cttgcagaag gctcagattg ttaaattaat   2520
caaattttca aaagagcacc caatcacgtt agcaattggc gatggtgcaa atgatgtcag   2580
catgattctg gaagcgcacg tgggcatagg tgtcatcggc aaggaaggcc gccaggctgc   2640
caggaacagc gactatgcaa tcccaaagtt taagcatttg aagaagatgc tgcttgttca   2700
cgggcatttt tattacatta ggatctctga gctcgtgcag tacttcttct ataagaacgt   2760
ctgcttcatc ttccctcagt ttttatacca gttcttctgt gggttttcac aacagacttt   2820
gtaccacacc gcgtatctga ccctctacaa catcagcttc acctccctcc ccatcctcct   2880
gtacagcctc atggagcagc atgttggcat tgacgtgctc aagagagacc cgaccctgta   2940
cagggacgtc gccaagaatg ccctgctgcg ctggcgcgtg ttcatctact ggacgctcct   3000
gggactgttt gacgcactgg tgttcttctt tggtgcttat ttcgtgtttg aaaatacaac   3060
tgtgacaagc aacgggcaga tatttggaaa ctggacgttt ggaacgctgg tattcaccgt   3120
gatggtgttc acagttacac taaagcttgc attggacaca cactactgga cttggatcaa   3180
ccattttgtc atctgggggt cgctgctgtt ctacgttgtc ttttcgcttc tctggggagg   3240
agtgatctgg ccgttcctca actaccagag gatgtactac gtgttcatcc agatgctgtc   3300
cagcgggccc gcctggctgg ccatcgtgct gctggtgacc atcagcctcc ttcccgacgt   3360
cctcaagaaa gtcctgtgcc ggcagtcgtg gccaacagca acagagagag tccagactaa   3420
gagccagtgc ctttctgtcg agcagtcaac catctcttatg cttctcaga cttccagcag   3480
cctgagtttc tgatggaaca agagcccagg ctaccagagc acctgtccct cggccgcctg   3540
gtacagctcc cactctcagc aggtgacact cgcggcctgg aaggagaagg tgtccacgga   3600
gccccacccc atcctcggcg gttcccatca ccactgacgt tccatcccaa gtcacagctg   3660
ccctaggtcc cgtgtgggaa tgctcgtgtg atggatggtc ctaagcctgt ggagactgtg   3720
cacgtgcctc ttcctggccc ccagcaggca aggagggggg tcacaggcct tgccctcgag   3780
catggcaccc tggccgcctg gacccagcac tgtggttgtt gagccacacc agtggcctct   3840
gggcattcgg ctcaacgcag gagggacatt ctgctgcccc accctgcgcg ctgtcatgca   3900
gaggccattc ccccaggcct gtgtcttcac ccacctgcca tcattggcct tgctgtcac   3960
tgggagagaa gagccgtcca gggacccatg gtggcccaca tgtggatgcc acatgctgct   4020
gtttcctgct tgcccggcca ccaccatgc cctccatagg gtgaggtgga gccatggtgg   4080
tgcgtccttt actcaacaac cctccaatcc ggatgctgtg ggaagggccg ggtcactcgg   4140
ataccatcat ccctgcggat gcaccgcgt accctgctca tctgggagtg gtttccctgc   4200
ggttacgtcc aagcccggct gcctgtgtg ttggggctgg ctgagtttcg gtctcccat   4260
caccggccgc ctcgtggaga aggcagtgcc acgtgggagg acaaggccac gccggcagct   4320
tccagccctg ccgcagaagt gccaggatgt ccatcagcca ctcgccaggg cggcggagccg   4380
tcagtccact gttacgggag aatgttgatt tcgcgggtgc gagggccggg agacagatac   4440
ttggctgtga tgagcagaca tcctctgtcc ccgtggaggg gtcaacacca aggtggtgtt   4500
cgtgcaccag aacctgtctc gggctgacgg gggtggcaca caggacacgg gtggatccca   4560
acaggcagca ccgcacctct gcccgcctcc cgcactgcag ctccgcccgc cgggctctgc   4620
gtccccacgt ccctcgtcc catccccacg tcccctcatc ccgtcacctc gtccccacat   4680
ccccttgccc cgtcacctcg tcctcatgtc cccttgtcct gtcacctcgt ccccacgtcc   4740
cctcgtctcc tcatcccac gtcctctcgt cccttgtcc cgtcccaca taccctcgtc   4800
cccatgtccc cacgcagggc tctccttcgt cttaggatct gtccagcgct gctctgggtg   4860
ggttagcaac cccaggggctg ctgtgatagg aagtccctgt tgttctccgt actggcattt   4920
ctatttctag aaaataatatt tgacatagcc ttaatggtcc ttaaagaaga catttcagtg   4980
tgagattcag acttcagacg ctgaaactgc tgcctttcag gaaagcacca ccaacgctgg   5040
aggaggagcc ggccctcacg cccgcccgc gccacgctgt ggaacgggc tccggcaagt   5100
gaaacccaga ggggtgtttcc gaggtgcctcga acagtaggta ttttttggaag ctcagatttc   5160
accatttgat tgtataatct tttacctata aaatatttat ttgaagtaga gggtaaatca   5220
gcggtaagaa cagtgaacac agtggttggg ataaataag gtgacaaaca tcacaccaaa   5280
gatgagggta gcgagcaact ggcttgagca gacagaacgg ggaagactcc actctgtccc   5340
gagggccag ccgcaggcgt ccccagggcc acctgccct gaggtccttg tgtggccgcg   5400
ctggcttggc agccctgccc acgctgcccc cgcaaacaat ggtgtgtgcg ttttacagc   5460
ccttttagg aacccaatat gggcataaat gtaacacctg tagcggggc agattctctg   5520
tatgttcagt taacaaatta tttgtaatgt atttttttag aaatcttaaa attgcctttg   5580
cactgaagta ttttcatagc tgttttatatc tcttttattc atttatttaa catactgtct   5640
aattttaaaa ataggttttt aaagctttca tttttaagtt tatgaaattt tggccactttt   5700
acatttagat tctggtgaga gttttgactg aatgttccaa tctctgatga atgcgaattt   5760
tcagatttga ttttattctc tacacacacc tcttcttttc ttggtatttc tggtggcagt   5820
gattagttga acagcacatt taaggcacga taatttgcta cactttttct ttacaatttg   5880
ttgcaatttc atctgctttc tatgtttcat tgttaattgc catccttcag ccttaaaaat   5940
agaagattct cacgtgaagg tttagtaagt tgggtcccag ctctgcctgt gtggagatag   6000
tcaccatgta cctctgacaa caagtttag tgtgaaagtc actaaacttt tacacactcc   6060
caaacgtctt tttaaaaatt gcttgggaaa ttattaaatg aatgtgcctg atgatttgaa   6120
atagacaagg ggcacgagat aaaaaagaaa aggatgagaa gatcctcagt gaatgacgtt   6180
gcagggtctt catgcaattt tccacctcgc agtagttagt atttacttgc cttaaactaa   6240
ctttgaagca agtaatgtca actttgagca ctttgttgag ttttgaaaaa tcttatttgt   6300
tgctgcacag gttaataaat tatcaattg taattcagca tgttggtcag agacacggtc   6360
actgattcac acccagtccc tgccacagac cgtctccagac acgcacagtg ggcctgctgc   6420
atgattcaca cccagtccct gccacagacc gtctccagac cgcacagtgg cctgctgca   6480
tgattcacac ccagtccctg ccacagaccg tctccagaca gcacagtggg cctgctgcat   6540
gcgtgttacc tggcttttgg ctccacgctc actcatagcc atgtccacat ggggccttgc   6600
acacaggatc actcacatat gtacatgtac ccaccacaaa cgtgcaagct cctgcacaca   6660
tgcatgcaca caaacgtgta cacaagtgtg agctcctaca cgcatacaca cacacacgtg   6720
tacatgcacc aaagcatgtg tgacctacag acatgcagca catgcacgtg tacacatacc   6780
acagacacgc gtgtgcatgc tcctacacaa tacatatgca catatcatga acagcgtaag   6840
ttcctacaca cggacgtgtg atacacacat gcatgtacag gtaagcacac atgtacaagc   6900
tcctacaggc ttgctctcac acacgtgtat gcacagcaga gagacgtatg agcttctact   6960
gcacacatgc acacacacac gcacacgtac attcactaca aacgtgcagc ctcctgcaca   7020
cgtgcacatt catgtgtaca ccacaaatga gttcccagac gtgtaaacac acgtgcacac   7080
```

```
atcgtacaca tgtgagctcc cacacgtaca cacagatgca catggacaca ccccaaacac   7140
gcacaggctc ctacacacat gcacacacgt gtacaccaca aacgagctcc cagacatgta   7200
aacacacgtc tcccacacgt gagctcccac acgtacacat gcacatgtac gcaccacaaa   7260
cacatgcgca ggctcctgca ggcgtgaata cacacatgca cacacatata cacacatgtg   7320
ccacaaacaa gtgcacactg tcctggtgtc ctgcactgca tcctgcctcc ttgctgaggg   7380
gccccctgtga gaggcctctg gatgggcatg ggaagatggg ctccctggcc cccagcccat   7440
gcctcctgg gatgaagagt cccctcctg gcagaatgtc tgggctttgc agagcaggcc   7500
ccgggggtga agtcgcagct tcacttacac cagctgctct gtgagcaagg cttggtgccc   7560
tggacaaggc ccttcccctt tagggaggtc cagcctcgca agctgaaacc tcccctcggc   7620
tcagccctat accaggcggc cacagcagga ctggccacac ccacgccgca cctcatccgt   7680
gcacgcgtcg gagcacggcc agccttccgc cacgagccag ctgggaaggg ccgcggccgc   7740
ctaaagcccc agtcaaccca gcctgtgtct gagcagacag ggcgaacaag caggccacac   7800
cgtctcgagg gaggaggcca gatgcggcca gcgtctccaa cagggtgacc atccgctcgg   7860
cttgctgagc gtttaaacaa atgtttagac aggctgtggg gactcccctg agttgagcct   7920
tggccagggg tccggtgctg tcgcgggaaa cctccagcct tgttcttcaa accactcagc   7980
tcatgtgttt tgcactgact agtactgaat aatacaacca ctcttattta atgttagtat   8040
tatttatttg acaactcagt gtctaacagc ttgatatgca ggtccttgca tcctacattt   8100
ctttaggaag ttacccattt gtaactttaa aaacaggaaa aatatcagtt ggcaaatgca   8160
atcttttttt tttttaagct aaaggtgggt gaactggaat gaaaatcttt ctgatgttgt   8220
gtctataagc agccttgatg ggatatgtta gaagtgtcat gaaagtgtga ttctactttt   8280
gcagaaaaat ctaaagatca atttatatag ctttatttt tactttatca aagtatacag   8340
aatttaata tgcatatat gtgtctgact taaaattata atgtctgcgt caccatttaa   8400
aatgtctgtt cattatgtaa tgtaataaaa gaaggtcttc aaaaatgtat ttaacatgaa   8460
tggtatccat agttgtcatc atcataaata ctggagttta ttttaaatt attaaacata   8520
gtaggtgcat aacataaat cagtctccac acagtaacat ttaactgata attcattaat   8580
cagctttgaa aaattaaatt gttaattaaa ccaatctaat atttcagtaa agtttatttt   8640
gtatgcttct gtttttaact tttatttctg tagataaact gactggataa tattatattg   8700
gacttttctc tagattatct aagcaggaga cctgaatctg cttgcaataa agaataaaag   8760
tctgcttcag tttctttata aagaaactca cacaa                              8795

SEQ ID NO: 26           moltype = AA   length = 1134
FEATURE                 Location/Qualifiers
source                  1..1134
                        mol_type = protein
                        organism = Homo sapiens
SEQUENCE: 26
MDCSLVRTLV HRYCAGEENW VDSRTIYVGH REPPPGAEAY IPQRYPDNRI VSSKYTFWNF   60
IPKNLFEQFR RVANFYFLII FLVQLIIDTP TSPVTSGLPL FFVITVTAIK QGYEDWLRHK  120
ADNAMNQCPV HFIQHGKLVR KQSRKLRVGD IVMVKEDETF PCDLIFLSSN RGDGTCHVTT  180
ASLDGESSHK THYAVQDTKG FHTEEDIGGL HATIECEQPQ PDLYKFVGRI NVYSDLNDPV  240
VRPLGSENLL LRGATLKNTE KIFGVAIYTG METKMALNYQ SKSQKRSAVE KSMNAFLIVY  300
LCILISKALI NTVLKYMWQS EPFRDEPWYN QKTESERQRN LFLKAFTDFL AFMVLFNYII  360
PVSMYVTVEM QKFLGSYFIT WDEDMFDEET GEGPLVNTSD LNEELGQVEY IFTDKTGTLT  420
ENNMEFKECC IEGHVYVPHV ICNGQVLPES SGIDMIDSSP SVNGREREEL FFRALCLCHT  480
VQVKDDDSVD GPRKSPDGGK SCVYISSSPD EVALVEGVQR LGFTYLRLKD NYMEILNREN  540
HIERFELLEI LSFDSVRRRM SVIVKSATGE IYLFCKGADS SIFPRVIEGK VDQIRARVER  600
NAVEGLRTLC VAYKRLIQEE YEGICKLLQA AKVALQDREK KLAEAYEQIE KDLTLLGATA  660
VEDRLQEKAA DTIEALQKAG IKVWVLTGDK METAAATCYA CKLFRRNTQL LELTTKRIEE  720
QSLHDVLFEL SKTVLRHSGS LTRDNLSGLS ADMQDYGLII DGAALSLIMK PREDGSSGNY  780
RELFLEICRS CSAVLCCRMA PLQKAQIVKL IKFSKEHPIT LAIGDGANDV SMILEAHVGI  840
GVIGKEGRQA ARNSDYAIPK FKHLKKMLLV HGHFYYIRIS ELVQYFFYKN VCFIFPQFLY  900
QFFCGFSQQT LYDTAYLTLY NISFTSLPIL LYSLMEQHVG IDVLKRDPTL YRDVAKNALL  960
RWRVFIYWTL LGLFDALVFF FGAYFVFENT TVTSNGQIFG NWTFGTLVFT VMVFTVTLKL 1020
ALDTHYWTWI NHFVIWGSLL FYVVFSLLWG GVIWPFLNYQ RMYYVFIQML SSGPAWLAIV 1080
LLVTISLLPD VLKKVLCRQL WPTATERVQT KSQCLSVEQS TIFMLSQTSS SLSF        1134

SEQ ID NO: 27           moltype = DNA   length = 4575
FEATURE                 Location/Qualifiers
source                  1..4575
                        mol_type = genomic DNA
                        organism = Homo sapiens
SEQUENCE: 27
tttccgcagt taggggctgc tatttcaacg cagggagata aaagaaaaa aacacttgct    60
cttctacccc gctaaaaaca ctcatcctag ggagcacgcc agcatttgca gcgttcgggg   120
cagggccact cggcctgcgg ccgttgcact ggctggaagc tggcaggcga tcacggttga   180
ttggctcggg tgcggtccaa gggcagcaac gccttcggcg ggccgcctag ggtgattggc   240
tgctgcagcc caccccctag ccggtttggt gggcggcgaa gctggattg gtggagctaa   300
gagctggctc agtttcagcg ctggctcttc gtgcatggca gagatggcga ctgcgactcg   360
gctgctgggg tggcgtgtgg cgagctgagg gctgcggccg ccgcttgccg gcttcgtttc   420
ccagcggggcc cactcgcttt tgcccgtgga cgatgcaatc aatgggctaa gcgaggagca   480
gaggcaggaa ttttggaagc agctgggaaa cctgggcgta ttgggcatca cagcccctgt   540
tcagtatggc ggctccggcc tgggctacct ggagcatgtg ctggtgatgg aggagatatc   600
ccgagcttcc ggagcagtgg ggctcagtta cggtgcccac tccaacctct gcatcaacca   660
gcttgtgcc aatgggaatg aggccagaa agagaagtat ctccggcagc tgatcagtgg   720
tgagtacatc ggagccctgg ccatgagtga gccaatgcaa ggctctgatg ttgtctctat   780
gaagctcaaa gcgaaaaga aaggaaatca ctacatcctg aatggcaaca agttctggat   840
cactaatggc cctgatgctg acgtcctgat tgtctatgcc aagacagatc tggctgctgt   900
gccagcttct cggggcatca cagccttcat tgtggagaag ggtatgcctg gctttagcac   960
ctctaagaag ctggacaagc tggggatgag gggctctaac acctgtgagc taatctttga  1020
```

```
agactgcaag attcctgctg ccaacatcct gggccatgag aataaggtg tctacgtgct    1080
gatgagtggg ctggacctgg agcggctggt gctggccggg gggcctcttg ggctcatgca    1140
agcggtcctg gaccacacca ttccctacct gcacgtgagg gaagcctttg gccagaagat    1200
cggccacttc cagttgatgc aggggaagat ggctgacatg tacacccgcc tcatggcgtg    1260
tcggcagtat gtctacaatg tcgccaaggc ctgcgatgag gacggcattg ca ctgctaagga   1320
ctgtgcaggt gtgattcttt actcagctga gtgtgccaca caggtagccc tggacggcat    1380
tcagtgtttt ggtggcaatg gctacatcaa tgactttccc atgggccgct tcttcgaga    1440
tgccaagctg tatgagatag gggctgggac cagcgaggtg aggcggctgg tcatcggcag    1500
agccttcaat gcagactttc actagtcctg agacccttcg cccccttttc ctgcacctag    1560
tggcctttct tgggaagtag agatgtggcg gctttcccac cctgcccaca gcaggccctc    1620
ctgcccagct gctcttgtca gccctctggc ctctggatga ggttgagttc tccacaacag    1680
ctcccaagca tcatgggcct cgcagccggg cctgtgccac ggctagtgtt gtgtgattta    1740
aaatggactc agcaggaagc atattgtctg gggattgttg ggacaggttt tggtgactct    1800
gtgcccttgc tctctaactt ctgagcccac ctcccagggt aggcacctgg gggcatgcag    1860
gtgcccacct cccagggtag gcacctgggg gcatgcaggt acccacctct ttctcttggg    1920
tgaggctctg gcaaggagat ctctctgctc aagcacagca gaatcatggc ccctctccat    1980
gaattggaac ttggtacagg ttaagtatcc ctaatcctga aatctgaaac acttgtggtt    2040
ccaagcattt tggataaggc aaattcaact ttcagtctct tttctgggg aaaaaaataa    2100
taaacctagc ctagccaggc gtggtggctc atgcttgtaa tcccagcact tcaggaggct    2160
gagatgggtg gatcacctga ggtcaggagt tcaagaccag cctggccaac atgtggaaac    2220
ctcgcctcaa ctaaaaatag aaaaaaatta gttgggcatg tggtgggca cctgtaatcc    2280
cagctacttc aggaggctga ggcaggagaa ttacttgaac ccaggaggcg gacgttgcag    2340
tgagccgagc ttgtgccatt gcactccagc ctgggcgaca agagcaaaac tcttcaaaaa    2400
acaaaacaaa acaaaaaaac cctggcccttt gtttcttcca gtttctagag gtatcagctc    2460
ctagcagctt atgaacacat atgcttgctt ggccaggcaa ggtggtgtgt gcctgtaatc    2520
ccagcacttt gggaggccaa ggcaggtgga tcacttgcag tcaggagttc aagaccagcc    2580
tgtccaacgt ggtgaaaccc catctctact aaaaatacaa aaattagcca ggggtggtgg    2640
tgcacgtctg taatcccagc tactcaggag gctgaggcag gagaatcact tgaacccggg    2700
aggtggaggt tgcaatgagc caatatgaca ccgctgcagt ccagcctggg ccatagagtg    2760
agactctgtc tcaaaaaagg aaagaaaaat aggctgacta cagtgactaca tgcctgtaat    2820
cccaacactt tgggaggccg aggcaggtgg atcacgaggt caggagttca agaccagcct    2880
ggccaagatg gtaaaacctc gtctctacta aaaatacaaa aattagccag gtgtggtggc    2940
aggctcctgt aatcccagct actcaggagg ctgaggcaga gaattgcttg aacccgggag    3000
gcagagtttg cagtgagcca gatcacacc actgcactcc ggcctgggca acagagcgag    3060
actctgtctc aaaaaataat aggccaggca tggtggctca acgtctgtaa tcccagcact    3120
ttgggaggcc gaggcgggca gatcacaagg tcaggagttc gagaccagcc tgacgaccaa    3180
catggtgaaa cctcgtctct actaaaaata caaaaattag ccaggcctgg tggcacgcgc    3240
ctgtaatccc agttacacag aagactgagg caggagaatc gcttgaacgc aggaggcaga    3300
ggttgcagga gctgagatcg cgccattgca ctccagcctg ggcaacagag tgagactctg    3360
tctcaaaaaa taataataaa ataaatgaac acacatgctg ctgagtccgc aggggggca    3420
gagcagagga cagcgtgctt ttgtgtactg ttggaagact ggctcctcct gtacagcacc    3480
tctgagccct tgtgcaccgc cctgccacgg gcaccatcca gtcctggccg tgtgaccacc    3540
cacagctgac tgggcagca gcacaggccc tacccgacga ggccggagtt ggctcgcatg    3600
actccagctg aggctgcctg tgtacatttc tccagatacc ctatggctaa ttttgttata    3660
actgcacagt ggctgctgcc atttttgtatt aaatatattg tgaaacaaac ctatctgggg    3720
agaagcaatc tacttgccgc tgcttcctgt ctggatccag cttgtgtcct tggagagtgg    3780
ctggcccagg tcctattcct gtcctccagc ccgttcttc atgagggaca ggaaggtaaa    3840
atcagccctt aggagagagg tctcagcctc ccttttcccag atctcccagt gagttttaaa    3900
ggaagcaggg agcccagagt gctaagttct tacagccaga aggaagctta tagatttctg    3960
aaaaccgccc ctttgttttt aaaagatca acacaatttg actttctcaa ggtcaaaacg    4020
aactagaatc cagatctgct catggcaaaa atggggtgt tctgagaatt ccagctttga    4080
gccgcactgt acagcagtct ggatagagtg tgatctgaga agggaatggg tctgggttgt    4140
tccacccctt ccgagttcca aaaagaggga actggttttc ttggttctca gcccagcagc    4200
acctatcctg gctcttggtc ctggcctgca gccaagtgct gttcctagcc tgaggcttga    4260
gacaggtggg gttggctcct caccaacccc agttccgtc catcctgagg gcaagatcct    4320
gggctcatag gcagtcccctt tcacttcctt gtcttgctcc ctgctatgtt ggagatgaat    4380
gtgactaaaa gggccatctt gctggcttaa tgtgtggctg gagagaccag cctggagaca    4440
atgtggcaaa atggggcgct tcatccagtc tgtctaagcc ctgtcgactt ggggaggtga    4500
tttctttcct ggttctatat gtgaagcaaa ataaatgttt taaaattaaa agcaaaaaaa    4560
acaaaatgaa ccatg                                                    4575

SEQ ID NO: 28          moltype = AA   length = 396
FEATURE                Location/Qualifiers
source                 1..396
                       mol_type = protein
                       organism = Homo sapiens
SEQUENCE: 28
MAEMATATRL LGWRVASWRL RPPLAGFVSQ RAHSLLPVDD AINGLSEEQR QEFWKQLGNL     60
GVLGITAPVQ YGGSGLGYLE HVLVMEEISR ASGAVGLSYG AHSNLCINQL VRNGNEAQKE    120
KYLPKLISGE YIGALAMSEP NAGSDVVSMK LKAEKKGNHY ILNGNKFWIT NGPDADVLIV    180
YAKTDLAAVP ASRGITAFIV EKGMPGFSTS KKLDKLGMRG SNTCELIFED CKIPAANILG    240
HENKGVYVLM SGLDLERLVL AGGPLGLMQA VLDHTIPYLH VREAFGQKIG HFQLMQGKMA    300
DMYTRLMACR QYVYNVAKAC DEGHCTAKDC AGVILYSAEC ATQVALDGIQ CFGGNGYIND    360
FPMGRFLRDA KLYEIGAGTS EVRRLVIGRA FNADFH                              396

SEQ ID NO: 29          moltype = DNA   length = 4286
FEATURE                Location/Qualifiers
source                 1..4286
                       mol_type = genomic DNA
```

```
                        organism = Homo sapiens
SEQUENCE: 29
caacttccgg gtcaaaggtg cctgagccgg cgggtcccct gtgtccgccg cggctgtcgt    60
cccccgctcc cgccacttcc ggggtcgcag tcccgggcat ggagccgcga ccgtgaggcg   120
ccgctggacc cgggacgacc tgcccagtcc ggccgcgcc ccacgtcccg gtctgtgtcc   180
cacgcctgca gctggaatgg aggctctctg gacccfttag aaggcacccc tgccctcctg   240
aggtcagctg agcggttaat gcggaaggtt aagaaactgc gcctggacaa ggagaacacc   300
ggaagttgga gaagcttctc gctgaattcc gaggggctg agaggatggc caccaccggg   360
accccaacgg ccgaccgagg cgacgcagcc gccacagatg acccggccgc ccgcttccag   420
gtgcagaagc actcgtggga cgggctccgg agcatcatcc acggcagccg caagtactcg   480
ggcctcattg tcaacaaggc gccccacgac ttccagtttg tgcagaagac ggatgagtct   540
gggccccact cccaccgcct ctactacctg ggaatgccat atggcagccg agagaactcc   600
ctcctctact ctgagattcc caagaaggtc cggaaagagg ctctgctgct cctgtcctgg   660
aagcagatgc tggatcattt ccaggcacg ccccaccatg gggtctactc tcgggaggag   720
gagctgctga gggagcggaa acgcctgggg gtcttcggca tcacctccta cgacttccac   780
agcgagagtg gcctcttcct cttccaggcc agcaacagcc tcttccactg ccgcgacggc   840
ggcaagaacg gcttcatggt gtcccctatg aaaccgctgg aaatcaagac ccagtgctca   900
gggcccggga tggaccccaa aatctgccct gccgaccctg ccttcttctc cttcatcaat   960
aacagcgacc tgtgggtggc caacatcgag acaggcgagg agcggcggct gaccttctgc  1020
caccaaggtt tatccaatgt cctggatgac cccaagtctg cgggtgtggc caccttcgtc  1080
atacaggaag agttcgaccg cttcactggg tactggtggt gccccacagc ctcctgggaa  1140
ggttcagagg gcctcaagac gctgcgaatc ctgtatgagg aagtcgatga gtccgaggtg  1200
gaggtcattc acgtccctc tcctgcgcta gaagaaaagga agacggactc gtatcggtac  1260
cccaggacag gcagcaagaa tcccaagatt gccttgaaac tggctgagtt ccagactgac  1320
agccagggca agatcgtctc gacccaggag aaggagctgg tgcagcccft cagctcgctg  1380
ttcccgaagg tggagtacat cgccagggcc gggtggacca gggatggcaa atacgcctgg  1440
gccatgttcc tggaccggcc ccagcagtgg ctccagctcg tcctcctccc cccggccctg  1500
ttcatcccga gcacagagaa tgaggagcag cggctagcct ctgccagagc tgtccccagg  1560
aatgtccagc cgtatgtggt gtacgaggag gtcaccaacg tctggatcaa tgttcatgac  1620
atcttctatc ccttccccca atcagaggga gaggacgact tctgctttct ccgcgccaat  1680
gaatgcaaga ccggcttctg ccatttgtac aaagtcaccg ccgttttaaa atcccagggc  1740
tacgattgga gtgagccctt cagccccggg gaagatgaat ttaagtgccc cattaaggaa  1800
gagattgctc tgaccagcgg tgaatgggag gttttggcga ggcacggctc caagatctgg  1860
gtcaatgagg agaccaagct ggtgtacttc caggggacca aggacacgcc gctggagcac  1920
cacctctacg tggtcagcta tgaggcggcc ggcgagatcg tacgcctcac cacgcccggc  1980
ttctccccata gctgctccat gagccagaac ttcgacatgt tcgtcagcca ctacagcagc  2040
gtgagcacgc cgccctgcgt gcacgtctac aagctgagcg gccccgacga cgaccccctg  2100
cacaagcagc ccgcttctg ggctagcatg atggaggcag ccagctgccc cccggattat  2160
gttcctccag agatcttcca tttccacacg cgctcggatg tgcggctcta cggcatgatc  2220
tacaagcccc acgccttgca gccagggaag aagcacccca ccgtcctctt tgtatatgga  2280
ggcccccagg tgcagctggt gaataactcc ttcaaaggca tcaagtactt gcggctcaac  2340
acactggcct cctgggcta cgccgtggtt gtgattgacg gcaggggctc ctgtcagcga  2400
gggcttcggt tcgaagggc cctgaaaaac caaatgggac aggtggagat cgaggaccag  2460
gtggagggcc tgcagttcgt ggccgagaag tatggcttca tcgacctgag ccgagttgcc  2520
atccatggct ggtcctacgg gggcttcctc tcgctcatgg ggctaatcca caagcccag  2580
gtgttcaagg tggccatcgc gggtgccccg gtcaccgtct ggatggccta cgacacaggg  2640
tacactgagc gctacatgga cgtccctgag aacaaccagc acggctatga ggcgggttcc  2700
gtggccctgc acgtggagaa gctgcccaat gagcccaacc gcttgcttat cctccacgac  2760
ttcctggacg aaaacgtgca cttttttccac acaaacttcc tcgtctccca actgatccga  2820
gcagggaaac cttaccagct ccagatctac cccaacgaga gacacagtat tcgctgcccc  2880
gagtcgggcg agcactatga agtcacgttg ctgcactttc tacaggaata cctctgagcc  2940
tgcccaccgg gagccgccac atcacagcac aagtggctgc agcctccgcg gggaaccagg  3000
cgggaggac tgagtggccc gcgggcccca gtgaggcact tgtcccgcc cagcgctggc  3060
cagccccgag gagccgctgc cttcaccgcc ccgacgcctt ttatccttt ttaaacgctc  3120
ttgggtttta tgtccgctgc ttcttggttg ccagacaga gagatggtgg tctcgggcca  3180
gccctcctc tccccgcctt ctgggaggag gaggtcacac gctgatgggc actgaggagg  3240
ccagaagaga ctcagaggag cgggctgcct tccgcctggg gctccctgtg acctctcagt  3300
cccctggccc ggccagccac cgtccccagc acccaagcat gcaattgcct gtccccccg  3360
gccagcctcc ccaacttgat gtttgtgttt tgtttgggg gatattttc ataattattt  3420
aaaagacagg ccgggcgcgg tggctcacgt ctgtaatccc agcactttgg gaggctgagg  3480
cgggcggatc acctgaggtt gggagttcaa gaccagcctg gccaacatgg gaaaccccg  3540
tctctactaa aaatacaaaa aattagccgg gtgtggtggc gcgtgcctat aatcccagct  3600
actcgggagg ctgaggcagg agaatcgctt gaacccggga ggtggaggtt gcggtgagcc  3660
aagatcgcac cattgcactc cagcctgggc aacaagacg aaatctgtc tcaaaataaa  3720
taaaaaataa aagacagaaa gcaagggtg cctaaatcta gacttggggt ccacaccggg  3780
cagcggggtt gcaacccagc acctggtagg ctccattct tcccaagccc gagcagaggg  3840
tcatgcgggc cccacaggag aagcggccag ggcccgcggg gggcaccacc tgtggacagc  3900
cctcctgtcc ccaagcttc aggcaggcac tgaaacgcac cgaacttcca cgctctgctg  3960
gtcagtggcg gctgtccct cccagccca gccgccaac cacatgtgtc tgcctgaccc  4020
gtacacacca ggggttccgg ggttgggagc tgaaccatcc ccacctcagg gttatatttc  4080
cctctcccct tccctccccg ccaagagctc tgccaggggc gggcaaaaaa aaagtaaaa  4140
agaaaagaaa aaaaaaaaa agaaacaaac cacctctaca tattatgaa agaaaatatt  4200
tttgtcgatt cttattcttt tataattatg cgtggaagaa gtagacacat taaacgattc  4260
cagttggaaa aaaaaaaaaa aaaaaa                                      4286

SEQ ID NO: 30      moltype = AA   length = 892
FEATURE            Location/Qualifiers
source             1..892
                   mol_type = protein
```

```
                    organism = Homo sapiens
SEQUENCE: 30
MRKVKKLRLD KENTGSWRSF SLNSEGAERM ATTGTPTADR GDAAATDDPA ARFQVQKHSW   60
DGLRSIIHGS RKYSGLIVNK APHDFQFVQK TDESGPHSHR LYYLGMPYGS RENSLLYSEI  120
PKKVRKEALL LLSWKQMLDH FQATPHHGVY SREEELLRER KRLGVFGITS YDFHSESGLF  180
LFQASNSLFH CRDGGKNGFM VSPMKPLEIK TQCSGPRMDP KICPADPAFF SFINNSDLWV  240
ANIETGEERR LTFCHQGLSN VLDDPKSAGV ATFVIQEEFD RFTGYWWCPT ASWEGSEGLK  300
TLRILYEEVD ESEVEVIHVP SPALEERKTD SYRYPRTGSK NPKIALKLAE FQTDSQGKIV  360
STQEKELVQP FSSLFPKVEY IARAGWTRDG KYAWAMFLDR PQQWLQLVLL PPALFIPSTE  420
NEEQRLASAR AVPRNVQPYV VYEEVTNVWI NVHDIFYPFP QSEGEDELCF LRANECKTGF  480
CHLYKVTAVL KSQGYDWSEP FSPGEDEFKC PIKEEIALTS GEWEVLARHG SKIWVNEETK  540
LVYFQGTKDT PLEHHLYVVS YEAAGEIVRL TTPGFSHSCS MSQNFDMFVS HYSSVSTPPC  600
VHVYKLSGPD DDPLHKQPRF WASMMEAASC PPDYVPPEIF HPFHTRSDVRL YGMIYKPHAL  660
QPGKKHPTVL FVYGGPQVQL VNNSFKGIKY LRLNTLASLG YAVVVIDGRG SCQRGLRFEG  720
ALKNQMGQVE IEDQVEGLQF VAEKYGFIDL SRVAIHGWSY GGFLSLMGLI HKPQVFKVAI  780
AGAPVTVWMA YDTGYTERYM DVPENNQHGY EAGSVALHVE KLPNEPNRLL ILHGFLDENV  840
HFFHTNFLVS QLIRAGKPYQ LQIYPNERHS IRCPESGEHY EVTLLHFLQE YL          892

SEQ ID NO: 31           moltype = DNA  length = 2113
FEATURE                 Location/Qualifiers
source                  1..2113
                        mol_type = genomic DNA
                        organism = Homo sapiens
SEQUENCE: 31
actcaccctc cggcttcctg tcggggcttt ctcagcccca ccccacgttt ggacatttgg    60
agcatttcct tccctgacag ccggacctgg gactgggctg gggccctggc ggatggagac   120
atgctgcccc tgctgctgct gcccctgctg tggggggggt ccctgcagga gaagccagtg   180
tacgagctgc aagtgcagaa gtcggtgacg gtgcaggagg gcctgtgcgt ccttgtgccc   240
tgctccttct cttaccctg gagatcctgg tattcctctc ccccactcta cgtctactgg    300
ttccgggacg gggagatccc atactacgct gaggttgtgg ccacaaacaa cccagacaga   360
agagtgaagc cagagaccca gggccgattc cgcctccttg gggatgtcca agaagaac    420
tgctccctga gcatcggaga tgccagaatg gaggacacgg gaagctattt cttccgcgtg   480
gagagaggaa gggatgtaaa atatagctac caacagaata agctgaactt ggaggtgaca   540
gccctgatag agaaacccga catccacttt ctggagtccgg ccgcccccata              600
aggctgagct gcagccttcc aggatcctgt gaagcgggac cacctctcac attcctgtg    660
acggggaatg ccctcagccc cctgaccccc gagaccaccc gctcctcgga gctcaccctc   720
accccaggc ccgaggacca tggcaccaac ctcacctgtc aggtgaaacg ccaaggagct   780
caggtgacca cggagagaac tgtccagctc aatgtctcct atgctccaca gaacctcgcc   840
atcagcatct tcttcagaaa tggcacaggc acagccctgc ggatcctgag caatggcatg   900
tcggtgccca tccaggaggg ccagtccctg ttcctcgcct gcacagttga cagcaacccc   960
cctgcctcac tgagctggtt ccgggaggga aaagccctca atccttccca gacctcaatg  1020
tctgggaccc tggagctgcc taacatagga gctagagagg aggggaatt cacctgccgg   1080
gttcagcatc cgctgggctc ccagcacctg tccttcatcc tttctgtgca gagaagctcc  1140
tcttcctgca tatgtgtaac tgagaaacag cagggctcct ggcccctcgt cctcaccctg  1200
atcaggggg ctctcatggg ggctggcttc ctcctcacct atggcctcac ctggatctac  1260
tataccaggt gtggaggccc ccagcagagc agggctgaga ggcctggctg agcccctccc  1320
gctcaagaca gaactgaggt gtggacactt agccctgtgg gacacatgca ggacatcact  1380
gtcagcttct ttctgaaagc tcacatccca ctgactaccc ctcttttcct tcctgcccca  1440
tacccctct acttattccc ctctgcttgt gagtcttgcc ccaccacacc tgcatcccca  1500
tctgcacccc atccctctc cacctgccct tctcttcct ctcatccac catctccagc   1560
cctgtgaagg gaatgtactt tcggtcttat acccccatta cccattaccc aaaagttacc  1620
tttttttt ttttttttt ttgagacaga gtctcactct gttgcacagg ctggagttca  1680
gtggcacaat ctccgttcac tgcaacctcc acctctgggg ttcaagcaat tctcctgcct  1740
cagcctccct agtagctggg attacaggtg cctgccacca catccagtta attttttttt  1800
tttgtatgtt agtagagatg gggttttacc atgttggcca ggtctcgaac tcctgacctc  1860
aagcaatcca ctgcattggc ctcccaaagt gctggcatta caggtatgag ccaccgtgcc  1920
tggctgccaa aagttacctt cttaacactt gaatttctgg tctcctcagc ttccctatcc   1980
atataggcac agagaggcag catttgtttt ccagttaaaa ctctacctca ttgtgattat  2040
tatccaatac aattgttaca aaataagtaa aacttttatg aaacaataca acataactga  2100
ttttactctt taa                                                      2113

SEQ ID NO: 32           moltype = AA  length = 396
FEATURE                 Location/Qualifiers
source                  1..396
                        mol_type = protein
                        organism = Homo sapiens
SEQUENCE: 32
MLPLLLLPLL WGGSLQEKPV YELQVQKSVT VQEGLCVLVP CSFSYPWRSW YSSPPLYVYW   60
FRDGEIPYYA EVVATNNPDR RVKPETQGRF RLLGDVQKKN CSLSIGDARM EDTGSYFFRV  120
ERGRDVKYSY QQNKLNLEVT ALIEKPDIHF LEPLESGRPT RLSCSLPGSC EAGPPLTFSW  180
TGNALSPLDP ETTRSSELTL TPRPEDHGTN LTCQVKRQGA QVTTERTVQL NVSYAPQNLA  240
ISIFFRNGTG TALRILSNGM SVPIQEGQSL FLACTVDSNP PASLSWFREG KALNPSQTSM  300
SGTLELPNIG AREGGEFTCR VQHPLGSQHL SFILSVQRSS SSCICVTEKQ QGSWPLVLTL  360
IRGALMGAGF LLTYGLTWIY YTRCGGPQQS RAERPG                              396

SEQ ID NO: 33           moltype = DNA  length = 4045
FEATURE                 Location/Qualifiers
source                  1..4045
                        mol_type = genomic DNA
```

```
                      organism = Homo sapiens
SEQUENCE: 33
cgcccacgcc cggcgcccg accgcggagg actccccgag ccccgcccgc catggcccgg    60
atcccgacgg ccgccctggg ttgcatcagc ctcctctgcc tgcagctccc tggctcgctg   120
tcccgcagcc tgggcgggga cccgcgaccc gtcaaaccca gggagccccc agcccggagc   180
ccttccagca gcctgcagcc caggcacccc gcacccgac ctgtggtctg gaagcttcac    240
cgggccctcc aggcacagag gggtgccggc ctggccctg ttatgggtca gcctctccgg    300
gatggtggcc gccaacactc gggcccccga agacactcgg gccccgcag gacccaagcc    360
cagctcctgc gagtgggctg tgtgctgggc acctgccagg tgcagaatct cagccaccgc   420
ctgtggcaac tcatgggacc ggccggccgg caggactcag ctcctgtgga ccccagcagc   480
ccccacagct atggctgagg tggggccggg ccacacccct gcccatccca gccagggtgc   540
tgtgcccccg tccagagctg cagctgagcc ccatctgaag cccagtccct cggagctgca   600
gacagcaggt cctgcagcaa caatacctgc acggctttgc acacgtaaac ctaggctggt   660
ctacacgcag tgctggtacg tcaaggagcc taaacaccct gaaattgtga cccctgggtg   720
gacagctgcc agacacagct ggcggcagca ccagatgcta agcgcttcag agaggaggtg   780
tctgcccaga gatgtggagc agaagctggg ccctgaacac acggggccat gtctggacga   840
gcaggggaga gaggctgaac tggccagaag tggccctcc gctgctggtc cagtcagact    900
gaagcccggc cttgtgcctg ggctgttcct gctctcatgc acaaccagcc cttccacgtg   960
cctgcctgtg ggacaggagg gggagcgtgg gatgctgtag cccccgggt tgggcaaggg   1020
aaggatggtg gccctccaga ggtcatgaag ggacctctgt ggctccagct gccaaccctg   1080
gagcccgac cgaggtggcc atggagactc cacctggatc ccctgtagga ggccaggag    1140
gggaactcag cagttcagga gccaccccaa accattctgg gacaggaca cccctttcta   1200
ccccagggca gggcagggct gggtggggca agatccccca gcccgactag acccacctca   1260
cctgaagggg gtgagaccct tgttggcagc cagacaaggg tggggctcca caggcagcac   1320
aggcgcccca ccaccaccca gtttggggac ccagtgggac caggtgcggg ggcagagggt   1380
gacttaccaa gagccaggga gggcagccca ggcccaagtg acagcaagaa caagaaccac   1440
tgccggcgtg cacagacttg tgtgtgtgtcc ttccctgggg ggacggggga ctcacatgtg   1500
cctgccactg gagcctctca accgtccagc agaacacggg gttcagaaag gctccttct    1560
gctatttagc gaacactgag catttaattt acaaatgttt gctagggtca ccctctcggc   1620
catcccagga gggtcgccat gatcacccca actctagagg ccgcagcaga gctcaggaca   1680
ttccccccaca gagcttgccc ctcagttcct acctccaagg gggagggtcc tggaagcgcc   1740
cacccaggcg ccgcccctgt gcttgctccc cgagctcagg gattgccgag tccacgtaac   1800
tgacctgtac tccacgaggc cctgtgggaa cggtccaggc tggtcctgcc ctgtggaggc   1860
ctccgtgcac tgagagatgt actaggattg cagcaaaggt ggtcagggtg atgggccgca   1920
cagcgaggca gtcaaggcca gctccctggg agaagcactg ggtcaggtga ggtctgagga   1980
cagcaggcct tccctagggg aaggagctgg gagtgccaag gccccaggtg cacaggaggc   2040
gtggctgctg agaggctgca gggtggaggg gcctcggcct cagagtcatg tgccctgtga   2100
ccactgaagg gtgtcagcag agcacacggc atgaggacag agggaggggc acgggagtg    2160
aaggaggggg ccctgggcg aggctcgggg gtcaggagct cagcgtccgc tactcagccc   2220
agccaaaacc ctcccagacg tctcctctcc tgcctgggca aagtccagct ggcaccccg    2280
tctgggggcct gcctgtggtc agggccaagt gttccctcct ccaggaaagc ctttaccctc   2340
ctcatgccct gtagtcagga ggccgcctgc tgtaaccctc cgtgtcgcct cgggtgcgaa   2400
atcagaccca cctgacacca tcacgcggag gcccagcagc acctgcaccc acttccagct   2460
gctctggcca aaatctccgc tcggccaggc cccgtggctc acacctgtaa tcctagcaca   2520
ttgggaggcc aaggcaggca catcacctga gttcaggagt tcaagaccag cctgccaac    2580
atggtgaaat cccgtctcta ctaaaaacag aaaattatcc gggcgtggtg gcacatgact   2640
gtaatcccag ctactcagga ggctgaggca ggaggatcac ttgaacctgg gaggcggagg   2700
ttgcagtgag ctgagattgc gccattgcac tccagcctgg gcaacaagag caaaattctg   2760
cctcaaaaaa aaaaatagta ataatacaaa aattagctgg gcgtggtggc acatgccagt   2820
aattccatct actcggagg ctgaggcagg agaatcgtca agcccggga ggtggaggtt    2880
gcagtgagcc cagatggcgc tgctgcactc aagcttggat gacagagcaa gactccgttt   2940
caaaaaaaaa aaacctcctc tcttccttca caccttcctc tgaatcccac ccggtcccac   3000
ctcctgaacc tatccagaca ccttctcctg acccaggcac cacctgcttt cggggcgatg   3060
gccgtagcct cctcccaggc acctgtctgc atccctctgg ccagtgcatg ctgagcacgt   3120
gacctacccg tgttgggaca cgtgaggata cagccttgac cccaggggc tgacattcta    3180
gggggagata gaaggagaca aacgtagaag gtagaataag tgggtggtgg agtggcaggg   3240
agtgctgagt gccacaggaa gtcagacaag gaagggagagt gtgggcagg tgccgtttaa    3300
atggggggcg ctgggtctc ctcacagttg cttctcagct cagctgtgcc aggatcttgt    3360
tgagtcaggt cagctgccca cagccctctt gcctgacccc tgaagcccag aactctgatc   3420
ttcacagccc taggtatggc cccagcaccc cactgccctc tcctctgccc cagccgactg   3480
ctgttcccag acttccctgg ccacgctcca agacgccagc tctgccgcgg gcactttgtt   3540
ctcacggtgt cctccatgcc tgcagggccc atgcatggga agttcgcttg cggcctggg    3600
tgttggcggt tccgtgcctg ctccaactct ccgtgaggcc cctctcccag agcctgacac   3660
actctgtggc cgaactctag gcaggtgccc ctgagtcctt tcctcgacga ggcctgaccc   3720
catccccatc ctcgctgggc ccgccgaccc cggtgttagc aagaatcctc taaatcagtt   3780
tatgagaat tacccacccct cgatatctga tccattcct catctcccac ccttgatctc    3840
atcaccctgc cggcctcctg caagatcctc attgagccac tccagtgaga tcccccctac   3900
cctcgaaggc cgccctaaca acttcccatc cgctgacccc tccaacgcca tcaatctcca   3960
gctgtggttg ttgaactcgg aggtgagctc ctctcaccac tctcttgaat aaagctttc    4020
tcaccatttt aaaaaaaaaa aaaaa                                          4045

SEQ ID NO: 34     moltype = AA  length = 148
FEATURE           Location/Qualifiers
source            1..148
                  mol_type = protein
                  organism = Homo sapiens
SEQUENCE: 34
MARIPTAALG CISLLCLQLP GSLSRSLGGD PRPVKPREPP ARSPSSSLQP RHPAPRPVVW    60
KLHRALQAQR GAGLAPVMGQ PLRDGGRQHS GPRRHSGPRR TQAQLLRVGC VLGTCQVQNL  120
```

SHRLWQLMGP AGRQDSAPVD PSSPHSYG                                                148

SEQ ID NO: 35           moltype = DNA   length = 3406
FEATURE                 Location/Qualifiers
source                  1..3406
                        mol_type = genomic DNA
                        organism = Homo sapiens
SEQUENCE: 35
aggcgggcgg agcgaggggt ggaggggcgc gcgcgaacgg gcgggcgagc aagcgagcgg    60
cgtctccacc agcatctgcc gcggccgcct ttgcccgaag cccgggggacg aaccgacgga   120
ccgaccgcct ggcgcacgga cgcgggcgct cgctttgtgt tcggggctag cgtcggcgag   180
gcttgagctt gcagcgcgcg gcttccctgc tttctcgcgg ccaccccggc tccgccggcc   240
tcggcgcgcg aggggctgga ggtgcgggag ccgctctccg ccggtcggtc cccgcgcggc   300
tgagcccagg ccgccagcgc cgcggccccg tgcggtgtcc ctgagctcct gctccccgcc   360
gggctgctcc gagcaacggt gcttcggagc tccaaactcg ggctgccggg gcaagtgtct   420
tcatgaaccc agaggatgtc cgggaagcac tacaagggtc ctgaagtcag ttgttgcatc   480
aaatacttca tatttggctt caatgtcata ttttggtttt tgggaataac atttcttgga   540
attggactgt gggcatggaa tgaaaaagga gttctgtcca acatctcttc catcaccgat   600
ctcggcggct ttgacccagt ttggctcttc cttgtggtgg gaggagtgat gttcattttg   660
ggatttgcag ggtgcattgg agcgctacgg gaaaacactt tccttctcaa gtttttttct   720
gtgttcctgg gaattatttt cttcctggag ctcactgccg gagttctagc atttgttttc   780
aaagactgga tcaaagacca gctgtatttc tttataaaca acaacatcag agcatatgtg   840
gatgacattg atttgcaaaa cctcatagac ttcacccagg aatattggca gtgctgtggg   900
gcttttggag ctgatgattg gaacctaaat atttacttca attgcacaga ttccaatgca   960
agtcgagagc gatgtggcgt tccattctcc tgctgcacta agatcccgc agaagatgtc  1020
atcaacactc agtgtggcta tgatgccagg caaaaaccag agttgacca gcagattgta  1080
atctacacga aaggctgtgt gccccagttt gagaagtggt tgcaggacaa tttaaccatc  1140
gttgctggta ttttcatagg cattgcattg ctgcagatat ttgggatatg cctgcccag   1200
aatttggtta gcgatatcga agctgtcagg gcgagctggt agaccccctg caaccgctgc  1260
tgcagacacc tggacagacc cagctttcgg gaccctccg cgtgccgaac tgatcttcga  1320
gctgcatgga cctaatcaca gatgcagcct gcagtcccgc ctaatggagc tgccattagg  1380
ggagtgtaaa actgggaaat gctgctcact gacagaatta aaaaaaaaaa taaccagtat  1440
gaaagtcgtt gcgccgtgaa tctctactgt agccatgaat ttatgacag ttagatgctt   1500
accaaaaaag aaaaaaaggg agggtagggg acccagatgt acttgaatgt gcagaaaata  1560
cattcttgtc ctcatcttcc gtaattggag ggctgggaga ggcagctttg ctcttcacca  1620
caccttggac ggaccaccett cttctctgttc catggcctga aggagtgcat ctcctcaaag  1680
actcagcccc tcacctggga gggcagtggt tgtgggcat ccctccatgt acattttagg   1740
aaacacttgc aactctcatc tgaagaagaa aacaactcat ctttgggttc agattttgtg  1800
atggtattca gcaagtcact tgggcgagca cacttggtct atcctggaaa gtctccttga  1860
aagagaagtt gtgtatttca tgtgcaccga gcaagggcat tggaagacgt catgaggctg  1920
tattttagca ggactgatcg tttttctaag tagacctgag ctttgtttat cagtgaaatt  1980
caaggagaaa atgaggttaa tgaagaggta tcagttaaat atcccctttct tctcaccctg  2040
ccaaaattag cagttggatt tttgaaaact ctggaatatt ctgggtcatt ttgttttgta  2100
tgtttgttgt ttttcgtctt ccaaaggtga aagctatgat acagttccac ttaaatttta  2160
gtgtttctt actcagctca agcattaatt tttgattaag tcttaatctg catgaccgtg  2220
gaatctgaat ccatcatctc cctttcctgc cagcttttct acaaacattg aaatatgtta  2280
tttggtcagc acttatttcc taggttcaca gccttgggag gttgtggcat gtcctcccag  2340
tctggctggg aagagaccag ctgtaccatc caaatgcttc cctggtcttg atgatctctt  2400
ccagagtcga tctgagtggc cttttctgca ccctccccttt ctttctcttt gaatggaatt  2460
aaacccaatt tggaaacaac attgacccag tcaaagctt ctaatggtttt ctttttcttc   2520
ctccagtttt agtttgcttt tattaaaaaa agaaaatagt gcatggccat agctccttca  2580
gttctcttat tgcagactaa ccatcaggat ggtatcaaag cacaaatact ttggagggga  2640
atgcgttgaa ctgggcaag tactctgtaa cacaaagtgg gaaacacttt cctggtgctg   2700
ccgctcctgc cccacttta ggtgggaggg acgagttttg ccctctagat tttaatccag   2760
ctggtgtcca ccggatgttg ccctcctggg gagcagatat cagtctgtgg aactctggga  2820
aaaccacagg cacatttttc ggtgcgcagca gatttgccag cacataactg ggcagcagc   2880
tagaatactt tgtggaaatt aagcgaggtt ttccatttca gccccatggt gcatggtggt  2940
ggccgatgaa tgtgtcagtc tgctcagaga aggacaaaa aggaaattat tttcaaaact  3000
gtgttcactg tttgggtgtg tgtatggctc tgcatgtgtg tgttttttgtc tctgtatagg  3060
tagaggtatt cacatcttac tccgactgta aggttgtctt acttcatctc tgccccacc   3120
acagttgcca ttttgtaatg tccttccaac atggagaaga cacgagctct ctccagttgg   3180
catcatttgt cttttttgtt gattgcctca ttctccagtg aactccatct ggccaattga  3240
ttcagaatca ggcaagatcc ctgccctttg gcacatccac tgaaaggcca aacagcaagt  3300
ccgagtgagt tttaaatatt aattaatcac cctttatttt ttacacttga gagtgattgt  3360
aataaaggct gtcattaata aacttggttc taccttaaaa aaaaaa                 3406

SEQ ID NO: 36           moltype = DNA   length = 5882
FEATURE                 Location/Qualifiers
source                  1..5882
                        mol_type = genomic DNA
                        organism = Homo sapiens
SEQUENCE: 36
atcaaatttc aactccaggc agtccttcca gccatgtggg ttcagcggaa agagaagcaa    60
aaccactctt cctaaaatgt tagaagctgc tcttcgctta ccttgggcc tttgcattgg   120
gagctgtttt tcacatcaaa gaatatgtgc tgaatggaat tttagtattt tgctgtcgtt   180
ttaatatttt cgtctggtct tcctcagttc ttccagacgc tttctgagag aatggggca    240
ggagctctag ccatctgtca aagtaaagca gcggttcggc tgaaagaaga catgaaaaag   300
atagtggcag tgccattaaa tgaacagaag gatttttacct atcagaagtt atttggagtc   360
agtctccaag aacttgaacg gcaggggctc accgagaatg gcattccagc agtagtgtgg   420

```
aatatagtgg aatatttgac gcagcatgga cttacccaag aaggtctttt tagggtgaat    480
ggtaacgtga aggtggtgga acaacttcga ctgaagttcg agagtggagt gcccgtggag    540
ctcgggaagg acggtgatgt ctgctcagca gccagtctgt tgaagctgtt tctgagggag    600
ctgcctgaca gtctgatcac ctcagcgttg cagcctcgat tcattcaact ctttcaggat    660
ggcagaagta atgttcagga gagtagctta agagacttaa taaaagagct gccagacacc    720
cactactgcc tcctcaagta cctttgccag ttcttgacaa aagtagccaa gcatcatgtg    780
cagaatcgca tgaatgttca caatctcgcc actgtatttg ggccaaattg ctttcatgtg    840
ccacctgggc ttgaaggcat gaaggaacag gacctgtgca acaagataat ggctaaaatt    900
ctagaaaatt acaatacccct gtttgaagta gagtatacag aaaatgatca tctgagatgt    960
gaaaacctgg ctaggcttat catagtaaaa gaggtctatt ataagaactc cctgcccatc   1020
cttttaacaa gaggcttaga aagagacatg ccaaaaccac ctccaaaaac caagatccca   1080
aaatccagga gtgagggatc tattcaggcc cacagagtac tgcaaccaga gctatctgat   1140
ggcattcctc agctcagctt gcggctaagt tatagaaaag cctgcttgga agacatgaat   1200
tcagcagagg gtgctattag tgccaagttg gtacccagtt cacaggaaga tgaaagacct   1260
ctgtcacctt tctatttgag tgctcatgta ccccaagtca gcaatgtgtc tgcaaccgga   1320
gaactcttag aaagaaccat ccgatcagct gtagaacaac atctttttga tgttaataac   1380
tctggaggtc aaagttcaga ggactcagaa tctggaacaa tatcagcatc ttctgccaca   1440
tctgccagac agcgccgcg ccagtccaag gagcaggatg aagttcgaca tgggaggac   1500
aagggactta tcaacaaaga aaatactcct tctgggttca accaccttga tgattgtatt   1560
ttgaatactc aggaagtcga aaaggtacac aaaaatactt ttggttgtgc tggagaaagg   1620
agcaagccta aacgtcagaa atccagtact aaactttctg agcttcatga caatcaggac   1680
ggtcttgtga atatggaaag tctcaattcc acacgatctc atgagagaac tggacctgat   1740
gattttgaat ggatgtctga tgaaggaaa ggaaatgaaa aagatggtgg acacactcag   1800
cattttgaga gccccacaat gaagatccag gagcatccca gcctatctga caccaaacag   1860
cagagaaatc aagatgccgg tgaccaggag gagagctttg tctccgaagt gccccagtcg   1920
gacctgactg cattgtgtga tgaaaagaac tgggaagagc ctatccctgc tttctcctcc   1980
tggcagcggg agaacagtga ctctgatgaa gcccaccct cgccgcaggc tgggcgcctg   2040
atccgtcagc tgctggacga agacagcgac cccatgctct ctcctcggtt ctacgcttat   2100
gggcagagca ggcaataccct ggatgacaca gaagtgcctc cttccccacc aaactcccat   2160
tctttcatga ggcggcgaag ctcctctctg gggtcctatg atgatgagca aggagacctg   2220
acacctgccc agctcacacg aaggattcag agccttaaaa agaagatccg gaagtttgaa   2280
gatagattcg aagaagagaa gaagtacaga ccttcccaca gtgacaaagc agccaatccg   2340
gaggttctga atggacaaa tgaccttgcc aaattccgga gacaacttaa gaatcaaaa   2400
ctaaagatat ctgaagagaa cctaactccc aggatgcggc agcgaagcaa cacactccc   2460
aagagttttg gttcccaact tgagaaagaa gatgagaaga agcaagagct ggtggataaa   2520
gcaataaagc ccagtgttga agccacattg gaatctattc agaggaagct ccaggagaag   2580
cgagcggaaa gcagccgccc tgaggacatt aaggatatga ccaaagacca gattgctaat   2640
gagaaagtgg ctctgcagaa agctctgtta tattatgaaa gcattcatgg acggccggta   2700
acaaagaacg aacggcaggt gatgaagcca ctatacgaca ggtaccggct ggtcaaacag   2760
atcctctccc gagctaacac catacccatc attggttccc cctccagcaa gcggagaagc   2820
cctttgctgc agcaattat cgagggcgaa actgcttcct tcttcaagga gataaaggaa   2880
gaagaggagg ggtcagaaga cgatagcaat gtgaagccag acttcatggt cactctgaaa   2940
accgatttca gtgcacgatg cttttctggac caattcgaat atgacgctga tggatttatt   3000
tccccaatgg atgataaaat accatcaaaa tgcagccagg acacagggct ttcaaatctc   3060
catgctgcct caatacctga actcctggaa cacctccagg aaatgagaga agaaaagaaa   3120
aggattcgaa agaaacttcg ggattttgaa gacaactttt tcagacagaa tggaagaaat   3180
gtccagaagg aagaccgcac tcctatggct gaagaataca gtgaaatata gcacataag   3240
gcgaaactga ggctcctgga ggtgctcatc agcaagagag acactgattc caagtccatg   3300
tgaggggcat ggccaagcac aggggctggg cagctgcggt gagagtttac tgtccccaga   3360
gaaagtgcag ctctggaagg cagccttggg gctggccctg caaagcatgc agcccttctg   3420
cctctagacc atttggcatc ggctcctgtt tccattgcgt gccttagaaa ctggctggaa   3480
gaagacaatg tgacctgact taggcatttt gtaattggaa agtcaagact gcagtatgtg   3540
cacatgcgca cgcgcatgca cgcacacaca cacacagtag tggagctttc ctaacactag   3600
cagagattaa tcactacatt agacaacact catctacaga gaatatacac tgttcttccc   3660
tggataactg agaaacaaga gaccattctc tgtctaactg tgataaaaac aagctcagga   3720
ctttattcta tagagcaaac ttgctgtgga gggccatgct ctccttggac ccagttaact   3780
gcaaacgtgc attggagccc tatttgctgc cgctgccatt ctagtgacct ttccacagag   3840
ctgcgccttc ctcacgtgtg tgaaaggttt tccccttcag ccctcaggta gatggaagct   3900
gcatctgccc acgatggcag tgcagtcatc atcttcagga tgtttcttca ggacttcctc   3960
agctgacaag gaattttggt ccctgcctag gaccgggtca tctgcagagg acagagagat   4020
ggtaagcagc tgtatgaatg ctgattttaa aaccaggtca tgggagaaga gcctggagat   4080
tctttcctga acactgactg cacttaccag tctgatttta tcgtcaaaca ccaagccagg   4140
ctagcatgct catggcaatc tgtttggggc tgttttgttg tggcactagc caaacataaa   4200
ggggcttaag tcagcctgca tacagaggat cggggagaa aggggcctgt gttctcagcc   4260
tcctgagtac ttaccagagt ttaatttttt taaaaaaat ctgcactaaa atccccaaac   4320
tgacaggtaa atgtagccct cagagctcag cccaaggcag aatctaaatc acactatttt   4380
cgagatcatg tataaaaaga aaaaaagaa gtcatgctgt gtggcaatt ataatttttt   4440
tcaaagactt tgtcacaaaa ctgtctatat tagacatttt ggagggacca ggaaatgtaa   4500
gacaccaaat cctccatctc ttcagtgtgc ctgatgtcac ctcatgattt gctgttactt   4560
ttttaactcc tgcgccaagg acagtggggtt ctgtgtccac cttgtgctt tgcgaggccg   4620
agcccaggca tctgctcgcc tgccacggct gaccagagaa ggtgcttcag gagctctgcc   4680
ttagacgacg tgttacagta tgaacacaca gcagaggcac cctcgtatgt tttgaaagtt   4740
gccttctgaa agggcacagt tttaaggaaa agaaaaagaa tgtaaaacta tactgacccg   4800
ttttcagttt taagggtcg tgagaaactg gctggtccaa tgggatttac agcaacattt   4860
tccattgctg aagtgaggta gcagctctct tctgtcagct gaatgttaag gatgggaaa   4920
aagaatgcct ttaagtttgc tcttaatcgt atggaagctt gagctatgtg ttggaagtgc   4980
cctggtttta atccatacac aaagacggta cataatccta caggtttaaa tgtacataaa   5040
aatatagttt ggaattcttt gctctactgt ttacattgca gattgctata atttcaagga   5100
gtgagattat aaataaaatg atgcacttta ggatgttccc tatttttgaa atctgaacat   5160
```

```
gaatcattca catgaccaaa aattgtgttt ttttaaaaat acatgtctag tctgtccttt    5220
aatagctctc ttaaataagc tatgatatta atcagatcat taccagttag cttttaaagc    5280
acatttgttt aagactatgt ttttggaaaa atacgctaca gaattttttt ttaagctaca    5340
aataaatgag atgctactaa ttgttttgga atctgttgtt tctgccaaag gtaaattaac    5400
taaagattta ttcaggaatc cccatttgaa tttgtatgat tcaataaaag aaaacaccaa    5460
gtaagttata taaaataaat tgtgtatgag atgttgtgtt ttcctttgta atttccacta    5520
actaactaac taacttatat tcttcatgga atggagccca gaagaaatga gaggaagccc    5580
ttttcacact agatcttatt tgaagaaatg tttgttagtc agtcagtcag tggtttctgg    5640
ctctgccgag ggagatgtgt tccccagcaa ccatttctgc agcccagaat ctcaaggcac    5700
tagaggcggt gtcttaatta attggcttca caaagacaaa atgctctgga ctgggatttt    5760
tcctttgctg tgttgggaat atgtgtttat taattagcac atgccaacaa aataaatgtc    5820
aagagttatt tcataagtgt aagtaaactt aagaattaaa gagtgcagac ttataatttt    5880
ca                                                                  5882

SEQ ID NO: 37           moltype = AA   length = 1023
FEATURE                 Location/Qualifiers
source                  1..1023
                        mol_type = protein
                        organism = Homo sapiens
SEQUENCE: 37
MGAGALAICQ SKAAVRLKED MKKIVAVPLN EQKDFTYQKL FGVSLQELER QGLTENGIPA    60
VVWNIVEYLT QHGLTQEGLF RVNGNVKVVE QLRLKFESGV PVELGKDGDV CSAASLLKLF   120
LRELPDSLIT SALQPRFIQL FQDGRNDVQE SSLRDLIKEL PDTHYCLLKY LCQFLTKVAK   180
HHVQNRMNVH NLATVFGPNC FHVPPGLEGM KEQDLCNKIM AKILENYNTL FEVEYTENDH   240
LRCENLARLI IVKEVYYKNS LPILLTRGLE RDMPKPPPKT KIPKSRSEGS IQAHRVLQPE   300
LSDGIPQLSL RLSYRKACLE DMNSAEGAIS AKLVPSSGED ERPLSPFYLS AHVPQVSNVS   360
ATGELLERTI RSAVEQHLFD VNNSGGQSSE DSESGTLSAS SATSARQRRR QSKEQDEVRH   420
GRDKGLINKE NTPSGFNHLD DCILNTQEVE KVHKNTFGCA GERSKPKRQK SSTKLSELHD   480
NQDGLVNMES LNSTRSHERT GPDDFEWMSD ERKGNEKDGG HTQHFESPTM KIQEHPSLSD   540
TKQQRNQDAG DQEESFVSEV PQSDLTALCD EKNWEEPIPA FSSWQRENSD SDEAHLSPQA   600
GRLIRQLLDE DSDPMLSPRF YAYGQSRQYL DDTEVPPSPP NSHSFMRRRS SSLGSYDDEQ   660
EDLTPAQLTR RIQSLKKKIR KFEDRFEEEK KYRPSHSDKA ANPEVLKWTN DLAKFRRQLK   720
ESKLKISEED LTPRMRQRSN TLPKSFGSQL EKEDEKKQEL VDKAIKPSVE ATLESIQRKL   780
QEKRAESSRP EDIKDMTKDQ IANEKVALQK ALLYYESIHG KPVTKNERQV MKPLYDRYRL   840
VKQILSRANT IPIIGSPSSK RRSPLLQPII EGETASFFKE IKEEEEGSED DSNVKPDFMV   900
TLKTDFSARC FLDQFEDDAD GFISPMDDKI PSKCSQDTGL SNLHAASIPE LLEHLQEMRE   960
EKKRIRKKLR DFEDNFFRQN GRNVQKEDRT PMAEEYSEYK HIKAKLRLLE VLISKRDTDS  1020
KSM                                                                1023

SEQ ID NO: 38           moltype = DNA   length = 4988
FEATURE                 Location/Qualifiers
source                  1..4988
                        mol_type = genomic DNA
                        organism = Homo sapiens
SEQUENCE: 38
attgaggagc agaaggagta gggtgcgggg gaggaggagg agcgccttta gtgctgcagc      60
agctgctgct ctgattggcc cggtggttca gctgcttccc tggaacaaaa ggtcaaagtg     120
gactgcagtg taaatgtaga gaagcagccg ataaaatagc attgcctgaa gaagtttgga     180
ggctgagagc agcagtagac tggccaactg cagagcaagt tgtttctcca gccgtgcggt     240
gcagcctcat gcccccaacc cagcttagcc actgtaagaa gacgttcact gtacagacga     300
ccaaacttgc cgtggaagag acagttgtga gattcccttg caaatttaca tacgagaatg     360
gcttgtgaaa tcatgcctct gcaaagtgct catgtacccc aagtcagcaa tgtgtctgca     420
accggagaac tcttagaaag aaccatccga tcagctgtag aacaacatct ttttgatgtt     480
aataactctg gaggtcaaag ttcagaggac tcagaatctg gaacactatc agcatcttct     540
gccacatctg ccagacagcg ccgccgccag tccaaggagc aggatgaagt tcgacatggg     600
agagacaagg gacttatcaa caaagaaaat actccttctg ggttcaacca ccttgatgat     660
tgtatcttga atactcagga agtcgaaaag gtacacaaaa atactttggg ttgtgctgga     720
gaaaggagca agcctaaacg tcagaaatcc agtactaaac tttctgagct tcatgacaat     780
caggacggtc ttgtgaatat ggaaagtctc aattccaacc gatctcatga gagaactgga     840
cctgatgatt ttgaatggat gtctgatgaa aggaaaggaa atgaaaaaga tggtggacac     900
actcagcatt ttgagagccc cacaatgaag atccaggagc atcccagcct atctgacacc     960
aaacagcaga gaaatcaaga tgccggtgac caggaggaga gctttgtctc cgaagtgccc    1020
cagtcggacc tgactgcatt gtgtgatgaa aagaactggg aagagcctat ccctgctttc    1080
tcctcctggc agcgggagaa cagtgactct gatgaagccc acctctcgcc gcaggctggg    1140
cgcctgatcc gtcagctgct ggacgaagac agcgacccca tgctctctcc tcggttctac    1200
gcttatgggc agagcaggca atacctggat gacacagaag tgcctccttc cccaccaaac    1260
tcccattctt tcatgaggcg gcgaagctcc tctctggggt cctatgatga tgagcaagag    1320
gacctgacac ctgcccagct cacacgaagg attcagagcc ttaaaaagaa gatccggaag    1380
tttgaagata gattcgaaga agagaagaag tacagacctt cccacagtga caaagcagcc    1440
aatccggagg ttctgaaatg gacaaatgac cttgccaaat tccggagaca acttaaagaa    1500
tcaaaactaa agatatctga agaggaccta actcccagga tgcggcagcg aagcaacaca    1560
ctccccaaga gttttggttc ccaacttgag aagaagatga gaagaagca agagctggtg    1620
gataaagcaa taaagcccag tgttgaagcc acattggaat ctattcagag gaagctccag    1680
gagaagcgag cggaaagcag ccgccctgag gacattaagg atatgaccaa ggacagcagt    1740
gctaatgaga aagtgcctct gcagaaagct ctgttatatt atgaaagcat tcatggacgg    1800
ccggtaacaa agaacgaacg gcaggtgatg aagccactat acgacaggta ccggctggtc    1860
aaacagatcc tctcccgagc taacaccata cccatcattg gttcccctc cagcaagcgg    1920
agaagcccct tgctgcagcc aattatcgag ggcgaaactg cttcctttt caaggagata    1980
aaggaagaag aggaggggtc agaagacgat agcaatgtga agccagactt catggtcact    2040
```

```
ctgaaaaccg atttcagtgc acgatgcttt ctggaccaat tcgaagatga cgctgatgga    2100
tttatttccc caatggatga taaaatacca tcaaaatgca gccaggacac agggctttca    2160
aatctccatg ctgcctcaat acctgaactc ctggaacacc tccaggaaat gagagaagaa    2220
aagaaaagga ttcgaaagaa acttcgggat tttgaagaca cttttttcag acagaatgga    2280
agaaatgtcc agaaggaaga ccgcactcct atggctgaag aatacagtga atataagcga    2340
ataaaggcga aactgaggct cctggaggtg ctcatcagca agagagacac tgattccaag    2400
tccatgtgag gggcatggcc aagcacaggg ggctggcagc tgcggtgaga gtttactgtc    2460
cccagagaaa gtgcagctct ggaaggcagc cttggggctg gccctgcaaa gcatgcagcc    2520
cttctgcctc tagaccattt ggcatcggct cctgtttcca ttgcctgcct tagaaactgg    2580
ctggaagaag acaatgtgac ctgacttagg cattttgtaa ttggaaagtc aagactgcag    2640
tatgtgcaca tgcgcacgcg catgcacgca cacacacaca cagtagtgga gctttcctaa    2700
cactagcaga gattaatcac tacattagac aacactcatc tacagagaat atacactgtt    2760
cttccctgga taactgagaa acaagagacc attctctgtc taactgtgat aaaaacaagc    2820
tcaggacttt attctataga gcaaactttgc tgtggaggcc catgctctcc ttggacccag    2880
ttaactgcaa acgtgcattg gagcccctatt tgctgccgct gccattctag tgacctttcc    2940
acagagctgc gccttcctca cgtgtgtgaa aggttttccc cttcagccct caggtagatg    3000
gaagctgcat ctgcccacga tggcagtgca gtcatcatct tcaggatgtt tcttcaggac    3060
ttcctcagct gacaaggaat tttgctccct gcctaggacc gggtcatctg cagaggacag    3120
agagatggta agcagctgta tgaatgctga ttttaaaacc aggtcatggg agaagagcct    3180
ggagattctt tcctgaacac tgactgcact taccagtctg attttatcgt caaacaccaa    3240
gccaggctag catgctcatg gcaatctgtt tggggctgtt tgttgtggc actagccaaa    3300
cataaagggg cttaagtcag cctgcataca gaggatcggg agagaaggg gcctgtgttc    3360
tcagcctcct gagtacttac cagagtttaa ttttttttaaa aaaaatctgc actaaaatcc    3420
ccaaactgac aggtaaatgt agccctcaga gctcagccca aggcagaatc taaatcacac    3480
tattttcgag atcatgtata aaagaaaaa aagaagtca tgctgtgtgg ccaattataa    3540
ttttttcaa agactttgtc acaaaactgt ctatattaga cattttggag ggaccaggaa    3600
atgtaagaca ccaaatcctc catctcttca gtgtgcctga tgtcacctca tgatttgctg    3660
ttactttttt aactcctgcg ccaaggacag tgggttctgt gtccacccttt gtgctttgcg    3720
aggccgagcc caggcatctg ctcgcctgcc acggctgacc agagaaggtg cttcaggagc    3780
tctgccttag cacgacgtgtt acagtatgaa cacacagg aggcaccctc gtatgttttc    3840
aaagttgcct tctgcaaaggg cacagttttta aggaaaagaa aaagaatgta aaactatct    3900
gacccgttt cagttttaaa gggtcgtgag aaactggctg gtccaatggg atttacagca    3960
acattttcca ttgctgaagt gaggtagcag ctctcttctg tcagctgaat gttaaggatg    4020
gggaaaaga atgcctttaa gtttgctctt aatcgtatgg aagcttgagc tatgtgttgg    4080
aagtgccctg gttttaatcc atacacaaag acggtacata atcctacagg tttaaatgta    4140
cataaaaata tagtttggaa ttctttgctc tactgtttac attgcagatt gctataattt    4200
caaggagtga gattataaat aaaatgatgc actttaggat gttcctatt tttgaaatct    4260
gaacatgaat cattcacatg accaaaaatt gtgttttttt aaaaatacat gtctagtctg    4320
tcctttaata gctctcttaa ataagctatg atattaatca gatcattacc agttagcttt    4380
taaagcacat ttgtttaaga ctatgttttt ggaaaaatac gctacagaat ttttttttaa    4440
gctacaaata aatgagatgc tactaattgt tttggaatct gttgtttctg ccaaaggtaa    4500
attaactaaa gatttattca ggaatcccca tttgaatttg tatgattcaa taaaagaaaa    4560
caccaagtaa gttatataaa aaaattgtg tatgaagtgt tgtgttttcc tttgtaattt    4620
ccactaacta actaactaac ttatattctt catggaatgg agcccagaag aaatgagagg    4680
aagccctttt cacactagat cttatttgaa gaaatgtttg ttagtcagtc agtcagtggt    4740
ttctggctct gccgagggag atgtgttccc cagcaaccat ttctgcagcc cagaatctca    4800
aggcactaga ggcggtgtct taattaattg gcttcacaaa gacaaaatgc tctggactgg    4860
gattttccct ttgctgtgtt gggaatatgt gtttattaat tagcacatgc caacaaaata    4920
aatgtcaaga gttatttcat aagtgtaagt aaacttaaga attaaagagt gcagacttat    4980
aattttca                                                           4988
```

SEQ ID NO: 39          moltype = AA    length = 683
FEATURE                 Location/Qualifiers
source                  1..683
                         mol_type = protein
                         organism = Homo sapiens
SEQUENCE: 39
```
MACEIMPLQS AHVPQVSNVS ATGELLERTI RSAVEQHLFD VNNSGGQSSE DSESGTLSAS     60
SATSARQRRR QSKEQDEVRH GRDKGLINKE NTPSGFNHLD DCILNTQEVE KVHKNTFGCA    120
GERSKPKRQK SSTKLSELHD NQDGLVNMES LNSTRSHERT GPDDFEWMSD ERKGNEKDGG    180
HTQHFESPTM KIQEHPSLSD TKQQRNQDAG DQEESFVSEV PQSDLTALCD EKNWEEPIPA    240
FSSWQRENSD SDEAHLSPQA GRLIRQLLDE DSDPMLSPRF YAYGQSRQYL DDTEVPPSPP    300
NSHSFMRRRS SSLGSYDDEQ EDLTPAQLTR RIQSLKKKIR KFEDRFEEEK KYRPSHSDKA    360
ANPEVLKWTN DLAKFRRQLK ESKLKISEED LTPRMQRSN TLPKSFGSQL EKEDEKKQEL    420
VDKAIKPSVE ATLESIQRKL QEKRAESSRP EDIKDMTKDQ IANEKVALQK ALLYYESIHG    480
RPVTKNERQV MKPLYDRYRL VKQILSRANT IPIIGSPSSK RRSPLLQPII EGETASFFKE    540
IKEEEGSED DSNVKPDFMV TLKTDFSARC FLDQFEDDAD GFISPMDDKI PSKCSQDTGL    600
SNLHAASIPE LLEHLQEMRE EKKRIRKKLR DFEDNFFRQN GRNVQKEDRT PMAEEYSEYK    660
HIKAKLRLLE VLISKRDTDS KSM                                          683
```

SEQ ID NO: 40          moltype = DNA    length = 4946
FEATURE                 Location/Qualifiers
source                  1..4946
                         mol_type = genomic DNA
                         organism = Homo sapiens
SEQUENCE: 40
```
attgaggagc agaaggagta gggtgcgggg gaggaggagg agcgccttta gtgctgcagc     60
agctgctgct ctgattggcc cggtggttca gctgcttccc tggaacaaaa ggtcaaagtg    120
gactgcagtg taaatgtaga gaagcagccg ataaaatagc attgcctgaa gaagtttgga    180
```

```
ggctgagagc agcagtagac tggccaactg cagagcaagt tgtttctcca gccgtgcggt    240
gcagcctcat gcccccaacc cagcttagcc actgtaagaa gacgttcact gtacagacga    300
ccaaacttgc cgtggaagag acagttgtga gattcccttg caaatttaca tacgagaatg    360
gcttgtgaaa tcatgcctct gcaaagttca caggaagatg aaagacctct gtcacctttc    420
tatttgagtg ctcatgtacc ccaagtcagc aatgtgtctg caaccggaga actcttagaa    480
agaaccatcc gatcagctgt agaacaacat cttttgatg ttaataactc tggaggtcaa     540
agttcagagg actcagaatc tggaacacta tcagcatctt ctgccacatc tgccagacag    600
cgccgccgcc agtccaagga gcaggatgaa gttcgacatg ggagagacaa gggacttatc    660
aacaaagaaa atactccttc tgggttcaac caccttagta ttgtattttt gaatactcaa    720
gaagtcgaaa aggtacacaa aaatactttt ggttgtgctg gagaaaggag caagcctaaa    780
cgtcagaaat ccagtactaa actttctgag cttcatgaca atcaggacgg tcttgtgaat    840
atggaaagtc tcaattccac acgatctcat gagagaactg gacctgatga ttttgaatgg    900
atgtctgatg aaaggaaagg aaatgaaaaa gatggtggac acactcagca ttttgagagc    960
cccacaatga agatccagga gcatcccagc ctatctgaca ccaaacagca gagaaatcaa   1020
gatgccggtg accaggagga gagctttgtc tccgaagtgc cccagtcgga cctgactgca   1080
ttgtgtgatg aaaagaactg ggaagagcct atccctgctt tctcctcctg gcagcgggag   1140
aacagtgact ctgatgaagc ccacctctcg ccgcaggctg ggcgcctgat ccgtcagctg   1200
ctggacgaag acagcgaccc catgctctct cctcggttct acgcttatgg gcagagcagg   1260
caatacctgg atgacacaga agtgcctcct tccccaccaa actcccattc tttcatgagg   1320
cggcgaagct cctctctggg gtcctatgat gatgagcaag aggacctgac acctgcccag   1380
ctcacacgaa ggattcagag ccttaaaaag aagatccgga gtttgaaga tagattcgaa    1440
gaagagaaga agtacagacc ttcccacagt gacaaagcag ccaatccgga ggttctgaaa   1500
tggacaaatg accttgccaa attccggaga caacttaaag aatcaaaact aaagatatct   1560
gaagaggacc taactcccag gatgcggcag cgaagcaaca cactcccaa gagttttggt     1620
tcccaacttg agaagaagaa tgaagaagaa caagagctgg tggataaagc aataaagccc   1680
agtgttgaag ccacattgga atctattcag aggaaagtcc aggaaaagca agcggaaagc   1740
agccgccctg aggacattaa ggatatgacc aaagaccaga ttgctaatga gaaagtggct   1800
ctgcagaaag ctctgttata ttatgaaagc attcatggac ggccggtaac aaagaacgaa   1860
cggcaggtga tgaagccact atacgacagg taccggctgg tcaaacagat cctctcccga   1920
gctaacacca tacccatcat tgaagaagag gaggggtcag aagacgatag caatgtgaag   1980
ccagacttca tggtcactct gaaaaccgat ttcagtgcac gatgctttct ggaccaattc   2040
gaagatgacg ctgatggatt tatttcccca atggatgata aaataccatc aaaatgcagc   2100
caggacacag ggcttttcaaa tctccatgct gcctcaatac ctgaactcct ggaacacctc   2160
caggaaatga gagaagaaaa gaaaaggatt cgaaagaaac ttcgggattt tgaagacaac   2220
tttttcagac agaatggaag aaatgtccag aaggaagacc gcactcctat ggctgaagaa   2280
tacagtgaat ataagcacat aaaggcgaaa ctgaggctcc tggaggtgct catcagcaag   2340
agagacactg attccaagtc catgtgaggg gcatggccaa gcacaggggg ctggcagctg   2400
cggtgagagt ttactgtccc cagagaaagt gcagctctgg aaggcagcct tggggctggc   2460
cctgcaaagc atgcagccct tctgcctcta gaccatttga tcaggctcc tgtttccatt    2520
gcctgcctta gaaactggct ggaagaagac aatgtgacct gacttaggca ttttgtaatt   2580
ggaaagtcaa gactgcagta tgtgcacatg cgcacgcgca tgcacgcaca cacacacaca   2640
gtagtggagc tttcctaaca ctagcagaga ttaatcacta cattagacaa cactcatcta   2700
cagagaatat acactgttct tccctggata actgagaaac aagagaccat tctctgtcta   2760
actgtgataa aaacaagctc aggacttat tctatagagc aaacttgctg tggagggcca    2820
tgctctcctt ggacccagtt aactgcaaac gtgcattgga gccctatttg ctgccgctgc   2880
cattctagtg accttttccac agagctgcgc cttcctcacg tgtgtgaaag gttttcccct   2940
tcagccctca ggtagatgga agctgcatct gcccacgatg gcagtgcagt catcatcttc   3000
aggatgtttc ttcaggactt cctcagctga caaggaattt tggtcccgtc ctaggaccgg   3060
gtcatctgca gaggacagag agatggtaag cagctgtatg aatgctgatt ttaaaaccag   3120
gtcatggag aagagcctgg agattctttc ctgaacactg actgcactta ccagtctgat     3180
tttatcgtca aacaccaagc caggctagca tgctcatgc aatctgtttg gggctgtttt     3240
gttgtggcac tagccaaaca taaagggggct taagtcagcc tgcatacaga ggatcgggga   3300
gagaagggc ctgtgttctc agcctcctga gtacttacca gagtttaatt ttttttaaaa     3360
aaatctgcac taaaatcccc aaactgacag gtaaatgtag ccctcagagc tcagcccaag   3420
gcagaatcta aatcacacta ttttcgagat catgtataaa agaaaaaaaa agaagtcatg   3480
ctgtgtggcc aattataatt ttttcaaag actttgtcac aaaactgtct atattagaca    3540
ttttggaggg accaggaaat gtaagacacc aaatcctcca tctcttcagt gtgcctgatg   3600
tcacctcatg atttgctgtt actttttttaa ctcctgcgcc aaggacagtg ggttctgtgt   3660
ccaccttgt gctttgcgag gccgagccca ggcatctgct cgcctgccac ggctgaccag    3720
agaaggtgct tcaggagctc tgccttagac gacgtgttac agtatgaaca cacagcagag   3780
gcaccctcgt atgttttgaa agttgccttc tgaaagggca cagttttaag gaaaagaaaa   3840
agaatgtaaa actatactga cccgttttca gttttaaagg gtcgtgagaa actggctggt   3900
ccaatgggat ttacagcaac attttccatt gctgaagtga ggtagcagct ctcttctgtc   3960
agctgaattgt taaggatggg gaaaaagaat gcctttaagt ttgctcttaa tcgtatggaa   4020
gcttgagcta tgtgttggaa gtgccctggt tttaatccat acacaaagac ggtacataat   4080
cctacaggtt taaatgtaca taaaaatata gtttggaatt ctttgctcta ctgtttacat   4140
tgcagattgc tataatttca aggagtgaga ttataaataa aatgatgcac tttaggatgt   4200
ttcctatttt tgaaatctga acatgaatca ttcacatgac caaaaattgt gtttttttaa   4260
aaatacatgt ctagtctgtc ctttaatagc tctcttaaat aagctatgat attaatcaga   4320
tcattaccag ttagcttta aagcacattt gtttaagact atgttttgg aaaaatacgc      4380
tacagaattt ttttttaagc tacaaataaa tgagatgcta ctaattgttt tggaatctgt   4440
tgtttctgcc aaaggtaaat taactaaaga tttattcagg aatccccatt tgaatttgta   4500
tgattcaata aaagaaaaca ccaagtaagt tatataaaat aaattgtgta tgagatgttg   4560
tgttttcctt tgtaatttcc actaactaac taactaactt atattcttca tggaatggag   4620
cccagaagaa atgagaggaa gccctttca cactagatct tatttgaaga atgtttgtt     4680
agtcagtcag tcagtggttt ctggctctgc cgagggagag tgttcccca gcaaccattt    4740
ctgcagccca gaatctcaag gcactagagg cggtgtctta attaattggc ttcacaaaga   4800
caaaatgctc tggactggga ttttttcctttt gctgtgttgg gaatatgtgt ttattaatta   4860
gcacatgcca acaaaataaa tgtcaagagt tatttcataa gtgtaagtaa acttaagaat   4920
```

```
taaagagtgc agacttataa ttttca                                              4946

SEQ ID NO: 41           moltype = AA  length = 669
FEATURE                 Location/Qualifiers
source                  1..669
                        mol_type = protein
                        organism = Homo sapiens
SEQUENCE: 41
MACEIMPLQS SQEDERPLSP FYLSAHVPQV SNVSATGELL ERTIRSAVEQ HLFDVNNSGG    60
QSSEDSESGT LSASSATSAR QRRRQSKEQD EVRHGRDKGL INKENTPSGF NHLDDCILNT   120
QEVEKVHKNT FGCAGERSKP KRQKSSTKLS ELHDNQDGLV NMESLNSTRS HERTGPDDFE   180
WMSDERKGNE KDGGHTQHFE SPTMKIQEHP SLSDTKQQRN QDAGDQEESF VSEVPQSDLT   240
ALCDEKNWEE PIPAFSSWQR ENSDSDEAHL SPQAGRLIRQ LLDEDSDPML SPRFYAYGQS   300
RQYLDDTEVP PSPPNSHSFM RRRSSSLGSY DDEQEDLTPA QLTRRIQSLK KKIRKFEDRF   360
EEEKKYRPSH SDKAANPEVL KWTNDLAKFR RQLKESKLKI SEEDLTPRMR QRSNTLPKSF   420
GSQLEKEDEK KQELVDKAIK PSVEATLESI QRKLQEKRAE SSRPEDIKDM TKDQIANEKV   480
ALQKALLYYE SIHGRPVTKN ERQVMKPLYD RYRLVKQILS RANTIPIIEE EEGSEDDSNV   540
KPDFMVTLKT DFSARCFLDQ FEDDADGFIS PMDDKIPSKC SQDTGLSNLH AASIPELLEH   600
LQEMREEKKR IRKKLRDFED NFFRQNGRNV QKEDRTPMAE EYSEYKHIKA KLRLLEVLIS   660
KRDTDSKSM                                                          669

SEQ ID NO: 42           moltype = DNA  length = 4946
FEATURE                 Location/Qualifiers
source                  1..4946
                        mol_type = genomic DNA
                        organism = Homo sapiens
SEQUENCE: 42
attgaggagc agaaggagta gggtgcgggg gaggaggagg agcgccttta gtgctgcagc     60
agctgctgct ctgattggcc cggtggttca gctgcttccc tggaacaaaa ggtcaaagtg    120
gactgcagtg taaatgtaga gaagcagccg ataaaatagc attgcctgaa gaagtttgga   180
ggctgagagc agcagtagac tggccaactg cagagcaagt tgtttctcca gccgtgcggt    240
gcagcctcat gccccaacc cagcttagcc actgtaagaa gacgttcact gtacagacga    300
ccaaacttgc cgtggaagag acagttgtga gattcccttg caaatttaca tacgagaatg    360
gcttgtgtaa tcatgcctct gcaaagactc ttagaaagaa ccatccgatc agctgtgaa    420
caacatcttt ttgatgttaa taactctgga ggtcaaagtt cagaggactc agaatctgga    480
acactatcag catcttctgc cacatctgcc agacagcgcc gccgccagtc caaggagcag    540
gatgaagttc gacatgggag agacaaggga cttatcaaca agaaaaatac tccttctggg    600
ttcaaccacc ttgatgattg tatttttgaat actcaggaag tcgaaaaggt acacaaaaat    660
actttggtt gtgctggaga aaggagcaag cctaaacgtc agaaatccag tactaaactt    720
tctgagcttc atgacaatca ggacggtctt gtgaatatgg aaagtctcaa ttccacacga    780
tctcatgaga gaactggacc tgatgatttt aatggatgt ctgatgaaag gaaggaaat    840
gaaaaagatg gtggacacac tcagcatttt gagagcccca atgaagat ccaggagcat    900
cccagcctat ctgacaccaa acagcagaga aatcaagatg gcgaggagag    960
```

```
gtcatgggag aagagcctgg agattctttc ctgaacactg actgcactta ccagtctgat 3180
tttatcgtca aacaccaagc caggctagca tgctcatggc aatctgtttg gggctgtttt 3240
gttgtggcac tagccaaaca taaaggggct taagtcagcc tgcatacaga ggatcgggga 3300
gagaaggggc ctgtgttctc agcctcctga gtacttacca gagtttaatt ttttttaaaa 3360
aaatctgcac taaaatcccc aaactgacag gtaaatgtag ccctcagagc tcagcccaag 3420
gcagaatcta aatcacacta ttttcgagat catgtataaa aagaaaaaaa agaagtcatg 3480
ctgtgtggcc aattataatt tttttcaaag actttgtcac aaaactgtct atattagaca 3540
ttttggaggg accaggaaat gtaagacacc aaatcctcca tctcttcagt gtgcctgatg 3600
tcacctcatg atttgctgtt actttttttaa ctcctgcgcc aaagacagtg ggttctgtgt 3660
ccacctttgt gctttgcgag gccgagccca ggcatctgct cgcctgccac ggctgaccag 3720
agaaggtgct tcaggagctc tgccttagac gacgtgttac agtatgaaca cacagcagag 3780
gcaccctcgt atgttttgaa agttgccttc tgaaagggca cagttttaag gaaaagaaaa 3840
agaatgtaaa actatactga cccgttttca gttttaaagg gtcgtgagaa actggctggt 3900
ccaatgggat ttacagcaac attttccatt gctgaagtga ggtagcagct ctcttcgtc 3960
agctgaatgt taaggatggg gaaaaagaat gcctttaagt ttgctcttaa tcgtatggaa 4020
gcttgagcta tgtgttggaa gtgccctggt tttaatccat acacaaagac ggtacataat 4080
cctacaggtt taaatgtaca taaaatata gtttggaatt ctttgctcta ctgtttcat 4140
tgcagattgc tataatttca aggagtgaga ttataaataa aatgatgcac tttaggatgt 4200
ttcctatttt tgaaatctga acatgaatca ttcacatgac caaaaattgt gttttttaa 4260
aaatacatgt ctagtctgtc ctttaatagc tctcttaaat aagctatgat attaatcaga 4320
tcattaccag ttagctttta aagcacattt gtttaagact atgttttttgg aaaaatacgc 4380
tacagaattt tttttaagc tacaaataaa tgagatgcta ctaattgttt tggaatctgt 4440
tgtttctgcc aaaggtaaat taactaaaga tttattcagg aatccccatt tgaatttgta 4500
tgattcaata aaagaaaaca ccaagtaagt tatataaaat aaattgtgta tgagatgttg 4560
tgttttcctt tgtaatttcc actaactaac taactaactt atattcttca tggaatggag 4620
cccagaagaa atgagaggaa gcccttttca cactagatct tatttgaaga aatgtttgtt 4680
agtcagtcag tcagtggttt ctggctctgc cgagggagt gtgttcccca gcaaccatt 4740
ctgcagccca gaatcaag gcactagagg cggtgtctta attaattggc ttcacaaaga 4800
caaaatgctc tggactggga tttttccttt gctgtgttgg aatatgtgt ttattaatta 4860
gcacatgcca acaaaataaa tgtcaagagt tatttcataa gtgtaagtaa acttaagaat 4920
taaagagtgc agacttataa ttttca                                     4946

SEQ ID NO: 43           moltype = AA  length = 669
FEATURE                 Location/Qualifiers
source                  1..669
                        mol_type = protein
                        organism = Homo sapiens
SEQUENCE: 43
MACEIMPLQR LLERTIRSAV EQHLFDVNNS GGQSSEDSES GTLSASSATS ARQRRRQSKE  60
QDEVRHGRDK GLINKENTPS GFNHLDDCIL NTQEVEKVHK NTFGCAGERS KPKRQKSSTK 120
LSELHDNQDG LVNMESLNST RSHERTGPDD FEWMSDERKG NEKDGGHTQH FESPTMKIQE 180
HPSLSDTKQQ RNQDAGDQEE SFVSEVPQSD LTALCDEKNW EEPIPAFSSW QRENSDSDEA 240
HLSPQAGRLI RQLLDEDSDP MLSPRFYAYG QSRQYLDDTE VPPSPPNSHS FMRRRSSSLG 300
SYDDEQEDLT PAQLTRRIQS LKKKIRKFED RFEEEKKYRP SHSDKAANPE VLKWTNDLAK 360
FRRQLKESKL KISEEDLTPR MRQRSNTLPK SFGSQLEKED EKKQELVDKA IKPSVEATLE 420
SIQRKLQEKR AESSRPEDIK DMTKDQIANE KVALQKALLY YESIHGRPVT KNERQVMKPL 480
YDRYRLVKQI LSRANTIPII GSPSSKRRSP LLQPIIEGET ASFFKEIKEE EEGSEDDSNV 540
KPDFMVTLKT DFSARCFLDQ FEDDADGFIS PMDDKIPSKC SQDTGLSNLH AASIPELLEH 600
LQEMREEKKR IRKKLRDFED NFFRQNGRNV QKEDRTPMAE EYSEYKHIKA KLRLLEVLIS 660
KRDTDSKSM                                                        669

SEQ ID NO: 44           moltype = DNA  length = 9802
FEATURE                 Location/Qualifiers
source                  1..9802
                        mol_type = genomic DNA
                        organism = Homo sapiens
SEQUENCE: 44
aagaaaccgg ccaggtgtgg cctaggcgcc cagtgccagc ggggaggaga ctcgctccgc   60
cgccgaccaa caccaacacc cagctccgac gcagctcctc tgcgcccttg ccgccctccg  120
agccacagct ttcctcccgc tcctgccccc ggccccgtcgc cgtctccgcg ctcgcagcgg  180
cctcgggagg gcccaggtag cgagcagcga cctcgcgagc cttccgcact cccgcccggt  240
tccccggccg tccgcctatc cttggccccc tccgctttct ccgcgccggc ccgcctcgct  300
tatgcctcgg cgctgagccg ctctcccgat tgcccgccga catgagctgc aacgaggct  360
cccacccgcg gatcaacact ctgggccgca tgatccgcgc cgagtctgcc ccggacctgc  420
gctacgaggt gaccagcggc ggcggggggca ccagcaggat gtactattct cggcgcggcc  480
tgatcaccga ccagaactcg gacggctact gtcaaaccgg cacgatgtcc aggcaccaga  540
accagaacac catccaggag ctgctgcaga actgctccga ctgcttgatg cgagcagagc  600
tcatcgtgca gcctgaattg aagtatgaag atggaataca actgactcgg agtcgagaat  660
tggatgagtg ttttgcccag tgccaatgacc aaatggaaat cctcgacagg ttgatcagag  720
agatgcggca gatgggccag ccctgtgatg cttaccagaa aaggcttctt cagctccaag  780
agcaaatgcg agccctttat aaagccatca gtgtccctcg agtccgcagg ccagctcca  840
agggtggtga aggctacact tgtcagagtg gctctggctg ggatgagttc accaaacatg  900
tcaccagtga atgtttgggg tggatgaggc agcaaaggc ggagatggac atggtggcct  960
gggggtggga cctgggctca gtggagcgac acattaacac ccaccgtgga atccacaact 1020
ccatcggcga ctatcgctgg cagctgacca aatcaaagc cgacctgcgc gagaaatctg 1080
cgatctacca gttggaggag gagtatgaaa acctgctgaa agcgtccttt gagaggatgg 1140
atcacctgcg acagctgcag aacatcattc aggccacgtc cagggagatc atgtggatca 1200
atgactgcga ggaggaggag ctgctgtacg actggaacga caagaacacc aacatcgctc 1260
agaaacagga ggccttctcc atacgcatga gtcaactgga agttaaagaa aaagagctca 1320
```

```
ataagctgaa acaagaaagt gaccaacttg tcctcaatca gcatccagct tcagacaaaa 1380
ttgaggccta tatggacact ctgcagacgc agtggagttg gattcttcag atcaccaagt 1440
gcattgatgt tcatctgaaa gaaaatgctg cctactttca gttttttgaa gaggcgcagt 1500
ctactgaagc ataccgaag gggctccagg actccatcag gaagaagtac ccctgcgaca 1560
agaacatgcc cctgcagcac ctgctggaac agatcaagga gctggagaa gaacgagaga 1620
aaatccttga atacaagcgt caggtgcaga acttggtaaa caagtctaag aagattgtac 1680
agctgaagcc tcgtaaccca gactacagaa gcaataaacc cattattctc agagctctct 1740
gtgactacaa acaagatcag aaaatcgtgc ataaggggga tgagtgtatc ctgaaggaca 1800
acaacgagcg cagcaagtgg tacgtgacgg gcccgggagg cgttgacatg cttgttcct 1860
ctgtgggggct gatcatccct cctccgaacc cactggccgt ggacctctct tgcaagattg 1920
agcagtacta cgaagccatc ttggctctgt ggaaccagct ctacatcaac atgaagagcc 1980
tggtgtcctg gcactactgc atgattgaca tagagaagat caggggccatg acaatcgcca 2040
agctgaaaac aatgcggcag gaagattaca tgaagacgat agccgacctt gagttacatt 2100
accaagagtt catcagaaat agccaaggct cagagatgtt tggagatgat gacaagcaga 2160
aaatacagtc tcagttcacc gatgcccaga agcattacca gaccctggtc attcagctcc 2220
ctggctatcc ccagcaccag acagtgacca caactgaaat cactcatcat ggaacctgcc 2280
aagatgtcaa ccataataaa gtaattgaaa ccaacagaga aaatgacaag caagaaacat 2340
ggatgctgat ggagctgcga aagattcgca ggcagataga gcactgcgag gcaggatga 2400
ctctcaaaaa cctccctcta gcagaccagg gatcttctca ccacatcaca gtgaaaatta 2460
acgagcttaa gagtgtgcag aatgattcac aagcaattgc tgaggttctc aaccagctta 2520
aagatatgct tgccaacttc agaggttctg aaaagtactg ctatttacag aatgaagtat 2580
ttggactatt tcagaaactg gaaaatatca atggtgttac agatggctac ttaaatagct 2640
tatgcacagt aagggcactg ctccaggcta ttctccaaac agaagacatg ttaaaggttt 2700
atgaagccag gctcactgag gaggaaactg tctgcctgga cctggataaa gtggaagctt 2760
accgctgtgg actgaagaaa ataaaaatg acttgaactt gaagaagtcg ttgttggcca 2820
ctatgaagac agaactacag aaagcccagc agatccactc tcagacttca cagcagtatc 2880
cactttatga tctggacttg ggcaagttcg gtgaaaaagt cacacagctg acagaccgct 2940
ggcaaaggat agataaacag atcgacttta ggttatggga cctggagaaa caaatcaagc 3000
aattgaggaa ttatcgtgat aactatcagg ctttctgcaa gtggctctat gatgctaaac 3060
gccgccagga ttccttagaa tccatgaaat ttggagattc caacacagtc atgcggtttt 3120
tgaatgagca gaagaacttg cacagtgaaa tatctggcaa acgagacaaa tcagaggaag 3180
tacaaaaaat tgctgaactt tgcgccaatt caattaagga ttatgagctc cagctggcct 3240
catacacctc aggactggaa actctgctga acatacctat caagaggacc atgattcagt 3300
cccctttctgg ggtgattctg caagaggctg cagatgttca tgctcggtac attgaactac 3360
ttacaagatc tggagactat tacaggttct taagtgagat gctgaagagt ttggaagatc 3420
tgaagctgaa aaaataccaag atcgaagttt tggaagagga gctcagactg gcccgagatg 3480
ccaactcgga aaactgtaat aagaacaaat tcctggatca gaacctgcag aaataccagg 3540
cagagtgttc ccagttcaaa gcgaagcttg cgagcctgga ggagctgaag agacaggctg 3600
agctggatgg gaagtcggct aagcaaaatc tagacaagtc ctacggccaa ataaaagaac 3660
tcaatgagaa gatcacccga ctgacttatg agattgaaga tgaaaagaga agaagaaaat 3720
ctgtggaaga cagatttgac caacagaaga atgactatga ccaactgcag aaagcaaggc 3780
aatgtgaaaa ggagaacctt ggttggcaga aattagagtc tgagaaagcc atcaaggaga 3840
aggagtacga gattgaaagg ttgaggggttc tactgcagga agaaggcacc cggaaggaga 3900
aatatgaaaa tgagctggca aaggtaagaa accactataa tgaggagatg agtaatttaa 3960
ggaacaagta tgaaacagag attaacatta cgaagaccac catcaaggag atatccatgc 4020
aaaaagagga tgattccaaa aatcttagaa accagcttga tagactttca agggaaaatc 4080
gagatctgaa ggatgaaatt gtcaggctca atgacagcat cttgcaggcc actgagcagc 4140
gaaggcgagc tgaagaaaac gcccttcagc aaaaggcctg tggctctgag ataatgcaga 4200
agaagcagca tctggagata gaactgaagc aggtcatgca gcagcgctct gaggacaatg 4260
cccggcacaa gcagtccctg gaggaggctg ccaagaccat tcaggacaaa aataaggaga 4320
tcgagagact caaagctgag tttcaggagg aggccaagcg ccgctgggaa tatgaaaatg 4380
aactgagtaa ggtaagaaac aatttatgatg aggagatcat tagcttaaaa aatcagtttg 4440
agaccgagat caacatcacc aagaccacca tccaccagct caccatgcag aaggaagagg 4500
ataccagtgg ctaccgggct cagatagaca atctcacccg agaaaacagg agcttatctg 4560
aagaaataaa gaggctgaag aacactctaa cccagaccac agagaatctc aggagggtga 4620
aagaagacat ccaacagcaa aaggccactg gctctgaggt gtctcagagg aaacagcagc 4680
tggaggttga gctgagacaa gtcactcaga tgcgaacaga ggagagcgta agatataagc 4740
aatctccttga tgatgctgcc aaaaccatcc aggataaaaa caaggagata gaaaggttaa 4800
aacaactgat cgacaaagaa acaaatgacc ggaaatgcct ggaagatgaa aacgcgagat 4860
tacaaagggt ccagtatgac ctgcagaaag caaacagtag tgcgacggag acaataaaca 4920
aactgaaggt tcaggagcaa gaactgacac gcctgaggat cgactatgaa agggtttccc 4980
aggagaggac tgtgaaggac caggatatca cgcggttcca gaactctctg aaagagctgc 5040
agctgcagaa gcagaaggtg aagaggagc tgaatcggct gaagaggacc gcgtcagaag 5100
actcctgcaa gaggaagaag ctggaggaag agctggaagg catgagggg tcgctgaagg 5160
agcaagccat caaaatcacc aacctgaccc agcagctgga gcaggcatcc attgttaaga 5220
agaggagtga ggatgacctc cggcagcaga gggacgtgct ggatggccac ctgagggaaa 5280
agcagaggac ccaggaagag ctgaggaggc tctcttctga ggtcgaggcc ctgaggcggc 5340
agttactcca ggaacaggaa agtgtcaaac aagctcactt gaggaatgag catttccaga 5400
aggcgataga agataaaagc agaagcttaa atgaaagcaa aatagaaatt gagaggctgc 5460
agtctctcac agagaacctg accaaggagc acttgatgtt agaagaagaa ctgcggaacc 5520
tgaggctgga gtacgatgac ctgagggagag gacgaagcga agcggacagt gataaaaatg 5580
caaccatctt ggaactaagg agccagctgc agatcagcaa caaccggacc ctggaactgc 5640
aggggctgat taatgattta cagagagaga gggaaatttg agacaggaa attgagaaat 5700
tccaaaagca ggctttagag gcatctaata ggattcagga atcaaagaat cagtgtactc 5760
aggtggtaca ggaaagagag agccttctgt tgaaatcaa agtcctggag caagacaagg 5820
caaggctgca gaggctggag gatgagctga atcgtgcaaa atcaactcta gaggcagaaa 5880
ccaggggtgaa acagcgcctg gagtgtgaga acagcaaat tcagaatgac ctgaatcagt 5940
ggaagactca atattcccgc aaggaggagg ctattaggaa gatagaatcg gaaagagaaa 6000
agagtgagag agagaagaac agtcttagga gtgagatcga aagactccaa gcagagatca 6060
```

```
agagaattga agagaggtgc aggcgtaagc tggaggattc taccaggag  acacagtcac   6120
agttagaaac agaacgctcc cgatatcaga gggagattga taaactcaga cagcgcccat   6180
atgggtccca tcgagagacc cagactgagt gtgagtggac cgttgacacc tccaagctgg   6240
tgtttgatgg gctgaggaag aaggtgacag caatgcagct ctatgagtgt cagctgatcg   6300
acaaaacaac cttggacaaa ctattgaagg ggaagaagtc agtggaagaa gttgcttctg   6360
aaatccagcc attccttcgg ggtgcaggat ctatcgctgg agcatctgct tctcctaagg   6420
aaaaatactc tttggtagag gccaagagaa agaaattaat cagcccagaa tccacagtca   6480
tgcttctgga ggcccaggca gctacaggtg gtataattga tccccatcgg aatgagaagc   6540
tgactgtcga cagtgccata gctcgggacc tcattgactt cgatgaccgt cagcagatat   6600
atgcagcaga aaaagctatc actgttttg atgatccatt ttcaggcaag acagtatctg   6660
tttcagaagc catcaagaaa aatttgattg atagagaaac cggaatgcgc ctgctggaag   6720
cccagattgc ttcagggggt gtagtagacc ctgtgaacag tgtcttttg ccaaaagatg   6780
tcgccttggc ccggggggctg attgatagag atttgtatcg atccctgaat gatccccgag   6840
atagtcagaa aaactttgtg gatccagtca ccaaaaagaa ggtcagttac gtgcagctga   6900
aggaacggtg cagaatcgaa ccacatactg gtctgctctt gctttcagta cagaagagaa   6960
gcatgtcctt ccaaggaatc agacaacctg tgaccgtcac tgagctagta gattctggta   7020
tattgagacc gtccactgtc aatgaactgg aatctggtca gatttcttat gacgaggttg   7080
gtgagaat taaggacttc ctccaggggt caagctgcag gcaggcata tacaatgaga   7140
ccacaaaaca gaagcttggc atttatgagg ccatgaaaat tggcttagtc cgacctggta   7200
ctgctctgga gttgctggaa gcccaagcag ctactggctt tatagtggat cctgttagca   7260
acttgaggtt accagtggag gaagcctaca agagaggtct ggtgggcatt gagttcaaag   7320
agaagctcct gtctgcagaa cgagctgtca ctgggtataa tgatcctgaa acaggaaaca   7380
tcatctcttt gttccaagcc atgaataagg aactcatcga aaagggccac ggtattcgct   7440
tattagaagc acagatcgca accgggggga tcattgaccc aaaggagagc catcgtttac   7500
cagttgacat agcatataag aggggctatt tcaatgagga actcagtgag attctctcag   7560
atccaagtga tgataccaaa ggatttttg accccaacac tgaagaaaat cttacctatc   7620
tgcaactaaa agaagatgc attaaggatg aggaaacagg gctctgtctt ctgcctctga   7680
aagaaaagaa gaaacaggtg cagacatcac aaaagaatac cctcaggaag cgtagagtgg   7740
tcatagttga cccagaaacc aataaagaaa tgtctgttca ggaggcctac aagaagggcc   7800
taattgatta tgaaaccttc aaagaactgt gtgagcagga atgtgaatgg gaagaaataa   7860
ccatcacggg atcagatggc tccaccaggg tggtcctggt agatagaaag acaggcagtc   7920
agtatgatat tcaagatgct attgacaagg gccttgttga caggaagttc tttgatcagt   7980
accgatccgg cagcctcagc ctcactcaat ttgctgacat gatctccttg aaaatggtg   8040
tcggcaccag cagcagcatg ggcagtggtg tcagcgatga tgttttttagc agctccgac   8100
atgaatcagt aagtaagatt tccaccatat ccagcgtcag gaattaacc ataaggacga   8160
gctctttttc agacacctg gaagaatcga gccccattgc agccatcttt gacacagaaa   8220
acctggagaa aatctccatt acagaaggta tagagcgggg catcgttgac agcatcacgg   8280
gtcagagggct tctggaggct caggcctgca caggtggcat catccaccca accacgggcc   8340
agaagctgtc acttcaggac gcagtctccc agggtgtgat tgaccaagac atggccacca   8400
ggctgaagcc tgctcagaaa gccttcatag gcttcgaggg tgtgaaggga aagaagaaga   8460
tgtcagcagc agaggcagtg aaagaaaaat ggctcccgta tgaggctggc cagcgcttcc   8520
tggagttcca gtacctcacg ggaggtcttg ttgacccgga agtgcatggg aggataagca   8580
ccgaagaagc catccggaag gggttcatag atggccgcgc cgcacagagg ctgcaagaca   8640
ccagcagcta tgccaaaatc ctgacctgcc ccaaaaccaa attaaaaata tcctataagg   8700
atgccataaa tcgctccatg gtagaagata tcactgggct gcgccttctg gaagccgcct   8760
ccgtgtcgtc caagggctta cccagccctt acaacatgtc ttcggctccg gggtcccgct   8820
ccggctcccg ctcgggatct cgctccggat ctcgctccgg gtcccgcagt gggtcccgga   8880
gaggaagctt tgacgccaca gggaattctt cctactctta ttcctactca tttagcagta   8940
gttctattgg gcactagtag tcagttggga gtggttgcta tacctgact tcatttatat   9000
gaatttccac tttattaaat aatagaaaag aaaatcccgg tgcttgcagt agagtgatag   9060
gacattctat gcttacagaa aatatagcca tgattgataa caaatagtaa aggctgttct   9120
ggcttttat cttcttagct catcttaaat aagcagtaca cttggatgca gtgcgtctga   9180
agtgctaatc agttgtaaca atagcacaaa tcgaacttag gatttgtttc ttctcttctg   9240
tgtttcgatt tttgatcaat tctttaattt tggaagccta taatacagtt ttctattctt   9300
ggagataaaa attaaatgga tcactgatat tttagtcatt ctgcttctca tctaaatatt   9360
tccatattct gtattaggag aaaattaccc tcccagcacc agcccccctc tcaaaccccc   9420
aacccaaaac caagcatttt ggaatgagtc tcctttagtt tcagagtgtg gattgtataa   9480
cccatatact cttcgatgta cttgtttggt ttggtattaa tttgactgtg catgacagcg   9540
gcaatctttt ctttggtcaa agttttctgt ttatttgct tgtcatattc gatgtactt   9600
aaggtgtctt tatgaagttt gctattctgg caataaact ttagacttt gaagtgttttg   9660
tgttttaatt taatatgttt ataagcatgt ataacatttt agcatatttt tatcataggt   9720
ctaaaaatat ttgtttacta aatacctgtg aagaaatacc attaaaaaac tatttggttc   9780
tgaattctta ctagaaaaaa aa                                          9802

SEQ ID NO: 45         moltype = AA  length = 2871
FEATURE               Location/Qualifiers
source                1..2871
                      mol_type = protein
                      organism = Homo sapiens
SEQUENCE: 45
MSCNGGSHPR INTLGRMIRA ESGPDLRYEV TSGGGGTSRM YYSRRGVITD QNSDGYCQTG    60
TMSRHQNQNT IQELLQNCSD CLMRAELIVQ PELKYGDGIQ LTRSRELDEC FAQANDQMEI   120
LDSLIREMRQ MGQPCDAYQK RLLQLQEQMR ALYKAISVPR VRRASSKGGG GYTCQSGSGW   180
DEFTKHVTSE CLGWMRQQRA EMDMVAWGVD LASVEQHINS HRGIHNSIGD YRWQLDKIKA   240
DLREKSAIYQ LEEEYENLLK ASFERMDHLR QLQNIIQATS REIMWINDCE EEELLYDWSD   300
KNTNIAQKQE AFSIRMSQLE VKEKELNKLK QESDQLVLNQ HPASDKIEAY MDTLQTQWSW   360
ILQITKCIDV HLKENAAYFQ FFEEAQSTEA YLKGLQDSIR KKYPCDKNMP LQHLLEQIKE   420
LEKEREKILE YKRQVQNLVN KSKKIVQLKP RNPDYRSNKP IILRALCDYK QDQKIVHKGD   480
ECILKDNNER SKWYVTGPGG VDMLVPSVGL IIPPPNPLAV DLSCKIEQYY EAILALWNQL   540
```

```
YINMKSLVSW HYCMIDIEKI RAMTIAKLKT MRQEDYMKTI ADLELHYQEF IRNSQGSEMF    600
GDDDKRKIQS QFTDAQKHYQ TLVIQLPGYP QHQTVTTTEI THHGTCQDVN HNKVIETNRE    660
NDKQETWMLM ELQKIRRQIE HCEGRMTLKN LPLADQGSSH HITVKINELK SVQNDSQAIA    720
EVLNQLKDML ANFRGSEKYC YLQNEVFGLF QKLENINGVT DGYLNSLCTV RALLQAILQT    780
EDMLKVYEAR LTEEETVCLD LDKVEAYRCG LKKIKNDLNL KKSLLATMKT ELQKAQQIHS    840
QTSQQYPLYD LDLGKFGEKV TQLTDRWQRI DKQIDFRLWD LEKQIKQLRN YRDNYQAFCK    900
WLYDAKRRQD SLESMKFGDS NTVMRFLNEQ KNLHSEISGK RDKSEEVQKI AELCANSIKD    960
YELQLASYTS GLETLLNIPI KRTMIQSPSG VILQEAADVH ARYIELLTRS GDYYRFLSEM   1020
LKSLEDLKLK NTKIEVLEEE LRLARDANSE NCNKNKFLDQ NLQKYQAECS QFKAKLASLE   1080
ELKRQAELDG KSAKQNLDKC YGQIKELNEK ITRLTYEIED EKRRRKSVED RFDQQKNDYD   1140
QLQKARQCEK ENLGWQKLES EKAIKEKEYE IERLRVLLQE EGTRKREYEN ELAKVRNHYN   1200
EEMSNLRNKY ETEINITKTT IKEISMQKED DSKNLRNQLD RLSRENRDLK DEIVRLNDSI   1260
LQATEQRRRA EENALQQKAC GSEIMQKKQH LEIELKQVMQ QRSEDNARHK QSLEEAAKTI   1320
QDKNKEIERL KAEFQEEAKR RWEYENELSK VRNNYDEEII SLKNQFETEI NITKTTIHQL   1380
TMQKEEDTSG YRAQIDNLTR ENRSLSEEIK RLKNTLTQTT ENLRRVEEDI QQQKATGSEV   1440
SQRKQQLEVE LRQVTQMRTE ESVRYKQSLD DAAKTIQDKN KEIERLKQLI DKETNDRKCL   1500
EDENARLQRV QYDLQKANSS ATETINKLKV QEQELTRLRI DYERVSQERT VKDQDITRFQ   1560
NSLKELQLQK QKVEEELNRL KRTASEDSCK RKKLEEELEG MRRSLKEQAI KITNLTQQLE   1620
QASIVKKRSE DDLRQQRDVL DGHLREKQRT QEELRRLSSE VEALRRQLLQ EQESVKQAHL   1680
RNEHFQKAIE DKSRSLNESK IEIERLQSLT ENLTKEHLML EEELRNLRLE YDDLRRGRSE   1740
ADSDKNATIL ELRSQLQISN NRTLELQGLI NDLREREENL RQEIEKFKQQ ALEASNRIQE   1800
SKNQCTQVVQ ERESLLVKIK VLEQDKARLQ RLEDELNRAK STLEAETRVK QRLECEKQQI   1860
QNDLNQWKTQ YSRKEEAIRK IESEREKSER EKNSLRSEIE RLQAEIKRIE ERCRRKLEDS   1920
TRETQSQLET ERSRYQREID KLRQRPYGSH RETQTECEWT VDTSKLVFDG LRKKVTAMQL   1980
YECQLIDKTT LDKLLGKKS VEEVASEIQP FLRGAGSIAG ASASPKEKYS LVEAKRKKLI   2040
SPESTVMLLE AQAATGGIID PHRNEKLTVD SAIARDLIDF DDRQQIYAAE KAITGFDDPF   2100
SGKTVSVSEA IKKNLIDRET GMRLLEAQIA SGGVVDPVNS VFLPKDVALA RGLIDRDLYR   2160
SLNDPRDSQK NFVDPVTKKK VSYVQLKERC RIEPHTGLLL LSVQKRSMSF QGIRQPVTVT   2220
ELVDSGILRP STVNELESGQ ISYDEVGERI KDFLQGSSCI AGIYNETTKQ KLGIYEAMKI   2280
GLVRPGTALE LLEAQAATGF IVDPVSNLRL PVEEAYKRGL VGIEFKEKLL SAERAVTGYN   2340
DPETGNIISL FQAMNKELIE KGHGIRLLEA QIATGGIIDP KESHRLPVDI AYKRGYFNEE   2400
LSEILSDPSD DTKGFFDPNT EENLTYLQLK ERCIKDEETG LCLLPLKEKK KQVQTSQKNT   2460
LRKRRVVIVD PETNKEMSVQ EAYKKGLIDY ETFKELCEQE CEWEEITITG SDGSTRVVLV   2520
DRKTGSQYDI QDAIDKGLVD RKFFDQYRSG SLSLTQFADM ISLKNGVGTS SSMGSGVSDD   2580
VFSSSRHESV SKISTISSVR NLTIRSSSFS DTLEESSPIA AIFDTENLEK ISITEGIERG   2640
IVDSITGQRL LEAQACTGGI IHPTTGQKLS LQDAVSQGVI DQDMATRLKP AQKAFIGFEG   2700
VKGKKKMSAA EAVKEKWLPY EAGQRFLEFQ YLTGGLVDPE VHGRISTEEA IRKGFIDGRA   2760
AQRLQDTSSY AKILTCPKTK LKISYKDAIN RSMVEDITGL RLLEAASVSS KGLPSPYNMS   2820
SAPGSRSGSR SGSRSGSRSG SRSGSRRGSF DATGNSSYSY SYSFSSSSIG H            2871

SEQ ID NO: 46        moltype = DNA   length = 8473
FEATURE              Location/Qualifiers
source               1..8473
                     mol_type = genomic DNA
                     organism = Homo sapiens
SEQUENCE: 46
aagaaaccgg ccaggtgtgg cctaggcgcc cagtgccagc ggggaggaga ctcgctccgc     60
cgccgaccaa caccaacacc cagctccgac gcagctcctc tgcgcccttg ccgccctccg    120
agccacagct ttcctcccgc tcctgccccc ggcccgtcgc cgtctccgcg ctcgcagcgg    180
cctcgggagg gcccaggtag cgagcagcga cctcgcgagc cttccgcact cccgccggtt    240
tccccgccg tccgcctatc cttggccccc tccgcttttct ccgcgccggc ccgcctccgt    300
tatgcctcgg cgctgagccg ctctcccgat tgcccgccga catgagctgc aacggaggct    360
cccacccgcg gatcaacact ctgggccgca tgatccgcgc cgagtctggc ccggacctgc    420
gctacgaggt gaccagcggc ggcggggca ccagcaggat gtactattct cggcgcggcg    480
tgatcaccga ccgaactcg gacggctact gtcaaaccgc gacgatgtcc aggcaccaga    540
accagaacac catccaggag ctgctgcaga actgctccga ctgcttgatg cgagcagagc    600
tcatcgtgca gcctgaattg aagtatgag atggaataca actgactcgg agtcgagaat    660
tggatgagtg ttttgcccag gccaatgacc aaatggaaat cctcgacagc ttgatcagag    720
agatgcggca gatgggccag ccctgtgatg cttaccagaa aaggcttctt cagctccaag    780
agcaaatgcg agcccttttat aaagccatca gtgtccctcg agtccgcagg gccagctcca    840
agggtggtgg aggctacact tgtcagagtg gctctggctg ggatgagttc accaaacatg    900
tcaccagtga atgtttgggg tggatgaggc agcaaagggc ggagatggac atggtggcct    960
ggggtgtgga cctggcctca gtggagcagc acattaacag ccaccgggc atccacaact   1020
ccatcggcga ctatcaggct cagctggaca aaatcaaagc cgacctggac gagaaatctg   1080
cgatctacca gttggaggag gagtatgaaa acctgctgaa agcgtccttt gagaggatgg   1140
atcacctgcg acagctgcag aacatcattc aggccacgtc cagggagatc atgtggatca   1200
atgactgcga ggaggaggag ctgctgtacg actggagcga caagaacacc aacatcgctc   1260
agaaacagga ggccttctcc atacgcatga gtcaactgga agttaaagaa aaagagctca   1320
ataagctgaa acaagaaagt gaccaacttg tcctcaatca gcatccagct tcagacaaaa   1380
ttgaggccta tatggacact ctgcagacgc agtggagttg gattcttcag atcaccaagt   1440
gcattgatgt tcatctgaaa gaaaatgctg cctactttca gttttttgaa gaggcgcagt   1500
ctactgaagc atacctgaag gggctccagg actccatcag gaagaagtac ccctgcgaca   1560
agaacatgcc cctgcagcac ctgctggaac agatcaagga gctggagaaa gaacgagaga   1620
aatcctga atacaagcgt caggtcaga acttggtaaa caagtctaag agaagttac   1680
agctgaagcc tcgtaaccca gactacagaa gcaataaacc cattattctc agagctctct   1740
gtgactacaa acaagatcag aaaatcgtgc ataagggga tgagtgtatc ctgaaggaca   1800
acaacgagcg cagcaagtgg tacgtgacgg gcccgggagg cgttgacatg cttgttcct   1860
ctgtggggct gatcatccct cctccgaacc cactggccgt ggacctctct tgcaagattg   1920
agcagtacta cgaagccatc ttggctctgt ggaaccagct ctacatcaac atgaagagcc   1980
```

```
tggtgtcctg gcactactgc atgattgaca tagagaagat cagggccatg acaatcgcca    2040
agctgaaaac aatgcggcag gaagattaca tgaagacgat agccgacctt gagttacatt    2100
accaagagtt catcagaaat agccaaggct cagagatgtt tggagatgat gacaagcgga    2160
aaatacagtc tcagttcacc gatgcccaga agcattacca gaccctggtc attcagctcc    2220
ctggctatcc ccagcaccag acagtgacca caactgaact cactcatcat ggaacctgcc    2280
aagatgtcaa ccataataaa gtaattgaaa ccaacagaga aaatgacaag caagaaacat    2340
ggatgctgat ggagctgcag aagattcgca ggcagataga gcactgcgag ggcaggatga    2400
ctctcaaaaa cctccctcta gcagaccagg gatcttctca ccacatcaca gtgaaaatta    2460
acgagcttaa gagtgtgcag aatgattcac aagcaattgc tgaggttctc aaccagctta    2520
aagatatgct tgccaacttc agaggttctg aaaagtactg ctatttacag aatgaagtat    2580
ttggactatt tcagaaactg gaaaatatca atggtgttac agatggctac ttaaatagct    2640
tatgcacagt aagggcactg ctccaggcta ttctccaaac agaagacatg ttaaaggttt    2700
atgaagccag gctcactgag gaggaaactg tctgcctgga cctggataaa gtggaagctt    2760
accgctgtgg actgaagaaa ataaaaaatg acttgaactt gaagaagtcg ttgttggcca    2820
ctatgaagac agaactacag aaagcccagc agatccactc tcagacttca cagcagtatc    2880
cactttatga tctggacttg ggcaagttcg gtgaaaaagt cacacagctg acagaccgct    2940
ggcaaaggat agataaacag atcgacttta ggttatggga cctggagaaa caaatcaagc    3000
aattgaggaa ttatcgtgat aactatcagg cttctctgca gtggctctat gatgctaaac    3060
gccgccagga ttccttagaa tccatgaaat ttggagattc caacacagtc atgcggtttt    3120
tgaatgagca gaagaacttg cacagtgaaa tatctggcaa acgagacaaa tcagaggaag    3180
tacaaaaaat tgctgaactt tgcgccaatt caattaagga ttatgagctc cagctggcct    3240
catacaccct aggactggaa actctgctga acataccatt caaggagacc atgattcagt    3300
cccttctgg ggtgattctg caagaggctg cagatgttca tgctcggtac attgaactac    3360
ttacaagatc tggagactat tacaggttct taagtgagat gctgaagagt ttggaagatc    3420
tgaagctgaa aaataccaag atcgaagttt tggaaggga gctcagactg gcccgagatg    3480
ccaactcgga aaactgtaat aagaacaaat tcctggatca gaacctgcag aaataccagg    3540
cagagtgttc ccagttcaaa gcgaagcttg cgagcctgga ggagctgaag agacaggctg    3600
agctggatgg gaagtcggct aagcaaaatc tagacaagtg ctacgccaa ataaaagaac    3660
tcaatgagaa gatcacccga ctgacttatg agattgaaga tgaaaagaga agaagaaaat    3720
ctgtgtgaaca cagatttgac caacagaaga atgactatga ccaactgcag aaagcaaggc    3780
aatgtgaaaa ggagaaccctt ggttggcaga aattagagtc tgagaaagcc atcaaggaga    3840
aggagtacga gattgaaagg ttgagggttc tactgcagga agaaggcacc cggaagagag    3900
aatatgaaaa tgagctggca aaggtaagaa accactataa tgaggagatg agtaatttaa    3960
ggaacaagta tgaaacagag attaacatta cgaagaccac catcaaggag atatccatgc    4020
aaaaagagga tgattccaaa aatcttagaa accagcttga tagactttca agggaaaatc    4080
gagatctgaa ggatgaaatt gtcaggctca atgacagcat cttgcaggcc actgagcagc    4140
gaaggcgagc tgaagaaaac gcccttcagc aaaaggcctg tggctctgag ataatgcaga    4200
agaagcagca tctggagata gaactgaagc aggtcatgca gcagcgctct gaggacaatg    4260
cccggacaca gcagtccctg gaggaggctg ccaagaccat tcaggacaaa aataaggaga    4320
tcgagagact caaagctgag tttcaggagg aggccaagcg ccgctgggaa tatgaaaatg    4380
aactgagtaa ggcatctaat aggattcagg aatcaaagaa tcagtgtact caggtggtac    4440
aggaaagaga gagccttctg gtgaaaatca aagtcctgga gcaagacaag gcaaggctgc    4500
agaggctgga ggatgagctg aatcgtgcaa aatcaactct agaggcagaa accagggtga    4560
aacagcgcct ggagtgtgag aaacagcaaa ttcagaatga cctgaatcag tggaagactc    4620
aatattcccg caaggaggag gctattagga agatagaatc ggaaagaaa aagagtgaga    4680
gagagaagaa cagtcttagg agtgagatcg aaagactcca agcagagatc aagagaattg    4740
aagagaggtg caggcgtaag ctggaggatt ctaccaggga gacacagtca cagttagaaa    4800
cagaacgctc ccgatatcag agggagattg ataaactcag acagcgccca tatgggtccc    4860
atcgagagac ccagactgag tgtgagtgga ccgttgacac ctccaagctg gtgtttgatg    4920
ggctgaggaa gaaggtgaca gcaatgcagc tctatgagtg tcagctgatc gacaaaacaa    4980
ccttgacaa actattgaag gggaagaagt cagtggaaga agttgcttct gaaatccagc    5040
cattccttcg gggtgcagga tctatccgctg gagcatctgc ttctcctaag gaaaaatact    5100
ctttggtaga ggccaagaga aagaaattaa tcagcccaga atccacagtc atgcttctgg    5160
aggcccaggc agctacaggt ggtataattg atccccatcg gaatgagaag ctgactgtcg    5220
acagtgccat agctcgggac ctcattgact tcgatgaccg tcagcagata tatgcagcag    5280
aaaaagctat cactggtttt tgatgatccat ttttcaggcaa gacagtatct gtttcagaag    5340
ccatcaagaa aaattgatt gatagagaaa ccggaatgcg cctgctggaa gcccagattg    5400
cttcaggggg tgtagtagac cctgtgaaca gtgtctttt tgccaaagat gtcgccttgg    5460
cccggggct gattgataga gatttgtatc gatccctgaa tgatcccga tgatcgtcaga gatagtcgga    5520
aaaactttgt ggatccagtc accaaaaaga aggtcagtta cgtgcagctg aaggaacggt    5580
gcagaatcga accacatact ggtctgctct tgctttcagt acagaagaga agcatgtcct    5640
tccaaggaat cagacaacct gtgaccgtca ctgagctagt agattctggt atattgagac    5700
cgtccactgt caatgaactg gaatctggtc agatttctta tgacgaggtt ggtgagagaa    5760
ttaaggactt cctccagggt tcaagctgca tagcagcat atacaatgag accacaaaac    5820
agaagcttgg catttatgag gccatgaaaa ttggcttagt ccgacctggt actgctctgg    5880
agttgctgga agcccaagca gctactggct ttatagtgga tcctgttagc aacttgaggt    5940
taccagtgga ggaagcctac aagagaggtc tggtgggcat tgagttcaaa gagaagctcc    6000
tgtctgcaga acgagctgtc actgggtata atgatcctga aacaggaaac atcatctctt    6060
tgttccaagc catgaataag gaactcatgg aaaagggcca cggtattcgc ttattagaag    6120
cacagatcgc aaccgggggg atcattgacc caaaggagag ccatcgttta ccagttgaca    6180
tagcatataa gaggggctat ttcaatgagg aactcagtga gattctctca gatccaagtg    6240
atgataccaa aggattttt gaccccaaca ctgaagaaaa tcttacctat ctgcaactaa    6300
aagaaagatg cattaaggat gaggaaacag gctctgtctc tctgcctctg aaagaaaaga    6360
agaaacaggt gcagacatca caaaagaata ccctcaggaa gcgtagagtg gtcatagttg    6420
acccagaaac caataaagaa atgtctgttc aggaggccta caagaagggc ctaattgatt    6480
atgaaacctt caaagaactg tgtgagcagg aatgtgaatg ggaagaaata accatcacgg    6540
gatcagatgc ctccaccagg gtggtcctgg tagatagaaa gacaggcagt cagtatgata    6600
ttcaagatgc tattgacaag ggccttgttg acaggaagtt ctttgatcag taccgatccg    6660
gcagcctcag cctcactcaa tttgctgaca tgatctcctt gaaaaatggt gtcggcacca    6720
```

-continued

```
gcagcagcat gggcagtggt gtcagcgatg atgttttag cagctcccga catgaatcag 6780
taagtaagat ttccaccata tccagcgtca ggaatttaac cataaggagc agctcttttt 6840
cagacaccct ggaagaatcg agccccattg cagccatctt tgacacagaa aacctggaga 6900
aaatctccat tacagaaggt atagagcggg gcatcgttga cagcatcacg ggtcagaggc 6960
ttctggaggc tcaggcctgc acaggtggca tcatccaccc aaccacggc cagaagctgt 7020
cacttcagga cgcagtctcc caggtgtga ttgaccaaga catggccacc aggctgaagc 7080
ctgctcagaa agccttcata ggcttcgagg gtgtgaaggg aaagaagaag atgtcagcag 7140
cagaggcagt gaaagaaaaa tggctcccgt atgaggctgg ccagcgcttc ctggagttcc 7200
agtacctcac gggaggtctt gttgaccggg aagtgcatgg gaggataagc accgaagaag 7260
ccatccggaa ggggttcata gatggccgcg ccgcacagag gctgcaagac accagcagct 7320
atgccaaaat cctgacctgc cccaaaacca aattaaaaat atcctataag gatgccataa 7380
atcgctccat ggtagaagat atcactgggc tgcgccttct ggaagccgcc tccgtgtcgt 7440
ccaagggctt acccagccct tacaacatgt cttcggctcc ggggtcccgc tccggctccc 7500
gctcgggatc tcgctccgga tctcgctccg ggtcccgcag tgggtcccgg agaggaagct 7560
ttgacgccac agggaattct tcctactctt attcctactc atttagcagt agttctattg 7620
ggcactagta gtcagttggg agtggttgct ataccttgac ttcatttata tgaatttcca 7680
ctttattaaa taatagaaaa gaaaatcccg gtgcttgcag tagagtgata ggacattcta 7740
tgcttacaga aaatatagcc atgattgaaa tcaaatagta aaggctgttc tggctttta 7800
tcttcttagc tcatcttaaa taagcagtac acttggatgc agtgcgtctg aagtgctaat 7860
cagttgtaac aatagcacaa atcgaactta ggatttgttt cttctcttct gtgtttcgat 7920
ttttgatcaa ttctttaatt ttggaagcct ataatacagt tttctattct tggagataaa 7980
aattaaatgg atcactgata ttttagtcat tctgcttctc atctaaatat ttccatattc 8040
tgtattagga gaaaattacc ctcccagcac cagcccccct ctcaaacccc caacccaaaa 8100
ccaagcattt tggaatgagt ctcctttagt ttcagagtgt ggattgtata acccatatac 8160
tcttcgatgt acttgtttgg tttggtatta atttgactgt gcatgacagc ggcaatcttt 8220
tctttggtca aagttttctg tttatttgc ttgtcatatt cgatgtactt taaggtgtct 8280
ttatgaagtt tgctattctg gcaataaact tttagacttt tgaagtgttt gtgttttaat 8340
ttaatatgtt tataagcatg tataaacatt tagcatattt ttatcatagg tctaaaaata 8400
tttgtttact aaatacctgt gaagaaatac cattaaaaaa ctatttggtt ctgaattctt 8460
actagaaaaa aaa                                                    8473
```

```
SEQ ID NO: 47        moltype = AA  length = 2428
FEATURE              Location/Qualifiers
source               1..2428
                     mol_type = protein
                     organism = Homo sapiens
SEQUENCE: 47
MSCNGGSHPR INTLGRMIRA ESGPDLRYEV TSGGGGTSRM YYSRRGVITD QNSDGYCQTG   60
TMSRHQNQNT IQELLQNCSD CLMRAELIVQ PELKYGDGIQ LTRSRELDEC FAQANDQMEI  120
LDSLIREMRQ MGQPCDAYQK RLLQLQEQMR ALYKAISVPR VRRASSKGGG GYTCQSGSGW  180
DEFTKHVTSE CLGWMRQQRA EMDMVAWGVD LASVEQHINS HRGIHNSIGD YRWQLDKIKA  240
DLREKSAIYQ LEEEYENLLK ASFERMDHLR REIMWINDCE EEELLYDWSD              300
KNTNIAQKQE AFSIRMSQLE VKEKELNKLK QESDQLVLNQ HPASDKIEAY MDTLQTQWSW  360
ILQITKCIDV HLKENAAYFQ FFEEAQSTEA YLKGLQDSIR KKYPCDKNMP LQHLLEQIKE  420
LEKEREKILE YKRQVQNLVN KSKKIVQLKP RNPDYRSNKP IILRALCDYK QDQKIVHKGD  480
ECILKDNNER SKWYVTGPGG VDMLVPSVGL IIPPPNPLAV DLSCKIEQYY EAILALWNQL  540
YINMKSLVSW HYCMIDIEKI RAMTIAKLKT MRQEDYMKTI ADLELHYQEF IRNSQGSEMF  600
GDDDKRKIQS QFTDAQKHYQ TLVIQLPGYP QHQTVTTTEI THHGTCQDVN HNKVIETNRE  660
NDKQETWMLM ELQKIRRQIE HCEGRMTLKN LPLADQGSSH HITVKINELK SVQNDSQAIA  720
EVLNQLKDML ANFRGSEKYC YLQNEVFGLF QKLENINGVT DGYLNSLCTV RALLQAILQT  780
EDMLKVYEAR LTEEETVCLD LDKVEAYRCG LKKIKNDLNL KKSLLATMKT ELQKAQQIHS  840
QTSQQYPLYD LDLGKFGEKV TQLTDRWQRI DKQIDFRLWD LEKQIKQLRN YRDNYQAFCK  900
WLYDAKRRQD SLESMKFGDS NTVMRFLNEQ KNLHSEISGK RDKSEEVQKI AELCANSIKD  960
YELQLASYTS GLETLLNIPI KRTMIQSPSG VILQEAADVH ARYIELLTRS GDYYRFLSEM 1020
LKSLEDLKLK NTKIEVLEEE LRLARDANSE NCNKNKFLDQ NLQKYQAECS QFKAKLASLE 1080
ELKRQAELDG KSAKQNLDKC YGQIKELNEK ITRLTYEIED EKRRKSVED RFDQQKNDYD 1140
QLQKARQCEK ENLGWQKLES EKAIKEKEYE IERLRVLLQE EGTRKREYEN ELAKVRNHYN 1200
EEMSNLRNKY ETEINITKTT IKEISMQKED DSKNLRNQLD RLSRENRDLK DEIVRLNDSI 1260
LQATEQRRRA EENALQQKAC GSEIMQKKQH LEIELKQVMQ QRSEDNARHK QSLEEAAKTI 1320
QDKNKEIERL KAEFQEEAKR RWEYENELSK ASNRIQESKN QCTQVVQERE SLLVKIKVLE 1380
QDKARLQRLE DELNRAKSTL EAETRVKQRL ECEKQQIQND LNQWKTQYSR KEEAIRKIES 1440
EREKSEREKN SLRSEIERLQ AEIKRIEERC RRKLEDSTRE TQSQLETERS RYQREIDKLR 1500
QRPYGSHRET QTECEWTVDT SKLVFDGLRK KVTAMQLYEC QLIDKTTLDK LLKGKKSVEE 1560
VASEIQPFLR GAGSIAGASA SPKEKYSLVE AKRKKLISPE STVMLLEAQA ATGGIIDPHR 1620
NEKLTVDSAI ARDLIDFDDR QQIYAAEKAI TGFDDPFSGK TVSVSEAIKK NLIDRETGMR 1680
LLEAQIASGG VVDPVNSVFL PKDVALARGL IDRDLYRSLN DPRDSQKNFV DPVTKKKVSY 1740
VQLKERCRIE PHTGLLLLSV QKRSMSFQGI RQPVTVTELV DSGILRPSTV NELESGQISY 1800
DEVGERIKDF LQGSSCIAGI YNETTKQKLG IYEAMKIGLV RPGTALELLE AQAATGFIVD 1860
PVSNLRLPVE EAYKRGLVGI EFKEKLLSAE RAVTGYNDPE TGNIISLFQA MNKELIEKGH 1920
GIRLLEAQIA TGGIIDPKES HRLPVDIAYK RGYFNEELSE ILSDPSDDTK GFFDPNTEEN 1980
LTYLQLKERC IKDEETGLCL LPLKEKKKQV TQSQKNTLRK RRVVIVDPET NKEMSVQEAY 2040
KKGLIDYETF KELCEQECEW EEITITGSDG STRVVLVDRK TGSQYDIQDA IDKGLVDRKF 2100
FDQYRSGSLS LTQFADMISL KNGVGTSSSM GSGVSDDVFS SSRHESVSKI STISSVRNLT 2160
IRSSSFSDTL EESSPIAAIF DTENLEKISI TEGIERGIVD SITGQRLLEA QACTGGIIHP 2220
TTGQKLSLQD AVSQGVIDQD MATRLKPAQK AFIGFEGVKG KKKMSAAEAV KEKWLPYEAG 2280
QRFLEFQYLT GGLVDPEVHG RISTEEAIRK GFIDGRAAQR LQDTSSYAKI LTCPKTKLKI 2340
SYKDAINRSM VEDITGLRLL EAASVSSKGL PSPYNMSSAP GSRSGSRSGS RSGSRSGSRS 2400
GSRRGSFDAT GNSSYSYSYS FSSSSIGH                                   2428
```

```
SEQ ID NO: 48            moltype = DNA   length = 8768
FEATURE                  Location/Qualifiers
source                   1..8768
                         mol_type = genomic DNA
                         organism = Homo sapiens
SEQUENCE: 48
gcggccgcac tagtacccccg gagcccatgg gcgcgccgag ccgggcgcgg gggcgctgaa    60
cggcggagcg ggagcggccg gaggagccat ggactgcagc ctcgtgcgga cgctcgtgca   120
cagatactgt gcaggagaag agaattgggt ggacagcagg accatctacg tgggacacag   180
ggagccacct ccgggcgcag aggcctacat cccacagaga tacccagaca acaggatcgt   240
ctcgtccaag tacacatttt ggaactttat acccaagaat ttatttgaac aattcagaag   300
agtagccaac tttttatttcc ttatcatatt tctggtgcag ttgattattg atacacccac   360
aagtccagtg acaagcggac ttccactctt ctttgtcatt actgtgacgg ctatcaaaca   420
gggttatgaa gactggcttc gacataaagc agacaatgac atgaaccagt gtcctgttca   480
tttcattcag cacggcaagc tcgttcggaa acaaagtcga aagctgcgag ttggggacat   540
tgtcatggtt aaggaggacg agacctttcc ctgcgacttg atcttccttt ccagcaaccg   600
gggagatggg acgtgccacg tcaccaccgc cagcttggat ggagaatcca gccataaaac   660
gcattacgcg gtccaggaca ccaaaggctt ccacacagag gaggatatcg gcggacttca   720
cgccaccatc gagtgtgagc agccccagcc cgacctctac aagttcgtgg gtcgcatcaa   780
cgtttacagt gacctgaatg accccgtggt gaggcccta ggatcggaaa acctgctgct   840
tagaggagct acactgaaga acactgagaa aatctttggt gtggctattt acgggaat    900
ggaaaccaag atgccattaa attatcaatc aaaatctcag aagcgatctg ccgtggaaa    960
atcgatgaat gcgttcctca ttgtgtatct ctgcattctg atcagcaaag ccctgataaa   1020
cactgtgctg aaatacatgt ggcagagtga gcccttcgg gatgagccgt ggtataatca   1080
gaaaacggag tcgaaaggc agaggaatct gttcctcaag gcattcacgg acttcctggc   1140
cttcatggtc ctctttaact acatcatccc tgtgtccata tacgtcacgg tcgagatgca   1200
gaagttcctc ggctcttact tcatcaccctg ggacgaagac atgtttgacg aggagactgg   1260
cgaggggcct ctggtgaaca cgtcggacct caatgaagag ctgggacagg tggagtacat   1320
cttcacagac aagaccggca ccctcacgga aaacaacatg gagttcaagg agtgctgcat   1380
cgaaggccat gtctacgtgc cccacgtcat ctgcaacggg caggtcctcc cagagtcgtc   1440
aggaatcgac atgattgact cgtccccag cgtcaacggg agggagcgcg aggagctgtt   1500
tttccgggcc ctctgtctct gccacaccgt ccaggtgaaa gacgatgaca gcgtagacgg   1560
ccccaggaaa tcgccggacg gggggaaatc ctgtgtgtac atctcatcct cgcccgacga   1620
ggtggcgctg gtcgaaggtg tccagagact tggctttacc tacctaaggc tgaaggacaa   1680
ttacatggag atattaaaca gggagaacca catcgaaagg tttgaattgc tggaaattt    1740
gagttttgac tcagtcagaa ggagaatgag tgtaattgta aaatctgcta caggagaaat   1800
ttatctgtttt tgcaaaggag cagattcttc gatattcccc cgagtgatag aaggcaaagt   1860
tgaccagatc cgagccagag tggagcgtaa cgcagtggag gggctccgaa ctttgtgtgt   1920
tgcttataaa aggctgatcc aagaagaata tgaaggcatt tgtaagctgc tgcaggctgc   1980
caaagtggcc cttcaagatc gagagaaaaa gttagcagaa gccatgagc aaatagaaga    2040
agatcttact ctgcttggtg ctacagctgt tgaggaccgg ctgcaggaga aagctgcaga   2100
caccatcgag gccctgcaga aggccgggat caaagtctgg gttctcacgg agacaagat    2160
ggagccggcc gcggccacgt gctacgcctg caagctcttc cgcaggaaca cgcagctgct   2220
ggagctgacc accaagagga tcgaggagca gagcctgcac gacgtcctgt tcgagctgag   2280
caagacggtc ctgcgccaca gcgggagcct gaccagagac aacctgtccg gactttcagc   2340
agatatgcag gactacggtt taattatcga cggagctgca ctgtctctga taatgaagcc   2400
tcgagaagac gggagttccg gcaactacag ggagctcttc ctggaaatct gccggagctg   2460
cagcgcggtg ctctgctgcc gcatggcgcc cttgcagaag gctcagattg ttaaattaat   2520
caaattttca aaagagcacc caatcacgtt agcaattggc gatggtgcaa atgatgtcag   2580
catgattctg gaagcgcacg tgggcatagg tgtcatcggc aaggaaggcc gccaggctgc   2640
caggaacagc gactatgcaa tcccaaagtt taagcatttg aagaagatgc tgcttgttca   2700
cgggcattt tattacatta ggatctctga gctcgtgcag tacttcttct ataagaacgt   2760
ctgcttcatc ttccctcagt ttttataca gttcttctgt gggttttcac aacagacttt   2820
gtacgacacc cgctatctga ccctctacaa catcagcttc acctccctcc catcctcct    2880
gtacagcctc atggagcagc atgttggcat tgacgtgctc aagagagacc cgaccctgta   2940
cagggacgtc gccaagaatg ccctgctgcg ctggcgcgtg ttcatctact ggacgctcct   3000
gggactgttt gacgcactgg tgttcttctt tggtgcttat ttcgtgtttg aaaatacaac   3060
tgtgacaagc aacgggcaga tatttggaaa ctggacgttt ggaacgctgg tattcaccgt   3120
gatggtgttc acagttacac taaagcttgc attggacaca cactactgga cttggatcaa   3180
ccattttgtc atctggggg cgctgctgtt ctacttgtc ttttcgcttc tctggggggag    3240
agtgatctgg ccgttcctca actaccagag gatgtactac gtgttcatcc agatgctgtc   3300
cagcgggccc gcctggctgg ccatcgtgct gctggtgacc atcagcctcc ttcccgacgt   3360
cctcaagaaa gtcctgtgcc ggcagctgtg gccaacagca acagagagag tccagaatgg   3420
gtgcgcacag cctcgggacc gcgactcaga attcaccccct cttgcctctc tgcagagccc   3480
aggctaccag agcacctgtc cctcggccgc ctggtacagca tcccactctc agcaggtgac   3540
actcgcggcc tggaaggaga aggtgtccac ggagccccca cccatcctcg gcggttccca   3600
tcaccactgc agttccatcc caagtcacag ctgcccttagg tcccgtgtgg aatgctcgt    3660
gtgatgcatg gtcctaagcc tgtggagact gtgcacgtgc ctcttcctgg ccccagcag    3720
gcaaggaggg gggtcacagg ccttgcctc gagcatggca cccctggccgc ctggaccccag   3780
cactgtggtt gttgagccac accagtggcc tctgggcatt cggctcaacg caggagggac   3840
attctgctgg cccaccctgc gcgctgtcat gcagaggcca ttccccccagg ctgtgtcttt   3900
cacccacctg ccatcattgg cctttgctgt cactgggaga aagagccgt ccagggaccc    3960
atggtggccc acatgtggat gccacatgct gctgtttcct gcttgcccgg ccaccaccca   4020
tgccctccat aggtaggt ggagccatg tggtgcgtcc tttactcaac aaccctccaa    4080
tccggatgct gtgggaaggg ccgggtcact cggataccat catccctgcg gatgcaccgc   4140
cgtaccctgc tcatctggga gtggtttccc tgcggttacg tccaagcccg cctgccctgt   4200
gtgttgggc tggctgagtt tcggtctccc catcaccggc cgcctcgtgg agaaggcagt   4260
gccacgtggg aggacaaggc cacgccggca gcttccagcc ctgccgcaga agtgccagga   4320
tgtccatcag ccactcgcca gggcacggag ccgtcagtcc actgttacgg agaatgttga   4380
```

```
atttcgcggg tgcgagggcc gggagacaga tacttggctg tgatgagcag acatcctctg   4440
tccccgtgga ggggtcaaca ccaaggtggt gttcgtgcac cagaacctgt ctcgggctga   4500
cgggggtggc acacaggaca cgggtggatc ccaacaggca gcaccgcacc tctgcccgcc   4560
tcccgcactg cagctccgcc cgccgggctc tgcgtcccca cgtcccctcg tcccatcccc   4620
acgtccccto atcccgtcac ctcgtcccca catcccottg ccccgtcacc tcgtcctcat   4680
gtcccottgt cctgtcacct cgtcccacg tccctcgtc tcctcatccc cacgtcctct   4740
cgtccottg tcccgtcccc acataccctg gtcccatgt cccacgcag ggctctcctt   4800
cgtcttagga tctgtccagc gctgctctgg gtgggttagc aaccccaggg ctgctgtgat   4860
aggaagtccc tgttgttctc cgtactggca tttctatttc tagaaataat atttgacata   4920
gccttaatgg tccttaaaga agacatttca gtgtgagatt cagacttcag acgctgaaac   4980
tgctgccttt caggaaagca ccaccaacgc tggaggagga gccggccctc acgcccgccc   5040
cgccgccacgc tgtggaacgg ggctccggca agtgaaaccc agagggtgtt tccgaggtgc   5100
tcgacagtag gtattttttgg aagctcagat ttcaccattt gattgtataa tcttttacct   5160
ataaaatatt tatttgaagt agagggtaaa tcagcggtaa gaacagtgaa cacagtggtt   5220
gggataaaat aaggtgacaa acatcacacc aaagatgagg gtagcgagca actggcttga   5280
gcagacagaa cggggaagac tccactctgt cccgaggggc cagccgcagg cgtcocccagg   5340
gccaccctgc cctgaggtcc ttgtgtggcc gccctggctt ggcagccctg cccacgctgc   5400
ccccgcaaac aatggtgtgt gcgttttttac agccottttt aggaacccaa tatgggcata   5460
aatgtaacac ctgtagcggg ggcagattct ctgtatgttc agttaacaaa ttatttgtaa   5520
tgtatttttt tagaaatctt aaaattgcct ttgcactgaa gtattttcat agctgtttat   5580
atctctttta ttcattatt taacatactg tctaatttta aaaataggtt tttaaagctt   5640
tcattttaa gtttatgaaa ttttggccac tttacattta gattctggtg agagttttga   5700
ctgaatgttc caatctctga tgaatgcgaa ttttcagatt tgattttatt ctctacacac   5760
acctcttctt ttcttggtat ttctggtggc agtgattagt tgaacagcac atttaaggca   5820
cgataatttg ctacacttt tctttacaat ttgttgcaat ttcatctgct ttctatgttt   5880
cattgttaat tgccatccct cagcottaaa aatagaagat tctcacgtga aggtttagta   5940
agttgggtcc cagctctgcc tgtgtggaga tagtccaccat gtacctctga caacaagttt   6000
tagtgtgaaa gtcactaaac ttttacacac tcccaaacgt ctttttaaaa attgcttggg   6060
aaattattaa atgaatgtgc ctgatgattt gaaatagaca aggggcacga gataaaaaag   6120
aaaaggatga gaagatcctc agtgaatgac gttgcagggt cttcatgcaa ttttccacct   6180
cgcagtagtt agtatttact tgccttaaac taacttttgaa gcaagtaatg tcaactttga   6240
gcactttgtt gagttttgaa aaatcttatt tgttgctgca caggttaata aattatcaat   6300
ttgtaattca gcatgttggt cagagacacg gtcactgatt cacacccagt ccctgccaca   6360
gaccgtctca gacacgcaca gtgggcctgc tgcatgattc acacccagtc cctgccacag   6420
accgtctcag acacgcacag tgggcctgct gcatgattca cacccagtcc ctgccacaga   6480
ccgtctcaga cacgcacagt gggcctgctg catgcgtgtt acctggcttt tggctccacg   6540
ctcactcata gccatgtcca catggggct tgcacacagg atcactcaca tatgtacatg   6600
tacccaccac aaacgtgcaa gctcctgcac acatgcatgc acacaaacgt gtacacaagt   6660
gtgagctcct acacgcatac acacacacac gtgtacatgc accaaagcat gtgtgaccta   6720
cagacatgca gaacatgcac gtgtacacat accacagaca cgcgtgtgca tgctcctaca   6780
caatacatat gcacatatca tgaacagcgt aagttcctac acacgacgt gtgatacaca   6840
catgcatgta caggtaagca cacatgtaca agctcctaca ggcttgctct cacacacgtg   6900
tgtcacagc agagagacgt atgagcttct actgcacaca tgcacacaca cacgcacacg   6960
tacattcact acaaacgtgc agcctcctgc acacgtgcac attcatgtgt acaccacaaa   7020
tgagttccca gacgtgtaaa cacacgtgca cacatcgtac acatgtgagc tcccacacgt   7080
acacacagat gcacatggac acaccccaaa cacgcacagg ctcctacaca catgcacaca   7140
cgtgtacacc acaaacgagc tcccagacat gtaaacacac gtctcccaca gctgagctcc   7200
cacacgtaca catgcacatg tacgcaccac aaaacacatgc gcaggctcct gcaggcgtga   7260
atacacacat gcacacacat atacacacat gtgccacaaa caagtgcaca ctgtcctggt   7320
gtcctgcact gcatcctgcc tccttgctga ggggcccctg tgagaggcct ctggatgggc   7380
atgggaagat gggctccctg gcccccagcc catgcctccc tgggatgaag agtccccctc   7440
ctggcagaat gtctgggctt tgcagagcag gccccggggg tgaagtcgca gcttcactta   7500
caccagctgc tctgtgagca aggcttggtg ccctggacaa ggcccttccc ctttagggag   7560
gtccagcctc gcaagctgaa acctcccctc ggctcagccc tataccaggc ggccacagca   7620
ggactggcca caccacgcc gcacctcatc cgtgcacgcg tcggagcacg gccagcctc   7680
cgccacgagc cagctgggaa gggccgcggc cgcctaaagc cccagtcaac ccagcctgtg   7740
tctgagcaga cagggcgaac aagcaggcca caccgtctcg agggaggagg ccagatgcgg   7800
ccagcgtctc caacagggtg accatccgct cggcttgctg agcgtttaaa caaatgttta   7860
gacaggctgt ggggactccc ctgagttgag ccttggccag gggtccggtg ctgtcgcggg   7920
aaacctccag ccttgttctt caaaccactc agctcatgtg ttttgcactg actagtactg   7980
aataatacaa ccactcttat ttaatgttag tattatttat ttgacaactc agtgtctaac   8040
agcttgatat gcaggtcctt gcatcctaca tttcttttagg aagttaccca tttgtaactt   8100
taaaaacagg aaaaatatca gttggcaaat gcaatcttt tttttttaa gctaaaggtg   8160
ggtgaactgg aatgaaaatc tttctgatgt tgtgtctata agcagccttg atgggatatg   8220
ttagaagtgt catgaaagtg tgattctact tttgcagaaa aatctaaaga tcaatttata   8280
tagctttatt ttttactta tcaaagtata cagaatttta atatgcatat attgtgtctg   8340
acttaaaatt ataatgtctg cgtcaccatt taaaatgtct gttcattatg taatgtaata   8400
aaagaaggtc ttcaaaaatg tatttaacat gaatggtatc catgtttgtc atcatcataa   8460
atactggagt ttatttttaa attattaaac atagtaggtg cattaacata aatcagtctc   8520
cacacagtaa catttaactg ataattcatt aatcagcttt gaaaaattaa attgttaatt   8580
aaaccaatct aacatttcag taaagtttat tttgtatgct tctgttttta actttttattt   8640
ctgtagataa actgactgga taatattata ttggactttt ctctagatta tctaagcagg   8700
agacctgaat ctgcttgcaa taaagaataa agtctgcttt cagtttcttt ataaagaaac   8760
tcacacaa                                                            8768

SEQ ID NO: 49        moltype = AA   length = 1191
FEATURE              Location/Qualifiers
source               1..1191
                     mol_type = protein
```

```
                    organism = Homo sapiens
SEQUENCE: 49
MDCSLVRTLV  HRYCAGEENW  VDSRTIYVGH  REPPPGAEAY  IPQRYPDNRI  VSSKYTFWNF   60
IPKNLFEQFR  RVANFYFLII  FLVQLIIDTP  TSPVTSGLPL  FFVITVTAIK  QGYEDWLRHK  120
ADNAMNQCPV  HFIQHGKLVR  KQSRKLRVGD  IVMVKEDETF  PCDLIFLSSN  RGDGTCHVTT  180
ASLDGESSHK  THYAVQDTKG  FHTEEDIGGL  HATIECEQPQ  PDLYKFVGRI  NVYSDLNDPV  240
VRPLGSENLL  LRGATLKNTE  KIFGVAIYTG  METKMALNYQ  SKSQKRSAVE  KSMNAFLIVY  300
LCILISKALI  NTVLKYMWQS  EPFRDEPWYN  QKTESERQRN  LFLKAFTDFL  AFMVLFNYII  360
PVSMYVTVEM  QKFLGSYFIT  WDEDMFDEET  GEGPLVNTSD  LNEELGQVEY  IFTDKTGTLT  420
ENNMEFKECC  IEGHVYVPHV  ICNGQVLPES  SGIDMIDSSP  SVNGREREEL  FFRALCLCHT  480
VQVKDDDSVD  GPRKSPDGGK  SCVYISSSPD  EVALVEGVQR  LGFTYLRLKD  NYMEILNREN  540
HIERFELLEI  LSFDSVRRRM  SVIVKSATGE  IYLFCKGADS  SIFPRVIEGK  VDQIRARVER  600
NAVEGLRTLC  VAYKRLIQEE  YEGICKLLQA  AKVALQDREK  KLAEAYEQIE  KDLTLLGATA  660
VEDRLQEKAA  DTIEALQKAG  IKVWVLTGDK  METAAATCYA  CKLFRRNTQL  LELTTKRIEE  720
QSLHDVLFEL  SKTVLRHSGS  LTRDNLSGLS  ADMQDYGLII  DGAALSLIMK  PREDGSSGNY  780
RELFLEICRS  CSAVLCCRMA  PLQKAQIVKL  IKFSKEHPIT  LAIGDGANDV  SMILEAHVGI  840
GVIGKEGRQA  ARNSDYAIPK  FKHLKKMLLV  HGHFYYIRIS  ELVQYFFYKN  VCFIFPQFLY  900
QFFCGFSQQT  LYDTAYLTLY  NISFTSLPIL  LYSLMEQHVG  IDVLKRDPTL  YRDVAKNALL  960
RWRVFIYWTL  LGLFDALVFF  FGAYPVFENT  TVTSNGQIFG  NWTFGTLVFT  VMVFTVTLKL 1020
ALDTHYWTWI  NHFVIWGSLL  FYVVFSLLWG  GVIWPFLNYQ  RMYYVFIQML  SSGPAWLAIV 1080
LLVTISLLPD  VLKKVLCRQL  WPTATERVQN  GCAQPRDRDS  EFTPLASLQS  PGYQSTCPSA 1140
AWYSSHSQQV  TLAAWKEKVS  TEPPPILGGS  HHHCSSIPSH  SCPRSRVGML  V          1191

SEQ ID NO: 50          moltype = DNA   length = 4673
FEATURE                Location/Qualifiers
source                 1..4673
                       mol_type = genomic DNA
                       organism = Homo sapiens
SEQUENCE: 50
tttccgcagt taggggctgc tatttcaacg cagggagata aaaagaaaaa aacacttgct   60
cttctacccc gctaaaaaca ctcatcctag ggagcacgcc agcatttgca gcgttcgggg  120
cagggccact cggcctgcgg ccgttgcact ggctggaagc tggcaggcga tcacggttga  180
ttggctcggt tgcggtccaa gggcagcaac gccttcggcg ggccgcctag ggtgattggc  240
tgctgcagcc cacccctag ccggtttggt gggcggcgaa gcctggattg gtggagctaa  300
gagctggctc agtttcagcg ctggctcttc gtgcatggca gagatggcga ctgcgactcg  360
gctgctgggg tggcgtgtgg cgagctggag gctgcggccg ccgcttgccg gcttcgtttc  420
ccagcgggcc cactcgcttt tgcccgtgga cgatgcaatc aatgggctaa gcgaggagca  480
gaggcagctt cgtcagacca tggctaagtt ccttcaggag cacctggccc caaggccca   540
ggagatcgat cgcagcaatg agttcaagaa cctgcgagaa ttttggaagc agctgggaa   600
cctgggcgta ttgggcatca cagccccgt tcagtatggc ggctccgcc tgggctacct   660
ggagcatgtg ctggtgatgg aggagatatc ccgagcttcc ggagcagtgg ggctcagtta  720
cggtgcccac tccaacctct gcatcaacca gcttgtacgc aatgggaatg aggcccagaa  780
agagaagtat ctcccgaagc tgatcagtgg tgagtacatc gaggccctgg ccatgagtga  840
gcccaatgca ggctctgatg ttgtctctat gaagctcaaa gcggaaaaga aggaaatca   900
ctacatcctg aatggcaaca agttctggat cactaatggc cctgatgctg acgtcctgat  960
tgtctatgcc aagacagatc tggctgctgt gccagcttct cggggcatca cagccttcat 1020
tgtggaagag ggtatgcctg gctttagcac ctctaagaag ctggacaagc tggggatgag 1080
gggctctaac acctgtgagc taatctttga agactgcaag attcctgctg ccaacatcct 1140
gggccatgag aataagggtg tctacgtgct gatgagtggg ctggacctgg agcggctggt 1200
gctggccggg gggcctcttg ggctcatgca agcggtcctg gaccacacca ttccctacct 1260
gcacgtgagg gaagcctttg gccagaagat cggccacttc cagttgatgc aggggaagat 1320
ggctgacatg tacacccgcc tcatggcgtg tcggcagtat gtctacaatg tcgccaaggc 1380
ctgcgatgag ggccattgca ctgctaagga ctgtgcaggt gtgattcttt actcagctga 1440
gtgtgccaca caggtagccc tggacggcat tcagtgtttt ggtggcaatg gctacatcaa 1500
tgacttccc atgggccgct tcttcgaga tgccaagctg tatgagatag gggctgggac 1560
cagcgaggtg aggcggctgg tcatcggcag agccttcaat gcagactttc actagtcctg 1620
agacccttcg ccccctttc ctgcacctag tggcctttct tgggaagtag agatgtggcg 1680
gctttcccac cctgcccaca gcaggccctc ctgcccagct gctcttgtca gccctctggc 1740
ctctggatga ggttgagttc tccacaacag ctcccaagca tcatgggcct cgcagccggg 1800
cctgtgccac ggctagtgtt gtgtgattta aaatgactc agcaggaagc atattgctg   1860
gggattgttg gacaggttt tggtgactct gtgcccttgc tctctaactt ctgagcccac 1920
ctcccagggt aggcacctgg gggcatgcag gtgcccacct cccagggtag gcacctggg   1980
gcatgcaggt acccacctct ttctcttggg tgaggctctg gcaaggagat ctctctgctc 2040
aagcacagca gaatcatggc ccctctccat gaattggaac ttggtacagg ttaagtatcc 2100
ctaatcctga aatctgaaac acttgtggtt ccaagcattt tggataaggc aaattcaact 2160
ttcagtctct tttctggggg aaaaaaataa taaacctagc ctagcaggc gtggtggctc 2220
atgcttgtaa tcccagcact tcaggaggct gagatgggtg gatcacctga ggtcaggagt 2280
tcaagaccag cctggccaac atgtggaaac ctcgcctcaa ctaaaaatag aaaaaaatta 2340
gttgggcatg gtggtgggca cctgtaatcc cagctactc aggaggctga ggcaggagaa 2400
ttacttgaac ccaggaggcg gacgttgcag tgagccgagc ttgtgccatt gcactccagc 2460
ctgggcgaca gagcaaaac tcttcaaaaa acaaaacaaa acaaaaaaac cctgcccttt 2520
gtttcttcca gtttctagag gtatcagctc ctagcagctt atgaacacat atgcttgctt 2580
ggccaggcaa ggtggtgtgt gcctgtaatc ccagcacttt gggaggccaa ggcaggtgga 2640
tcacttgagg tcaggagttc aagaccagcc tgtccaacgt ggtgaaaccc catctctact 2700
aaaaatacaa aaattagcca ggggtggtgg tgcacgcctg taatcccagc tactcaggag 2760
gctgaggcag gagaatcact tgaacccggg aggtggaggt tgcaatgagc caatatgaca 2820
ccgctgcagt ccagcctggg ccatagagtg agactctgtc tcaaaaaagg aaagaaaaat 2880
aggctggca cagtgactca tgcctgtaat cccaacactt tgggaggccg aggcaggtgg 2940
atcacgaggt caggagttca agaccagcct ggccaagatg gtaaaacctc gtctctacta 3000
```

-continued

```
aaaatacaaa aattagccag gtgtggtggc aggctcctgt aatcccagct actcaggagg  3060
ctgaggcaga gaattgcttg aacccggag gcagagtttg cagtgagcca agatcacacc  3120
actgcactcc agcttggacg acagagcgag actctgtctc aaaaaataat aggccaggca  3180
tggtggctca acgtctgtaa tcccagcact ttgggaggcc gaggcgggca gatcacaagg  3240
tcaggagttc gagaccagcc tgacgaccaa catggtgaaa cctcgtctct actaaaaata  3300
caaaaattag ccaggcctgg tggcacgcgc ctgtaatccc agttacacag aagactgagg  3360
caggagaatc gcttgaacgc aggaggcaga ggttgcagga gctgagatcg cgccattgca  3420
ctccagcctg ggcaacagag tgagactctg tctcaaaaaa taataataaa ataaatgaac  3480
acacatgctg ctgagtccgc aggggggca gagcagagga cgtgcgtgtt ttgtgtactg  3540
ttggaagact ggctcctcct gtacagcacc tctgagccct tgtgcaccgc cctgccacgg  3600
gcaccatcca gtcctggccg tgtgaccacc cacagctgac tgggcagcag gcacaggccc  3660
tacccgagca ggccggagtt ggctcgcatg actccagctg aggctgcctg tgtacatttc  3720
tccagatacc ctatggctaa ttttgttata actgcacagt ggctgctgcc attttgtatt  3780
aaatatattg tgaaacaaac ctatctgggg agaagcaatc tgcttcctgt  3840
ctggatccag cttgtgtcct tggagagtgg ctggcccagg tcctattcct gtcctccagc  3900
ccgttctttc atgagggaca ggaagtaaa atcagccctt aggagagagg tctcagcctc  3960
cctttcccag atctcccagt gagttttaaa ggaagcaggg agcccagagt gctaagttct  4020
tacagccaga aggaagctta tagattctg aaaaccgccc ctttgttttt aaaaagatca  4080
acacaatttg actttctcaa ggtcaaaacg aactagaatc cagatctgct catggcaaaa  4140
atgggggtgt tctgagaatt ccagctttgg gccgcactgt acagcagtct ggatagagtg  4200
tgatctgaga agggaatggg tctggggtgt tccaccccttt ccgagttcca aaaagaggga  4260
actggtttc ttggttctca gcccagcagc acctatcctg gctcttggtc ctggcctgca  4320
gccaagtgct gttcctagcc tgaggcttga cacaggtggg gttggctcct caccaacccc  4380
agttccgtcc catcctgagg gcaagatcct gggctcatag gcagtccctt tcacttcctt  4440
gtcttgctcc ctgctatgtt ggagatgaat gtgactaaaa gggccatctt gctggcttaa  4500
tgtgtggctg gagagaccag cctggagaca atgtggcaaa atgggcgct tcatccagtc  4560
tgtctaagcc ctgtcgactt ggggaggtga tttctttcct ggttctatat gtgaagcaaa  4620
ataaatgttt taaaattaaa agcaaaaaa acaaatgaa ccatgaaaaa aaa  4673

SEQ ID NO: 51         moltype = AA   length = 426
FEATURE               Location/Qualifiers
source                1..426
                      mol_type = protein
                      organism = Homo sapiens
SEQUENCE: 51
MAEMATATRL LGWRVASWRL RPPLAGFVSQ RAHSLLPVDD AINGLSEEQR QLRQTMAKFL   60
QEHLAPKAQE IDRSNEFKNL REFWKQLGNL GVLGITAPVQ YGGSGLGYLE HVLVMEEISR  120
ASGAVGLSYG AHSNLCINQL VRNGNEAQKE KYLPKLISGE YIGALAMSEP NAGSDVVSMK  180
LKAEKKGNHY ILNGNKFWIT NGPDADVLIV YAKTDLAAVP ASRGITAFIV EKGMPGFSTS  240
KKLDKLGMRG SNTCELIFED CKIPAANILG HENKGVYVLM SGLDLERLVL AGGPLGLMQA  300
VLDHTIPYLH VREAFGQKIG HFQLMQGKMA DMYTRLMACR QYVYNVAKAC DEGHCTAKDC  360
AGVILYSAEC ATQVALDGIQ CFGGNGYIND FPMGRFLRDA KLYEIGAGTS EVRRLVIGRA  420
FNADFH                                                            426

SEQ ID NO: 52         moltype = AA   length = 268
FEATURE               Location/Qualifiers
source                1..268
                      mol_type = protein
                      organism = Homo sapiens
SEQUENCE: 52
MSGKHYKGPE VSCCIKYFIF GFNVIFWFLG ITFLGIGLWA WNEKGVLSNI SSITDLGGFD   60
PVWLFLVVGG VMFILGFAGC IGALRENTFL LKFFSVFLGI IFFLELTAGV LAFVFKDWIK  120
DQLYFFINNN IRAYRDDIDL QNLIDFTQEY WQCCGAFGAD DWNLNIYFNC TDSNASRERC  180
GVPFSCCTKD PAEDVINTQC GYDARQKPEV DQQIVIYTKG CVPQFEKWLQ DNLTIVAGIF  240
IGIALLQIFG ICLAQNLVSD IEAVRASW                                    268

SEQ ID NO: 53         moltype = DNA   length = 3583
FEATURE               Location/Qualifiers
source                1..3583
                      mol_type = genomic DNA
                      organism = Homo sapiens
SEQUENCE: 53
ctgggcccca gcgaggcggt ggggcggggc ggggcggggc gggcgcgca gcaggagcga   60
gtggggccgc ccgccgggcc gcggacactg tcgcccgggcg caacaaggct  120
acgcagaaga accccttga ctgaagcaat ggagggggg ccagctgtct gctgccagga  180
tcctcgggca gagctggtag aacgggtggc agccatcgat gtgactcact ggaggaggc  240
agatggtggc ccagagccta ctagaaacg tgtggacccc ccaccacggg ccagagctgc  300
ctctgtgatc cctggcagta cttcaagact gctcccagcc cggctagc tctcagcag  360
gaagctttcc ctacaggagc ggccagcagg aagctatctg gaggcgcagg ctgggcctta  420
tgccacgggg cctgccagcc acatctcccc ccgggcctgg cggaggccca ccatcgagtc  480
ccaccacgtg gccatctcag atgcagagga ctgcgtgcag ctgaccagt acaagctgca  540
gagtgagatt ggcaagggtg cctacggtgt ggtgaggctg gcctacaacg aaagtgaaga  600
cagacactat gcaatgaaag tcctttccaa aaagaagtta ctgaagcagt atggctttcc  660
agtcccct ccccgagg ggtccagge tgccagcca agcagtgct  720
gccccctggag cgggtgtacc aggagattgc catcctgaag aagctggacc acgtgaatgt  780
ggtcaaactg atcgaggtcc tggatgaccc agctgaggac aacctctatt tggtgtttga  840
cctcctgaga aaggggcccg tcatggaagt gcccctgtgac aagcccttct cggaggcca  900
agctcgcctc tacctgcggg acgtcatcct gggcctcgag tacttgcact gccagaagat  960
cgtccacagg gacatcaagc catccaacct gctcctgggg gatgatgggc acgtgaagat 1020
```

```
cgccgacttt ggcgtcagca accagtttga ggggaacgac gctcagctgt ccagcacggc    1080
gggaacccca gcattcatgg cccccgaggc catttctgat tccggccaga gcttcagtgg    1140
gaaggccttg gatgtatggg ccactggcgt cacgttgtac tgctttgtct atgggaagtg    1200
cccattcatc gacgatttca tcctggccct ccacaggaag atcaagaatg agcccgtggt    1260
gtttcctgag gagccagaaa tcagcgagga gctcaaggac ctgatcctga agatgttaga    1320
caagaatccc gagacgagaa ttggggtgcc agacatcaag ttgcacccct gggtgaccaa    1380
gaacggggag gagcccttc cttcggagga ggagcactgc agcgtggtgg aggtgacaga    1440
ggaggaggtt aagaactcag tcaggctcat ccccagctgg accacggtga tcctggtgaa    1500
gtccatgctg aggaagcgtt cctttgggaa cccgtttgag ccccaagcac ggagggaaga    1560
gcgatccatg tctgctccag gaaacctact ggtgaaagaa gggtttggtg aaggggcaga    1620
gagcccagag ctccccggcg tccaggaaga cgaggctgca tcctgagccc ctgcatgcac    1680
ccagggccac ccggcagcac actcatcccg cgcctccaga ggcccacccc tcatgcaaca    1740
gccgccccg caggcagggg gctggggact gcagcccac tcccgcccct cccccatcgt    1800
gctgcatgac ctccacgcac gcacgtccag ggacagctgg gaatgtatgt catttgggt    1860
cttgggggca gggctccac gaggccatcc tcctcttctt ggacctcctt ggcctggaccc    1920
attctgtggg gaaaccgggt gcccatggag cctcagaaat gccacccggc tggttggcat    1980
ggcctggggc aggaggcaga ggcaggagac caagatggca ggtggaggcc aggcttacca    2040
caacggaaga gacctcccgc tggggccggg caggcctggc tcagctgcca caggcatatg    2100
gtggagaggg gggtaccctg cccaccttgg ggtggtggca ccagagctct tgtctattca    2160
gacgctggta tggggctcg gacccctcac tggggacagg gccagtgttg gagaattctg    2220
attccttttt tgttgtcttt tactttttgtt tttaacctgg gggttcgggg agaggccctg    2280
cttgggaaca tctcacgagc tttcctacat cttccgtggt tcccagcaca gcccaagatt    2340
atttggcagc caagtggatg gaactaactt tcctggactg tgtttcgcat tcggcgttat    2400
ctggaaagtg gactgaacgg aatcaagctc tgagcagagg cctgaagcgg aagcaccaca    2460
tcgtccctgc ccatctcact ctctcccttg atgatgcccc tagagctgag gctggagaag    2520
acaccaggc tgactttgac cgagggccat ggacgcgaca ggcctgtgc cctgcgcag    2580
ctgaaataac tggaacccag cctctcctcc tacaccggcc tacccatctg ggcccaagag    2640
ctgcactcac actcctacaa cgaaggacaa actgtccagg tcggagggat cacgagacac    2700
agaacctgga ggggtgtgca cgctggcagg tggcctctgc ggcaattgcc tcaccctgag    2760
gacatcagca gtcagcctgc tcagagcggg ggtgctggga cgcgtgcaga cacagctctt    2820
ccggagcagc cttcacccttc tctctgggat cagtgtccgg ctggccgacg tggcatttgc    2880
tgaccgaatg ctcatagagg ttgacccca cagggtcacg caggactcgg acactgccct    2940
ggaaacatga tggacaagg gcttttggcc acaggtgtgg gtgtcctgtt ggaggagggc    3000
ttgtttggag aagggaggct ggctggggga gaaacccga tcccgctgca tctccgcgcc    3060
tgtgggtgca tgtcgcgtgc tcatctgttg cacacagctc actcgtatgt cctgcactgg    3120
tacatgcatc tgtaatacag tttctacgtc tatttaaggc taggagccga atgtgcccca    3180
ttgtcagtgg gtccacgttt ctccccggct cctctgggct aaggcagtgt ggcccgaagc    3240
ttaaaaagtt actcggtact gtttttaaga acactttat agagttagtg gaaggcaagt    3300
taagagccaa tcactgatcc ccaagtgttt cttgagcatc tggtctgggg gaccacttt    3360
gatcggaccc acccttggaa agctcagggg taggcccagg tgggatgctc accctgtcac    3420
tgagggtttt ggttggcatc gttgtttttg aatgtagcac aagcgatgag caaactctat    3480
aagagtgttt taaaaattaa cttcccagga agtgagttaa aaacaataaa agcccttct    3540
tgagttaaaa agaaaaaaaa aaaaaaaaaa aaaaaaaaaa aaa    3583

SEQ ID NO: 54          moltype = AA  length = 505
FEATURE                Location/Qualifiers
source                 1..505
                       mol_type = protein
                       organism = Homo sapiens
SEQUENCE: 54
MEGGPAVCCQ DPRAELVERV AAIDVTHLEE ADGGPEPTRN GVDPPPRARA ASVIPGSTSR    60
LLPARPSLSA RKLSLQERPA GSYLEAQAGP YATGPASHIS PRAWRRPTIE SHHVAISDAE   120
DCVQLNQYKL QSEIGKGAYG VVRLAYNESE DRHYAMKVLS KKKLLKQYGF PRRPPPRGSQ   180
AAQGGPAKQL LPLERVYQEI AILKKLDHVN VVKLIEVLDD PAEDNLYLVF DLLRKGPVME   240
VPCDKPFSEE QARLYLRDVI LGLEYLHCQK IVHRDIKPSN LLLGDDGHVK IADFGVSNQF   300
EGNDAQLSST AGTPAFMAPE AISDSGQSFS GKALDVWATG VTLYCFVYGK CPFIDDFILA   360
LHRKIKNEPV VFPEEPEISE ELKDLILKML DKNPETRIGV PDIKLHPWVT KNGEEPLPSE   420
EEHCSVVEVT EEEVKNSVRL IPSWTTVILV KSMLRKRSFG NPFEPQARRE ERSMSAPGNL   480
LVKEGFGEGG KSPELPGVQE DEAAS   505

SEQ ID NO: 55          moltype = DNA  length = 3529
FEATURE                Location/Qualifiers
source                 1..3529
                       mol_type = genomic DNA
                       organism = Homo sapiens
SEQUENCE: 55
agcagaacag agtatgcaat ttgggaagct gtggtgtggc tgcagtggag agttcccaac    60
aaggctacgc agaagaaccc ccttgactga agcaatggag ggggtccag ctgtctgctg   120
ccaggatcct cgggcagagc tggtagaacg ggtgacgac atgatgtga ctcacttgga   180
ggaggcagat ggtggcccag agcctactag aaacggtgtg gacccccac acgggccag   240
agctgcctct gtgatccctg gcagtacttc aagactgctc ccagcccggc ctagcctctc   300
agccaggaag ctttccctac aggagcggcc agcaggaagc tatctggagg cgcaggctgg   360
gccttatgcc acggggcctg ccagccacat ctccccccgg gcctggcgga ggcccaccat   420
cgagtcccac cacgtggcca tctcagatgc agaggactgg gtgcaggtga accagtacaa   480
gctgcagagt gagattggca agggtgccta cggtgtggtg aggctggcct acaacgaaag   540
tgaagacaga cactatgcaa tgaaagtcct ttccaaaaag aagttactga agcagtatgg   600
cttttccacgt cgcccccccc cgagagggtc ccaggctgcc cagggaggac cagccaagca   660
gctgctgccc ctggagcggg tgtaccagga gattgccatc ctgaagaagc tggaccacgt   720
gaatgtggtc aaactgatcg aggtcctgga tgacccagct gaggacaacc tctatttggt   780
```

```
gtttgacctc ctgagaaagg ggcccgtcat ggaagtgccc tgtgacaagc ccttctcgga    840
ggagcaagct cgcctctacc tgcgggacgt catcctgggc ctcgagtact tgcactgcca    900
gaagatcgtc cacagggaca tcaagccatc caacctgctc ctgggggatg atgggcacgt    960
gaagatcgcc gactttggcg tcagcaacca gtttgagggg aacgacgctc agctgtccag   1020
cacggcggga accccagcat tcatggcccc cgaggccatt tctgattccg gccagagctt   1080
cagtgggaag gccttggatg tatgggccac tggcgtcacg ttgtactgct ttgtctatgg   1140
gaagtgccca ttcatcgacg atttcatcct ggccctccac aggaagatca agaatgagcc   1200
cgtggtgttt cctgaggagc cagaaatcag cgaggagctc aaggacctga tcctgaagat   1260
gttagacaag aatcccgaga cgagaattgg ggtgccagac atcaagttgc acccttgggt   1320
gaccaagaac gggggaggagc cccttccttc ggaggaggag cactgcagcg tggtggaggt   1380
gacagaggag gaggttaaga actcagtcag gctcatcccc agctggacca cggtgatcct   1440
ggtgaagtcc atgctgagga agcgttcctt tgggaacccg tttgagcccc aagcacggag   1500
ggaagagcga tccatgtctg ctccaggaaa cctactggtg aaagaagggt ttggtgaagg   1560
gggcaagagc ccagagctcc ccggcgtcca gaaagcagg gctgcatcct gagcccctgc   1620
atgcacccag ggccaccgg cagcacactc atcccgcgcc tccagaggcc caccctcat    1680
gcaacagccg ccccgcagg cagggggctg ggactgcag cccactccc gccctcccc     1740
catcgtgctg catgacctcc acgcacgcac gtccaggac agactggaat gtatgtcatt   1800
tggggtcttg ggggcagggc tcccacgagg ccatcctcct cttcttggac ctccttggcc   1860
tgacccattc tgtggggaaa ccgggtgccc atggagcctc agaaatgcca cccggctggt   1920
tggcatggcc tggggcagga ggcagaggca ggagaccaag atggcaggtg gaggccaggc   1980
ttaccacaac ggaagagacc tcccgctggg gccgggcagg cctggctcag ctgccacagg   2040
catatggtgg agaggggggt accctgccca ccttgggtg gtggcaccag agctcttgtc   2100
tattcagacg ctggtatggg ggctcggacc cctcactggg gacagggcca gtgttggaga   2160
attctgattc cttttttgtt gtctttact tttgttttta acctgggggt tcggggagag   2220
gccctgcttg ggaacatctc acgagctttc ctacatcttc cgtggttccc agcacagccc   2280
aagattattt ggcagccaag tggatggaac taactttcct gactgtgtt tcgcattcgg   2340
cgttatctgg aaagtggact gaacggaatc aagctctgag cagaggcctg aagcggaagc   2400
accacatcgt ccctgcccat ctcactctct cccttgatga tgcccctaga gctgaggctg   2460
gagaagacac cagggctgac tttgaccgag ggccatggac gcgacaggcc tgtgccctg    2520
cgcatgctga aataactgga acccagcctc tcctcctaca ccggcctacc catctgggcg   2580
caagagctgc actcacactc ctacaacgaa ggacaaactg tccaggtcgg agggatcacg   2640
agacacagaa cctggagggg tgtgcacgct ggcaggtggc ctctgcggca attgcctcac   2700
cctgaggaca tcagcagtca gcctgctcag agcgggggtg ctggagcgcg tgcagacaca   2760
gctcttccgg agcagccttc accttctctc tgggatcagt gtccggctgg ccgacgtggc   2820
atttgctgac cgaatgctca tagaggttga ccccacagg gtcaccgagg actcggacac   2880
tgccctggaa acatggatgg acaagggctt ttggccacag gtgtgggtgt cctgttggag   2940
gagggcttgt ttggagaagg gaggctggct gggggagaaa cccggatccc gctgcatctc   3000
cgcgcctgtg ggtgcatgtc gcgtgctcat ctgttgcaca cagctcactc gtatgtcctg   3060
cactggtaca tgcatctatt atacagtttc tacgtctatt taaggctagg agccgaatgt   3120
gccccattgt cagtgggtcc acgtttctcc ccggctcctc tgggctaagg cagtgtggcc   3180
cgaagcttaa aaagttactc ggtactgttt taagaacac ttttatagag ttagtggaag    3240
gcaagttaag agccaatcac tgatcccaa gtgtttcttg agcatctggt ctgggggac     3300
cactttgatc ggacccaccc ttggaaagct caggggtagg cccaggtggg atgctcaccc   3360
tgtcactgag ggttttggtt ggcatcgttg ttttgaatg tagcacaagc gatgagcaaa    3420
ctctataaga gtgttttaaa aattaacttc ccaggaagtg agttaaaaac aataaaagcc    3480
ctttcttgag ttaaaagaa aaaaaaaaaa aaaaaaaaa aaaaaaaa                   3529

SEQ ID NO: 56          moltype = AA   length = 532
FEATURE                Location/Qualifiers
source                 1..532
                       mol_type = protein
                       organism = Homo sapiens
SEQUENCE: 56
MQFGKLWCGC SGEFPTRLRR RTPLTEAMEG GPAVCCQDPR AELVERVAAI DVTHLEEADG    60
GPEPTRNGVD PPPRARAASV IPGSTSRLLP ARPSLSARKL SLQERPAGSY LEAQAGPYAT   120
GPASHISPRA WRRPTIESHH VAISDAEDCV QLNQYKLQSE IGKGAYGVVR LAYNESEDRH   180
YAMKVLSKKK LLKQYGFPRR PPPRGSQAAQ GGPAKQLLPL ERVYQEIAIL KKLDHVNVVK   240
LIEVLDDPAE DNLYLVFDLL RKGPVMEVPC DKPFSEEQAR LYLRDVILGL EYLHCQKIVH   300
RDIKPSNLLL GDDGHVKIAD FGVSNQFEGN DAQLSSTAGT PAFMAPEAIS DSGQSFSGKA   360
LDVWATGVTL YCFVYGKCPF IDDFILALHR KIKNEPVVFP EEPEISEELK DLILKMLDKN   420
PETRIGVPDI KLHPWVTKNG EEPLPSEEEH CSVVEVTEEE VKNSVRLIPS WTTVILVKSM   480
LRKRSFGNPF EPQARREERS MSAPGNLLVK EGFGEGGKSP ELPGVQEDEA AS           532

SEQ ID NO: 57          moltype = DNA   length = 2535
FEATURE                Location/Qualifiers
source                 1..2535
                       mol_type = genomic DNA
                       organism = Homo sapiens
SEQUENCE: 57
ctgggcccca gcgaggcggt ggggcggggc ggggcggggc ggggcgcgca gcaggagcga     60
gtggggccgc ccgccgggcc gcggacactg tcgcccggcg cccaggttcc caacaaggct    120
acgcagaaga accccttga ctgaagcaat ggaggggggt ccagctgtct gctgccagga     180
tcctcgggca gagctggtag aacgggtggc agccatcgat gtgactcact ggaggaggc     240
agatggtgga ccgagagccta ctagaaacgg tgtggaccccc gccaccaggg cagagctgg   300
ctctgtgatc cctggcagta cttcaagact gctcccagcc cggcctagcc tctcagcag    360
gaagctttcc ctacaggagc ggccagcagg aagctatctg gaggcgcagg ctgggcctta   420
tgccacgggg cctgccagcc acatctcccc ccggcctgg cggaggccca ccatcgtc      480
ccaccacgtg gccatctcag atgcagagga ctgcgtgcag ctgaaccagt acaagctgca   540
gagtgagatt ggcaagggtg cctacggtgt ggtgaggctg gcctacaacg aaagtgaaga   600
```

```
cagacactat gcaatgaaag tcctttccaa aaagaagtta ctgaagcagt atggctttcc    660
acgtcgccct cccccgagag ggtcccaggc tgcccaggga ggaccagcca agcagctgct    720
gcccctggag cgggtgtacc aggagattgc catcctgaag aagctggacc acgtgaatgt    780
ggtcaaactg atcgaggtcc tggatgaccc agctgaggac aacctctatt tggccctgca    840
gaaccaggcc cagaatatcc agttagattc aacaaatgcc gccaagcccc actccctgct    900
tccctctgag cagcaagaca gtggatccac gtgggctgcg cgctcagtgt ttgacctcct    960
gagaaagggg cccgtcatgg aagtgccctg tgacaagccc ttctcggagg agcaagctcg   1020
cctctacctg cgggacgtca tcctgggcct cgagtacttg cactgccaga gatcgtcca   1080
cagggacatc aagccatcca acctgctcct gggggatgat gggcacgtga agatcgccga   1140
ctttggcgtc agcaaccagt ttgagggaa cgacgctcag ctgtccagca cggcgggaac   1200
cccagcattc atggccccg aggccatttc tgattccggc cagagcttca gtgggaaggc   1260
cttggatgta tgggccactg gcgtcacgtt gtactgcttt gtctatggga agtgcccatt   1320
catcgacgat ttcatcctgg ccctccacag gaagatcaag aatgagcccg tggtgtttcc   1380
tgaggagcca gaaatcagcg aggagctcaa ggacctgatc ctgaagatgt tagacaagaa   1440
tcccgagacg agaattgggg tgccagacat caagttgcac ccttgggtga ccaagaacgg   1500
ggaggagccc cttccttcgg aggaggagca ctgcagcgtg gtggaggtga caggaggagga   1560
ggttaagaac tcagtcaggc tcatcccag ctggaccacg gtgatcctgg tgaagtccat   1620
gctgaggaag cgttcctttg gaaccccaa tgagcccccaa gcacggaggg aagagcgatc   1680
catgtctgct ccaggaaacc tactggtgta agtactggtg gccaggagac tgccgggcac   1740
tccctgagt tggtgggga ggtctgaggc ccatcctccc actctcactg tcgttgggcc   1800
aaggccagag cctggggact tggccaggtc tcggtgttgg ccccatttgc atctctgtcc   1860
ccaaggttag tcgggctag aagggacctt ttgggcccag ctcttgcttc attcctgggg   1920
ccagcatccc tcacacacac acttccaggg atgaggagct cacgcagccc ctccatggga   1980
caggaagacc cttcttccat gcagcttgat gtcactctct cactgggtcc agcccctctg   2040
gggcttcaaa tctgtggccc cctcagccct tgcagcctg cagaggttt gcagacaggc   2100
tgatgttggc ttcctgtagg aggctggcgg gctgtagagg aggggtgctg ggccctgctg   2160
ctggccctgg ggactgttgg ctgctctccc aagtgcccca ggctgcctgc agccattgct   2220
ggggctctgt gcccagtcag cactttgtga gtgcttgttc agtgagtaag cagggacagg   2280
ctggccggtg gaccacggga gaggaaccccg cattggccga gggctcccta tggtgagcca   2340
cgcctgtggg ttcaccacct cctaggaggg tccagaaaag cagctcccca agcctgtgcg   2400
cctcgtcctc agcagatcca ccttcttcac tataataaaaa gccagtctgg gatgctaaaa   2460
aaaaaaaaaa aaaaaaaaaa aaaaaaaaaa aaaaaaaaaa aaaaaaaaaa aaaaaaaaaa   2520
aaaaaaaaaa aaaaa                                                   2535

SEQ ID NO: 58           moltype = AA   length = 520
FEATURE                 Location/Qualifiers
source                  1..520
                        mol_type = protein
                        organism = Homo sapiens
SEQUENCE: 58
MEGGPAVCCQ DPRAELVERV AAIDVTHLEE ADGGPEPTRN GVDPPPRARA ASVIPGSTSR    60
LLPARPSLSA RKLSLQERPA GSYLEAQAGP YATGPASHIS PRAWRRPTIE SHHVAISDAE   120
DCVQLNQYKL QSEIGKGAYG VVRLAYNESE DRHYAMKVLS KKKLLKQYGF PRRPPPRGSQ   180
AAQGGPAKQL LPLERVYQEI AILKKLDHVN VVKLIEVLDD PAEDNLYLAL QNQAQNIQLD   240
STNIAKPHSL LPSEQQDSGS TWAARSVFDL LRKGPVMEVP CDKPFSEEQA RLYLRDVILG   300
LEYLHCQKIV HRDIKPSNLL LGDDHVKIA DFGVSNQFEG NDAQLSSTAG TPAFMAPEAI   360
SDSGQSFSGK ALDVWATGVT LYCFVYGKCP FIDDFILALH RKIKNEPVVF PEEPEISEEL   420
KDLILKMLDK NPETRIGVPD IKLHPWVTKN GEEPLPSEEE HCSVVEVTEE EVKNSVRLIP   480
SWTTVILVKS MLRKRSFGNP FEPQARREER SMSAPGNLLV                        520

SEQ ID NO: 59           moltype = DNA   length = 1153
FEATURE                 Location/Qualifiers
source                  1..1153
                        mol_type = genomic DNA
                        organism = Homo sapiens
SEQUENCE: 59
gaaaacacca aatcaaccat aggtccaaga acaattgtct ctggacggca gctatgcgac    60
tcaccgtgct gtgtgctgtg tgcctgctgc ctggcagcct ggcctgccg ctgcctcagg   120
aggcgggagg catgagtgag ctacagtggg aacaggctca ggactatctc aagagatttt   180
atctctatga ctcagaaaca aaaatgcca acagtttaga agccaaactc aaggagatgc   240
aaaaattctt tggcctacct ataactgaa tgttaaactc ccgcgtcata gaaataatgc   300
agaagcccag atgtggagtg ccagatgttg cagaatactc actatttcca aatagcccaa   360
aatggacttc caaagtggtc acctacagga tcgtatcata tactcgagac ttaccgcata   420
ttacagtgga tcgattagtg tcaaaggctt taaacatgtg gacggcaagag atccccctga   480
atttcaggaa agttgtatgg ggaactgctg acatcatgat tggctttgcg cgaggagctc   540
atggggactc ctaccatttt gatgggccag gaaacacggt ggctcatgcc tttgcgcctg   600
ggacaggtct cggaggagat gctcacttcg atgaggatga acgctggacg gatggtagca   660
gtctagggat taacttcctg tatgctgcaa ctcatgaact tggccattct ttgggtatgg   720
gacattcctc tgatcctaat gcagtgatgt atccaacta tggaaatgga gatccccaaa   780
attttaaact ttcccaggat gatattaaag gcattcagaa actatatgga aagagaagta   840
attcaagaaa gaaatagaaa cttcaggcag aacatccatt cattcattca ttggattgta   900
tatcattgtt gcacaatcag aattgataag cactgttcct ccactccatt tagcaattat   960
gtcaccctt tttattgcag ttggttttttg aatgtctttc actccttta aggataaact  1020
ccttatggt gtgactgtgt cttattcatc tatacttgca gtgggtagat gtcaataaat  1080
gttacataca caaataaata aaatgtttat tccatgtaa atttaaaaaa aaaaaaaaaa  1140
aaaaaaaaaa aaa                                                    1153

SEQ ID NO: 60           moltype = AA   length = 267
FEATURE                 Location/Qualifiers
```

```
source              1..267
                    mol_type = protein
                    organism = Homo sapiens
SEQUENCE: 60
MRLTVLCAVC LLPGSLALPL PQEAGGMSEL QWEQAQDYLK RFYLYDSETK NANSLEAKLK    60
EMQKFFGLPI TGMLNSRVIE IMQKPRCGVP DVAEYSLFPN SPKWTSKVVT YRIVSYTRDL   120
PHITVDRLVS KALNMWGKEI PLHFRKVVWG TADIMIGFAR GAHGDSYPFD GPGNTLAHAF   180
APGTGLGGDA HFDEDERWTD GSSLGINFLY AATHELGHSL GMGHSSDPNA VMYPTYGNGD   240
PQNFKLSQDD IKGIQKLYGK RSNSRKK                                      267

SEQ ID NO: 61       moltype = DNA  length = 451
FEATURE             Location/Qualifiers
source              1..451
                    mol_type = genomic DNA
                    organism = Homo sapiens
SEQUENCE: 61
gggttgcgga gggtgggcct gggaggggtg gtggccattt tttgtctaac cctaactgag    60
aagggcgtag gcgccgtgct tttgctcccc gcgcgctgtt tttctcgctg actttcagcg   120
ggcggaaaag cctcggcctg ccgccttcca ccgttcattc tagagcaaac aaaaaatgtc   180
agctgctggc ccgttcgccc ctcccgggga cctgcggcgg gtcgcctgcc cagccccga   240
acccccgcctg gaggccgcgg tcggcccggg gcttctccgg aggcacccac tgccaccgcg   300
aagagttggg ctctgtcagc cgcgggtctc tcgggggcga gggcgaggtt caggcctttc   360
aggccgcagg aagaggaacg gagcgagtcc ccgcgcgcgg cgcgattccc tgagctgtgg   420
gacgtgcacc caggactcgg ctcacacatg c                                 451
```

BIOMARKERS FOR THE DIAGNOSIS AND TREATMENT OF FIBROTIC LUNG DISEASE

RELATED APPLICATIONS

This application is a continuation of U.S. patent application Ser. No. 16/624,500, filed Dec. 19, 2019, which application is a National Stage Application, filed under 35 U.S.C. § 371, of PCT/US2018/039573, filed Jun. 26, 2018, which claims the benefit of provisional application U.S. Ser. No. 62/525,087, filed Jun. 26, 2017 and U.S. Ser. No. 62/525,088, filed Jun. 26, 2017, the contents of each of which are herein incorporated by reference in their entirety.

GOVERNMENT SUPPORT

This invention was made with government support under grant number HL097163, HL123442, and HL138131 awarded by National Institutes of Health and grant number W81XWH-17-1-0597 awarded by Department of Defense. The government has certain rights in the invention.

INCORPORATION OF SEQUENCE LISTING

The Sequence Listing XML associated with this application is provided electronically in XML format and is hereby incorporated by reference into the specification. The name of the XML file containing the Sequence Listing XML is "UNCO-018_C01US_SeqList_ST26.xml". The XML file is 227,030 bytes, created on Sep. 7, 2022, and is being submitted electronically via USPTO Patent Center.

FIELD OF THE DISCLOSURE

The disclosure is directed to molecular biology, genetics, and therapeutics for fibrotic lung disease.

BACKGROUND

Fibrotic pulmonary diseases are progressive and irreversible. Standard therapies are mere palliative as they cannot address the underlying disease mechanism once the subject has progressed to a point at which symptoms are present. Thus, there is a long-felt but unmet need in the field for a method of treating asymptomatic subjects as well as those who are at risk of developing fibrotic pulmonary diseases to prevent onset of the disease, delay onset of the disease, or reduce the severity of disease symptoms. The methods of the disclosure provide a preventative or efficacious treatment, as opposed to a merely palliative treatment, for asymptomatic subjects as well as those subjects at risk of developing the disease.

SUMMARY

The disclosure provides a method of treating a fibrotic lung disease in a subject comprising administering to the subject an effective amount of a therapeutic agent, wherein the subject is asymptomatic and wherein the subject is at risk of developing the fibrotic lung disease.

In some embodiments of the methods of the disclosure, the subject presents radiographic Usual Interstitial Pneumonia (UIP). In some embodiments, the subject has fibrotic interstitial lung disease (FILD). In some embodiments, the subject has a blood relative with familial interstitial pneumonia (FIP). In some embodiments, including those embodiments wherein the subject has a blood relative with familial interstitial pneumonia (FIP), the blood relative is a sibling. Alternatively, or in addition, in some embodiments, the subject has a mutation in a sequence encoding Mucin 5B (MUC5B), Telomerase RNA Component (TERC), Family with sequence similarity 13 member A (FAM13A), Telomerase Reverse Transcriptase (TERT), Desmoplakin (DSP), Zinc-alpha 2-Glycoprotein 1 (AZGP1), Oligonucleotide/oligosaccharide-binding Fold Containing 1 (OBFC1), ATPase Phospholipid Transporting 11A (ATP11A), Isovaleryl-CoA dehydrogenase (IVD)/Dispatched RND Transporter Family Member 2 (DISP2), Dipeptidyl Peptidase 9 (DPP9), Sialic Acid Binding Ig-Like Lectin 14 (SIGLEC14), Adrenomedullin 2 (ADM2), Tetraspanin 5 (TSPAN5), Calcium/Calmodulin-Dependent Protein Kinase 1 (CAMKK1), zinc finger with KRAB and SCAN domains 1 (ZKSCAN1), isovaleryl-CoA dehydrogenase (IVD), ATPase phospholipid transporting 11A (AK025511) or Matrix Metalloprotease-7 (MMP-7).

In some embodiments of the methods of the disclosure, the subject has a mutation in a sequence encoding MUC5B, TERC, FAM13A, TERT, DSP, AZGP1, OBFC1, ATP11A, IVD/DISP2, DPP9, SIGLEC14, ADM2, TSPAN5, CAMKK1 or MMP-7.

In some embodiments of the methods of the disclosure, the subject has a mutation in a nucleic acid or amino acid sequence encoding a gene or gene product that is upregulated in a subject having a fibrotic pulmonary disease of the disclosure. In some embodiments of the methods of the disclosure, the subject has a mutation in a nucleic acid or amino acid sequence encoding Leukotriene A4 Hydrolase (LTA4H), Surfactant Protein B (SFTPB), Breast Cancer Anti-Estrogen Resistance 3 (BCAR3), C-X-C motif Chemokine Ligand 13 (CXCL13), EPH Receptor A2 (EPHA2), Serum Amyloid A1 (SAA1), Phospholipase A2 Group IIA (PLA2G2A), Insulin-Like Growth Factor Binding Protein 3 (IGFBP3), C-C Motif Chemokine Ligand 28 (CCL28), S100 Calcium Binding Protein A12 (S100A12), Thromboxane A Synthase 1 (TBXAS1), Leukocyte Cell Derived Chemotaxin 1 (LECT1), Complement C3 (C3), Gastrin Releasing Peptide (GRP), C-Reactive Protein (CRP), Vitrin (VIT), Insulin-Like Growth Factor Binding Protein 1 (IGFBP1), Family with Sequence Similarity 173 Member A (FAM173A), Natriuretic Peptide A (NPPA), Secreted Frizzled Related Protein 1 (SFRP1), Ezrin (EZR), Inter-Alpha-Trypsin Inhibitor Heavy Chain Family Member 5 (ITIH5), Pleckstrin and Sec7 Domain Containing 2 (PSD2), Galectin 3 Binding Protein (LGALS3BP), Catenin Beta 1 (CTNNB1), Chromodomain Y Like 2 (CDYL2), Matrix Metallopeptidase 7 (MMP7), Apolipoprotein B (APOB), Proline and Arginine Rich End Leucine Rich Repeat Protein (PRELP), Eukaryotic Translation Initiation Factor 1A, X-linked (EIF1AX), Mesencephalic Astrocyte Derived Neurotrophic Factor (MANF), TNF Receptor Superfamily Member 13C (TNFRSF13C), Deformed Epidermal Autoregulatory Factor 1 transcription factor (DEAF1), Tumor Protein Translationally-Controlled 1 (TPT1), Unc-5 Netrin Receptor B (UNC5B), Phosphatidylethanolamine Binding Protein 1 (PEBP1), Syntaxin 8 (STX8), Polymeric Immunoglobulin Receptor (PIGR), Adenine Phosphoribosyltransferase (APRT), Matrix Metallopeptidase 3 (MMP3), Galectin 7 (LGALS7), Bruton Tyrosine Kinase (BTK), NSFL1 Cofactor (NSFL1C), FER Tyrosine Kinase (FER), Regenerating Family Member 1 Beta (REG1B), SMAD Family Member 2 (SMAD2), Interleukin 1 Receptor Like 1 (IL1RL1), C-C Motif Chemokine Ligand 18 (CCL18), Acid Phosphatase 2 Lysosomal (ACP2), Eukaryotic Translation Initiation Factor 4E Family Member 2 (EIF4E2), Neurexin 3 (NRXN3), IGF Like Family Member 1 (IGFL1), NME/NM23 Nucleoside Diphosphate Kinase 1 (NME1), Potassium Voltage-Gated Channel Isk-Related Family Member 1-Like (KCNE1L) or Neurexophilin 2 (NXPH2).

In some embodiments of the methods of the disclosure, the subject has a mutation in a nucleic acid or amino acid sequence encoding a gene or gene product that is down-regulated in a subject having a fibrotic pulmonary disease of the disclosure. In some embodiments of the methods of the disclosure, the subject has a mutation in a nucleic acid or amino acid sequence encoding Surfactant Protein D (SFTPD), Glyceraldehyde-3-Phosphate Dehydrogenase (GAPDH), Histone Cluster 1 H1 Family Member C (HIST1H1C), YTH Domain Containing 1 (YTHDC1), Plexin A1 (PLXNA1), Serine Peptidase Inhibitor Kazal Type 6 (SPINK6), LDL Receptor Related Protein Associated Protein 1 (LRPAP1), Secretoglobin Family 3A Member 1 (SCGB3A1), H2A Histone Family Member Z (H2AFZ) or Chromosome 1 Open Reading Frame 162 (C1orf162).

In some embodiments of the methods of the disclosure, the subject has a mutation in a sequence encoding MUC5B. In some embodiments, the mutation is a polymorphism in a sequence encoding a MUC5B promoter. In some embodiments, the polymorphism is rs35705950 comprising (SEQ ID NO: 7).

In some embodiments of the methods of the disclosure, the human subject has a mutation in a sequence encoding TERC. In some embodiments, the mutation is a polymorphism in a sequence encoding TERC or a regulatory sequence thereof. In some embodiments the polymorphism is rs6793295 comprising (SEQ ID NO: 1).

In some embodiments of the methods of the disclosure, the human subject has a mutation in a sequence encoding intronic FAM13A. In some embodiments, the mutation is a polymorphism in a sequence encoding intronic FAM13A or a regulatory sequence thereof. In some embodiments, the polymorphism is rs2609260.

In some embodiments of the methods of the disclosure, the human subject has a mutation in a sequence encoding intronic TERT. In some embodiments, the mutation is a polymorphism in a sequence encoding intronic TERT or a regulatory sequence thereof. In some embodiments, the polymorphism is rs4449583.

In some embodiments of the methods of the disclosure, the human subject has a mutation in a sequence encoding intronic DSP. In some embodiments, the mutation is a polymorphism in a sequence encoding intronic DSP or a regulatory sequence thereof. In some embodiments, the polymorphism is rs2076295.

In some embodiments of the methods of the disclosure, the human subject has a mutation in a sequence encoding intronic ZKSCAN1. In some embodiments, the mutation is a polymorphism in a sequence encoding intronic ZKSCAN1 or a regulatory sequence thereof. In some embodiments, the polymorphism is rs6963345.

In some embodiments of the methods of the disclosure, the human subject has a mutation in a sequence encoding intronic OBFC1. In some embodiments, the mutation is a polymorphism in a sequence encoding intronic OBFC1 or a regulatory sequence thereof. In some embodiments, the polymorphism is rs2488000.

In some embodiments of the methods of the disclosure, the human subject has a mutation in a sequence encoding an AK025511 3' UTR. In some embodiments, the mutation is a polymorphism in a sequence encoding an AK025511 3' UTR or a regulatory sequence thereof. In some embodiments, the polymorphism is rs1278769.

In some embodiments of the methods of the disclosure, the human subject has a mutation in a sequence encoding IVD. In some embodiments, the mutation is a polymorphism in a sequence encoding intronic IVD or a regulatory sequence thereof. In some embodiments, the polymorphism is rs35700143.

In some embodiments of the methods of the disclosure, the human subject has a mutation in a sequence encoding intronic DPP9. In some embodiments, the mutation is a polymorphism in a sequence encoding intronic DPP9 or a regulatory sequence thereof. In some embodiments, the polymorphism is rs12610495.

In some embodiments of the methods of the disclosure, the subject has a mutation in a sequence encoding FAM13A. In some embodiments, the mutation is a polymorphism in a sequence encoding FAM13A or a regulatory sequence thereof. In some embodiments the polymorphism is rs2609255 comprising (SEQ ID NO: 2).

In some embodiments of the methods of the disclosure, the subject has a mutation in a sequence encoding TERT. In some embodiments, the mutation is a polymorphism in a sequence encoding TERT or a regulatory sequence thereof. In some embodiments the polymorphism is rs2736100 comprising (SEQ ID NO: 3).

In some embodiments of the methods of the disclosure, the subject has a mutation in a sequence encoding DSP. In some embodiments, the mutation is a polymorphism in a sequence encoding DSP or a regulatory sequence thereof. In some embodiments the polymorphism is rs2076295 comprising (SEQ ID NO: 4).

In some embodiments of the methods of the disclosure, the subject has a mutation in a sequence encoding AZGP1. In some embodiments, the mutation is a polymorphism in a sequence encoding AZGP1 or a regulatory sequence thereof. In some embodiments the polymorphism is rs4727443 comprising (SEQ ID NO: 5).

In some embodiments of the methods of the disclosure, the subject has a mutation in a sequence encoding OBFC1. In some embodiments, the mutation is a polymorphism in a sequence encoding OBFC1 or a regulatory sequence thereof. In some embodiments the polymorphism is rs11191865 comprising (SEQ ID NO: 6).

In some embodiments of the methods of the disclosure, the subject has a mutation in a sequence encoding ATP11A. In some embodiments, the mutation is a polymorphism in a sequence encoding ATP11A or a regulatory sequence thereof. In some embodiments the polymorphism is rs12787690 comprising (SEQ ID NO: 8).

In some embodiments of the methods of the disclosure, the subject has a mutation in a sequence encoding IVD/DISP2. In some embodiments, the mutation is a polymorphism in a sequence encoding IVD/DISP2 or a regulatory sequence thereof. In some embodiments the polymorphism is rs2034650 comprising (SEQ ID NO: 9).

In some embodiments of the methods of the disclosure, the subject has a mutation in a sequence encoding DPP9. In some embodiments, the mutation is a polymorphism in a sequence encoding DPP9 or a regulatory sequence thereof. In some embodiments the polymorphism is rs12610495 comprising (SEQ ID NO: 10).

In some embodiments of the methods of the disclosure, the fibrotic lung disease is pulmonary fibrosis, idiopathic pulmonary fibrosis (IPF), an interstitial lung abnormality (ILA), or an asymptomatic ILA. In some embodiments, the fibrotic lung disease is pulmonary fibrosis or IPF. In some embodiments, the fibrotic lung disease is IPF.

In some embodiments of the methods of the disclosure, the therapeutic agent comprises a N-acetylcysteine, pirfenidone, and nintedanib.

In some embodiments of the methods of the disclosure, the therapeutic agent comprises pirfenidone. In some embodiments, the effective dosage is administered orally as a capsule or a tablet. In some embodiments, including those embodiments wherein the therapeutic agent comprises pirfenidone, the effective dosage is about 2400 mg/day. In some embodiments, the effective dosage is administered according to an escalating dosage regimen. In some embodiments, including those embodiments wherein the therapeutic agent comprises pirfenidone, the escalating dosage regimen comprises (a) administering to the subject about 800 mg of pirfenidone per day for a first week; (b) administering to the subject about 1600 mg of pirfenidone per day for a second week; and (c) administering to the subject about 2400 mg of pirfenidone per day for the remainder of the treatment. In some embodiments, including those embodiments wherein the therapeutic agent comprises pirfenidone, the escalating dosage regimen comprises (a) administering to the subject a capsule or tablet comprising about 250 mg of pirfenidone three times a day for a first week; (b) administering to the subject two capsules or tablets comprising about 250 mg of pirfenidone three times a day for a second week; and (c) administering to the subject three capsules or tablets comprising about 250 mg of pirfenidone three times a day for the remainder of the treatment. In some embodiments of the escalating dosage regimen, the capsule or tablet comprises 267 mg of pirfenidone.

In some embodiments of the methods of the disclosure, the therapeutic agent comprises nintedanib. In some embodiments, the effective dosage is administered orally as a capsule or a tablet. In some embodiments, including those embodiments wherein the therapeutic agent comprises nintedanib, the effective dosage is about 300 mg/day. In some embodiments, the effective dosage is about 150 mg administered twice per day, wherein the daily doses are administered about 12 hours apart from one another. In some embodiments, including those embodiments wherein the therapeutic agent comprises nintedanib, the effective dosage is about 200 mg/day. In some embodiments, the effective dosage is about 100 mg administered twice per day, wherein the daily doses are administered about 12 hours apart from one another. In some embodiments, including those embodiments wherein the therapeutic agent comprises nintedanib, the effective dosage is administered according to a modified or interrupted dosage regimen. In some embodiments, the modified or interrupted dosage regimen comprises (a) administering to the subject about 300 mg of nintedanib per day until the subject presents an elevated level of liver enzymes compared to a control level of liver enzymes; (b) administering to the subject about 200 mg of nintedanib per day until the subject presents the control level of liver enzymes; and (c) administering to the subject about 300 mg of nintedanib per day for the remainder of the treatment; wherein the control level of liver enzymes is a level detected in the subject prior to an initiation of the treatment. In some embodiments, including those embodiments wherein the therapeutic agent comprises nintedanib, the modified or interrupted regimen comprises (a) administering to the subject a capsule or tablet comprising about 150 mg of nintedanib twice per day until the subject presents an elevated level of liver enzymes compared to a control level of liver enzymes; (b) administering to the subject two capsules or tablets comprising about 100 mg twice per day until the subject presents an elevated level of liver enzymes compared to a control level of liver enzymes; and (c) administering to the subject a capsule or tablet comprising about 150 mg of nintedanib twice per day for the remainder of the treatment; wherein the control level of liver enzymes is a level detected in the subject prior to an initiation of the treatment.

In some embodiments of the methods of the disclosure, the therapeutic agent prevents the onset or development of a sign or symptom of the fibrotic lung disease.

In some embodiments of the methods of the disclosure, the therapeutic agent delays the onset or development of a sign or symptom of the fibrotic lung disease when compared to the expected onset of the sign or symptom in the absence of treatment with the therapeutic agent.

In some embodiments of the methods of the disclosure, the therapeutic agent reduces the severity of a sign or symptom of the fibrotic lung disease when compared to the expected severity of the sign or symptom in the absence of treatment with the therapeutic agent.

In some embodiments of the methods of the disclosure, the therapeutic agent reduces the severity of a sign or symptom of the fibrotic lung disease when compared to the expected severity of the sign or symptom in the absence of treatment with the therapeutic agent.

In some embodiments of the methods of the disclosure, the at least one sign of the fibrotic lung disease is detectable before the subject presents a symptom of the fibrotic lung disease. In some embodiments, the at least one sign comprises gradual or unintended weight loss, clubbing of the fingers or toes, rapid and shallow breathing, fibrotic lesions in one or both lungs detectable by radiography, or a cough. In some embodiments, the symptom comprises shortness of breath during exercise, shortness of breath at rest, a dry and hacking cough, repeated bouts of coughing, and uncontrollable bouts of coughing.

In some embodiments of the methods of the disclosure, the method prevents the onset of a secondary condition associated with a severe form of the fibrotic lung disease. In some embodiments, a secondary condition comprises a collapsed lung, an infected lung, a blood clot in a lung, lung cancer, respiratory failure, pulmonary hypertension, heart failure or death.

The disclosure provides a method of identifying a therapeutic agent or target thereof for the treatment of a fibrotic lung disease, comprising administering to a non-human subject a dose of a composition that modifies transcription or translation of a sequence encoding Mucin 5B (MUC5B), Telomerase RNA Component (TERC), Family with sequence similarity 13 member A (FAM13A), Telomerase Reverse Transcriptase (TERT), Desmoplakin (DSP), Zinc-alpha 2-Glycoprotein 1 (AZGP1), Oligonucleotide/oligosaccharide-binding Fold Containing 1 (OBFC1), ATPase Phospholipid Transporting 11A (ATP11A), Isovaleryl-CoA dehydrogenase (IVD)/Dispatched RND Transporter Family Member 2 (DISP2), Dipeptidyl Peptidase 9 (DPP9), Sialic Acid Binding Ig-Like Lectin 14 (SIGLEC14), Adrenomedullin 2 (ADM2), Tetraspanin 5 (TSPAN5), Calcium/Calmodulin-Dependent Protein Kinase Kinase 1 (CAMKK1) or Matrix Metalloprotease-7 (MMP-7), wherein the dose of the composition is tolerable to the non-human subject and wherein the dose of the composition is therapeutically effective.

In some embodiments of the methods of identifying a therapeutic agent or target thereof for the treatment of a fibrotic lung disease of the disclosure, the method of identifying a therapeutic agent or target thereof for the treatment of a fibrotic lung disease, comprising administering to a non-human subject a composition that modifies an activity of a product of a sequence encoding MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, wherein the dose of the composition is tolerable to the non-human subject and wherein the dose of the composition is therapeutically effective.

In some embodiments of the methods of identifying a therapeutic agent or target thereof for the treatment of a fibrotic lung disease of the disclosure, the composition that modifies transcription or translation decreases or inhibits transcription or translation.

In some embodiments of the methods of identifying a therapeutic agent or target thereof for the treatment of a fibrotic lung disease of the disclosure, the composition decreases or inhibits transcription or translation of a sequence encoding a gene selected from the group consisting of Leukotriene A4 Hydrolase (LTA4H), Surfactant Protein B (SFTPB), Breast Cancer Anti-Estrogen Resistance 3 (BCAR3), C-X-C motif Chemokine Ligand 13 (CXCL13), EPH Receptor A2 (EPHA2), Serum Amyloid A1 (SAA1), Phospholipase A2 Group IIA (PLA2G2A), Insulin-Like Growth Factor Binding Protein 3 (IGFBP3), C-C Motif Chemokine Ligand 28 (CCL28), S100 Calcium Binding Protein A12 (S100A12), Thromboxane A Synthase 1 (TBXAS1), Leukocyte Cell Derived Chemotaxin 1 (LECT1), Complement C3 (C3), Gastrin Releasing Peptide (GRP), C-Reactive Protein (CRP), Vitrin (VIT), Insulin-Like Growth Factor Binding Protein 1 (IGFBP1), Family with Sequence Similarity 173 Member A (FAM173A), Natriuretic Peptide A (NPPA), Secreted Frizzled Related Protein 1 (SFRP1), Ezrin (EZR), Inter-Alpha-Trypsin Inhibitor Heavy Chain Family Member 5 (ITIH5), Pleckstrin and Sec7 Domain Containing 2 (PSD2), Galectin 3 Binding Protein (LGALS3BP), Catenin Beta 1 (CTNNB1), Chromodomain Y Like 2 (CDYL2), Matrix Metallopeptidase 7 (MMP7), Apolipoprotein B (APOB), Proline and Arginine Rich End Leucine Rich Repeat Protein (PRELP), Eukaryotic Translation Initiation Factor 1A, X-linked (EIF1AX), Mesencephalic Astrocyte Derived Neurotrophic Factor (MANF), TNF Receptor Superfamily Member 13C (TNFRSF13C), Deformed Epidermal Autoregulatory Factor 1 transcription factor (DEAF1), Tumor Protein Translationally-Controlled 1 (TPT1), Unc-5 Netrin Receptor B (UNC5B), Phosphatidylethanolamine Binding Protein 1 (PEBP1), Syntaxin 8 (STX8), Polymeric Immunoglobulin Receptor (PIGR), Adenine Phosphoribosyltransferase (APRT), Matrix Metallopeptidase 3 (MMP3), Galectin 7 (LGALS7), Bruton Tyrosine Kinase (BTK), NSFL1 Cofactor (NSFL1C), FER Tyrosine Kinase (FER), Regenerating Family Member 1 Beta (REG1B), SMAD Family Member 2 (SMAD2), Interleukin 1 Receptor Like 1 (IL1RL1), C-C Motif Chemokine Ligand 18 (CCL18), Acid Phosphatase 2 Lysosomal (ACP2), Eukaryotic Translation Initiation Factor 4E Family Member 2 (EIF4E2), Neurexin 3 (NRXN3), IGF Like Family Member 1 (IGFL1), NME/NM23 Nucleoside Diphosphate Kinase 1 (NME1), Potassium Voltage-Gated Channel Isk-Related Family Member 1-Like (KCNE1L) or Neurexophilin 2 (NXPH2).

In some embodiments of the methods of identifying a therapeutic agent or target thereof for the treatment of a fibrotic lung disease of the disclosure, the composition increases or activates transcription or translation of a sequence encoding a gene selected from the group consisting of Surfactant Protein D (SFTPD), Glyceraldehyde-3-Phosphate Dehydrogenase (GAPDH), Histone Cluster 1 H1 Family Member C (HIST1H1C), YTH Domain Containing 1 (YTHDC1), Plexin A1 (PLXNA1), Serine Peptidase Inhibitor Kazal Type 6 (SPINK6), LDL Receptor Related Protein Associated Protein 1 (LRPAP1), Secretoglobin Family 3A Member 1 (SCGB3A1), H2A Histone Family Member Z (H2AFZ) or Chromosome 1 Open Reading Frame 162 (C1orf162).

In some embodiments of the methods of identifying a therapeutic agent or target thereof for the treatment of a fibrotic lung disease of the disclosure, the composition that modifies an activity decreases or inhibits the activity.

In some embodiments of the methods of identifying a therapeutic agent or target thereof for the treatment of a fibrotic lung disease of the disclosure, the composition decreases or inhibits the activity of a sequence encoding a gene selected from Leukotriene A4 Hydrolase (LTA4H), Surfactant Protein B (SFTPB), Breast Cancer Anti-Estrogen Resistance 3 (BCAR3), C-X-C motif Chemokine Ligand 13 (CXCL13), EPH Receptor A2 (EPHA2), Serum Amyloid A1 (SAA1), Phospholipase A2 Group IIA (PLA2G2A), Insulin-Like Growth Factor Binding Protein 3 (IGFBP3), C-C Motif Chemokine Ligand 28 (CCL28), 5100 Calcium Binding Protein A12 (S100A12), Thromboxane A Synthase 1 (TBXAS1), Leukocyte Cell Derived Chemotaxin 1 (LECT1), Complement C3 (C3), Gastrin Releasing Peptide (GRP), C-Reactive Protein (CRP), Vitrin (VIT), Insulin-Like Growth Factor Binding Protein 1 (IGFBP1), Family with Sequence Similarity 173 Member A (FAM173A), Natriuretic Peptide A (NPPA), Secreted Frizzled Related Protein 1 (SFRP1), Ezrin (EZR), Inter-Alpha-Trypsin Inhibitor Heavy Chain Family Member 5 (ITIH5), Pleckstrin and Sec7 Domain Containing 2 (PSD2), Galectin 3 Binding Protein (LGALS3BP), Catenin Beta 1 (CTNNB1), Chromodomain Y Like 2 (CDYL2), Matrix Metallopeptidase 7 (MMP7), Apolipoprotein B (APOB), Proline and Arginine Rich End Leucine Rich Repeat Protein (PRELP), Eukaryotic Translation Initiation Factor 1A, X-linked (EIF1AX), Mesencephalic Astrocyte Derived Neurotrophic Factor (MANF), TNF Receptor Superfamily Member 13C (TNFRSF13C), Deformed Epidermal Autoregulatory Factor 1 transcription factor (DEAF1), Tumor Protein Translationally-Controlled 1 (TPT1), Unc-5 Netrin Receptor B (UNC5B), Phosphatidylethanolamine Binding Protein 1 (PEBP1), Syntaxin 8 (STX8), Polymeric Immunoglobulin Receptor (PIGR), Adenine Phosphoribosyltransferase (APRT), Matrix Metallopeptidase 3 (MMP3), Galectin 7 (LGALS7), Bruton Tyrosine Kinase (BTK), NSFL1 Cofactor (NSFL1C), FER Tyrosine Kinase (FER), Regenerating Family Member 1 Beta (REG1B), SMAD Family Member 2 (SMAD2), Interleukin 1 Receptor Like 1 (IL1RL1), C-C Motif Chemokine Ligand 18 (CCL18), Acid Phosphatase 2 Lysosomal (ACP2), Eukaryotic Translation Initiation Factor 4E Family Member 2 (EIF4E2), Neurexin 3 (NRXN3), IGF Like Family Member 1 (IGFL1), NME/NM23 Nucleoside Diphosphate Kinase 1 (NME1), Potassium Voltage-Gated Channel Isk-Related Family Member 1-Like (KCNE1L) or Neurexophilin 2 (NXPH2).

In some embodiments of the methods of identifying a therapeutic agent or target thereof for the treatment of a fibrotic lung disease of the disclosure, the composition that modifies an activity increases or activates the activity.

In some embodiments of the methods of identifying a therapeutic agent or target thereof for the treatment of a fibrotic lung disease of the disclosure, the composition increases or activates the activity of a sequence encoding Surfactant Protein D (SFTPD), Glyceraldehyde-3-Phosphate Dehydrogenase (GAPDH), Histone Cluster 1 H1 Family Member C (HIST1H1C), YTH Domain Containing 1 (YTHDC1), Plexin A1 (PLXNA1), Serine Peptidase Inhibitor Kazal Type 6 (SPINK6), LDL Receptor Related Protein Associated Protein 1 (LRPAP1), Secretoglobin Family 3A Member 1 (SCGB3A1), H2A Histone Family Member Z (H2AFZ) or Chromosome 1 Open Reading Frame 162 (C1orf162).

In some embodiments of the methods of identifying a therapeutic agent or target thereof for the treatment of a fibrotic lung disease of the disclosure, the non-human subject is a mammal.

In some embodiments of the methods of identifying a therapeutic agent or target thereof for the treatment of a fibrotic lung disease of the disclosure, the mammal is genetically-modified.

In some embodiments of the methods of the disclosure, the genetically-modified mammal is a model organism for the fibrotic lung disease.

In some embodiments of the methods of identifying a therapeutic agent or target thereof for the treatment of a fibrotic lung disease of the disclosure, the fibrotic lung disease is pulmonary fibrosis, idiopathic pulmonary fibrosis (IPF), an interstitial lung abnormality (ILA), or an asymptomatic ILA.

In some embodiments of the methods of identifying a therapeutic agent or target thereof for the treatment of a fibrotic lung disease of the disclosure, the fibrotic lung disease is pulmonary fibrosis or IPF.

In some embodiments of the methods of identifying a therapeutic agent or target thereof for the treatment of a fibrotic lung disease of the disclosure, the fibrotic lung disease is IPF.

In some embodiments of the methods of identifying a therapeutic agent or target thereof for the treatment of a fibrotic lung disease of the disclosure, the non-human subject carries a mutation in a sequence encoding MUC5B.

In some embodiments of the methods of identifying a therapeutic agent or target thereof for the treatment of a fibrotic lung disease of the disclosure, the mutation comprises a polymorphism in a sequence encoding a MUC5B promoter.

In some embodiments of the methods of identifying a therapeutic agent or target thereof for the treatment of a fibrotic lung disease of the disclosure, the polymorphism is rs35705950.

In some embodiments of the methods of identifying a therapeutic agent or target thereof for the treatment of a fibrotic lung disease of the disclosure, the non-human subject carries a mutation in a sequence encoding TERC, FAM13A, TERT, DSP, ZKSCAN1, AZGP1, OBFC1, MUC5B, AK025511, ATP11A, IVD/DISP2, DPP9, SIGLEC14, ADM2, TSPAN5, CAMKK1 or MMP-7.

In some embodiments of the methods of identifying a therapeutic agent or target thereof for the treatment of a fibrotic lung disease of the disclosure, the composition prevents the onset or development of a sign or symptom of the fibrotic lung disease.

In some embodiments of the methods of identifying a therapeutic agent or target thereof for the treatment of a fibrotic lung disease of the disclosure, the composition delays the onset or development of a sign or symptom of the fibrotic lung disease when compared to the expected onset of the sign or symptom in the absence of treatment with the composition.

In some embodiments of the methods of identifying a therapeutic agent or target thereof for the treatment of a fibrotic lung disease of the disclosure, the composition delays the onset or development of a sign or symptom of the fibrotic lung disease when compared to the expected onset of the sign or symptom when treated using a standard therapeutic intervention.

In some embodiments of the methods of identifying a therapeutic agent or target thereof for the treatment of a fibrotic lung disease of the disclosure, the composition reduces the severity of a sign or symptom of the fibrotic lung disease when compared to the expected severity of the sign or symptom in the absence of treatment with the composition.

In some embodiments of the methods of identifying a therapeutic agent or target thereof for the treatment of a fibrotic lung disease of the disclosure, the composition reduces the severity of a sign or symptom of the fibrotic lung disease when compared to the expected severity of the sign or symptom when treated using a standard therapeutic intervention.

In some embodiments of the methods of identifying a therapeutic agent or target thereof for the treatment of a fibrotic lung disease of the disclosure, the standard therapeutic intervention comprises a N-acetylcysteine, pirfenidone, and nintedanib.

In some embodiments of the methods of identifying a therapeutic agent or target thereof for the treatment of a fibrotic lung disease of the disclosure, the standard therapeutic intervention comprises pirfenidone.

In some embodiments of the methods of identifying a therapeutic agent or target thereof for the treatment of a fibrotic lung disease of the disclosure, an effective dosage of pirfenidone is about 2400 mg/day.

In some embodiments of the methods of identifying a therapeutic agent or target thereof for the treatment of a fibrotic lung disease of the disclosure, the effective dosage is administered orally as a capsule or a tablet.

In some embodiments of the methods of identifying a therapeutic agent or target thereof for the treatment of a fibrotic lung disease of the disclosure, the effective dosage is administered three times per day.

In some embodiments of the methods of identifying a therapeutic agent or target thereof for the treatment of a fibrotic lung disease of the disclosure, the effective dosage is administered according to an escalating dosage regimen.

In some embodiments of the methods of identifying a therapeutic agent or target thereof for the treatment of a fibrotic lung disease of the disclosure, the escalating dosage regimen comprises, administering to the non-human subject about 800 mg of pirfenidone per day for a first week; administering to the non-human subject about 1600 mg of pirfenidone per day for a second week; and administering to the non-human subject about 2400 mg of pirfenidone per day for the remainder of the treatment.

In some embodiments of the methods of identifying a therapeutic agent or target thereof for the treatment of a fibrotic lung disease of the disclosure, the escalating dosage regimen comprises, administering to the non-human subject a capsule or tablet comprising about 250 mg of pirfenidone three times a day for a first week; administering to the non-human subject two capsules or tablets comprising about 250 mg of pirfenidone three times a day for a second week; and administering to the non-human subject three capsules or tablets comprising about 250 mg of pirfenidone three times a day for the remainder of the treatment.

In some embodiments of the methods of identifying a therapeutic agent or target thereof for the treatment of a fibrotic lung disease of the disclosure, the capsule or tablet comprises 267 mg of pirfenidone.

In some embodiments of the methods of identifying a therapeutic agent or target thereof for the treatment of a fibrotic lung disease of the disclosure, the standard therapeutic intervention comprises nintedanib.

In some embodiments of the methods of identifying a therapeutic agent or target thereof for the treatment of a fibrotic lung disease of the disclosure, an effective dosage of nintedanib is administered orally as a capsule or a tablet.

In some embodiments of the methods of identifying a therapeutic agent or target thereof for the treatment of a fibrotic lung disease of the disclosure, the effective dosage is about 300 mg/day.

In some embodiments of the methods of identifying a therapeutic agent or target thereof for the treatment of a fibrotic lung disease of the disclosure, the effective dosage is about 150 mg administered twice per day, wherein the daily doses are administered about 12 hours apart from one another.

In some embodiments of the methods of identifying a therapeutic agent or target thereof for the treatment of a fibrotic lung disease of the disclosure, the effective dosage is about 200 mg/day.

In some embodiments of the methods of identifying a therapeutic agent or target thereof for the treatment of a fibrotic lung disease of the disclosure, the effective dosage is about 100 mg administered twice per day, wherein the daily doses are administered about 12 hours apart from one another.

In some embodiments of the methods of identifying a therapeutic agent or target thereof for the treatment of a fibrotic lung disease of the disclosure, the non-human subject presents at least one sign of the fibrotic lung disease.

In some embodiments of the methods of identifying a therapeutic agent or target thereof for the treatment of a fibrotic lung disease of the disclosure, the at least one sign comprises gradual or unintended weight loss, clubbing of the fingers or toes, rapid and shallow breathing, fibrotic lesions in one or both lungs detectable by radiography, or a cough.

In some embodiments of the methods of identifying a therapeutic agent or target thereof for the treatment of a fibrotic lung disease of the disclosure, the compound prevents the onset of a secondary condition associated with a severe form of the fibrotic lung disease.

In some embodiments of the methods of identifying a therapeutic agent or target thereof for the treatment of a fibrotic lung disease of the disclosure, the compound prevents the onset for at 1 year, 2 years, 3 years, 4 years, 5 years or any whole or fractional number of years in between.

In some embodiments of the methods of identifying a therapeutic agent or target thereof for the treatment of a fibrotic lung disease of the disclosure, secondary condition comprises a collapsed lung, an infected lung, a blood clot in a lung, lung cancer, respiratory failure, pulmonary hypertension, heart failure or death.

The disclosure provides a composition for the treatment of a fibrotic lung disease identified by a method of the disclosure, including, a method of identifying a therapeutic agent or target thereof for the treatment of a fibrotic lung disease of the disclosure.

The disclosure provides a method of treating fibrotic lung disease in a human subject of the disclosure comprising administering a therapeutically effective amount of a composition identified by a method of the disclosure, wherein the subject is asymptomatic and wherein the subject is at risk of developing the fibrotic lung disease. In some embodiments, the subject is wild type (e.g. does not comprises a mutation or a sequence variation) with respect to a nucleic acid or amino acid sequence encoding one or more of TERC, FAM13A, TERT, DSP, ZKSCAN1, AZGP1, OBFC1, MUC5B, AK025511, ATP11A, IVD/DISP2, DPP9, SIGLEC14, ADM2, TSPAN5, CAMKK1 or MMP-7.

In some embodiments of the methods of treating fibrotic lung disease in a human subject of the disclosure by administering a composition identified by a method of the disclosure, the human subject presents radiographic Usual Interstitial Pneumonia (UIP).

In some embodiments of the methods of treating fibrotic lung disease in a human subject of the disclosure by administering a composition identified by a method of the disclosure, wherein the human subject has fibrotic interstitial lung disease (FILD).

In some embodiments of the methods of treating fibrotic lung disease in a human subject of the disclosure by administering a composition identified by a method of the disclosure, wherein the human subject has a blood relative with familial interstitial pneumonia (FIP).

In some embodiments of the methods of treating fibrotic lung disease in a human subject of the disclosure by administering a composition identified by a method of the disclosure, wherein the blood relative is a sibling.

In some embodiments of the methods of treating fibrotic lung disease in a human subject of the disclosure by administering a composition identified by a method of the disclosure, wherein the human subject has a mutation or a sequence variation in a nucleic acid or an amino acid sequence encoding TERC, FAM13A, TERT, DSP, ZKSCAN1, AZGP1, OBFC1, MUC5B, AK025511, ATP11A, IVD/DISP2, DPP9, SIGLEC14, ADM2, TSPAN5, CAMKK1 or MMP-7.

In some embodiments of the methods of treating fibrotic lung disease in a human subject of the disclosure by administering a composition identified by a method of the disclosure, the mutation comprises a polymorphism in a sequence encoding a MUC5B promoter.

In some embodiments of the methods of treating fibrotic lung disease in a human subject of the disclosure by administering a composition identified by a method of the disclosure, the polymorphism is rs35705950.

In some embodiments of the methods of treating fibrotic lung disease in a human subject of the disclosure by administering a composition identified by a method of the disclosure, the fibrotic lung disease is pulmonary fibrosis, idiopathic pulmonary fibrosis (IPF), an interstitial lung abnormality (ILA), or an asymptomatic ILA.

In some embodiments of the methods of treating fibrotic lung disease in a human subject of the disclosure by administering a composition identified by a method of the disclosure, the fibrotic lung disease is pulmonary fibrosis or IPF.

In some embodiments of the methods of treating fibrotic lung disease in a human subject of the disclosure by administering a composition identified by a method of the disclosure, the fibrotic lung disease is IPF.

In some embodiments of the methods of treating fibrotic lung disease in a human subject of the disclosure by administering a composition identified by a method of the disclosure, the method prevents the onset of a secondary condition associated with a severe form of the fibrotic lung disease.

In some embodiments of the methods of treating fibrotic lung disease in a human subject of the disclosure by administering a composition identified by a method of the disclosure, a secondary condition comprises a collapsed lung, an infected lung, a blood clot in a lung, lung cancer, respiratory failure, pulmonary hypertension, heart failure or death.

BRIEF DESCRIPTION OF THE DRAWINGS

FIG. 2A-B is a pair of volcano plots showing serum sample quality control using Principal component analysis (PCA). FIG. 2A shows before outlier exclusion and FIG. 2B shows after outlier exclusion.

FIG. 7A is a series of graphs and FIG. 7B is a series of confocal images showing that the concentration of Muc5b is directly related to the fibroproliferative response to bleomycin. Representative images from second harmonic generation (SHG) demonstrate increased lung collagen (red) in transgenic mice following bleomycin injury.

FIG. 13 is a table describing the baseline characteristics of patients with rheumatoid arthritis.

FIG. 14 is a table describing the genotypic association of MUC5B rs35705950 single nucleotide polymorphism in patients with RA, with and without interstitial lung disease FIG. 15 is a table describing the dominant genotypic association of MUC5B rs35705950 single nucleotide polymorphism in patients with RA-ILD and a usual interstitial pneumonia or possible usual interstitial pneumonia pattern (RA-UIP) and in patients with RA-ILD and a pattern inconsistent with usual interstitial pneumonia (RA non-UIP).

FIG. 19A-D is a series of photographs depicting High-resolution CT (HRCT) images of: 19A) chest from a study subject whose scan was read as normal, without signs of interstitial lung disease or fibrosis. 19B) HRCT image from subject who was categorized as having "Probable Fibrotic ILD." 19C) Representative HRCT image from subject who was characterized as having "Definite Fibrotic ILD." 19D) HRCT image from a case of previously diagnosed, established Idiopathic Pulmonary Fibrosis (IPF) in one of the study families.

FIG. 20 is a table depicting a summary of characteristics of study subjects used in quantitative CT Analyses.

FIG. 21A-F is a series of photographs depicting representative axial HRCT images visually assessed as "No Fibrosis" (21A), "Probable Fibrotic ILD" (21C) and "Definite Fibrotic ILD" (E). Below each is the corresponding quantitative HRCT results for the above scan: (21B) "No Fibrosis" fibrosis extent 1.7% (fibrosis score=0.55), (21D) "Probable Fibrotic ILD" fibrosis extent 18.5% (fibrosis score 2.92), (F) "Definite Fibrotic ILD" fibrosis extent 35.5% (fibrosis score 3.60), Classification results color coded as follows: green=normal lung, blue=airway, yellow=reticular abnormality, magenta=ground glass opacity, red=honeycombing.

FIG. 22 is a table depicting Screening Cohort Subject Characteristics. *DNA available on a total of 489 subjects (404 No Fibrosis and 75 PrePF subjects). Odds ratios reported in this table were calculated from a mixed effects logistic regression model including age (as a continuous variable), male sex, ever smoker (yes/no), and MUC5B promoter variant (r535705950) genotype. *In the reported model, rs35705950 coded as a dominant allele; in log-additive genetic model, p=0.05, as well.

FIG. 23 is a table depicting patterns of CT abnormalities in scans with probable or definite fibrotic ILD. *Because a confident single diagnosis was relatively uncommon, most cases included consideration of several patterns. For this reason, the percentages add up to more than 100%.

FIG. 5A depicts ROC curves for visual diagnosis compared to log HAA scores. FIG. 5B depicts ROC Curves for visual diagnosis compared to fibrosis scores. ROC analysis showed that fibrosis score discriminates subjects with visual diagnosis of PrePF. Average area under the curve (AUC) in fivefold cross validation was 0.85 (range 0.83-0.87) and average accuracy, sensitivity, and specificity in the test partitions were 0.83 (range 0.74-0.86), 0.74 (range 0.56-0.92) and 0.84 (range 0.76-0.89) respectively. Optimal threshold for fibrosis score ranged from 1.40-1.42. FIG. 5C depicts Density plots of fibrosis scores for visually diagnosed PrePF (pink) and No Fibrosis (blue) scans—the fibrosis score optimal threshold is indicated with the red line (1.40).

FIG. 26 is a series of tables depicting Dyspnea questionnaire data. FIG. 26A depicts breathlessness responses for the cohort. FIG. 26B depicts breathlessness responses by Visual CT diagnosis.

FIG. 28 is a table depicting subject characteristics based on Quantitative Fibrosis Score. Clinical characteristics and genotype breakdown of subjects with quantitative HRCT analyses. The cutoff of 1.4 for the logarithm of fibrosis score is based on analyses presented in the text. *p-value compares characteristic between groups. Linear regression values regress fibrosis score on age, male sex, smoking history, and MUC5B promoter variant. **In the reported model, rs35705950 coded as a dominant allele given small number of TT subjects.

FIG. 29 is a table depicting an exploratory genetic association study of 13 pulmonary fibrosis susceptibility variants in RA-ILD.

DETAILED DESCRIPTION OF THE DISCLOSURE

Figure 1:
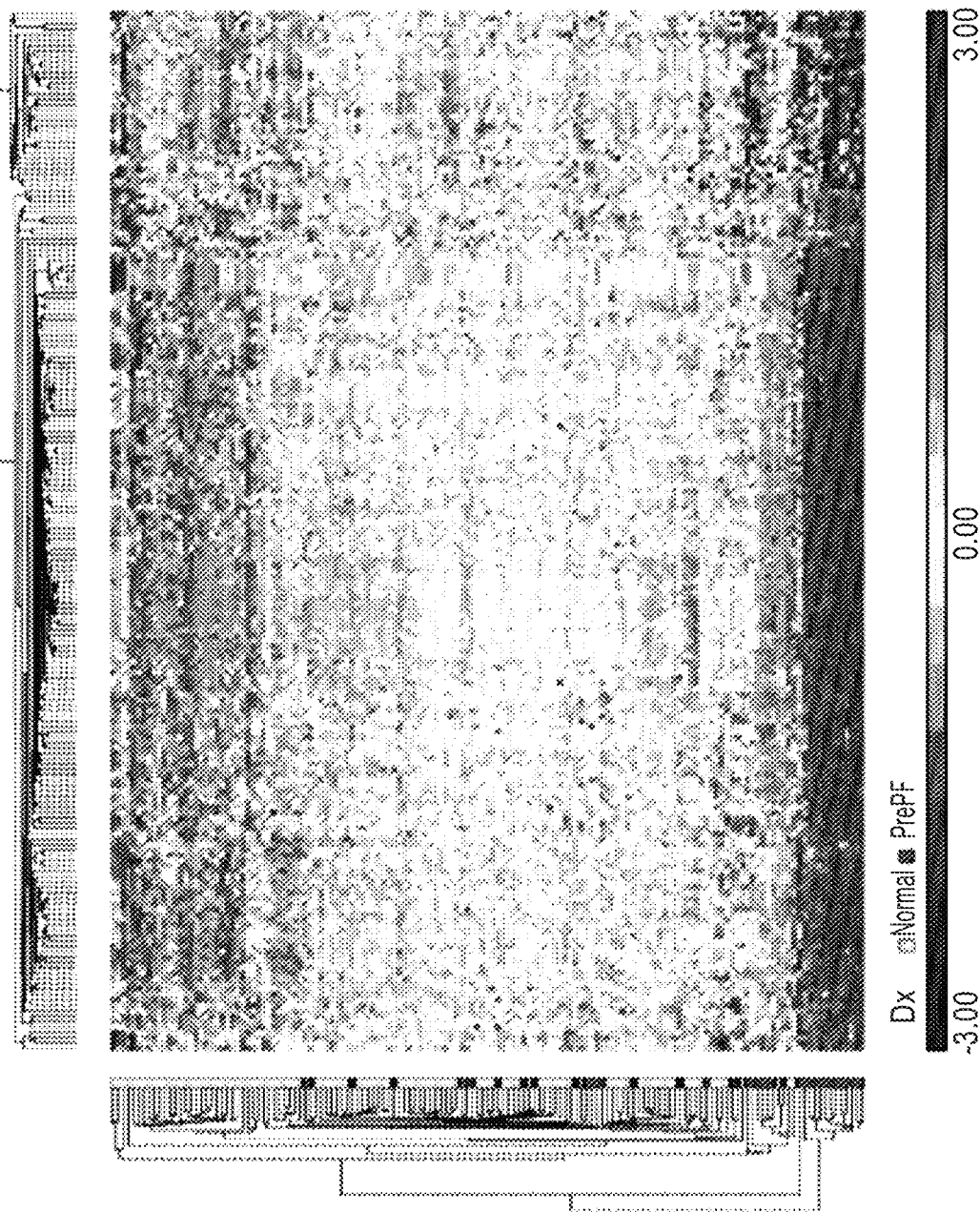
FIG. 1 is a map depicting an exemplary hierarchical clustering of differentially expressed genes for pre-pulmonary fibrosis subjects and normal subjects.

The present disclosure provides a method of treating a fibrotic lung disease in a subject comprising administering to the subject an effective amount of a therapeutic agent, wherein the subject is asymptomatic and wherein the subject is at risk of developing the fibrotic lung disease.

Methods of Identifying a Therapeutic Agent of the Disclosure or Target Thereof

The disclosure provides a method of identifying a therapeutic agent or target thereof for the treatment of a fibrotic lung disease, comprising administering to a non-human subject a dose of a composition that modifies transcription or translation of a sequence encoding Mucin 5B (MUC5B), Telomerase RNA Component (TERC), Family with sequence similarity 13 member A (FAM13A), Telomerase Reverse Transcriptase (TERT), Desmoplakin (DSP), Zinc-alpha 2-Glycoprotein 1 (AZGP1), Oligonucleotide/oligosaccharide-binding Fold Containing 1 (OBFC1), ATPase Phospholipid Transporting 11A (ATP11A), Isovaleryl-CoA dehydrogenase (IVD)/Dispatched RND Transporter Family Member 2 (DISP2), Dipeptidyl Peptidase 9 (DPP9), Sialic Acid Binding Ig-Like Lectin 14 (SIGLEC14), Adrenomedullin 2 (ADM2), Tetraspanin 5 (TSPAN5), Calcium/Calmodulin-Dependent Protein Kinase Kinase 1 (CAMKK1) or Matrix Metalloprotease-7 (MMP-7), wherein the dose of the composition is tolerable to the non-human subject and wherein the dose of the composition is therapeutically effective.

The disclosure provides method of identifying a therapeutic agent or target thereof for the treatment of a fibrotic lung disease, comprising administering to a non-human subject a composition that modifies an activity of a product of a sequence encoding MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, wherein the dose of the composition is tolerable to the non-human subject and wherein the dose of the composition is therapeutically effective.

In some embodiments of the methods of the disclosure, the composition that modifies transcription or translation decreases or inhibits transcription or translation. In some embodiments, the composition decreases or inhibits transcription or translation of a sequence encoding a gene selected from the group consisting of Leukotriene A4 Hydrolase (LTA4H), Surfactant Protein B (SFTPB), Breast Cancer Anti-Estrogen Resistance 3 (BCAR3), C-X-C motif Chemokine Ligand 13 (CXCL13), EPH Receptor A2 (EPHA2), Serum Amyloid A1 (SAA1), Phospholipase A2 Group IIA (PLA2G2A), Insulin-Like Growth Factor Binding Protein 3 (IGFBP3), C-C Motif Chemokine Ligand 28 (CCL28), 5100 Calcium Binding Protein A12 (S100A12), Thromboxane A Synthase 1 (TBXAS1), Leukocyte Cell Derived Chemotaxin 1 (LECT1), Complement C3 (C3), Gastrin Releasing Peptide (GRP), C-Reactive Protein (CRP), Vitrin (VIT), Insulin-Like Growth Factor Binding Protein 1 (IGFBP1), Family with Sequence Similarity 173 Member A (FAM173A), Natriuretic Peptide A (NPPA), Secreted Frizzled Related Protein 1 (SFRP1), Ezrin (EZR), Inter-Alpha-Trypsin Inhibitor Heavy Chain Family Member 5 (ITIH5), Pleckstrin and Sec7 Domain Containing 2 (PSD2), Galectin 3 Binding Protein (LGALS3BP), Catenin Beta 1 (CTNNB1), Chromodomain Y Like 2 (CDYL2), Matrix Metallopeptidase 7 (MMP7), Apolipoprotein B (APOB), Proline and Arginine Rich End Leucine Rich Repeat Protein (PRELP), Eukaryotic Translation Initiation Factor 1A, X-linked (EIF1AX), Mesencephalic Astrocyte Derived Neurotrophic Factor (MANF), TNF Receptor Superfamily Member 13C (TNFRSF13C), Deformed Epidermal Autoregulatory Factor 1 transcription factor (DEAF1), Tumor Protein Translationally-Controlled 1 (TPT1), Unc-5 Netrin Receptor B (UNCSB), Phosphatidylethanolamine Binding Protein 1 (PEBP1), Syntaxin 8 (STX8), Polymeric Immunoglobulin Receptor (PIGR), Adenine Phosphoribosyltransferase (APRT), Matrix Metallopeptidase 3 (MMP3), Galectin 7 (LGALS7), Bruton Tyrosine Kinase (BTK), NSFL1 Cofactor (NSFL1C), FER Tyrosine Kinase (FER), Regenerating Family Member 1 Beta (REG1B), SMAD Family Member 2 (SMAD2), Interleukin 1 Receptor Like 1 (IL1RL1), C-C Motif Chemokine Ligand 18 (CCL18), Acid Phosphatase 2 Lysosomal (ACP2), Eukaryotic Translation Initiation Factor 4E Family Member 2 (EIF4E2), Neurexin 3 (NRXN3), IGF Like Family Member 1 (IGFL1), NME/NM23 Nucleoside Diphosphate Kinase 1 (NME1), Potassium Voltage-Gated Channel Isk-Related Family Member 1-Like (KCNE1L) or Neurexophilin 2 (NXPH2).

In some embodiments of the methods of the disclosure, the composition that modifies transcription or translation increases or activates transcription or translation. In some embodiments, the composition increases or activates transcription or translation of a sequence encoding a gene selected from the group consisting of Surfactant Protein D (SFTPD), Glyceraldehyde-3-Phosphate Dehydrogenase (GAPDH), Histone Cluster 1 H1 Family Member C (HIST1H1C), YTH Domain Containing 1 (YTHDC1), Plexin A1 (PLXNA1), Serine Peptidase Inhibitor Kazal Type 6 (SPINK6), LDL Receptor Related Protein Associated Protein 1 (LRPAP1), Secretoglobin Family 3A Member 1 (SCGB3A1), H2A Histone Family Member Z (H2AFZ) or Chromosome 1 Open Reading Frame 162 (C1orf162).

In some embodiments of the methods of the disclosure, the composition that modifies an activity decreases or inhibits the activity. In some embodiments, the composition decreases or inhibits the activity of a sequence encoding a gene selected from Leukotriene A4 Hydrolase (LTA4H), Surfactant Protein B (SFTPB), Breast Cancer Anti-Estrogen Resistance 3 (BCAR3), C-X-C motif Chemokine Ligand 13 (CXCL13), EPH Receptor A2 (EPHA2), Serum Amyloid A1 (SAA1), Phospholipase A2 Group IIA (PLA2G2A), Insulin-Like Growth Factor Binding Protein 3 (IGFBP3), C-C Motif Chemokine Ligand 28 (CCL28), S100 Calcium Binding Protein A12 (S100A12), Thromboxane A Synthase 1 (TBXAS1), Leukocyte Cell Derived Chemotaxin 1 (LECT1), Complement C3 (C3), Gastrin Releasing Peptide (GRP), C-Reactive Protein (CRP), Vitrin (VIT), Insulin-Like Growth Factor Binding Protein 1 (IGFBP1), Family with Sequence Similarity 173 Member A (FAM173A), Natriuretic Peptide A (NPPA), Secreted Frizzled Related Protein 1 (SFRP1), Ezrin (EZR), Inter-Alpha-Trypsin Inhibitor Heavy Chain Family Member 5 (ITIH5), Pleckstrin and Sec7 Domain Containing 2 (PSD2), Galectin 3 Binding Protein (LGALS3BP), Catenin Beta 1 (CTNNB1), Chromodomain Y Like 2 (CDYL2), Matrix Metallopeptidase 7 (MMP7), Apolipoprotein B (APOB), Proline and Arginine Rich End Leucine Rich Repeat Protein (PRELP), Eukaryotic Translation Initiation Factor 1A, X-linked (EIF1AX), Mesencephalic Astrocyte Derived Neurotrophic Factor (MANF), TNF Receptor Superfamily Member 13C (TNFRSF13C), Deformed Epidermal Autoregulatory Factor 1 transcription factor (DEAF1), Tumor Protein Translationally-Controlled 1 (TPT1), Unc-5 Netrin Receptor B (UNC5B), Phosphatidylethanolamine Binding Protein 1 (PEBP1), Syntaxin 8 (STX8), Polymeric Immunoglobulin Receptor (PIGR), Adenine Phosphoribosyltransferase (APRT), Matrix Metallopeptidase 3 (MMP3), Galectin 7 (LGALS7), Bruton Tyrosine Kinase (BTK), NSFL1 Cofactor (NSFL1C), FER Tyrosine Kinase (FER), Regenerating Family Member 1 Beta (REG1B), SMAD Family Member 2 (SMAD2), Interleukin 1 Receptor Like 1 (IL1RL1), C-C Motif Chemokine Ligand 18 (CCL18), Acid Phosphatase 2 Lysosomal (ACP2), Eukaryotic Translation Initiation Factor 4E Family Member 2 (EIF4E2), Neurexin 3 (NRXN3), IGF Like Family Member 1 (IGFL1), NME/NM23 Nucleoside Diphosphate Kinase 1 (NME1), Potassium Voltage-Gated Channel Isk-Related Family Member 1-Like (KCNE1L) or Neurexophilin 2 (NXPH2).

In some embodiments of the methods of the disclosure, the composition that modifies an activity increases or activates the activity. In some embodiments, the composition increases or activates the activity of a sequence encoding Surfactant Protein D (SFTPD), Glyceraldehyde-3-Phosphate Dehydrogenase (GAPDH), Histone Cluster 1 H1 Family Member C (HIST1H1C), YTH Domain Containing 1 (YTHDC1), Plexin A1 (PLXNA1), Serine Peptidase Inhibitor Kazal Type 6 (SPINK6), LDL Receptor Related Protein Associated Protein 1 (LRPAP1), Secretoglobin Family 3A Member 1 (SCGB3A1), H2A Histone Family Member Z (H2AFZ) or Chromosome 1 Open Reading Frame 162 (C1orf162).

In some embodiments of the methods of the disclosure, the non-human subject is a mammal. In some embodiments, mammal is genetically-modified. In some embodiments, the genetically-modified mammal is a model organism for the fibrotic lung disease.

In some embodiments of the methods of the disclosure, the fibrotic lung disease is pulmonary fibrosis, idiopathic pulmonary fibrosis (IPF), an interstitial lung abnormality (ILA), or an asymptomatic ILA. In some embodiments, the fibrotic lung disease is pulmonary fibrosis or IPF. In some embodiments, the fibrotic lung disease is IPF.

In some embodiments of the methods of the disclosure, the non-human subject carries a mutation in a sequence encoding MUC5B. In some embodiments, the mutation comprises a polymorphism in a sequence encoding a MUC5B promoter. In some embodiments, the polymorphism is rs35705950. Alternatively, or in addition, in some embodiments, the non-human subject carries a mutation in a sequence encoding TERC, FAM13A, TERT, DSP, AZGP1, OBFC1, ATP11A, IVD/DISP2, DPP9, SIGLEC14, ADM2, TSPAN5, CAMKK1 or MMP-7.

In some embodiments of the methods of the disclosure, the composition prevents the onset or development of a sign or symptom of the fibrotic lung disease.

In some embodiments of the methods of the disclosure, the composition delays the onset or development of a sign or symptom of the fibrotic lung disease when compared to the expected onset of the sign or symptom in the absence of treatment with the composition. In some embodiments, the composition delays the onset or development of a sign or symptom of the fibrotic lung disease when compared to the expected onset of the sign or symptom when treated using a standard therapeutic intervention.

In some embodiments of the methods of the disclosure, the composition reduces the severity of a sign or symptom of the fibrotic lung disease when compared to the expected severity of the sign or symptom in the absence of treatment with the composition. In some embodiments, the composition reduces the severity of a sign or symptom of the fibrotic lung disease when compared to the expected severity of the sign or symptom when treated using a standard therapeutic intervention.

In some embodiments of the methods of the disclosure, the standard therapeutic intervention comprises a N-acetylcysteine, pirfenidone, and nintedanib.

In some embodiments of the methods of the disclosure, the standard therapeutic intervention comprises pirfenidone. In some embodiments, an effective dosage of pirfenidone is about 2400 mg/day. In some embodiments, the effective dosage is administered orally as a capsule or a tablet. In some embodiments, the effective dosage is administered three times per day. In some embodiments, the effective dosage is administered according to an escalating dosage regimen. In some embodiments, the escalating dosage regimen comprises (a) administering to the non-human subject about 800 mg of pirfenidone per day for a first week; (b) administering to the non-human subject about 1600 mg of pirfenidone per day for a second week; and (c) administering to the non-human subject about 2400 mg of pirfenidone per day for the remainder of the treatment. In some embodiments, the escalating dosage regimen comprises (a) administering to the non-human subject a capsule or tablet comprising about 250 mg of pirfenidone three times a day for a first week; (b) administering to the non-human subject two capsules or tablets comprising about 250 mg of pirfenidone three times a day for a second week; and (c) administering to the non-human subject three capsules or tablets comprising about 250 mg of pirfenidone three times a day for the remainder of the treatment. In some embodiments, the capsule or tablet comprises 267 mg of pirfenidone.

In some embodiments of the methods of the disclosure, the standard therapeutic intervention comprises nintedanib. In some embodiments, an effective dosage of nintedanib is administered orally as a capsule or a tablet. In some embodiments, the effective dosage is about 300 mg/day. In some embodiments, the effective dosage is about 150 mg administered twice per day, wherein the daily doses are administered about 12 hours apart from one another. In some embodiments, the effective dosage is about 200 mg/day. In some embodiments, the effective dosage is about 100 mg administered twice per day, wherein the daily doses are administered about 12 hours apart from one another.

In some embodiments of the methods of the disclosure, the non-human subject presents at least one sign of the fibrotic lung disease. In some embodiments, the at least one sign comprises gradual or unintended weight loss, clubbing of the fingers or toes, rapid and shallow breathing, fibrotic lesions in one or both lungs detectable by radiography, or a cough.

In some embodiments of the methods of the disclosure, the compound prevents the onset of a secondary condition associated with a severe form of the fibrotic lung disease. In some embodiments, the compound prevents the onset for at 1 year, 2 years, 3 years, 4 years, 5 years or any whole or fractional number of years in between. In some embodiments, the secondary condition comprises a collapsed lung, an infected lung, a blood clot in a lung, lung cancer, respiratory failure, pulmonary hypertension, heart failure or death.

The disclosure provides a composition for the treatment of a fibrotic lung disease identified by a method of the disclosure for identifying a therapeutic agent or target thereof for the treatment of a fibrotic lung disease.

Subjects of the Disclosure

The disclosure provides a method of treating a fibrotic lung disease in a human subject comprising administering to the subject the composition for the treatment of a fibrotic lung disease identified by a method of the disclosure for identifying a therapeutic agent or target thereof for the treatment of a fibrotic lung disease, wherein the subject is asymptomatic and wherein the subject is at risk of developing the fibrotic lung disease.

In some embodiments of the methods of treating a fibrotic lung disease in a human subject of the disclosure, the human subject presents radiographic Usual Interstitial Pneumonia (UIP). In some embodiments, the human subject has fibrotic interstitial lung disease (FILD). In some embodiments, the human subject has a blood relative with familial interstitial pneumonia (FIP). In some embodiments, the blood relative is a sibling. Alternatively, or in addition, in some embodiments, the human subject has a mutation in a sequence encoding MUC5B, TERC, FAM13A, TERT, DSP, AZGP1, OBFC1, ATP11A, IVD/DISP2, DPP9, SIGLEC14, ADM2, TSPAN5, CAMKK1 or MMP-7. In some embodiments, the mutation comprises a polymorphism in a sequence encoding a MUC5B promoter. In some embodiments, the polymorphism is rs35705950.

In some embodiments of the methods of treating a fibrotic lung disease in a human subject of the disclosure, the fibrotic lung disease is pulmonary fibrosis, idiopathic pulmonary fibrosis (IPF), an interstitial lung abnormality (ILA), or an asymptomatic ILA. In some embodiments, the fibrotic lung disease is pulmonary fibrosis or IPF. In some embodiments, the fibrotic lung disease is IPF.

In some embodiments of the methods of treating a fibrotic lung disease in a human subject of the disclosure, the method prevents the onset of a secondary condition associated with a severe form of the fibrotic lung disease. In some embodiments, the secondary condition comprises a collapsed lung, an infected lung, a blood clot in a lung, lung cancer, respiratory failure, pulmonary hypertension, heart failure or death.

Idiopathic Pulmonary Fibrosis (IPF)

IPF is localized to the lung and is characterized by a pattern of heterogeneous, subpleural patches of fibrotic, remodeled lung, and often results in death within 3-5 years of diagnosis. IPF affects 5 million people worldwide, disproportionately affects men, is associated with cigarette smoking, increases with age, is inexplicably increasing in prevalence, and is likely underdiagnosed. Most patients with IPF are discovered in the advanced stage when little can be done to influence survival. There is a critical unmet need in idiopathic pulmonary fibrosis (IPF) for an early detection and prevention of IPF. Earlier diagnosis of IPF detects subjects with a lower burden of fibrotic lung disease providing an opportunity for secondary prevention of this progressive disease and changes the clinical approach to patients with IPF from palliative to preventive.

Early detection and prevention of idiopathic pulmonary fibrosis (IPF) is critical. As demonstrated herein, treatment of subjects at risk for developing PrePF is based on two central concepts of first, understanding that PrePF is essential for primary and secondary prevention of IPF and second, that similar to asymptomatic family members of familial IPF (FIP; ≥2 family members with IPF), asymptomatic family members of sporadic IPF represent an at-risk population for PrePF. These central concepts are supported by the observation that 1) IPF has a pre-symptomatic phase and PrePF appears to be a harbinger of IPF, 2) familial and sporadic IPF are similar etiologically, 3) MUC5B promoter variant is critical to early disease recognition and 4) identification of PrePF represents an opportunity to prevent extensive lung fibrosis. As shown herein, a common gain-of-function MUC5B promoter variant rs35705950 is a strong risk factor (genetic and otherwise), accounting for at least 30% of the total risk of developing IPF. The MUC5B promoter variant rs35705950 may be used to identify individuals with PrePF. MUC5B promoter variant rs35705950 is also predictive of radiographic progression of PrePF and is present in over 50% of non-Hispanic white patients with IPF and is also associated with unique clinical and biological IPF phenotypes. PrePF can be predicted using a combination of clinical risk factors, the MUC5B promoter variant rs35705950, and a panel of biomarkers. This disclosure provides methods of treating subjects with Preclinical Pulmonary Fibrosis (PrePF) and who may also be at risk for developing IPF. The methods of the disclosure fundamentally change the clinical approach to treating subjects with IPF, shifting the focus from a merely palliative to a proactive and preventive therapy.

Rheumatoid Arthritis-Associated Interstitial Lung Disease (RA-ILD)

Rheumatoid arthritis (RA) is a common inflammatory and autoimmune disease that is associated with progressive impairment, systemic complications and increased mortality. Interstitial lung disease (RA-ILD) is detected in up to 60% of patients with RA on high-resolution computed-tomography (HRCT), is clinically significant in 10%, and is a leading cause of morbidity and mortality in patients with RA.

RA-ILD shares several characteristics with idiopathic pulmonary fibrosis (IPF), including common environmental risk factors, the high prevalence of the usual interstitial pneumonia (UIP) pattern, the progressive nature of the disease, and poor survival. The hypothesis of a shared genetic background between IPF and RA-ILD was recently suggested by a whole-exome sequencing (WES) genetic association study in patients with RA-ILD, revealing an excess of mutations in genes in RA-ILD previously associated with familial interstitial pneumonia (FIP) including TERT, RTEL1, PARN and SFTPC.

The common gain-of-function promoter variant rs3570595013 of the gene encoding mucin5B (MUC5B) is the strongest genetic risk factor for IPF, observed in at least 50% of the cases of IPF and accounting for 30% of the risk of developing this disease. The MUC5B promoter variant is associated with increased expression of MUC5B in lung parenchyma of unaffected controls and cases of IPF. Consequently, it is hypothesized that the MUC5B promoter variant rs35705950 would also contribute to the occurrence of RA-ILD. To test this hypothesis, a multi-ethnic association study of the MUC5B promoter variant and RA-ILD in seven distinct case series was performed.

The MUC5B promoter variant rs35705950, the strongest genetic risk factor for IPF, is also a strong risk factor for RA-ILD, especially among those with radiographic evidence of UIP. Of note, the effect of the MUC5B promoter variant on the development of ILD associated with RA was similar in magnitude and direction to that observed in IPF.

The relationship between the MUC5B promoter variant and RA-ILD may be specific to UIP and may not be generalizable to other autoimmune conditions of the lung. The MUC5B promoter variant has not been found to be associated with risk of ILDs linked to systemic sclerosis or autoimmune myositis. Unlike these other types of ILD, RA-ILD shares more characteristics with IPF, notably the increased frequency of the UIP pattern (both radiologic and histologic), an increased prevalence of male sex and older age, and genetic susceptibility as assessed by an excess of mutations in genes linked to FIP in a cohort of RA-ILD, and now the MUC5B promoter variant rs35705950.

The disclosure demonstrates that the MUC5B promoter variant is a risk factor for UIP, and not simply limited to IPF and RA-ILD. In fact, emerging studies have identified the MUC5B promoter variant as a risk factor for chronic hypersensitivity pneumonitis, another condition known to have a sub-phenotype of UIP. Further, since HRCT underestimates the presence of ILD and the UIP pattern of fibrosis, our point estimates for association with the MUC5B variant are likely conservative. Similar to IPF, early forms of RA-ILD can be identified using the MUC5B promoter variant as biomarker.

The disclosure demonstrates that Muc5b is overexpressed by the bronchoalveolar epithelia and MUC5B mRNA is co-expressed by cells expressing surfactant protein C, as has been shown in IPF. These findings suggest either type 2 alveolar epithelial cells can express MUC5B or that in patients with RA-ILD, the cells in the distal airspace dedifferentiate. Importantly, the disclosure demonstrates for the first time that cells that overexpress MUC5B are undergoing ER stress, a recognized mechanism of cell injury and repair. In aggregate, these findings indicate that the gain-of-function MUC5B promoter variant rs35705950 injures alveolar epithelia by inducing ER stress.

RA-ILD is a complex genetic phenotype with the minor allele of the MUC5B promoter variant rs35705950 identified as a risk factor for the disease. The odds ratios for the association of MUC5B promoter variant with RA-ILD is equivalent to that observed with IPF and substantively higher than those for the most other common risk variants for RA-ILD, including cigarette smoking and the human leukocyte antigen locus for RA.

The MUC5B promoter variant is a risk factor for UIP in general and may prove relevant beyond RA-ILD and IPF.

Expression of MUC5B in the bronchoalveolar epithelia co-incident with markers of ER stress suggest that the MUC5B promoter variant may be causing pulmonary fibrosis by initiating microscopic foci of injury and repair.

The MUC5B promoter variant appears to predict ILD in the RA population, identifying potential opportunities for early ILD detection in patients with RA.

Preclinical Idiopathic Pulmonary Fibrosis

Better understanding and recognition of early pulmonary fibrosis is critical because medical therapies have been shown to slow progression, not to reverse or even stabilize established fibrosis—therefore, intervention before irreversible fibrosis has become extensive has the potential to improve quality of life and decrease morbidity. While IPF affects approximately 5 million people worldwide, between 1.8 and 14% of the general population ≥50 years of age have radiologic findings of undiagnosed pulmonary fibrosis. Large cohort studies indicate that interstitial lung abnormalities, postulated to represent early pulmonary fibrosis, are associated with increased mortality, and that most of these abnormalities progress over time. Members of families with 2 or more cases of pulmonary fibrosis (FIP, Familial Interstitial Pneumonia) have been identified as an "at-risk" population. In a previous study of FIP relatives, 14% had interstitial lung abnormalities on high resolution computed tomography (HRCT), and 35% had an abnormal transbronchial biopsy indicating interstitial lung disease.

HRCT provides visualization of the lung parenchyma and plays a key role in the diagnosis of the Idiopathic Interstitial Pneumonias (IIPs), including IPF. Currently, visual diagnosis by thoracic radiologists, in conjunction with multidisciplinary clinical conference, is the gold standard for diagnosing TIPS. However, visual assessment is imprecise and hampered by inter-observer variation. Quantitative HRCT (qHRCT) evaluation provides measures of fibrosis extent that, in subjects diagnosed with IPF, correlate with degree of physiologic impairment at baseline, and may be more sensitive to subtle changes in disease status than routinely used physiological metrics. The design and utility of quantitative methods in the context of early forms of fibrotic ILD requires further study. Deep learning methods have been increasingly used in imaging to identify and classify CT patterns, and may be particularly valuable in detection of early lung fibrosis.

PrePF is prevalent among FIP relatives, and a texture-based quantitative method of HRCT analyses is useful in identifying these abnormalities in this population, and key risk factors, including the MUC5B promoter variant, predict those at risk of this disease. PrePF subjects are older, more likely to be male, and more likely to have smoked than the unaffected subjects; additionally, the gain-of-function MUC5B promoter variant rs35705950, which has been shown in prior studies to be associated with pulmonary fibrosis, is more common in PrePF subjects when compared to their unaffected family members. Given the subtlety of the fibrotic change in many of these cases of PrePF, the high prevalence of potential UIP pattern on HRCT scan suggests that PrePF subjects may progress to IPF over time.

Methods for Detecting a Genetic Variant

The present disclosure also provides methods of detecting the biomarkers of the present disclosure. Methods of detecting a genetic variant are further described in US Application US 2016-0060701A1 (the contents of which are incorporated herein by reference in their entirety). The practice of the present disclosure employs, unless otherwise indicated, conventional methods of analytical biochemistry, microbiology, molecular biology and recombinant DNA techniques within the skill of the art. Such techniques are explained fully in the literature. (See, e.g., Sambrook, J. et al. Molecular Cloning: A Laboratory Manual. 3rd, ed., Cold Spring Harbor Laboratory, Cold Spring Harbor Laboratory Press, Cold Spring Harbor, N. Y., 2000; DNA Cloning: A Practical Approach, Vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); CRC Handbook of Parvoviruses, Vol. I & II (P. Tijessen, ed.); Fundamental Virology, 2nd Edition, Vol. I & II (B. N. Fields and D. M. Knipe, eds.)).

The methods of the invention are not limited to any particular way of detecting the presence or absence of a genetic variant (e.g. SNP) and can employ any suitable method to detect the presence or absence of a variant(s), of which numerous detection methods are known in the art. Dynamic allele-specific hybridization (DASH) can be used to detect a genetic variant. DASH genotyping takes advantage of the differences in the melting temperature in DNA that results from the instability of mismatched base pairs. The process can be vastly automated and encompasses a few simple principles. Thus, the aspects and embodiments described herein provide methods for assessing the presence or absence of SNPs in a sample (e.g. biological sample) from a subject suspected of having or developing an interstitial lung disease (e.g., because of family history). In certain embodiments, one or more SNPs are screened in one or more samples from a subject. The SNPs can be associated with one or more genes, e.g., one or more genes or other genes associated with mucous secretions as disclosed herein.

Typically, the target genomic segment is amplified and separated from non-target sequence, e.g., through use of a biotinylated primer and chromatography. A probe that is specific for the particular allele is added to the amplification product. The probe can be designed to hybridize specifically to a variant sequence or to the dominant allelic sequence. The probe can be either labeled with or added in the presence of a molecule that fluoresces when bound to double-stranded DNA. The signal intensity is then measured as temperature is increased until the Tm can be determined. A non-matching sequence (either genetic variant or dominant allelic sequence, depending on probe design), will result in a lower than expected Tm.

DASH genotyping relies on a quantifiable change in Tm, and is thus capable of measuring many types of mutations, not just SNPs. Other benefits of DASH include its ability to work with label free probes and its simple design and performance conditions.

Molecular beacons can also be used to detect a genetic variant. This method makes use of a specifically engineered single-stranded oligonucleotide probe. The oligonucleotide is designed such that there are complementary regions at each end and a probe sequence located in between. This design allows the probe to take on a hairpin, or stem-loop, structure in its natural, isolated state. Attached to one end of the probe is a fluorophore and to the other end a fluorescence quencher. Because of the stem-loop structure of the probe, the fluorophore is in close proximity to the quencher, thus preventing the molecule from emitting any fluorescence. The molecule is also engineered such that only the probe sequence is complementary to the targeted genomic DNA sequence.

If the probe sequence of the molecular beacon encounters its target genomic DNA sequence during the assay, it will anneal and hybridize. Because of the length of the probe sequence, the hairpin segment of the probe will be denatured in favor of forming a longer, more stable probe-target hybrid. This conformational change permits the fluorophore and quencher to be free of their tight proximity due to the hairpin association, allowing the molecule to fluoresce.

If on the other hand, the probe sequence encounters a target sequence with as little as one non-complementary nucleotide, the molecular beacon will preferentially stay in its natural hairpin state and no fluorescence will be observed, as the fluorophore remains quenched. The unique design of these molecular beacons allows for a simple diagnostic assay to identify SNPs at a given location. If a molecular beacon is designed to match a wild-type allele and another to match a mutant of the allele, the two can be used to identify the genotype of an individual. If only the first probe's fluorophore wavelength is detected during the assay then the individual is homozygous to the wild type. If only the second probe's wavelength is detected then the individual is homozygous to the mutant allele. Finally, if both wavelengths are detected, then both molecular beacons must be hybridizing to their complements and thus the individual must contain both alleles and be heterozygous.

A microarray can also be used to detect genetic variants. Hundreds of thousands of probes can be arrayed on a small chip, allowing for many genetic variants or SNPs to be interrogated simultaneously. Because SNP alleles only differ in one nucleotide and because it is difficult to achieve optimal hybridization conditions for all probes on the array, the target DNA has the potential to hybridize to mismatched probes. This can be addressed by using several redundant probes to interrogate each SNP. Probes can be designed to have the SNP site in several different locations as well as containing mismatches to the SNP allele. By comparing the differential amount of hybridization of the target DNA to each of these redundant probes, it is possible to determine specific homozygous and heterozygous alleles.

Restriction fragment length polymorphism (RFLP) can be used to detect genetic variants and SNPs. RFLP makes use of the many different restriction endonucleases and their high affinity to unique and specific restriction sites. By performing a digestion on a genomic sample and determining fragment lengths through a gel assay it is possible to ascertain whether or not the enzymes cut the expected restriction sites. A failure to cut the genomic sample results in an identifiably larger than expected fragment implying that there is a mutation at the point of the restriction site which is rendering it protected from nuclease activity.

PCR- and amplification-based methods can be used to detect genetic variants. For example, tetra-primer PCR employs two pairs of primers to amplify two alleles in one PCR reaction. The primers are designed such that the two primer pairs overlap at a SNP location but each matches perfectly to only one of the possible alleles. As a result, if a given allele is present in the PCR reaction, the primer pair specific to that allele will produce product but not the alternative allele with a different allelic sequence. The two primer pairs can be designed such that their PCR products are of a significantly different length allowing for easily distinguishable bands by gel electrophoresis, or such that they are differently labeled.

Primer extension can also be used to detect genetic variants. Primer extension first involves the hybridization of a probe to the bases immediately upstream of the SNP nucleotide followed by a 'mini-sequencing' reaction, in which DNA polymerase extends the hybridized primer by adding a base that is complementary to the SNP nucleotide. The incorporated base that is detected determines the presence or absence of the SNP allele. Because primer extension is based on the highly accurate DNA polymerase enzyme, the method is generally very reliable. Primer extension is able to genotype most SNPs under very similar reaction conditions making it also highly flexible. The primer extension method is used in a number of assay formats, and can be detected using e.g., fluorescent labels or mass spectrometry.

Primer extension can involve incorporation of either fluorescently labeled ddNTP or fluorescently labeled deoxynucleotides (dNTP). With ddNTPs, probes hybridize to the target DNA immediately upstream of SNP nucleotide, and a single, ddNTP complementary to the SNP allele is added to the 3' end of the probe (the missing 3'-hydroxyl in didioxynucleotide prevents further nucleotides from being added). Each ddNTP is labeled with a different fluorescent signal allowing for the detection of all four alleles in the same reaction. With dNTPs, allele-specific probes have 3' bases which are complementary to each of the SNP alleles being interrogated. If the target DNA contains an allele complementary to the 3' base of the probe, the target DNA will completely hybridize to the probe, allowing DNA polymerase to extend from the 3' end of the probe. This is detected by the incorporation of the fluorescently labeled dNTPs onto the end of the probe. If the target DNA does not contain an allele complementary to the probe's 3' base, the target DNA will produce a mismatch at the 3' end of the probe and DNA polymerase will not be able to extend from the 3' end of the probe.

The iPLEX® SNP genotyping method takes a slightly different approach, and relies on detection by mass spectrometer. Extension probes are designed in such a way that many different SNP assays can be amplified and analyzed in a PCR cocktail. The extension reaction uses ddNTPs as above, but the detection of the SNP allele is dependent on the actual mass of the extension product and not on a fluorescent molecule. This method is for low to medium high throughput, and is not intended for whole genome scanning.

Primer extension methods are, however, amenable to high throughput analysis. Primer extension probes can be arrayed on slides allowing for many SNPs to be genotyped at once. Broadly referred to as arrayed primer extension (APEX), this technology has several benefits over methods based on differential hybridization of probes. Comparatively, APEX methods have greater discriminating power than methods using differential hybridization, as it is often impossible to obtain the optimal hybridization conditions for the thousands of probes on DNA microarrays (usually this is addressed by having highly redundant probes).

Oligonucleotide ligation assays can also be used to detect genetic variants. DNA ligase catalyzes the ligation of the 3' end of a DNA fragment to the 5' end of a directly adjacent DNA fragment. This mechanism can be used to interrogate a SNP by hybridizing two probes directly over the SNP polymorphic site, whereby ligation can occur if the probes are identical to the target DNA. For example, two probes can be designed; an allele-specific probe which hybridizes to the target DNA so that its 3' base is situated directly over the SNP nucleotide and a second probe that hybridizes the template upstream (downstream in the complementary strand) of the SNP polymorphic site providing a 5' end for the ligation reaction. If the allele-specific probe matches the target DNA, it will fully hybridize to the target DNA and ligation can occur. Ligation does not generally occur in the presence of a mismatched 3' base. Ligated or unligated products can be detected by gel electrophoresis, MALDI-TOF mass spectrometry or by capillary electrophoresis.

The 5'-nuclease activity of Taq DNA polymerase can be used for detecting genetic variants. The assay is performed concurrently with a PCR reaction and the results can be read in real-time. The assay requires forward and reverse PCR primers that will amplify a region that includes the SNP polymorphic site. Allele discrimination is achieved using FRET, and one or two allele-specific probes that hybridize to the SNP polymorphic site. The probes have a fluorophore linked to their 5' end and a quencher molecule linked to their 3' end. While the probe is intact, the quencher will remain in close proximity to the fluorophore, eliminating the fluorophore's signal. During the PCR amplification step, if the allele-specific probe is perfectly complementary to the SNP allele, it will bind to the target DNA strand and then get degraded by 5'-nuclease activity of the Taq polymerase as it extends the DNA from the PCR primers. The degradation of the probe results in the separation of the fluorophore from the quencher molecule, generating a detectable signal. If the allele-specific probe is not perfectly complementary, it will have lower melting temperature and not bind as efficiently. This prevents the nuclease from acting on the probe.

Förster resonance energy transfer (FRET) detection can be used for detection in primer extension and ligation reactions where the two labels are brought into close proximity to each other. It can also be used in the 5'-nuclease reaction, the molecular beacon reaction, and the invasive cleavage reactions where the neighboring donor/acceptor pair is separated by cleavage or disruption of the stem-loop structure that holds them together. FRET occurs when two conditions are met. First, the emission spectrum of the fluorescent donor dye must overlap with the excitation wavelength of the acceptor dye. Second, the two dyes must be in close proximity to each other because energy transfer drops off quickly with distance. The proximity requirement is what makes FRET a good detection method for a number of allelic discrimination mechanisms.

A variety of dyes can be used for FRET, and are known in the art. The most common ones are fluorescein, cyanine dyes (Cy3 to Cy7), rhodamine dyes (e.g. rhodamine 6G), the Alexa series of dyes (Alexa 405 to Alexa 730). Some of these dyes have been used in FRET networks (with multiple donors and acceptors). Optics for imaging all of these require detection from UV to near IR (e.g. Alex 405 to Cy7), and the Atto series of dyes (Atto-Tec GmbH). The Alexa series of dyes from Invitrogen cover the whole spectral range. They are very bright and photostable.

Example dye pairs for FRET labeling include Alexa-405/Alex-488, Alexa-488/Alexa-546, Alexa-532/Alexa-594, Alexa-594/Alexa-680, Alexa-594/Alexa-700, Alexa-700/Alexa-790, Cy3/Cy5, Cy3.5/Cy5.5, and Rhodamine-Green/Rhodamine-Red, etc. Fluorescent metal nanoparticles such as silver and gold nanoclusters can also be used (Richards et al. (2008) J Am Chem Soc 130:5038-39; Vosch et al. (2007) Proc Natl Acad Sci USA 104:12616-21; Petty and Dickson (2003) J Am Chem Soc 125:7780-81 Available filters, dichroics, multichroic mirrors and lasers can affect the choice of dye.

In Vitro Complexes

Provided herein are nucleic acid complexes, e.g., formed in in vitro assays to indicate the presence of a genetic variant sequence. One of skill will understand that a nucleic acid complex can also be formed to detect the presence of a dominant allelic sequence, depending on the design of the probe or primer, e.g., in assays to distinguish homozygous and heterozygous subjects.

In some embodiments, the complex comprises a first nucleic acid hybridized to a genetic variant nucleic acid, wherein the genetic variant nucleic acid is a genetic variant in a gene selected from MUC5B, TERC, FAM13A, TERT, DSP, AZGP1, OBFC1, ATP11A, IVD/DISP2, DPP9, SIGLEC14, ADM2, TSPAN5, CAMKK1 or MMP-7. In some embodiments, the genetic variant nucleic acid is an amplification product. In some embodiments, the genetic variant nucleic acid is on genomic DNA, e.g., from a subject that has or is suspected of having an interstitial lung disease. In some embodiments, the first nucleic acid is an amplification product or a primer extension product. In some embodiments, the first nucleic acid is labeled. In some embodiments, the nucleic acid complex further comprises a second nucleic acid hybridized to the genetic variant nucleic acid. In some embodiments, the second nucleic acid is labeled e.g., with a FRET or other fluorescent label. In some embodiments, the first and second nucleic acids form a FRET pair when hybridized to a genetic variant sequence.

In some embodiments, the nucleic acid complex further comprises an enzyme, such as a DNA polymerase (e.g., standard DNA polymerase or thermostable polymerase such as Taq) or ligase.

The present disclosure includes but is not limited to the following embodiments:

A method for determining if an individual is predicted to develop and/or progress rapidly with an interstitial pneumonia comprising: detecting in a biological sample from the individual, at least one of: a) the presence of a marker polymorphism selected from the group consisting of: rs35705950; and/or, b) a level of gene expression of a marker gene or plurality of marker genes selected from the group consisting of: a marker gene having at least 95% sequence identity with at least one sequence selected from the group consisting of MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, or homologs or variants thereof; c) polypeptides encoded by the marker genes of b) d) fragments of polypeptides of c); and e) a polynucleotide which is fully complementary to at least a portion of a marker gene of b); wherein the presence of the plurality of markers is indicative of whether an individual will develop a disease. In some embodiments, the genes detected share 100% sequence identity with the corresponding marker gene in b). In some embodiments, the presence or level of at least one of the plurality of markers is determined and compared to a standard level or reference set. In some embodiments, the standard level or reference set is determined according to a statistical procedure for risk prediction. In some embodiments, the statistical procedure for risk prediction comprises using the sum of the gene expression of the marker or markers or the presence or absence of a set of markers, weighted by a Proportional Hazards coefficient. In some embodiments, the presence of the at least one marker is determined by detecting the presence or absence or expression level of a polypeptide. In some embodiments, the method further comprises detecting the presence of the polypeptide using a reagent that specifically binds to the polypeptide or a fragment thereof. In some embodiments, the reagent is selected from the group consisting of an antibody, an antibody derivative, and an antibody fragment. In some embodiments, the presence of the marker is determined by obtaining the sequence of genomic DNA at the locus of the polymorphism. In some embodiments, the presence of the marker is determined by obtaining RNA from the biological sample; generating cDNA from the RNA; amplifying the cDNA with probes or primers for marker genes; obtaining from the amplified cDNA the expression levels of the genes or gene expression products in the sample. In some embodiments, the individual is a human.

In some embodiments, the method further comprises: a) comparing the expression level of the marker gene or plurality of marker genes in the biological sample to a control level of the marker gene(s) selected from the group consisting of: a control level of the marker gene that has been correlated with interstitial lung disease, the risk of developing interstitial lung disease, or having a interstitial lung disease; and a control level of the marker that has been correlated with slow or no progression of interstitial lung disease, or low risk of developing an interstitial lung disease; and b) selecting the individual as being predicted to progress rapidly in the development of interstitial pneumonia, if the expression level of the marker gene in the individual's biological sample is statistically similar to, or greater than, the control level of expression of the marker gene that has been correlated with interstitial lung disease, or c) selecting the individual as being predicted to not develop interstitial lung disease, or to progress slowly, if the level of the marker gene in the individual's biological sample is statistically less than the control level of the marker gene that has been correlated with interstitial lung disease.

In some embodiments, the method further comparing the presence of a polymorphism, in the biological sample to a set of genetic variants or polymorphic markers from an individual or control group having developed interstitial lung disease, and, selecting the individual as being predicted to develop or to progress with interstitial pneumonia if the polymorphic markers present in the biological sample are identical to or statistically similar to a set of polymorphic markers from the individual or control group or, selecting the individual as being predicted to develop or rapidly progress with interstitial pneumonia, if the polymorphic markers present in the biological sample are not identical to or statistically similar to the set of genetic variants or polymorphic markers from the individual or control group.

A method for monitoring the progression of interstitial lung disease in a subject, comprising: i) measuring expression levels of a plurality of gene markers in a first biological sample obtained from the subject, wherein the plurality of markers comprise a plurality of markers selected from the group consisting of: a marker gene having at least 95% sequence identity with a sequence selected from the group consisting of a) MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, or homologs or variants thereof; c) fragments of polypeptides of d); and e) a polynucleotide which is fully complementary to at least a portion of a marker gene of b); ii) measuring expression levels of the plurality of markers in a second biological sample obtained from the subject; and iii) comparing the expression level of the marker measured in the first sample with the level of the marker measured in the second sample. In some embodiments, the marker genes detected share 100% sequence identity with the corresponding marker gene in a). In some embodiments, the method further comprises performing a follow-up step selected from the group consisting of CT scan of the chest and pathological examination of lung tissues from the subject. In some embodiments, the first biological sample from the subject is obtained at a time to, and the second biological sample from the subject is obtained at a later time $t_1$. In some embodiments, the first biological sample and the second biological sample are obtained from the subject are obtained more than once over a range of times.

A method of assessing the efficacy of a treatment for interstitial lung disease or interstitial pneumonia in a subject, the method comprising comparing: i) the expression level of a marker measured in a first sample obtained from the subject at a time to, wherein the marker is selected from the group consisting of a) a marker gene having at least 95% sequence identity with a sequence selected from the group consisting of MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, or homologs or variants thereof; b) polypeptides encoded by the marker genes of a) c) fragments of polypeptides of b); and d) a polynucleotide which is fully complementary to at least a portion of a marker gene of a); ii) the level of the marker in a second sample obtained from the subject at time $t_1$; and, iii) performing a follow-up step selected from CT scan of the chest and pathological examination of lung tissues from the subject; wherein a decrease in the level of the marker in the second sample relative to the first sample is an indication that the treatment is efficacious for treating interstitial pneumonia in the subject. In some embodiments, the genes detected share 100% sequence identity with the corresponding marker gene in a). In some embodiments, the time t0 is before the treatment has been administered to the subject, and the time t1 is after the treatment has been administered to the subject. In some embodiments, the comparing is repeated over a range of times.

An assay system for predicting individual prognosis therapy for interstitial pneumonia comprising a means to detect at least one of: a) the presence of a marker polymorphism selected from the group consisting of: rs35705950; and/or, b) a level of gene expression of a marker gene or plurality of marker genes selected from the group consisting of: a marker gene having at least 95% sequence identity with a sequence selected from the group consisting of MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, or homologs or variants thereof; c) polypeptides encoded by the marker genes of b) d) fragments of polypeptides of c); and e) a polynucleotide which is fully complementary to at least a portion of a marker gene of b). In some embodiments, the means to detect comprises nucleic acid probes comprising at least 10 to 50 contiguous nucleic acids of the marker polymorphisms or gene(s), or complementary nucleic acid sequences thereof. In some embodiments, the means to detect comprises binding ligands that specifically detect polypeptides encoded by the marker genes. In some embodiments, the genes detected share 100% sequence identity with the corresponding marker gene in b).

In some embodiments, the means to detect comprises at least one of nucleic acid probe and binding ligands disposed on an assay surface. In some embodiments, the assay surface comprises a chip, array, or fluidity card. In some embodiments, the probes comprise complementary nucleic acid sequences to at least 10 to 50 nucleic acid sequences of the marker genes. In some embodiments, the binding ligands comprise antibodies or binding fragments thereof. In some embodiments, the assay system further comprises: a control selected from information containing a predetermined control level or set of genetic variants or polymorphic markers that has been correlated with diagnosis, development, progression, or life expectancy in interstitial lung disease patients.

A method of detecting a level of gene expression of one or more marker genes in a human subject with interstitial pneumonia, comprising, optionally, obtaining a biological sample from a human individual with interstitial pneumonia; detecting the level of expression of a gene selected from MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, or homologs or variants thereof, in one or more cells from the biological sample from the individual. In some embodiments, the method further comprises detecting the level of expression of a gene selected from MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, or homologs or variants thereof, in one or more cells from the biological sample from the individual. In some embodiments, the method further comprises detecting the level of expression of a gene selected from MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, or homologs or variants thereof in one or more cells from the biological sample from the individual.

A method of treating an interstitial lung disease in a subject in need of such treatment, comprising: detecting a level of one or more marker genes selected from MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, or homologs or variants thereof in a biological sample obtained from the human subject; and, administering an effective amount of an effective treatment. In some embodiments, the method further comprises detecting the level of expression of a gene selected from MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, or homologs or variants thereof, in one or more cells from the biological sample from the individual. In some embodiments, the method further comprises detecting the level of expression of a gene selected from MUC5B, TERC, FAM13A, TERT, DSP, AZGP1, OBFC1, ATP11A, IVD/DISP2, DPP9, SIGLEC14, ADM2, TSPAN5, CAMKK1 or MMP-7, or homologs or variants thereof, in one or more cells from the biological sample from the individual.

Detection of Genetic Variants

Methods of detecting a genetic variant are further described, for example, in U.S. Pat. No. 8,673,565 (the contents of which are herein incorporated by reference in their entirety). Genetic variations in the mucin genes are associated with pulmonary diseases. These genetic variations can be found in any part of the gene, e.g., in the regulatory regions, introns, or exons. Relevant genetic variations may also be found the intergene regions, e.g., in sequences between mucin genes. Insertions, substitutions, and deletions are included in genetic variants. Single nucleotide polymorphisms (SNPs) are exemplary genetic variants.

In particular, 14 independent SNPs are associated with pulmonary disorders (e.g. FIP or IPF). The studies disclosed herein demonstrate that presence of one or more of these SNPs associated with MUC5B can lead to predisposition to a pulmonary disorder. In addition, in some embodiments, if present, some of these SNPs are related to a transcription factor binding site. The transcription factor binding site can effect modulation of MUC5B expression, for example E2F3 loss, and HOXA9 and PAX-2 generation.

The disclosure thus provides methods for assessing the presence or absence of SNPs in a sample from a subject suspected of having or developing a pulmonary disorder (e.g., because of family history). In certain embodiments, one or more SNPs are screened in one or more samples from a subject. The SNPs can be associated with one or more genes, e.g., one or more MUC genes or other genes associated with mucous secretion. In some embodiments, a MUC gene associated SNP is associated with MUC5B and/or another MUC gene, such as MUC5AC or MUC1. SNPs contemplated for diagnostic, treatment, or prognosis can include SNPs found within a MUC gene and/or within a regulatory or promoter region associated with a MUC gene. For example, one or more SNPs can include, but are not limited to, detection of the SNPs of MUC5B alone or in combination with other genetic variations or SNPs and/or other diagnostic or prognostic methods.

Methods for detecting genetic variants such as a SNP are known in the art, e.g., Southern or Northern blot, nucleotide array, amplification methods, etc. Primers or probes are designed to hybridize to a target sequence. For example, genomic DNA can be screened for the presence of an identified genetic element of using a probe based upon one or more sequences, e.g., using a probe with substantial identity to a subsequence of the MUC5B gene. Expressed RNA can also be screened, but may not include all relevant genetic variations. Various degrees of stringency of hybridization may be employed in the assay. As the conditions for hybridization become more stringent, there must be a greater degree of complementarity between the probe and the target for duplex formation to occur. Thus, high stringency conditions are typically used for detecting a SNP.

Thus, in some embodiments, a genetic variant MUC5B gene in a subject is detected by contacting a nucleic acid in a sample from the subject with a probe having substantial identity to a subsequence of the MUC5B gene, and determining whether the nucleic acid indicates that the subject has a genetic variant MUC5B gene. In some cases, the sample can be processed prior to amplification, e.g., to separate genomic DNA from other sample components. In some cases, the probe has at least 90, 92, 94, 95, 96, 98, 99, or 100% identity to the MUC5B gene subsequence. Typically, the probe is between 10-500 nucleotides in length, e.g., 10-100, 10-40, 10-20, 20-100, 100-400, etc. In the case of detecting a SNP, the probe can be even shorter, e.g., 8-20 nucleotides in length. In some cases, the MUC5B gene sequence to be detected includes at least 8 contiguous nucleotides, e.g., at least 10, 15, 20, 25, 30, 35 or more contiguous nucleotides. In some embodiments, the sequence to be detected includes 8 contiguous nucleotides, e.g., at least 10, 15, 20, 25, 30, 35 or more contiguous nucleotides.

The degree of stringency can be controlled by temperature, ionic strength, pH and/or the presence of a partially denaturing solvent such as formamide. For example, the stringency of hybridization is conveniently varied by changing the concentration of formamide within the range up to and about 50%. The degree of complementarity (sequence identity) required for detectable binding will vary in accordance with the stringency of the hybridization medium and/or wash medium. In certain embodiments, in particular for detection of a particular SNP, the degree of complementarity is about 100 percent. In other embodiments, sequence variations can result in <100% complementarity, <90% complementarity probes, <80% complementarity probes, etc., in particular, in a sequence that does not involve a SNP. In some examples, e.g., detection of species homologs, primers may be compensated for by reducing the stringency of the hybridization and/or wash medium.

High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. Other exemplary conditions are disclosed in the following Examples. It is understood that the temperature and ionic strength of a desired stringency are determined in part by the length of the particular nucleic acid(s), the length and nucleotide content of the target sequence(s), the charge composition of the nucleic acid(s), and by the presence or concentration of formamide, tetramethylammonium chloride or other solvent(s) in a hybridization mixture. Nucleic acids can be completely complementary to a target sequence or exhibit one or more mismatches.

Nucleic acids of interest can also be amplified using a variety of known amplification techniques. For instance, polymerase chain reaction (PCR) technology may be used to amplify target sequences (e.g., genetic variants) directly from DNA, RNA, or cDNA. In some embodiments, a stretch of nucleic acids is amplified using primers on either side of a targeted genetic variation, and the amplification product is then sequenced to detect the targeted genetic variation (using, e.g., Sanger sequencing, Pyrosequencing, Nextgen® sequencing technologies). For example, the primers can be designed to hybridize to either side of the upstream regulatory region of the MUC5B gene, and the intervening sequence determined to detect a SNP in the promoter region. In some embodiments, one of the primers can be designed to hybridize to the targeted genetic variant. In some cases, a genetic variant nucleotide can be identified using RT-PCR, e.g., using labeled nucleotide monomers. In this way, the identity of the nucleotide at a given position can be detected as it is added to the polymerizing nucleic acid. The Scorpion™ system is a commercially available example of this technology.

Thus, in some embodiments, a genetic variant MUC5B gene in a subject is detected by amplifying a nucleic acid in a sample from the subject to form an amplification product, and determining whether the amplification product indicates a genetic variant MUC5B gene. In some cases, the sample can be processed prior to amplification, e.g., to separate genomic DNA from other sample components. In some cases, amplifying comprises contacting the sample with amplification primers having substantial identity to MUC5B genomic subsequences, e.g., at least 90, 92, 94, 95, 96, 98, 99, or 100% identity. Typically, the sequence to be amplified is between 30-1000 nucleotides in length, e.g., 50-500, 50-400, 100-400, 50-200, 100-300, etc. In some cases, the sequence to be amplified or detected includes at least 8 contiguous nucleotides, e.g., at least 10, 15, 20, 25, 30, 35 or more contiguous nucleotides. In some embodiments, the sequence to be amplified or detected includes 8 contiguous nucleotides, e.g., at least 10, 15, 20, 25, 30, 35 or more contiguous nucleotides. In some aspects, the contiguous nucleotides include nucleotide 28.

Amplification techniques can also be useful for cloning nucleic acid sequences, to make nucleic acids to use as probes for detecting the presence of a target nucleic acid in samples, for nucleic acid sequencing, for control samples, or for other purposes. Probes and primers are also readily available from commercial sources, e.g., from Invitrogen, Clonetech, etc.

Detection of Expression Levels

Expression of a given gene, e.g., MUC5B or another mucin, pulmonary disease marker, or standard (control), is typically detected by detecting the amount of RNA (e.g., mRNA) or protein. Sample levels can be compared to a control level.

Methods for detecting RNA are largely cumulative with the nucleic acid detection assays described above. RNA to be detected can include mRNA. In some embodiments, a reverse transcriptase reaction is carried out and the targeted sequence is then amplified using standard PCR. Quantitative PCR (qPCR) or real time PCR (RT-PCR) is useful for determining relative expression levels, when compared to a control. Quantitative PCR techniques and platforms are known in the art, and commercially available (see, e.g., the qPCR Symposium website, available at qpersymposium.com). Nucleic acid arrays are also useful for detecting nucleic acid expression. Customizable arrays are available from, e.g., Affimatrix. An exemplary human MUC5B mRNA sequence, e.g., for probe and primer design, can be found at GenBank Accession No. AF086604.1.

Protein levels can be detected using antibodies or antibody fragments specific for that protein, natural ligands, small molecules, aptamers, etc. An exemplary human MUC5B sequence, e.g., for screening a targeting agent, can be found at UniProt Accession No. O00446.

Antibody based techniques are known in the art, and described, e.g., in Harlow & Lane (1988) Antibodies: A Laboratory Manual and Harlow (1998) Using Antibodies: A Laboratory Manual; Wild, The Immunoassay Handbook, 3d edition (2005) and Law, Immunoassay: A Practical Guide (1996). The assay can be directed to detection of a molecular target (e.g., protein or antigen), or a cell, tissue, biological sample, liquid sample or surface suspected of carrying an antibody or antibody target.

A non-exhaustive list of immunoassays includes: competitive and non-competitive formats, enzyme linked immunosorption assays (ELISA), microspot assays, Western blots, gel filtration and chromatography, immunochromatography, immunohistochemistry, flow cytometry or fluorescence activated cell sorting (FACS), microarrays, and more. Such techniques can also be used in situ, ex vivo, or in vivo, e.g., for diagnostic imaging.

Aptamers are nucleic acids that are designed to bind to a wide variety of targets in a non-Watson Crick manner. An aptamer can thus be used to detect or otherwise target nearly any molecule of interest, including a pulmonary disease associated protein. Methods of constructing and determining the binding characteristics of aptamers are well known in the art. For example, such techniques are described in U.S. Pat. Nos. 5,582,981, 5,595,877 and 5,637,459. Aptamers are typically at least 5 nucleotides, 10, 20, 30 or 40 nucleotides in length, and can be composed of modified nucleic acids to improve stability. Flanking sequences can be added for structural stability, e.g., to form 3-dimensional structures in the aptamer.

Protein detection agents described herein can also be used as a treatment and/or diagnosis of pulmonary disease or predictor of disease progression, e.g., propensity for survival, in a subject having or suspected of developing a pulmonary disorder. In certain embodiments, MUC5B antibodies can be used to assess MUC5B protein levels in a subject having or suspected of developing a pulmonary disorder. It is contemplated herein that antibodies or antibody fragments may be used to modulate MUC5B production in a subject having or suspected of developing a pulmonary disease. In certain embodiments, one or more agents capable of modulating MUC5B may be used to treat a subject having or suspected of developing a pulmonary disorder. One or more antibodies or antibody fragments may be generated to detect one or more of the SNPs disclosed herein by any method known in the art.

In certain embodiments, MUC5B diagnostic tests may include, but are not limited to, alone or in combination, analysis of rs35705950 SNP in MUC5B gene, MUC5B mRNA levels, and/or MUC5B protein levels.

Additional Pulmonary Disease Markers

The above methods of detection can be applied to additional pulmonary disease markers. That is, the expression level or presence of genetic variants of at least one additional pulmonary disease marker gene can be determined, or the activity of the marker protein can be determined, and compared to a standard control for the pulmonary disease marker. The examination of additional pulmonary disease markers can be used to confirm a diagnosis of pulmonary disease, monitor disease progression, or determine the efficacy of a course of treatment in a subject.

In some cases, pulmonary disease is indicated by an increased number of lymphocytes, e.g., CD4+CD28- cells.

Genetic variations in the following genes are associated with pulmonary disease: Surfactant Protein A2, Surfactant Protein B, Surfactant Protein C, TERC, TERT, IL-1RN, IL-1α, IL-1β, TNF, Lymphotoxin a, TNF-RII, IL-10, IL-6, IL-12, IFNγ, TGFβ, CR1, ACE, IL-8, CXCR1, CXCR2, MUC1 (KL6), or MUC5AC. Thus, the invention further includes methods of determining whether the genome of a subject comprises a genetic variant of at least one gene selected from these genes. The presence of a genetic variant indicates that the subject has or is at risk of developing pulmonary disease. Said determining can optionally be combined with determining whether the genome of the subject comprises a genetic variant MUC5B gene, or determining whether the subject has an elevated level of MUC5B RNA or protein to confirm or strengthen the diagnosis or prognosis.

Abnormal expression in the following genes can also be indicative of pulmonary disease: Surfactant Protein A, Surfactant Protein D, KL-6/MUC1, CC16, CK-19, Ca 19-9, SLX, MCP-1, MIP-1a, ITAC, glutathione, type III procollagen peptide, sIL-2R, ACE, neopterin, beta-glucuronidase, LDH, CCL-18, CCL-2, CXCL12, MMP7, and osteopontin. Thus, the expression of one of these genes can be detected and compared to a control, wherein an abnormal expression level indicates that the subject has or is at risk of developing pulmonary disease. Said determining can optionally be combined with determining whether the genome of the subject comprises a genetic variant MUC5B gene, or determining whether the subject has an elevated level of MUC5B RNA or protein to confirm or strengthen the diagnosis or prognosis.

Biomarkers

The present disclosure provides a peripheral blood biomarker profile for IPF to demonstrate the use of a predictive biomarker profile in cases of preclinical pulmonary fibrosis (PrePF) derived from families with familial IPF. The present disclosure also provides biomarker identification for association between each genetic, epigenetic or protein (gene product) biomarker with PrePF and the predictive value of the combination of biomarkers associated with PrePF.

A large cohort of families with familial IPF for genetic research was established, including 937 families with ≥2 cases of IPF, and 2375 family members that have been previously phenotyped as unaffected. This study focuses on subjects with PrePF to elucidate the processes active in early disease pathogenesis and to predict or prevent the irreversible fibroproliferative process. Genetic risk factors, especially the MUC5B promoter variant, identifies individuals with preclinical interstitial changes on chest CT scan that progress and are associated with reduced survival. Biomarkers may be used to identify those subjects with PrePF among those at-risk for IPF. Given the irreversible nature of IPF, even approved treatments (pirfenidone and nintedanib) only modestly slow progression and have not been shown to alter the 3-5 year survival. Pirfenidone and nintedanib are effective in patients with mild disease, suggesting that patients with PrePF may be targeted for early intervention, before most of the lung has been irreversibly remodeled.

Table 1 below shows additional gene expression changes present in subjects with IPF compared to controls. Specifically, the expression of the genes listed in Table 1 are upregulated in IPF compared to the expression of these same genes in control subjects. Accordingly, the discovery of elevated expression levels of one or more genes listed in Table 1 compared to a control in an asymptomatic subject may indicate that the subject has PrePF and/or that the subject is at risk for developing IPF.

In some embodiments of the methods of the disclosure, the subject has a mutation in a nucleic acid or amino acid sequence encoding a gene or gene product that is upregulated in a subject having a fibrotic pulmonary disease of the disclosure. In some embodiments of the methods of the disclosure, the subject has a mutation in a nucleic acid or amino acid sequence encoding Leukotriene A4 Hydrolase (LTA4H), Surfactant Protein B (SFTPB), Breast Cancer Anti-Estrogen Resistance 3 (BCAR3), C-X-C motif Chemokine Ligand 13 (CXCL13), EPH Receptor A2 (EPHA2), Serum Amyloid A1 (SAA1), Phospholipase A2 Group IIA (PLA2G2A), Insulin-Like Growth Factor Binding Protein 3 (IGFBP3), C-C Motif Chemokine Ligand 28 (CCL28), 5100 Calcium Binding Protein A12 (S100A12), Thromboxane A Synthase 1 (TBXAS1), Leukocyte Cell Derived Chemotaxin 1 (LECT1), Complement C3 (C3), Gastrin Releasing Peptide (GRP), C-Reactive Protein (CRP), Vitrin (VIT), Insulin-Like Growth Factor Binding Protein 1 (IGFBP1), Family with Sequence Similarity 173 Member A (FAM173A), Natriuretic Peptide A (NPPA), Secreted Frizzled Related Protein 1 (SFRP1), Ezrin (EZR), Inter-Alpha-Trypsin Inhibitor Heavy Chain Family Member 5 (ITIH5), Pleckstrin and Sec7 Domain Containing 2 (PSD2), Galectin 3 Binding Protein (LGALS3BP), Catenin Beta 1 (CTNNB1), Chromodomain Y Like 2 (CDYL2), Matrix Metallopeptidase 7 (MMP7), Apolipoprotein B (APOB), Proline and Arginine Rich End Leucine Rich Repeat Protein (PRELP), Eukaryotic Translation Initiation Factor 1A, X-linked (EIF1AX), Mesencephalic Astrocyte Derived Neurotrophic Factor (MANF), TNF Receptor Superfamily Member 13C (TNFRSF13C), Deformed Epidermal Autoregulatory Factor 1 transcription factor (DEAF1), Tumor Protein Translationally-Controlled 1 (TPT1), Unc-5 Netrin Receptor B (UNCSB), Phosphatidylethanolamine Binding Protein 1 (PEBP1), Syntaxin 8 (STX8), Polymeric Immunoglobulin Receptor (PIGR), Adenine Phosphoribosyltransferase (APRT), Matrix Metallopeptidase 3 (MMP3), Galectin 7 (LGALS7), Bruton Tyrosine Kinase (BTK), NSFL1 Cofactor (NSFL1C), FER Tyrosine Kinase (FER), Regenerating Family Member 1 Beta (REG1B), SMAD Family Member 2 (SMAD2), Interleukin 1 Receptor Like 1 (IL1RL1), C-C Motif Chemokine Ligand 18 (CCL18), Acid Phosphatase 2 Lysosomal (ACP2), Eukaryotic Translation Initiation Factor 4E Family Member 2 (EIF4E2), Neurexin 3 (NRXN3), IGF Like Family Member 1 (IGFL1), NME/NM23 Nucleoside Diphosphate Kinase 1 (NME1), Potassium Voltage-Gated Channel Isk-Related Family Member 1-Like (KCNE1L) or Neurexophilin 2 (NXPH2).

TABLE 1

| TARGET_GENE_SYMBOL | ORGANISM | p-value | B-H q-value | Fold Change |
|---|---|---|---|---|
| LTA4H | Human | 8.70E-43 | 3.13E-39 | 3.912 |
| SFTP8 | Human | 1.17E-37 | 2.10E-34 | 3.399 |
| BCAR3 | Human | 4.28E-25 | 3.85E-22 | 2.906 |
| CXCL13 | Human | 1.30E-29 | 1.56E-26 | 2.904 |
| EPHA2 | Human | 9.62E-23 | 6.93E-20 | 2.651 |
| SAA1 | Human | 6.01E-07 | 7.84E-06 | 2.631 |
| PLA2G2A | Human | 8.19E-21 | 2.95E-18 | 2.171 |
| Igfbp3 | Mouse | 1.18E-18 | 2.66E-16 | 2.149 |
| CCL28 | Human | 1.22E-22 | 7.30E-20 | 2.135 |
| S100A12 | Human | 1.06E-20 | 3.45E-18 | 2.125 |
| TBXAS1 | Human | 1.60E-21 | 7.20E-19 | 2.11 |
| LECT1 | Human | 4.17E-19 | 1.00E-16 | 2.082 |
| C3 | Human | 7.08E-07 | 8.95E-06 | 2.062 |
| GRP | Human | 8.35E-09 | 1.66E-07 | 1.988 |
| CSP | Human | 1.36E-08 | 2.61E-07 | 1.957 |
| VIT | Human | 2.47E-17 | 4.45E-15 | 1.929 |
| IGFBP1 | Human | 4.32E-11 | 1.56E-09 | 1.914 |
| FAM173A | Human | 2.19E-13 | 1.84E-11 | 1.904 |
| NPPA | Human | 5.02E-12 | 2.58E-10 | 1.877 |
| SFRP1 | Human | 1.74E-20 | 5.23E-18 | 1.866 |
| EZR | Human | 6.41E-10 | 1.72E-08 | 1.809 |
| ITIH5 | Human | 5.11E-21 | 2.04E-18 | 1.705 |
| PSD2 | Human | 5.38E-18 | 1.08E-15 | 1.689 |
| LGALS38P | Human | 8.06E-22 | 4.15E-19 | 1.678 |
|  |  | 1.18E-05 | 0.000102 | 1.668 |
| CTNNB1 | Human | 5.66E-12 | 2.87E-10 | 1.625 |
| CDYL2 | Human | 4.11E-07 | 5.59E-06 | 1.622 |
| MMP7 | Human | 1.56E-19 | 4.02E-17 | 1.621 |
| APOB | Human | 8.73E-13 | 6.42E-11 | 1.597 |
| PRELP | Human | 1.13E-10 | 3.53E-09 | 1.595 |
| EIF1AX | Human | 2.13E-06 | 2.31E-05 | 1.59 |
| MANF | Human | 0.00458 | 0.015006 | 1.585 |
| TNFRSF13C | Human | 1.77E-11 | 7.31E-10 | 1.573 |
| C3 | Human | 2.40E-16 | 3.93E-14 | 1.566 |
| DEAF1 | Human | 0.000221 | 0.001192 | 1.565 |
| TPT1 | Human | 1.22E-12 | 7.82E-11 | 1.548 |
| UNC5B | Human | 2.06E-34 | 2.18E-12 | 1.547 |
| PEBP1 | Human | 4.92E-11 | 1.72E-09 | 1.544 |
| STX8 | Human | 8.82E-12 | 4.13E-10 | 1.537 |
| PIGR | Human | 1.29E-09 | 3.19E-08 | 1.532 |
| APRT | Human | 1.51E-07 | 2.26E-06 | 1.525 |
| MMP3 | Human | 9.50E-07 | 1.15E-05 | 1.524 |
| LGALS7 | Human | 7.51E-05 | 0.000474 | 1.514 |
| BTK | Human | 1.47E-09 | 3.52E-08 | 1.511 |
| NSFL1C | Human | 7.33E-11 | 2.40E-09 | 1.506 |
| FER | Human | 2.24E-07 | 3.24E-06 | 1.503 |
| REG1B | Human | 6.68E-11 | 2.25E-09 | 1.502 |
| SMAD2 | Human | 4.39E-10 | 1.25E-08 | 1.493 |
| IL1RL1 | Human | 9.55E-07 | 1.15E-05 | 1.492 |
| CCL18 | Human | 1.25E-13 | 1.07E-11 | 1.491 |
| ACP2 | Human | 3.73E-08 | 6.33E-07 | 1.488 |
| EIF4E2 | Human | 1.67E-12 | 1.02E-10 | 1.483 |
| NRXN3 | Human | 2.33E-17 | 4.42E-15 | 1.48 |
| IGFL1 | Human | 5.07E-10 | 1.40E-08 | 1.474 |
| NME1 | Human | 1.43E-10 | 4.39E-09 | 1.463 |
| KCNE1L | Human | 3.93E-20 | 1.09E-17 | 1.462 |
| NXPH2 | Human | 9.66E-30 | 2.47E-08 | 1.451 |

Table 2 below shows additional gene expression changes present in subjects with IPF compared to controls. Specifically, the expression of the genes listed in Table 2 are downregulated in IPF compared to the expression of these same genes in control subjects. Accordingly, the discovery of decreased expression levels of one or more genes listed in Table 2 compared to a control in an asymptomatic subject may indicate that the subject has PrePF and/or that the subject is at risk for developing IPF.

In some embodiments of the methods of the disclosure, the subject has a mutation in a nucleic acid or amino acid sequence encoding a gene or gene product that is down-regulated in a subject having a fibrotic pulmonary disease of the disclosure. In some embodiments of the methods of the disclosure, the subject has a mutation in a nucleic acid or amino acid sequence encoding Surfactant Protein D (SFTPD), Glyceraldehyde-3-Phosphate Dehydrogenase (GAPDH), Histone Cluster 1 H1 Family Member C (HIST1H1C), YTH Domain Containing 1 (YTHDC1), Plexin A1 (PLXNA1), Serine Peptidase Inhibitor Kazal Type 6 (SPINK6), LDL Receptor Related Protein Associated Protein 1 (LRPAP1), Secretoglobin Family 3A Member 1 (SCGB3A1), H2A Histone Family Member Z (H2AFZ) or Chromosome 1 Open Reading Frame 162 (C1orf162).

TABLE 2

| TARGET_GENE_SYMBOL | ORGANISM | p-value | B-H q-value | Fold Change |
|---|---|---|---|---|
| SFTPD | Human | 8.19E-15 | 9.83E-13 | -2.262 |
| GAPDH | Human | 1.46E-09 | 3.52E-08 | -2.096 |
| HIST1H1C | Human | 3.68E-18 | 7.80E-16 | -2.011 |
|  |  | 3.63E-16 | 5.69E-14 | -1.964 |
| YTHDC1 | Human | 1.19E-11 | 5.38E-10 | -1.699 |
| PLXNA1 | Human | 1.64E-12 | 1.02E-10 | -1.64 |
| SPINK6 | Human | 3.68E-07 | 5.04E-06 | -1.635 |
| LRPAP1 | Human | 2.65E-15 | 3.53E-13 | -1.521 |
| SCGB3A1 | Human | 3.35E-07 | 4.61E-06 | -1.518 |
| H2AFZ | Human | 3.91E-14 | 3.91E-12 | -1.501 |
|  |  | 2.95E-11 | 1.16E-09 | -1.493 |
| C1orf162 | Human | 1.29E-84 | 7.52E-04 | -1.458 |

In some embodiments of the methods of the disclosure, the subject having PrePF or at risk of developing IPF has a mutation in a sequence encoding MUC5B, TERC, FAM13A, TERT, DSP, AZGP1, OBFC1, ATP11A, IVD/DISP2, DPP9, SIGLEC14, ADM2, TSPAN5, CAMKK1 or MMP-7.

In some embodiments of the methods of the disclosure, the subject having PrePF or at risk of developing IPF has a mutation in a sequence encoding Telomerase RNA Component (TERC). In some embodiments the polymorphism is rs6793295 comprising (SEQ ID NO: 1).

```
                                        (SEQ ID NO: 1)
            AGAAAGAAGT CATGAAAGTA GGAACCACAT

TTTTACTCAT CTTTCTGTCT CCAGCAAGCA

GCTTACTGCT TTTCATACAC ATTTTGCTTT

TATTACTCAT GATTTCAAAG GTGTAATGGT

TCAGCCACAT CAATGTAACA AACAGTTCAC

ACTGGGCTCT TATAGTCTGG CCTTTAAAAC

CTTCACTATT TATGCTTTCA TCTTAACTAC

TTTGACCCTC ACAGGTTTAC TCACTAAGAA

CTTGAGTTTC AAGAGAAAAG ATGACATGTT
```

-continued
```
TGCTGCTTAA ACAAGCAATA TCTAAAAGCA

TATTTAGTTA TAAACGTCTT ACCAAGAATT

GATATAATTT TCATTTAAAC ATTTTTATAA

ATAGTAGTTT ACAAGATATA GTAAGTACAT

CTCTAAAAAT ACAGTGTATT CATGTACCTT

GACATAAACT TGTAGTAGTA CCTTAGTTTT

ATTCATGTTG TTATATTAAC TACCATCACT

TTGAATACAT ACCTGTTCAC
```

B
```
GTACAGTATA GGTCGGTTTA GGTTTATTGC

CTTAATTGCT TGGTTTTGAG TTAGTACTGT

AGCAAATGCT ATCACACTTT GCATTCCCTA

AAAACAGGTA AATTCATTAA GGAAACAGAC

AAAGTATATA ATAATCTCGC TACATAAATA

TTTCAAGATC AGCTATCTGC ATTCTGATAA

AATTGTTTTT AAAATTTAAG CATTCCTTGG

ACTTTGAATT GTAAGTTGAT CAAATTCAAA

AATGAATTGT TACTGTATTC TTCTCTCCTG

GCCCTAAAAT CTATCTAAAA CATGGCATGG

GGAGTTTCTT AATGTTTCAG TGTCCATTTC

CTGGGTGTTT CCCTCTAGGT TTTTTTTCCT

CACCCCTCAA GCTTCTATGT GGATCCCAGC

TAGAGCTCAT ACTACTTATC CAACACACAT

CATTGTGCAA GCACTCTTTT ATATTCATAC

TAGTACTTTT AAGTGTGTGT GCGGTGGGAA

AAGGTTACCA ATCACATTTT
```

In some embodiments of the methods of the disclosure, the subject having PrePF or at risk of developing IPF has a mutation in a sequence encoding Family with sequence similarity 13 member A (FAM13A). In some embodiments the polymorphism is rs2609255 comprising (SEQ ID NO: 2).

```
                                    (SEQ ID NO: 2)
GTATTCATCA ACTCCTATTT CATTCCCTCT TCCTGTGCTC

ACTGGAAGAT GACATTTCCC AGACTTCCAA GAATGTTACT

GAGTTCTGGA ATGTAAGTAG AAGGGATAAG TATCACTTCT

GTGCTGTGGC GGTTATGGAC CTGTGAACTT TGCACACGCC

TTCTATCTTC TTTTTCAGTG TCCATTTCAG AGGGCATGTT

TTCAGATGAA ACCAGTAGAA GATGGAAGCA GCCTGTGACT

AGAATCACTG CTTAGGGTCT TGCTGCCTAG GAATCCCACT

CTACCTGCAA CAGACTGTGA AGAACCGAG AAATACACTG

ATTTTGAACA TAGCCCATAC TATAATGGGG ATGTTTGTTA

CAGCAGTTAG CATTAAAAAC CTTGGCTAGG CATTGGTCAT

AATTGTAGAA CACAGCAAAT GAAGGGAAAC TGGAACATAG

AGGCCAGTGA GAACTTTAGG GTTAATGAAA AATGAGGGCA

ACCAGGATAA TTTGGTTCTT
```

K
```
GCCAAATAGG AAGGTGAAAC CAAAGGTAGA CTGGAGGTCA

GAAAATCAGT CCAGCACATG TGATGTTTTC ATTTAGTTGC

CTGTATGTCT GTCTGGTCTC CAGCTCAGCC TGGCTCCTTG

AGGTAAGAGG CAGTGGCTGT TCACCTTTGC ATCCCAGCAC

CTGGCATACA ATAGATGGGA TGAAATGTTC AAACTGAGCC

TAAGCTTCAG GGTGCTTATC AAAGCAGGGA AGATACACAA

GAGGAGATGA TTCAGGTCCA GGGCAGGTCA GGTATCTAAA

CCCAGTCTCT TAGGAAGCTG GATCCTCCGA ACCAGGGAGA

ACAAGCTGGA TATGCACTGG ATTTCCCAGC AGTACTGATC

TAGAGACTCT CATAGAGTCC CTTTTATTCC TTGGCCTAGG

GTTACAACTG CTTATAGCAT CTGGAAAGAC TCAACACCTC

AAAAGAGACT TTCAGTAGAT ACAGCAAATA CACTCATGGA

ATTGATAATT AAGCTTCAAT
```

In some embodiments of the methods of the disclosure, the subject having PrePF or at risk of developing IPF has a mutation in a sequence encoding Telomerase Reverse Transcriptase (TERT). In some embodiments the polymorphism is rs2736100 comprising (SEQ ID NO: 3).

```
                                    (SEQ ID NO: 3)
ATTGTCGTTG TTTGCTTTTG TTTATTGAGA CAGTCTCACT

CTGTCACCCA GGCTGGAGTG TAATGGCACA ATCTCGGCTC

ACTGCAACCT CTGCCTCCTC GGTTCAAGCA GTTCTCATTC

CTCAACCTCA TGAGTAGCTG GGATTACAGG CGCCCACCAC

CACGCCTGGC TAATTTTTGT ATTTTTAGTA GAGATAGGCT

TTCACCATGT TGGCCAGGCT GGTCTCAAAC TCCTGACCTC

AAGTGATCTG CCCGCCTTGG CCTCCCACAG TGCTGGGATT

ACAGGTGCAA GCCACCGTGC CCGGCATACC TTGATCTTTT

AAAATGAAGT CTGAAACATT GCTACCCTTG TCCTGAGCAA

TAAGACCCTT AGTGTATTTT AGCTCTGGCC ACCCCCCAGC

CTGTGTGCTG TTTTCCCTGC TGACTTAGTT CTATCTCAGG

CATCTTGACA CCCCCACAAG CTAAGCATTA TTAATATTGT

TTTCCGTGTT GAGTGTTTCT
```

K
```
TAGCTTTGCC CCCGCCCTGC TTTTCCTCCT TTGTTCCCCG

TCTGTCTTCT GTCTCAGGCC CGCCGTCTGG GGTCCCCTTC

CTTGTCCTTT GCGTGGTTCT TCTGTCTTGT TATTGCTGGT

AAACCCCAGC TTTACCTGTG CTGGCCTCCA TGGCATCTAG
```

-continued

```
CGACGTCCGG GGACCTCTGC TTATGATGCA CAGATGAAGA

TGTGGAGACT CACGAGGAGG GCGGTCATCT TGGCCCGTGA

GTGTCTGGAG CACCACGTGG CCAGCGTTCC TTAGCCAGTG

AGTGACAGCA ACGTCCGCTC GGCCTGGGTT CAGCCTGGAA

AACCCCAGGC ATGTCGGGGT CTGGTGGCTC CGCGGTGTCG

AGTTTGAAAT CGCGCAAACC TGCGGTGTGG CGCCAGCTCT

GACGGTGCTG CCTGGCGGGG GAGTGTCTGC TTCCTCCCTT

CTGCTTGGGA ACCAGGACAA AGGATGAGGC TCCGAGCCGT

TGTCGCCCAA CAGGAGCATG
```

In some embodiments of the methods of the disclosure, the subject having PrePF or at risk of developing IPF has a mutation in a sequence encoding Desmoplakin (DSP). In some embodiments the polymorphism is rs2076295 comprising (SEQ ID NO: 4).

```
                                        (SEQ ID NO: 4)
ATTTGGGAAC CTTTAAAAAA TATTCTGGCT TCAAAAATAC

TCCATATTTA CATCTTTGGT TCTATCTGAA GTAAAGCCGT

GATGGTGTGC GTAAGTGAAA CAGGTGCAAA GGGGCAACAA

CAAAGGGCGC CTCTCTTTGT CTTTGTGTCG CAGGCGGAGA

TGGACATGGT GGCCTGGGGT GTGGACCTGG CCTCAGTGGA

GCAGCACATT AACAGCCACC GGGGCATCCA CAACTCCATC

GGCGACTATC GCTGGCAGCT GGACAAAATC AAAGCCGACC

TGGTACTTGT CTGTGTTTCA TTTTAGAGTC TTCAAAATAT

CTACCGAAGG ATCGTGTAAT TACTCAATCC CAGGGAGTTT

CTTCTGAAAC ATTGCTATTA TTTCTTTCCC AGAAGACTGG

AAATGTTTAG AAATCCCACT TCTTAAATGG GGAAGTGGAA

TCAGTAGCCC TATTAGAGAT TATGTTAACA CTTGAAGAGG

AGTTAAACCA GAGGCTGAGG

K

TGTGCAAACA CTCATTTGCA GTTTGTGAAT AAGTCTCTTT

AGGGGTGGCA GTTTGTTTCT GCGGTAAGCA GAACATCTTT

TTGAATAGGG GAAATGCAAC AGTCTTATAC AGTAGTTTGT

GTCATTGGTG AATCCTTTCC TAGGTGGTAA TTAAAACATT

ATTTCTACTG AGCAAAGCCA TATGTCATCC CGACACCCGC

TCCCATGCTG AAAAAAGTCA GACTTGAAAC TGGGTTGAGA

ATTACAGCAT AAAATCATAA CTGATCTTAA GTGCTTAGTT

TCCCGCAGGT CTCTACACTT GTAAATCACT AAACTTTTTT

TTTTTTTTTT TACCTGAGAC CATAGCTTCT CATCCTCATT

TCTTCTTCTG GCTTTTTGGG GCTTACTTTT GTCCACCTGA

GCCCCTGACC AACTTTCTCC TTCATTTCTC TAAGACCTAG

GGAATCCTAA ATGATGTCTT TAAACTTTAA GACAATTTTC

TAACACGTGA GTCTTTAAGT
```

In some embodiments of the methods of the disclosure, the subject having PrePF or at risk of developing IPF has a mutation in a sequence encoding Zinc-alpha 2-Glycoprotein 1 (AZGP1). In some embodiments the polymorphism is rs4727443 comprising (SEQ ID NO: 5).

```
                                        (SEQ ID NO: 5)
CCCAACCCAA ATAAGCACTA TAACCTCTTG TTATTCACTT

CTCATGCAAC CAGTCTTCTG TTCTCTGTGA GTCTTTAGGA

AATGAGGAGC ATGATCTTCT AGCAGTAAAA CACCTGTAGA

GAATTGCCTT ATGTTTTTTG TTTGTTTATT TGTTTGTGTG

CTTTGGTTTG GTTTGCTTTT TTTTTTTTTT TTTTTTTTTT

TTTGAGATGG AGTCTCGCCC TGTTGCCCAG GCTGGAGTGT

AGTGGCGAAA TCTCGGCTCA CTGCAACCTC CACCTCCCTG

GTTCAAGCAA TTCCCCTGTC TCAGCCTCCC GAGTAGCTGA

GATTACAGGT GCACACCACC ACGCCCGGCT AATTTTTTTG

TATTTTTAGT AGAGATGGGG TTTCACCATG TTGGCCAGAC

TGGTCTCGAA CTTCTGACCT CAGGCAATCC GCCTGCCTCA

GCCTCCCAAA GCGCTGGGAT TACAGGCATG AGCCACTGCG

CCCCGCCTCC ATGTTAATCA

M

TCTTTCTGAT TTCAAATAAC TCATTATCCC CATGACCTTA

TGGATTTGTT TTTCCTCTTC ATCCACAAAA TTCTCCAGAG

AAGTCTCCCT TGTTATCTCT TGGCTGTGCT TTCTATCTCA

CCAGTTATCT TTCTCCAAAG AGCTTCCTCT GCAAAGAAGC

TTTGTATATG AAGACCATGT GGGGGCTGAA TCAAGACCAA

GTTTCACAAC CTAAAAGTAG TTCACAAAGC TTCCTTGCCT

CTATTCTCTG CAAATCTGTA AACTCTTCAG CTGACCCAAT

TTCTCTCTTT AGCCTTCAGA GATTATTTTA TTTTATTTTA

TTTCATTTCA TTTCATTTCA TTTTGACAGA ATCTAGCTCT

GTCGCCCAGG CTGGAGTGCA GTGGCACCAT CTTTGCTCAC

TGCAACCTCC CCCTCACAGG TTCAAGCAAC TGTCCTGCCT

CAGCCTCCCG AGTAGCTGGG ATTACAGGCG TGAGCCACCA

CGCCCAGCTG ATTTTTTTTT
```

In some embodiments of the methods of the disclosure, the subject having PrePF or at risk of developing IPF has a mutation in a sequence encoding Oligonucleotide/oligosaccharide-binding Fold Containing 1 (OBFC1). In some embodiments the polymorphism is rs11191865 comprising (SEQ ID NO: 6).

(SEQ ID NO: 6)

```
CCTCTACTGC CGTACACCCC ACCACTCAGC CTTGGAGTGC
CTGTGTGCAG AGCAGGGCTG AGGCATGGTG CTGCTTTGGT
GGTCTAGGTT TGCTGCAGGG CCAGGTGGCC TGAGCTCCAG
GCAGGATCTC TGGCTGCACT CAGCCCTTTC TGCCTCCCCA
AATGCTCTAT ATCACTATTT GTACACTGAG CAGAGTAAAG
TTAGAGAGAA CTGTTTTATA GAATAGGGCT GGCCCCCGCT
CCCCTGGCCT ACGTGATGGT CCTTCCTGGC TGCCAGGTAC
TTGTTTGTAT TAGAGACAGA CACTCCACAG GGTCTGTTGT
GGCCCACAGC ACATAGGCAA TCAGAGGCAG AAAGCAGAGC
TGTTTGGACC CACAGAGGGC CGGCTGTCTG CCACTGAAAT
GTCTTTCCAG TTGGTTGAGA AGCAGCAGGA TGCTCTGCTG
GTGATGTCTG AAAGTCCAG GATTCTTTGG GTCTCCAAGG
AGATCCTAGC ATATACCACT
R
TCGTGGTTTT AATAAAGAGC AAAAACACTT TCAGATGGGG
AGAAGAGTGG AACAAAAGGT ATTCTTCCTG GGTTGAAGTC
TGGGGGAAAG GCATTGAGAA GACTGGGCTA ATGGCACAAA
CCAATGAAGT ACTCAAGTCA CCTGTGATGG AGGCCAGTCA
TCCAATGGTA TCAACTTTGT ATGTGGCAAC ACTTAATAAA
AATCTGAACA GGTCTTCACT TGTGGACACA GTAGACTTTC
TTGAAAAAGG ACAGAAAAGT GAGCCCTGTG AATTTTCATC
TCACGGACTG ACAACAATGA CTTGCCTTTA AGGACAGTCA
CTCAAGATGA AGATGCAACA AAACCCTTCC AGTTCCAAGT
GGCTGATGAA AAAAAAAAAA TCTTAAAAGC ATCACAGAAC
AACGGAGAAA GAGATCAGAA GACTATAACA GATAGTTTGA
ATTTTAAAAC TCAGAGAAAA GCAACTGAGG AGGAAATACA
CTGCTTAGAA AGAAGAAACT
```

In some embodiments of the methods of the disclosure, the subject having PrePF or at risk of developing IPF has a mutation in a sequence encoding Mucin 5B (MUC5B). In some embodiments the polymorphism is rs35705950 comprising (SEQ ID NO: 7).

SEQ ID NO: 7)
```
TGGACGGCCT CTGAAGGGGT CTGTGGGGTC CTGGACGGGT
CCCCATTCAT GGCAGGATTA ACCCCCCTCG GGTTCTGTGT
GGTCCAGGCC GCCCCTTTGT CTCCACTGCC CCCTGGCCAG
AATGAGGGAC AGTGACCCAC CCAGGGCTGG GCCTGGCTCA
GACTCCGTCA GAGCCGCAGG GCAAGTTCCT GGCACGTCCG
AGGTGGGAGG CTCCTCTGCG CTCCAGGAGG CTGTGCCTGG
CCCCCCTTCC CGGCAGGAAC CGGCTGTGTC CCTTTCCTTC
CTTTATCTTC TGTTTTCAGC
```

D

```
CCTTCAACTG TGAAGAGGTG AACTCTTCAA ACACGCTGAG
CAAACAGGCC CGACTCCCAG GGCCGCATCC GGGATGTCTC
AATAGCTGTG GCCTTGACGT CCACCTCGGA CCCCTGCCCC
GGACCCAGCC CAGTTCCCAA TGGGCCCTCT GCCCGGGGAG
GTGCCTAGTG GGAGGGACGA GGGCAAAGTC GGGGCCCCCA
CTTGTTTGGT GTCACTGTGT GCCAGCGGCC ACTGGCGGGC
GAGGCTGTTC CAGGGTGGAG GCGGGGAGGG TTGGACCACA
GGCACTGAGC GGGGACAGAG
```

In some embodiments of the methods of the disclosure, the subject having PrePF or at risk of developing IPF has a mutation in a sequence encoding ATPase Phospholipid Transporting 11A (ATP11A). In some embodiments the polymorphism is rs12787690 comprising (SEQ ID NO: 8).

(SEQ ID NO: 8)
```
GTCATTGGTC AAATGTGGCC TGTATCTAAA TTCCAACTGT
TAGAATCATA GACATCTAGA GCTTACGTCA GTTTTAGATA
TTTCTTATGA ATTCTCAGAA TTCATAGATT CTCATTTTTA
TTCTTAGACT TCTCAGATAT TCCGTTTTTG ATAGTATACC
CTTCTGAGTC TAATATGTCC TAAAGTGCGA ACTTGTACAA
TTTtttttttt tttttttttt ttttttttttt t
```

K

```
tgataaggag ttttactctg tcacccaggc tggagtgcag
tgacccgatc tcggctcact gcaacctctg cctcccgggt
tcaagtgatt gtgatgtctc agtctcccaa gtagctggga
ttacaggctc ctgccaccac atgcctagct aattgttata
ctttagtaga aatgggctt cgccgtgtta gtcaggctgg
tcttgtactc ctgacctcag ttgatctgcc taccttggcc
cccaaggtgc tgggattaca ggcatgagcc accgcgcctg
accCAGCTTC TTAAATTATT CTGGGCCACC AGTAATGTGA
ATCATGtaaa ttaaaatata taattaaaCA AAATCATATA
GCGATTAGAG ATAATAGTTG TGAAATGCTT GAAAAATCAT
AGGCATTTAA TAAATAGAAG CCATTCCAAT TAGGATTCTT
CTTGATTTTT TTTCAAGACC AAAAAAATAC TCttttaaat
atttattata ataCTCCATG
```

In some embodiments of the methods of the disclosure, the subject having PrePF or at risk of developing IPF has a mutation in a sequence encoding Isovaleryl-CoA dehydrogenase (IVD)/Dispatched RND Transporter Family Member 2 (DISP2). In some embodiments the polymorphism is rs2034650 comprising (SEQ ID NO: 9).

(SEQ ID NO: 9)

```
aggctgcagt tagtcatgac tgcgcgctgc actccagcct gggtgacaaa gtgaggccct gtctcaaaaa caataaaaaa TTTAAAAGAG CTGAGCATGG AGGCcacttt gggaggctga ggcaggcaga tctcttaagc ccaggagtct gagaccagcc tgggcgacat gatgaagccc catctctaca aaaaatacaa aaaaattagc tgagctttat ggcaaatccc tgtaatccca gttacctagg aggcccaggc aggaagatgg cttgagccca aaaggttgag gctgtagtga gctgtgatca tgaacagagt gagaccctgt ttcaaaacaa aatgaaaaac aaacaaacaa aaaaaCCAAG AAAACAAGAA AACAAAAACT ATACAATGAT GAGCCAAAAA GCAAGATATG GAAGAatata tatatatata tatatatata tataGTATGA GTCCAGCTAT AGAAAGTTTG

AAATCAGGCA ACCTAAACAA TATTGTTCAG GGATCTATAC

AGAGGCAGGA AGCCATTGAG AAAGGTAAGG GGAGGATTAT

CACCAAATTC AGGATGGTGG CTCCCCTGGG GAGAATATGT

CAAGGAGGGG CACATGGGCT TGGAATACTG TCTTCATTGA

CCTGCGTGTT GGGTACACAG GAGTTTGTTA TTTTTCACAC

TGCATATGTG CATGTATATA CTCTCCCATA TATACCATGC

ATTTCACACA AGAACACAAA GGCTGTGTGG CTCTGCTCTG

CCCCTTTCCC CTTCCAGCTC CCATTCTCGT C

Y

TCAGCTAGCA GAGGAGGGTC AGGGTCTTTT AGCACAGCTT

CCTTCTGTCT CTGAGTGGGT CAGAGGAGTA CGGGGATGAG

GGCCTCCCTT CTGCGGCTGG GCTCTGGCCA CTCCAGGGTG

GGAAGGCCTG GAGAAACAG GGCCAGGCAA AGCCGGCTGG

CCCTGCTGTT TCTGCCAATG CTGGGATTAG GCCAGGGCTC

TGGCCCACCT GTCATTTCAC TCATTCAGCA TGAACATAGC

CACTGAGCAC TTACTGTGAG CCCCGGGTGC TATTGGGAGA

GTTCAGATAA GTGAGAGAGG GTCTTTGACC TCAAAGATCT

TACAGAGAGG ACCGTATACA CAAATAACAG TATACCAGCA

AAATGTGAGC TAAGTGTCAT GTGACTACTC atctactctt tcaataaata tttgttgtgc acctattaca tgccaggaac tgtgctggat ggtgatcatg taaagacagt caaatcacag tcctagctct cagattcaca gcctgcctaa tgctggggaa acTGGAAT
```

In some embodiments of the methods of the disclosure, the subject having PrePF or at risk of developing IPF has a mutation in a sequence encoding Dipeptidyl Peptidase 9 (DPP9). In some embodiments the polymorphism is rs12610495 comprising (SEQ ID NO: 10).

```
                                         (SEQ ID NO: 10)
CCAGCCAGAA GGGGCGCAGT TTGTTAGTTC AGCTCCTCCT

GAGACAGAAA TAAAGACACG AACCAAAGGA CATCAGCACT

TACAGGGCTC TCAGGTCACA CACAGGATGT CCGCGCCCAC

TGCAGAGCTG CAGGTCCCCT CCAGGGCAGT GGGGAGCCAC

AAGCAGCGTT AGGCAGCGGC TGGGACCAGG ACCGCCTGAG

CACTCAAGAA CCCCCACTGC CCCAAGCACT GCTGGCAGCA

AGCCCAGAAA ACTGAGCCCG GGGAGCTCCT CTGAGCGGCC

TAAGCACCCC TCTAAGCTGT GCTGCCCCAA TTCAAGCCTG

GCTCACGGCA GCAAAGAAAA AATGTGACCT TCGGAGCTCC

CAAAGGGGCC ACCCATAAGC TGAGAGCCTG CCCGGAAGCA

CTTATAGACC CGCGTGGCTT GTTTTCATTG CAAAGAACAA

TAAAAATTAT CTTGCCTCTG ATCACCACTG ATAGCCCAAG

AAGCAAAAAT TCGATCCCGG

D

GATGAGAAAT GAAATGAAAC ATCGCGAGAA ACTTCCAGGA

ATCTTCTGGA TGTGGCTAGA CTCTTTAGCT TGAGCTTCCA

GACAGGCCGA GGCTTGGTGC TGGAGCCTGG CCCTCCGCTG

ACCTCTCTTC TACCCGGGGG CACAGCCCGG ATTGCAGAGA

GGCTGGCGCA AGAGTGAGGG AGCGAGGGCT AGCCTGTGAT

GGGCTTTCTC CACCTAGCAC CACCCTATGC TGTGGCTCAG

GGGAGTCAAG AGTTTACACA GCTGCAGAGA TGGATTCCAG

GCCACTTACT CAAGTCTACC TACTCCTTCC TTCGGCCAAT

CAGCTGGGTG CCTCTGCGGC CTGTGACACC ACCAGCAAAC

AGCTCCAGAC CTCCTAGCAT GGTCTCTGTC AAGGCTGGGT

GGCAGATCTG TGATCTCCTT TTTAAATTTT TCATTTTTTT

TAAGAGATGG GGTCTTGCTA TATTGCCCAG GCTGGTCTCA

AACTCCTGGG CTCCAGCGAT
```

In some embodiments of the methods of the disclosure, the wild type human MUC5B gene of the disclosure consists of or comprises the nucleic acid sequence (Genbank Accession number: NM_002458.2):

(SEQ ID NO: 11)

```
   1 cacccggccc ggctccctcc ctgcccgtcc ccgtccccc accccgtgcca gcccccagga
  61 tgggtgcccc gagcgcgtgc cggacgctgg tgttggctct ggcggccatg ctcgtggtgc
 121 cgcaggcaga gacccagggc cctgtggagc cgagctggga gaatgcaggg cacaccatgg
 181 atggcggtgc cccgacgtcc tcgcccaccc ggcgcgtgag ctttgttcca cccgtcactg
 241 tcttccccag cctgagcccc ctgaacccgg cgcacaatgg gcgggtgtgc agcacctggg
 301 gtgacttcca ctacaagacc ttcgacggcg acgtcttccg cttccctggc ctttgcaact
 361 acgtgttctc tgagcactgc cgcgccgcct acgaggactt caacgtccag ctacgccgag
 421 gcctagtggg ctccaggcct gtggtcaccc gtgttgtcat caaggcccag gggctggtgc
 481 tggaggcgtc caacggctcc gtcctcatca atgggcagcg ggaggagctg ccttacagcc
 541 gcactggcct cctggtggag cagagcgggg actacatcaa ggtcagcatc cggctggtgc
 601 tgacattcct gtggaacgga gaggacagtg ccctgctgga gctggatccc aaatacgcca
 661 accagacctg tggcctgtgt gggacttca acggcctccc ggccttcaac gagttctatg
 721 cccacaacgc caggctgacc ccgctccagt ttgggaacct gcagaagttg gatgggccca
 781 cggagcagtg cccggacccg ctgcccttgc cggccggcaa ctgcacggac gaggagggca
 841 tctgccaccg caccctgctg gggccggcct ttgcggagtg ccacgcactg gtggacagca
 901 ctgcgtacct ggccgcctgc gcccaggacc tgtgccgctg ccccaccctg ccgtgtgcca
 961 cctttgtgga atactcacgc cagtgcgccc acgcgggggg ccagccgcgg aactggaggt
1021 gccctgagct ctgccccgg acctgccccc tcaacatgca gcaccaggag tgtggctcac
1081 cctgcacgga cacctgctcc aaccccagc gcgcgcagct ctgcgaggac cactgtgtgg
1141 acggctgctt ctgcccccca ggcacggtgc tggatgacat cacgcactct ggctgcctgc
1201 ccctcgggca gtgcccctgc acccacggcg gccgcaccta cagcccgggc acctccttca
1261 acaccacctg cagctcctgc acctgctccg gggggctatg gcagtgccag gacctgccgt
1321 gccctggcac ctgctctgtg cagggcgggg cccacatctc cacctatgat gagaaactct
1381 acgacctgca tgtgactgc agctacgttc tgtccaagaa atgtgccgac agcagcttca
1441 ccgtgctggc tgagctgcgg aagtgcggcc tgacggacaa cgagaactgc ctgaaagcgg
1501 tgacgctcag cctggacggc ggggacacgg ccatccgggt ccaagcggac ggcggcgtgt
1561 tcctcaactc catctacacg cagctgcccc tgtcggcagc caacatcacc ctgttcacac
1621 cctcgagctt cttcatcgtg gtgcagacag gcctggggct gcagctgctg gtgcagctgg
1681 tgccactcat gcaggtgttt gtcaggctgg accccgccca ccagggccag atgtgcggcc
1741 tgtgtgggaa cttcaaccag aaccaggctg acgacttcac ggccctcagc ggggtggtgg
1801 aggccacggg cgcagccttc gccaacacct ggaaggccca ggctgcctgt gccaatgcca
1861 ggaacagctt tgaggacccc tgctccctca gtgtggagaa tgagaactac gcccggcact
1921 ggtgctcgcg cctgaccgat cccaacagtg ccttctcgcg ctgccactcc atcatcaacc
1981 ccaagcccct tcactcgaac tgcatgtttg acacctgcaa ctgtgagcgg agcgaggact
2041 gcctgtgcgc cgcgctgtcc tcctatgtgc acgcctgtgc cgccaagggc gtacagctca
2101 gcgactggag ggacggcgtc tgcaccaagt acatgcagaa ctgccccaag tcccagcgct
2161 acgcctacgt ggtggatgcc tgccagccca cttgccgcgg cctgagtgag gccgacgtca
2221 cctgcagcgt ttccttcgtg cctgtggacg gctgcacctg cccgcgggc accttcctca
2281 atgacgcggg cgcctgtgtg cccgcccagg agtgcccctg ctacgctcac ggcaccgtgc
2341 tggctcctgg agaggtggtg cacgacgagg gcgccgtgtg ttcatgtacg ggtgggaagc
```

-continued

```
2401 taagctgcct gggagcctct ctgcagaaaa gcacagggtg tgcagccccc atggtgtacc
2461 tggactgcag caacagctcg gcgggcaccc ctggggccga gtgcctccgg agctgccaca
2521 cgctggacgt gggctgtttc agcacacact gcgtgtccgg ctgtgtctgt ccccgggcc
2581 tggtgtcgga tgggagtggg gctgcattg ccgaggagga ctgcccctgt gtgcacaacg
2641 aggccaccta caagcctgga gagaccatca gggtcgactg caacacctgc acctgcagga
2701 accggaggtg ggagtgcagc caccggctct gcctgggcac ctgcgtggcc tacggggatg
2761 gccacttcat caccttgat ggcgatcgct acagctttga aggcagctgc gagtacatct
2821 tggcccagga ctactgtggg acaacacca cccacgggac cttccgcatc gtcaccgaga
2881 acatcccctg tgggaccacc ggcaccacct gctccaaggc catcaagctc ttcgtggaga
2941 gctacgagct gatcctccaa gaggggacct taaggcggt ggcgagaggg ccgggtgggg
3001 acccacccta caagatacgc tacatgggga tcttcctggt catcgagacc cacgggatgg
3061 ccgtgtcctg gaccggaag accagcgtgt tcatccgact gcaccaggac tacaagggca
3121 gggtctgcgg cctgtgcggg aacttcgacg acaatgccat caatgacttt gccacgcgta
3181 gccggtccgt ggtgggggac gcactggagt ttgggaacag ctggaagctc tccccctcct
3241 gcccggacgc cctggcaccc aaggacccct gcacggccaa ccccttccgc aagtcctggg
3301 cccagaagca gtgcagcatc ctccacggcc ccaccttcgc cgcctgccgc tcccaggttg
3361 actccaccaa gtactacgag gcctgcgtga acgacgcgtg tgcctgcgac tcgggtggcg
3421 actgcgagtg tttctgcacg gctgtggctg cctacgccca ggcctgccac gacgcgggcc
3481 tgtgtgtgtc ctgcggact ccggacacct gcccttgtt ctgtgacttc tacaacccac
3541 atggggctg tgagtggcac taccagccct gcggggcacc ctgcctaaaa acctgccgga
3601 accccagtgg gcactgcctg gtggacctgc ctggcctgga aggctgctac ccgaagtgcc
3661 cacccagcca gcccttcttc aatgaggacc agatgaagtg cgtggcccag tgtggctgct
3721 acgacaagga cggaaactac tatgacgtcg gtgcaagggt ccccacagcg gagaactgcc
3781 agagctgtaa ctgcacaccc agtggcatcc agtgcgctca cagccttgag gcctgcacct
3841 gcacctatga ggacaggacc tacagctacc aggacgtcat ctacaacacc accgatgggc
3901 ttggcgcctg cttgatcgcc atctgcggaa gcaacggcac catcatcagg aaggctgtgg
3961 catgtcctgg aactccagcc acaacgccat tcaccttcac caccgcctgg tcccccact
4021 ccacgacaag cccggcctc ccggtctcca ccgtgtgtgt ccgcgaggtc tgccgctggt
4081 ccagctggta caatgggcac cgcccagagc ccggcctggg aggcggagac tttgagacgt
4141 ttgaaaacct gaggcagaga gggtaccagg tatgccctgt gctggctgac atcgagtgcc
4201 gggcggcgca gcttcccgac atgccgctgg aggagctggg ccagcaggtg gactgtgacc
4261 gcatgcgggg gctgatgtgc gccaacagcc aacagagtcc cccgctctgt cacgactacg
4321 agctgcgggt tctctgctgc gaatacgtgc cctgtggccc ctccccggcc ccaggcacca
4381 gccctcagcc ctccctcagt gccagcacgg agcctgctgt gcctacccca acccagacca
4441 cagcaaccga aaagaccacc ctatgggtga ccccgagcat ccggtcgacg gcggccctca
4501 cctcgcagac tgggtccagc tcaggcccg tgacggtcac cccctcggcc caggtaccca
4561 ccacctgcca gccccggtgt cagtggacag agtggtttga tgaggactac cccaagtctg
4621 aacaacttgg aggggacgtt gagtcctacg ataagatcag ggccgctgga gggcacttat
4681 gccagcagcc taaggacata gagtgccagg ccgagagctt cccaactgg accctggcac
4741 aggtggggca gaaggtgcac tgtgacgtcc acttcggcct ggtgtgcagg aactgggagc
4801 aggagggcgt cttcaagatg tgctacaact acaggatccg ggtcctctgc tgcagtgacg
```

-continued

```
4861 accactgcag gggacgtgcc acaaccccgc caccgaccac agagctggag acggccacca
4921 ccaccaccac ccaggccctg ttctcaacgc cgcagcctac gagtagcccg gggctgacca
4981 gggctccccc ggccagcacc acagcagtcc ccaccctctc agaaggactg acatccccca
5041 gatacacaag cacccttggt acagccacca cgggaggccc cacgacgcct gcaggctcca
5101 cagaacccac tgtcccaggg gtggccacat ccacccttcc aacacgctca gcccttccag
5161 ggacgacggg gagcttgggc acatggcgcc cctcacagcc acccacgctg ccccaacaa
5221 caatggcaac ctccagagct cgcccgacag gcacagccag caccgcttcc aaagagccgc
5281 tgaccacgag cctggcgcca cactcacga gcgagctgtc cacctctcag gccgagacca
5341 gcacgcccag gacagagacg acaatgagcc ccttgactaa caccaccacc agccagggca
5401 cgacccgctg tcaaccgaag tgtgagtgga cagagtggtt tgacgtggac ttcccaacct
5461 caggggttgc aggcggggac atggaaactt ttgaaaacat cagggctgct gggggcaaga
5521 tgtgctgggc accaaagagc atagagtgcc gggcggagaa ctaccccgag gtaagcatcg
5581 accaggtcgg gcaggtgctg acctgcagcc tggagacggg gctgacctgc aagaacgaag
5641 accagacagg caggttcaac atgtgcttca actacaacgt gcgtgtgctt tgctgtgacg
5701 actacagcca ctgccccagt accccagcca ccagctccac ggccacgccc tcctcaactc
5761 cggggacgac ctggatcctc acaaagccga ccacaacagc cactacgact gcgtccactg
5821 gatccacggc cacccgacc tccaccctga aacagctcc ccctcccaaa gtgctgacca
5881 ccacgccac cacacccaca gtcaccagct ccaaagccac tccctcctcc agtccaggga
5941 ctgcaaccgc ccttccagca ctgagaagca cagccaccac acccacagct accagcgtta
6001 cacccatccc ctcttcctcc ctgggcacca cctggacccg cctatcacag accaccacac
6061 ccacggccac catgtccaca gccacaccct cctccactcc agagactgcc cacacctcca
6121 cagtgcttac cgccacggcc accacaactg gggccaccgg ctctgtggcc accccctcct
6181 ccaccccagg aacagctcac actaccaaag tgccaactac cacaaccacg ggcttcacag
6241 ccacccctc ctccagccca gggacggcac tcacgcctcc agtgtggatc agcacaacca
6301 ccacacccac aaccagaggc tccacggtga ccccctcctc catcccgggg accacccaca
6361 ccgccacagt gctgaccacc accaccacaa ctgtggccac tggttctatg caacaccct
6421 cctctagcac acagaccagt ggtactcccc catcactgac caccacggcc actacgatca
6481 cggccaccgg ctccaccacc aaccctcct caactcctgg acaactccc atcccccag
6541 tgctgaccac caccgccacc acacctgcag ccaccagcaa cacagtgact ccctcctctg
6601 ccctagggac cacccacaca ccccagtgc cgaacaccat ggccaccaca cacgggcgat
6661 ccctgccccc cagcagtccc cacacggtgc gcacagcctg gacttcggcc acctcgggca
6721 tcttgggcac cacccacatc acagagcctt ccacggtgac ttcccacacc ctagcagcaa
6781 ccaccggtac cacccagcac tcgactccag ccctttccag ccctcaccct agcagcagaa
6841 ccaccgagtc accccttct ccagggacga ccaccccggg ccacaccacg gccacctcca
6901 ggaccacagc cacggccaca cccagcaaga cccgcacctc gaccctgctg cccagcagcc
6961 ccacatcggc ccccataacc acggtggtga ccatgggctg tgagcccag tgtgcctggt
7021 cagagtggct ggactacagc tacccccatgc cggggccctc tggcggggac tttgacacct
7081 actccaacat ccgtgcggcc ggaggggccg tctgtgagca gcccctgggc ctcgagtgcc
7141 gtgcccaggc ccagcctggt gtccccctgc gggagttggg ccaggtcgtg gaatgcagcc
7201 tggactttgg cctggtctgc aggaaccgtg agcaggtggg gaagttcaag atgtgcttca
```

-continued

```
7261 actatgaaat ccgtgtgttc tgctgcaact acggccactg ccccagcacc ccggccacca 7321 gctctacggc catgccctcc tccactccgg ggacgacctg gatcctcaca gagctgacca 7381 caacagccac tacgactgag tccactggat ccacggccac ccgtcctcc accccaggga 7441 ccacctggat cctcacagag ccgagcacta cagccaccgt gacggtgccc accggatcca 7501 cggccaccgc ctcctccacc caggcaactg ctggcacccc acatgtgagc accacggcca 7561 cgacacccac agtcaccagc tccaaagcca ctcccttctc cagtccaggg actgcaaccg 7621 cccttccagc actgagaagc acagccacca cacccacagc taccagcttt acagccatcc 7681 cctcctcctc cctgggcacc acctggaccc gcctatcaca gaccaccaca cccacggcca 7741 ccatgtccac agccacaccc tcctccactc cagagactgt ccacacctcc acagtgctta 7801 ccaccacggc caccacaacc ggggccaccg gctctgtggc cacccctcc tccaccccag 7861 gaacagctca cactaccaaa gtgctgacta ccacaaccac gggcttcaca gccacccct 7921 cctccagccc agggacggca cgcacgcttc cagtgtggat cagcacaacc accacaccca 7981 caaccagagg ttccacggtg accccctcct ccatcccggg gaccaccac accccacag 8041 tgctgaccac caccaccaca actgtggcca ctggttctat ggcaacaccc tcctctagca 8101 cacagaccag tggtactccc ccatcactga ccaccgggc cactacgatc acggccaccg 8161 gctccaccac caaccccctcc tcaactccag ggacaacacc tatcccccca gtgctgacca 8221 ccaccgccac cacacctgca gccaccagca gcagtgac tccctcctct gccctaggga 8281 ccacccacac accccagtg ccgaacacca cggccaccac acacgggcga tccctgtccc 8341 ccagcagtcc ccacacgtg cgcacagcct ggacttcggc cacctcaggc accttgggca 8401 ccacccacat cacagagcct tccacgggga cttcccacac cccagcagca accaccggta 8461 ccacccagca ctcgactcca gccctgtcca gccctcaccc tagcagcagg accaccgagt 8521 cacccccttc tccagggacg accaccccgg ccacaccag gccacctcc aggaccacgg 8581 ccacggccac acccagcaag acccgcacct cgaccctgct gcccagcagc cccacatcgg 8641 ccccaataac cacggtggtg accatgggct gtgagcccca gtgtgcctgg tcagagtggc 8701 tggactacag ctaccccatg ccggggccct ctggcgggga ctttgacacc tactccaaca 8761 tccgtgcggc cggaggggcc gtctgtgagc agccctggg cctcgagtgc cgtgcccagg 8821 cccagcctgg tgtcccctg cgggagttgg gccaggtcgt ggaatgcagc ctggactttg 8881 gcctggtctg caggaaccgt gagcaggtgg ggaagttcaa gatgtgcttc aactatgaaa 8941 tccgtgtgtt ctgctgcaac tacggccact gccccagcac ccgggccacc agctctacgg 9001 ccacgccctc ctccactcca gggacgacct ggatcctcac agagcagacc acagcagcca 9061 ctacgaccgc aaccactgga tccacggcca tccgtcctc caccccggga acagctcccc 9121 ctcccaaagt gctgaccagc acggccacca cacccacagc caccagttcc aaagccactt 9181 cctcctccag tccaaggact gcaaccaccc ttccagtgct gacaagcaca gccaccaaat 9241 ccacagctac cagctttaca cccatccct ccttcaccct tgggaccacc gggaccctcc 9301 cagaacagac caccacaccc atggccacca tgtccacaat ccacccctcc tccactccgg 9361 agaccaccca cacctccaca gtgctgacca cgaaggccac cacgacaagg gccaccagtt 9421 ccatgtccac cccctcctcc actccgggga cgacctggat cctcacagag ctgaccacag 9481 cagccactac aactgcagcc actggcccca cggccacccc gtcctccacc cagggacca 9541 cctggatcct cacagagccc agcactacag ccaccgtgac ggtgccacc ggatccacgg 9601 ccaccgcctc ctccacccgg gcaactgctg gcaccctcaa agtgctgacc agcacggcca 9661 ccacacccac agtcatcagc tccagagcca ctcccttctc cagtccaggg actgcaaccg
```

-continued

```
  9721  cccttccagc actgagaagc acagccacca cacccacagc taccagcgtt acagccatcc
  9781  cctcttcctc cctgggcacc gcctggaccc gcctatcaca gaccaccaca cccacggcca
  9841  ccatgtccac agccacaccc tcctctactc cagagactgt ccacacctcc acagtgctta
  9901  ccaccacgac caccacaacc agggccaccg gctctgtggc cacccccctcc tccaccccag
  9961  gaacagctca cactaccaaa gtgccgacta ccacaaccac gggcttcaca gccaccccct
 10021  cctccagccc agggacggca ctcacgcctc cagtgtggat cagcacaacc accacaccca
 10081  caaccagagg ctccacggtg acccctcct ccatcccggg gaccacccac accgccacag
 10141  tgctgaccac caccaccaca actgtggcca ctggttctat ggcaacaccc tcctctagca
 10201  cacagaccag tggtactccc ccatcactga ccaccacggc cactacgatc acagccaccg
 10261  gctccaccac caacccctcc tcaactccag gacaactcc catccccca gtgctgacca
 10321  ccaccgccac cacacctgca gccaccagca gcacagtgac tccctcctct gccctaggga
 10381  ccacccacac acccccagtg ccgaacacca cggccaccac acacgggcgg tccctgcccc
 10441  ccagcagtcc ccacacggtg cgcacagcct ggacttcggc cacctcgggc atcttgggca
 10501  ccacccacat cacagagcct tccacggtga cttcccacac cccagcagca accaccagta
 10561  ccacccagca ctcgactcca gccctgtcca gccctcaccc tagcagcagg accaccgagt
 10621  cacccccttc tccagggacg accaccccgg ccacaccag gggcacctcc aggaccacag
 10681  ccacagccac acccagcaag acccgcacct cgaccctgct gcccagcagc cccacatcgg
 10741  cccccataac cacggtggtg accacgggct gtgagcccca gtgtgcctgg tcagagtggc
 10801  tggactacag ctaccccatg ccggggccct ctggcgggga ctttgacacc tactccaaca
 10861  tccgtgcggc cggaggggca gtctgtgagc agcccctggg cctcgagtgc cgtgcccagg
 10921  cccagcctgg tgtcccctg cgggagttgg gccaggtcgt ggaatgcagc ctggactttg
 10981  gctggtctg caggaaccgt gagcaggtgg ggaagttcaa gatgtgcttc aactatgaaa
 11041  tccgtgtgtt ctgctgcaac tacggccact gccccagcac cccggccacc agctctacgg
 11101  ccacgccctc ctcaactccg gggacgacct ggatcctcac aaagctgacc acaacagcca
 11161  ctacgactga gtccactgga tccacggcca ccccgtcctc cacccagg accacctgga
 11221  tcctcacaga gccgagcact acagccaccg tgacggtgcc caccggatcc acggccaccg
 11281  cctcctccac ccaggcaact gctggcaccc cacatgtgag caccacggcc acgacaccca
 11341  cagtcaccag ctccaaagcc actcccttct ccagtccagg gactgcaacc gcccttccag
 11401  cactgagaag cacagccacc acccccacag ctaccagctt tacagccatc ccctcctcct
 11461  ccctgggcac cacctggacc cgcctatcac agaccaccac acccacggcc accatgtcca
 11521  cagccacacc ctcctccact ccagagactg cccacacctc cacagtgctt accaccacgg
 11581  ccaccacaac cagggccacc ggctctgtgg ccacccctc ttccacccca ggaacagctc
 11641  acactaccaa agtgccgact accacaacca cgggcttcac agtcacccc tcctccagcc
 11701  cagggacggc acgcacgcct ccagtgtgga tcagcacaac caccacaccc acaaccagtg
 11761  gctccacggt gaccccctcc tccgtcccgg ggaccaccca cacccccaca gtgctgacca
 11821  ccaccaccac aactgtggcc actggttcta tggcaacacc ctcctctagc acacagacca
 11881  gtggtactcc cccatcactg atcaccacgg ccactacgat cacggccacc ggctccacca
 11941  ccaacccctc ctcaactcca gggacaacac ctatccccc agtgctgacc accaccgcca
 12001  ccacacctgc agccaccagc agcacagtga ctccctcctc tgccctaggg accacccaca
 12061  cacccccagt gccgaacacc acggccacca cacacgggcg atccctgtcc cccagcagtc
```

-continued

```
12121  cccacacggt gcgcacagcc tggacttcgg ccacctcagg caccttgggc accacccaca
12181  tcacagagcc ttccacgggg acttcccaca ccccagcagc aaccaccggt accacccagc
12241  actcgactcc agccctgtcc agccctcacc ctagcagcag gaccaccgag tcaccccctt
12301  ccccagggac gaccacccccg ggccacacca cggccacctc caggaccacg gccacggcca
12361  cacccagcaa gacccgcacc tcgaccctgc tgcccagcag ccccacatcg gcccccataa
12421  ccacggtggt gaccacgggc tgtgagcccc agtgtgcctg gtcagagtgg ctggactaca
12481  gctaccccat gccggggccc tctggcgggg actttgacac ctactccaac atccgtgcgg
12541  ccggagggc cgtctgtgag cagcccctgg gcctcgagtg ccgtgcccag gccagcctg
12601  gtgtcccct gggggagttg gccaggtcg tggaatgcag cctggacttt ggcctggtct
12661  gcaggaaccg tgagcaggtg gggaagttca agatgtgctt caactatgaa atccgtgtgt
12721  tctgctgcaa ctacggccac tgccccagca ccccggccac cagctctacg gccatgccct
12781  cctccactcc ggggacgacc tggatcctca cagagctgac cacaacagcc actacgactg
12841  catccactgg atccacggcc accccgtcct ccaccccggg aacagctccc cctcccaaag
12901  tgctgaccag cccggccacc acacccacag ccaccagttc caaagccact tcctcctcca
12961  gtccaaggac tgcaaccacc cttccagtgc tgacaagcac agccaccaaa tccacagcta
13021  ccagcgttac acccatcccc tcctccaccc ttgggaccac cgggaccctc ccagaacaga
13081  ccaccacacc cgtggccacc atgtccacaa tccaccccctc ctccactccg gagaccaccc
13141  acacctccac agtgctgacc acgaaggcca ccacgacaag ggccaccagt tccacgtcca
13201  cccctcctc cactccgggg acgacctgga tcctcacaga gctgaccaca gcagccacta
13261  caactgcagc cactggcccc acggccaccc cgtcctccac cccagggacc acctggatcc
13321  tcacagagct gaccacaaca gccactacga ctgcgtccac tggatccacg gccaccccgt
13381  cctccacccc agggaccacc tggatcctca cagagccgag cactacagcc accgtgacgg
13441  tgcccaccgg atccacggcc accgcctcct ccacccaggc aactgctggc accccacatg
13501  tgagcaccac ggccacgaca cccacagtca ccagctccaa agccactccc tcctccagtc
13561  cagggactgc aactgcccctt ccagcactga aagcacagc caccacaccc acagctacca
13621  gctttacagc catcccctcc tcctccctgg gcaccacctg gacccgccta tcacagacca
13681  ccacacccac ggccaccatg tccacagcca cccctcctc cactccagag actgtccaca
13741  cctccacagt gcttaccgcc acggccacca caaccggggc caccggctct gtggccaccc
13801  cctcctccac cccaggaaca gctcacacta ccaaagtgcc gactaccaca accacgggct
13861  tcacagccac ccctcctcc agcccaggga cggcactcac gcctccagtg tggatcagca
13921  caaccaccac acccacaacc accacaccca aaccagtgg ctccacggtg acccctcct
13981  ccatcccggg gaccacccac accgccagag tgctgaccac caccaccaca actgtggcca
14041  ctggttctat ggcaacaccc tcctctagca cacagaccag tggtactccc ccatcactga
14101  ccaccacggc cactacgatc acggccaccg gctccaccac caaccccctcc tcaactccag
14161  ggacaacacc catcaccca gtgctgacca gcacggccac cacacccgca gccaccagct
14221  ccaaagccac ttcctcctcc agtccaagga ctgcaaccac ccttccagtg ctgacaagca
14281  cagccacaaa atccacagct accagctttta cacccatccc ctcctccacc ctgtggacca
14341  cgtggaccgt cccagcacag accaccacac cctgtccacc catgtccaca atccacacct
14401  cctctactcc agagaccacc cacacctcca cagtgctgac caccacagcc accatgacaa
14461  gggccaccaa ttccacggcc acacctcct ccactctggg gacgaccccgg atcctcactg
14521  agctgaccac aacagccact acaactgcag ccactggatc cacggccacc ctgtcctcca
```

-continued

```
14581  ccccagggac cacctggatc ctcacagagc cgagcactat agccaccgtg atggtgccca
14641  ccggttccac ggccaccgcc tcctccactc tgggaacagc tcacacccc aaagtggtga
14701  ccaccatggc cactatgccc acagccactg cctccacggt tcccagctcg tccaccgtgg
14761  ggaccacccg cacccctgca gtgctcccca gcagcctgcc aaccttcagc gtgtccactg
14821  tgtcctcctc agtcctcacc accctgagac ccactggctt ccccagctcc cacttctcta
14881  ctccctgctt ctgcagggca tttggacagt ttttctcgcc cggggaagtc atctacaata
14941  agaccgaccg agccggctgc catttctacg cagtgtgcaa tcagcactgt gacattgacc
15001  gcttccaggg cgcctgtccc acctccccac cgccagtgtc ctccgccccg ctgtcctcgc
15061  cctcccctgc ccctggctgt gacaatgcca tccctctccg gcaggtgaat gagacctgga
15121  ccctggagaa ctgcacggtg gccaggtgcg tgggtgacaa ccgtgtcgtc ctgctggacc
15181  caaagcctgt ggccaacgtc acctgcgtga caagcacct gcccatcaaa gtgtcggacc
15241  cgagccagcc ctgtgacttc cactatgagt gcgagtgcat ctgcagcatg tggggcggct
15301  cccactattc caccttttgac ggcacctctt acaccttccg gggcaactgc acctatgtcc
15361  tcatgagaga gatccatgca cgctttggga atctcagcct ctacctggac aaccactact
15421  gcacggcctc tgccactgcc gctgccgccc gctgccccg cgccctcagc atccactaca
15481  agtccatgga tatcgtcctc actgtcacca tggtgcatgg aaggaggag ggcctgatcc
15541  tgtttgacca aattccggtg agcagcggtt tcagcaagaa cggcgtgctt gtgtctgtgc
15601  tggggaccac caccatgcgt gtggacattc ctgccctggg cgtgagcgtc accttcaatg
15661  gccaagtctt ccaggcccgg ctgccctaca gcctcttcca caacaacacc gagggccagt
15721  gcggcacctg caccaacaac cagagggacg actgtctcca gcggacggga accactgccg
15781  ccagttgcaa ggacatggcc aagacgtggc tggtccccga cagcagaaag gatggctgct
15841  gggccccgac tggcacaccc cccactgcca gccccgcagc ccggtgtct agcacaccca
15901  ccccaccccc atgcccacca cagccgctct gtgatctgat gctgagccag gtctttgctg
15961  agtgccacaa ccttgtgccc ccgggcccat tcttcaacgc ctgcatcagc gaccactgca
16021  ggggccgcct tgaggtgccc tgccagagcc tggaggctta cgcagagctc tgccgcgccc
16081  ggggagtgtg cagtgactgg cgaggtgcaa ccggtggcct gtgcgacctc acctgcccac
16141  ccaccaaagt gtacaagcca tgcggcccca tacagcctgc cacctgcaac tctaggaacc
16201  agagcccaca gctggagggg atggcggagg gctgcttctg ccctgaggac cagatcctct
16261  tcaacgcaca catgggcatc tgcgtgcagg cctgccctg cgtgggaccc gatgggtttc
16321  ctaaatttcc cggggagcgg tgggtcagca actgccagtc ctgcgtgtgt gacgagggtt
16381  cagtgtcggt gcagtgcaag cccctgccct gtgacgccca gggtcagccc ccgccgtgca
16441  accgtcccgg cttcgtaacc gtgaccaggc ccgggccga aacccctgc tgccccgaga
16501  cggtgtgcgt gtgcaacaca accacctgcc cccagagcct gcctgtgtgc ccgccagggc
16561  aggagtccat ctgcacccag gaggagggcg actgctgtcc caccttccgc tgcagacctc
16621  agctgtgttc gtacaatggc accttctacg gggttggtgc aaccttccca ggcgcccttc
16681  cctgccacat gtgtacctgc ctctctgggg acacccagga cccaacggtg caatgtcagg
16741  aggatgcctg caacaatact acctgtcccc agggctttga gtacaagaga gtggccgggc
16801  agtgctgtgg ggagtgcgtc cagaccgcct gcctcacgcc cgatggccag ccagtccagc
16861  tgaatgaaac ctgggtcaac agccatgtgg acaactgcac cgtgtacctc tgtgaggctg
16921  agggtggagt ccatttgctg accccacagc ctgcatcctg cccagatgtg tccagctgca
```

-continued

```
16981 gggggagcct caggaaaacc ggctgctgct actcctgtga ggaggactcc tgtcaagtcc 17041 gcatcaacac gaccatcctg tggcaccagg gctgcgagac cgaggtcaac atcaccttct 17101 gcgagggctc ctgccccgga gcgtccaagt actcagcaga ggcccaggcc atgcagcacc 17161 agtgcacctg ctgccaggag aggcgggtcc acgaggagac ggtgcccttg cactgtccta 17221 acggctcagc catcctgcac acctacaccc acgtggatga gtgtggctgc acgcccttct 17281 gtgtccctgc gcccatggct cccccacaca cccgtggctt cccggcccag gaggccactg 17341 ctgtctgaga cgttctgcc tccatcccca tgctctgtcc acctggagcc aggatgtgca 17401 ttgtctgatc atgaaaacct tgggcctcct ctgcggagcc ccccggcctg tgtgtggcac 17461 cccgcgctcc gtgctcctgc tgcccacccc gtgggtgaaa ccggcccag aagggtgagg 17521 ggccagcagg acccctttcg ggagggcgcc actcaggagt cctaccctgg gagagcctgt 17581 ggcccacctt ggccttgccc ctccctgatg tcactgggac gccctggaac aaactaagca 17641 tgtgcgggcc tatgtgtccc tgccacggcc ggagcgcccg cgcagcacgg attccagctg 17701 gccacgtccg gccgctgggg cagacaggct ggtccaggca aggccagctg ctgccaggaa 17761 gctgcgacag gcaaggcggc cgcctgtcca tgcctgctgc agggtaactc agggctgagg 17821 tcgcaacggc caggtcagag aggggtcagc atcccaaagc cccctctgct caacccagcc 17881 cagttttgca aataaaccct gagcattgag tacgtt
```

In some embodiments of the methods of the disclosure, the wild type human MUC5B gene of the disclosure consists of or comprises the amino acid sequence (Genbank Accession number: NP_002449.2):

(SEQ ID NO: 12)
```
   1 mgapsacrtl vlalaamlvv pqaetqgpve pswenaghtm dggaptsspt rrvsfvppvt 61 vfpslsplnp ahngrvcstw gdfhyktfdg dvfrfpglcn yvfsehcraa yedfnvqlrr 121 glvgsrpvvt rvvikaqglv leasngsvli ngqreelpys rtgllveqsg dyikvsirlv 181 ltflwngeds alleldpkya nqtcglcgdf nglpafnefy ahnarltplq fgnlqkldgp 241 teqcpdplpl pagnctdeeg ichrtllgpa faechalvds taylaacaqd lcrcptcpca 301 tfveysrqca haggqprnwr cpelcprtcp lnmqhqecgs pctdtcsnpq raqlcedhcv 361 dgcfcppgtv lddithsgcl plgqcpcthg grtyspgtsf nttcssctcs gglwqcqdlp 421 cpgtcsvqgg ahistydekl ydlhgdcsyv lskkcadssf tvlaelrkcg ltdnenclka 481 vtlsldggdt airvqadggv flnsiytqlp lsaanitlft pssffivvqt glglqllvql 541 vplmqvfvrl dpahqgqmcg lcgnfnqnqa ddftalsgvv eatgaafant wkaqaacana 601 rnsfedpcsl svenenyarh wcsrltdpns afsrchsiin pkpfhsncmf dtcncersed 661 clcaalssyv hacaakgvql sdwrdgvctk ymqncpksqr yayvvdacqp tcrglseadv 721 tcsysfvpvd gctcpagtfl ndagacvpaq ecpcyahgtv lapgevvhde gavcsctggk 781 lsclgaslqk stgcaapmvy ldcsnssagt pgaeclrsch tldvgcfsth cvsgcvcppg 841 lvsdgsggci aeedcpcvhn eatykpgeti rvdcntctcr nrrwecshrl clgtcvaygd 901 ghfitfdgdr ysfegsceyi laqdycgdnt thgtfrivte nipcgttgtt cskaiklfve 961 syelilqegt fkavargpgg dppykirymg iflviethgm ayswdrktsv firlhqdykg 1021 rvcglcgnfd dnaindfatr srsvvgdale fgnswklsps cpdalapkdp ctanpfrksw 1081 aqkqcsilhg ptfaacrsqv dstkyyeacv ndacacdsgg dcecfctava ayaqachdag 1141 lcvswrtpdt cplfcdfynp hggcewhyqp cgapclktcr npsghclvdl pglegcypkc
```

-continued

```
1201 ppsqpffned qmkcvaqcgc ydkdgnyydv garvptaenc qscnctpsgi qcahsleact
1261 ctyedrtysy qdviynttdg lgacliaicg sngtiirkav acpgtpattp ftfttawvph
1321 sttspalpvs tvcvrevcrw sswynghrpe pglgggdfet fenlrqrgyq vcpvladiec
1381 raaqlpdmpl eelgqqvdcd rmrglmcans qqspplchdy elrvlcceyv pcgpspapgt
1441 spqpslsast epavptptqt tatekttlwv tpsirstaal tsqtgsssgp vtvtpsapgt
1501 ttcqprcqwt ewfdedypks eqlggdvesy dkiraagghl cqqpkdiecq aesfpnwtla
1561 qvgqkvhcdv hfglvcrnwe qegvfkmcyn yrirvlccsd dhcrgrattp pptteletat
1621 ttttqalfst pqptsspglt rappasttav ptlsegltsp rytstlgtat tggpttpags
1681 teptvpgvat stlptrsalp gttgslgtwr psqpptlapt tmatsrarpt gtastaskep
1741 lttslaptlt selstsqaet stprtettms pltntttsqg ttrcqpkcew tewfdvdfpt
1801 sgvaggdmet feniraaggk mcwapksiec raenypevsi dqvgqvltcs letgltckne
1861 dqtgrfnmcf nynvrvlccd dyshcpstpa tsstatpsst pgttwiltkp tttatttast
1921 gstatptstl rtapppkvlt ttattptvts skatpssspg tatalpalrs tattptatsv
1981 tpipssslgt twtrlsqttt ptatmstatp sstpetahts tvltatattt gatgsvatps
2041 stpgtahttk vpttttgft atpssspgta ltppvwistt ttpttrgstv tpssipgtth
2101 tatvltttt tvatgsmatp ssstqtsgtp psltttatti tatgsttnps stpgttpipp
2161 vltttattpa atsntvtpss algtthtppv pntmatthgr slppssphtv rtawtsatsg
2221 ilgtthitep stvtshtlaa ttgttqhstp alssphpssr ttesppspgt ttpghttats
2281 rttatatpsk trtstllpss ptsapittvv tmgcepqcaw sewldysypm pgpsggdfdt
2341 ysniraagga vceqplglec raqaqpgvpl relgqvvecs ldfglvcrnr eqvgkfkmcf
2401 nyeirvfccn yghcpstpat sstampsstp gttwiltelt ttatttestg statpsstpg
2461 ttwiltepst tatvtvptgs tatasstqat agtphvstta ttptvtsska tpfsspgtat
2521 alpalrstat tptatsftai pssslgttwt rlsqtttpta tmstatpsst petvhtstvl
2581 tttatttgat gsvatpsstp gtahttkvlt ttttgftatp ssspgtartl pvwistttp
2641 ttrgstvtps sipgtthtpt vltttttva tgsmatpsss tqtsgtppsl tttattitat
2701 gsttnpsstp gttpippvlt ttattpaats stvtpssalg tthtppvpnt tatthgrsls
2761 pssphtvrta wtsatsgtlg tthitepstg tshtpaattg ttqhstpals sphpssrtte
2821 sppspgtttp ghtratsrtt atatpsktrt stllpsspts apittvvtmg cepqcawsew
2881 ldysypmpgp sggdfdtysn iraaggavce qplglecraq aqpgvplrel gqvvecsldf
2941 glvcrnreqv gkfkmcfnye irvfccnygh cpstpatsst atpsstpgtt wilteqttaa
3001 tttattgsta ipsstpgtap ppkvltstat tptatsskat sssprtatt lpvltstatk
3061 statsftpip sftlgttgtl peqtttpmat mstihpsstp etthtstvlt tkatttrats
3121 smstpsstpg ttwilteltt aatttaatgp tatpsstpgt twiltepstt atvtvptgst
3181 atasstrata gtlkvltsta ttptvissra tpssspgtat alpalrstat tptatsvtai
3241 pssslgtawt rlsqtttpta tmstatpsst petvhtstvl ttttttrat gsvatpsstp
3301 gtahttkvpt ttttgftatp ssspgtaltp pvwistttp ttrgstvtps sipgtthtat
3361 vlttttva tgsmatpsss tqsgtppsl tttattitat gsttnpsstp gttpippvlt
3421 ttattpaats stvtpssalg tthtppvpnt tatthgrslp pssphtvrta wtsatsgilg
3481 tthitepstv tshtpaatts ttqhstpals sphpssrtte sppspgtttp ghtrgtsrtt
3541 atatpsktrt stllpsspts apittvvttg cepqcawsew ldysypmpgp sggdfdtysn
3601 iraaggavce qplglecraq aqpgvplrel gqvvecsldf glvcrnreqv gkfkmcfnye
```

-continued

```
3661  irvfccnygh cpstpatsst atpsstpgtt wiltklttta tttestgsta tpsstpgttw 3721  iltepsttat vtvptgstat asstqatagt phvsttattp tvtsskatpf sspgtatalp 3781  alrstattpt atsftaipss slgttwtrls qtttptatms tatpsstpet ahtstvlttt 3841  atttratgsv atpsstpgta httkvptttt tgftvtpsss pgtartppvw isttttptts 3901  gstvtpssvp gtthtptvlt tttttvatgs matpssstqt sgtppslitt attitatgst 3961  tnpsstpgtt pippvlttta ttpaatsstv tpssalgtth tppvpnttat thgrslspss 4021  phtvrtawts atsgtlgtth itepstgtsh tpaattgttq hstpalssph pssrttespp 4081  spgtttpght tatsrttata tpsktrtstl lpssptsapi ttvvttgcep qcawsewldy 4141  sypmpgpsgg dfdtysnira aggavceqpl glecraqaqp gvplgelgqv vecsldfglv 4201  crnreqvgkf kmcfnyeirv fccnyghcps tpatsstamp sstpgttwil teltttattt 4261  astgstatps stpgtapppk vltspattpt atsskatsss sprtattlpv ltstatksta 4321  tsvtpipsst lgttgtlpeq tttpvatmst ihpsstpett htstvlttka tttratssts 4381  tpsstpgttw iltelttaat ttaatgptat psstpgttwi lteltttatt tastgstatp 4441  sstpgttwil tepsttatvt vptgstatas stqatagtph vsttattptv tsskatpsss 4501  pgtatalpal rstattptat sftaipsssl gttwtrlsqt ttptatmsta tpsstpetvh 4561  tstvltatat ttgatgsvat psstpgtaht tkvpttttg ftatpssspg taltppvwis 4621  ttttpttttp ttsgstvtps sipgtthtar vlttttttva tgsmatpsss tqtsgtppsl 4681  tttattitat gsttnpsstp gttpitpvlt stattpaats skatsssspr tattlpvlts 4741  tatkstatsf tpipsstlwt twtvpaqttt pmstmstiht sstpetthts tvltttatmt 4801  ratnstatps stlgttrilt elttttattta atgstatlss tpgttwilte pstiatvmvp 4861  tgstatasst lgtahtpkvv ttmatmptat astvpssstv gttrtpavlp sslptfsvst 4921  vsssvlttlr ptgfpsshfs tpcfcrafgq ffspgeviyn ktdragchfy avcnqhcdid 4981  rfqgacptsp ppvssaplss pspapgcdna iplrqvnetw tlenctvarc vgdnrvvlld 5041  pkpvanvtcv nkhlpikvsd psqpcdfhye cecicsmwgg shvstfdgts ytfrgnctyv 5101  lmreiharfg nlslyldnhy ctasataaaa rcpralsihy ksmdivltvt mvhgkeegli 5161  lfdqipvssg fskngvlvsv lgtttmrvdi palgvsvtfn gqvfqarlpy slfhnntegq 5221  cgtctnnqrd dclqrdgtta asckdmaktw lvpdsrkdgc waptgtppta spaapvsstp 5281  tptpcppqpl cdlmlsqvfa echnlvppgp ffnacisdhc rgrlevpcqs leayaelcra 5341  rgvcsdwrga tgglcdltcp ptkvykpcgp iqpatcnsrn qspqlegmae gcfcpedqil 5401  fnahmgicvq acpcvgpdgf pkfpgerwvs ncqscvcdeg svsvqckplp cdaqgqpppc 5461  nrpgfvtvtr praenpccpe tvcvcntttc pqslpvcppg qesictqeeg dccptfrcrp 5521  qlcsyngtfy gvgatfpgal pchmctclsg dtqdptvqcq edacnnttcp qgfeykrvag 5581  qccgecvqta cltpdgqpvq lnetwvnshv dnctvylcea eggvhlltpq pascpdvssc 5641  rgslrktgcc ysceedscqv rinttilwhq gcetevnitf cegscpgask ysaeaqamqh 5701  qctccqerry heetvplhcp ngsailhtyt hvdecgctpf cvpapmapph trgfpaqeat 5761  av
```

In some embodiments of the methods of the disclosure, the wild type human TERT gene of the disclosure consists of or comprises the nucleic acid sequence (Genbank Accession number: NM_198253.2, transcript variant 1):

(SEQ ID NO: 13)

```
   1 caggcagcgc tgcgtcctgc tgcgcacgtg ggaagccctg gccccggcca ccccgcgat
  61 gccgcgcgct ccccgctgcc gagccgtgcg ctccctgctg cgcagccact accgcgaggt
 121 gctgccgctg gccacgttcg tgcggcgcct ggggcccag ggctggcggc tggtgcagcg
 181 cggggacccg gcggctttcc gcgcgctggt ggcccagtgc ctggtgtgcg tgccctggga
 241 cgcacggccg ccccccgccg ccccctcctt ccgccaggtg tcctgcctga aggagctggt
 301 ggcccgagtg ctgcagaggc tgtgcgagcg cggcgcgaag aacgtgctgg ccttcggctt
 361 cgcgctgctg gacggggccc gcggggggccc ccccgaggcc ttcaccacca gcgtgcgcag
 421 ctacctgccc aacacggtga ccgacgcact gcggggggagc ggggcgtggg ggctgctgct
 481 gcgccgcgtg ggcgacgacg tgctggttca cctgctggca cgctgcgcgc tctttgtgct
 541 ggtggctccc agctgcgcct accaggtgtg cgggccgccg ctgtaccagc tcggcgctgc
 601 cactcaggcc cggccccgc cacacgctag tggaccccga aggcgtctgg gatgcgaacg
 661 ggcctggaac catagcgtca gggaggccgg ggtccccctg ggcctgccag ccccgggtgc
 721 gaggaggcgc gggggcagtg ccagccgaag tctgccgttg cccaagaggc ccaggcgtgg
 781 cgctgcccct gagccggagc ggacgcccgt tgggcagggg tcctgggccc acccgggcag
 841 gacgcgtgga ccgagtgacc gtggtttctg tgtggtgtca cctgccagac ccgccgaaga
 901 agccacctct ttggagggtg cgctctctgg cacgcgccac tcccacccat ccgtgggccg
 961 ccagcaccac gcgggccccc catccacatc gcggccacca cgtccctggg acacgccttg
1021 tcccccggtg tacgccgaga ccaagcactt cctctactcc tcaggcgaca aggagcagct
1081 gcggccctcc ttcctactca gctctctgag gcccagcctg actggcgctc ggaggctcgt
1141 ggagaccatc tttctgggtt ccaggccctg gatgccaggg actccccgca ggttgccccg
1201 cctgccccag cgctactggc aaatgcggcc cctgtttctg gagctgcttg gaaccacgc
1261 gcagtgcccc tacggggtgc tcctcaagac gcactgcccg ctgcgagctg cggtcacccc
1321 agcagccggt gtctgtgccc gggagaagcc ccagggctct gtggcggccc ccgaggagga
1381 ggacacagac cccgtcgcc tggtgcagct gctccgccag cacagcagcc cctggcaggt
1441 gtacggcttc gtgcgggcct gcctgcgccg gctggtgccc ccaggcctct ggggctccag
1501 gcacaacgaa cgccgcttcc tcaggaacac caagaagttc atctccctgg ggaagcatgc
1561 caagctctcg ctgcaggagc tgacgtggaa gatgagcgtg cgggactgcg cttggctgcg
1621 caggagccca gggttggct gtgttccggc cgcagagcac cgtctgcgtg aggagatcct
1681 ggccaagttc ctgcactggc tgatgagtgt gtacgtcgtc gagctgctca ggtctttctt
1741 ttatgtcacg gagaccacgt ttcaaaagaa caggctcttt ttctaccgga agagtgtctg
1801 gagcaagttg caaagcattg gaatcagaca gcacttgaag agggtgcagc tgcgggagct
1861 gtcggaagca gaggtcaggc agcatcggga agccaggccc gccctgctga cgtccagact
1921 ccgcttcatc cccaagcctg acgggctgcg gccgattgtg aacatggact acgtcgtggg
1981 agccagaacg ttccgcagag aaaagagggc cgagcgtctc acctcgaggg tgaaggcact
2041 gttcagcgtg ctcaactacg agcgggcgcg gcgccccggc ctcctgggcg cctctgtgct
2101 gggcctggac gatatccaca gggcctggcg caccttcgtg ctgcgtgtgc gggcccagga
2161 cccgccgcct gagctgtact ttgtcaaggt ggatgtgacg ggcgcgtacg acaccatccc
```

```
2221 ccaggacagg ctcacggagg tcatcgccag catcatcaaa ccccagaaca cgtactgcgt 2281 gcgtcggtat gccgtggtcc agaaggccgc ccatgggcac gtccgcaagg ccttcaagag 2341 ccacgtctct accttgacag acctccagcc gtacatgcga cagttcgtgg ctcacctgca 2401 ggagaccagc ccgctgaggg atgccgtcgt catcgagcag agctcctccc tgaatgaggc 2461 cagcagtggc ctcttcgacg tcttcctacg cttcatgtgc caccacgccg tgcgcatcag 2521 gggcaagtcc tacgtccagt gccagggggat cccgcagggc tccatcctct ccacgctgct 2581 ctgcagcctg tgctacggcg acatggagaa caagctgttt gcggggattc ggcgggacgg 2641 gctgctcctg cgtttggtgg atgatttctt gttggtgaca cctcacctca cccacgcgaa 2701 aaccttcctc aggaccctgg tccgaggtgt ccctgagtat ggctgcgtgg tgaacttgcg 2761 gaagacagtg gtgaacttcc ctgtagaaga cgaggccctg ggtggcacgg cttttgttca 2821 gatgccggcc cacggcctat tcccctggtg cggcctgctg ctggataccc ggaccctgga 2881 ggtgcagagc gactactcca gctatgcccg gacctccatc agagccagtc tcaccttcaa 2941 ccgcggcttc aaggctggga ggaacatgcg tcgcaaactc tttggggtct tgcggctgaa 3001 gtgtcacagc ctgtttctgg atttgcaggt gaacagcctc cagacggtgt gcaccaacat 3061 ctacaagatc ctcctgctgc aggcgtacag gtttcacgca tgtgtgctgc agctcccatt 3121 tcatcagcaa gtttggaaga accccacatt tttcctgcgc gtcatctctg acacggcctc 3181 cctctgctac tccatcctga aagccaagaa cgcagggatg tcgctggggg caagggcgc 3241 cgccggccct ctgccctccg aggccgtgca gtggctgtgc caccaagcat tcctgctcaa 3301 gctgactcga caccgtgtca cctacgtgcc actcctgggg tcactcagga cagcccagac 3361 gcagctgagt cggaagctcc cggggacgac gctgactgcc ctggaggccg cagccaaccc 3421 ggcactgccc tcagacttca agaccatcct ggactgatgg ccacccgccc acagccaggc 3481 cgagagcaga caccagcagc cctgtcacgc cgggctctac gtcccaggga gggaggggcg 3541 gcccacaccc aggcccgcac cgctgggagt ctgaggcctg agtgagtgtt tggccgaggc 3601 ctgcatgtcc ggctgaaggc tgagtgtccg gctgaggcct gagcgagtgt ccagccaagg 3661 gctgagtgtc cagcacacct gccgtcttca cttccccaca ggctggcgct cggctccacc 3721 ccagggccag cttttcctca ccaggagccc ggcttccact cccacatag gaatagtcca 3781 tccccagatt cgccattgtt caccctcgc cctgccctcc tttgccttcc accccacca 3841 tccaggtgga gaccctgaga aggaccctgg gagctctggg aatttggagt gaccaaaggt 3901 gtgccctgta cacaggcgag gaccctgcac ctggatgggg gtccctgtgg gtcaaattgg 3961 ggggaggtgc tgtgggagta aaatactgaa tatatgagtt tttcagtttt gaaaaaaa
```

In some embodiments of the methods of the disclosure, the wild type human TERT gene of the disclosure consists of or comprises the amino acid sequence (Genbank Accession number: NP_937983.2, transcript variant 1):

(SEQ ID NO: 14)
```
  1 mpraprcrav rsllrshyre vlplatfvrr lgpqgwrlvq rgdpaafral vaqclvcvpw 61 darpppaaps frqvsclkel varvlqrlce rgaknvlafg falldgargg ppeafttsvr 121 sylpntvtda lrgsgawgll lrrvgddvlv hllarcalfv lvapscayqv cgpplyqlga 181 atqarpppha sgprrrlgce rawnhsvrea gvplglpapg arrggsasr slplpkrprr 241 gaapepertp vgqgswahpg rtrgpsdrgf cvvsparpae eatslegals gtrhshpsvg 301 rqhhagppst srpprpwdtp cppvyaetkh flyssgdkeq lrpsfllssl rpsltgarrl
```

```
 361 vetiflgsrp wmpgtprrlp rlpqrywqmr plflellgnh aqcpygvllk thcplraavt 421 paagvcarek pqgsvaapee edtdprrlvq llrqhsspwq vygfvraclr rlvppglwgs 481 rhnerrflrn tkkfislgkh aklslqeltw kmsvrdcawl rrspgvgcvp aaehrlreei 541 lakflhwlms vyvvellrsf fyvtettfqk nrlffyrksv wsklqsigir qhlkrvqlre 601 lseaevrqhr earpalltsr lrfipkpdgl rpivnmdyvv gartfrrekr aerltsrvka 661 lfsvinyera rrpgllgasv lglddihraw rtfvlrvraq dpppelyfvk vdvtgaydti 721 pqdrltevia siikpqntyc vrryavvqka ahghvrkafk shvstltdlq pymrqfvahl 781 qetsplrdav vieqssslne assglfdvfl rfmchhavri rgksyvqcqg ipqgsilstl 841 lcslcygdme nklfagirrd glllrlvddf llvtphltha ktflrtivrg vpeygcvvnl 901 rktvvnfpve dealggtafv qmpahglfpw cglildtrtl evqsdyssya rtsirasltf 961 nrgfkagrnm rrklfgvlrl kchslfldlq vnslqtvctn iykilllqay rfhacvlqlp 1021 fhqqvwknpt fflrvisdta slcysilkak nagmslgakg aagplpseav qwlchqafll 1081 kltrhrvtyv pllgslrtaq tqlsrklpgt tltaleaaan palpsdfkti ld
```

In some embodiments of the methods of the disclosure, the wild type human TERT gene of the disclosure consists of or comprises the nucleic acid sequence (Genbank Accession number: NM_001193376.1, transcript variant 2):

```
                                                             (SEQ ID NO: 15)
   1 caggcagcgc tgcgtcctgc tgcgcacgtg ggaagccctg gccccggcca ccccgcgat 61 gccgcgcgct cccgctgcc gagccgtgcg ctccctgctg cgcagccact accgcgaggt 121 gctgccgctg ccacgttcg tgcggcgcct ggggccccag ggctggcggc tggtgcagcg 181 cggggacccg gcggctttcc gcgcgctggt ggcccagtgc ctggtgtgcg tgccctggga 241 cgcacggccg ccccccgccg cccctcctt ccgccaggtg tcctgcctga aggagctggt 301 ggcccgagtg ctgcagaggc tgtgcgagcg cggcgcgaag aacgtgctgg ccttcggctt 361 cgcgctgctg gacggggccc gcgggggccc ccccgaggcc ttcaccacca gcgtgcgcag 421 ctacctgccc aacacggtga ccgacgcact gcggggagc ggggcgtggg ggctgctgct 481 gcgccgcgtg ggcgacgacg tgctggttca cctgctggca cgctgcgcgc tctttgtgct 541 ggtggctccc agctgcgcct accaggtgtg cgggccgccg ctgtaccagc tcggcgctgc 601 cactcaggcc cggccccgc cacacgctag tggaccccga aggcgtctgg gatgcgaacg 661 ggcctggaac catagcgtca gggaggccgg ggtccccctg ggcctgccag ccccgggtgc 721 gaggaggcgc gggggcagtg ccagccgaag tctgccgttg cccaagaggc caggcgtgg 781 cgctgcccct gagccggagc ggacgcccgt tgggcagggg tcctgggccc acccgggcag 841 gacgcgtgga ccgagtgacc gtggtttctg tgtggtgtca cctgccagac ccgccgaaga 901 agccacctct ttggagggtg cgctctctgg cacgcgccac tcccacccat ccgtgggccg 961 ccagcaccac gcgggccccc catccacatc gcggccacca cgtccctggg acacgccttg 1021 tcccccggtg tacgccgaga ccaagcactt cctctactcc tcaggcgaca aggagcagct 1081 gcggccctcc ttcctactca gctctctgag gcccagcctg actggcgctc ggaggctcgt 1141 ggagaccatc tttctgggtt ccaggccctg gatgccaggg actccccgca ggttgccccg 1201 cctgccccag cgctactggc aaatgcggcc cctgtttctg gagctgcttg gaaccacgc 1261 gcagtgcccc tacggggtgc tcctcaagac gcactgccg ctgcgagctg cggtcacccc 1321 agcagccggt gtctgtgccc gggagaagcc ccagggctct gtggcggccc ccgaggagga
```

-continued

```
1381 ggacacagac cccgtcgcc tggtgcagct gctccgccag cacagcagcc cctggcaggt 1441 gtacggcttc gtgcgggcct gcctgcgccg gctggtgccc ccaggcctct ggggctccag 1501 gcacaacgaa cgccgcttcc tcaggaacac caagaagttc atctccctgg ggaagcatgc 1561 caagctctcg ctgcaggagc tgacgtggaa gatgagcgtg cgggactgcg cttggctgcg 1621 caggagccca ggggttggct gtgttccggc cgcagagcac cgtctgcgtg aggagatcct 1681 ggccaagttc ctgcactggc tgatgagtgt gtacgtcgtc gagctgctca ggtctttctt 1741 ttatgtcacg gagaccacgt ttcaaaagaa caggctcttt ttctaccgga agagtgtctg 1801 gagcaagttg caaagcattg gaatcagaca gcacttgaag agggtgcagc tgcgggagct 1861 gtcggaagca gaggtcaggc agcatcggga agccaggccc gccctgctga cgtccagact 1921 ccgcttcatc cccaagcctg acgggctgcg gccgattgtg aacatggact acgtcgtggg 1981 agccagaacg ttccgcagag aaaagagggc cgagcgtctc acctcgaggg tgaaggcact 2041 gttcagcgtg ctcaactacg agcgggcgcg gcgccccggc ctcctgggcg cctctgtgct 2101 gggcctggac gatatccaca gggcctggcg caccttcgtg ctgcgtgtgc gggcccagga 2161 cccgccgcct gagctgtact ttgtcaaggt ggatgtgacg ggcgcgtacg acaccatccc 2221 ccaggacagg ctcacggagg tcatcgccag catcatcaaa ccccagaaca cgtactgcgt 2281 gcgtcggtat gccgtggtcc agaaggccgc ccatgggcac gtccgcaagg ccttcaagag 2341 ccacgtctct accttgacag acctccagcc gtacatgcga cagttcgtgg ctcacctgca 2401 ggagaccagc ccgctgaggg atgccgtcgt catcgagcag agctcctccc tgaatgaggc 2461 cagcagtggc ctcttcgacg tcttcctacg cttcatgtgc caccacgccg tgcgcatcag 2521 gggcaagtcc tacgtccagt gccaggggat cccgcagggc tccatcctct ccacgctgct 2581 ctgcagcctg tgctacggcg acatggagaa caagctgttt gcggggattc ggcgggacgg 2641 gctgctcctg cgtttggtgg atgatttctt gttggtgaca cctcacctca cccacgcgaa 2701 aaccttcctc agctatgccc ggacctccat cagagccagt ctcaccttca accgcggctt 2761 caaggctggg aggaacatgc gtcgcaaact ctttgggtc ttgcggctga agtgtcacag 2821 cctgtttctg gatttgcagg tgaacagcct ccagacggtg tgcaccaaca tctacaagat 2881 cctcctgctg caggcgtaca ggtttcacgc atgtgtgctg cagctcccat tcatcagca 2941 agtttggaag aacccacat ttttcctgcg cgtcatctct gacacggcct ccctctgcta 3001 ctccatcctg aaagccaaga acgcagggat gtcgctgggg gccaagggcg ccgccggccc 3061 tctgccctcc gaggccgtgc agtggctgtg ccaccaagca ttcctgctca agctgactcg 3121 acaccgtgtc acctacgtgc cactcctggg gtcactcagg acagcccaga cgcagctgag 3181 tcggaagctc ccgggacga cgctgactgc cctggaggcc gcagccaacc cggcactgcc 3241 ctcagacttc aagaccatcc tggactgatg gccacccgcc cacagccagg ccgagagcag 3301 acaccagcag ccctgtcacg ccgggctcta cgtcccaggg agggaggggc ggcccacacc 3361 caggcccgca ccgctgggag tctgaggcct gagtgagtgt ttggccgagg cctgcatgtc 3421 cggctgaagg ctgagtgtcc ggctgaggcc tgagcgagtg tccagccaag gctgagtgt 3481 ccagcacacc tgccgtcttc acttccccac aggctggcgc tcggctccac cccagggcca 3541 gcttttcctc accaggagcc cggcttccac tccccacata ggaatagtcc atccccagat 3601 tcgccattgt tcacccctcg ccctgccctc ctttgccttc cacccccacc atccaggtgg 3661 agaccctgag aaggaccctg ggagctctgg gaatttggag tgaccaaagg tgtgccctgt 3721 acacaggcga ggacctgca cctggatggg ggtccctgtg ggtcaaattg gggggaggtg 3781 ctgtgggagt aaaatactga atatatgagt ttttcagttt tgaaaaaaa
```

In some embodiments of the methods of the disclosure, the wild type human TERT gene of the disclosure consists of or comprises the amino acid sequence (Genbank Accession number: NP_001180305.1, transcript variant 2):

(SEQ ID NO: 16)

```
   1 mpraprcrav rsllrshyre vlplatfvrr lgpqgwrlvq rgdpaafral vaqclvcvpw
  61 darpppaaps frqvsclkel varvlqrlce rgaknvlafg falldgargg ppeafttsvr
 121 sylpntvtda lrgsgawgll lrrvgddvlv hllarcalfv lvapscayqv cgpplyqlga
 181 atqarpppha sgprrrlgce rawnhsvrea gvplglpapg arrggsasr  slplpkrprr
 241 gaapepertp vgqgswahpg rtrgpsdrgf cvvsparpae eatslegals gtrhshpsvg
 301 rqhhagppst srpprpwdtp cppvyaetkh flyssgdkeq lrpsfllssl rpsltgarrl
 361 vetiflgsrp wmpgtprrlp rlpqrywqmr plflellgnh aqcpygvllk thcplraavt
 421 paagvcarek pqgsvaapee edtdprrlvq llrqhsspwq vygfvraclr rlvppglwgs
 481 rhnerrflrn tkkfislgkh aklslqeltw kmsvrdcawl rrspgvgcvp aaehrlreei
 541 lakflhwlms vyvvellrsf fyvtettfqk nrlffyrksv wsklqsigir qhlkrvqlre
 601 lseaevrqhr earpalltsr lrfipkpdgl rpivnmdyvv gartfrrekr aerltsrvka
 661 lfsvlnyera rrpgllgasv lglddihraw rtfvlrvraq dpppelyfvk vdvtgaydti
 721 pqdrltevia siikpqntyc vrryavvqka ahghvrkafk shvstltdlq pymrqfvahl
 781 qetsplrdav vieqssslne assglfdvfl rfmchhavri rgksyvqcqg ipqgsilstl
 841 lcslcygdme nklfagirrd glllrlvddf llvtphltha ktflsyarts irasltfnrg
 901 fkagrnmrrk lfgvlrlkch slfldlqvns lqtvctniyk illlqayrfh acvlqlpfhq
 961 qvwknptffl rvisdtaslc ysilkaknag mslgakgaag plpseavqwl chqafllklt
1021 rhrvtyvpll gslrtaqtql srklpgttlt aleaaanpal psdfktild
```

In some embodiments of the methods of the disclosure, the wild type human FAM13A gene of the disclosure consists of or comprises the nucleic acid sequence (Genbank Accession number: NM_014883.3, transcript variant 1):

(SEQ ID NO: 36)

```
   1 atcaaatttc aactccaggc agtccttcca gccatgtggg ttcagcggaa agagaagcaa
  61 aaccactctt cctaaaatgt tagaagctgc tcttcgctta ccttggggcc tttgcattgg
 121 gagctgtttt tcacatcaaa gaatatgtgc tgaatggaat tttagtattt tgctgtcgtt
 181 ttaatatttt cgtctggtct tcctcagttc ttccagacgt tttctgagag aatgggggca
 241 ggagctctag ccatctgtca aagtaaagca gcggttcggc tgaaagaaga catgaaaaag
 301 atagtggcag tgccattaaa tgaacagaag gattttacct atcagaagtt atttggagtc
 361 agtctccaag aacttgaacg gcagggactc accgagaatg gcattccagc agtagtgtgg
 421 aatatagtgg aatatttgac gcagcatgga cttacccaag aaggtctttt tagggtgaat
 481 ggtaacgtga aggtggtgga acaacttcga ctgaagttcg agagtggagt gcccgtggag
 541 ctcgggaagg acggtgatgt ctgctcagca gccagtctgt tgaagctgtt tctgagggag
 601 ctgcctgaca gtctgatcac ctcagcgttg cagcctcgat tcattcaact ctttcaggat
 661 ggcagaaatg atgttcagga gagtagctta agagacttaa taaaagagct gccagacacc
 721 cactactgcc tcctcaagta cctttgccag ttcttgacaa agtagccaa  gcatcatgtg
 781 cagaatcgca tgaatgttca caatctcgcc actgtatttg ggccaaattg ctttcatgtg
 841 ccacctgggc ttgaaggcat gaaggaacag gacctgtgca acaagataat ggctaaaatt
```

-continued

```
 901 ctagaaaatt acaataccct gtttgaagta gagtatacag aaaatgatca tctgagatgt
 961 gaaaacctgg ctaggcttat catagtaaaa gaggtctatt ataagaactc cctgcccatc
1021 cttttaacaa gaggcttaga aagagacatg ccaaaaccac ctccaaaaac caagatccca
1081 aaatccagga gtgagggatc tattcaggcc cacagagtac tgcaaccaga gctatctgat
1141 ggcattcctc agctcagctt gcggctaagt tatagaaaag cctgcttgga agacatgaat
1201 tcagcagagg gtgctattag tgccaagttg gtacccagtt cacaggaaga tgaaagacct
1261 ctgtcacctt tctatttgag tgctcatgta ccccaagtca gcaatgtgtc tgcaaccgga
1321 gaactcttag aaagaaccat ccgatcagct gtagaacaac atcttttga tgttaataac
1381 tctggaggtc aaagttcaga ggactcagaa tctggaacac tatcagcatc ttctgccaca
1441 tctgccagac agcgccgccg ccagtccaag gagcaggatg aagttcgaca tgggagagac
1501 aagggactta tcaacaaaga aaatactcct tctgggttca accaccttga tgattgtatt
1561 ttgaatactc aggaagtcga aaaggtacac aaaaatactt ttggttgtgc tggagaaagg
1621 agcaagccta aacgtcagaa atccagtact aaactttctg agcttcatga caatcaggac
1681 ggtcttgtga atatggaaag tctcaattcc acacgatctc atgagagaac tggacctgat
1741 gattttgaat ggatgtctga tgaaaggaaa ggaaatgaaa aagatggtgg acacactcag
1801 cattttgaga gccccacaat gaagatccag gagcatccca gcctatctga caccaaacag
1861 cagagaaatc aagatgccgg tgaccaggag gagagctttg tctccgaagt gccccagtcg
1921 gacctgactg cattgtgtga tgaaaagaac tgggaagagc ctatccctgc tttctcctcc
1981 tggcagcggg agaacagtga ctctgatgaa gcccacctct cgccgcaggc tgggcgcctg
2041 atccgtcagc tgctggacga agacagcgac cccatgctct ctcctcggtt ctacgcttat
2101 gggcagagca ggcaataccct ggatgacaca gaagtgcctc cttccccacc aaactcccat
2161 tctttcatga ggcggcgaag ctcctctctg gggtcctatg atgatgagca agaggacctg
2221 acacctgccc agctcacacg aaggattcag agccttaaaa agaagatccg gaagtttgaa
2281 gatagattcg aagaagagaa gaagtacaga ccttcccaca gtgacaaagc agccaatccg
2341 gaggttctga aatggacaaa tgaccttgcc aaattccgga gacaacttaa agaatcaaaa
2401 ctaaagatat ctgaagagga cctaactccc aggatgcggc agcgaagcaa cacactcccc
2461 aagagttttg gttcccaact tgagaaagaa gatgagaaga agcaagagct ggtggataaa
2521 gcaataaagc ccagtgttga agccacattg gaatctattc agaggaagct ccaggagaag
2581 cgagcggaaa gcagccgccc tgaggacatt aaggatatga ccaaagacca gattgctaat
2641 gagaaagtgg ctctgcagaa agctctgtta tattatgaaa gcattcatgg acggccggta
2701 acaaagaacg aacggcaggt gatgaagcca ctatacgaca ggtaccggct ggtcaaacag
2761 atcctctccc gagctaacac catacccatc attggttccc cctccagcaa gcggagaagc
2821 cctttgctgc agccaattat cgagggcgaa actgcttcct tcttcaagga gataaaggaa
2881 gaagaggagg ggtcagaaga cgatagcaat gtgaagccag acttcatggt cactctgaaa
2941 accgatttca gtgcacgatg ctttctggac caattcgaag atgacgctga tggatttatt
3001 tccccaatgg atgataaaat accatcaaaa tgcagccagg acacaggggct ttcaaatctc
3061 catgctgcct caatacctga actcctggaa cacctccagg aaatgagaga agaaaagaaa
3121 aggattcgaa agaaacttcg ggatttgaa gacaacttt tcagacagaa tggaagaaat
3181 gtccagaagg aagaccgcac tcctatggct gaagaataca gtgaatataa gcacataaag
3241 gcgaaactga ggctcctgga ggtgctcatc agcaagagag acactgattc caagtccatg
3301 tgaggggcat ggccaagcac aggggggctgg cagctgcggt gagagtttac tgtccccaga
```

-continued

```
3361  gaaagtgcag ctctggaagg cagccttggg gctggccctg caaagcatgc agcccttctg
3421  cctctagacc atttggcatc ggctcctgtt tccattgcct gccttagaaa ctggctggaa
3481  gaagacaatg tgacctgact taggcatttt gtaattggaa agtcaagact gcagtatgtg
3541  cacatgcgca cgcgcatgca cgcacacaca cacacagtag tggagctttc ctaacactag
3601  cagagattaa tcactacatt agacaacact catctacaga gaatatacac tgttcttccc
3661  tggataactg agaaacaaga gaccattctc tgtctaactg tgataaaaac aagctcagga
3721  ctttattcta tagagcaaac ttgctgtgga gggccatgct ctccttggac ccagttaact
3781  gcaaacgtgc attggagccc tatttgctgc cgctgccatt ctagtgacct ttccacagag
3841  ctgcgccttc ctcacgtgtg tgaaaggttt tccccttcag ccctcaggta gatggaagct
3901  gcatctgccc acgatggcag tgcagtcatc atcttcagga tgtttcttca ggacttcctc
3961  agctgacaag gaattttggt ccctgcctag gaccgggtca tctgcagagg acagagagat
4021  ggtaagcagc tgtatgaatc ctgattttaa aaccaggtca tgggagaaga gcctggagat
4081  tctttcctga acactgactg cacttaccag tctgatttta tcgtcaaaca ccaagccagg
4141  ctagcatgct catggcaatc tgtttgggggc tgttttgttg tggcactagc caaacataaa
4201  ggggcttaag tcagcctgca tacagaggat cggggagaga aggggcctgt gttctcagcc
4261  tcctgagtac ttaccagagt ttaatttttt taaaaaaaat ctgcactaaa atccccaaac
4321  tgacaggtaa atgtagccct cagagctcag cccaaggcag aatctaaatc acactatttt
4381  cgagatcatg tataaaaaga aaaaaaagaa gtcatgctgt gtggccaatt ataatttttt
4441  tcaaagactt tgtcacaaaa ctgtctatat tagacatttt ggagggacca ggaaatgtaa
4501  gacaccaaat cctccatctc ttcagtgtgc ctgatgtcac ctcatgattt gctgttactt
4561  ttttaactcc tgcgccaagg acagtgggtt ctgtgtccac ctttgtgctt tgcgaggccg
4621  agcccaggca tctgctcgcc tgccacggct gaccagagaa ggtgcttcag gagctctgcc
4681  ttagacgacg tgttacagta tgaacacaca gcagaggcac cctcgtatgt tttgaaagtt
4741  gccttctgaa agggcacagt tttaaggaaa agaaaaagaa tgtaaaacta tactgacccg
4801  ttttcagttt taaagggtcg tgagaaactg gctggtccaa tgggatttac agcaacattt
4861  tccattgctg aagtgaggta gcagctctct tctgtcagct gaatgttaag gatggggaaa
4921  aagaatgcct ttaagtttgc tcttaatcgt atggaagctt gagctatgtg ttggaagtgc
4981  cctggtttta atccatacac aaagacggta cataatccta caggtttaaa tgtacataaa
5041  aatatagttt ggaattcttt gctctactgt ttacattgca gattgctata atttcaagga
5101  gtgagattat aaataaaatg atgcacttta ggatgtttcc tattttttgaa atctgaacat
5161  gaatcattca catgaccaaa aattgtgttt ttttaaaaat acatgtctag tctgtccttt
5221  aatagctctc ttaaataagc tatgatatta atcagatcat taccagttag cttttaaagc
5281  acatttgttt aagactatgt ttttggaaaa atacgctaca gaattttttt ttaagctaca
5341  aataaatgag atgctactaa ttgttttgga atctgttgtt tctgccaaag gtaaattaac
5401  taaagattta ttcaggaatc cccatttgaa tttgtatgat tcaataaaag aaaacaccaa
5461  gtaagttata taaataaat tgtgtatgag atgttgtgtt ttcctttgta atttccacta
5521  actaactaac taacttatat tcttcatgga atggagccca gaagaaatga gaggaagccc
5581  ttttcacact agatcttatt tgaagaaatg tttgttagtc agtcagtcag tggtttctgg
5641  ctctgccgag ggagatgtgt tccccagcaa ccatttctgc agcccagaat ctcaaggcac
5701  tagaggcggt gtcttaatta attggcttca caaagacaaa atgctctgga ctgggatttt
```

-continued

```
5761 tcctttgctg tgttgggaat atgtgtttat taattagcac atgccaacaa aataaatgtc 5821 aagagttatt tcataagtgt aagtaaactt aagaattaaa gagtgcagac ttataattt 5881 ca
```

In some embodiments of the methods of the disclosure, the wild type human FAM13A gene of the disclosure consists of or comprises the amino acid sequence (Genbank Accession number: NP_055698.2, transcript variant 1):

(SEQ ID NO: 37)
```
   1 mgagalaicq skaavrlked mkkivavpln eqkdftyqkl fgvslqeler qgltengipa
  61 vvwniveylt qhgltqeglf rvngnvkvve qlrlkfesgv pvelgkdgdv csaasllklf
 121 lrelpdslit salqprfiql fqdgrndvqe sslrdlikel pdthycllky lcqfltkvak
 181 hhvqnrmnvh nlatvfgpnc fhvppglegm keqdlcnkim akilenyntl feveytendh
 241 lrcenlarli ivkevyykns lpilltrgle rdmpkpppkt kipksrsegs iqahrvlqpe
 301 lsdgipqlsl rlsyrkacle dmnsaegais aklvpssqed erplspfyls ahvpqvsnvs
 361 atgellerti rsaveqhlfd vnnsggqsse dsesgtlsas satsarqrrr qskeqdevrh
 421 grdkglinke ntpsgfnhld dcilntqeve kvhkntfgca gerskpkrqk sstklselhd
 481 nqdglvnmes lnstrshert gpddfewmsd erkgnekdgg htqhfesptm kigehpslsd
 541 tkqqrnqdag dqeesfvsev pqsdltalcd eknweepipa fsswqrensd sdeahlspqa
 601 grlirqllde dsdpmlsprf yaygqsrqyl ddtevppspp nshsfmrrrs sslgsyddeq
 661 edltpaqltr riqslkkkir kfedrfeeek kyrpshsdka anpevlkwtn dlakfrrqlk
 721 esklkiseed ltprmrqrsn tlpksfgsql ekedekkqel vdkaikpsve atlesiqrkl
 781 qekraessrp edikdmtkdq ianekvalqk allyyesihg rpvtknerqv mkplydryrl
 841 vkqilsrant ipiigspssk rrspllqpii egetasffke ikeeeegsed dsnvkpdfmv
 901 tlktdfsarc fldqfeddad gfispmddki pskcsqdtgl snlhaasipe llehlqemre
 961 ekkrirkklr dfednffrqn grnvqkedrt pmaeeyseyk hikaklrlle vliskrdtds
1021 ksm
```

In some embodiments of the methods of the disclosure, the wild type human FAM13A gene of the disclosure consists of or comprises the nucleic acid sequence (Genbank Accession number: NM_001015045.2, transcript variant 2):

(SEQ ID NO: 17)
```
  1 attgaggagc agaaggagta gggtgcgggg gaggaggagg agcgccttta gtgctgcagc
 61 agctgctgct ctgattggcc cggtggttca gctgcttccc tggaacaaaa ggtcaaagtg
121 gactgcagtg taaatgtaga gaagcagccg ataaaatagc attgcctgaa gaagtttgga
181 ggctgagagc agcagtagac tggccaactg cagagcaagt tgtttctcca gccgtgcggt
241 gcagcctcat gcccccaacc cagcttagcc actgtaagaa gacgttcact gtacagacga
301 ccaaacttgc cgtggaagag acagttgtga gattcccttg caaatttaca tacgagaatg
361 gcttgtgaaa tcatgcctct gcaaagttca caggaagatg aaagacctct gtcaccttc
421 tatttgagtg ctcatgtacc ccaagtcagc aatgtgtctg aaccggaga actcttagaa
481 agaaccatcc gatcagctgt agaacaacat ctttttgatg ttaataactc tggaggtcaa
541 agttcagagg actcagaatc tggaacacta tcagcatctt ctgccacatc tgccagacag
601 cgccgccgcc agtccaagga gcaggatgaa gttcgacatg ggagagacaa gggacttatc
```

-continued

```
 661 aacaaagaaa atactccttc tgggttcaac caccttgatg attgtatttt gaatactcag
 721 gaagtcgaaa aggtacacaa aaatactttt ggttgtgctg gagaaaggag caagcctaaa
 781 cgtcagaaat ccagtactaa actttctgag cttcatgaca atcaggacgg tcttgtgaat
 841 atggaaagtc tcaattccac acgatctcat gagagaactg gacctgatga ttttgaatgg
 901 atgtctgatg aaaggaaagg aaatgaaaaa gatggtggac acactcagca ttttgagagc
 961 cccacaatga agatccagga gcatcccagc ctatctgaca ccaaacagca gagaaatcaa
1021 gatgccggtg accaggagga gagctttgtc tccgaagtgc cccagtcgga cctgactgca
1081 ttgtgtgatg aaaagaactg ggaagagcct atccctgctt tctcctcctg gcagcgggag
1141 aacagtgact ctgatgaagc ccacctctcg ccgcaggctg gcgcctgat ccgtcagctg
1201 ctggacgaag acagcgaccc catgctctct cctcggttct acgcttatgg gcagagcagg
1261 caatacctgg atgacacaga agtgcctcct tccccaccaa actcccattc tttcatgagg
1321 cggcgaagct cctctctggg gtcctatgat gatgagcaag aggacctgac acctgcccag
1381 ctcacacgaa ggattcagag ccttaaaaag aagatccgga gtttgaaga tagattcgaa
1441 gaagagaaga agtacagacc ttcccacagt gacaaagcag ccaatccgga ggttctgaaa
1501 tggacaaatg accttgccaa attccggaga caacttaaag aatcaaaact aaagatatct
1561 gaagaggacc taactcccag gatgcggcag cgaagcaaca cactccccaa gagttttggt
1621 tcccaacttg agaaagaaga tgagaagaag caagagctgg tggataaagc aataaagccc
1681 agtgttgaag ccacattgga atctattcag aggaagctcc aggagaagcg agcggaaagc
1741 agccgccctg aggacattaa ggatatgacc aaagaccaga ttgctaatga gaaagtggct
1801 ctgcagaaag ctctgttata ttatgaaagc attcatggac ggccggtaac aaagaacgaa
1861 cggcaggtga tgaagccact atacgacagg taccggctgg tcaaacagat cctctcccga
1921 gctaacacca tacccatcat tggttccccc tccagcaagc ggagaagccc tttgctgcag
1981 ccaattatcg agggcgaaac tgcttccttc ttcaaggaga taaaggaaga agaggagggg
2041 tcagaagacg atagcaatgt gaagccagac ttcatggtca ctctgaaaac cgatttcagt
2101 gcacgatgct ttctggacca attcgaagat gacgctgatg gatttatttc cccaatggat
2161 gataaaatac catcaaaatg cagccaggac acagggcttt caaatctcca tgctgcctca
2221 atacctgaac tcctggaaca cctccaggaa atgagagaag aaaagaaaag gattcgaaag
2281 aaacttcggg attttgaaga caacttttc agacagaatg gaagaaatgt ccagaaggaa
2341 gaccgcactc ctatggctga agaatacagt gaatataagc acataaaggc gaaactgagg
2401 ctcctggagg tgctcatcag caagagagac actgattcca gtccatgtg agggcatgg
2461 ccaagcacag ggggctggca gctgcggtga gagtttactg tccccagaga aagtgcagct
2521 ctggaaggca gccttgggc tggccctgca aagcatgcag cccttctgcc tctagaccat
2581 ttggcatcgg ctcctgtttc cattgcctgc cttagaaact ggctggaaga agacaatgtg
2641 acctgactta ggcatttgt aattggaaag tcaagactgc agtatgtgca catgcgcacg
2701 cgcatgcacg cacacacaca cacagtagtg gagctttcct aacactagca gagattaatc
2761 actacattag acaacactca tctacagaga atatacactg ttcttccctg gataactgag
2821 aaacaagaga ccattctctg tctaactgtg ataaaaacaa gctcaggact ttattctata
2881 gagcaaactt gctgtggagg gccatgctct ccttggaccc agttaactga aaacgtgcat
2941 tggagcccta tttgctgccg ctgccattct agtgaccttt ccacagagct gcgccttcct
3001 cacgtgtgtg aaaggttttc cccttcagcc ctcaggtaga tggaagctgc atctgcccac
```

```
-continued
3061 gatggcagtg cagtcatcat cttcaggatg tttcttcagg acttcctcag ctgacaagga 3121 attttggtcc ctgcctagga ccgggtcatc tgcagaggac agagagatgg taagcagctg 3181 tatgaatgct gattttaaaa ccaggtcatg ggagaagagc ctggagattc tttcctgaac 3241 actgactgca cttaccagtc tgattttatc gtcaaacacc aagccaggct agcatgctca 3301 tggcaatctg tttgggctg ttttgttgtg gcactagcca aacataaagg ggcttaagtc 3361 agcctgcata cagaggatcg gggagagaag gggcctgtgt tctcagcctc ctgagtactt 3421 accagagttt aattttttta aaaaaatct gcactaaaat ccccaaactg acaggtaaat 3481 gtagccctca gagctcagcc caaggcagaa tctaaatcac actattttcg agatcatgta 3541 taaaaagaaa aaaagaagt catgctgtgt ggccaattat aattttttc aaagactttg 3601 tcacaaaact gtctatatta gacattttgg agggaccagg aaatgtaaga caccaaatcc 3661 tccatctctt cagtgtgcct gatgtcacct catgatttgc tgttactttt ttaactcctg 3721 cgccaaggac agtgggttct gtgtccacct ttgtgctttg cgaggccgag cccaggcatc 3781 tgctcgcctg ccacggctga ccagagaagg tgcttcagga gctctgcctt agacgacgtg 3841 ttacagtatg aacacacagc agaggcaccc tcgtatgttt tgaaagttgc cttctgaaag 3901 ggcacagttt taaggaaaag aaaaagaatg taaaactata ctgacccgtt ttcagtttta 3961 aagggtcgtg agaaactggc tggtccaatg ggatttacag caacattttc cattgctgaa 4021 gtgaggtagc agctctcttc tgtcagctga atgttaagga tggggaaaaa gaatgccttt 4081 aagtttgctc ttaatcgtat ggaagcttga gctatgtgtt ggaagtgccc tggttttaat 4141 ccatacacaa agacggtaca taatcctaca ggtttaaatg tacataaaaa tatagtttgg 4201 aattctttgc tctactgttt acattgcaga ttgctataat ttcaaggagt gagattataa 4261 ataaaatgat gcactttagg atgtttccta tttttgaaat ctgaacatga atcattcaca 4321 tgaccaaaaa ttgtgttttt ttaaaaatac atgtctagtc tgtcctttaa tagctctctt 4381 aaataagcta tgatattaat cagatcatta ccagttagct tttaaagcac atttgtttaa 4441 gactatgttt ttggaaaaat acgctacaga attttttttt aagctacaaa taaatgagat 4501 gctactaatt gttttggaat ctgttgtttc tgccaaaggt aaattaacta aagatttatt 4561 caggaatccc catttgaatt tgtatgattc aataaaagaa acaccaagt aagttatata 4621 aaataaattg tgtatgagat gttgtgtttt cctttgtaat ttccactaac taactaacta 4681 acttatattc ttcatggaat ggagcccaga agaaatgaga ggaagccctt ttcacactag 4741 atcttatttg aagaaatgtt tgttagtcag tcagtcagtg gtttctggct ctgccgaggg 4801 agatgtgttc cccagcaacc atttctgcag cccagaatct caaggcacta gaggcggtgt 4861 cttaattaat tggcttcaca aagacaaaat gctctggact gggattttc ctttgctgtg 4921 ttgggaatat gtgtttatta attagcacat gccaacaaaa taaatgtcaa gagttatttc 4981 ataagtgtaa gtaaacttaa gaattaaaga gtgcagactt ataatttca
```

In some embodiments of the methods of the disclosure, the wild type human FAM13A gene of the disclosure consists of or comprises the amino acid sequence (Genbank Accession number: NP_001015045.1, transcript variant 2):

```
                                                     (SEQ ID NO: 18)
  1 maceimplqs sqederplsp fylsahvpqv snvsatgell ertirsaveq hlfdvnnsgg 61 qssedsesgt lsassatsar qrrqskeqd evrhgrdkgl inkentpsgf nhlddcilnt 121 qevekvhknt fgcagerskp krqksstkls elhdnqdglv nmeslnstrs hertgpddfe
```

-continued

```
181 wmsderkgne kdgghtqhfe sptmkigehp slsdtkqqrn qdagdqeesf vsevpqsdlt 241 alcdeknwee pipafsswqr ensdsdeahl spqagrlirq lldedsdpml sprfyaygqs 301 rqylddtevp psppnshsfm rrrssslgsy ddeqedltpa qltrriqslk kkirkfedrf 361 eeekkyrpsh sdkaanpevl kwtndlakfr rqlkesklki seedltprmr qrsntlpksf 421 gsqlekedek kqelvdkaik psveatlesi qrklqekrae ssrpedikdm tkdqianekv 481 alqkallyye sihgrpvtkn erqvmkplyd ryrlvkqils rantipiigs psskrrspll 541 qpiiegetas ffkeikeeee gseddsnvkp dfmvtlktdf sarcfldqfe ddadgfispm 601 ddkipskcsq dtglsnlhaa sipellehlq emreekkrir kklrdfednf frqngrnvqk 661 edrtpmaeey seykhikakl rllevliskr dtdsksm
```

In some embodiments of the methods of the disclosure, the wild type human FAM13A gene of the disclosure consists of or comprises the nucleic acid sequence (Genbank Accession number: NM_001265578.1, transcript variant 3):

(SEQ ID NO: 38)
```
   1 attgaggagc agaaggagta gggtgcgggg gaggaggagg agcgccttta gtgctgcagc 61 agctgctgct ctgattggcc cggtggttca gctgcttccc tggaacaaaa ggtcaaagtg 121 gactgcagtg taaatgtaga gaagcagccg ataaaatagc attgcctgaa gaagtttgga 181 ggctgagagc agcagtagac tggccaactg cagagcaagt tgtttctcca gccgtgcggt 241 gcagcctcat gcccccaacc cagcttagcc actgtaagaa gacgttcact gtacagacga 301 ccaaacttgc cgtggaagag acagttgtga gattcccttg caaatttaca tacgagaatg 361 gcttgtgaaa tcatgcctct gcaaagtgct catgtacccc aagtcagcaa tgtgtctgca 421 accggagaac tcttagaaag aaccatccga tcagctgtag aacaacatct ttttgatgtt 481 aataactctg gaggtcaaag ttcagaggac tcagaatctg aacactatc agcatcttct 541 gccacatctg ccagacagcg ccgccgccag tccaaggagc aggatgaagt tcgacatggg 601 agagacaagg gacttatcaa caaagaaaat actccttctg ggttcaacca ccttgatgat 661 tgtattttga atactcagga agtcgaaaag gtacacaaaa atacttttgg ttgtgctgga 721 gaaaggagca agcctaaacg tcagaaatcc agtactaaac tttctgagct tcatgacaat 781 caggacggtc ttgtgaatat ggaaagtctc aattccacac gatctcatga gagaactgga 841 cctgatgatt ttgaatggat gtctgatgaa aggaaaggaa atgaaaaaga tggtggacac 901 actcagcatt ttgagagccc cacaatgaag atccaggagc atcccagcct atctgacacc 961 aaacagcaga gaaatcaaga tgccggtgac caggaggaga gctttgtctc cgaagtgccc 1021 cagtcggacc tgactgcatt gtgtgatgaa aagaactggg aagagcctat ccctgctttc 1081 tcctcctggc agcgggagaa cagtgactct gatgaagccc acctctcgcc gcaggctggg 1141 cgcctgatcc gtcagctgct ggacgaagac agcgacccca tgctctctcc tcggttctac 1201 gcttatgggc agagcaggca atacctggat gacacagaag tgcctccttc cccaccaaac 1261 tcccattctt tcatgaggcg gcgaagctcc tctctggggt cctatgatga tgagcaagag 1321 gacctgacac ctgcccagct cacacgaagg attcagagcc ttaaaagaa gatccggaag 1381 tttgaagata gattcgaaga agaagaag tacagacctt cccacagtga caaagcagcc 1441 aatccggagg ttctgaaatg gacaaatgac cttgccaaat tccggagaca acttaaagaa 1501 tcaaaactaa agatatctga gaggaccta actcccagga tgcggcagcg aagcaacaca 1561 ctcccccaaga gttttggttc ccaacttgag aaagaagatg agaagaagca agagctggtg
```

```
1621  gataaagcaa taaagcccag tgttgaagcc acattggaat ctattcagag gaagctccag 1681  gagaagcgag cggaaagcag ccgccctgag gacattaagg atatgaccaa agaccagatt 1741  gctaatgaga aagtggctct gcagaaagct ctgttatatt atgaaagcat tcatggacgg 1801  ccggtaacaa agaacgaacg gcaggtgatg aagccactat acgacaggta ccggctggtc 1861  aaacagatcc tctcccgagc taacaccata cccatcattg gttcccctc cagcaagcgg 1921  agaagcccctt tgctgcagcc aattatcgag ggcgaaactg cttccttctt caaggagata 1981  aaggaagaag aggagggtc agaagacgat agcaatgtga agccagactt catggtcact 2041  ctgaaaaccg atttcagtgc acgatgcttt ctggaccaat tcgaagatga cgctgatgga 2101  tttatttccc caatggatga taaaatacca tcaaaatgca gccaggacac agggctttca 2161  aatctccatg ctgcctcaat acctgaactc ctggaacacc tccaggaaat gagagaagaa 2221  aagaaaagga ttcgaaagaa acttcgggat tttgaagaca acttttttcag acagaatgga 2281  agaaatgtcc agaaggaaga ccgcactcct atggctgaag aatacagtga atataagcac 2341  ataaaggcga aactgaggct cctggaggtg ctcatcagca agagagacac tgattccaag 2401  tccatgtgag gggcatggcc aagcacaggg ggctggcagc tgcggtgaga gtttactgtc 2461  cccagagaaa gtgcagctct ggaaggcagc cttggggctg ccctgcaaa gcatgcagcc 2521  cttctgcctc tagaccattt ggcatcggct cctgtttcca ttgcctgcct tagaaactgg 2581  ctggaagaag acaatgtgac ctgacttagg cattttgtaa ttggaaagtc aagactgcag 2641  tatgtgcaca tgcgcacgcg catgcacgca cacacacaca cagtagtgga gctttcctaa 2701  cactagcaga gattaatcac tacattagac aacactcatc tacagagaat atacactgtt 2761  cttccctgga taactgagaa acaagagacc attctctgtc taactgtgat aaaaacaagc 2821  tcaggacttt attctataga gcaaacttgc tgtggagggc catgctctcc ttggacccag 2881  ttaactgcaa acgtgcattg gagccctatt tgctgccgct gccattctag tgacctttcc 2941  acagagctgc gccttcctca cgtgtgtgaa aggttttccc cttcagccct caggtagatg 3001  gaagctgcat ctgcccacga tggcagtgca gtcatcatct tcaggatgtt tcttcaggac 3061  ttcctcagct gacaaggaat tttggtccct gcctaggacc gggtcatctg cagaggacag 3121  agagatggta agcagctgta tgaatgctga ttttaaaacc aggtcatggg agaagagcct 3181  ggagattctt tcctgaacac tgactgcact taccagtctg attttatcgt caaacaccaa 3241  gccaggctag catgctcatg gcaatctgtt tggggctgtt ttgttgtggc actagccaaa 3301  cataaagggg cttaagtcag cctgcataca gaggatcggg gagagaaggg gcctgtgttc 3361  tcagcctcct gagtacttac cagagtttaa ttttttttaaa aaaaatctgc actaaaatcc 3421  ccaaactgac aggtaaatgt agccctcaga gctcagccca aggcagaatc taaatcacac 3481  tattttcgag atcatgtata aaagaaaaa aaagaagtca tgctgtgtgg ccaattataa 3541  ttttttttcaa agactttgtc acaaaactgt ctatattaga cattttggag ggaccaggaa 3601  atgtaagaca ccaaatcctc catctcttca gtgtgcctga tgtcacctca tgatttgctg 3661  ttactttttt aactcctgcg ccaaggacag tgggttctgt gtccacctttt gtgctttgcg 3721  aggccgagcc caggcatctg ctcgcctgcc acggctgacc agagaaggtg cttcaggagc 3781  tctgccttag acgacgtgtt acagtatgaa cacacagcag aggcaccctc gtatgttttg 3841  aaagttgcct tctgaaaggg cacagttta aggaaaagaa aagaatgta aaactatact 3901  gacccgtttt cagtttttaaa gggtcgtgag aaactggctg gtccaatggg atttacagca 3961  acattttcca ttgctgaagt gaggtagcag ctctcttctg tcagctgaat gttaaggatg 4021  gggaaaaaga atgccttaaa gtttgctctt aatcgtatgg aagcttgagc tatgtgttgg
```

```
4081 aagtgccctg gttttaatcc atacacaaag acggtacata atcctacagg tttaaatgta 4141 cataaaaata tagtttggaa ttctttgctc tactgtttac attgcagatt gctataattt 4201 caaggagtga gattataaat aaaatgatgc actttaggat gtttcctatt tttgaaatct 4261 gaacatgaat cattcacatg accaaaaatt gtgtttttt aaaaatacat gtctagtctg 4321 tcctttaata gctctcttaa ataagctatg atattaatca gatcattacc agttagcttt 4381 taaagcacat ttgtttaaga ctatgttttt ggaaaaatac gctacagaat ttttttttaa 4441 gctacaaata aatgagatgc tactaattgt tttggaatct gttgtttctg ccaaaggtaa 4501 attaactaaa gatttattca ggaatcccca tttgaatttg tatgattcaa taaaagaaaa 4561 caccaagtaa gttatataaa ataaattgtg tatgagatgt tgtgttttcc tttgtaattt 4621 ccactaacta actaactaac ttatattctt catggaatgg agcccagaag aaatgagagg 4681 aagccctttt cacactagat cttatttgaa gaaatgtttg ttagtcagtc agtcagtggt 4741 ttctggctct gccgagggag atgtgttccc cagcaaccat ttctgcagcc cagaatctca 4801 aggcactaga ggcggtgtct taattaattg gcttcacaaa gacaaaatgc tctggactgg 4861 gatttttcct ttgctgtgtt gggaatatgt gtttattaat tagcacatgc caacaaaata 4921 aatgtcaaga gttatttcat aagtgtaagt aaacttaaga attaaagagt gcagacttat 4981 aattttca
```

In some embodiments of the methods of the disclosure, the wild type human FAM13A gene of the disclosure consists of or comprises the amino acid sequence (Genbank Accession number: NP_001252507.1, transcript variant 3):

(SEQ ID NO: 39)
```
  1 maceimplqs ahvpqvsnvs atgellerti rsaveqhlfd vnnsggqsse dsesgtlsas 61 satsarqrrr qskeqdevrh grdkglinke ntpsgfnhld dcilntqeve kvhkntfgca 121 gerskpkrqk sstklselhd nqdglvnmes lnstrshert gpddfewmsd erkgnekdgg 181 htqhfesptm kigehpslsd tkqqrnqdag dqeesfvsev pqsdltalcd eknweepipa 241 fsswqrensd sdeahlspqa grlirqllde dsdpmlsprf yayggsrqyl ddtevppspp 301 nshsfmrrrs sslgsyddeq edltpaqltr riqslkkkir kfedrfeeek kyrpshsdka 361 anpevlkwtn dlakfrrqlk esklkiseed ltprmrqrsn tlpksfgsql ekedekkqel 421 vdkaikpsve atlesiqrkl qekraessrp edikdmtkdq ianekvalqk allyyesihg 481 rpvtknerqv mkplydryrl vkqilsrant ipiigspssk rrspllqpii egetasffke 541 ikeeeegsed dsnvkpdfmv tlktdfsarc fldqfeddad gfispmddki pskcsqdtgl 601 snlhaasipe llehlqemre ekkrirkklr dfednffrqn grnvqkedrt pmaeeyseyk 661 hikaklrlle vliskrdtds ksm
```

In some embodiments of the methods of the disclosure, the wild type human FAM13A gene of the disclosure consists of or comprises the nucleic acid sequence (Genbank Accession number: NM_001265579.1, transcript variant 4):

(SEQ ID NO: 40)
```
  1 attgaggagc agaaggagta gggtgcgggg gaggaggagg agcgccttta gtgctgcagc 61 agctgctgct ctgattggcc cggtggttca gctgcttccc tggaacaaaa ggtcaaagtg 121 gactgcagtg taaatgtaga gaagcagccg ataaaatagc attgcctgaa gaagtttgga
```

```
 181   ggctgagagc agcagtagac tggccaactg cagagcaagt tgtttctcca gccgtgcggt 241   gcagcctcat gcccccaacc cagcttagcc actgtaagaa gacgttcact gtacagacga 301   ccaaacttgc cgtggaagag acagttgtga gattcccttg caaatttaca tacgagaatg 361   gcttgtgaaa tcatgcctct gcaaagttca caggaagatg aaagacctct gtcaccttc 421   tatttgagtg ctcatgtacc ccaagtcagc aatgtgtctg caaccggaga actcttagaa 481   agaaccatcc gatcagctgt agaacaacat cttttgatg ttaataactc tggaggtcaa 541   agttcagagg actcagaatc tggaacacta tcagcatctt ctgccacatc tgccagacag 601   cgccgccgcc agtccaagga gcaggatgaa gttcgacatg ggagagacaa gggacttatc 661   aacaaagaaa atactccttc tgggttcaac caccttgatg attgtatttt gaatactcag 721   gaagtcgaaa aggtacacaa aaatactttt ggttgtgctg gagaaaggag caagcctaaa 781   cgtcagaaat ccagtactaa actttctgag cttcatgaca atcaggacgg tcttgtgaat 841   atggaaagtc tcaattccac acgatctcat gagagaactg gacctgatga ttttgaatgg 901   atgtctgatg aaaggaaagg aaatgaaaaa gatggtggac acactcagca ttttgagagc 961   cccacaatga agatccagga gcatcccagc ctatctgaca ccaaacagca gagaaatcaa 1021   gatgccggtg accaggagga gagctttgtc tccgaagtgc cccagtcgga cctgactgca 1081   ttgtgtgatg aaaagaactg ggaagagcct atccctgctt ctcctcctg gcagcgggag 1141   aacagtgact ctgatgaagc ccacctctcg ccgcaggctg gcgcctgat ccgtcagctg 1201   ctggacgaag acagcgaccc catgctctct cctcggttct acgcttatgg gcagagcagg 1261   caatacctgg atgcacagga agtgcctcct tccccaccaa actcccattc tttcatgagg 1321   cggcgaagct cctctctggg gtcctatgat gatgagcaag aggacctgac acctgcccag 1381   ctcacacgaa ggattcagag ccttaaaaag aagatccgga gtttgaaga tagattcgaa 1441   gaagagaaga agtacagacc ttcccacagt gacaaagcag ccaatccgga ggttctgaaa 1501   tggacaaatg accttgccaa attccggaga caacttaaag aatcaaaact aaagatatct 1561   gaagaggacc taactcccag gatgcggcag cgaagcaaca cactccccaa gagttttggt 1621   tcccaacttg agaaagaaga tgagaagaag caagagctgg tggataaagc aataaagccc 1681   agtgttgaag ccacattgga atctattcag aggaagctcc aggagaagcg agcggaaagc 1741   agccgccctg aggacattaa ggatatgacc aaagaccaga ttgctaatga aaagtggct 1801   ctgcagaaag ctctgttata ttatgaaagc attcatggac ggccggtaac aaagaacgaa 1861   cggcaggtga tgaagccact atacgacagg taccggctgg tcaaacagat cctctcccga 1921   gctaacacca tacccatcat tgaagaagag gagggtcag aagacgatag caatgtgaag 1981   ccagacttca tggtcactct gaaaaccgat ttcagtgcac gatgctttct ggaccaattc 2041   gaagatgacg ctgatggatt tattcccca atggatgata aaataccatc aaaatgcagc 2101   caggacacag ggctttcaaa tctccatgct gcctcaatac ctgaactcct ggaacacctc 2161   caggaaatga gagaagaaaa gaaaaggatt cgaaagaaac ttcgggattt tgaagacaac 2221   ttttcagac agaatggaag aaatgtccag aaggaagacc gcactcctat ggctgaagaa 2281   tacagtgaat ataagcacat aaaggcgaaa ctgaggctcc tggaggtgct catcagcaag 2341   agagacactg attccaagtc catgtgaggg gcatggccaa gcacagggg ctggcagctg 2401   cggtgagagt ttactgtccc cagagaaagt gcagctctgg aaggcagcct tggggctggc 2461   cctgcaaagc atgcagccct tctgcctcta gaccatttgg catcggctcc tgtttccatt 2521   gcctgcctta gaaactggct ggaagaagac aatgtgacct gacttaggca ttttgtaatt 2581   ggaaagtcaa gactgcagta tgtgcacatg cgcacgcgca tgcacgcaca cacacacaca
```

```
2641  gtagtggagc tttcctaaca ctagcagaga ttaatcacta cattagacaa cactcatcta
2701  cagagaatat acactgttct tccctggata actgagaaac aagagaccat tctctgtcta
2761  actgtgataa aaacaagctc aggactttat tctatagagc aaacttgctg tggagggcca
2821  tgctctcctt ggacccagtt aactgcaaac gtgcattgga gccctatttg ctgccgctgc
2881  cattctagtg accttttccac agagctgcgc cttcctcacg tgtgtgaaag gttttcccct
2941  tcagccctca ggtagatgga agctgcatct gcccacgatg gcagtgcagt catcatcttc
3001  aggatgtttc ttcaggactt cctcagctga caaggaattt tggtccctgc ctaggaccgg
3061  gtcatctgca gaggacagag agatggtaag cagctgtatg aatgctgatt ttaaaaccag
3121  gtcatgggag aagagcctgg agattctttc ctgaacactg actgcactta ccagtctgat
3181  tttatcgtca aacaccaagc caggctagca tgctcatggc aatctgtttg gggctgtttt
3241  gttgtggcac tagccaaaca taaagggggct taagtcagcc tgcatacaga ggatcgggga
3301  gagaagggggc ctgtgttctc agcctcctga gtacttacca gagtttaatt ttttttaaaaa
3361  aaatctgcac taaaatcccc aaactgacag gtaaatgtag ccctcagagc tcagcccaag
3421  gcagaatcta aatcacacta ttttcgagat catgtataaa aagaaaaaaa agaagtcatg
3481  ctgtgtggcc aattataatt tttttcaaag actttgtcac aaaactgtct atattagaca
3541  ttttggaggg accaggaaat gtaagacacc aaatcctcca tctcttcagt gtgcctgatg
3601  tcacctcatg atttgctgtt acttttttaa ctcctgcgcc aaggacagtg ggttctgtgt
3661  ccaccttttgt gctttgcgag gccgagccca ggcatctgct cgcctgccac ggctgaccag
3721  agaaggtgct tcaggagctc tgccttagac gacgtgttac agtatgaaca cacagcagag
3781  gcaccctcgt atgttttgaa agttgccttc tgaaagggca cagttttaag gaaaagaaaa
3841  agaatgtaaa actatactga cccgttttca gttttaaagg gtcgtgagaa actggctggt
3901  ccaatgggat ttacagcaac attttccatt gctgaagtga ggtagcagct ctcttctgtc
3961  agctgaatgt taaggatggg gaaaaagaat gcctttaagt ttgctcttaa tcgtatggaa
4021  gcttgagcta tgtgttggaa gtgccctggt tttaatccat acacaaagac ggtacataat
4081  cctacaggtt taaatgtaca taaaaatata gtttggaatt ctttgctcta ctgtttacat
4141  tgcagattgc tataatttca aggagtgaga ttataaataa aatgatgcac tttaggatgt
4201  ttcctatttt tgaaatctga acatgaatca ttcacatgac caaaaattgt gttttttaa
4261  aaatacatgt ctagtctgtc ctttaatagc tctcttaaat aagctatgat attaatcaga
4321  tcattaccag ttagctttta aagcacattt gtttaagact atgttttttgg aaaaatacgc
4381  tacagaattt tttttaagc tacaaataaa tgagatgcta ctaattgttt tggaatctgt
4441  tgtttctgcc aaagtaaat taactaaaga tttattcagg aatccccatt tgaattttgta
4501  tgattcaata aaagaaaaca ccaagtaagt tatataaaat aaattgtgta tgagatgttg
4561  tgttttcctt tgtaatttcc actaactaac taactaactt atattcttca tggaatggag
4621  cccagaagaa atgagaggaa gcccttttca cactagatct tatttgaaga aatgtttgtt
4681  agtcagtcag tcagtggttt ctggctctgc cgagggagat gtgttcccca gcaaccattt
4741  ctgcagccca gaatctcaag gcactagagg cggtgtctta attaattggc ttcacaaaga
4801  caaaatgctc tggactggga ttttttcctttt gctgtgttgg gaatatgtgt ttattaatta
4861  gcacatgcca acaaaataaa tgtcaagagt tatttcataa gtgtaagtaa acttaagaat
4921  taaagagtgc agacttataa ttttca
```

In some embodiments of the methods of the disclosure, the wild type human FAM13A gene of the disclosure consists of or comprises the amino acid sequence (Genbank Accession number: NP_001252508.1, transcript variant 4):

(SEQ ID NO: 41)

```
  1 maceimplqs sqederplsp fylsahvpqv snvsatgell ertirsaveq hlfdvnnsgg
 61 qssedsesgt lsassatsar qrrrqskeqd evrhgrdkgl inkentpsgf nhlddcilnt
121 qevekvhknt fgcagerskp krqksstkls elhdnqdglv nmeslnstrs hertgpddfe
181 wmsderkgne kdgghtqhfe sptmkigehp slsdtkqqrn qdagdqeesf vsevpqsdlt
241 alcdeknwee pipafsswqr ensdsdeahl spqagrlirq lldedsdpml sprfyaygqs
301 rqylddtevp psppnshsfm rrrssslgsy ddeqedltpa qltrriqslk kkirkfedrf
361 eeekkyrpsh sdkaanpevl kwtndlakfr rqlkesklki seedltprmr qrsntlpksf
421 gsqlekedek kqelvdkaik psveatlesi qrklqekrae ssrpedikdm tkdqianekv
481 alqkallyye sihgrpvtkn erqvmkplyd ryrlvkqils rantipiiee eegseddsnv
541 kpdfmvtlkt dfsarcfldq feddadgfis pmddkipskc sqdtglsnlh aasipelleh
601 lqemreekkr irkklrdfed nffrqngrnv qkedrtpmae eyseykhika klrllevlis
661 krdtdsksm
```

In some embodiments of the methods of the disclosure, the wild type human FAM13A gene of the disclosure consists of or comprises the nucleic acid sequence (Genbank Accession number: NM_001265580.1, transcript variant 5):

(SEQ ID NO: 42)

```
   1 attgaggagc agaaggagta gggtgcgggg gaggaggagg agcgccttta gtgctgcagc
  61 agctgctgct ctgattggcc cggtggttca gctgcttccc tggaacaaaa ggtcaaagtg
 121 gactgcagtg taaatgtaga gaagcagccg ataaatagc attgcctgaa gaagtttgga
 181 ggctgagagc agcagtagac tggccaactg cagagcaagt tgtttctcca gccgtgcggt
 241 gcagcctcat gcccccaacc cagcttagcc actgtaagaa gacgttcact gtacagacga
 301 ccaaacttgc cgtggaagag acagttgtga gattcccttg caaatttaca tacgagaatg
 361 gcttgtgaaa tcatgcctct gcaaagactc ttagaaagaa ccatccgatc agctgtagaa
 421 caacatcttt ttgatgttaa taactctgga ggtcaaagtt cagaggactc agaatctgga
 481 acactatcag catcttctgc cacatctgcc agacagcgcc gccgccagtc caggagcag
 541 gatgaagttc gacatgggag agacaaggga cttatcaaca agaaaatac tccttctggg
 601 ttcaaccacc ttgatgattg tattttgaat actcaggaag tcgaaaggt acacaaaaat
 661 acttttggtt gtgctggaga aaggagcaag cctaaacgtc agaaatccag tactaaactt
 721 tctgagcttc atgacaatca ggacggtctt gtgaatatgg aaagtctcaa ttccacacga
 781 tctcatgaga gaactggacc tgatgatttt gaatggatgt ctgatgaaag gaaaggaaat
 841 gaaaaagatg gtggacacac tcagcatttt gagagcccca caatgaagat ccaggagcat
 901 cccagcctat ctgacaccaa acagcagaga aatcaagatg ccggtgacca ggaggagagc
 961 tttgtctccg aagtgcccca gtcggacctg actgcattgt gtgatgaaaa gaactgggaa
1021 gagcctatcc ctgctttctc ctcctggcag cgggagaaca gtgactctga tgaagcccac
1081 ctctcgccgc aggctgggcg cctgatccgt cagctgctgg acgaagacag cgaccccatg
1141 ctctctcctc ggttctacgc ttatgggcag agcaggcaat acctggatga cacagaagtg
1201 cctccttccc caccaaaactc ccattctttc atgaggcggc gaagctcctc tctggggtcc
```

```
                            -continued
1261  tatgatgatg agcaagagga cctgacacct gcccagctca cacgaaggat tcagagcctt 1321  aaaaagaaga tccggaagtt tgaagataga ttcgaagaag agaagaagta cagaccttcc 1381  cacagtgaca aagcagccaa tccggaggtt ctgaaatgga caaatgacct tgccaaattc 1441  cggagacaac ttaaagaatc aaaactaaag atatctgaag aggacctaac tcccaggatg 1501  cggcagcgaa gcaacacact ccccaagagt tttggttccc aacttgagaa agaagatgag 1561  aagaagcaag agctggtgga taaagcaata aagcccagtg ttgaagccac attggaatct 1621  attcagagga agctccagga gaagcgagcg gaaagcagcc gccctgagga cattaaggat 1681  atgaccaaag accagattgc taatgagaaa gtggctctgc agaaagctct gttatattat 1741  gaaagcattc atggacggcc ggtaacaaag aacgaacggc aggtgatgaa gccactatac 1801  gacaggtacc ggctggtcaa acagatcctc tcccgagcta acaccatacc catcattggt 1861  tccccctcca gcaagcggag aagccctttg ctgcagccaa ttatcgaggg cgaaactgct 1921  tccttcttca aggagataaa ggaagaagag gaggggtcag aagacgatag caatgtgaag 1981  ccagacttca tggtcactct gaaaaccgat ttcagtgcac gatgctttct ggaccaattc 2041  gaagatgacg ctgatggatt tatttcccca atggatgata aaataccatc aaaatgcagc 2101  caggacacag ggctttcaaa tctccatgct gcctcaatac ctgaactcct ggaacacctc 2161  caggaaatga gagaagaaaa gaaaaggatt cgaaagaaac ttcgggattt tgaagacaac 2221  tttttcagac agaatggaag aaatgtccag aaggaagacc gcactcctat ggctgaagaa 2281  tacagtgaat ataagcacat aaaggcgaaa ctgaggctcc tggaggtgct catcagcaag 2341  agagacactg attccaagtc catgtgaggg gcatggccaa gcacaggggg ctggcagctg 2401  cggtgagagt ttactgtccc cagagaaagt gcagctctgg aaggcagcct tggggctggc 2461  cctgcaaagc atgcagccct tctgcctcta gaccatttgg catcggctcc tgtttccatt 2521  gcctgcctta gaaactggct ggaagaagac aatgtgacct gacttaggca ttttgtaatt 2581  ggaaagtcaa gactgcagta tgtgcacatg cgcacgcgca tgcacgcaca cacacacaca 2641  gtagtggagc tttcctaaca ctagcagaga ttaatcacta cattagacaa cactcatcta 2701  cagagaatat acactgttct tccctggata actgagaaac aagagaccat tctctgtcta 2761  actgtgataa aaacaagctc aggactttat tctatagagc aaacttgctg tggagggcca 2821  tgctctcctt ggacccagtg aactgcaaac gtgcattgga gccctatttg ctgccgctgc 2881  cattctagtg acctttccac agagctgcgc cttcctcacg tgtgtgaaag gttttcccct 2941  tcagccctca ggtagatgga agctgcatct gcccacgatg gcagtgcagt catcatcttc 3001  aggatgtttc ttcaggactt cctcagctga caaggaattt tggtccctgc ctaggaccgg 3061  gtcatctgca gaggacagag agatggtaag cagctgtatg aatgctgatt ttaaaaccag 3121  gtcatgggag aagagcctgg agattctttc ctgaacactg actgcactta ccagtctgat 3181  tttatcgtca acaccaagc caggctagca tgctcatggc aatctgtttg ggctgttttt 3241  gttgtggcac tagccaaaca taagggggct taagtcagcc tgcatacaga ggatcgggga 3301  gagaaggggc ctgtgttctc agcctcctga gtacttacca gagtttaatt ttttaaaaa 3361  aaatctgcac taaaatcccc aaactgacag gtaaatgtag ccctcagagc tcagcccaag 3421  gcagaatcta aatcacacta ttttcgagat catgtataaa aagaaaaaaa agaagtcatg 3481  ctgtgtggcc aattataatt ttttcaaag actttgtcac aaaactgtct atattagaca 3541  ttttggaggg accaggaaat gtaagacacc aaatcctcca tctcttcagt gtgcctgatg 3601  tcacctcatg atttgctgtt acttttttaa ctcctgcgcc aaggacagtg ggttctgtgt 3661  ccacctttgt gctttgcgag gccgagccca ggcatctgct cgcctgccac ggctgaccag
```

-continued

```
3721  agaaggtgct tcaggagctc tgccttagac gacgtgttac agtatgaaca cacagcagag 3781  gcaccctcgt atgttttgaa agttgccttc tgaaagggca cagttttaag gaaaagaaaa 3841  agaatgtaaa actatactga cccgttttca gttttaaagg gtcgtgagaa actggctggt 3901  ccaatgggat ttacagcaac attttccatt gctgaagtga ggtagcagct ctcttctgtc 3961  agctgaatgt taaggatggg gaaaaagaat gcctttaagt ttgctcttaa tcgtatggaa 4021  gcttgagcta tgtgttggaa gtgccctggt tttaatccat acacaaagac ggtacataat 4081  cctacaggtt taaatgtaca taaaaatata gtttggaatt ctttgctcta ctgtttacat 4141  tgcagattgc tataatttca aggagtgaga ttataaataa aatgatgcac tttaggatgt 4201  ttcctatttt tgaaatctga acatgaatca ttcacatgac caaaaattgt gttttttaa 4261  aaatacatgt ctagtctgtc ctttaatagc tctcttaaat aagctatgat attaatcaga 4321  tcattaccag ttagctttta aagcacattt gtttaagact atgttttgg aaaaatacgc 4381  tacagaattt ttttttaagc tacaaataaa tgagatgcta ctaattgttt tggaatctgt 4441  tgtttctgcc aaaggtaaat taactaaaga tttattcagg aatccccatt tgaatttgta 4501  tgattcaata aaagaaaaca ccaagtaagt tatataaaat aaattgtgta tgagatgttg 4561  tgttttcctt tgtaatttcc actaactaac taactaactt atattcttca tggaatggag 4621  cccagaagaa atgagaggaa gcccttttca cactagatct tatttgaaga aatgtttgtt 4681  agtcagtcag tcagtggttt ctggctctgc cgagggagat gtgttcccca gcaaccattt 4741  ctgcagccca gaatctcaag gcactagagg cggtgtctta attaattggc ttcacaaaga 4801  caaaatgctc tggactggga ttttcccttt gctgtgttgg gaatatgtgt ttattaatta 4861  gcacatgcca acaaaataaa tgtcaagagt tatttcataa gtgtaagtaa acttaagaat 4921  taaagagtgc agacttataa ttttca
```

In some embodiments of the methods of the disclosure, the wild type human FAM13A gene of the disclosure consists of or comprises the amino acid sequence (Genbank Accession number: NP_001252509.1, transcript variant 5):

(SEQ ID NO: 43)
```
  1 maceimplqr llertirsav eqhlfdvnns ggqssedses gtlsassats arqrrrqske 61 qdevrhgrdk glinkentps gfnhlddcil ntqevekvhk ntfgcagers kpkrqksstk 121 lselhdnqdg lvnmeslnst rshertgpdd fewmsderkg nekdgghtqh fesptmkiqe 181 hpslsdtkqq rnqdagdqee sfvsevpqsd ltalcdeknw eepipafssw qrensdsdea 241 hlspqagrli rqlldedsdp mlsprfyayg qsrqylddte vppsppnshs fmrrrssslg 301 syddeqedlt paqltrriqs lkkkirkfed rfeeekkyrp shsdkaanpe vlkwtndlak 361 frrqlkeskl kiseedltpr mrqrsntlpk sfgsqleked ekkqelvdka ikpsveatle 421 siqrklqekr aessrpedik dmtkdqiane kvalqkally yesihgrpvt knerqvmkpl 481 ydryrlvkqi lsrantipii gspsskrrsp llqpiieget asffkeikee eegseddsnv 541 kpdfmvtlkt dfsarcfldq feddadgfis pmddkipskc sqdtglsnlh aasipelleh 601 lqemreekkr irkklrdfed nffrqngrnv qkedrtpmae eyseykhika klrllevlis 661 krdtdsksm
```

In some embodiments of the methods of the disclosure, the wild type human DSP gene of the disclosure consists of or comprises the nucleic acid sequence (Genbank Accession number: NM_004415.3, transcript variant 1):

(SEQ ID NO: 44)

```
   1 aagaaaccgg ccaggtgtgg cctaggcgcc cagtgccagc ggggaggaga ctcgctccgc
  61 cgccgaccaa caccaacacc cagctccgac gcagctcctc tgcgcccttg ccgccctccg
 121 agccacagct ttcctcccgc tcctgccccc ggcccgtcgc cgtctccgcg ctcgcagcgg
 181 cctcgggagg gcccaggtag cgagcagcga cctcgcgagc cttccgcact cccgcccggt
 241 tccccggccg tccgcctatc cttggccccc tccgctttct ccgcgccggc ccgcctcgct
 301 tatgcctcgg cgctgagccg ctctcccgat tgcccgccga catgagctgc aacggaggct
 361 cccacccgcg gatcaacact ctgggccgca tgatccgcgc cgagtctggc ccggacctgc
 421 gctacgaggt gaccagcggc ggcgggggca ccagcaggat gtactattct cggcgcggcg
 481 tgatcaccga ccagaactcg gacggctact gtcaaaccgg cacgatgtcc aggcaccaga
 541 accagaacac catccaggag ctgctgcaga actgctccga ctgcttgatg cgagcagagc
 601 tcatcgtgca gcctgaattg aagtatggag atggaataca actgactcgg agtcgagaat
 661 tggatgagtg ttttgcccag gccaatgacc aaatggaaat cctcgacagc ttgatcagag
 721 agatgcggca gatgggccag ccctgtgatg cttaccagaa aaggcttctt cagctccaag
 781 agcaaatgcg agcccttat aaagccatca gtgtccctcg agtccgcagg gccagctcca
 841 agggtggtgg aggctacact tgtcagagtg gctctggctg ggatgagttc accaaacatg
 901 tcaccagtga atgtttgggg tggatgaggc agcaaagggc ggagatggac atggtggcct
 961 ggggtgtgga cctggcctca gtggagcagc acattaacag ccaccggggc atccacaact
1021 ccatcggcga ctatcgctgg cagctggaca aaatcaaagc cgacctgcgc gagaaatctg
1081 cgatctacca gttggaggag gagtatgaaa acctgctgaa agcgtccttt gagaggatgg
1141 atcacctgcg acagctgcag aacatcattc aggccacgtc cagggagatc atgtggatca
1201 atgactgcga ggaggaggag ctgctgtacg actggagcga caagaacacc aacatcgctc
1261 agaaacagga ggccttctcc atacgcatga gtcaactgga agttaaagaa aaagagctca
1321 ataagctgaa acaagaaagt gaccaacttg tcctcaatca gcatccagct tcagacaaaa
1381 ttgaggccta tatggacact ctgcagacgc agtggagttg gattcttcag atcaccaagt
1441 gcattgatgt tcatctgaaa gaaaatgctg cctactttca gttttttgaa gaggcgcagt
1501 ctactgaagc atacctgaag gggctccagg actccatcag gaagaagtac ccctgcgaca
1561 agaacatgcc cctgcagcac ctgctggaac agatcaagga gctggagaaa gaacgagaga
1621 aaatccttga atacaagcgt caggtgcaga acttggtaaa caagtctaag aagattgtac
1681 agctgaagcc tcgtaaccca gactacagaa gcaataaacc cattattctc agagctctct
1741 gtgactacaa acaagatcag aaaatcgtgc ataagggga tgagtgtatc ctgaaggaca
1801 acaacgagcg cagcaagtgg tacgtgacgg gcccggggag cgttgacatg cttgttccct
1861 ctgtggggct gatcatccct cctccgaacc cactggccgt ggacctctct tgcaagattg
1921 agcagtacta cgaagccatc ttggctctgt ggaaccagct ctacatcaac atgaagagcc
1981 tggtgtcctg gcactactgc atgattgaca tagagaagat cagggccatg acaatcgcca
2041 agctgaaaac aatgcggcag gaagattaca tgaagacgat agccgacctt gagttacatt
2101 accaagagtt catcagaaat agccaaggct cagagatgtt tggagatgat gacaagcgga
2161 aaatacagtc tcagttcacc gatgcccaga agcattacca gaccctggtc attcagctcc
```

-continued

```
2221 ctggctatcc ccagcaccag acagtgacca caactgaaat cactcatcat ggaacctgcc
2281 aagatgtcaa ccataataaa gtaattgaaa ccaacagaga aaatgacaag caagaaacat
2341 ggatgctgat ggagctgcag aagattcgca ggcagataga gcactgcgag ggcaggatga
2401 ctctcaaaaa cctcccctcta gcagaccagg gatcttctca ccacatcaca gtgaaaatta
2461 acgagcttaa gagtgtgcag aatgattcac aagcaattgc tgaggttctc aaccagctta
2521 aagatatgct tgccaacttc agaggttctg aaaagtactg ctatttacag aatgaagtat
2581 ttggactatt tcagaaactg gaaaatatca atggtgttac agatggctac ttaaatagct
2641 tatgcacagt aagggcactg ctccaggcta ttctccaaac agaagacatg ttaaaggttt
2701 atgaagccag gctcactgag gaggaaactg tctgcctgga cctggataaa gtggaagctt
2761 accgctgtgg actgaagaaa ataaaaaatg acttgaactt gaagaagtcg ttgttggcca
2821 ctatgaagac agaactacag aaagcccagc agatccactc tcagacttca cagcagtatc
2881 cactttatga tctggacttg ggcaagttcg gtgaaaaagt cacacagctg acagaccgct
2941 ggcaaaggat agataaacag atcgacttta ggttatggga cctggagaaa caaatcaagc
3001 aattgaggaa ttatcgtgat aactatcagg ctttctgcaa gtggctctat gatgctaaac
3061 gccgccagga ttccttagaa tccatgaaat ttggagattc caacacagtc atgcggtttt
3121 tgaatgagca gaagaacttg cacagtgaaa tatctggcaa acgagacaaa tcagaggaag
3181 tacaaaaaat tgctgaactt tgcgccaatt caattaagga ttatgagctc cagctggcct
3241 catacacctc aggactggaa actctgctga acatacctat caagaggacc atgattcagt
3301 cccttctgg ggtgattctg caagaggctg cagatgttca tgctcggtac attgaactac
3361 ttacaagatc tggagactat tacaggttct taagtgagat gctgaagagt ttggaagatc
3421 tgaagctgaa aaataccaag atcgaagttt ggaagagga gctcagactg gcccgagatg
3481 ccaactcgga aaactgtaat aagaacaaat tcctggatca gaacctgcag aaataccagg
3541 cagagtgttc ccagttcaaa gcgaagcttg cgagcctgga ggagctgaag agacaggctg
3601 agctggatgg gaagtcggct aagcaaaatc tagacaagtg ctacggccaa ataaaagaac
3661 tcaatgagaa gatcacccga ctgacttatg agattgaaga tgaaaagaga agaagaaat
3721 ctgtggaaga cagatttgac caacagaaga atgactatga ccaactgcag aaagcaaggc
3781 aatgtgaaaa ggagaacctt ggttggcaga aattagagtc tgagaaagcc atcaaggaga
3841 aggagtacga gattgaaagg ttgagggttc tactgcagga agaaggcacc cggaagagag
3901 aatatgaaaa tgagctggca aaggtaagaa accactaaa tgaggagatg agtaatttaa
3961 ggaacaagta tgaaacagag attaacatta cgaagaccac catcaaggag atatccatgc
4021 aaaaagagga tgattccaaa aatcttagaa accagcttga tagactttca agggaaaatc
4081 gagatctgaa ggatgaaatt gtcaggctca atgacagcat cttgcaggcc actgagcagc
4141 gaaggcgagc tgaagaaaac gcccttcagc aaaaggcctg tggctctgag ataatgcaga
4201 agaagcagca tctggagata gaactgaagc aggtcatgca gcagcgctct gaggacaatg
4261 cccggcacaa gcagtccctg gaggaggctg ccaagaccat tcaggacaaa ataaggaga
4321 tcgagagact caaagctgag tttcaggagg aggccaagcg ccgctgggaa tatgaaaatg
4381 aactgagtaa ggtaagaaac aattatgatg aggagatcat tagcttaaaa aatcagtttg
4441 agaccgagat caacatcacc aagaccacca tccaccagct caccatgcag aaggaagagg
4501 ataccagtgg ctaccgggct cagatagaca atctcacccg agaaaacagg agcttatctg
4561 aagaaataaa gaggctgaag aacactctaa cccagaccac agagaatctc aggagggtgg
4621 aagaagacat ccaacagcaa aaggccactg ctctgaggt gtctcagagg aaacagcagc
```

-continued

```
4681  tggaggttga gctgagacaa gtcactcaga tgcgaacaga ggagagcgta agatataagc
4741  aatctcttga tgatgctgcc aaaaccatcc aggataaaaa caaggagata gaaaggttaa
4801  aacaactgat cgacaaagaa acaaatgacc ggaaatgcct ggaagatgaa aacgcgagat
4861  tacaaagggt ccagtatgac ctgcagaaag caaacagtag tgcgacggag acaataaaca
4921  aactgaaggt tcaggagcaa gaactgacac gcctgaggat cgactatgaa agggtttccc
4981  aggagaggac tgtgaaggac caggatatca cgcggttcca gaactctctg aaagagctgc
5041  agctgcagaa gcagaaggtg aagaggagc tgaatcggct gaagaggacc gcgtcagaag
5101  actcctgcaa gaggaagaag ctggaggaag agctggaagg catgaggagg tcgctgaagg
5161  agcaagccat caaaatcacc aacctgaccc agcagctgga gcaggcatcc attgttaaga
5221  agaggagtga ggatgacctc cggcagcaga gggacgtgct ggatggccac ctgagggaaa
5281  agcagaggac ccaggaagag ctgaggaggc tctcttctga ggtcgaggcc ctgaggcggc
5341  agttactcca ggaacaggaa agtgtcaaac aagctcactt gaggaatgag catttccaga
5401  aggcgataga agataaaagc agaagcttaa atgaaagcaa aatagaaatt gagaggctgc
5461  agtctctcac agagaacctg accaaggagc acttgatgtt agaagaagaa ctgcggaacc
5521  tgaggctgga gtacgatgac ctgaggagag gacgaagcga agcggacagt gataaaaatg
5581  caaccatctt ggaactaagg agccagctgc agatcagcaa caaccggacc ctggaactgc
5641  aggggctgat taatgattta cagagagaga gggaaaattt gagacaggaa attgagaaat
5701  tccaaaagca ggctttagag gcatctaata ggattcagga atcaaagaat cagtgtactc
5761  aggtggtaca ggaaagagag agccttctgg tgaaaatcaa agtcctggag caagacaagg
5821  caaggctgca gaggctggag gatgagctga atcgtgcaaa atcaactcta gaggcagaaa
5881  ccagggtgaa acagcgcctg gagtgtgaga acagcaaat tcagaatgac ctgaatcagt
5941  ggaagactca atattcccgc aaggaggagg ctattaggaa gatagaatcg gaaagagaaa
6001  agagtgagag agagaagaac agtcttagga gtgagatcga aagactccaa gcagagatca
6061  agagaattga agagaggtgc aggcgtaagc tggaggattc taccagggag acacagtcac
6121  agttagaaac agaacgctcc cgatatcaga gggagattga taaactcaga cagcgcccat
6181  atgggtccca tcgagagacc cagactgagt gtgagtggac cgttgacacc tccaagctgg
6241  tgtttgatgg gctgaggaag aaggtgacag caatgcagct ctatgagtgt cagctgatcg
6301  acaaaacaac cttggacaaa ctattgaagg ggaagaagtc agtggaagaa gttgcttctg
6361  aaatccagcc attccttcgg ggtgcaggat ctatcgctgg agcatctgct tctcctaagg
6421  aaaaatactc tttggtagag gccaagagaa agaaattaat cagcccagaa tccacagtca
6481  tgcttctgga ggcccaggca gctacaggtg gtataattga tccccatcgg aatgagaagc
6541  tgactgtcga cagtgccata gctcgggacc tcattgactt cgatgaccgt cagcagatat
6601  atgcagcaga aaaagctatc actggttttg atgatccatt ttcaggcaag acagtatctg
6661  tttcagaagc catcaagaaa aatttgattg atagagaaac cggaatgcgc ctgctggaag
6721  cccagattgc ttcagggggt gtagtagacc ctgtgaacag tgtcttttg ccaaaagatg
6781  tcgccttggc ccgggggctg attgatagag atttgtatcg atccctgaat gatccccgag
6841  atagtcagaa aaactttgtg gatccagtca ccaaaaagaa ggtcagttac gtgcagctga
6901  aggaacggtg cagaatcgaa ccacatactg gtctgctctt gctttcagta cagaagagaa
6961  gcatgtcctt ccaaggaatc agacaacctg tgaccgtcac tgagctagta gattctggta
7021  tattgagacc gtccactgtc aatgaactgg aatctggtca gatttcttat gacgaggttg
```

-continued

```
7081 gtgagagaat taaggacttc ctccagggtt caagctgcat agcaggcata tacaatgaga
7141 ccacaaaaca gaagcttggc atttatgagg ccatgaaaat tggcttagtc cgacctggta
7201 ctgctctgga gttgctggaa gcccaagcag ctactggctt tatagtggat cctgttagca
7261 acttgaggtt accagtggag gaagcctaca agagaggtct ggtgggcatt gagttcaaag
7321 agaagctcct gtctgcagaa cgagctgtca ctgggtataa tgatcctgaa acaggaaaca
7381 tcatctcttt gttccaagcc atgaataagg aactcatcga aaagggccac ggtattcgct
7441 tattagaagc acagatcgca accgggggga tcattgaccc aaaggagagc catcgtttac
7501 cagttgacat agcatataag aggggctatt tcaatgagga actcagtgag attctctcag
7561 atccaagtga tgataccaaa ggatttttg accccaacac tgaagaaaat cttacctatc
7621 tgcaactaaa agaaagatgc attaaggatg aggaaacagg gctctgtctt ctgcctctga
7681 aagaaaagaa gaaacaggtg cagacatcac aaaagaatac cctcaggaag cgtagagtgg
7741 tcatagttga cccagaaacc aataaagaaa tgtctgttca ggaggcctac aagaagggcc
7801 taattgatta tgaaaccttc aaagaactgt gtgagcagga atgtgaatgg gaagaaataa
7861 ccatcacggg atcagatggc tccaccaggg tggtcctggt agatagaaag acaggcagtc
7921 agtatgatat tcaagatgct attgacaagg ccttgttga caggaagttc tttgatcagt
7981 accgatccgg cagcctcagc ctcactcaat tgctgacat gatctccttg aaaaatggtg
8041 tcggcaccag cagcagcatg ggcagtggtg tcagcgatga tgtttttagc agctcccgac
8101 atgaatcagt aagtaagatt tccaccatat ccagcgtcag gaatttaacc ataaggagca
8161 gctcttttc agacaccctg gaagaatcga gcccattgc agccatcttt gacacagaaa
8221 acctggagaa aatctccatt acagaaggta tagagcgggg catcgttgac agcatcacgg
8281 gtcagaggct tctggaggct caggcctgca caggtggcat catccaccca accacgggcc
8341 agaagctgtc acttcaggac gcagtctccc agggtgtgat tgaccaagac atggccacca
8401 ggctgaagcc tgctcagaaa gccttcatag gcttcgaggg tgtgaaggga aagaagaaga
8461 tgtcagcagc agaggcagtg aaagaaaaat ggctcccgta tgaggctggc cagcgcttcc
8521 tggagttcca gtacctcacg ggaggtcttg ttgacccgga agtgcatggg aggataagca
8581 ccgaagaagc catccggaag gggttcatag atggccgcgc cgcacagagg ctgcaagaca
8641 ccagcagcta tgccaaaatc ctgacctgcc ccaaaaccaa attaaaaata tcctataagg
8701 atgccataaa tcgctccatg gtagaagata tcactgggct gcgccttctg gaagccgcct
8761 ccgtgtcgtc caagggctta cccagcccctt acaacatgtc ttcggctccg ggtcccgct
8821 ccggctcccg ctcgggatct cgctccggat ctcgctccgg gtccgcagt gggtcccgga
8881 gaggaagctt gacgccaca gggaattctt cctactctta ttcctactca tttagcagta
8941 gttctattgg gcactagtag tcagttggga gtggttgcta taccttgact tcatttatat
9001 gaatttccac tttattaaat aatagaaaag aaaatcccgg tgcttgcagt agagtgatag
9061 gacattctat gcttacagaa aatatagcca tgattgaaat caaatagtaa aggctgttct
9121 ggcttttat cttcttagct catcttaaat aagcagtaca cttggatgca gtgcgtctga
9181 agtgctaatc agttgtaaca atagcacaaa tcgaacttag gatttgtttc ttctcttctg
9241 tgtttcgatt tttgatcaat tctttaattt tggaagccta taatacagtt ttctattctt
9301 ggagataaaa attaaatgga tcactgatat tttagtcatt ctgcttctca tctaaatatt
9361 tccatattct gtattaggag aaaattaccc tcccagcacc agccccctc tcaaaccccc
9421 aacccaaaac caagcatttt ggaatgagtc tcctttagtt tcagagtgtg gattgtataa
9481 cccatatact cttcgatgta cttgtttggt ttggtattaa tttgactgtg catgacagcg
```

-continued

```
9541 gcaatctttt ctttggtcaa agttttctgt ttattttgct tgtcatattc gatgtacttt 9601 aaggtgtctt tatgaagttt gctattctgg caataaaact ttagactttt gaagtgtttg 9661 tgttttaatt taatatgttt ataagcatgt ataaacattt agcatatttt tatcataggt 9721 ctaaaaatat ttgtttacta aatacctgtg aagaaatacc attaaaaaac tatttggttc 9781 tgaattctta ctagaaaaaa aa
```

In some embodiments of the methods of the disclosure, the wild type human DSP gene of the disclosure consists of or comprises the amino acid sequence (Genbank Accession number: NP_004406.2, transcript variant 1):

(SEQ ID NO: 45)

```
   1 mscngghpr  intlgrmira esgpdlryev tsggggtsrm yysrrgvitd qnsdgycqtg 61 tmsrhqnqnt iqellqncsd clmraelivq pelkygdgiq ltrsreldec faqandqmei 121 ldsliremrq mgqpcdayqk rllqlqeqmr alykaisvpr vrrasskggg gytcqsgsgw 181 deftkhvtse clgwmrqqra emdmvawgvd lasveqhins hrgihnsigd yrwqldkika 241 dlreksaiyq leeeyenllk asfermdhlr qlqniiqats reimwindce eeellydwsd 301 kntniaqkqe afsirmsqle vkekelnklk qesdqlvinq hpasdkieay mdtlqtqwsw 361 ilqitkcidv hlkenaayfq ffeeaqstea ylkglqdsir kkypcdknmp lqhlleqike 421 lekerekile ykrqvqnlvn kskkivqlkp rnpdyrsnkp iilralcdyk qdqkivhkgd 481 ecilkdnner skwyvtgpgg vdmlvpsvgl iipppnplav dlsckieqyy eailalwnql 541 yinmkslvsw hycmidieki ramtiaklkt mrqedymkti adlelhyqef irnsqgsemf 601 gdddkrkiqs qftdaqkhyq tlviqlpgyp qhqtvtttei thhgtcqdvn hnkvietnre 661 ndkqetwmlm elqkirrqie hcegrmtlkn lpladqgssh hitvkinelk svqndsgqia 721 evlnqlkdml anfrgsekyc ylqnevfglf qkleningvt dgylnslctv rallqailqt 781 edmlkvyear lteeetvcld ldkveayrcg lkkikndlnl kksllatmkt elqkaqqihs 841 qtsqqyplyd ldlgkfgekv tqltdrwqri dkqidfrlwd lekqikqlrn yrdnyqafck 901 wlydakrrqd slesmkfgds ntvmrflneq knlhseisgk rdkseevqki aelcansikd 961 yelqlasyts glletllnipi krtmiqspsg vilqeaadvh aryielltrs gdyyrflsem 1021 lksledlklk ntkievleee lrlardanse ncnknkfldq nlqkyqaecs qfkaklasle 1081 elkrqaeldg ksakqnldkc ygqikelnek itrltyeied ekrrrksved rfdqqkndyd 1141 qlqkarqcek enlgwqkles ekaikekeye ierlrvllqe egtrkreyen elakvrnhyn 1201 eemsnlrnky eteinitktt ikeismqked dsknlrnqld rlsrenrdlk deivrlndsi 1261 lqateqrrra eenalqqkac gseimqkkqh leielkqvmq qrsednarhk qsleeaakti 1321 qdknkeierl kaefqeeakr rweyenelsk vrnnydeeii slknqfetei nitkttihql 1381 tmqkeedtsg yraqidnltr enrslseeik rlkntltqtt enlrrveedi qqqkatgsev 1441 sqrkqqleve lrqvtqmrte esvrykqsld daaktiqdkn keierlkqli dketndrkcl 1501 edenarlqry qydlqkanss atetinklkv qeqeltrlri dyervsgert vkdqditrfq 1561 nslkelqlqk qkveeelnrl krtasedsck rkkleeeleg mrrslkeqai kitnitqqle 1621 qasivkkrse ddlrqqrdvl dghlrekqrt qeelrrlsse vealrrqllq eqesvkqahl 1681 rnehfqkaie dksrslnesk ieierlqslt enitkehlml eeelrnlrle yddlrrgrse 1741 adsdknatil elrsqlqisn nrtlelqggli ndlqrerenl rqeiekfqkq aleasnriqe 1801 sknqctqvvq eresllvkik vleqdkarlq rledelnrak stleaetrvk qrlecekqqi
```

-continued

```
1861  qndlnqwktq ysrkeeairk ieserekser eknslrseie rlqaeikrie ercrrkleds
1921  tretqsqlet ersrygreid klrqrpygsh retqtecewt vdtsklvfdg lrkkvtamql
1981  yecqlidktt ldkllkgkks veevaseiqp flrgagsiag asaspkekys lveakrkkli
2041  spestvmlle aqaatggiid phrnekltvd saiardlidf ddrqqiyaae kaitgfddpf
2101  sgktvsvsea ikknlidret gmrlleaqia sggvvdpvns vflpkdvala rglidrdlyr
2161  slndprdsqk nfvdpvtkkk vsyvqlkerc riephtglll lsvqkrsmsf qgirqpvtvt
2221  elvdsgilrp stvnelesgq isydevgeri kdflqgssci agiynettkq klgiyeamki
2281  glvrpgtale lleaqaatgf ivdpvsnlrl pveeaykrgl vgiefkekll saeravtgyn
2341  dpetgniisl fqamnkelie kghgirllea qiatggiidp keshrlpvdi aykrgyfnee
2401  lseilsdpsd dtkgffdpnt eenltylqlk ercikdeetg lcllplkekk kqvqtsqknt
2461  lrkrrvvivd petnkemsvq eaykkglidy etfkelceqe ceweeititg sdgstrvvlv
2521  drktgsqydi qdaidkglvd rkffdqyrsg slsltqfadm islkngvgts ssmgsgvsdd
2581  vfsssrhesv skistissvr nltirsssfs dtleesspia aifdtenlek isitegierg
2641  ivdsitgqrl leaqactggi ihpttgqkls lqdaysqgvi dqdmatrlkp aqkafigfeg
2701  vkgkkkmsaa eavkekwlpy eagqrflefq yltgglvdpe vhgristeea irkgfidgra
2761  aqrlqdtssy akiltcpktk lkisykdain rsmveditgl rlleaasvss kglpspynms
2821  sapgsrsgsr sgsrsgsrsg srsgsrrgsf datgnssysy sysfssssig h
```

In some embodiments of the methods of the disclosure, the wild type human DSP gene of the disclosure consists of or comprises the nucleic acid sequence (Genbank Accession number: NM_001008844.2, transcript variant 2):

(SEQ ID NO: 19)

```
   1  aagaaaccgg ccaggtgtgg cctaggcgcc cagtgccagc ggggaggaga ctcgctccgc
  61  cgccgaccaa caccaacacc cagctccgac gcagctcctc tgcgcccttg ccgccctccg
 121  agccacagct ttcctcccgc tcctgccccc ggcccgtcgc cgtctccgcg ctcgcagcgg
 181  cctcgggagg gcccaggtag cgagcagcga cctcgcgagc cttccgcact cccgcccggt
 241  tccccggccg tccgcctatc cttggccccc tccgctttct ccgcgccggc ccgcctcgct
 301  tatgcctcgg cgctgagccg ctctcccgat tgcccgccga catgagctgc aacggaggct
 361  cccacccgcg gatcaacact ctgggccgca tgatccgcgc cgagtctggc ccggacctgc
 421  gctacgaggt gaccagcggc ggcggggggca ccagcaggat gtactattct cggcgcggcg
 481  tgatcaccga ccagaactcg gacggctact gtcaaaccgg cacgatgtcc aggcaccaga
 541  accagaacac catccaggag ctgctgcaga actgctccga ctgcttgatg cgagcagagc
 601  tcatcgtgca gcctgaattg aagtatggag atggaataca actgactcgg agtcgagaat
 661  tggatgagtg ttttgcccag gccaatgacc aaatggaaat cctcgacagc ttgatcagag
 721  agatgcggca gatgggccag ccctgtgatg cttaccagaa aaggcttctt cagctccaag
 781  agcaaatgcg agcccttat aaagccatca gtgtccctcg agtccgcagg gccagctcca
 841  agggtggtgg aggctacact tgtcagagtg gctctggctg ggatgagttc accaaacatg
 901  tcaccagtga atgtttgggg tggatgaggc agcaagggc ggagatggac atggtggcct
 961  ggggtgtgga cctggcctca gtggagcagc acattaacag ccaccgggc atccacaact
1021  ccatcggcga ctatcgctgg cagctggaca aaatcaaagc cgacctgcgc gagaaatctg
1081  cgatctacca gttggaggag gagtatgaaa acctgctgaa agcgtccttt gagaggatgg
```

-continued

```
1141  atcacctgcg acagctgcag aacatcattc aggccacgtc cagggagatc atgtggatca
1201  atgactgcga ggaggaggag ctgctgtacg actggagcga caagaacacc aacatcgctc
1261  agaaacagga ggccttctcc atacgcatga gtcaactgga agttaaagaa aaagagctca
1321  ataagctgaa acaagaaagt gaccaacttg tcctcaatca gcatccagct tcagacaaaa
1381  ttgaggccta tatggacact ctgcagacgc agtggagttg gattcttcag atcaccaagt
1441  gcattgatgt tcatctgaaa gaaaatgctg cctactttca gttttttgaa gaggcgcagt
1501  ctactgaagc ataccctgaag gggctccagg actccatcag gaagaagtac ccctgcgaca
1561  agaacatgcc cctgcagcac ctgctggaac agatcaagga gctggagaaa gaacgagaga
1621  aaatccttga atacaagcgt caggtgcaga acttggtaaa caagtctaag aagattgtac
1681  agctgaagcc tcgtaaccca gactacagaa gcaataaacc cattattctc agagctctct
1741  gtgactacaa acaagatcag aaaatcgtgc ataagggga tgagtgtatc ctgaaggaca
1801  acaacgagcg cagcaagtgg tacgtgacgg gcccgggagg cgttgacatg cttgttccct
1861  ctgtggggct gatcatccct cctccgaacc cactggccgt ggacctctct tgcaagattg
1921  agcagtacta cgaagccatc ttggctctgt ggaaccagct ctacatcaac atgaagagcc
1981  tggtgtcctg gcactactgc atgattgaca tagagaagat cagggccatg acaatcgcca
2041  agctgaaaac aatgcggcag gaagattaca tgaagacgat agccgacctt gagttacatt
2101  accaagagtt catcagaaat agccaaggct cagagatgtt tggagatgat gacaagcgga
2161  aaatacagtc tcagttcacc gatgcccaga agcattacca gaccctggtc attcagctcc
2221  ctggctatcc ccagcaccag acagtgacca caactgaaat cactcatcat ggaacctgcc
2281  aagatgtcaa ccataataaa gtaattgaaa ccaacagaga aaatgacaag caagaaacat
2341  ggatgctgat ggagctgcag aagattcgca ggcagataga gcactgcgag gcaggatga
2401  ctctcaaaaa cctccctcta gcagaccagg gatcttctca ccacatcaca gtgaaaatta
2461  acgagcttaa gagtgtgcag aatgattcac aagcaattgc tgaggttctc aaccagctta
2521  aagatatgct tgccaacttc agaggttctg aaaagtactg ctatttacag aatgaagtat
2581  ttggactatt tcagaaactg gaaaatatca atggtgttac agatggctac ttaaatagct
2641  tatgcacagt aagggcactg ctccaggcta ttctccaaac agaagacatg ttaaaggttt
2701  atgaagccag gctcactgag gaggaaactg tctgcctgga cctggataaa gtggaagctt
2761  accgctgtgg actgaagaaa ataaaaaatg acttgaactt gaagaagtcg ttgttggcca
2821  ctatgaagac agaactacag aaagcccagc agatccactc tcagacttca cagcagtatc
2881  cactttatga tctggacttg ggcaagttcg gtgaaaaagt cacacagctg acagaccgct
2941  ggcaaaggat agataaacag atcgacttta ggttatggga cctggagaaa caaatcaagc
3001  aattgaggaa ttatcgtgat aactatcagg ctttctgcaa gtggctctat gatgctaaac
3061  gccgccagga ttccttagaa tccatgaaat ttggagattc aacacagtc atgcggtttt
3121  tgaatgagca gaagaacttg cacagtgaaa tatctggcaa acgagacaaa tcagaggaag
3181  tacaaaaaat tgctgaactt tgcgccaatt caattaagga ttatgagctc cagctggcct
3241  catacacctc aggactggaa actctgctga acatacctat caagaggacc atgattcagt
3301  ccccttctgg ggtgattctg caagaggctg cagatgttca tgctcggtac attgaactac
3361  ttacaagatc tggagactat tacaggttct taagtgagat gctgaagagt ttggaagatc
3421  tgaagctgaa aaataccaag atcgaagttt tggaagagga gctcagactg gcccgagatg
3481  ccaactcgga aaactgtaat aagaacaaat tcctggatca gaacctgcag aaataccagg
```

```
3541 cagagtgttc ccagttcaaa gcgaagcttg cgagcctgga ggagctgaag agacaggctg 3601 agctggatgg gaagtcggct aagcaaaatc tagacaagtg ctacggccaa ataaaagaac 3661 tcaatgagaa gatcacccga ctgacttatg agattgaaga tgaaaagaga agaagaaaat 3721 ctgtggaaga cagatttgac caacagaaga atgactatga ccaactgcag aaagcaaggc 3781 aatgtgaaaa ggagaacctt ggttggcaga aattagagtc tgagaaagcc atcaaggaga 3841 aggagtacga gattgaaagg ttgagggttc tactgcagga agaaggcacc cggaagagag 3901 aatatgaaaa tgagctggca aaggcatcta ataggattca ggaatcaaag aatcagtgta 3961 ctcaggtggt acaggaaaga gagagcctte tggtgaaaat caaagtcctg gagcaagaca 4021 aggcaaggct gcagaggctg gaggatgagc tgaatcgtgc aaaatcaact ctagaggcag 4081 aaaccagggt gaaacagcgc ctggagtgtg agaaacagca aattcagaat gacctgaatc 4141 agtggaagac tcaatattcc cgcaaggagg aggctattag gaagatagaa tcggaaagag 4201 aaaagagtga gagagagaag aacagtctta ggagtgagat cgaaagactc caagcagaga 4261 tcaagagaat tgaagagagg tgcaggcgta agctggagga ttctaccagg gagacacagt 4321 cacagttaga aacagaacgc tcccgatatc agagggagat tgataaactc agacagcgcc 4381 catatgggtc ccatcgagag acccagactg agtgtgagtg gaccgttgac acctccaagc 4441 tggtgtttga tgggctgagg aagaaggtga cagcaatgca gctctatgag tgtcagctga 4501 tcgacaaaac aaccttggac aaactattga aggggaagaa gtcagtggaa gaagttgctt 4561 ctgaaatcca gccattcctt cggggtgcag gatctatcgc tggagcatct gcttctccta 4621 aggaaaaata ctctttggta gaggccaaga gaaagaaatt aatcagccca gaatccacag 4681 tcatgcttct ggaggcccag gcagctacag gtggtataat tgatccccat cggaatgaga 4741 agctgactgt cgacagtgcc atagctcggg acctcattga cttcgatgac cgtcagcaga 4801 tatatgcagc agaaaaagct atcactggtt ttgatgatcc attttcaggc aagacagtat 4861 ctgtttcaga agccatcaag aaaaatttga ttgatagaga accggaatg cgcctgctgg 4921 aagcccagat tgcttcaggg ggtgtagtag accctgtgaa cagtgtctt ttgccaaaag 4981 atgtcgcctt ggcccggggg ctgattgata gagatttgta tcgatccctg aatgatcccc 5041 gagatagtca gaaaaacttt gtggatccag tcaccaaaaa gaaggtcagt tacgtgcagc 5101 tgaaggaacg gtgcagaatc gaaccacata ctggtctgct cttgctttca gtacagaaga 5161 gaagcatgtc cttccaagga atcagacaac ctgtgaccgt cactgagcta gtagattctg 5221 gtatattgag accgtccact gtcaatgaac tggaatctgg tcagatttct tatgacgagg 5281 ttggtgagag aattaaggac ttcctccagg gttcaagctg catagcaggc atatacaatg 5341 agaccacaaa acagaagctt ggcatttatg aggccatgaa aattggctta gtccgacctg 5401 gtactgctct ggagttgctg gaagcccaag cagctactgg ctttatagtg atcctgtta 5461 gcaacttgag gttaccagtg gaggaagcct acaagagagg tctggtgggc attgagttca 5521 aagagaagct cctgtctgca gaacgagctg tcactgggta taatgatcct gaaacaggaa 5581 acatcatctc tttgttccaa gccatgaata aggaactcat cgaaaagggc cacggtattc 5641 gcttattaga agcacagatc gcaaccgggg ggatcattga cccaaaggag agccatcgtt 5701 taccagttga catagcatat aagagggggct atttcaatga ggaactcagt gagattctct 5761 cagatccaag tgatgatacc aaaggatttt ttgaccccaa cactgaagaa atcttacct 5821 atctgcaact aaaagaaaga tgcattaagg atgaggaaac agggctctgt cttctgcctc 5881 tgaaagaaaa gaagaaacag gtgcagacat cacaaaagaa taccctcagg aagcgtagag 5941 tggtcatagt tgacccagaa accaataaag aaatgtctgt tcaggaggcc tacaagaagg
```

-continued

```
6001 gcctaattga ttatgaaacc ttcaaagaac tgtgtgagca ggaatgtgaa tgggaagaaa
6061 taaccatcac gggatcagat ggctccacca gggtggtcct ggtagataga aagacaggca
6121 gtcagtatga tattcaagat gctattgaca agggccttgt tgacaggaag ttctttgatc
6181 agtaccgatc cggcagcctc agcctcactc aatttgctga catgatctcc ttgaaaaatg
6241 gtgtcggcac cagcagcagc atgggcagtg tgtcagcga tgatgttttt agcagctccc
6301 gacatgaatc agtaagtaag atttccacca tatccagcgt caggaattta accataagga
6361 gcagctcttt ttcagacacc ctggaagaat cgagccccat tgcagccatc tttgacacag
6421 aaaacctgga gaaaatctcc attacagaag gtatagagcg gggcatcgtt gacagcatca
6481 cgggtcagag gcttctggag gctcaggcct gcacaggtgg catcatccac ccaaccacgg
6541 gccagaagct gtcacttcag gacgcagtct cccagggtgt gattgaccaa gacatggcca
6601 ccaggctgaa gcctgctcag aaagccttca taggcttcga gggtgtgaag ggaagaaga
6661 agatgtcagc agcagaggca gtgaaagaaa aatggctccc gtatgaggct ggccagcgct
6721 tcctggagtt ccagtacctc acgggaggtc ttgttgaccc ggaagtgcat gggaggataa
6781 gcaccgaaga agccatccgg aaggggttca tagatggccg cgccgcacag aggctgcaag
6841 acaccagcag ctatgccaaa atcctgacct gccccaaaac caaattaaaa atatcctata
6901 aggatgccat aaatcgctcc atggtagaag atatcactgg gctgcgcctt ctggaagccg
6961 cctccgtgtc gtccaagggc ttacccagcc cttacaacat gtcttcggct ccggggtccc
7021 gctccggctc ccgctcggga tctcgctccg gatctcgctc cgggtcccgc agtgggtccc
7081 ggagaggaag ctttgacgcc acagggaatt cttcctactc ttattcctac tcatttagca
7141 gtagttctat tgggcactag tagtcagttg ggagtggttg ctataccttg acttcattta
7201 tatgaatttc cactttatta aataatagaa aagaaaatcc cggtgcttgc agtagagtga
7261 taggacattc tatgcttaca gaaaatatag ccatgattga aatcaaatag taaaggctgt
7321 tctggctttt tatcttctta gctcatctta aataagcagt acacttggat gcagtgcgtc
7381 tgaagtgcta atcagttgta acaatagcac aaatcgaact taggatttgt ttcttctctt
7441 ctgtgtttcg atttttgatc aattctttaa ttttggaagc ctataataca gttttctatt
7501 cttggagata aaaattaaat ggatcactga tattttagtc attctgcttc tcatctaaat
7561 atttccatat tctgtattag gagaaaatta ccctcccagc accagccccc ctctcaaacc
7621 cccaacccaa aaccaagcat tttggaatga gtctccttta gtttcagagt gtggattgta
7681 taacccatat actcttcgat gtacttgttt ggtttggtat taatttgact gtgcatgaca
7741 gcggcaatct tttctttggt caaagttttc tgtttatttt gcttgtcata ttcgatgtac
7801 tttaaggtgt ctttatgaag tttgctattc tggcaataaa cttttagact tttgaagtgt
7861 ttgtgtttta atttaatatg tttataagca tgtataaaca tttagcatat ttttatcata
7921 ggtctaaaaa tatttgttta ctaaatacct gtgaagaaat accattaaaa aactatttgg
7981 ttctgaattc ttactagaaa aaaaa
```

In some embodiments of the methods of the disclosure, the wild type human DSP gene of the disclosure consists of or comprises the amino acid sequence (Genbank Accession number: NP_001008844.1, transcript variant 2):

(SEQ ID NO: 20)

```
   1 mscnggshpr intlgrmira esgpdlryev tsggggtsrm yysrrgvitd qnsdgycqtg
  61 tmsrhqnqnt iqellqncsd clmraelivq pelkygdgiq ltrsreldec faqandqmei
 121 ldsliremrq mgqpcdayqk rllqlqeqmr alykaisvpr vrrasskggg gytcqsgsgw
 181 deftkhvtse clgwmrqqra emdmvawgvd lasveqhins hrgihnsigd yrwqldkika
 241 dlreksaiyq leeeyenllk asfermdhlr qlqniiqats reimwindce eeellydwsd
 301 kntniaqkqe afsirmsqle vkekelnklk qesdqlvinq hpasdkieay mdtlqtqwsw
 361 ilqitkcidv hlkenaayfq ffeeaqstea ylkglqdsir kkypcdknmp lqhlleqike
 421 lekerekile ykrqvqnlvn kskkivqlkp rnpdyrsnkp iilralcdyk qdqkivhkgd
 481 ecilkdnner skwyvtgpgg vdmlvpsvgl iipppnplav dlsckieqyy eailalwnql
 541 yinmkslvsw hycmidieki ramtiaklkt mrqedymkti adlelhyqef irnsqgsemf
 601 gdddkrkiqs qftdaqkhyq tiviqlpgyp qhqtvtttei thhgtcqdvn hnkvietnre
 661 ndkqetwmlm elqkirrqie hcegrmtlkn lpladqgssh hitvkinelk svqndsgaia
 721 evinqlkdml anfrgsekyc ylqnevfglf qkleningvt dgylnslctv rallqailqt
 781 edmlkvyear lteeetvcld ldkveayrcg lkkikndlnl kksllatmkt elqkaqqihs
 841 qtsqqyplyd ldlgkfgekv tqltdrwqri dkqidfrlwd lekqikqlrn yrdnyqafck
 901 wlydakrrqd slesmkfgds ntvmrflneq knlhseisgk rdkseevqki aelcansikd
 961 yelqlasyts gletllnipi krtmiqspsg vilqeaadvh aryielltrs gdyyrflsem
1021 lksledlklk ntkievleee lrlardanse ncnknkfldq nlqkyqaecs qfkaklasle
1081 elkrqaeldg ksakqnldkc ygqikelnek itrltyeied ekrrrksved rfdqqkndyd
1141 qlqkarqcek enlgwqkles ekaikekeye ierlrvllqe egtrkreyen elakasnriq
1201 esknqctqvv qeresllvki kvleqdkarl qrledelnra kstleaetrv kqrlecekqq
1261 iqndlnqwkt qysrkeeair kieserekse reknslrsei erlqaeikri eercrrkled
1321 stretqsqle tersrygrei dklrqrpygs hretqtecew tvdtsklvfd glrkkvtamq
1381 lyecqlidkt tldkllkgkk sveevaseiq pflrgagsia gasaspkeky slveakrkkl
1441 ispestvmll eaqaatggii dphrnekltv dsaiardlid fddrqqiyaa ekaitgfddp
1501 fsgktvsvse aikknlidre tgmrlleaqi asggvvdpvn svflpkdval arglidrdly
1561 rslndprdsq knfvdpvtkk kvsyvqlker criephtgll llsvqkrsms fqgirqpvtv
1621 telvdsgilr pstvnelesg qisydevger ikdflqgssc iagiynettk qklgiyeamk
1681 iglvrpgtal elleaqaatg fivdpvsnlr lpveeaykrg lvgiefkekl lsaeravtgy
1741 ndpetgniis lfqamnkeli ekghgirlle aqiatggiid pkeshrlpvd iaykrgyfne
1801 elseilsdps ddtkgffdpn teenitylql kercikdeet glcllplkek kkqvqtsqkn
1861 tlrkrrvviv dpetnkemsv qeaykkglid yetfkelceq eceweeitit gsdgstrvvl
1921 vdrktgsqyd iqdaidkglv drkffdqyrs gslsltqfad mislkngvgt sssmgsgvsd
1981 dvfsssrhes vskistissv rnltirsssf sdtleesspi aaifdtenle kisitegier
2041 givdsitgqr lleaqactgg iihpttgqkl slqdavsqgv idqdmatrlk paqkafigfe
2101 gvkgkkkmsa aeavkekwlp yeagqrflef qyltgglvdp evhgristee airkgfidgr
2161 aaqrlqdtss yakiltcpkt klkisykdai nrsmveditg lrlleaasvs skglpspynm
2221 ssapgsrsgs rsgsrsgsrs gsrsgsrrgs fdatgnssys ysysfssssi gh
```

In some embodiments of the methods of the disclosure, the wild type human DSP gene of the disclosure consists of or comprises the nucleic acid sequence (Genbank Accession number: NM_001319034.1, transcript variant 3):

(SEQ ID NO: 46)

```
   1 aagaaaccgg ccaggtgtgg cctaggcgcc cagtgccagc ggggaggaga ctcgctccgc 61 cgccgaccaa caccaacacc cagctccgac gcagctcctc tgcgcccttg ccgccctccg 121 agccacagct ttcctcccgc tcctgccccc ggcccgtcgc cgtctccgcg ctcgcagcgg 181 cctcgggagg gcccaggtag cgagcagcga cctcgcgagc cttccgcact cccgcccggt 241 tccccggccg tccgcctatc cttggccccc tccgctttct ccgcgccggc ccgcctcgct 301 tatgcctcgg cgctgagccg ctctcccgat tgcccgccga catgagctgc aacggaggct 361 cccacccgcg gatcaacact ctgggccgca tgatccgcgc cgagtctggc ccggacctgc 421 gctacgaggt gaccagcggc ggcggggggca ccagcaggat gtactattct cggcgcggcg 481 tgatcaccga ccagaactcg gacggctact gtcaaaccgg cacgatgtcc aggcaccaga 541 accagaacac catccaggag ctgctgcaga actgctccga ctgcttgatg cgagcagagc 601 tcatcgtgca gcctgaattg aagtatggag atggaataca actgactcgg agtcgagaat 661 tggatgagtg ttttgcccag gccaatgacc aaatggaaat cctcgacagc ttgatcagag 721 agatgcggca gatgggccag ccctgtgatg cttaccagaa aaggcttctt cagctccaag 781 agcaaatgcg agccctttat aaagccatca gtgtccctcg agtccgcagg gccagctcca 841 agggtggtgg aggctacact tgtcagagtg gctctggctg ggatgagttc accaaacatg 901 tcaccagtga atgtttgggg tggatgaggc agcaaagggc ggagatggac atggtggcct 961 ggggtgtgga cctggcctca gtggagcagc acattaacag ccaccgggc atccacaact 1021 ccatcggcga ctatcgctgg cagctggaca aaatcaaagc cgacctgcgc gagaaatctg 1081 cgatctacca gttggaggag gagtatgaaa acctgctgaa agcgtccttt gagaggatgg 1141 atcacctgcg acagctgcag aacatcattc aggccacgtc cagggagatc atgtggatca 1201 atgactgcga ggaggaggag ctgctgtacg actggagcga caagaacacc aacatcgctc 1261 agaaacagga ggccttctcc atacgcatga gtcaactgga agttaaagaa aaagagctca 1321 ataagctgaa acaagaaagt gaccaacttg tcctcaatca gcatccagct tcagacaaaa 1381 ttgaggccta tatggacact ctgcagacgc agtggagttg gattcttcag atcaccaagt 1441 gcattgatgt tcatctgaaa gaaaatgctg cctactttca gttttttgaa gaggcgcagt 1501 ctactgaagc ataccctgaag gggctccagg actccatcag gaagaagtac ccctgcgaca 1561 agaacatgcc cctgcagcac ctgctggaac agatcaagga gctggagaaa gaacgagaga 1621 aaatccttga atacaagcgt caggtgcaga acttggtaaa caagtctaag aagattgtac 1681 agctgaagcc tcgtaaccca gactacagaa gcaataaacc cattattctc agagctctct 1741 gtgactacaa acaagatcag aaaatcgtgc ataaggggga tgagtgtatc ctgaaggaca 1801 acaacgagcg cagcaagtgg tacgtgacgg gcccgggagg cgttgacatg cttgttccct 1861 ctgtggggct gatcatccct cctccgaacc cactggccgt ggacctctct tgcaagattg 1921 agcagtacta cgaagccatc ttggctctgt ggaaccagct ctacatcaac atgaagagcc 1981 tggtgtcctg gcactactgc atgattgaca tagagaagat cagggccatg acaatcgcca 2041 agctgaaaac aatgcggcag gaagattaca tgaagacgat agccgacctt gagttacatt 2101 accaagagtt catcagaaat agccaaggct cagagatgtt tggagatgat gacaagcgga 2161 aaatacagtc tcagttcacc gatgcccaga agcattacca gaccctggtc attcagctcc
```

-continued

```
2221 ctggctatcc ccagcaccag acagtgacca caactgaaat cactcatcat ggaacctgcc
2281 aagatgtcaa ccataataaa gtaattgaaa ccaacagaga aaatgacaag caagaaacat
2341 ggatgctgat ggagctgcag aagattcgca ggcagataga gcactgcgag ggcaggatga
2401 ctctcaaaaa cctcccctcta gcagaccagg gatcttctca ccacatcaca gtgaaaatta
2461 acgagcttaa gagtgtgcag aatgattcac aagcaattgc tgaggttctc aaccagctta
2521 aagatatgct tgccaacttc agaggttctg aaaagtactg ctatttacag aatgaagtat
2581 ttggactatt tcagaaactg gaaaatatca atggtgttac agatggctac ttaaatagct
2641 tatgcacagt aagggcactg ctccaggcta ttctccaaac agaagacatg ttaaaggttt
2701 atgaagccag gctcactgag gaggaaactg tctgcctgga cctggataaa gtggaagctt
2761 accgctgtgg actgaagaaa ataaaaaatg acttgaactt gaagaagtcg ttgttggcca
2821 ctatgaagac agaactacag aaagcccagc agatccactc tcagacttca cagcagtatc
2881 cactttatga tctggacttg ggcaagttcg gtgaaaaagt cacacagctg acagaccgct
2941 ggcaaaggat agataaacag atcgacttta ggttatggga cctggagaaa caaatcaagc
3001 aattgaggaa ttatcgtgat aactatcagg ctttctgcaa gtggctctat gatgctaaac
3061 gccgccagga ttccttagaa tccatgaaat ttggagattc caacacagtc atgcggtttt
3121 tgaatgagca gaagaacttg cacagtgaaa tatctggcaa acgagacaaa tcagaggaag
3181 tacaaaaaat tgctgaactt tgcgccaatt caattaagga ttatgagctc cagctggcct
3241 catacacctc aggactggaa actctgctga acatacctat caagaggacc atgattcagt
3301 cccttctgg ggtgattctg caagaggctg cagatgttca tgctcggtac attgaactac
3361 ttacaagatc tggagactat tacaggttct aagtgagat gctgaagagt ttggaagatc
3421 tgaagctgaa aaataccaag atcgaagttt ggaagagga gctcagactg gcccgagatg
3481 ccaactcgga aaactgtaat aagaacaaat tcctggatca gaacctgcag aaataccagg
3541 cagagtgttc ccagttcaaa gcgaagcttg cgagcctgga ggagctgaag agacaggctg
3601 agctggatgg gaagtcggct aagcaaaatc tagacaagtg ctacggccaa ataaaagaac
3661 tcaatgagaa gatcaccga ctgacttatg agattgaaga tgaaaagaga agaagaaat
3721 ctgtggaaga cagatttgac caacagaaga atgactatga ccaactgcag aaagcaaggc
3781 aatgtgaaaa ggagaacctt ggttggcaga aattagagtc tgagaaagcc atcaaggaga
3841 aggagtacga gattgaaagg ttgagggttc tactgcagga agaaggcacc cggaagagag
3901 aatatgaaaa tgagctggca aaggtaagaa accactaaa tgaggagtg agtaatttaa
3961 ggaacaagta tgaaacagag attaacatta cgaagaccac catcaaggag atatccatgc
4021 aaaaagagga tgattccaaa aatcttagaa accagcttga tagactttca agggaaaatc
4081 gagatctgaa ggatgaaatt gtcaggctca atgacagcat cttgcaggcc actgagcagc
4141 gaaggcgagc tgaagaaaac gcccttcagc aaaaggcctg tggctctgag ataatgcaga
4201 agaagcagca tctggagata gaactgaagc aggtcatgca gcagcgctct gaggacaatg
4261 cccggcacaa gcagtccctg gaggaggctg ccaagaccat tcaggacaaa ataaggaga
4321 tcgagagact caaagctgag tttcaggagg aggccaagcg ccgctgggaa tatgaaaatg
4381 aactgagtaa ggcatctaat aggattcagg aatcaaagaa tcagtgtact caggtggtac
4441 aggaaagaga gagccttctg gtgaaaatca agtcctgga gcaagacaag gcaaggctgc
4501 agaggctgga ggatgagctg aatcgtgcaa atcaactct agaggcagaa accagggtga
4561 aacagcgcct ggagtgtgag aaacagcaaa ttcagaatga cctgaatcag tggaagactc
4621 aatattcccg caaggaggag gctattagga agatagaatc ggaaagagaa aagagtgaga
```

-continued

```
4681 gagagaagaa cagtcttagg agtgagatcg aaagactcca agcagagatc aagagaattg 4741 aagagaggtg caggcgtaag ctggaggatt ctaccaggga gacacagtca cagttagaaa 4801 cagaacgctc ccgatatcag agggagattg ataaactcag acagcgccca tatgggtccc 4861 atcgagagac ccagactgag tgtgagtgga ccgttgacac ctccaagctg gtgtttgatg 4921 ggctgaggaa gaaggtgaca gcaatgcagc tctatgagtg tcagctgatc gacaaaacaa 4981 ccttggacaa actattgaag gggaagaagt cagtggaaga agttgcttct gaaatccagc 5041 cattccttcg gggtgcagga tctatcgctg gagcatctgc ttctcctaag gaaaaatact 5101 ctttggtaga ggccaagaga aagaaattaa tcagcccaga atccacagtc atgcttctgg 5161 aggcccaggc agctacaggt ggtataattg atccccatcg gaatgagaag ctgactgtcg 5221 acagtgccat agctcgggac ctcattgact tcgatgaccg tcagcagata tatgcagcag 5281 aaaaagctat cactggtttt gatgatccat tttcaggcaa gacagtatct gtttcagaag 5341 ccatcaagaa aaatttgatt gatagagaaa ccggaatgcg cctgctggaa gcccagattg 5401 cttcaggggg tgtagtagac cctgtgaaca gtgtcttttt gccaaaagat gtcgccttgg 5461 cccgggggct gattgataga gatttgtatc gatccctgaa tgatccccga gatagtcaga 5521 aaaactttgt ggatccagtc accaaaaaga aggtcagtta cgtgcagctg aaggaacggt 5581 gcagaatcga accacatact ggtctgctct tgctttcagt acagaagaga agcatgtcct 5641 tccaaggaat cagacaacct gtgaccgtca ctgagctagt agattctggt atattgagac 5701 cgtccactgt caatgaactg gaatctggtc agatttctta tgacgaggtt ggtgagagaa 5761 ttaaggactt cctccagggt tcaagctgca tagcaggcat atacaatgag accacaaaac 5821 agaagcttgg catttatgag gccatgaaaa ttggcttagt ccgacctggt actgctctgg 5881 agttgctgga agcccaagca gctactggct ttatagtgga tcctgttagc aacttgaggt 5941 taccagtgga ggaagcctac aagagaggtc tggtgggcat tgagttcaaa gagaagctcc 6001 tgtctgcaga acgagctgtc actgggtata atgatcctga aacaggaaac atcatctctt 6061 tgttccaagc catgaataag gaactcatcg aaaagggcca cggtattcgc ttattagaag 6121 cacagatcgc aaccgggggg atcattgacc caaaggagag ccatcgtttta ccagttgaca 6181 tagcatataa gaggggctat ttcaatgagg aactcagtga gattctctca gatccaagtg 6241 atgataccaa aggatttttt gaccccaaca ctgaagaaaa tcttacctat ctgcaactaa 6301 aagaaagatg cattaaggat gaggaaacag ggctctgtct tctgcctctg aaagaaaaga 6361 agaaacaggt gcagacatca caaaagaata ccctcaggaa gcgtagagtg gtcatagttg 6421 acccagaaac caataaagaa atgtctgttc aggaggccta caagaagggc ctaattgatt 6481 atgaaacctt caaagaactg tgtgagcagg aatgtgaatg ggaagaaata accatcacgg 6541 gatcagatgg ctccaccagg gtggtcctgg tagatagaaa gacaggcagt cagtatgata 6601 ttcaagatgc tattgacaag ggccttgttg acaggaagtt ctttgatcag taccgatccg 6661 gcagcctcag cctcactcaa tttgctgaca tgatctcctt gaaaaatggt gtcggcacca 6721 gcagcagcat gggcagtggt gtcagcgatg atgtttttag cagctcccga catgaatcag 6781 taagtaagat ttccaccata tccagcgtca ggaatttaac cataaggagc agctctttt 6841 cagacaccct ggaagaatcg agcccccattg cagccatctt gacacagaa aacctggaga 6901 aaatctccat tacagaaggt atagagcggg gcatcgttga cagcatcacg ggtcagaggc 6961 ttctggaggc tcaggcctgc acaggtggca tcatccaccc aaccacgggc cagaagctgt 7021 cacttcagga cgcagtctcc cagggtgtga ttgaccaaga catggccacc aggctgaagc
```

```
                                              -continued
7081 ctgctcagaa agccttcata ggcttcgagg gtgtgaaggg aaagaagaag atgtcagcag 7141 cagaggcagt gaaagaaaaa tggctcccgt atgaggctgg ccagcgcttc ctggagttcc 7201 agtacctcac gggaggtctt gttgacccgg aagtgcatgg gaggataagc accgaagaag 7261 ccatccggaa ggggttcata gatggccgcg ccgcacagag gctgcaagac accagcagct 7321 atgccaaaat cctgacctgc cccaaaacca aattaaaaat atcctataag gatgccataa 7381 atcgctccat ggtagaagat atcactgggc tgcgccttct ggaagccgcc tccgtgtcgt 7441 ccaagggctt acccagccct tacaacatgt cttcggctcc ggggtcccgc tccggctccc 7501 gctcgggatc tcgctccgga tctcgctccg ggtcccgcag tgggtcccgg agaggaagct 7561 ttgacgccac agggaattct tcctactctt attcctactc atttagcagt agttctattg 7621 ggcactagta gtcagttggg agtggttgct ataccttgac ttcatttata tgaatttcca 7681 ctttattaaa taatagaaaa gaaaatcccg gtgcttgcag tagagtgata ggacattcta 7741 tgcttacaga aaatatagcc atgattgaaa tcaaatagta aaggctgttc tggcttttta 7801 tcttcttagc tcatcttaaa taagcagtac acttggatgc agtgcgtctg aagtgctaat 7861 cagttgtaac aatagcacaa atcgaactta ggatttgttt cttctcttct gtgtttcgat 7921 ttttgatcaa ttctttaatt ttggaagcct ataatacagt tttctattct tggagataaa 7981 aattaaatgg atcactgata ttttagtcat tctgcttctc atctaaatat ttccatattc 8041 tgtattagga gaaaattacc ctcccagcac cagccccccct ctcaaacccc caacccaaaa 8101 ccaagcattt tggaatgagt ctcctttagt ttcagagtgt ggattgtata acccatatac 8161 tcttcgatgt acttgtttgg tttggtatta atttgactgt gcatgacagc ggcaatcttt 8221 tctttggtca aagttttctg tttattttgc ttgtcatatt cgatgtactt taaggtgtct 8281 ttatgaagtt tgctattctg gcaataaact tttagacttt tgaagtgttt gtgttttaat 8341 ttaatatgtt tataagcatg tataaacatt tagcatattt ttatcatagg tctaaaaata 8401 tttgtttact aaatacctgt gaagaaatac cattaaaaaa ctatttggtt ctgaattctt 8461 actagaaaaa aaa
```

In some embodiments of the methods of the disclosure, the wild type human DSP gene of the disclosure consists of or comprises the amino acid sequence (Genbank Accession number: NP_001305963.1, transcript variant 3):

```
                                                                    (SEQ ID NO: 47)
  1 mscnggshpr intlgrmira esgpdlryev tsggggtsrm yysrrgvitd qnsdgycqtg 61 tmsrhqnqnt iqellqncsd clmraelivq pelkygdgiq ltrsreldec faqandqmei 121 ldsliremrq mgqpcdayqk rllqlqeqmr alykaisvpr vrrasskggg gytcqsgsgw 181 deftkhvtse clgwmrqqra emdmvawgvd lasveqhins hrgihnsigd yrwqldkika 241 dlreksaiyq leeeyenllk asfermdhlr qlqniiqats reimwindce eeellydwsd 301 kntniaqkqe afsirmsqle vkekelnklk qesdqlvlnq hpasdkieay mdtlqtqwsw 361 ilqitkcidv hlkenaayfq ffeeaqstea ylkglqdsir kkypcdknmp lqhlleqike 421 lekerekile ykrqvqnlvn kskkivqlkp rnpdyrsnkp iilralcdyk qdqkivhkgd 481 ecilkdnner skwyvtgpgg vdmlvpsvgl iipppnplav dlsckieqyy eailalwnql 541 yinmkslvsw hycmidieki ramtiaklkt mrqedymkti adlelhyqef irnsqgsemf 601 gdddkrkiqs qftdaqkhyq tlviqlpgyp qhqtvtttei thhgtcqdvn hnkvietnre 661 ndkqetwmlm elqkirrqie hcegrmtlkn lpladqgssh hitvkinelk svqndsqaia
```

```
 721 evlnqlkdml anfrgsekyc ylqnevfglf qkleningvt dgylnslctv rallqailqt 781 edmlkvyear lteeetvcld ldkveayrcg lkkikndlnl kksllatmkt elqkaqqihs 841 qtsqqyplyd ldlgkfgekv tqltdrwqri dkqidfrlwd lekqikqlrn yrdnyqafck 901 wlydakrrqd slesmkfgds ntvmrflneq knlhseisgk rdkseevqki aelcansikd 961 yelqlasyts gletllnipi krtmiqspsg vilqeaadvh aryielltrs gdyyrflsem 1021 lksledlklk ntkievleee lrlardanse ncnknkfldq nlqkyqaecs qfkaklasle 1081 elkrqaeldg ksakqnldkc ygqikelnek itrltyeied ekrrrksved rfdqqkndyd 1141 qlqkarqcek enlgwqkles ekaikekeye ierlrvllqe egtrkreyen elakvrnhyn 1201 eemsnlrnky eteinitktt ikeismqked dsknlrnqld rlsrenrdlk deivrlndsi 1261 lqateqrrra eenalqqkac gseimqkkqh leielkqvmq qrsednarhk qsleeaakti 1321 qdknkeierl kaefqeeakr rweyenelsk asnriqeskn qctqvvqere sllvkikvle 1381 qdkarlqrle delnrakstl eaetrvkqrl ecekqqiqnd lnqwktqysr keeairkies 1441 ereksereekn slrseierlq aeikrieerc rrkledstre tqsqleters ryqreidklr 1501 qrpygshret qtecewtvdt sklvfdglrk kvtamqlyec qlidkttldk llkgkksvee 1561 vaseiqpflr gagsiagasa spkekyslve akrkklispe stvmlleaqa atggiidphr 1621 nekltvdsai ardlidfddr qqiyaaekai tgfddpfsgk tvsyseaikk nlidretgmr 1681 lleaqiasgg vvdpvnsvfl pkdvalargl idrdlyrsln dprdsqknfv dpvtkkkvsy 1741 vqlkercrie phtglllsv qkrsmsfqgi rqpvtvtelv dsgilrpstv nelesgqisy 1801 devgerikdf lqgssciagi ynettkqklg iyeamkiglv rpgtalelle aqaatgfivd 1861 pvsnlrlpve eaykrglvgi efkekllsae ravtgyndpe tgniislfqa mnkeliekgh 1921 girlleaqia tggiidpkes hrlpvdiayk rgyfneelse ilsdpsddtk gffdpnteen 1981 ltylqlkerc ikdeetglcl lplkekkkqv qtsqkntlrk rrvvivdpet nkemsvqeay 2041 kkglidyetf kelceqecew eeititgsdg strvvlvdrk tgsqydiqda idkglvdrkf 2101 fdqyrsgsls ltqfadmisl kngvgtsssm gsgvsddvfs ssrhesvski stissvrnlt 2161 irsssfsdtl eesspiaaif dtenlekisi tegiergivd sitgqrllea qactggiihp 2221 ttgqklslqd aysqgvidqd matrlkpaqk afigfegvkg kkkmsaaeav kekwlpyeag 2281 qrflefqylt gglvdpevhg risteeairk gfidgraaqr lqdtssyaki ltcpktklki 2341 sykdainrsm veditglrll eaasysskgl pspynmssap gsrsgsrsgs rsgsrsgsrs 2401 gsrrgsfdat gnssysysys fssssigh
```

In some embodiments of the methods of the disclosure, the wild type human AZGP1 gene of the disclosure consists of or comprises the nucleic acid sequence (Genbank Accession number: NM_001185.3):

(SEQ ID NO: 21)

```
   1 ccattggcct gtagattcac ctcccctggg cagggcccca ggacccagga taatatctgt
  61 gcctcctgcc cagaaccctc caagcagaca caatggtaag aatggtgcct gtcctgctgt
 121 ctctgctgct gcttctgggt cctgctgtcc cccaggagaa ccaagatggt cgttactctc
 181 tgacctatat ctacactggg ctgtccaagc atgttgaaga cgtccccgcg tttcaggccc
 241 ttggctcact caatgacctc cagttcttta gatacaacag taaagacagg aagtctcagc
 301 ccatgggact ctggagacag gtggaaggaa tggaggattg gaagcaggac agccaacttc
 361 agaaggccag ggaggacatc tttatggaga ccctgaaaga catcgtggag tattacaacg
 421 acagtaacgg gtctcacgta ttgcaggaa ggtttggttg tgagatcgag aataacagaa
 481 gcagcggagc attctggaaa tattactatg atggaaagga ctacattgaa ttcaacaaag
 541 aaatcccagc ctgggtcccc ttcgacccag cagcccagat aaccaagcag aagtgggagg
 601 cagaaccagt ctacgtgcag cgggccaagg cttacctgga ggaggagtgc cctgcgactc
 661 tgcggaaata cctgaaatac agcaaaaata tcctggaccg gcaagatcct ccctctgtgg
 721 tggtcaccag ccaccaggcc ccaggagaaa agaagaaact gaagtgcctg gcctacgact
 781 tctacccagg gaaaattgat gtgcactgga ctcgggccgg cgaggtgcag gagcctgagt
 841 tacggggaga tgttcttcac aatggaaatg gcacttacca gtcctgggtg gtggtggcag
 901 tgccccgca ggacacagcc ccctactcct gccacgtgca gcacagcagc ctggcccagc
 961 ccctcgtggt gccctgggag gccagctagg aagcaagggt tggaggcaat gtgggatctc
1021 agacccagta gctgccttc ctgcctgatg tgggagctga accacagaaa tcacagtcaa
1081 tggatccaca aggcctgagg agcagtgtgg ggggacagac aggaggtgga tttggagacc
1141 gaagactggg atgcctgtct tgagtagact tggacccaaa aaatcatctc accttgagcc
1201 cacccccacc ccattgtcta atctgtagaa gctaataaat aatcatccct ccttgcctag
1261 cataaaaaaa aaaaaaaa
```

In some embodiments of the methods of the disclosure, the wild type human AZGP1 gene of the disclosure consists of or comprises the nucleic acid sequence (Genbank Accession number: NP_001176.1):

(SEQ ID NO: 22)

```
  1 mvrmvpvlls lllllgpavp qenqdgrysl tyiytglskh vedvpafqal gslndlqffr
 61 ynskdrksqp mglwrqvegm edwkqdsqlq karedifmet lkdiveyynd sngshvlqgr
121 fgceiennrs sgafwkyyyd gkdyiefnke ipawvpfdpa aqitkqkwea epvyvqraka
181 yleeecpatl rkylkyskni ldrqdppsvv vtshqapgek kklkclaydf ypgkidvhwt
241 ragevqepel rgdvlhngng tyqswvvvav ppqdtapysc hvqhsslaqp lvvpweas
```

In some embodiments of the methods of the disclosure, the wild type human OBFC1 gene of the disclosure consists of or comprises the nucleic acid sequence (Genbank Accession number: NM_024928):

(SEQ ID NO: 23)

```
   1 aaatgcgctg gcggggagac cggggttggt ccctggcggg gcaggggcg ggctcaggcc
  61 ggaactccag agacgacctc agccaactgc tcctgcgccg ggcggggtcg tcgccgccag
 121 cggctccgag cgccggaagg gccaggtctc agggctcctg gagctgcagg cggcgggagg
 181 ggctacaaat gcttgactca gtgatgcaga accttcaga gttagctgga agccacagcc
 241 ctgcctcttg atgcagcctg gatccagccg gtgtgaagag gagacccctt ccctcttgtg
 301 gggtttggat cctgtgtttc tagcctttgc aaaactctac atcagggata tcctggacat
 361 gaaggagtcc cgccaggtgc caggtgtatt tttgtacaat ggacatccaa taaaacaggt
 421 agatgtcttg ggaactgtca ttggagtgag agaaagagat gctttctaca gttatggagt
 481 ggatgacagc actggagtta taaactgcat ctgctggaaa aagttgaata ctgagtctgt
 541 atcagctgct ccaagtgcag caagagagct cagcttaacc tcacaactta agaagctaca
 601 agagaccatt gagcagaaaa caaagataga gatcgggac acgatccgag tcagaggcag
 661 tatccgcaca tacagagaag agcgagagat tcatgccacc acttactata aagtggacga
 721 cccagtgtgg aacattcaaa ttgcaaggat gcttgagctg cccactatct acaggaaagt
 781 ttatgaccag ccttttcaca gctcagccct agagaaagaa gaggcactaa gcaatccagg
 841 cgccctggac ctccccagtc tcacgagttt gctgagtgaa aaagccaaag aattcctcat
 901 ggagaacaga gtgcagagct tttaccagca ggagctggaa atggtggagt ctttgctgtc
 961 ccttgccaat cagcctgtga ttcacagtgc ctcctccgac caagtgaatt ttaagaagga
1021 caccacttcc aaggcaattc atagtatatt taagaatgct atacaactgc tgcaggaaaa
1081 aggacttgtt ttccagaaag atgatggttt tgataaccta tactatgtaa ccagagaaga
1141 caaagacctg cacagaaaga tccaccggat cattcagcag gactgccaga accaaatca
1201 catggagaag ggctgtcact tcctgcacat cttggcctgt gctcgcctga gcatccgccc
1261 gggcctgagc gaggctgtgc tgcagcaagt tctggagctc ctggaggacc agagtgacat
1321 tgtcagcaca atggagcact actacacagc gttctgagca gagacacgca gaccagctga
1381 ggaggacaaa gataaggtgg cattcacccc caggctctga cttctcagcat catgcagggg
1441 cttatctgtc tggaggcagt tacctcataa taaactataa aatatagtca tcttgggaat
1501 gggatttggc ataaatgttg ttggctccct tctgtccact atgtccttgg tgtacaatga
1561 ctttgatctc agccatgaca caacaagaaa accctccctg ttgagctcct ggctggactg
1621 tgcgttgttc gcagagcaga atggggagga aacagtgttg gcagcttaac tgatgtgtgt
1681 ggttggagtc tcttccatgg caaagggaca ccacagggta gtgaacattc aggaactgag
1741 gggcatatgg cctgatcaca cagttctaag cttttcaaaa cttcaggtta tcagagacct
1801 tcctgtgggc ctctcttgct ggctaagaac cggtttaggg gagtagttct ccctggatga
1861 gtgcttacag tttctgtggc tcagttacca gcagtggggt tgagacctgg gtcgatgctc
1921 tttacaggcc tgcccagaga tgggaataaa cagggatcca cagcgtgact atgtgtttgt
1981 cattttcctt ttatttcctt gggaatcgaa aggtgtccca gtacatttcc ctgcacttac
2041 agaggtgcat gactaaatac attgtccctc gatgcccctg aagatcacgg aggcagtcag
2101 ccaattgcct ggcaggtggt agatgttatt ttcagggttg ccgctgagtg tgcaggatgt
2161 gctgacacca tccagacaaa gactcggtat gtgcccagac aggtgatgga gtcatgcttt
```

```
2221 tgctcagaat gacaaggtaa aggaaaaaca tctgaggtat gttgtaggcc tgttctgaca 2281 gcaaaatgac aaatccagcc agcaaaaata aagtgtggag aaagatttgg agttaattac 2341 agtcatttca cagaaggcac tgccttcgtc tgctgcattt gctcttgatg tgataagctc 2401 ttcgtggctc agctggagat cctttaggcc tggagagttg ctcctctctc cgtggaaaca 2461 ggacagtctt tatacgcaga agtccgctgc agctcgatac gtcaggctga gagctagaac 2521 cagtagattg cctcctgtca tagacttttg taatgatgca aacctttgct gatttctaac 2581 agtgattatg tagtggctgc cctgcatctt ctctgtgtac agaagggtcc ctagcataga 2641 gtctgcctgg aatgatgtcc tgggcagttc ttccttgagg tcagcagctg ttccacgttg 2701 aatgcatctg attagtgggg ctgcccagga aggagttcag aatcagaagg taaaagggc 2761 atacccttgc ctatagcaac tctgctctta ggggtttatc tcaaggagat ggctacacaa 2821 gtgtgaaagg atggttgcac aaggtgttca ttgctgtata atctagaatt ctatattggg 2881 gaaataccct atagggaaaa agttaattac ggttcttggg cacaatgaaa tactatgcag 2941 ctatgaaaaa aatgatgaaa gcagacagac agtgttgcca tggcacactg tccctagtag 3001 atttagtggg aagtagatag agttatagat ctgtttctat agtataacac cattatctac 3061 agctccctgt gtgtatgtat atatccgtag agagagtgta tatttctgca tggaggtctt 3121 tataaatgta gcacatgtac atatatatat atatacacac acacagtcga ccactcccTT 3181 ctcctggaag tactttccgc gtttggcttt caggacacca agctctctgg ttgctccttc 3241 tcaggttcct ttgttcagtg ctctgcctcc ctgaggactc agtcccagac ctcttttcta 3301 tctggcttgc tcactggggt gtctccagca gccacatgga ttataccatc tacatgctgt 3361 ctaacacctc agtttaaacc cagaatgggc ctcttccctg aactgcagac ccctatattc 3421 agtttgctac tgacatctcc acttaggtct ctaatggaca tctcagattt cacaggccca 3481 aagccaggct cccaattact cctgacccca ggcttgctcc tgatagtgac atgaggcagc 3541 caaatgccta ggcagagagg ggagggtccc aaatgaaacc ccacgttcaa gcaaagatca 3601 gcctgaaggc taaaagacca gattgctggt cctggatgaa acccaccacg cagagtggga 3661 acttctgttc ctgtttgccc acccttcccc aattgttctt tctgaataac gccttaacca 3721 atcgaatgtt gccttttcca gtaataccta cagcctgccc ctcccccat tctgagccca 3781 taaaaagacc cagactcccc catattaagg ggactttcct gcctttgggt aggggacca 3841 cccccacgtc tcctctctgt tgaaaactgt ttcatcactc aataaaactc ccagctttgc 3901 tcactcttcc actgtcagca cattctcatt cttctttggt gctgggcaag aactcaacca 3961 gtgtggaagc catacttggc ccaggcgggt gaagtgggcg ggccgtctcc tgcagcaggt 4021 agcatggtca agcgaggccc aggtgggccg tcaccagcca gaggtccctg gcttgcaaag 4081 tgaccgagaa aaaaatcctg tgccactcct ttggaaaatg tccctgattc aggaagaggt 4141 agctccatcc agttgctcaa accaaatcca ttggcttctt tctttctatc atacctcaca 4201 tccaatctgt ctgcaagtct tttggctcta ccttcagaat atctccagaa tcttaactgc 4261 ttcaccctcc tccccggcct cctcagtcct ctctgcttcc gccctggccc ctcttgggct 4321 gttcacagca cagcagctgt tgccaccctg ttaatgctcc cactctccta cagccttcgg 4381 tcttgcccca ggtaggagcc tgaggctgca cagaggtcag cacggccccg cttaccctgc 4441 cctcccagcc cagccgcacg ggccttgcac acatgcctcg gcatattcct gccttagggc 4501 tggtgctcct gctatttcct cttcccaggt aaccatgtga agtgcctccc tctgccctct 4561 ttccagcctt tacttgagtg tcaccttctc agtgaggcct gccctcattc ctctttcgct 4621 gtttgcaacc catctcctgt cccccttccc agaactccct ttcctacttc gttttcttc
```

-continued

```
4681 acagtacttg atactgccta acacactcca tggtttctta cttgccctgt ttattatttt
4741 cccccaatag acagaatgtt ccatgatggc agaattctct gttttgtttc cttccatgtc
4801 cccagcacct agaacagtgc ctgacgcatc tcctaagcaa tacgaccaat aagtatgtgt
4861 ctggctgcct tccggctgcc agtgtctgcc tctttcctag gggcagtggt tgcggggtg
4921 ctttctcaca tgtcttagta ggctgtgcag gctggaagtg ctcagaagtc acacccccag
4981 ggagcagcct cagccaacag cacccttggct gtaaatgccc cagctccctc gccctcaggt
5041 aagcattgct gaggcacacg ttccatactc ttttccacag ttcctccgtg ggactgagca
5101 ccacccagcc acccacagga gcagctaacc tgataaccac cagcctcacc ctccctgcct
5161 tacttccccg ctccccttta ccacatgctg acctcccaga tgcatttctt gctttccggt
5221 ctctgtctca ggattggctc ctggatgaac acaaactaac actatgttca caaatatatt
5281 tgggaaatgc tggatgaata attatacaca tcagacagat tactagaaat tctcaccaaa
5341 gggatgcaca tgttacctct gcatggtgag atctcaggtg cttttttaccc cacatagcta
5401 tcctttggca tttttataat tagcaagtgc tcactcttcc actgtcagta cattctcatt
5461 cttcttgggc gctggacaag aattcaaccg gtgtgtaagc cagactcggc ccgggcagtc
5521 tcaaactcct gactccttat ataatttcta caaaaattat aaagctattt cccactcccc
5581 accccacatt catgtaacct gaagcatgag taaaccaaga atgaggtagg cctctgtctt
5641 ctaagcaaca tcagaactct aagaacatga gggactctta gaaaactctc tggagctaac
5701 cacagctggg tcactgctca tgtactgaag accagccaga gggttcccct gaaaaggagg
5761 gaaactgagc aaacattctc cagttctctt agtgtgcaca tgtttcagga ggtgtgaacc
5821 ccacatgtag cttgtgtagg caagaagaca aatagtgcta ctgtctggtc aaggatttgt
5881 ttgaagagcc atgattatgc ccatatggta agccaccagt gctccccatc cctgtaagac
5941 acttctttct cattatttc tcctctgatg gtgtgccagg atgctggcca agagaagcca
6001 agtggaaaga aggctgttca gtgacaagga acctaagact tagtgccaag gactgaaacc
6061 aagtaaactt gtaattttcc atgatggaaa catctacact ttctcattag tggcctctac
6121 agcagttgcc ccaaagaagc gtctcattgt ttttttacta catttatgtg aagcatacag
6181 gcaaactcag aaagactgtg ataaggctcg ccagagatgc ctgcacaggt gctgggggaa
6241 aagcaggacc atcctgaagg gagatggtgt ctgtggacaa agaactctgc agtggttctt
6301 atttgcatga tttctgctgg tggaggctgt aaatgtgagc tcaaactccc acataagtga
6361 gttttcattg taatccagaa tgttttttaaa tcaccctact tctattgaac ttgcactatc
6421 atctgttaac ctctactgta tttattaaat aaacctgaat aggtaaatca cagtacagca
6481 aaa
```

In some embodiments of the methods of the disclosure, the wild type human OBFC1 gene of the disclosure consists of or comprises the amino acid sequence (Genbank Accession number: NP_079204.2):

(SEQ ID NO: 24)

```
  1 mqpgssrcee etpsllwgld pvflafakly irdildmkes rqvpgvflyn ghpikqvdvl
 61 gtvigvrerd afysygvdds tgvincicwk klntesvsaa psaarelslt sqlkklqeti
121 eqktkieigd tirvrgsirt yreereihat tyykvddpvw niqiarmlel ptiyrkvydq
181 pfhssaleke ealsnpgald lpsltsllse kakeflmenr vqsfyqqele mvesllslan
241 qpvihsassd qvnfkkdtts kaihsifkna iqllqekglv fqkddgfdnl yyvtredkdl
```

```
301  hrkihriiqq dcqkpnhmek gchflhilac arlsirpgls eavlqqvlel ledqsdivst 361  mehyytaf
```

In some embodiments of the methods of the disclosure, the wild type human ATP11A gene of the disclosure consists of or comprises the nucleic acid sequence (Genbank Accession number: NM_015205.2, transcript variant 1):

(SEQ ID NO: 25)
```
   1  gcggccgcac tagtaccccg gagcccatgg gcgcgccgag ccgggcgcgg gggcgctgaa
  61  cggcggagcg ggagcggccg gaggagccat ggactgcagc ctcgtgcgga cgctcgtgca
 121  cagatactgt gcaggagaag agaattgggt ggacagcagg accatctacg tgggacacag
 181  ggagccacct ccgggcgcag aggcctacat cccacagaga tacccagaca acaggatcgt
 241  ctcgtccaag tacacatttt ggaactttat acccaagaat ttatttgaac aattcagaag
 301  agtagccaac ttttatttcc ttatcatatt tctggtgcag ttgattattg atacacccac
 361  aagtccagtg acaagcggac ttccactctt ctttgtcatt actgtgacgg ctatcaaaca
 421  gggttatgaa gactggcttc gacataaagc agacaatgcc atgaaccagt gtcctgttca
 481  tttcattcag cacggcaagc tcgttcggaa acaaagtcga aagctgcgag ttggggacat
 541  tgtcatggtt aaggaggacg agacctttcc ctgcgacttg atcttccttt ccagcaaccg
 601  gggagatggg acgtgccacg tcaccaccgc cagcttggat ggagaatcca gccataaaac
 661  gcattacgcg gtccaggaca ccaaaggctt ccacacagag gaggatatcg gcggacttca
 721  cgccaccatc gagtgtgagc agccccagcc cgacctctac aagttcgtgg gtcgcatcaa
 781  cgtttacagt gacctgaatg accccgtggt gaggcccta ggatcggaaa acctgctgct
 841  tagaggagct acactgaaga cactgagaa aatctttggt gtggctattt acacgggaat
 901  ggaaaccaag atggcattaa attatcaatc aaaatctcag aagcgatctg ccgtggaaaa
 961  atcgatgaat gcgttcctca ttgtgtatct ctgcattctg atcagcaaag ccctgataaa
1021  cactgtgctg aaatacatgt ggcagagtga gcccttttcgg gatgagccgt ggtataatca
1081  gaaaacggag tcggaaaggc agaggaatct gttcctcaag gcattcacgg acttcctggc
1141  cttcatggtc ctctttaact acatcatccc tgtgtccatg tacgtcacgg tcagatgca
1201  gaagttcctc ggctcttact tcatcacctg ggacgaagac atgtttgacg aggagactgg
1261  cgaggggcct ctggtgaaca cgtcggacct caatgaagag ctgggacagg tggagtacat
1321  cttcacagac aagaccggca ccctcacgga aaacaacatg gagttcaagg agtgctgcat
1381  cgaaggccat gtctacgtgc cccacgtcat ctgcaacggg caggtcctcc cagagtcgtc
1441  aggaatcgac atgattgact cgtccccag cgtcaacggg agggagcgcg aggagctgtt
1501  tttccgggcc ctctgtctct gccacaccgt ccaggtgaaa gacgatgaca gcgtagacgg
1561  ccccaggaaa tcgccggacg gggggaaatc ctgtgtgtac atctcatcct cgcccgacga
1621  ggtggcgctg gtcgaaggtg tccagagact tggctttacc tacctaaggc tgaaggacaa
1681  ttacatggag atattaaaca gggagaacca catcgaaagg tttgaattgc tggaaatttt
1741  gagttttgac tcagtcagaa ggagaatgag tgtaattgta aaatctgcta caggagaaat
1801  ttatctgttt tgcaaaggag cagattcttc gatattcccc cgagtgatag aaggcaaagt
1861  tgaccagatc cgagccagag tggagcgtaa cgcagtggag gggctccgaa ctttgtgtgt
1921  tgcttataaa aggctgatcc aagaagaata tgaaggcatt tgtaagctgc tgcaggctgc
1981  caaagtggcc cttcaagatc gagagaaaaa gttagcagaa gcctatgagc aaatagagaa
```

-continued

```
2041 agatcttact ctgcttggtg ctacagctgt tgaggaccgg ctgcaggaga aagctgcaga 2101 caccatcgag gccctgcaga aggccgggat caaagtctgg gttctcacgg gagacaagat 2161 ggagacggcc gcggccacgt gctacgcctg caagctcttc cgcaggaaca cgcagctgct 2221 ggagctgacc accaagagga tcgaggagca gagcctgcac gacgtcctgt tcgagctgag 2281 caagacggtc ctgcgccaca gcgggagcct gaccagagac aacctgtccg actttcagc 2341 agatatgcag gactacggtt taattatcga cggagctgca ctgtctctga taatgaagcc 2401 tcgagaagac gggagttccg gcaactacag ggagctcttc ctggaaatct gccggagctg 2461 cagcgcggtg ctctgctgcc gcatggcgcc cttgcagaag gctcagattg ttaaattaat 2521 caaattttca aaagagcacc caatcacgtt agcaattggc gatggtgcaa atgatgtcag 2581 catgattctg gaagcgcacg tgggcatagg tgtcatcggc aaggaaggcc gccaggctgc 2641 caggaacagc gactatgcaa tcccaaagtt taagcatttg aagaagatgc tgcttgttca 2701 cgggcatttt tattacatta ggatctctga gctcgtgcag tacttcttct ataagaacgt 2761 ctgcttcatc ttccctcagt ttttatacca gttcttctgt gggttttcac aacagacttt 2821 gtacgacacc gcgtatctga ccctctacaa catcagcttc acctcctcc ccatcctcct 2881 gtacagcctc atggagcagc atgttggcat tgacgtgctc aagagagacc cgaccctgta 2941 cagggacgtc gccaagaatg ccctgctgcg ctggcgcgtg ttcatctact ggacgctcct 3001 gggactgttt gacgcactgg tgttcttctt tggtgcttat ttcgtgtttg aaaatacaac 3061 tgtgacaagc aacgggcaga tatttggaaa ctggacgttt ggaacgctgg tattcaccgt 3121 gatggtgttc acagttacac taaagcttgc attggacaca cactactgga cttggatcaa 3181 ccatttgtc atctgggggt cgctgctgtt ctacgttgtc ttttcgcttc tctggggagg 3241 agtgatctgg ccgttcctca actaccagag gatgtactac gtgttcatcc agatgctgtc 3301 cagcgggccc gcctggctgg ccatcgtgct gctggtgacc atcagcctcc ttcccgacgt 3361 cctcaagaaa gtcctgtgcc ggcagctgtg gccaacagca acagagagag tccagactaa 3421 gagccagtgc ctttctgtcg agcagtcaac catctttatg cttttctcaga cttccagcag 3481 cctgagtttc tgatggaaca agagcccagg ctaccagagc acctgtccct cggccgcctg 3541 gtacagctcc cactctcagc aggtgacact cgcggcctgg aaggagaagg tgtccacgga 3601 gcccccaccc atcctcggcg gttcccatca ccactgcagt tccatcccaa gtcacagctg 3661 ccctaggtcc cgtgtgggaa tgctcgtgtg atggatggtc ctaagcctgt ggagactgtg 3721 cacgtgcctc ttcctggccc ccagcaggca aggagggggg tcacaggcct tgccctcgag 3781 catggcaccc tggccgcctg acccagcac tgtggttgtt gagccacacc agtggcctct 3841 gggcattcgg ctcaacgcag gagggacatt ctgctggccc accctgcgcg ctgtcatgca 3901 gaggccattc ccccaggcct gtgtcttcac ccacctgcca tcattggcct tgctgtcac 3961 tgggagagaa gagccgtcca gggacccatg gtggcccaca tgtggatgcc acatgctgct 4021 gtttcctgct tgcccggcca ccacccatgc cctccatagg gtgaggtgga gccatggtgg 4081 tgcgtccttt actcaacaac cctccaatcc ggatgctgtg ggaagggccg ggtcactcgg 4141 ataccatcat ccctgcggat gcaccgccgt accctgctca tctgggagtg gtttccctgc 4201 ggttacgtcc aagcccgcct gccctgtgtg ttggggctgg ctgagtttcg gtctccccat 4261 caccggccgc ctcgtggaga aggcagtgcc acgtgggagg acaaggccac gccggcagct 4321 tccagccctg ccgcagaagt gccaggatgt ccatcagcca ctcgccaggg cacggagccg 4381 tcagtccact gttacgggag aatgttgatt tcgcgggtgc gagggccggg agacagatac
```

```
4441 ttggctgtga tgagcagaca tcctctgtcc ccgtggaggg gtcaacacca aggtggtgtt 4501 cgtgcaccag aacctgtctc gggctgacgg gggtggcaca caggacacgg gtggatccca 4561 acaggcagca ccgcacctct gcccgcctcc cgcactgcag ctccgcccgc cgggctctgc 4621 gtccccacgt ccctcgtcc catccccacg tccctcatc ccgtcacctc gtccccacat 4681 ccccttgccc cgtcacctcg tcctcatgtc cccttgtcct gtcacctcgt ccccacgtcc 4741 cctcgtctcc tcatcccac gtcctctcgt cccttgtcc cgtccccaca taccctcgtc 4801 cccatgtccc cacgcagggc tctccttcgt cttaggatct gtccagcgct gctctgggtg 4861 ggttagcaac cccagggctg ctgtgatagg aagtccctgt tgttctccgt actggcattt 4921 ctatttctag aaataatatt tgacatagcc ttaatggtcc ttaaagaaga catttcagtg 4981 tgagattcag acttcagacg ctgaaactgc tgcctttcag gaaagcacca ccaacgctgg 5041 aggaggagcc ggccctcacg cccgccccgc gccacgctgt ggaacggggc tccggcaagt 5101 gaaacccaga gggtgtttcc gaggtgctcg acagtaggta ttttggaag ctcagatttc 5161 accatttgat tgtataatct tttacctata aaatatttat ttgaagtaga gggtaaatca 5221 gcggtaagaa cagtgaacac agtggttggg ataaaataag gtgacaaaca tcacaccaaa 5281 gatgagggta gcgagcaact ggcttgagca gacagaacgg ggaagactcc actctgtccc 5341 gaggggccag ccgcaggcgt ccccagggcc accctgccct gaggtccttg tgtggccgcc 5401 ctggcttggc agccctgccc acgctgcccc cgcaaacaat ggtgtgtgcg ttttacagc 5461 cctttttagg aacccaatat gggcataaat gtaacacctg tagcgggggc agattctctg 5521 tatgttcagt taacaaatta tttgtaatgt atttttttag aaatcttaaa attgcctttg 5581 cactgaagta ttttcatagc tgtttatatc tcttttattc atttatttaa catactgtct 5641 aattttaaaa ataggttttt aaagctttca tttttaagtt tatgaaattt tggccacttt 5701 acatttagat tctggtgaga gttttgactg aatgttccaa tctctgatga atgcgaattt 5761 tcagatttga tttattctc tacacacacc tcttcttttc ttggtatttc tggtggcagt 5821 gattagttga acagcacatt taaggcacga taatttgcta cacttttcct ttacaatttg 5881 ttgcaatttc atctgctttc tatgtttcat tgttaattgc catccttcag ccttaaaaat 5941 agaagattct cacgtgaagg tttagtaagt tgggtcccag ctctgcctgt gtggagatag 6001 tcaccatgta cctctgacaa caagttttag tgtgaaagtc actaaacttt tacacactcc 6061 caaacgtctt tttaaaaatt gcttgggaaa ttattaaatg aatgtgcctg atgatttgaa 6121 atagacaagg ggcacgagat aaaaaagaaa aggatgagaa gatcctcagt gaatgacgtt 6181 gcagggtctt catgcaattt tccacctcgc agtagttagt atttacttgc cttaaactaa 6241 ctttgaagca agtaatgtca actttgagca ctttgttgag ttttgaaaaa tcttatttgt 6301 tgctgcacag gttaataaat tatcaatttg taattcagca tgttggtcag agacacggtc 6361 actgattcac acccagtccc tgccacagac cgtctcagac acgcacagtg ggcctgctgc 6421 atgattcaca cccagtccct gccacagacc gtctcagaca cgcacagtgg gcctgctgca 6481 tgattcacac ccagtccctg ccacagaccg tctcagacac gcacagtggg cctgctgcat 6541 gcgtgttacc tggcttttgg ctccacgctc actcatagcc atgtccacat ggggggcttgc 6601 acacaggatc actcacatat gtacatgtac ccaccacaaa cgtgcaagct cctgcacaca 6661 tgcatgcaca caaacgtgta cacaagtgtg agctcctaca cgcatacaca cacacacgtg 6721 tacatgcacc aaagcatgtg tgacctacag acatgcagaa catgcacgtg tacacatacc 6781 acagacacgc gtgtgcatgc tcctacacaa tacatatgca catatcatga acagcgtaag 6841 ttcctacaca cggacgtgtg atacacacat gcatgtacag gtaagcacac atgtacaagc
```

-continued

```
6901 tcctacaggc ttgctctcac acacgtgtat gcacagcaga gagacgtatg agcttctact
6961 gcacacatgc acacacacac gcacacgtac attcactaca aacgtgcagc ctcctgcaca
7021 cgtgcacatt catgtgtaca ccacaaatga gttcccagac gtgtaaacac acgtgcacac
7081 atcgtacaca tgtgagctcc cacacgtaca cacagatgca catggacaca ccccaaacac
7141 gcacaggctc ctacacacat gcacacacgt gtacaccaca aacgagctcc cagacatgta
7201 aacacacgtc tcccacacgt gagctcccac acgtacacat gcacatgtac gcaccacaaa
7261 cacatgcgca ggctcctgca ggcgtgaata cacacatgca cacacatata cacacatgtg
7321 ccacaaacaa gtgcacactg tcctggtgtc ctgcactgca tcctgcctcc ttgctgaggg
7381 gcccctgtga gaggcctctg gatgggcatg ggaagatggg ctccctggcc cccagcccat
7441 gcctccctgg gatgaagagt cccctcctg gcagaatgtc tgggctttgc agagcaggcc
7501 ccgggggtga agtcgcagct tcacttacac cagctgctct gtgagcaagg cttggtgccc
7561 tggacaaggc ccttcccctt tagggaggtc cagcctcgca agctgaaacc tccccctcggc
7621 tcagccctat accaggcggc cacagcagga ctggccacac ccacgccgca cctcatccgt
7681 gcacgcgtcg gagcacggcc agccttccgc cacgagccag ctgggaaggg ccgcggccgc
7741 ctaaagcccc agtcaaccca gcctgtgtct gagcagacag ggcgaacaag caggccacac
7801 cgtctcgagg gaggaggcca gatgcggcca gcgtctccaa cagggtgacc atccgctcgg
7861 cttgctgagc gtttaaacaa atgtttagac aggctgtggg gactccctg agttgagcct
7921 tggccagggg tccggtgctg tcgcgggaaa cctccagcct tgttcttcaa accactcagc
7981 tcatgtgttt tgcactgact agtactgaat aatacaacca ctcttattta atgttagtat
8041 tatttatttg acaactcagt gtctaacagc ttgatatgca ggtccttgca tcctacattt
8101 ctttaggaag ttacccattt gtaactttaa aaacaggaaa aatatcagtt ggcaaatgca
8161 atctttttt tttttaagct aaaggtgggt gaactggaat gaaaatcttt ctgatgttgt
8221 gtctataagc agccttgatg ggatatgtta gaagtgtcat gaaagtgtga ttctactttt
8281 gcagaaaaat ctaaagatca atttatatag ctttatttt tactttatca aagtatacag
8341 aattttaata tgcatatatt gtgtctgact taaaattata atgtctgcgt caccatttaa
8401 aatgtctgtt cattatgtaa tgtaataaaa gaaggtcttc aaaaatgtat ttaacatgaa
8461 tggtatccat agttgtcatc atcataaata ctggagttta tttttaaatt attaaacata
8521 gtaggtgcat taacataaat cagtctccac acagtaacat ttaactgata attcattaat
8581 cagctttgaa aaattaaatt gttaattaaa ccaatctaac atttcagtaa agtttatttt
8641 gtatgcttct gtttttaact tttatttctg tagataaact gactggataa tattatattg
8701 gacttttctc tagattatct aagcaggaga cctgaatctg cttgcaataa agaataaaag
8761 tctgcttcag tttctttata aagaaactca cacaa
```

In some embodiments of the methods of the disclosure, the wild type human ATP11A gene of the disclosure consists of or comprises the nucleic acid sequence (Genbank Accession number: NP_056020.2, transcript variant 1):

(SEQ ID NO: 26)

```
  1 mdcslvrtlv hrycageenw vdsrtiyvgh repppgaeay ipqrypdnri vsskytfwnf
 61 ipknlfeqfr rvanfyflii flvqliidtp tspvtsglpl ffvitvtaik qgyedwlrhk
121 adnamnqcpv hfiqhgklvr kqsrklrvgd ivmvkedetf pcdliflssn rgdgtchvtt
181 asldgesshk thyavqdtkg fhteediggl hatieceqpq pdlykfvgri nvysdlndpv
```

-continued

```
 241 vrplgsenll lrgatlknte kifgvaiytg metkmalnyq sksqkrsave ksmnaflivy 301 lciliiskali ntvlkymwqs epfrdepwyn qkteserqrn lflkaftdfl afmvlfnyii 361 pvsmyvtvem  qkflgsyfit wdedmfdeet gegplvntsd lneelgqvey iftdktgtlt 421 ennmefkecc  ieghvyvphv icngqvlpes sgidmidssp svngrereel ffralclcht 481 vqvkdddsvd  gprkspdggk scvyissspd evalvegvqr lgftylrlkd nymeilnren 541 hierfellei  lsfdsvrrrm svivksatge iylfckgads sifprviegk vdqirarver 601 naveglrtlc  vaykrliqee yegickllqa akvalqdrek klaeayeqie kdltllgata 661 vedrlqekaa  dtiealqkag ikvwvltgdk metaaatcya cklfrrntql lelttkriee 721 qslhdvlfel  sktvlrhsgs ltrdnlsgls admqdyglii dgaalslimk predgssgny 781 relfleicrs  csavlccrma plqkaqivkl ikfskehpit laigdgandv smileahvgi 841 gvigkegrqa  arnsdyaipk fkhlkkmllv hghfyyiris elvqyffykn vcfifpqfly 901 qffcgfsqqt  lydtayltly nisftslpil lyslmeqhvg idvlkrdptl yrdvaknall 961 rwrvfiywtl  lglfdalvff fgayfvfent tvtsngqifg nwtfgtlvft vmvftvtlkl 1021 aldthywtwi  nhfviwgsll fyvvfsllwg gviwpflnyq rmyyvfiqml ssgpawlaiv 1081 llvtisllpd  vlkkvlcrql wptatervqt ksqclsveqs tifmlsqtss slsf
```

In some embodiments of the methods of the disclosure, the wild type human ATP11A gene of the disclosure consists of or comprises the nucleic acid sequence (Genbank Accession number: NM_032189.3, transcript variant 2):

(SEQ ID NO: 48)
```
   1 gcggccgcac tagtaccccg gagcccatgg gcgcgccgag ccgggcgcgg gggcgctgaa 61 cggcggagcg ggagcggccg gaggagccat ggactgcagc ctcgtgcgga cgctcgtgca 121 cagatactgt gcaggagaag agaattgggt ggacagcagg accatctacg tgggacacag 181 ggagccacct ccgggcgcag aggcctacat cccacagaga tacccagaca acaggatcgt 241 ctcgtccaag tacacatttt ggaactttat acccaagaat ttatttgaac aattcagaag 301 agtagccaac ttttatttcc ttatcatatt tctggtgcag ttgattattg atacacccac 361 aagtccagtg acaagcggac ttccactctt ctttgtcatt actgtgacgg ctatcaaaca 421 gggttatgaa gactggcttc gacataaagc agacaatgcc atgaaccagt gtcctgttca 481 tttcattcag cacggcaagc tcgttcggaa acaaagtcga aagctgcgag ttggggacat 541 tgtcatggtt aaggaggacg agacctttcc ctgcgacttg atcttccttt ccagcaaccg 601 gggagatggg acgtgccacg tcaccaccgc cagcttggat ggagaatcca gccataaaac 661 gcattacgcg gtccaggaca ccaaaggctt ccacacagag gaggatatcg gcggacttca 721 cgccaccatc gagtgtgagc agccccagcc cgacctctac aagttcgtgg gtcgcatcaa 781 cgtttacagt gacctgaatg accccgtggt gaggccctta ggatcggaaa acctgctgct 841 tagaggagct acactgaaga acactgagaa aatctttggt gtggctattt acacgggaat 901 ggaaaccaag atggcattaa attatcaatc aaaatctcag aagcgatctg ccgtggaaaa 961 atcgatgaat gcgttcctca ttgtgtatct ctgcattctg atcagcaaag ccctgataaa 1021 cactgtgctg aaatacatgt ggcagagtga gccctttcgg gatgagccgt ggtataatca 1081 gaaaacggag tcggaaaggc agaggaatct gttcctcaag gcattcacgg acttcctggc 1141 cttcatggtc ctctttaact acatcatccc tgtgtccatg tacgtcacgg tcgagatgca 1201 gaagttcctc ggctcttact tcatcacctg ggacgaagac atgtttgacg aggagactgg
```

-continued

```
1261 cgaggggcct ctggtgaaca cgtcggacct caatgaagag ctgggacagg tggagtacat
1321 cttcacagac aagaccggca ccctcacgga aaacaacatg gagttcaagg agtgctgcat
1381 cgaaggccat gtctacgtgc cccacgtcat ctgcaacggg caggtcctcc cagagtcgtc
1441 aggaatcgac atgattgact cgtcccccag cgtcaacggg agggagcgcg aggagctgtt
1501 tttccgggcc ctctgtctct gccacaccgt ccaggtgaaa gacgatgaca gcgtagacgg
1561 ccccaggaaa tcgccggacg gggggaaatc ctgtgtgtac atctcatcct cgcccgacga
1621 ggtggcgctg gtcgaaggtg tccagagact tggctttacc tacctaaggc tgaaggacaa
1681 ttacatggag atattaaaca gggagaacca catcgaaagg tttgaattgc tggaaatttt
1741 gagttttgac tcagtcagaa ggagaatgag tgtaattgta aaatctgcta caggagaaat
1801 ttatctgttt tgcaaaggag cagattcttc gatattcccc cgagtgatag aaggcaaagt
1861 tgaccagatc cgagccagag tggagcgtaa cgcagtggag gggctccgaa ctttgtgtgt
1921 tgcttataaa aggctgatcc aagaagaata tgaaggcatt tgtaagctgc tgcaggctgc
1981 caaagtggcc cttcaagatc gagagaaaaa gttagcagaa gcctatgagc aaatagagaa
2041 agatcttact ctgcttggtg ctacagctgt tgaggaccgg ctgcaggaga agctgcaga
2101 caccatcgag gccctgcaga aggccgggat caaagtctgg gttctcacgg agacaagat
2161 ggagacggcc gcggccacgt gctacgcctg caagctcttc cgcaggaaca cgcagctgct
2221 ggagctgacc accaagagga tcgaggagca gagcctgcac gacgtcctgt tcgagctgag
2281 caagacggtc ctgcgccaca gcgggagcct gaccagagac aacctgtccg gactttcagc
2341 agatatgcag gactacggtt taattatcga cggagctgca ctgtctctga taatgaagcc
2401 tcgagaagac gggagttccg gcaactacag ggagctcttc ctggaaatct gccggagctg
2461 cagcgcggtg ctctgctgcc gcatggcgcc cttgcagaag gctcagattg ttaaattaat
2521 caaattttca aaagagcacc caatcacgtt agcaattggc gatggtgcaa atgatgtcag
2581 catgattctg gaagcgcacg tgggcatagg tgtcatcggc aaggaaggcc gccaggctgc
2641 caggaacagc gactatgcaa tcccaaagtt taagcatttg aagaagatgc tgcttgttca
2701 cgggcatttt tattacatta ggatctctga gctcgtgcag tacttcttct ataagaacgt
2761 ctgcttcatc ttccctcagt ttttatacca gttcttctgt gggttttcac aacagacttt
2821 gtacgacacc gcgtatctga ccctctacaa catcagcttc acctccctcc ccatcctcct
2881 gtacagcctc atggagcagc atgttggcat tgacgtgctc aagagagacc cgaccctgta
2941 cagggacgtc gccaagaatg ccctgctgcg ctggcgcgtg ttcatctact ggacgctcct
3001 gggactgttt gacgcactgg tgttcttctt tggtgcttat ttcgtgtttg aaaatacaac
3061 tgtgacaagc aacgggcaga tatttggaaa ctggacgttt ggaacgctgg tattcaccgt
3121 gatggtgttc acagttacac taaagcttgc attggacaca cactactgga cttggatcaa
3181 ccattttgtc atctgggggt cgctgctgtt ctacgttgtc ttttcgcttc tctggggagg
3241 agtgatctgg ccgttcctca actaccagag gatgtactac gtgttcatcc agatgctgtc
3301 cagcgggccc gcctggctgg ccatcgtgct gctggtgacc atcagcctcc ttcccgacgt
3361 cctcaagaaa gtcctgtgcc ggcagctgtg gccaacagca acagagagag tccagaatgg
3421 gtgcgcacag cctcgggacc gcgactcaga attcacccct cttgcctctc tgcagagccc
3481 aggctaccag agcacctgtc cctcggccgc ctggtacagc tcccactctc agcaggtgac
3541 actcgcggcc tggaaggaga aggtgtccac ggagccccca cccatcctcg gcggttccca
3601 tcaccactgc agttccatcc caagtcacag ctgccctagg tcccgtgtgg gaatgctcgt
```

-continued

```
3661 gtgatggatg gtcctaagcc tgtgggagact gtgcacgtgc ctcttcctgg ccccagcag
3721 gcaaggaggg gggtcacagg ccttgccctc gagcatggca ccctggccgc ctggacccag
3781 cactgtggtt gttgagccac accagtggcc tctgggcatt cggctcaacg caggagggac
3841 attctgctgg cccaccctgc gcgctgtcat gcagaggcca ttcccccagg cctgtgtctt
3901 cacccacctg ccatcattgg cctttgctgt cactgggaga gaagagccgt ccagggaccc
3961 atggtggccc acatgtggat gccacatgct gctgtttcct gcttgccgg ccaccaccca
4021 tgccctccat agggtgaggt ggagccatgg tggtgcgtcc tttactcaac aaccctccaa
4081 tccggatgct gtgggaaggg ccgggtcact cggataccat catccctgcg gatgcaccgc
4141 cgtaccctgc tcatctggga gtggtttccc tgcggttacg tccaagcccg cctgccctgt
4201 gtgttggggc tggctgagtt tcggtctccc catcaccggc cgcctcgtgg agaaggcagt
4261 gccacgtggg aggacaaggc cacgccggca gcttccagcc ctgccgcaga gtgccagga
4321 tgtccatcag ccactcgcca gggcacggag ccgtcagtcc actgttacgg gagaatgttg
4381 atttcgcggg tgcgagggcc gggagacaga tacttggctg tgatgagcag acatcctctg
4441 tccccgtgga ggggtcaaca ccaaggtggt gttcgtgcac cagaacctgt ctcgggctga
4501 cgggggtggc acacaggaca cgggtggatc caacaggca gcaccgcacc tctgcccgcc
4561 tcccgcactg cagctccgcc cgccgggctc tgcgtcccca cgtcccctcg tcccatcccc
4621 acgtccccctc atcccgtcac ctcgtcccca catccccttg ccccgtcacc tcgtcctcat
4681 gtccccttgt cctgtcacct cgtccccacg tccctcgtc cctcatccc cacgtcctct
4741 cgtccccttg tcccgtcccc acataccctc gtccccatgt cccacgcag gctctcctt
4801 cgtcttagga tctgtccagc gctgctctgg gtgggttagc aaccccaggg ctgctgtgat
4861 aggaagtccc tgttgttctc cgtactggca tttctatttc tagaaataat atttgacata
4921 gccttaatgg tccttaaaga agacatttca gtgtgagatt cagacttcag acgctgaaac
4981 tgctgccttt caggaaagca ccaccaacgc tggaggagga gccggccctc acgcccgccc
5041 cgcgccacgc tgtggaacgg gctccggca agtgaaaccc agagggtgtt tccgaggtgc
5101 tcgacagtag gtattttggg aagctcagat ttcaccattt gattgtataa tcttttacct
5161 ataaaatatt tatttgaagt agagggtaaa tcagcggtaa gaacagtgaa cacagtggtt
5221 gggataaaat aaggtgacaa acatcacacc aaagatgagg gtagcgagca actggcttga
5281 gcagacagaa cggggaagac tccactctgt cccgagggc cagccgcagg cgtccccagg
5341 gccaccctgc cctgaggtcc ttgtgtggcc gccctggctt ggcagccctg cccacgctgc
5401 ccccgcaaac aatggtgtgt gcgttttac agccctttt aggaacccaa tatgggcata
5461 aatgtaacac ctgtagcggg ggcagattct ctgtatgttc agttaacaaa ttatttgtaa
5521 tgtatttttt tagaaatctt aaaattgcct ttgcactgaa gtattttcat agctgtttat
5581 atctctttta ttcatttatt taacatactg tctaattta aaaataggtt tttaaagctt
5641 tcatttttaa gtttatgaaa ttttggccac tttacattta gattctggtg agagttttga
5701 ctgaatgttc caatctctga tgaatgcgaa ttttcagatt tgattttatt ctctacacac
5761 acctcttctt ttcttggtat ttctggtggc agtgattagt tgaacagcac atttaaggca
5821 cgataatttg ctacactttt tctttacaat ttgttgcaat ttcatctgct ttctatgttt
5881 cattgttaat tgccatcctt cagccttaaa aatagaagat tctcacgtga aggtttagta
5941 agttgggtcc cagctctgcc tgtgtggaga tagtcaccat gtacctctga caacaagttt
6001 tagtgtgaaa gtcactaaac ttttacacac tcccaaacgt cttttaaaa attgcttggg
6061 aaattattaa atgaatgtgc ctgatgattt gaaatagaca aggggcacga gataaaaaag
```

-continued

```
6121 aaaaggatga gaagatcctc agtgaatgac gttgcagggt cttcatgcaa ttttccacct
6181 cgcagtagtt agtatttact tgccttaaac taactttgaa gcaagtaatg tcaactttga
6241 gcactttgtt gagttttgaa aaatcttatt tgttgctgca caggttaata aattatcaat
6301 ttgtaattca gcatgttggt cagagacacg gtcactgatt cacacccagt ccctgccaca
6361 gaccgtctca gacacgcaca gtgggcctgc tgcatgattc acacccagtc cctgccacag
6421 accgtctcag acacgcacag tgggcctgct gcatgattca cacccagtcc ctgccacaga
6481 ccgtctcaga cacgcacagt gggcctgctg catgcgtgtt acctggcttt ggctccacg
6541 ctcactcata gccatgtcca catgggggct gcacacagg atcactcaca tatgtacatg
6601 tacccaccac aaacgtgcaa gctcctgcac acatgcatgc acacaaacgt gtacacaagt
6661 gtgagctcct acacgcatac acacacacac gtgtacatgc accaaagcat gtgtgaccta
6721 cagacatgca gaacatgcac gtgtacacat accacagaca cgcgtgtgca tgctcctaca
6781 caatacatat gcacatatca tgaacagcgt aagttcctac acgacgt gtgatacaca
6841 catgcatgta caggtaagca cacatgtaca agctcctaca ggcttgctct cacacacgtg
6901 tatgcacagc agagagacgt atgagcttct actgcacaca tgcacacaca cacgcacacg
6961 tacattcact acaaacgtgc agcctcctgc acacgtgcac attcatgtgt acaccacaaa
7021 tgagttccca gacgtgtaaa cacacgtgca cacatcgtac acatgtgagc tcccacacgt
7081 acacacagat gcacatggac acaccccaaa cacgcacagg ctcctacaca catgcacaca
7141 cgtgtacacc acaaacgagc tcccagacat gtaaacacac gtctcccaca cgtgagctcc
7201 cacacgtaca catgcacatg tacgcaccac aaacacatgc gcaggctcct gcaggcgtga
7261 atacacacat gcacacacat atacacacat gtgccacaaa caagtgcaca ctgtcctggt
7321 gtcctgcact gcatcctgcc tccttgctga ggggcccctg tgagaggcct ctggatgggc
7381 atgggaagat gggctccctg gcccccagcc catgcctccc tgggatgaag agtcccctc
7441 ctggcagaat gtctgggctt tgcagagcag gccccggggg tgaagtcgca gcttcactta
7501 caccagctgc tctgtgagca aggcttggtg ccctggacaa ggcccttccc ctttagggag
7561 gtccagcctc gcaagctgaa acctcccctc ggctcagccc tataccaggc ggccacagca
7621 ggactggcca cacccacgcc gcacctcatc cgtgcacgcg tcggagcacg gccagccttc
7681 cgccacgagc cagctgggaa gggccgcggc cgcctaaagc cccagtcaac ccagcctgtg
7741 tctgagcaga cagggcgaac aagcaggcca caccgtctcg agggaggagg ccagatgcgg
7801 ccagcgtctc caacagggtg accatccgct cggcttgctg agcgtttaaa caaatgttta
7861 gacaggctgt ggggactccc ctgagttgag ccttggccag gggtccggtg ctgtcgcggg
7921 aaacctccag ccttgttctt caaccactc agctcatgtg ttttgcactg actagtactg
7981 aataatacaa ccactcttat ttaatgttag tattatttat ttgacaactc agtgtctaac
8041 agcttgatat gcaggtcctt gcatcctaca tttctttagg aagttaccca tttgtaactt
8101 taaaaacagg aaaaatatca gttggcaaat gcaatctttt ttttttttaa gctaaaggtg
8161 ggtgaactgg aatgaaaatc tttctgatgt tgtgtctata agcagccttg atgggatatg
8221 ttagaagtgt catgaaagtg tgattctact tttgcagaaa aatctaaaga tcaatttata
8281 tagcttttatt ttttactttta tcaaagtata cagaattttta atatgcatat attgtgtctg
8341 acttaaaatt ataatgtctg cgtcaccatt taaaatgtct gttcattatg taatgtaata
8401 aaagaaggtc ttcaaaaatg tatttaacat gaatggtatc catagttgtc atcatcataa
8461 atactggagt ttatttttaa attattaaac atagtaggtg cattaacata aatcagtctc
```

-continued

```
8521 cacacagtaa catttaactg ataattcatt aatcagcttt gaaaaattaa attgttaatt 8581 aaaccaatct aacatttcag taaagtttat tttgtatgct tctgttttta acttttattt 8641 ctgtagataa actgactgga taatattata ttggactttt ctctagatta tctaagcagg 8701 agacctgaat ctgcttgcaa taagaataa aagtctgctt cagtttcttt ataaagaaac 8761 tcacacaa
```

In some embodiments of the methods of the disclosure, the wild type human ATP11A gene of the disclosure consists of or comprises the amino acid sequence (Genbank Accession number: NP_115565.3, transcript variant 2):

(SEQ ID NO: 49)
```
   1 mdcslvrtlv hrycageenw vdsrtiyvgh repppgaeay ipqrypdnri vsskytfwnf 61 ipknlfeqfr rvanfyflii flvqliidtp tspvtsglpl ffvitvtaik qgyedwlrhk 121 adnamnqcpv hfiqhgklvr kqsrklrvgd ivmvkedetf pcdliflssn rgdgtchvtt 181 asldgesshk thyavqdtkg fhteediggl hatieceqpq pdlykfvgri nvysdlndpv 241 vrplgsenll lrgatlknte kifgvaiytg metkmalnyq sksqkrsave ksmnaflivy 301 lciliskali ntvlkymwqs epfrdepwyn qkteserqrn lflkaftdfl afmvlfnyii 361 pvsmyvtvem qkflgsyfit wdedmfdeet gegplvntsd lneelgqvey iftdktgtlt 421 ennmefkecc ieghvyvphv icngqvlpes sgidmidssp svngrereel ffralclcht 481 vqvkdddsvd gprkspdggk scvyissspd evalvegvqr lgftylrlkd nymeilnren 541 hierfellei lsfdsvrrrm svivksatge iylfckgads sifprviegk vdqirarver 601 naveglrtlc vaykrliqee yegickllqa akvalqdrek klaeayeqie kdltllgata 661 vedrlqekaa dtiealqkag ikvwvltgdk metaaatcya cklfrrntql lelttkriee 721 qslhdvlfel sktvlrhsgs ltrdnlsgls admqdyglii dgaalslimk predgssgny 781 relfleicrs csavlccrma plqkaqivkl ikfskehpit laigdgandv smileahvgi 841 gvigkegrqa arnsdyaipk fkhlkkmllv hghfyyiris elvqyffykn vcfifpqfly 901 qffcgfsqqt lydtayltly nisftslpil lyslmeqhvg idvlkrdptl yrdvaknall 961 rwrvfiywtl lglfdalvff fgayfvfent tvtsngqifg nwtfgtlvft vmvftvtlkl 1021 aldthywtwi nhfviwgsll fyvvfsllwg gviwpflnyq rmyyvfiqml ssgpawlaiv 1081 llvtisllpd vlkkvlcrql wptatervqn gcaqprdrds eftplaslqs pgyqstcpsa 1141 awysshsqqv tlaawkekvs tepppilggs hhhcssipsh scprsrvgml v
```

In some embodiments of the methods of the disclosure, the wild type human IVD/DISP2 gene of the disclosure consists of or comprises the nucleic acid sequence (Genbank Accession number: NM_002225.3, transcript variant 1):

(SEQ ID NO: 50)
```
   1 tttccgcagt tagggctgc tatttcaacg cagggagata aaaagaaaaa aacacttgct 61 cttctacccc gctaaaaaca ctcatcctag ggagcacgcc agcatttgca gcgttcgggg 121 cagggccact cggcctgcgg ccgttgcact ggctggaagc tggcaggcga tcacggttga 181 ttggctcggg tgcggtccaa gggcagcaac gccttcggcg ggccgcctag ggtgattggc 241 tgctgcagcc cacccctag ccggtttggt gggcggcgaa gcctggattg gtggagctaa 301 gagctggctc agtttcagcg ctggctcttc gtgcatggca gagatggcga ctgcgactcg 361 gctgctgggg tggcgtgtgg cgagctggag gctgcggccg ccgcttgccg gcttcgtttc
```

-continued

```
 421 ccagcgggcc cactcgcttt tgcccgtgga cgatgcaatc aatgggctaa gcgaggagca
 481 gaggcagctt cgtcagacca tggctaagtt ccttcaggag cacctggccc caaggccca
 541 ggagatcgat cgcagcaatg agttcaagaa cctgcgagaa ttttggaagc agctggggaa
 601 cctgggcgta ttgggcatca cagcccctgt tcagtatggc ggctccggcc tgggctacct
 661 ggagcatgtg ctggtgatgg aggagatatc ccgagcttcc ggagcagtgg ggctcagtta
 721 cggtgcccac tccaacctct gcatcaacca gcttgtacgc aatgggaatg aggcccagaa
 781 agagaagtat ctcccgaagc tgatcagtgg tgagtacatc ggagccctgg ccatgagtga
 841 gcccaatgca ggctctgatg ttgtctctat gaagctcaaa gcggaaaaga aggaaatca
 901 ctacatcctg aatggcaaca agttctggat cactaatggc cctgatgctg acgtcctgat
 961 tgtctatgcc aagacagatc tggctgctgt gccagcttct cggggcatca cagccttcat
1021 tgtggagaag ggtatgcctg ctttagcac ctctaagaag ctggacaagc tggggatgag
1081 gggctctaac acctgtgagc taatctttga agactgcaag attcctgctg ccaacatcct
1141 gggccatgag aataagggtg tctacgtgct gatgagtggg ctggacctgg agcggctggt
1201 gctggccggg gggcctcttg ggctcatgca agcggtcctg gaccacacca ttccctacct
1261 gcacgtgagg gaagcctttg gccagaagat cggccacttc cagttgatgc aggggaagat
1321 ggctgacatg tacacccgcc tcatggcgtg tcggcagtat gtctacaatg tcgccaaggc
1381 ctgcgatgag ggccattgca ctgctaagga ctgtgcaggt gtgattcttt actcagctga
1441 gtgtgccaca caggtagccc tggacggcat tcagtgtttt ggtggcaatg ctacatcaa
1501 tgactttccc atgggccgct tcttcgaga tgccaagctg tatgagatag ggctgggac
1561 cagcgaggtg aggcggctgg tcatcggcag agccttcaat gcagactttc actagtcctg
1621 agacccttcg ccccctttc ctgcacctag tggcctttct tgggaagtag agatgtggcg
1681 gctttcccac cctgcccaca gcaggccctc ctgcccagct gctcttgtca gccctctggc
1741 ctctggatga ggttgagttc tccacaacag ctcccaagca tcatgggcct cgcagccggg
1801 cctgtgccac ggctagtgtt gtgtgattta aaatggactc agcaggaagc atattgtctg
1861 gggattgttg ggacaggttt tggtgactct gtgcccttgc tctctaactt ctgagcccac
1921 ctcccagggt aggcacctgg gggcatgcag gtgcccacct cccagggtag gcacctgggg
1981 gcatgcaggt acccacctct ttctcttggg tgaggctctg gcaaggagat ctctctgctc
2041 aagcacagca gaatcatggc ccctctccat gaattggaac ttggtacagg ttaagtatcc
2101 ctaatcctga aatctgaaac acttgtggtt ccaagcattt tggataaggc aaattcaact
2161 ttcagtctct tttctggggg aaaaaaataa taaacctagc ctagccaggc gtggtggctc
2221 atgcttgtaa tcccagcact tcaggaggct gagatgggtg gatcacctga ggtcaggagt
2281 tcaagaccag cctggccaac atgtggaaac ctcgcctcaa ctaaaaatag aaaaaaatta
2341 gttgggcatg tggtgggca cctgtaatcc cagctacttc aggaggctga ggcaggagaa
2401 ttacttgaac ccaggaggcg gacgttgcag tgagccgagc ttgtgccatt gcactccagc
2461 ctgggcgaca gagcaaaac tcttcaaaaa acaaaacaaa acaaaaaaac cctgcccctt
2521 gtttcttcca gtttctagag gtatcagctc ctagcagctt atgaacacat atgcttgctt
2581 ggccaggcaa ggtggtgtgt gcctgtaatc ccagcacttt gggaggccaa gcaggtgga
2641 tcacttgcag tcaggagttc aagaccagcc tgtccaacgt ggtgaaaccc catctctact
2701 aaaaatacaa aaattagcca ggggtggtgg tgcacgtctg taatcccagc tactcaggag
2761 gctgaggcag gagaatcact tgaacccggg aggtggaggt tgcaatgagc caatatgaca
```

```
-continued
2821 ccgctgcagt ccagcctggg ccatagagtg agactctgtc tcaaaaaagg aaagaaaaat 2881 aggctgggca cagtgactca tgcctgtaat cccaacactt tgggaggccg aggcaggtgg 2941 atcacgaggt caggagttca agaccagcct ggccaagatg gtaaaacctc gtctctacta 3001 aaaatacaaa aattagccag gtgtggtggc aggctcctgt aatcccagct actcaggagg 3061 ctgaggcaga gaattgcttg aacccgggag gcagagtttg cagtgagcca agatcacacc 3121 actgcactcc agcttggacg acagagcgag actctgtctc aaaaaataat aggccaggca 3181 tggtggctca acgtctgtaa tcccagcact ttgggaggcc gaggcgggca gatcacaagg 3241 tcaggagttc gagaccagcc tgacgaccaa catggtgaaa cctcgtctct actaaaaata 3301 caaaaattag ccaggcctgg tggcacgcgc ctgtaatccc agttacacag aagactgagg 3361 caggagaatc gcttgaacgc aggaggcaga ggttgcagga gctgagatcg cgccattgca 3421 ctccagcctg ggcaacagag tgagactctg tctcaaaaaa taataataaa ataaatgaac 3481 acacatgctg ctgagtccgc agggggggca gagcagagga cagcgtgctt ttgtgtactg 3541 ttggaagact ggctcctcct gtacagcacc tctgagccct tgtgcaccgc cctgccacgg 3601 gcaccatcca gtcctggccg tgtgaccacc cacagctgac tgggcagcag gcacaggccc 3661 tacccgagca ggccggagtt ggctcgcatg actccagctg aggctgcctg tgtacatttc 3721 tccagatacc ctatggctaa ttttgttata actgcacagt ggctgctgcc attttgtatt 3781 aaatatattg tgaaacaaac ctatctgggg agaagcaatc tacttgccgc tgcttcctgt 3841 ctggatccag cttgtgtcct tggagagtgg ctggcccagg tcctattcct gtcctccagc 3901 ccgttctttc atgagggaca ggaaggtaaa atcagccctt aggagagagg tctcagcctc 3961 cctttcccag atctcccagt gagttttaaa ggaagcaggg agcccagagt gctaagttct 4021 tacagccaga aggaagctta tagatttctg aaaaccgccc ctttgttttt aaaaagatca 4081 acacaatttg actttctcaa ggtcaaaacg aactagaatc cagatctgct catggcaaaa 4141 atggggtgt tctgagaatt ccagctttgg gccgcactgt acagcagtct ggatagagtg 4201 tgatctgaga agggaatggg tctgggttgt tccaccccctt ccgagttcca aaaagaggga 4261 actggttttc ttggttctca gcccagcagc acctatcctg gctcttggtc ctggcctgca 4321 gccaagtgct gttcctagcc tgaggcttga acaggtggg gttggctcct caccaacccc 4381 agttccgtcc catcctgagg gcaagatcct gggctcatag gcagtcccctt tcacttcctt 4441 gtcttgctcc ctgctatgtt ggagatgaat gtgactaaaa gggccatctt gctggcttaa 4501 tgtgtggctg gagagaccag cctggagaca atgtggcaaa atggggcgct tcatccagtc 4561 tgtctaagcc ctgtcgactt ggggaggtga tttctttcct ggttctatat gtgaagcaaa 4621 ataaatgttt taaattaaa agcaaaaaaa acaaaatgaa ccatgaaaaa aaa
```

In some embodiments of the methods of the disclosure, the wild type human IVD/DISP2 gene of the disclosure consists of or comprises the amino acid sequence (Genbank Accession number: transcript variant 1):

```
                                                        (SEQ ID NO: 51)
  1 maematatrl lgwrvaswrl rpplagfvsq rahsllpvdd ainglseeqr qlrqtmakfl 61 qehlapkage idrsnefknl refwkqlgnl gvlgitapvq yggsglgyle hvlvmeeisr 121 asgavglsyg ahsnlcinql vrngneaqke kylpklisge yigalamsep nagsdvvsmk 181 lkaekkgnhy ilngnkfwit ngpdadvliv yaktdlaavp asrgitafiv ekgmpgfsts 241 kkldklgmrg sntcelifed ckipaanilg henkgvyvlm sgldlerlvl aggplglmqa
```

-continued

```
301 vldhtipylh vreafgqkig hfqlmqgkma dmytrlmacr qyvynvakac deghctakdc 361 agvilysaec atqvaldgiq cfggngyind fpmgrflrda klyeigagts evrrlvigra 421 fnadfh
```

In some embodiments of the methods of the disclosure, the wild type human IVD/DISP2 gene of the disclosure consists of or comprises the nucleic acid sequence (Genbank Accession number: NM_001159508.1, transcript variant 2):

(SEQ ID NO: 27)
```
   1 tttccgcagt taggggctgc tatttcaacg cagggagata aaagaaaaa aacacttgct 61 cttctacccc gctaaaaaca ctcatcctag ggagcacgcc agcatttgca gcgttcgggg 121 cagggccact cggcctgcgg ccgttgcact ggctggaagc tggcaggcga tcacggttga 181 ttggctcggg tgcggtccaa gggcagcaac gccttcggcg ggccgcctag ggtgattggc 241 tgctgcagcc caccccctag ccggtttggt gggcggcgaa gcctggattg gtggagctaa 301 gagctggctc agtttcagcg ctggctcttc gtgcatggca gagatggcga ctgcgactcg 361 gctgctgggg tggcgtgtgg cgagctggag gctgcggccg ccgcttgccg gcttcgtttc 421 ccagcgggcc cactcgcttt gcccgtgga cgatgcaatc aatgggctaa gcgaggagca 481 gaggcaggaa ttttggaagc agctggggaa cctgggcgta ttgggcatca cagcccctgt 541 tcagtatggc ggctccggcc tgggctacct ggagcatgtg ctggtgatgg aggagatatc 601 ccgagcttcc ggagcagtgg ggctcagtta cggtgcccac tccaacctct gcatcaacca 661 gcttgtacgc aatgggaatg aggcccagaa agagaagtat ctcccgaagc tgatcagtgg 721 tgagtacatc ggagccctgg ccatgagtga gcccaatgca ggctctgatg ttgtctctat 781 gaagctcaaa gcggaaaaga aggaaatca ctacatcctg aatggcaaca agttctggat 841 cactaatggc cctgatgctg acgtcctgat tgtctatgcc aagacagatc tggctgctgt 901 gccagcttct cggggcatca cagccttcat tgtggagaag ggtatgcctg gctttagcac 961 ctctaagaag ctggacaagc tggggatgag gggctctaac acctgtgagc taatctttga 1021 agactgcaag attcctgctg ccaacatcct gggccatgag aataagggtg tctacgtgct 1081 gatgagtggg ctggacctgg agcggctggt gctggccggg gggcctcttg ggctcatgca 1141 agcggtcctg gaccacacca ttccctacct gcacgtgagg gaagcctttg gccagaagat 1201 cggccacttc cagttgatgc agggaagat ggctgacatg tacacccgcc tcatggcgtg 1261 tcggcagtat gtctacaatg tcgccaaggc ctgcgatgag ggccattgca ctgctaagga 1321 ctgtgcaggt gtgattcttt actcagctga gtgtgccaca caggtagccc tggacggcat 1381 tcagtgtttt ggtggcaatg gctacatcaa tgactttccc atgggccgct tcttcgaga 1441 tgccaagctg tatgagatag gggctgggac cagcgaggtg aggcggctgg tcatcggcag 1501 agccttcaat gcagactttc actagtcctg agacccttcg cccccttttc ctgcacctag 1561 tggcctttct tgggaagtag agatgtggcg gctttccac cctgcccaca gcaggccctc 1621 ctgcccagct gctcttgtca gccctctggc ctctggatga ggttgagttc tccacaacag 1681 ctcccaagca tcatgggcct cgcagccggg cctgtgccac ggctagtgtt gtgtgattta 1741 aaatggactc agcaggaagc atattgtctg gggattgttg ggacaggttt tggtgactct 1801 gtgcccttgc tctctaactt ctgagcccac ctcccagggt aggcacctgg gggcatgcag 1861 gtgcccacct cccagggtag gcacctgggg gcatgcaggt acccacctct ttctcttggg 1921 tgaggctctg gcaaggagat ctctctgctc aagcacagca gaatcatggc ccctctccat
```

-continued

```
1981 gaattggaac ttggtacagg ttaagtatcc ctaatcctga aatctgaaac acttgtggtt 2041 ccaagcattt tggataaggc aaattcaact ttcagtctct tttctggggg aaaaaaataa 2101 taaacctagc ctagccaggc gtggtggctc atgcttgtaa tcccagcact tcaggaggct 2161 gagatgggtg gatcacctga ggtcaggagt tcaagaccag cctggccaac atgtggaaac 2221 ctcgcctcaa ctaaaaatag aaaaaaatta gttgggcatg gtggtgggca cctgtaatcc 2281 cagctacttc aggaggctga ggcaggagaa ttacttgaac ccaggaggcg gacgttgcag 2341 tgagccgagc ttgtgccatt gcactccagc ctgggcgaca gagcaaaac tcttcaaaaa 2401 acaaaacaaa acaaaaaaac cctggccctt gtttcttcca gtttctagag gtatcagctc 2461 ctagcagctt atgaacacat atgcttgctt ggccaggcaa ggtggtgtgt gcctgtaatc 2521 ccagcacttt ggaggccaa ggcaggtgga tcacttgcag tcaggagttc aagaccagcc 2581 tgtccaacgt ggtgaaaccc catctctact aaaaatacaa aaattagcca gggtggtgg 2641 tgcacgtctg taatcccagc tactcaggag gctgaggcag gagaatcact tgaacccggg 2701 aggtggaggt tgcaatgagc caatatgaca ccgctgcagt ccagcctggg ccatagagtg 2761 agactctgtc tcaaaaagg aaagaaaaat aggctgggca cagtgactca tgcctgtaat 2821 cccaacactt tgggaggccg aggcaggtgg atcacgaggt caggagttca agaccagcct 2881 ggccaagatg gtaaaacctc gtctctacta aaaatacaaa aattagccag gtgtggtggc 2941 aggctcctgt aatcccagct actcaggagg ctgaggcaga gaattgcttg aacccgggag 3001 gcagagtttg cagtgagcca agatcacacc actgcactcc agcttggacg acagagcgag 3061 actctgtctc aaaaaataat aggccaggca tggtggctca acgtctgtaa tcccagcact 3121 ttgggaggcc gaggcgggca gatcacaagg tcaggagttc gagaccagcc tgacgaccaa 3181 catggtgaaa cctcgtctct actaaaaata caaaaattag ccaggcctgg tggcacgcgc 3241 ctgtaatccc agttacacag aagactgagg caggagaatc gcttgaacgc aggaggcaga 3301 ggttgcagga gctgagatcg cgccattgca ctccagcctg gcaacagag tgagactctg 3361 tctcaaaaaa taataataaa ataaatgaac acacatgctg ctgagtccgc agggggggca 3421 gagcagagga cagcgtgctt ttgtgtactg ttggaagact ggctcctcct gtacagcacc 3481 tctgagcct tgtgcaccgc cctgccacgg gcaccatcca gtcctggccg tgtgaccacc 3541 cacagctgac tgggcagcag gcacaggccc tacccgagca ggccggagtt ggctcgcatg 3601 actccagctg aggctgcctg tgtacatttc tccagatacc ctatggctaa ttttgttata 3661 actgcacagt ggctgctgcc attttgtatt aaatatattg tgaaacaaac ctatctgggg 3721 agaagcaatc tacttgccgc tgcttcctgt ctggatccag cttgtgtcct tggagagtgg 3781 ctggcccagg tcctattcct gtcctccagc ccgttctttc atgagggaca ggaaggtaaa 3841 atcagccctt aggagagagg tctcagcctc cctttccag atctcccagt gagttttaaa 3901 ggaagcaggg agcccagagt gctaagttct tacagccaga aggaagctta tagatttctg 3961 aaaaccgccc ctttgttttt aaaaagatca acacaatttg actttctcaa ggtcaaaacg 4021 aactagaatc cagatctgct catggcaaaa atgggggtgt tctgagaatt ccagctttgg 4081 gccgcactgt acagcagtct ggatagagtg tgatctgaga agggaatggg tctggggttgt 4141 tccacccctt ccgagttcca aaagaggga actggttttc ttggttctca gcccagcagc 4201 acctatcctg gctcttggtc ctggcctgca gccaagtgct gttcctagcc tgaggcttga 4261 gacaggtggg gttggctcct caccaacccc agttccgtcc catcctgagg gcaagatcct 4321 gggctcatag gcagtcccctt tcacttcctt gtcttgctcc ctgctatgtt ggagatgaat 4381 gtgactaaaa gggccatctt gctggcttaa tgtgtggctg gagagaccag cctggagaca
```

-continued

```
4441 atgtggcaaa atgggcgct tcatccagtc tgtctaagcc ctgtcgactt ggggaggtga 4501 tttctttcct ggttctatat gtgaagcaaa ataaatgttt taaaattaaa agcaaaaaaa 4561 acaaaatgaa ccatg
```

In some embodiments of the methods of the disclosure, the wild type human IVD/DISP2 gene of the disclosure consists of or comprises the nucleic acid sequence (Genbank Accession number: NP_001152980.1, transcript variant 2):

(SEQ ID NO: 28)
```
  1  maematatrl lgwrvaswrl rpplagfvsq rahsllpvdd ainglseeqr qefwkqlgnl 61  gvlgitapvq yggsglgyle hvlvmeeisr asgavglsyg ahsnlcinql vrngneaqke 121  kylpklisge yigalamsep nagsdvvsmk lkaekkgnhy ilngnkfwit ngpdadvliv 181  yaktdlaavp asrgitafiv ekgmpgfsts kkldklgmrg sntcelifed ckipaanilg 241  henkgvyvlm sgldlerlvl aggplglmqa vldhtipylh vreafgqkig hfqlmqgkma 301  dmytrlmacr qyvynvakac deghctakdc agvilysaec atqvaldgiq cfggngyind 361  fpmgrflrda klyeigagts evrrlvigra fnadfh
```

In some embodiments of the methods of the disclosure, the wild type human DPP9 gene of the disclosure consists of or comprises the nucleic acid sequence (Genbank Accession number: NM_139159.4):

(SEQ ID NO: 29)
```
   1 caacttccgg gtcaaaggtg cctgagccgg cgggtccct gtgtccgccg cggctgtcgt 61 cccccgctcc cgccacttcc ggggtcgcag tcccgggcat ggagccgcga ccgtgaggcg 121 ccgctggacc cgggacgacc tgcccagtcc ggccgccgcc ccacgtcccg gtctgtgtcc 181 cacgcctgca gctggaatgg aggctctctg gaccctttag aaggcacccc tgccctcctg 241 aggtcagctg agcggttaat gcggaaggtt aagaaactgc gcctggacaa ggagaacacc 301 ggaagttgga gaagcttctc gctgaattcc gaggggctg agaggatggc caccaccggg 361 accccaacgg ccgaccgagg cgacgcagcc gccacagatg acccggccgc ccgcttccag 421 gtgcagaagc actcgtggga cgggctccgg agcatcatcc acggcagccg caagtactcg 481 ggcctcattg tcaacaaggc gccccacgac ttccagtttg tgcagaagac ggatgagtct 541 gggccccact cccaccgcct ctactacctg gaatgccat atggcagccg agagaactcc 601 ctcctctact ctgagattcc caagaaggtc cggaaagagg ctctgctgct cctgtcctgg 661 aagcagatgc tggatcattt ccaggccacg ccccaccatg gggtctactc tcgggaggag 721 gagctgctga gggagcggaa acgcctgggg gtcttcggca tcacctccta cgacttccac 781 agcgagagtg gcctcttcct cttccaggcc agcaacagcc tcttccactg ccgcgacggc 841 ggcaagaacg gcttcatggt gtcccctatg aaaccgctgg aaatcaagac ccagtgctca 901 gggccccgga tggaccccaa aatctgccct gccgaccctg ccttcttctc cttcatcaat 961 aacagcgacc tgtgggtggc caacatcgag acaggcgagg agcggcggct gaccttctgc 1021 caccaaggtt tatccaatgt cctggatgac cccaagtctg cgggtgtggc caccttcgtc 1081 atacaggaag agttcgaccg cttcactggg tactggtggt gccccacagc ctcctgggaa 1141 ggttcagagg gcctcaagac gctgcgaatc ctgtatgagg aagtcgatga gtccgaggtg 1201 gaggtcattc acgtcccctc tcctgcgcta gaagaaggaa agacggactc gtatcggtac
```

-continued

```
1261 cccaggacag gcagcaagaa tcccaagatt gccttgaaac tggctgagtt ccagactgac 1321 agccagggca agatcgtctc gacccaggag aaggagctgg tgcagccctt cagctcgctg 1381 ttcccgaagg tggagtacat cgccagggcc gggtggaccc gggatggcaa atacgcctgg 1441 gccatgttcc tggaccggcc ccagcagtgg ctccagctcg tcctcctccc cccgccctg 1501 ttcatcccga gcacagagaa tgaggagcag cggctagcct ctgccagagc tgtccccagg 1561 aatgtccagc cgtatgtggt gtacgaggag gtcaccaacg tctggatcaa tgttcatgac 1621 atcttctatc ccttccccca atcagaggga gaggacgagc tctgctttct ccgcgccaat 1681 gaatgcaaga ccggcttctg ccatttgtac aaagtcaccg ccgttttaaa atcccagggc 1741 tacgattgga gtgagccctt cagcccccgg gaagatgaat ttaagtgccc cattaaggaa 1801 gagattgctc tgaccagcgg tgaatgggag gttttggcga ggcacggctc caagatctgg 1861 gtcaatgagg agaccaagct ggtgtacttc cagggcacca aggacacgcc gctggagcac 1921 cacctctacg tggtcagcta tgaggcggcc ggcgagatcg tacgcctcac cacgcccggc 1981 ttctcccata gctgctccat gagccagaac ttcgacatgt tcgtcagcca ctacagcagc 2041 gtgagcacgc cgccctgcgt gcacgtctac aagctgagcg ccccgacga cgaccccctg 2101 cacaagcagc ccgcttctg ggctagcatg atggaggcag ccagctgccc cccggattat 2161 gttcctccag agatcttcca tttccacacg cgctcggatg tgcggctcta cggcatgatc 2221 tacaagcccc acgccttgca gccagggaag aagcacccca ccgtcctctt tgtatatgga 2281 ggcccccagg tgcagctggt gaataactcc ttcaaaggca tcaagtactt gcggctcaac 2341 acactggcct ccctgggcta cgccgtggtt gtgattgacg gcaggggctc ctgtcagcga 2401 gggcttcggt tcgaaggggc cctgaaaaac caaatgggcc aggtggagat cgaggaccag 2461 gtggagggcc tgcagttcgt ggccgagaag tatggcttca tcgacctgag ccagttgcc 2521 atccatggct ggtcctacgg gggcttcctc tcgctcatgg ggctaatcca caagccccag 2581 gtgttcaagg tggccatcgc gggtgccccg gtcaccgtct ggatgcctag cgacacaggg 2641 tacactgagc gctacatgga cgtccctgag aacaaccagc acggctatga ggcgggttcc 2701 gtggccctgc acgtggagaa gctgcccaat gagcccaacc gcttgcttat cctccacggc 2761 ttcctggacg aaaacgtgca ctttttccac acaaacttcc tcgtctccca actgatccga 2821 gcagggaaac cttaccagct ccagatctac cccaacgaga gacacagtat tcgctgcccc 2881 gagtcgggcg agcactatga agtcacgttg ctgcactttc tacaggaata cctctgagcc 2941 tgcccaccgg gagccgccac atcacagcac aagtggctgc agcctccgcg ggaaccagg 3001 cgggagggac tgagtggccc gcgggcccca gtgaggcact ttgtcccgcc cagcgctggc 3061 cagccccgag gagccgctgc cttcaccgcc ccgacgcctt ttatcctttt ttaaacgctc 3121 ttgggttttta tgtccgctgc ttcttggttg ccgagacaga gagatggtgg tctcgggcca 3181 gcccctcctc tccccgcctt ctgggaggag gaggtcacac gctgatgggc actgagagg 3241 ccagaagaga ctcagaggag cgggctgcct tccgcctggg gctccctgtg acctctcagt 3301 cccctggccc ggccagccac cgtccccagc acccaagcat gcaattgcct gtcccccccg 3361 gccagcctcc ccaacttgat gtttgtgttt tgtttggggg gatattttc ataattattt 3421 aaaagacagg ccgggcgcgg tggctcacgt ctgtaatccc agcactttgg gaggctgagg 3481 cgggcggatc acctgaggtt gggagttcaa gaccagcctg ccaacatgg gaaaccccg 3541 tctctactaa aaatacaaaa aattagccgg gtgtggtggc gcgtgcctat aatcccagct 3601 actcgggagg ctgaggcagg agaatcgctt gaacccggga ggtggaggtt gcggtgagcc 3661 aagatcgcac cattgcactc cagcctgggc aacaagagcg aaactctgtc tcaaaataaa
```

-continued

```
3721  taaaaaataa aagacagaaa gcaaggggtg cctaaatcta gacttggggt ccacaccggg 3781  cagcggggtt gcaacccagc acctggtagg ctccatttct tcccaagccc gagcagaggg 3841  tcatgcgggc cccacaggag aagcggccag ggcccgcggg gggcaccacc tgtggacagc 3901  cctcctgtcc ccaagctttc aggcaggcac tgaaacgcac cgaacttcca cgctctgctg 3961  gtcagtggcg gctgtcccct ccccagccca gccgcccagc cacatgtgtc tgcctgaccc 4021  gtacacacca ggggttccgg ggttgggagc tgaaccatcc ccacctcagg gttatatttc 4081  cctctcccct tccctccccg ccaagagctc tgccaggggc gggcaaaaaa aaaagtaaaa 4141  agaaaagaaa aaaaaaaaaa agaaacaaac cacctctaca tattatggaa agaaaatatt 4201  tttgtcgatt cttattcttt tataattatg cgtggaagaa gtagacacat taaacgattc 4261  cagttggaaa aaaaaaaaaa aaaaaa
```

In some embodiments of the methods of the disclosure, the wild type human DPP9 gene of the disclosure consists of or comprises the amino acid sequence (Genbank Accession number: NP_631898.3):

```
                                                                (SEQ ID NO: 30)
  1  mrkvkklrld kentgswrsf slnsegaerm attgtptadr gdaaatddpa arfqvqkhsw 61  dglrsiihgs rkysglivnk aphdfqfvqk tdesgphshr lyylgmpygs rensllysei 121  pkkvrkeall llswkqmldh fqatphhgvy sreeellrer krlgvfgits ydfhsesglf 181  lfqasnslfh crdggkngfm vspmkpleik tqcsgprmdp kicpadpaff sfinnsdlwv 241  anietgeerr ltfchqglsn vlddpksagv atfviqeefd rftgywwcpt aswegseglk 301  tlrilyeevd esevevihvp spaleerktd syryprtgsk npkialklae fqtdsqgkiv 361  stqekelvqp fsslfpkvey iaragwtrdg kyawamfldr pqqwlqlvll ppalfipste 421  neeqrlasar avprnvqpyv vyeevtnvwi nvhdifypfp qsegedelcf lranecktgf 481  chlykvtavl ksqgydwsep fspgedefkc pikeeialts gewevlarhg skiwvneetk 541  lvyfqgtkdt plehhlyvvs yeaageivrl ttpgfshscs msqnfdmfvs hyssystppc 601  vhvyklsgpd ddplhkqprf wasmmeaasc ppdyvppeif hfhtrsdvrl ygmiykphal 661  qpgkkhptvl fvyggpqvql vnnsfkgiky lrlntlaslg yavvvidgrg scqrglrfeg 721  alknqmgqve iedqveglqf vaekygfidl srvaihgwsy ggflslmgli hkpqvfkvai 781  agapvtvwma ydtgyterym dvpennqhgy eagsvalhve klpnepnrll ilhgfldenv 841  hffhtnflvs qliragkpyq lqiypnerhs ircpesgehy evtllhflqe yl
```

In some embodiments of the methods of the disclosure, the wild type human SIGLEC14 gene of the disclosure consists of or comprises the nucleic acid sequence (Genbank Accession number: NM_001098612.1):

```
                                                                (SEQ ID NO: 31)
  1  actcaccctc cggcttcctg tcggggcttt ctcagcccca ccccacgttt ggacatttgg 61  agcatttcct tccctgacag ccggacctgg gactgggctg gggccctggc ggatggagac 121  atgctgcccc tgctgctgct gcccctgctg tggggggggt cctgcagga gaagccagtg 181  tacgagctgc aagtgcagaa gtcggtgacg gtgcaggagg gcctgtgcgt ccttgtgccc 241  tgctccttct cttaccccctg gagatcctgg tattcctctc ccccactcta cgtctactgg 301  ttccgggacg gggagatccc atactacgct gaggttgtgg ccacaaacaa cccagacaga
```

```
 361 agagtgaagc cagagaccca gggccgattc cgcctccttg gggatgtcca gaagaagaac 421 tgctccctga gcatcggaga tgccagaatg gaggacacgg gaagctattt cttccgcgtg 481 gagagaggaa gggatgtaaa atatagctac aacagaata agctgaactt ggaggtgaca 541 gccctgatag agaaacccga catccacttt ctggagcctc tggagtccgg ccgccccaca 601 aggctgagct gcagccttcc aggatcctgt gaagcgggac cacctctcac attctcctgg 661 acggggaatg ccctcagccc cctggacccc gagaccaccc gctcctcgga gtcaccctc 721 accccaggc ccgaggacca tggcaccaac ctcacctgtc aggtgaaacg ccaaggagct 781 caggtgacca cggagagaac tgtccagctc aatgtctcct atgctccaca gaacctcgcc 841 atcagcatct tcttcagaaa tggcacaggc acagccctgc ggatcctgag caatggcatg 901 tcggtgccca tccaggaggg ccagtccctg ttcctcgcct gcacagttga cagcaacccc 961 cctgcctcac tgagctggtt ccgggaggga aaagccctca atccttccca gacctcaatg 1021 tctgggaccc tggagctgcc taacatagga gctagagagg gagggaatt cacctgccgg 1081 gttcagcatc cgctgggctc ccagcacctg tccttcatcc tttctgtgca gagaagctcc 1141 tcttcctgca tatgtgtaac tgagaaacag cagggctcct ggcccctcgt cctcaccctg 1201 atcagggggg ctctcatggg ggctggcttc ctcctcacct atggcctcac ctggatctac 1261 tataccaggt gtggaggccc ccagcagagc agggctgaga ggcctggctg agcccctccc 1321 gctcaagaca gaactgaggt gtggacactt agccctgtgg gacacatgca ggacatcact 1381 gtcagcttct ttctggaagc tcacatccca ctgactaccc ctcttttcct tcctgcccca 1441 tacccttct acttattccc ctctgcttgt gagtcttgcc ccaccacacc tgcatcccca 1501 tctgcacccc atcccctctc cacctgccct tctcttccct ctccatccac catctccagc 1561 cctgtgaagg aatgtacttt tcggtcttat acccccatta cccattaccc aaaagttacc 1621 tttttttttt ttttttttt ttgagacaga gtctcactct gttgcacagg ctggagttca 1681 gtggcacaat ctccgttcac tgcaacctcc acctctgggg ttcaagcaat tctcctgcct 1741 cagcctccct agtagctggg attacaggtg cctgccacca catccagtta atttttttt 1801 tttgtatgtt agtagagatg gggtttttacc atgttggcca ggtctcgaac tcctgacctc 1861 aagcaatcca ctgcattggc ctcccaaagt gctggcatta caggtatgag ccaccgtgcc 1921 tggctgccaa aagttacctt cttaacactt gaatttctgg tctcctcagc ttccctatcc 1981 atataggcac agagaggcag catttgtttt ccagttaaaa ctctacctca ttgtgattat 2041 tatccaatac aattgttaca aaataagtaa aacttttatg aaacaataca acataactga 2101 ttttactctt taa
```

In some embodiments of the methods of the disclosure, the wild type human SIGLEC14 gene of the disclosure consists of or comprises the amino acid sequence (Genbank Accession number: NP_001092082.1):

(SEQ ID NO: 32)
```
  1 mlpllllpll wggslqekpv yelqvqksvt vqeglcvlvp csfsypwrsw ysspplyvyw 61 frdgeipyya evvatnnpdr rvkpetqgrf rllgdvqkkn cslsigdarm edtgsyffrv 121 ergrdvkysy qqnklnlevt aliekpdihf leplesgrpt rlscslpgsc eagppltfsw 181 tgnalspldp ettrsseltl tprpedhgtn ltcqvkrqga qvttertvql nvsyapqnla 241 isiffrngtg talrilsngm svpiqegqsl flactvdsnp paslswfreg kalnpsqtsm 301 sgtlelpnig areggeftcr vqhplgsqhl sfilsvqrss sscicvtekq qgswplvltl 361 irgalmgagf lltygltwiy ytrcggpqqs raerpg
```

In some embodiments of the methods of the disclosure, the wild type human ADM2 gene of the disclosure consists of or comprises the nucleic acid sequence (Genbank Accession number: NM_001253845.1):

(SEQ ID NO: 33)

```
   1 cgcccacgcc cggcgccccg accgcggagg actccccgag ccccgccgc catggcccgg
  61 atcccgacgg ccgccctggg ttgcatcagc ctcctctgcc tgcagctccc tggctcgctg
 121 tcccgcagcc tgggcgggga cccgcgaccc gtcaaaccca gggagccccc agcccggagc
 181 ccttccagca gcctgcagcc caggcacccc gcaccccgac ctgtggtctg aagcttcac
 241 cgggccctcc aggcacagag gggtgccggc ctggcccctg ttatgggtca gcctctccgg
 301 gatggtggcc gccaacactc gggcccccga agacactcgg gccccgcag gacccaagcc
 361 cagctcctgc gagtgggctg tgtgctgggc acctgccagg tgcagaatct cagccaccgc
 421 ctgtggcaac tcatgggacc ggccggccgg caggactcag ctcctgtgga ccccagcagc
 481 ccccacagct atggctgagg tggggccggg ccacacccct gcccatccca gccagggtgc
 541 tgtgcccccg tccagagctg cagctgagcc ccatctgaag cccagtccct cggagctgca
 601 gacagcaggt cctgcagcaa caatacctgc acggctttgc acacgtaaac ctaggctggt
 661 ctacacgcag tgctggtacg tcaaggagcc taaacaccct gaaattgtga cccctgggg
 721 gacagctgcc agacacagct ggcggcagca ccagatgcta agcgcttcag agaggaggtg
 781 tctgcccaga gatgtggagc agaagctggg ccctgaacac acggggccat gtctggacga
 841 gcagggagag gaggctgaac tggccagaag tggcccctcc gctgctggtc cagtcagact
 901 gaagcccggc cttgtgcctg ggctgttcct gctctcatgc acaaccagcc cttccacgtg
 961 cctgcctgtg ggacaggagg gggagcgtgg gatgctgtag ccccgggt tgggcaaggg
1021 aaggatggtg gccctccaga ggtcatgaag ggacctctgt ggctccagct gccaaccctg
1081 gagcccagac cgaggtggcc atggagactc cacctggatc ccctgtagga ggccagggag
1141 gggaactcag cagttcagga gccacccaa accattctgg gacaggaca cccctttcta
1201 ccccagggca gggcagggct gggtggggca agatccccca gcccgactag acccacctca
1261 cctgaagggg gtgagaccct tgttggcagc cagacaaggg tggggctcca caggcagcac
1321 aggcgcccca ccaccaccca gtttggggac ccagtgggac caggtgcggg ggcagagggt
1381 gacttaccaa gagccaggga gggcagccca ggcccaagtg acagcaagaa caagaaccac
1441 tgccggcgtg cacagacttg gtgtgtgtcc ttccctgggg ggacggggga ctcacatgtg
1501 cctgccactg gagcctctca accgtccagc agaacacggg gttcagaaag ggctccttct
1561 gctatttagc gaacactgag catttaattt acaaatgttt gctagggtca ccctctcggc
1621 catcccacga gggtcgccat gatcaccca actctagagg ccgcagcaga gctcaggaca
1681 ttcccccaca gagcttgccc ctcagttcct acctccaagg ggagggtcc tggaagcgcc
1741 cacccaggcg ccgcccctgt gcttgctccc cgagctcagg gattgccgag tccacgtaac
1801 tgacctgtac tccacgaggc cctgtgggaa cggtccaggc tggtcctgcc ctgtggaggc
1861 ctccgtgcac tgagagatgt actaggattg cagcaaaggt ggtcagggtg atgggccgca
1921 cagcgaggca gtcaaggcca gctccctggg agaagcactg ggtcaggtga ggtctgagga
1981 cagcaggcct tccctagggg aaggagctgg gagtgccaag gccccaggtg cacaggaggc
2041 gtggctgctg agaggctgca gggtggaggg gcctcggcct cagagtcatg tgccctgtga
2101 ccactgaagg gtgtcagcag agcacacggc atgaggacag agggaggggc acggggagtg
2161 aaggaggggg ccctggggca aggctcgggg gtcaggagct cagcgtccgc tactcagccc
```

-continued

```
2221 agccaaaacc ctcccagacg tctcctctcc tgcctgggca aagtccagct tggcaccccg 2281 tctggggcct gcctgtggtc agggccaagt gttccctcct ccaggaaagc ctttaccctc 2341 ctcatgccct gtagtcagga ggccgcctgc tgtaaccctc cgtgtcgcct cgggtgcgaa 2401 atcagaccca cctgacacca tcacgcggag gcccagcagc acctgcaccc acttccagct 2461 gctctggcca aaatctccgc tcggccaggc cccgtggctc acacctgtaa tcctagcaca 2521 ttgggaggcc aaggcaggca catcacctga gttcaggagt tcaagaccag cctggccaac 2581 atggtgaaat cccgtctcta ctaaaaacag aaaattatcc gggcgtggtg gcacatgact 2641 gtaatcccag ctactcagga ggctgaggca ggaggatcac ttgaacctgg gaggcggagg 2701 ttgcagtgag ctgagattgc gccattgcac tccagcctgg gcaacaagag caaaattctg 2761 cctcaaaaaa aaaatagta ataatacaaa aattagctgg gcgtggtggc acatgccagt 2821 aattccatct actcgggagg ctgaggcagg agaatcgtct aagcccggga ggtggaggtt 2881 gcagtgagcc cagatggcgc tgctgcactc aagcttggat gacagagcaa gactccgttt 2941 caaaaaaaaa aaacctcctc tcttccttca caccttcctc tgaatcccac ccggtcccac 3001 ctcctgaacc tatccagaca ccttctcctg acccaggcac cacctgcttt cggggcgatg 3061 gccgtagcct cctcccaggc acctgtctgc atccctctgg ccagtgcatg ctgagcacgt 3121 gacctacccg tgttgggaca cgtgaggata cagccttgac ccccaggggc tgacattcta 3181 gggggagata gaaggagaca aacgtagaag gtagaataag tgggtggtgg agtggcaggg 3241 agtgctgagt gccacaggaa gtcagacaag gaaggagagt gtggggcagg tgccgtttaa 3301 atgggggggcg ctggggtctc ctcacagttg cttctcagct cagctgtgcc aggatcttgt 3361 tgagtcaggt cagctgccca cagccctctt gcctgacccc tgaagcccag aactctgatc 3421 ttcacagccc taggtatggc cccagcaccc cactgccctc tctcctgccc cagccgactg 3481 ctgttcccag acttccctgg ccacgctcca agacgccagc tctgccgcgg cactttgtt 3541 ctcacggtgt cctccatgcc tgcagggccc atgcatggga agttgcgttg gcggcctggg 3601 tgttggcggt tccgtgcctg ctccaactct ccgtgaggcc cctctcccag agcctgacac 3661 actctgtggc cgaactctag gcaggtgccc ctgagtcctt tcctcgacga ggcctgaccc 3721 catccccatc ctcgctgggc ccgccgaccc cggtgttagc aagaatcctc taaatcagtt 3781 tatggagaat tacccaccct cgatatctga tcccattcct catctcccac ccttgatctc 3841 atcaccctgc cggcctcctg caagatcctc attgagccac tccagtgaga atcccctac 3901 cctcgaaggc cgccctaaca acttcccatc cgctgacccc tccaacgcca tcaatctcca 3961 gctgtggttg ttgaactcgg aggtgagctc ctctcaccac tctcttgaat aaagcttttc 4021 tcaccatttt aaaaaaaaaa aaaaa
```

In some embodiments of the methods of the disclosure, the wild type human ADM2 gene of the disclosure consists of or comprises the amino acid sequence (Genbank Accession number: NP_001240774.1):

```
                                                        (SEQ ID NO: 34)
  1  mariptaalg cisllclqlp gslsrslggd prpvkprepp arspssslqp rhpaprpvvw 61  klhralqaqr gaglapvmgq plrdggrqhs gprrhsgprr tqaqllrvgc vlgtcqvqnl 121  shrlwqlmgp agrqdsapvd pssphsyg
```

In some embodiments of the methods of the disclosure, the wild type human TSPAN5 gene of the disclosure consists of or comprises the nucleic acid sequence (Genbank Accession number: NM_005723.3):

```
                                                        (SEQ ID NO: 35)
   1 aggcgggcgg agcgaggggt gggagggcgc gcgcgaacgg gcgggcgagc aagcgagcgg
  61 cgtctccacc agcatctgcc gcggccgcct ttgcccgaag cccggggacg aaccgacgga
 121 ccgaccgcct ggcgcacgga cgcgggcgct cgctttgtgt tcggggctag cgtcggcgag
 181 gcttgagctt gcagcgcgcg gcttccctgc tttctcgcgg ccaccccggc tccggcggcc
 241 tcggcgcgcg aggggctgga ggtgcgggag ccgctctccg ccggtcggtc cccgcgcggc
 301 tgagcccagg ccgccagcgc cgcggccccg tgcggtgtcc ctgagctcct gctccccgcc
 361 gggctgctcc gagcaacggt gcttcggagc tccaaactcg ggctgccggg gcaagtgtct
 421 tcatgaaccc agaggatgtc cgggaagcac tacaagggtc ctgaagtcag ttgttgcatc
 481 aaatacttca tatttggctt caatgtcata ttttggtttt tgggaataac atttcttgga
 541 attggactgt gggcatggaa tgaaaaagga gttctgtcca acatctcttc catcaccgat
 601 ctcggcggct tgacccagt ttggctcttc cttgtggtgg gaggagtgat gttcattttg
 661 ggatttgcag ggtgcattgg agcgctacgg gaaaacactt tccttctcaa gttttttct
 721 gtgttcctgg gaattatttt cttcctggag ctcactgccg gagttctagc atttgttttc
 781 aaagactgga tcaaagacca gctgtatttc tttataaaca acaacatcag agcatatcgg
 841 gatgacattg atttgcaaaa cctcatagac ttcacccagg aatattggca gtgctgtggg
 901 gcttttggag ctgatgattg gaacctaaat atttacttca attgcacaga ttccaatgca
 961 agtcgagagc gatgtggcgt tccattctcc tgctgcacta aagatcccgc agaagatgtc
1021 atcaacactc agtgtggcta tgatgccagg caaaaaccag aagttgacca gcagattgta
1081 atctacacga aaggctgtgt gccccagttt gagaagtggt tgcaggacaa tttaaccatc
1141 gttgctggta ttttcatagg cattgcattg ctgcagatat ttgggatatg cctggcccag
1201 aatttggtta gcgatatcga agctgtcagg gcgagctggt agaccccctg caaccgctgc
1261 tgcaagacac tggacagacc cagctttcgg gacccctccg cgtgccgaac tgatcttcga
1321 gctgcatgga cctaatcaca gatgcagcct gcagtctcgc ctaatggagc tgccattagg
1381 ggagtgtaaa actgggaaat gctgctcact gacagaatta aaaaaaaaaa taaccagtat
1441 gaaagtcgtt gcgccgtgaa tctctactgt agccatgaat ttatgacag ttagatgctt
1501 accaaaaaag aaaaaaaggg agggtagggg acccagatgt acttgaatgt gcagaaaata
1561 cattcttgtc ctcatcttcc gtaattggag ggctgggaga ggcagctttg ctcttcacca
1621 caccttggac ggaccaccct ctttctgttc catggcctga aggagtgcat ctcctcaaag
1681 actcagcccc tcacctggga gggcagtggt ttgtgggcat ccctccatgt acattttagg
1741 aaacacttgc aactctcatc tgaagaagaa aacaactcat ctttgggttc agattttgtg
```

```
-continued
1801 atggtattca gcaagtcact tgggcgagca cacttggtct atcctggaaa gtctccttat 1861 aagagaagtt gtgtatttca tgtgcaccga gcaagggcat tggaagacgt catgaggctg 1921 tattttagca ggactgatcg tttttctaag tagacctgag ctttgtttat cagtgaaatt 1981 caaggagaaa atgaggttaa tgaagaggta tcagttaaat atcccttct tctcaccctg 2041 ccaaaattag cagttggatt tttggaaact ctggaatatt ctgggtcatt ttgttttgta 2101 tgtttgttgt ttttcgtctt ccaaaggtga aagctatgat acagttccac ttaaatttta 2161 gtgttttctt actcagctca agcattaatt tttgattaag tcttaatctg catgacctgt 2221 gaatctgaat ccatcatctc cctttcctgc cagcttttct acaaacattg aaatatgtta 2281 tttggtcagc acttatttcc taggttcaca gccttgggag gttgtggcat gtcctcccag 2341 tctggctggg aagagaccag ctgtaccatc caaatgcttc cctggtcttg atgatctctt 2401 ccagagtcga tctgagtggc cttttctgca ccctcccctt ctttctcttt gaatggaatt 2461 aaacccaatt tggaaacaac attgacccag tcaaaagctt ctaatggttt ctttttcttc 2521 ctccagtttt agtttgcttt tattaaaaaa agaaaatagt gcatggccat agctccttca 2581 gttctcttat tgcagactaa ccatcaggat ggtatcaaag cacaaatact ttggagggga 2641 atgcgttgaa ctggggcaag tactctgtaa cacaaagtgg gaaaccactt cctggtgctg 2701 ccgctcctgc ccccacttta ggtgggaggg acgagttttg ccctctagat tttaatccag 2761 ctggtgtcca ccgatgttg ccctcctggg gagcagatat cagtctgtgg aactctggga 2821 aaaccacagg cacatttttc ggtgcggaca gatttgccag cacataactg ggcagccagc 2881 tagaatactt tgtggaaatt aagcgaggtt ttccatttca gccccatggt gcatggtggt 2941 ggccgatgaa tgtgtcagtc tgctcagaga aaggacaaaa aggaaattat tttcaaaact 3001 gtgttcactg tttgggtgtg tgtatggctc tgcatgtgtg tgtttttgtc tctgtatagg 3061 tagaggtatt cacatcttac tccgactgta aggttgtctt acttcatctc tgcccccacc 3121 acagttgcca tttgtaatg tccttccaac atggagaaga cacgagctct ctccagttgg 3181 catcatttgt cttttttgtt gattgcctca ttctccagtg aactccatct ggccaattga 3241 ttcagaatca ggcaagatcc ctgccctttg gcacatccac tgaaaggcca aacagcaagt 3301 ccgagtgagt tttaaatatt aattaatcac cctttatttt ttacacttga gagtgattgt 3361 aataaaggct gtcattaata aacttggttc taccttaaaa aaaaaa
```

In some embodiments of the methods of the disclosure, the wild type human TSPAN5 gene of the disclosure consists of or comprises the amino acid sequence (Genbank Accession number: NP_005714.2):

```
                                                            (SEQ ID NO: 52)
  1 msgkhykgpe vsccikyfif gfnvifwflg itflgiglwa wnekgvlsni ssitdlggfd 61 pvwlflvvgg vmfilgfagc igalrentfl lkffsvflgi iffleltagv lafvfkdwik 121 dqlyffinnn irayrddidl qnlidftqey wqccgafgad dwnlniyfnc tdsnasrerc 181 gvpfscctkd paedvintqc gydarqkpev dqqiviytkg cvpqfekwlq dnltivagif 241 igiallqifg iclaqnlvsd ieavrasw
```

In some embodiments of the methods of the disclosure, the wild type human CAMKK1 gene of the disclosure consists of or comprises the nucleic acid sequence (Genbank Accession number: NM_032294.2, transcript variant 1):

(SEQ ID NO: 53)

```
   1 ctgggcccca gcgaggcggt ggggcggggc ggggcggggc ggggcgcgca gcaggagcga
  61 gtggggccgc ccgccgggcc gcggacactg tcgcccggcg cccaggttcc caacaaggct
 121 acgcagaaga accccccttga ctgaagcaat ggaggggggt ccagctgtct gctgccagga
 181 tcctcgggca gagctggtag aacgggtggc agccatcgat gtgactcact tggaggaggc
 241 agatggtggc ccagagccta ctagaaacgg tgtggacccc ccaccacggg ccagagctgc
 301 ctctgtgatc cctggcagta cttcaagact gctcccagcc cggcctagcc tctcagccag
 361 gaagctttcc ctacaggagc ggccagcagg aagctatctg gaggcgcagg ctgggcctta
 421 tgccacgggg cctgccagcc acatctcccc ccgggcctgg cggaggccca ccatcgagtc
 481 ccaccacgtg gccatctcag atgcagagga ctgcgtgcag ctgaaccagt acaagctgca
 541 gagtgagatt ggcaagggtg cctacggtgt ggtgaggctg gcctacaacg aaagtgaaga
 601 cagacactat gcaatgaaag tcctttccaa aaagaagtta ctgaagcagt atggctttcc
 661 acgtcgccct cccccgagag gtcccaggc tgcccaggga ggaccagcca agcagctgct
 721 gcccctggag cgggtgtacc aggagattgc catcctgaag aagctggacc acgtgaatgt
 781 ggtcaaactg atcgaggtcc tggatgaccc agctgaggac aacctctatt tggtgtttga
 841 cctcctgaga aaggggcccg tcatggaagt gccctgtgac aagcccttct cggaggagca
 901 agctcgcctc tacctgcggg acgtcatcct gggcctcgag tacttgcact gccagaagat
 961 cgtccacagg gacatcaagc catccaacct gctcctgggg gatgatgggc acgtgaagat
1021 cgccgacttt ggcgtcagca accagtttga ggggaacgac gctcagctgt ccagcacggc
1081 gggaacccca gcattcatgg ccccccgaggc catttctgat tccggccaga gcttcagtgg
1141 gaaggccttg gatgtatggg ccactggcgt cacgttgtac tgctttgtct atgggaagtg
1201 cccattcatc gacgatttca tcctggcccct ccacaggaag atcaagaatg agcccgtggt
1261 gtttcctgag gagccagaaa tcagcgagga gctcaaggac ctgatcctga agatgttaga
1321 caagaatccc gagacgagaa ttggggtgcc agacatcaag ttgcaccctt gggtgaccaa
1381 gaacggggag gagccccttc cttcggagga ggagcactgc agcgtggtgg aggtgacaga
1441 ggaggaggtt aagaactcag tcaggctcat ccccagctgg accacggtga tcctggtgaa
1501 gtccatgctg aggaagcgtt cctttgggaa cccgtttgag ccccaagcac ggagggaaga
1561 gcgatccatg tctgctccag gaaacctact ggtgaaagaa gggtttggtg aaggggggcaa
1621 gagcccagag ctccccggcg tccaggaaga cgaggctgca tcctgagccc ctgcatgcac
1681 ccagggccac ccggcagcac actcatcccg cgcctccaga ggcccacccc tcatgcaaca
1741 gccgcccccg caggcagggg gctggggact gcagcccac tcccgcccct ccccatcgt
1801 gctgcatgac ctccacgcac gcacgtccag ggacagactg gaatgtatgt catttgggt
1861 cttgggggca gggctcccac gaggccatcc tcctcttctt ggacctcctt ggcctgaccc
1921 attctgtggg gaaaccgggt gcccatggag cctcagaaat gccacccggc tggttggcat
1981 ggcctggggc aggaggcaga ggcaggagac caagatggca ggtggaggcc aggcttacca
2041 caacggaaga gacctcccgc tggggccggg caggcctggc tcagctgcca caggcatatg
2101 gtggagaggg gggtaccctg cccaccttgg ggtggtggca ccagagctct tgtctattca
2161 gacgctggta tgggggctcg gacccctcac tggggacagg gccagtgttg gagaattctg
```

```
                            -continued
2221 attcctttt   tgttgtcttt  tacttttgtt  tttaacctgg  gggttcgggg  agaggccctg 2281 cttgggaaca  tctcacgagc  tttcctacat  cttccgtggt  tcccagcaca  gcccaagatt 2341 atttggcagc  caagtggatg  gaactaactt  tcctggactg  tgtttcgcat  tcggcgttat 2401 ctggaaagtg  gactgaacgg  aatcaagctc  tgagcagagg  cctgaagcgg  aagcaccaca 2461 tcgtccctgc  ccatctcact  ctctcccttg  atgatgcccc  tagagctgag  gctggagaag 2521 acaccagggc  tgactttgac  cgagggccat  ggacgcgaca  ggcctgtggc  cctgcgcatg 2581 ctgaaataac  tggaacccag  cctctcctcc  tacaccggcc  tacccatctg  ggcccaagag 2641 ctgcactcac  actcctacaa  cgaaggacaa  actgtccagg  tcggagggat  cacgagacac 2701 agaacctgga  ggggtgtgca  cgctggcagg  tggcctctgc  ggcaattgcc  tcaccctgag 2761 gacatcagca  gtcagcctgc  tcagagcggg  ggtgctggag  cgcgtgcaga  cacagctctt 2821 ccggagcagc  cttcaccttc  tctctgggat  cagtgtccgg  ctggccgacg  tggcatttgc 2881 tgaccgaatg  ctcatagagg  ttgacccca   cagggtcacg  caggactcgg  acactgccct 2941 ggaaacatgg  atggacaagg  gcttttggcc  acaggtgtgg  gtgtcctgtt  ggaggagggc 3001 ttgtttggag  aagggaggct  ggctggggga  gaaacccgga  tcccgctgca  tctccgcgcc 3061 tgtgggtgca  tgtcgcgtgc  tcatctgttg  cacacagctc  actcgtatgt  cctgcactgg 3121 tacatgcatc  tgtaatacag  tttctacgtc  tatttaaggc  taggagccga  atgtgcccca 3181 ttgtcagtgg  gtccacgttt  ctccccggct  cctctgggct  aaggcagtgt  ggcccgaagc 3241 ttaaaaagtt  actcggtact  gtttttaaga  acacttttat  agagttagtg  gaaggcaagt 3301 taagagccaa  tcactgatcc  ccaagtgttt  cttgagcatc  tggtctgggg  ggaccacttt 3361 gatcggaccc  acccttggaa  agctcagggg  taggcccagg  tgggatgctc  accctgtcac 3421 tgagggtttt  ggttggcatc  gttgtttttg  aatgtagcac  aagcgatgag  caaactctat 3481 aagagtgttt  taaaaattaa  cttcccagga  agtgagttaa  aaacaataaa  agccctttct 3541 tgagttaaaa  agaaaaaaaa  aaaaaaaaaa  aaaaaaaaa   aaa
```

In some embodiments of the methods of the disclosure, the wild type human CAMKK1 gene of the disclosure consists of or comprises the amino acid sequence (Genbank Accession number: NP_115670.1, transcript variant 1):

```
                                                        (SEQ ID NO: 54)
  1  meggpavccq  dpraelverv  aaidvthlee  adggpeptrn  gvdppprara  asvipgstsr 61  llparpslsa  rklslqerpa  gsyleaqagp  yatgpashis  prawrrptie  shhvaisdae 121  dcvqlnqykl  qseigkgayg  vvrlaynese  drhyamkvls  kkkllkqygf  prrppprgsq 181  aaqggpakql  lplervyqei  ailkkldhvn  vvklievldd  paednlylvf  dllrkgpvme 241  vpcdkpfsee  qarlylrdvi  lgleylhcqk  ivhrdikpsn  lllgddghvk  iadfgvsnqf 301  egndaqlsst  agtpafmape  aisdsgqsfs  gkaldvwatg  vtlycfvygk  cpfiddfila 361  lhrkiknepv  vfpeepeise  elkdlilkml  dknpetrigv  pdiklhpwvt  kngeeplpse 421  eehcsvvevt  eeevknsvrl  ipswttvilv  ksmlrkrsfg  npfepqarre  ersmsapgnl 481  lvkegfgegg  kspelpgvqe  deaas
```

In some embodiments of the methods of the disclosure, the wild type human CAMKK1 gene of the disclosure consists of or comprises the nucleic acid sequence (Genbank Accession number: NM_172206.1, transcript variant 2):

(SEQ ID NO: 55)

```
   1 agcagaacag agtatgcaat ttgggaagct gtggtgtggc tgcagtggag agttcccaac
  61 aaggctacgc agaagaaccc ccttgactga agcaatggag gggggtccag ctgtctgctg
 121 ccaggatcct cgggcagagc tggtagaacg ggtggcagcc atcgatgtga ctcacttgga
 181 ggaggcagat ggtggcccag agcctactag aaacggtgtg acccccccac cacgggccag
 241 agctgcctct gtgatccctg gcagtacttc aagactgctc ccagcccggc ctagcctctc
 301 agccaggaag cttttcccta caggagcggcc agcaggaagc tatctggagg cgcaggctgg
 361 gccttatgcc acggggcctg ccagccacat ctcccccccgg gcctggcgga ggcccaccat
 421 cgagtcccac cacgtggcca tctcagatgc agaggactgc gtgcagctga accagtacaa
 481 gctgcagagt gagattggca agggtgccta cggtgtggtg aggctggcct acaacgaaag
 541 tgaagacaga cactatgcaa tgaaagtcct ttccaaaaag aagttactga agcagtatgg
 601 ctttccacgt cgccctcccc cgagagggtc ccaggctgcc cagggaggac cagccaagca
 661 gctgctgccc ctggagcggg tgtaccagga gattgccatc ctgaagaagc tggaccacgt
 721 gaatgtggtc aaactgatcg aggtcctgga tgacccagct gaggacaacc tctatttggt
 781 gtttgacctc ctgagaaagg gccccgtcat ggaagtgccc tgtgacaagc ccttctcgga
 841 ggagcaagct cgcctctacc tgcgggacgt catcctgggc ctcgagtact tgcactgcca
 901 gaagatcgtc cacagggaca tcaagccatc caacctgctc ctgggggatg atgggcacgt
 961 gaagatcgcc gactttggcg tcagcaacca gtttgagggg aacgacgctc agctgtccag
1021 cacggcggga acccccagcat tcatggcccc cgaggccatt tctgattccg gccagagctt
1081 cagtgggaag gccttggatg tatgggccac tggcgtcacg ttgtactgct ttgtctatgg
1141 gaagtgccca ttcatcgacg atttcatcct ggccctccac aggaagatca agaatgagcc
1201 cgtggtgttt cctgaggagc cagaaatcag cgaggagctc aaggacctga tcctgaagat
1261 gttagacaag aatcccgaga cgagaattgg ggtgccagac atcaagttgc accttgggt
1321 gaccaagaac ggggaggagc cccttccttc ggaggaggag cactgcagcg tggtggaggt
1381 gacagaggag gaggttaaga actcagtcag gctcatcccc agctggacca cggtgatcct
1441 ggtgaagtcc atgctgagga agcgttcctt tgggaacccg tttgagcccc aagcacggag
1501 ggaagagcga tccatgtctg ctccaggaaa cctactggtg aaagaagggt ttggtgaagg
1561 gggcaagagc ccagagctcc ccggcgtcca ggaagacgag gctgcatcct gagcccctgc
1621 atgcacccag ggccacccgg cagcacactc atcccgcgcc tccagaggcc caccctcat
1681 gcaacagccg ccccgcagg caggggctg gggactgcag ccccactccc gcccctcccc
1741 catcgtgctg catgacctcc acgcacgcac gtccagggac agactggaat gtatgtcatt
1801 tggggtcttg ggggcagggc tcccacgagg ccatcctcct cttcttggac ctccttggcc
1861 tgacccattc tgtggggaaa ccgggtgccc atggagcctc agaaatgcca cccggctggt
1921 tggcatggcc tggggcagga ggcagaggca ggagaccaag atggcaggtg gaggccaggc
1981 ttaccacaac ggaagagacc tcccgctggg gccgggcagg cctggctcag ctgccacagg
2041 catatggtgg agagggggt accctgccca ccttgggtg gtggcaccag agctcttgtc
2101 tattcagacg ctggtatggg ggctcggacc cctcactggg gacagggcca gtgttggaga
2161 attctgattc cttttttgtt gtcttttact tttgttttta acctgggggt tcggggagag
```

```
-continued
2221 gccctgcttg ggaacatctc acgagctttc ctacatcttc cgtggttccc agcacagccc 2281 aagattattt ggcagccaag tggatggaac taactttcct ggactgtgtt tcgcattcgg 2341 cgttatctgg aaagtggact gaacggaatc aagctctgag cagaggcctg aagcggaagc 2401 accacatcgt ccctgcccat ctcactctct cccttgatga tgcccctaga gctgaggctg 2461 gagaagacac cagggctgac tttgaccgag ggccatggac gcgacaggcc tgtggccctg 2521 cgcatgctga ataactgga acccagcctc tcctcctaca ccggcctacc catctgggcc 2581 caagagctgc actcacactc ctacaacgaa ggacaaactg tccaggtcgg agggatcacg 2641 agacacagaa cctggagggg tgtgcacgct ggcaggtggc ctctgcggca attgcctcac 2701 cctgaggaca tcagcagtca gcctgctcag agcgggggtg ctggagcgcg tgcagacaca 2761 gctcttccgg agcagccttc accttctctc tgggatcagt gtccggctgg ccgacgtggc 2821 atttgctgac cgaatgctca tagaggttga cccccacagg gtcacgcagg actcggacac 2881 tgccctggaa acatggatgg acaagggctt ttggccacag gtgtgggtgt cctgttggag 2941 gagggcttgt ttggagaagg gaggctggct gggggagaaa cccggatccc gctgcatctc 3001 cgcgcctgtg ggtgcatgtc gcgtgctcat ctgttgcaca cagctcactc gtatgtcctg 3061 cactggtaca tgcatctgta atacagtttc tacgtctatt taaggctagg agccgaatgt 3121 gccccattgt cagtgggtcc acgtttctcc ccggctcctc tgggctaagg cagtgtggcc 3181 cgaagcttaa aaagttactc ggtactgttt ttaagaacac ttttatagag ttagtggaag 3241 gcaagttaag agccaatcac tgatccccaa gtgtttcttg agcatctggt ctgggggac 3301 cactttgatc ggacccaccc ttggaaagct caggggtagg cccaggtggg atgctcaccc 3361 tgtcactgag ggttttggtt ggcatcgttg tttttgaatg tagcacaagc gatgagcaaa 3421 ctctataaga gtgttttaaa aattaacttc ccaggaagtg agttaaaaac aataaaagcc 3481 ctttcttgag ttaaaagaa aaaaaaaaa aaaaaaaaa aaaaaaaa
```

In some embodiments of the methods of the disclosure, the wild type human CAMKK1 gene of the disclosure consists of or comprises the amino acid sequence (Genbank Accession number: NP_757343.2, transcript variant 2):

```
                                                          (SEQ ID NO: 56)
  1 mqfgklwcgc sgefptrlrr rtplteameg gpavccqdpr aelvervaai dvthleeadg 61 gpeptrngvd pppraraasv ipgstsrllp arpslsarkl slgerpagsy leaqagpyat 121 gpashispra wrrptieshh vaisdaedcv qlnqyklqse igkgaygvvr laynesedrh 181 yamkvlskkk llkqygfprr ppprgsqaaq ggpakqllpl ervyqeiail kkldhvnvvk 241 lievlddpae dnlylvfdll rkgpvmevpc dkpfseeqar lylrdvilgl eylhcqkivh 301 rdikpsnlll gddghvkiad fgvsnqfegn daqlsstagt pafmapeais dsgqsfsgka 361 ldvwatgvtl ycfvygkcpf iddfilalhr kiknepvvfp eepeiseelk dlilkmldkn 421 petrigvpdi klhpwvtkng eeplpseeeh csvvevteee vknsvrlips wttvilvksm 481 lrkrsfgnpf epqarreers msapgnllvk egfgeggksp elpgvqedea as
```

In some embodiments of the methods of the disclosure, the wild type human CAMKK1 gene of the disclosure consists of or comprises the nucleic acid sequence (Genbank Accession number: NM_172207.2, transcript variant 3):

(SEQ ID NO: 57)

```
   1 ctgggcccca gcgaggcggt ggggcggggc ggggcggggc ggggcgcgca gcaggagcga
  61 gtggggccgc ccgccgggcc gcggacactg tcgcccggcg cccaggttcc caacaaggct
 121 acgcagaaga accccttga ctgaagcaat ggagggggt ccagctgtct gctgccagga
 181 tcctcgggca gagctggtag aacgggtggc agccatcgat gtgactcact tggaggaggc
 241 agatggtggc ccagagccta ctagaaacgg tgtggacccc ccaccacggg ccagagctgc
 301 ctctgtgatc cctggcagta cttcaagact gctcccagcc cggcctagcc tctcagccag
 361 gaagctttcc ctacaggagc ggccagcagg aagctatctg gaggcgcagg ctgggcctta
 421 tgccacgggg cctgccagcc acatctcccc ccgggcctgg cggaggccca ccatcgagtc
 481 ccaccacgtg gccatctcag atgcagagga ctgcgtgcag ctgaaccagt acaagctgca
 541 gagtgagatt ggcaagggtg cctacggtgt ggtgaggctg gcctacaacg aaagtgaaga
 601 cagacactat gcaatgaaag tcctttccaa aaagaagtta ctgaagcagt atggctttcc
 661 acgtcgccct cccccgagag gtcccaggc tgcccaggga ggaccagcca agcagctgct
 721 gccccctggag cgggtgtacc aggagattgc catcctgaag aagctggacc acgtgaatgt
 781 ggtcaaactg atcgaggtcc tggatgaccc agctgaggac aacctctatt tggccctgca
 841 gaaccaggcc cagaatatcc agttagattc aacaaatatc gccaagcccc actccctgct
 901 tccctctgag cagcaagaca gtggatccac gtgggctgcg cgctcagtgt ttgacctcct
 961 gagaaagggg cccgtcatgg aagtgccctg tgacaagccc ttctcggagg agcaagctcg
1021 cctctacctg cgggacgtca tcctgggcct cgagtacttg cactgccaga gatcgtcca
1081 cagggacatc aagccatcca acctgctcct gggggatgat gggcacgtga agatcgccga
1141 ctttggcgtc agcaaccagt ttgaggggaa cgacgctcag ctgtccagca cggcgggaac
1201 cccagcattc atggccccg aggccatttc tgattccggc cagagcttca gtgggaaggc
1261 cttggatgta tgggccactg gcgtcacgtt gtactgcttt gtctatggga agtgcccatt
1321 catcgacgat ttcatcctgg ccctccacag gaagatcaag aatgagcccg tggtgtttcc
1381 tgaggagcca gaaatcagcg aggagctcaa ggacctgatc ctgaagatgt tagacaagaa
1441 tcccgagacg agaattgggg tgccagacat caagttgcac ccttgggtga ccaagaacgg
1501 ggaggagccc cttccttcgg aggaggagca ctgcagcgtg gtgaggtga cagaggagga
1561 ggttaagaac tcagtcaggc tcatccccag ctggaccacg tgatcctgg tgaagtccat
1621 gctgaggaag cgttcctttg ggaacccgtt tgagccccaa gcacggaggg aagagcgatc
1681 catgtctgct ccaggaaacc tactggtgta agtactggtg ggccagggac tgccgggcac
1741 tccctggagt tgggtgggga ggtctgaggc ccatcctccc actctcactg tcgttgggcc
1801 aaggccagag cctggggact tggccaggtc tcggtgttgg ccccatttgc atctctgtcc
1861 ccaaggttag tcggggctag aagggacctt ttgggcccag ctcttgcttc attcctgggg
1921 ccagcatccc tcacacacac acttccaggg atgaggagct cacgcagccc ctccatggga
1981 caggaagacc cttcttccat gcagcttgat gtcactctct cactgggtcc agcccctctg
2041 gggcttcaaa tctgtggccc cctcagccct tggcagcctg gcagaggttt gcagacaggc
2101 tgatgttggc ttcctgtagg aggctggcgg gctgtagagg aggggtgctg gcccctctgc
2161 ctggccctgg ggactgttgg ctgctctccc aagtggccca ggctgcctgc agccattgct
```

-continued

```
2221 ggggctctgt gcccagtcag cactttgtga gtgcttgttc agtgagtaag cagggacagg 2281 ctggccggtg gaccacggga gaggaacccg cattggccga gggctcccta tggtgagcca 2341 cgcctgtggg ttcaccacct cctaggaggg tccagaaaag cagctcccca agcctgtgcg 2401 cctcgtcctc agcagatcca ccttcttcac tataataaaa gccagtctgg gatgctaaaa 2461 aaaaaaaaaa aaaaaaaaaa aaaaaaaaaa aaaaaaaaaa aaaaaaaaaa aaaaaaaaaa 2521 aaaaaaaaaa aaaaa
```

In some embodiments of the methods of the disclosure, the wild type human CAMKK1 gene of the disclosure consists of or comprises the amino acid sequence (Genbank Accession number: NP_757344.2, transcript variant 3):

(SEQ ID NO: 58)

```
  1 meggpavccq dpraelverv aaidvthlee adggpeptrn gvdppprara asvipgstsr 61 llparpslsa rklslqerpa gsyleaqagp yatgpashis prawrrptie shhvaisdae 121 dcvqlnqykl qseigkgayg vvrlaynese drhyamkvls kkkllkqygf prrppprgsq 181 aaqggpakql lplervyqei ailkkldhvn vvklievldd paednlylal qnqaqniqld 241 stniakphsl lpseqqdsgs twaarsvfdl lrkgpvmevp cdkpfseeqa rlylrdvilg 301 leylhcqkiv hrdikpsnll lgddghvkia dfgvsnqfeg ndaqlsstag tpafmapeai 361 sdsgqsfsgk aldvwatgvt lycfvygkcp fiddfilalh rkiknepvvf peepeiseel 421 kdlilkmldk npetrigvpd iklhpwvtkn geeplpseee hcsvvevtee evknsvrlip 481 swttvilvks mlrkrsfgnp fepqarreer smsapgnllv
```

In some embodiments of the methods of the disclosure, the wild type human MMP7 gene of the disclosure consists of or comprises the nucleic acid sequence (Genbank Accession number: NM_002423.4):

(SEQ ID NO: 59)

```
  1 gaaaacacca aatcaaccat aggtccaaga acaattgtct ctggacggca gctatgcgac 61 tcaccgtgct gtgtgctgtg tgcctgctgc ctggcagcct ggccctgccg ctgcctcagg 121 aggcgggagg catgagtgag ctacagtggg aacaggctca ggactatctc aagagatttt 181 atctctatga ctcagaaaca aaaaatgcca acagtttaga agccaaactc aaggagatgc 241 aaaaattctt tggcctacct ataactggaa tgttaaactc ccgcgtcata gaaataatgc 301 agaagcccag atgtggagtg ccagatgttg cagaatactc actatttcca aatagcccaa 361 aatggacttc caaagtggtc acctacagga tcgtatcata tactcgagac ttaccgcata 421 ttacagtgga tcgattagtg tcaaaggctt taaacatgtg gggcaaagag atcccctgc 481 atttcaggaa agttgtatgg ggaactgctg acatcatgat tggctttgcg cgaggagctc 541 atggggactc ctacccattt gatgggccag gaaacacgct ggctcatgcc tttgcgcctg 601 ggacaggtct cggaggagat gctcacttcg atgaggatga acgctggacg gatggtagca 661 gtctagggat taacttcctg tatgctgcaa ctcatgaact tggccattct ttgggtatgg 721 gacattcctc tgatcctaat gcagtgatgt atccaaccta tggaaatgga tcccccaaa 781 attttaaact ttcccaggat gatattaaag gcattcagaa actatatgga aagagaagta 841 attcaagaaa gaaatagaaa cttcaggcag aacatccatt cattcattca ttggattgta 901 tatcattgtt gcacaatcag aattgataag cactgttcct ccactccatt tagcaattat 961 gtcacccttt tttattgcag ttggttttg aatgtctttc actccttta aggataaact
```

```
-continued
1021  cctttatggt gtgactgtgt cttattcatc tatacttgca gtgggtagat gtcaataaat 1081  gttacataca caaataaata aaatgtttat tccatggtaa atttaaaaaa aaaaaaaaa 1141  aaaaaaaaaa aaa
```

In some embodiments of the methods of the disclosure, the wild type human MMP7 gene of the disclosure consists of or comprises the amino acid sequence (Genbank Accession number: NP_002414.1):

```
                                                               (SEQ ID NO: 60)
  1  mrltvlcavc llpgslalpl pqeaggmsel qweqaqdylk rfylydsetk nansleaklk 61  emqkffglpi tgmlnsrvie imqkprcgvp dvaeyslfpn spkwtskvvt yrivsytrdl 121  phitvdrlvs kalnmwgkei plhfrkvvwg tadimigfar gahgdsypfd gpgntlahaf 181  apgtglggda hfdederwtd gsslginfly aathelghsl gmghssdpna vmyptygngd 241  pqnfklsqdd ikgiqklygk rsnsrkk
```

In some embodiments of the methods of the disclosure, the wild type human TERC gene of the disclosure consists of or comprises the nucleic acid sequence (Genbank Accession number: NR_001566.1):

```
                                                               (SEQ ID NO: 61)
  1  gggttgcgga gggtgggcct gggaggggtg gtggccattt tttgtctaac cctaactgag 61  aagggcgtag gcgccgtgct tttgctcccc gcgcgctgtt tttctcgctg actttcagcg 121  ggcggaaaag cctcggcctg ccgccttcca ccgttcattc tagagcaaac aaaaaatgtc 181  agctgctggc ccgttcgccc ctcccgggga cctgcggcgg gtcgcctgcc cagcccccga 241  accccgcctg gaggccgcgg tcggcccggg gcttctccgg aggcacccac tgccaccgcg 301  aagagttggg ctctgtcagc cgcgggtctc tcggggggcga gggcgaggtt caggcctttc 361  aggccgcagg aagaggaacg gagcgagtcc ccgcgcgcgg cgcgattccc tgagctgtgg 421  gacgtgcacc caggactcgg ctcacacatg c
```

Definitions

The following definitions are included for the purpose of understanding the present subject matter and for constructing the appended patent claims. Abbreviations used herein have their conventional meaning within the chemical and biological arts.

Unless defined otherwise, technical and scientific terms used herein have the same meaning as commonly understood by a person of ordinary skill in the art. Any methods, devices and materials similar or equivalent to those described herein can be used in the practice of this disclosure. The following definitions are provided to facilitate understanding of certain terms used frequently herein and are not meant to limit the scope of the present disclosure.

As used herein, the term "FILD" refers to fibrotic interstitial lung disease.

As used herein, the term "FIP" refers to Familial Interstitial Pneumonia.

As used herein, the term "HRCT" refers to high-resolution CT (HRCT).

As used herein, the term "ILA" refers to asymptomatic interstitial lung abnormalities.

As used herein, the term "IPF" refers to idiopathic pulmonary fibrosis.

As used herein, the term "PBMC" refers to peripheral blood mononuclear cell.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions disclosed herein leads to the elimination of a sign or symptom, however, elimination is not required. Effective dosages are expected to decrease the severity of a sign or symptom. A sign is an objective indication of a medical condition that is observable or detectable by a medical professional or lay person (e.g. family member) (for example, with respect to fibrotic pulmonary disease, signs include, but are not limited to, changes in body weight, changes in body temperature and the presence of a fibrotic lesion in one or both lungs detectable by radiography).

A symptom is an indication of disease that may be a sign but may also be exclusively observable or subjectively experienced by the subject (for example, with respect to fibrotic pulmonary disease, symptoms may include but are not limited to, a dry or hacking cough, a sore throat, a tight chest, shortness of breath, and a feeling of exhaustion or malaise).

In one aspect, the terms "co-administered" and "co-administration" as relating to a subject refer to administering to the subject a compound of the invention or salt thereof along with a compound that may also treat the disorders or diseases contemplated within the invention. In one embodiment, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

A "disease" as used herein is a state of health of an animal or subject wherein the animal or subject cannot maintain homeostasis, and wherein if the disease is not ameliorated then the animal's or subject's health continues to deteriorate.

A "disorder" as used herein in an animal is a state of health in which the animal or subject is able to maintain homeostasis, but in which the animal's or subject's state of health is less favorable than it would be in the absence of the disorder. Left untreated, a disorder does not necessarily cause a further decrease in the animal's or subject's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "fibrotic lung disease" or "fibroid lung disease" or "pulmonary fibrosis" or "scarring of the lung" refers to a group of diseases characterized by the formation or development of excess fibrous connective tissue (fibrosis) in the lungs. Symptoms of pulmonary fibrosis are mainly: shortness of breath, particularly with exertion; chronic dry, hacking coughing; fatigue and weakness; chest discomfort; and loss of appetite and rapid weight loss. Pulmonary fibrosis may be a secondary effect of other diseases, most of them being classified as interstitial lung diseases, such as autoimmune disorders, viral infections or other microscopic injuries to the lung. Pulmonary fibrosis can also appear without any known cause ("idiopathic"). Idiopathic pulmonary fibrosis is a diagnosis of exclusion of a characteristic set of histologic/pathologic features known as usual interstitial pneumonia (UIP).

Diseases and conditions that may cause pulmonary fibrosis as a secondary effect include: inhalation of environmental and occupational pollutants (asbestosis, silicosis and gas exposure); hypersensitivity pneumonitis, most often resulting from inhaling dust contaminated with bacterial, fungal, or animal products; cigarette smoking; connective tissue diseases such as rheumatoid arthritis, SLE; scleroderma, sarcoidosis and Wegener's granulomatosis; infections; medications such as amiodarone, bleomycin (pingyangmycin), busulfan, methotrexate, apomorphine and nitrofurantoin; and radiation therapy to the chest.

As used herein, a "subject in need thereof" is a subject suffering from fibrotic lung disease relative to the population at large. For example, the subject is a patient who is or is about to be administered with comprising administering to the subject an effective amount of a therapeutic agent. For example, the subject is asymptomatic and is at risk of developing the fibrotic lung disease. A "subject" includes a mammal. The mammal can be e.g., any mammal, e.g., a human, primate, bird, mouse, rat, fowl, dog, cat, cow, horse, goat, camel, sheep or pig. Preferably, the mammal is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

Pharmaceutically acceptable carriers of the disclosure include, but are not limited to, pharmaceutically acceptable materials, compositions or carriers, such as a liquid or solid fillers, stabilizers, dispersing agents, suspending agents, diluents, excipients, thickening agents, solvents or encapsulating materials, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

Suitable forms for administration include forms suitable for systemic administration, oral administration, for example by a capsule or tablet. Once formulated, the compositions of the disclosure can be administered directly to the subject.

The term "prevent," "preventing" or "prevention," as used herein, means avoiding or delaying the onset of symptoms associated with a disease or condition in a subject that has not developed such symptoms at the time the administering of an agent or compound commences.

Compounds and Compositions

In some embodiments, compounds known to be useful in treating pulmonary fibrosis are useful within the methods of the invention. Non-limiting examples of such compounds are pirfenidone (5-methyl-1-phenylpyridin-2-one, or a salt or solvate thereof) and nintedanib (methyl (3Z)-3-{[(4-{methyl[(4-methylpiperazin-1-yl)acetyl]amino}phenyl) amino] (phenyl)methylidene}-2-oxo-2,3-dihydro-1H-indole-6-carboxylate, or a salt or solvate thereof).

In some embodiments, the subject identified as having MUC5B promoter polymorphism rs35705950 is administered a compound contemplated within the disclosure. In some embodiments, the subject is a mammal. In other embodiments, the mammal is a human.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation. Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

A suitable dose of a compound of the disclosure may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

In some embodiments of the methods of the disclosure, the therapeutic agent comprises pirfenidone. In some embodiments, the effective dosage is administered orally as a capsule or a tablet. In some embodiments, including those embodiments wherein the therapeutic agent comprises pirfenidone, the effective dosage is about 2400 mg/day. In some embodiments, the effective dosage is administered according to an escalating dosage regimen. In some embodiments, including those embodiments wherein the therapeutic agent comprises pirfenidone, the escalating dosage regimen comprises (a) administering to the subject about 800 mg of pirfenidone per day for a first week; (b) administering to the subject about 1600 mg of pirfenidone per day for a second week; and (c) administering to the subject about 2400 mg of pirfenidone per day for the remainder of the treatment. In some embodiments, including those embodiments wherein the therapeutic agent comprises pirfenidone, the escalating dosage regimen comprises (a) administering to the subject a capsule or tablet comprising about 250 mg of pirfenidone three times a day for a first week; (b) administering to the subject two capsules or tablets comprising about 250 mg of pirfenidone three times a day for a second week; and (c) administering to the subject three capsules or tablets comprising about 250 mg of pirfenidone three times a day for the remainder of the treatment. In some embodiments of the escalating dosage regimen, the capsule or tablet comprises 267 mg of pirfenidone.

In some embodiments of the methods of the disclosure, the therapeutic agent comprises nintedanib. In some embodiments, the effective dosage is administered orally as a capsule or a tablet. In some embodiments, including those embodiments wherein the therapeutic agent comprises nintedanib, the effective dosage is about 300 mg/day. In some embodiments, the effective dosage is about 150 mg administered twice per day, wherein the daily doses are administered about 12 hours apart from one another. In some embodiments, including those embodiments wherein the therapeutic agent comprises nintedanib, the effective dosage is about 200 mg/day. In some embodiments, the effective dosage is about 100 mg administered twice per day, wherein the daily doses are administered about 12 hours apart from one another. In some embodiments, including those embodiments wherein the therapeutic agent comprises nintedanib, the effective dosage is administered according to a modified or interrupted dosage regimen. In some embodiments, the modified or interrupted dosage regimen comprises (a) administering to the subject about 300 mg of nintedanib per day until the subject presents an elevated level of liver enzymes compared to a control level of liver enzymes; (b) administering to the subject about 200 mg of nintedanib per day until the subject presents the control level of liver enzymes; and (c) administering to the subject about 300 mg of nintedanib per day for the remainder of the treatment; wherein the control level of liver enzymes is a level detected in the subject prior to an initiation of the treatment. In some embodiments, including those embodiments wherein the therapeutic agent comprises nintedanib, the modified or interrupted regimen comprises (a) administering to the subject a capsule or tablet comprising about 150 mg of nintedanib twice per day until the subject presents an elevated level of liver enzymes compared to a control level of liver enzymes; (b) administering to the subject two capsules or tablets comprising about 100 mg twice per day until the subject presents an elevated level of liver enzymes compared to a control level of liver enzymes; and (c) administering to the subject a capsule or tablet comprising about 150 mg of nintedanib twice per day for the remainder of the treatment; wherein the control level of liver enzymes is a level detected in the subject prior to an initiation of the treatment.

In some embodiments, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it is preferable to include isotonic agents, for example, sugars, sodium chloride, or polyalcohols such as mannitol and sorbitol, in the composition.

It is also noted that the term "comprising" is intended to be open and permits but does not require the inclusion of additional elements or steps. When the term "comprising" is used herein, the terms "consisting essentially of" and "consisting" of are thus also encompassed and disclosed. Throughout the description, where compositions or combinations are described as having, including, or comprising specific components or steps, it is contemplated that compositions or combinations also consist essentially of, or consist of, the recited components. Similarly, where methods or processes are described as having, including, or comprising specific process steps, the processes also consist essentially of, or consist of, the recited processing steps.

All publications and patent documents cited herein are incorporated herein by reference as if each such publication or document was specifically and individually indicated to be incorporated herein by reference.

EXAMPLES

In order that the invention disclosed herein may be more efficiently understood, examples are provided below. It should be understood that these examples are for illustrative purposes only and are not to be construed as limiting the invention in any manner.

Example 1: Genetic Background of Asymptomatic Siblings of FIP Subjects

Asymptomatic siblings (>50 years old) of patients with established FIP underwent HRCT scan of the chest. HRCT scans were assessed for FILD by blinded thoracic radiologists; when possible, specific radiographic patterns were identified. PBMCs RNA and DNA were isolated. Genotyping for rs35705950 and microarray analysis were performed (SurePrint G3 Human Gene Expression Microarray). Data were analyzed using Partek Genomics Suite and RStudio. Four-hundred eighty-eight FIP siblings from 271 families were evaluated, 25 HRCT scans were excluded due to technically inadequacy, leaving 463 to be interpreted. Of these, 19% (n=88) met criteria for FILD. A subset of the positive FILD scans (n=58) were evaluated for specific interstitial patterns: the predominant radiographic finding was Usual Interstitial Pneumonia (UIP), documented as possible (n=37), probable (n=6), or definite (n=5) in 82.8% of these cases. DNA was available for 443 subjects (358 without and 85 with FILD). The minor allele (T) frequency (MAF) of rs35705950 was higher among those with evidence of FILD (MAF=0.29) than among those with normal appearing HRCT scans (MAF=0.21, p=0.005). The rs35705950 variant was associated with the presence of FILD (OR=1.90, 95% CI 1.10-3.30, p=0.02), and FILD was associated with age (OR=1.09, 95% CI 1.06-1.12, p=7.24×10−9), male sex (OR=1.81, 95% CI 1.04-3.16, p=0.04), and history of smoking (OR=1.94, 95% CI 1.11-3.40, p=0.02). Microarray analysis on PBMC RNA from 40 subjects with FILD and 105 unaffected siblings revealed 1,272 differentially expressed genes (FDR<0.05, fold-change>2); hierarchical clustering performed on the top 194 differentially expressed probes illustrates segregation of FILD subjects from unaffected siblings (FIG. 1).

Example 2: Role of MUC5B in Pathogenesis of IPF

Common genetic variants play major and similar roles in the development of both familial and sporadic IPF (Table 3), indicating a similar etiology for familial and sporadic IPF. A common gain-of-function MUC5B promoter variant rs35705950 is a strong risk factor (genetic and otherwise), accounting for at least 30% of the total risk of developing IPF (10) confirmed in independent studies, including a GWAS (OR for T (minor) allele=4.51; 95% CI=3.91-5.21; P=7.21×10-95); 3) rs35705950 may be used to identify individuals with PrePF and is predictive of radiographic progression of PrePF. MUC5B promoter variant rs35705950 is present in over 50% of non-Hispanic white (NHW) patients with IPF and is associated with unique biological and clinical IPF phenotypes. PrePF can be predicted using a combination of clinical risk factors, the MUC5B promoter variant rs35705950, and a panel of biomarkers.

TABLE 1

Common IPF risk variants identified by targeted sequencing of risk loci in 3,642 IPF cases and 4,442 unaffected controls

| Chrm | Common Variant | Nearest Gene | Annotation[a] | Minor Allele | MAF in cases | OR Aa vs AA (95% CI) | OR aa vs AA (95% CI) | P[b] |
|---|---|---|---|---|---|---|---|---|
| 3q26 | rs2293607 | TERC | 3' UTR | C | 0.2999 | 1.30 (1.18-1.43) | 1.79 (1.49-2.15) | $9.11 \times 10^{-13}$ |
| 4q22 | rs2609260 | FAM13A | Intronic | C | 0.2289 | 1.35 (1.22-1.50) | 1.96 (1.56-2.47) | $1.03 \times 10^{-13}$ |
| 5p15 | rs4449583 | TERT | Intronic | T | 0.2641 | 0.68 (0.62-0.75) | 0.46 (0.39-0.55) | $2.67 \times 10^{-25}$ |
| 6p24 | rs2076295 | DSP | Intronic | G | 0.5428 | 1.27 (1.14-1.42) | 2.08 (1.83-2.37) | $1.11 \times 10^{-29}$ |
| 7q22 | rs6963345 | ZKSCAN1 | Intronic | A | 0.4444 | 1.35 (1.22-1.50) | 1.73 (1.51-1.99) | $1.89 \times 10^{-15}$ |
| 10q24 | rs2488000 | OBFC1 | Intronic | T | 0.08 | 0.70 (0.62-0.79)[c] | | $7.13 \times 10^{-9}$ |
| 11p15 | rs35705950 | MUC5B | Promoter | T | 0.3533 | 5.45 (4.91-6.06) | 18.68 (13.34-6.17) | $9.60 \times 10^{-295}$ |
| 13q34 | rs1278769 | AK025511 | 3' UTR | A | 0.1996 | 0.77 (0.70-0.85) | 0.69 (0.56-0.86) | $7.48 \times 10^{-8}$ |
| 15q15 | rs35700143 | IVD | — | C | 0.4118 | 0.76 (0.68-0.84) | 0.63 (0.55-0.71) | $3.44 \times 10^{-12}$ |
| 19p13 | rs12610495 | DPP9 | Intronic | G | 0.3398 | 1.22 (1.11-1.35) | 1.59 (1.36-1.87) | $3.11 \times 10^{-9}$ |

OR, odds ratio. The minor allele is defined as the minor allele in the combined case and control group.
[a]Based on SNPDOC;
[b]P value adjusted for sex;
[c]OR resulting from dominant test.

Figure 5:
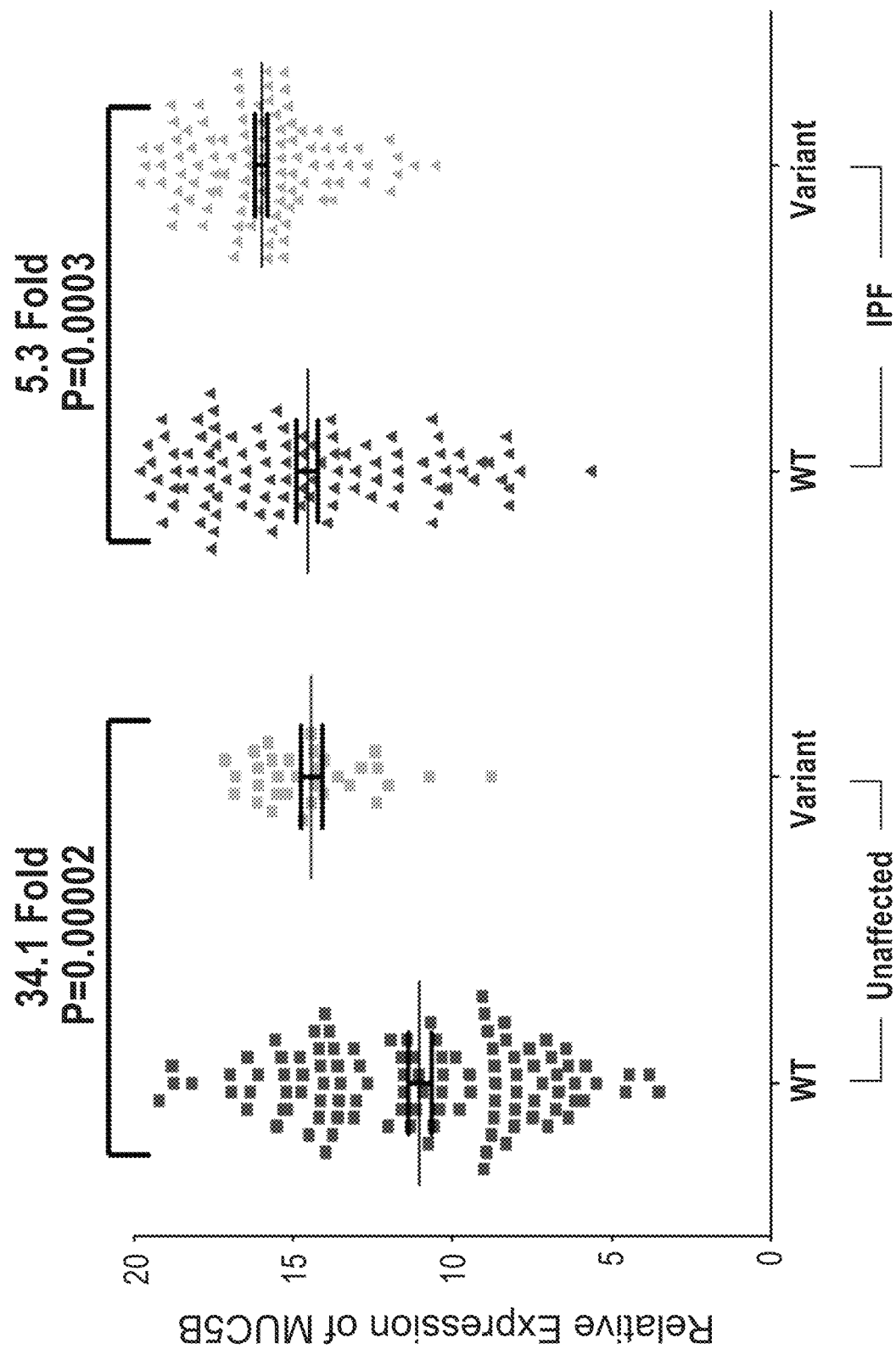
FIG. 5 is a graph showing MUC5B expression in IPF (N=203) and unaffected subjects (N=139) stratified by MUC5B promoter variant (r535705950) genotype.
Figure 6B:
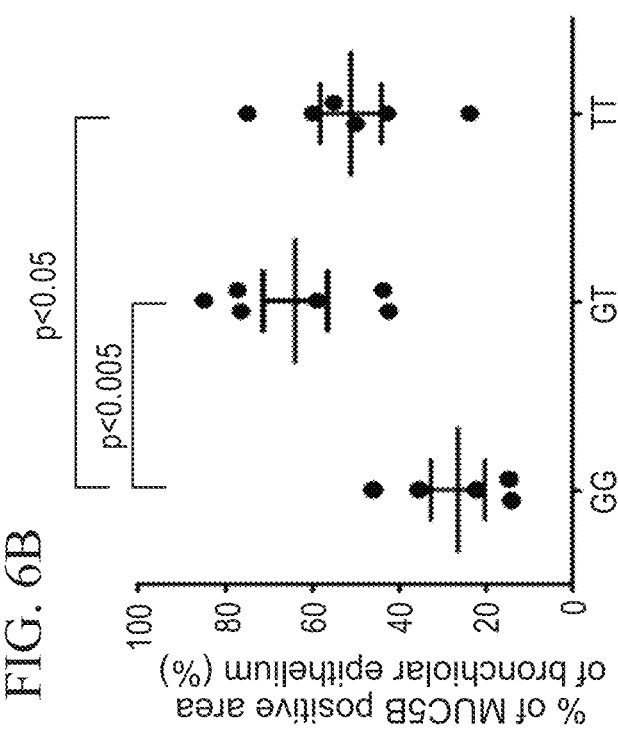
FIG. 6B is a graph showing the percentage of MUC5B positive area of bronchiolar epithelium. Unbiased stereological assessment of staining demonstrates that the volume fraction of stained airways (% positive area) is significantly greater in both the GT heterozygotes and the TT homozygotes.
Figure 6A:
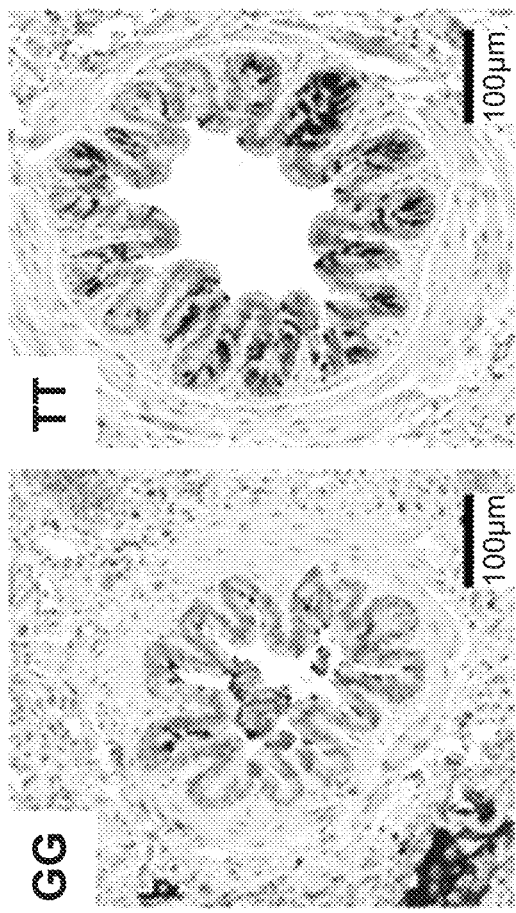
FIG. 6A is a microscopic image demonstrating that MUC5B is produced in bronchoalveolar epithelia of patients with IPF (brown staining in photomicrographs). Staining is increased in the airways of patients positive for rs35705950 (TT) compared to WT (GG).
Figure 7A:
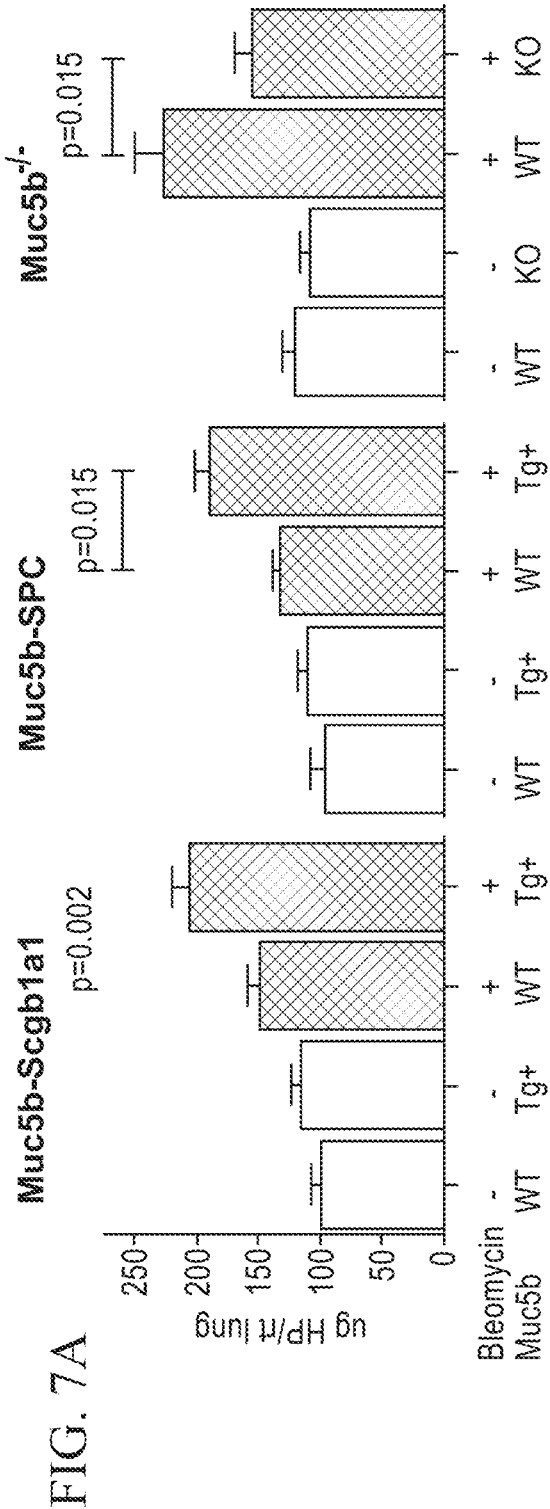
FIG. 7A-B is series of bar graphs showing that Scgb1a1- and SFPTC promoter show significant worsening of fibrosis (hydroxyproline) after bleomycin while Muc5b−/− mice are protected.
Figure 7B:
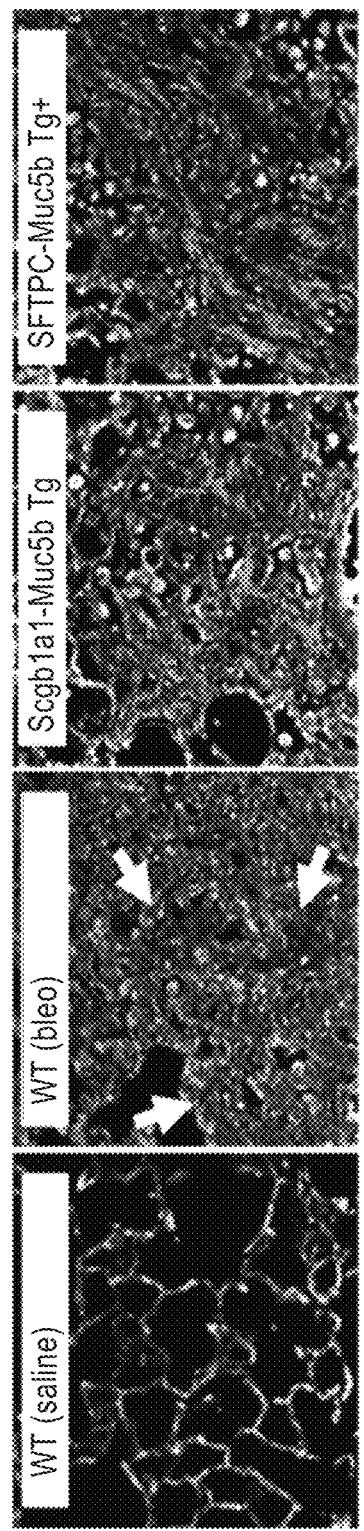
Figure 8:
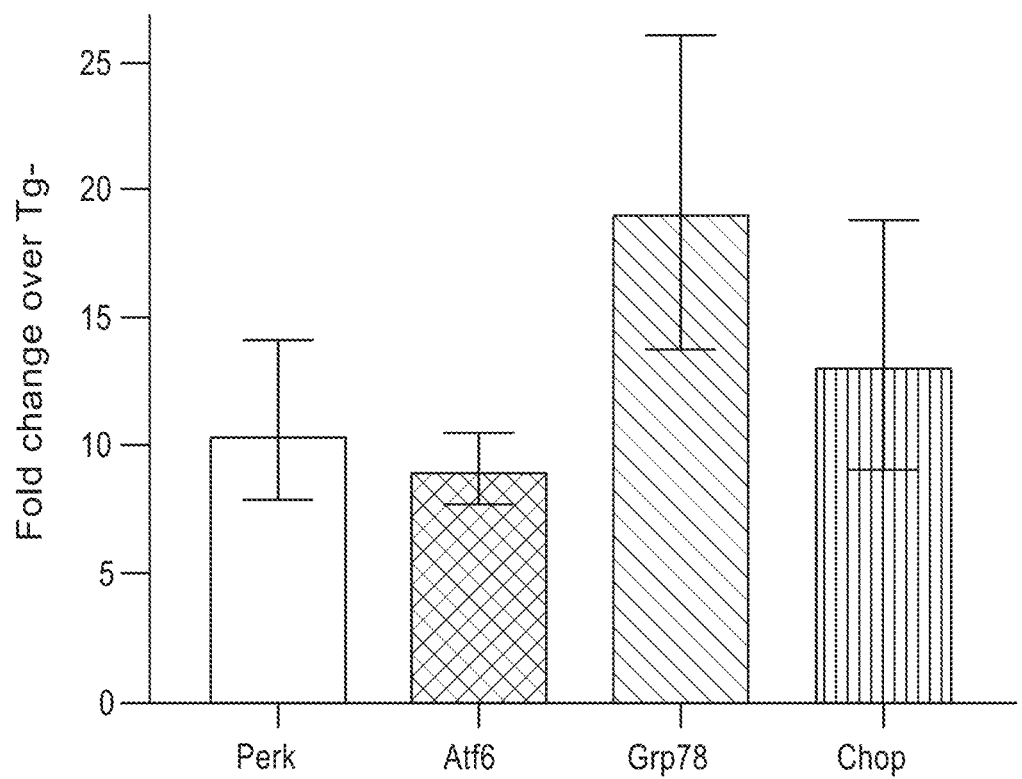
FIG. 8 is bar graph showing that the baseline expression of ER stress genes in lung tissue from WT and Scgb1a1 Muc5bTg mice. Muc5bTg mice have greater ER stress gene expression than their WT littermates (all genes in the ER stress pathway, with p<0.05). Bleomycin also induces ER stress (data not shown).
Figure 9:
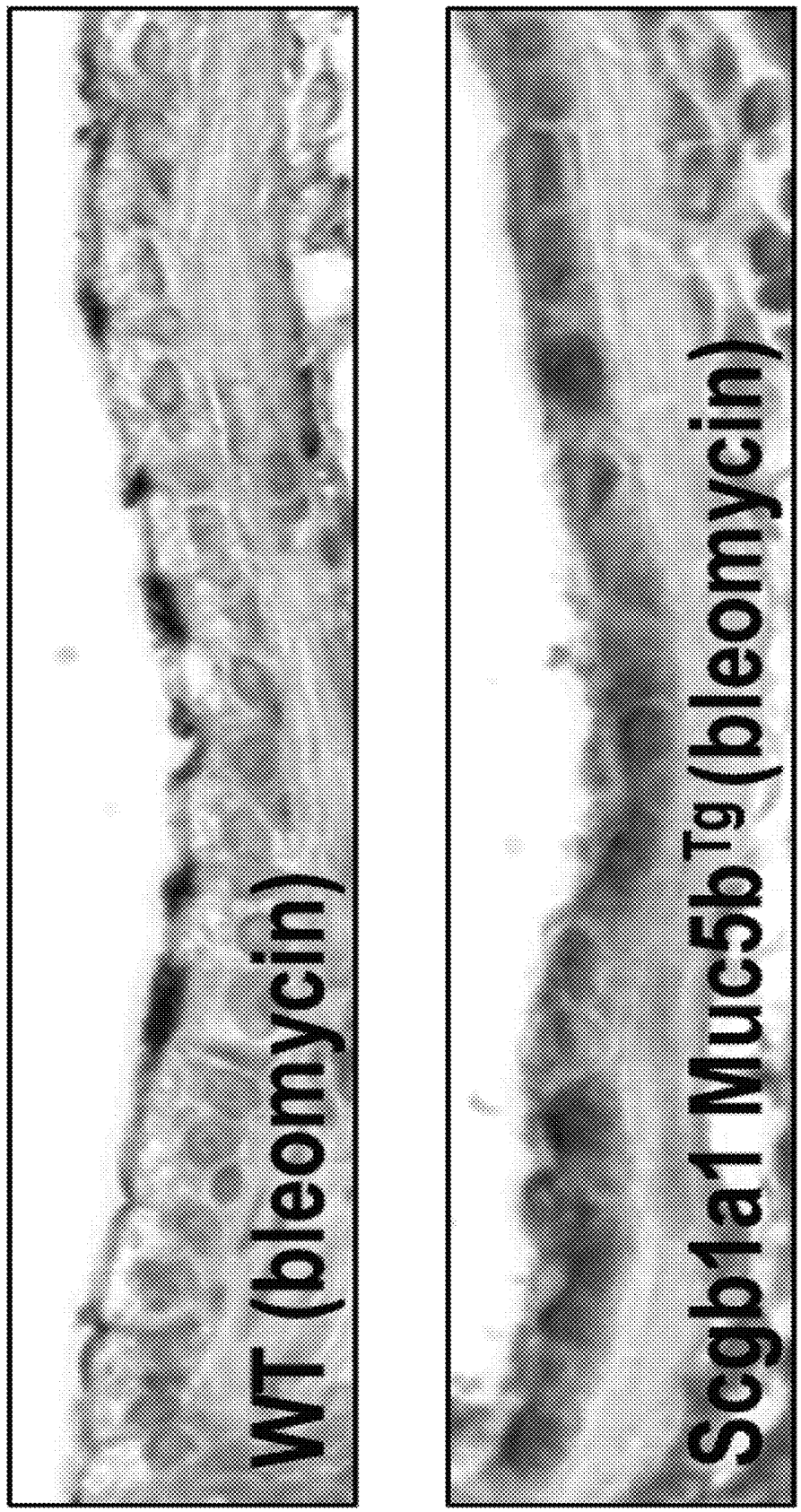
FIG. 9 is a pair of microscopic images showing enhanced CHOP (Ddit3) protein in wild type (WT, top photograph) and Scgb1a1-Muc5bTg mice (bottom photograph) after repeat bleomycin.
Figure 10:
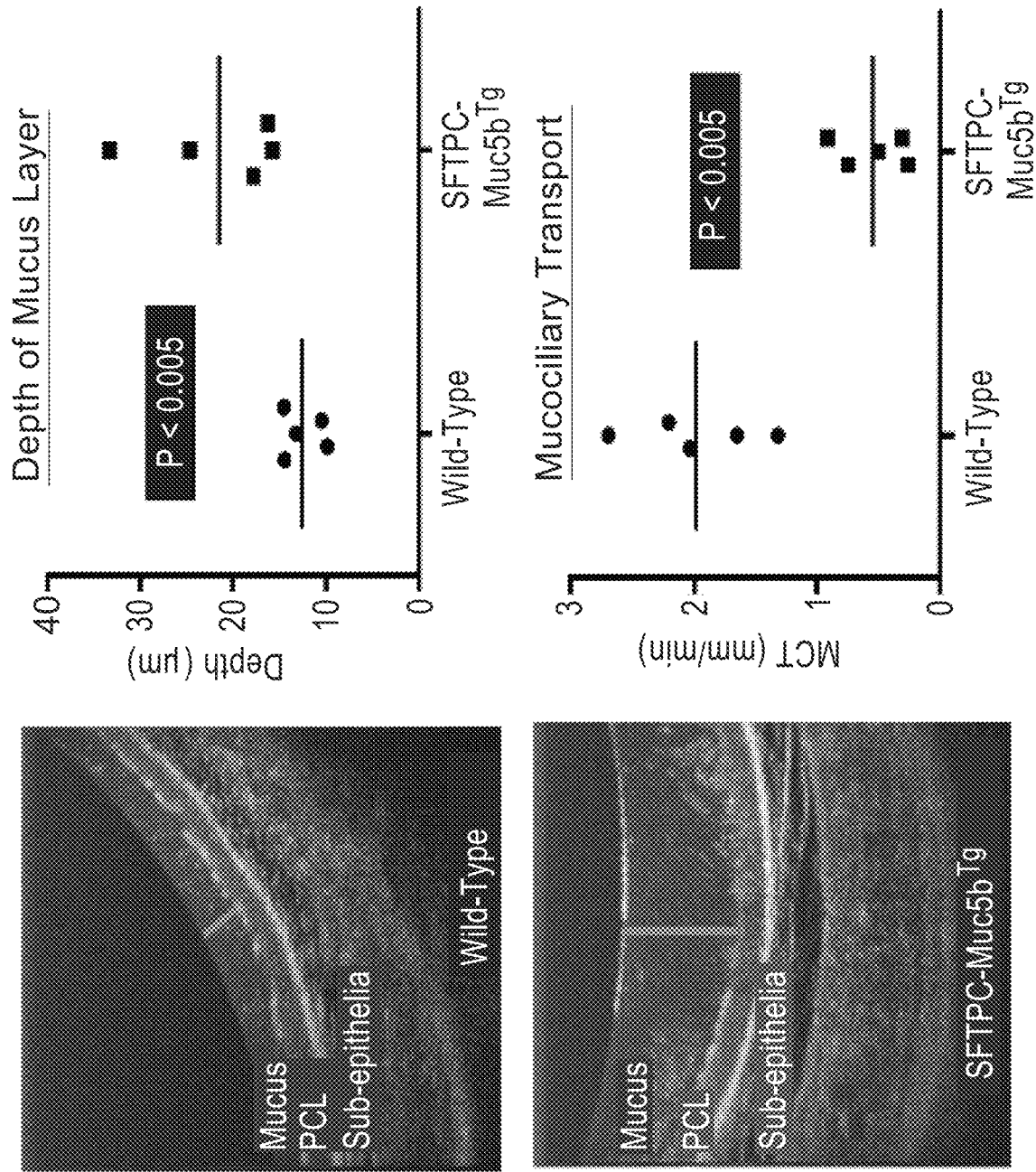
FIG. 10 is a pair of microscopic images and corresponding graphs showing the expanded mucus layer and decreased mucociliary transport in SFTPC-Muc5bTg mice compared to littermate wild-type mice. Statistical differences were assessed by Mann-Whitney U Test.

MUC5B is predicted is involved in the pathogenesis of IPF. FIG. 5 shows that MUC5B promoter variant is associated with enhanced MUC5B expression in both unaffected subjects and in patients with IPF and in IPF, MUC5B message and protein are expressed in bronchoalveolar epithelia (FIG. 6) and honeycomb cysts. In mice, the concentration of Muc5b is directly related to the fibroproliferative response to bleomycin (FIG. 7), Muc5b protein is expressed in the injured lung following bleomycin challenge, and enhanced production of Muc5b in mice appears to initiate endoplasmic reticulum (ER) stress in peripheral airways (FIGS. 8 and 9). Preliminary studies, also show that mucociliary clearance is decreased in mice that overexpress Muc5b (SFTPC-Muc5b$^{Tg}$) and in humans with IPF (FIG. 10).

Interstitial lung abnormalities on HRCT scans show asymptomatic relatives of patients with familial IPF and in the elderly. Similar to patients with IPF, interstitial lung abnormalities in asymptomatic subjects are associated with advanced age, cigarette smoking, reduced lung volume and decreased exercise tolerance. Moreover, the MUC5B promoter variant rs35705950 is associated with a higher prevalence of interstitial lung abnormalities on HRCT scan and is predictive of radiographic progression. Suggesting that interstitial lung abnormalities on HRCT scan are a precursor of IPF. However, interstitial lung abnormalities are not specific and include non-fibrotic and fibrotic HRCT defects, and consequently, the prevalence of interstitial lung abnormalities (>5% in the general population ≥50 years of age is orders of magnitude higher than IPF.

To address the non-specificity of interstitial lung abnormalities, a novel entity—Preclinical Pulmonary Fibrosis (PrePF) was used. PrePF is reported more frequently among smokers and in families with two or more cases of pulmonary fibrosis. In the Framingham population, data shows that PrePF is present in 1.8% of the general population ≥50 years of age (in contrast, interstitial lung abnormalities were seen in 6.7%) and that the MUC5B promoter variant rs35705950 is predictive of those with PrePF (OR=6.3 per allele [95% CI 3.1-12.7). As shown herein, among asymptomatic first-degree family members of familial interstitial pneumonia (FIP) 14% have fibrotic interstitial changes on CT scan and 35% have interstitial abnormalities on transbronchial biopsy. Moreover, in the Framingham population, it is shown that rs35705950 is predictive of radiographic progression of PrePF (OR=2.8 per allele [95% CI 1.8-4.4]) which is associated with a greater FVC decline (P=0.0001) and an increased risk of death (HR=3.7 [95% CI 1.3, 10.7]; P=0.02), indicating that in addition to having radiographic features of IPF, PrePF has similar risk factors (age, gender, smoking, and MUC5B variant) and a progressive clinical course. While the MUC5B promoter variant is predictive of PrePF, rs35705950 is present in ≈19% (minor allele frequency (MAF)=0.09) of the NHW population, however IPF occurs infrequently (<0.1%). Thus, additional biomarkers may be used in combination with rs35705950 identify PrePF within at-risk populations.

Figure 11:
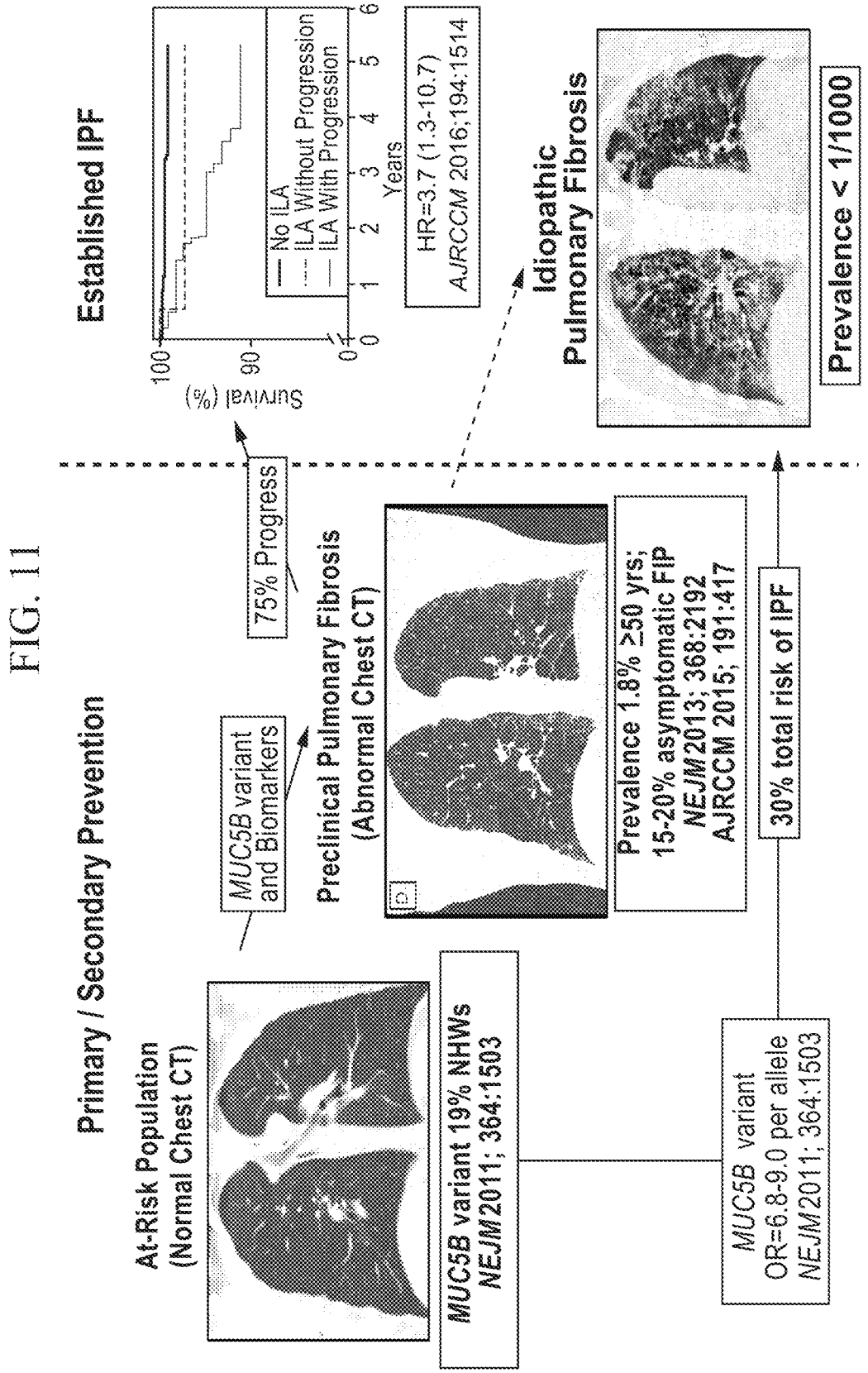
FIG. 11 is a series of schematic diagram showing that the MUC5B variant and other biomarkers can identify an at-risk population or those with PrePF, establishing the opportunity for primary and secondary prevention of IPF. The 'at-risk' population and the population with PrePF is large (19% with the MUC5B promoter variant and 1.8% of individuals ≥50 years of age respectively), IPF is diagnosed in a small population with established, end-stage disease and PrePF can be identified using the MUC5B variant rs35705950. Results indicate that PrePF (detected via chest CT scan) is associated with a poor prognosis suggesting that PrePF may be a harbinger of IPF.
Figure 12:
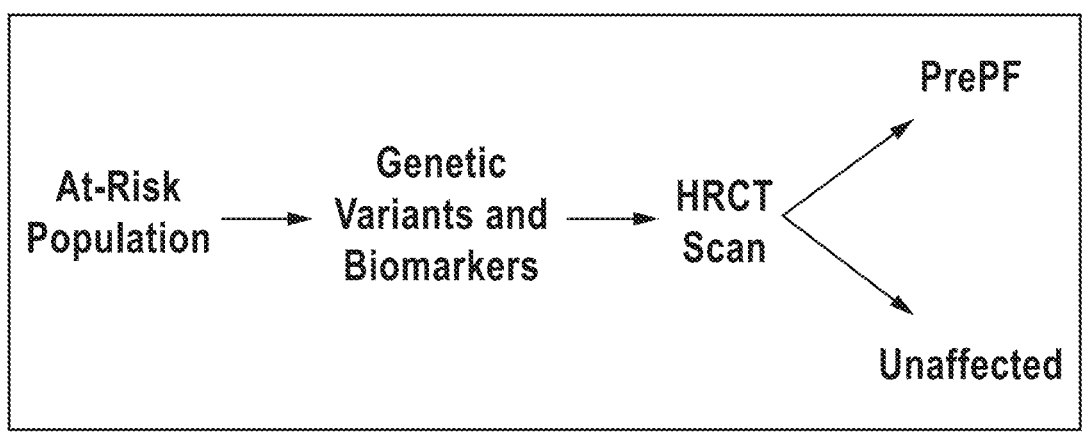
FIG. 12 is a schematic diagram showing a method of screening at-risk populations (family members of patients with IPF) to identify individuals with PrePF. Focus is placed on identifying the genetic variants and biomarkers that increase the yield of PrePF on HRCT scan, in addition to gender, age, and physiology scores.

The data provided herein suggest that 1) IPF is underdiagnosed; 2) PrePF is prevalent in at-risk populations; 3) approximately 75% of the cases of PrePF are progressive; 4) radiographic progression of PrePF is associated with increased morbidity and mortality; and 5) MUC5B variant rs35705950, peripheral blood biomarkers, clinical/biological, and radiographic screening should be useful in identifying those with PrePF (FIG. 11). While IPF takes years to develop, most patients with IPF are diagnosed in the advanced stage when little can be done to influence survival. Once the lung has undergone remodeling, the non-compliant, stiff lung matrix causes additional remodeling through activation of myofibroblasts, resulting in a feed-forward loop of lung remodeling. Earlier diagnosis of IPF detects subjects with a lower burden of fibrotic lung disease.

This disclosure provides a strategic approach to screening for early forms of IPF needs to be established (FIG. 11). While the MUC5B promoter variant is predictive of PrePF (defined as chest HRCT consistent with probable or definite fibrosis (e.g., bilateral subpleural reticular changes, honeycombing, or traction bronchiectasis) occurring in asymptomatic subjects ≥40 years of age that emerge from at-risk populations), the MUC5B promoter variant is present in ≈ 19% of the NHW population and IPF occurs infrequently (<0.1%). To study at-risk populations (asymptomatic siblings ≥40 years of age of patients with family or sporadic IPF), identification of genetic variants and biomarkers that increase the yield of patients with PrePF are used to establish screening tools and approaches that identify early stages of IPF. This approach changes the way IPF is diagnosed and treated, and is critical to developing interventions to prevent PrePF progression to established IPF. The methods provided in this disclosure fundamentally alter the clinical approach to patients with IPF from palliative to preventive (FIG. 10).

Example 3: Predictive Biomarker Profile for Established IPF

To address the development of a peripheral blood biomarker profile for IPF, an assay of the expression levels of >3700 plasma proteins was performed on plasma from 70 patients with established IPF and 70 controls. After controlling for multiple comparisons and appropriate co-variables, 57 proteins were up-regulated >1.5-fold (including surfactant proteins, MMP7, and C3) in the plasma of patients with IPF and 12 were significantly down-regulated (FIG. 2).

Example 4: Predictive Biomarker Profile for Early IPF

Figure 3:
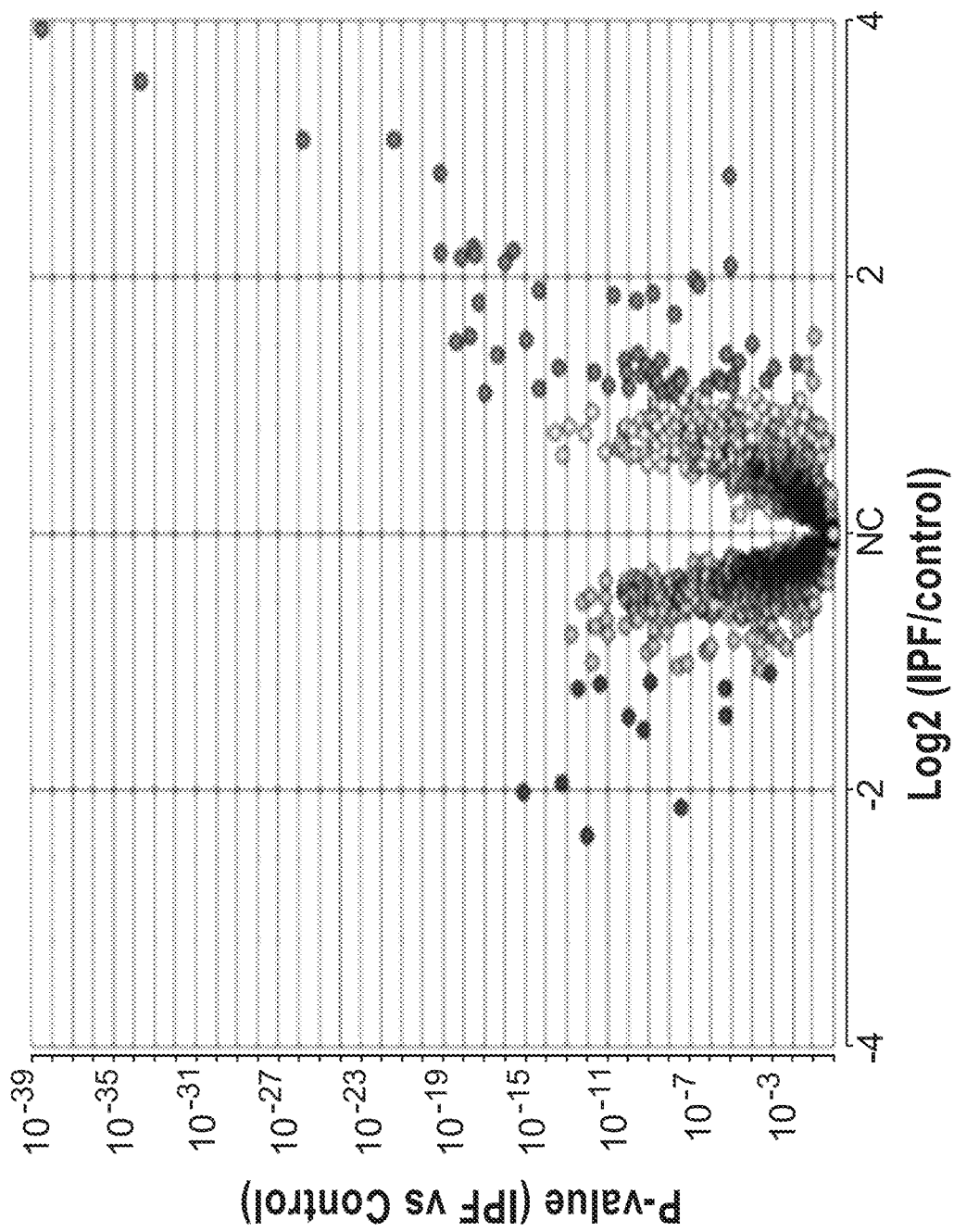
FIG. 3 is a volcano plot of 3315 plasma proteins, comparing results from 70 patients with established IPF and 70 controls. Solid red symbols represent 57 proteins that were significantly up-regulated and solid blue symbols 12 proteins that were significantly downregulated in patients with IPF after controlling for multiple comparisons and age/gender/smoking.
Figure 4:
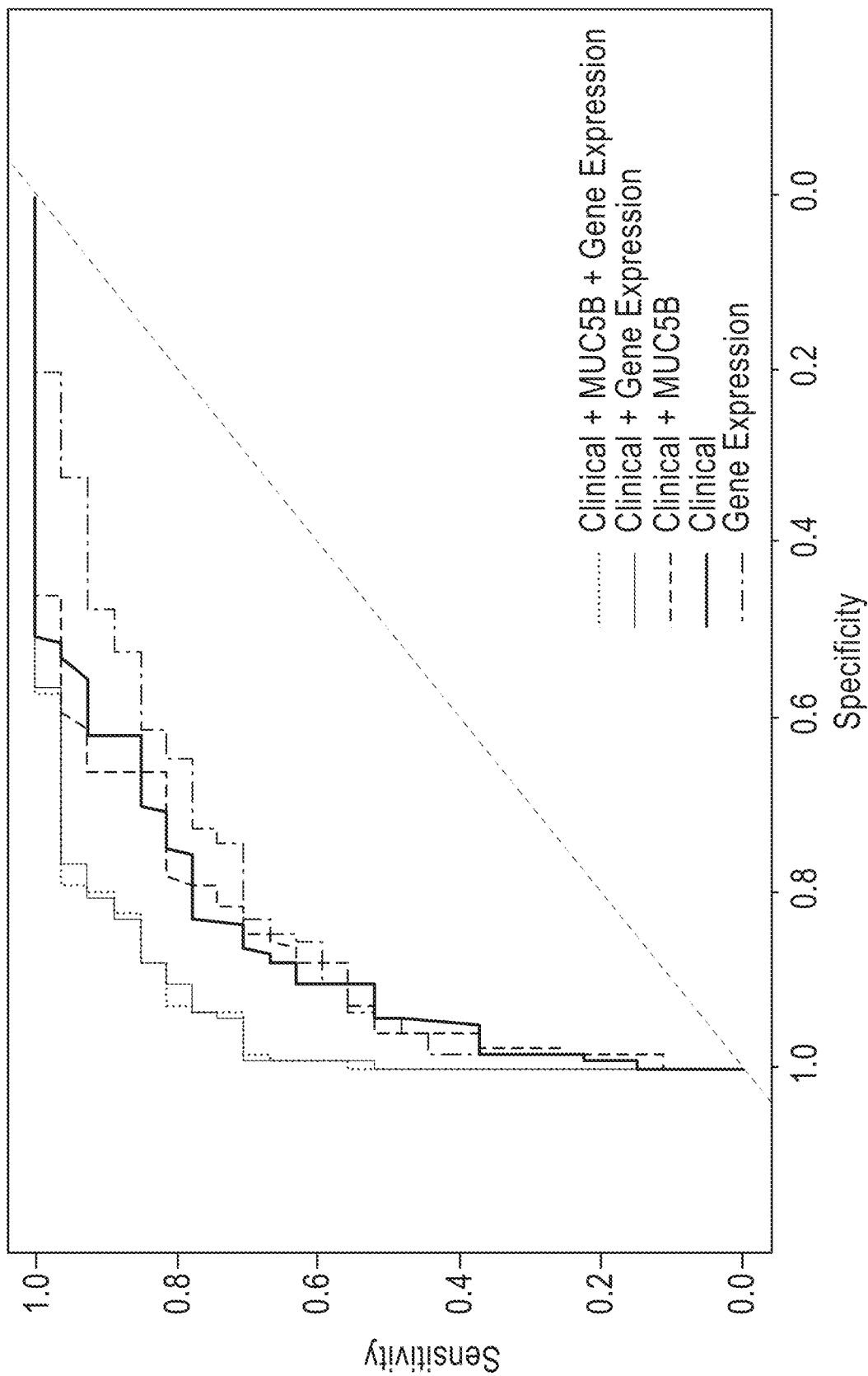
FIG. 4 is a survival plot showing receiver operator curves of predictive model for PrePF in asymptomatic relatives from FIP families. Area Under Curve (AUC) values for each model are as follows: Gene Expression alone (red)=0.83, Clinical Predictors (blue)=0.87, Clinical Predictors+MUC5B genotype (green)=0.87, Clinical Predictors+Gene Expression Score (yellow)=0.95, Clinical Predictors+MUC5B genotype+Gene Expression Score (black)=0.95, indicating that a peripheral blood biomarker panel may improve the diagnostic power of a predictive model for PrePF in an at-risk population.

To evaluate a predictive biomarker profile in cases of preclinical pulmonary fibrosis (PrePF) derived from families with familial IPF (≥2 cases of IPF in a family), HRCT scans were performed on 496 asymptomatic family members ≥40 years of age previously phenotyped as unaffected from 263 families with familial IPF. PrePF, consistent with the operational definition (defined as abnormalities on chest HRCT consistent with probable or definite fibrosis (e.g., bilateral subpleural reticular changes, honeycombing, or traction bronchiectasis) occurring in asymptomatic subjects ≥40 years that emerge from at-risk populations), was present in 77 (15.5%) of 496 asymptomatic individuals from families with familial IPF. The minor allele frequency (MAF) of the MUC5B promoter variant was 0.29 in those with PrePF versus 0.21 in those without fibrosis (P=0.025). Preliminary analysis of PBMC gene expression profiles evaluated by microarrays from 38 cases of PrePF and 187 subjects without fibrosis identified 16 genes significantly differentially expressed between the two groups (p-value <0.05 and >1.5 fold change). Among genes differentially expressed in PrePF are those involved in innate immunity and inflammatory responses (SIGLEC14), antibacterial effects (ADM2), growth and motility (TSPAN5), and protein phosyphorylation (CAMKK1). Moreover, PBMC gene expression appears to contribute to the ability to predict PrePF in an at-risk population (FIG. 3).

Additionally, RNA-sequencing analysis was performed on 40 PrePF subjects and 80 subjects with a normal HRCT scan. Sequencing of the polyA-enriched libraries was prepared using Illumina TrueSEQ reagents and multiplexing 10 samples on each lane of HiSEQ4000 to obtain on average 35-40 million reads per sample. This high coverage allows for the consideration of a broad dynamic range of mRNA transcripts for biomarker selection. Platform selection of serum and plasma samples from the same subjects are used for proteomic analysis.

Example 5: Biomarker Identification

To examine for association between each biomarkers and PrePF, a multivariable logistic regression model for PrePF with biomarkers and covariates is used for inclusion and a step-wise forward selection procedure is constructed. Variables stay in the model if associated at P≤0.01 after adjustment for the variables already in the model. Protein biomarkers that are significantly associated with established IPF and the top 20 differentially expressed genes in PrePF are considered for inclusion in a multivariable model. The number of potential biomarkers allowed in the joint model is restricted to approximately 20 given the number cases of PrePF expected. Secondarily, interactions between MUC5B genotype and the other biomarkers are tested for, which allow for the possibility that different biomarker profiles are diagnostic in IPF patients with/without the MUC5B risk allele.

Example 6: Predictive Ability of Biomarkers

To test the predictive value of the combination of biomarkers associated with PrePF, the observed expression and other biomarker values from those associated with PrePF in the siblings of FIP patients is used to obtain the probability, for each sibling, having PrePF.

Following, a construct receiver operating characteristic (ROC) curves (see M. S. Pepe et al., Phases of biomarker development for early detection of cancer. Journal of the National Cancer Institute 93, 1054-1061 (2001)), is used to choose the probability threshold that maximizes the area under the ROC curve. This probability threshold is used to classify each individual as predicted to have PrePF or not, allowing calculation of the sensitivity, specificity, positive predictive value, and negative predictive value of the predictive model. The properties of the predictive model(s) in the independent set of siblings of patients with IPF are evaluated. Different aliquots are run for 10 samples for each assay at each time the assays is run in order to use those 10 samples to evaluate the need for standardization of the absolute values for each assay over time. Either the raw or standardized values, for a given model, is used to observe biomarker values in the PrePF siblings and non-PrePF siblings to obtain the probability of being in the disease group based on the model parameters developed using the FIP siblings. The thresholds identified among the FIP siblings are used to classify each individual as predicted to have PrePF or not. This categorization allows for the calculation of the sensitivity, specificity, positive predictive value, and negative predictive value of the predictive model among the siblings of independent cases of IPF to that observed in the siblings of FIP cases.

Power is calculated to detect differences between those with and without PrePF assuming 500 siblings and 10% (N=50) with PrePF. Assuming $\alpha$=0.00005 (conservatively correcting for up to 1000 independent tests), we have 80% (90%) power to detect differences in protein or expression level of 0.74 (0.80) standard deviation between PrePF and unaffected siblings. These differences are larger than previously-observed protein and gene-expression levels in IPF patients and controls (see I. V. Yang et al., The peripheral blood transcriptome identifies the presence and extent of disease in idiopathic pulmonary fibrosis. PLoS One 7, e37708 (2012). With 50 PrePF and 450 unaffected, there is 90% power to bound the sensitivity of the biomarker-based classification of PrePF with a margin of error of 11% if the sensitivity is 65%, and 6.5% if the sensitivity is 95%; the margins of error for 65% and 95% sensitivity are 4.5% and 2.5%, respectively.

Example 7: MUC5B Promoter Variant r35705950 is a Risk Factor for Rheumatoid Arthritis—Interstitial Lung Disease Methods
Study Cohorts This study included a discovery cohort and multi-ethnic replication cohorts. The discovery cohort included patients with RA, with and without ILD (RA-noILD) as assessed by chest HRCT, and controls, from the French RA-ILD network. The multi-ethnic replication cohorts were obtained from six countries (China, Greece, Japan, Mexico, the Netherlands and United States). This included patients with RA-ILD and RA-noILD patients, and controls. All cases fulfilled the 2010 European League Against Rheumatism-American College of Rheumatology (EULAR-ACR) and/or 1987 ACR revised criteria for RA. The ILD status of patients with RA was established by chest HRCT images that were centrally reviewed by experienced readers for each participating cohort. There was one cohort, the RA-noILD cases from the USA1 cohort, which was determined by self-report. The chest HRCT ILD pattern was classified as UIP, possible UIP or inconsistent with UIP according to international criteria and all readers were blinded to the clinical and genetic data. The institutional review boards at each institution approved all protocols, and all patients provided written informed consent.

Genotyping

Genotyping of the MUC5B rs35705950 single nucleotide polymorphism (SNP) involved use of Taqman Genotyping Assays (Applied Biosystems, Foster City, CA, USA) as previously reported, by direct Sanger Sequencing or imputation from genome-wide association study data.

The additional common IPF risk variants on 3q26, 4q22, 5p15, 6p21.3, 6p24, 7q22, 10q24, 11p15.5, 13q34, 15q14-15, and 19p13 were genotyped by Taqman qPCR (Thermo Fisher Scientific, California) per the manufacturer's instructions.

Lung Tissue Analysis

In order to determine if MUC5B was expressed in RA-ILD ling tissue, we analyzed lung tissue was analyzed from nine patients with RA-ILD undergoing lung transplantation (University of California, San Francisco) compared to six unaffected controls with ILD (NHLBI Lung Tissue Research Consortium; https://ltrcpublic.com) or concordant expression of other relevant markers of pulmonary fibrosis. The tissue was formalin fixed, paraffin embedded and cut in 4 um sections. Tissue sections were deparaffinized in xylene, followed by dehydration in series of ethanol. Following citrate buffer antigen retrieval, slides were incubated overnight with primary antibodies against MUC5B (1:4000, Santa Cruz, Dallas, TX). Secondary antibody diluted 1:1000 tagged with HRP (Life Technologies) was visualized using an Aperio CS2 slide scanner (Leica, Buffalo Grove, IL).

Results

Study Cohorts

This case-control genetic study included 620 RA-ILD cases, 614 RA-noILD cases and 5448 unaffected controls. The discovery cohort included 118 RA-ILD cases, 105 RAnoILD cases and 1229 unaffected controls. The multi-ethnic replication sample included 502 RA-ILD, 509 RA-noILD cases and 4219 unaffected controls.

Characteristics of the Discovery Cohort

As compared with RA-noILD, patients with RA-ILD were more frequently male, older and more frequently smoked cigarettes (54.7% versus 36.1%) (FIG. 13). However, after adjusting for sex, the relationship between RA-ILD and cigarette smoking was no longer statistically significant (FIG. 13). After adjustment, RA-ILD and RA-noILD patients did not differ in rheumatoid factor (RF) and/or anti-citrullinated protein antibody (ACPA) positivity, erosive status of RA, exposure to methotrexate or the mean RA duration from diagnosis at inclusion in the cohort. Overall, 41% of patients with RA-ILD had a UIP or possible UIP HRCT pattern.

Figure 16A:
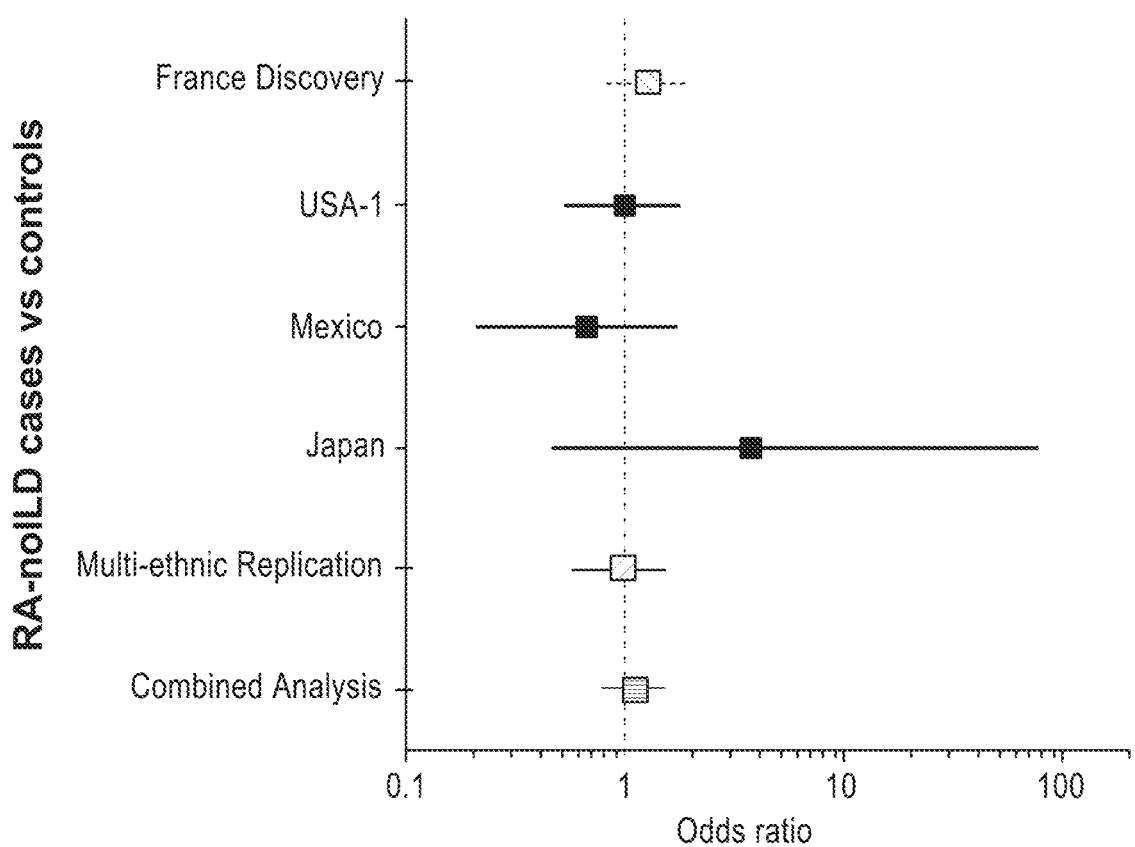
FIG. 16A is a forest plot of odds ratios {OR} and 95% confidence intervals {CI} depicting the lack of association of the MUC5B rs35705950 promoter variant with RA without 1LD {RA-noILD). The boxes indicate OR, and the horizontal lines indicate 95% CI for the best-fitting genetic model for each association test. The black dotted line represents a mean OR value of 1. The red boxes and red lines indicate the overall OR and 95% CI, respectively. For comparisons between RA cases and controls, the associations were adjusted for the country of origin and sex. For intra-RA cases comparisons, the associations were adjusted for the country of origin, sex, age at inclusion and smoking.
Figure 16B:
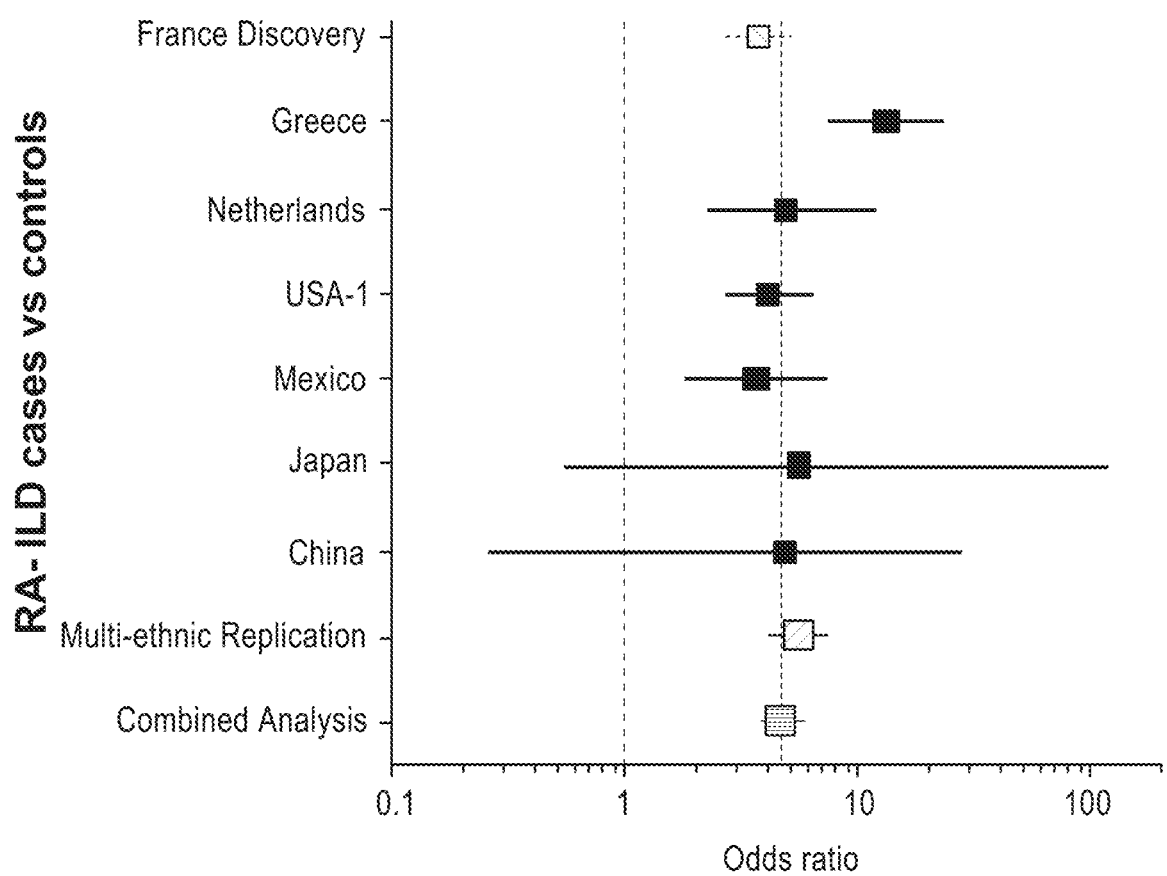
FIG. 16B is a forest plot of odds ratios (OR) and 95% confidence intervals {CI) depicting the additive genotypic association of the MUC5B rs 35705950 promoter variant with RA-ILD. The red dotted line represent the mean value of overall OR value. The boxes indicate OR, and the horizontal lines indicate 95% CI for the best-fitting genetic model for each association test. The black dotted line represents a mean OR value of 1. The red boxes and red lines indicate the overall OR and 95% CI, respectively. For comparisons between RA cases and controls, the associations were adjusted for the country of origin and sex. For intra-RA cases comparisons, the associations were adjusted for the country of origin, sex, age at inclusion and smoking.
Figure 16C:
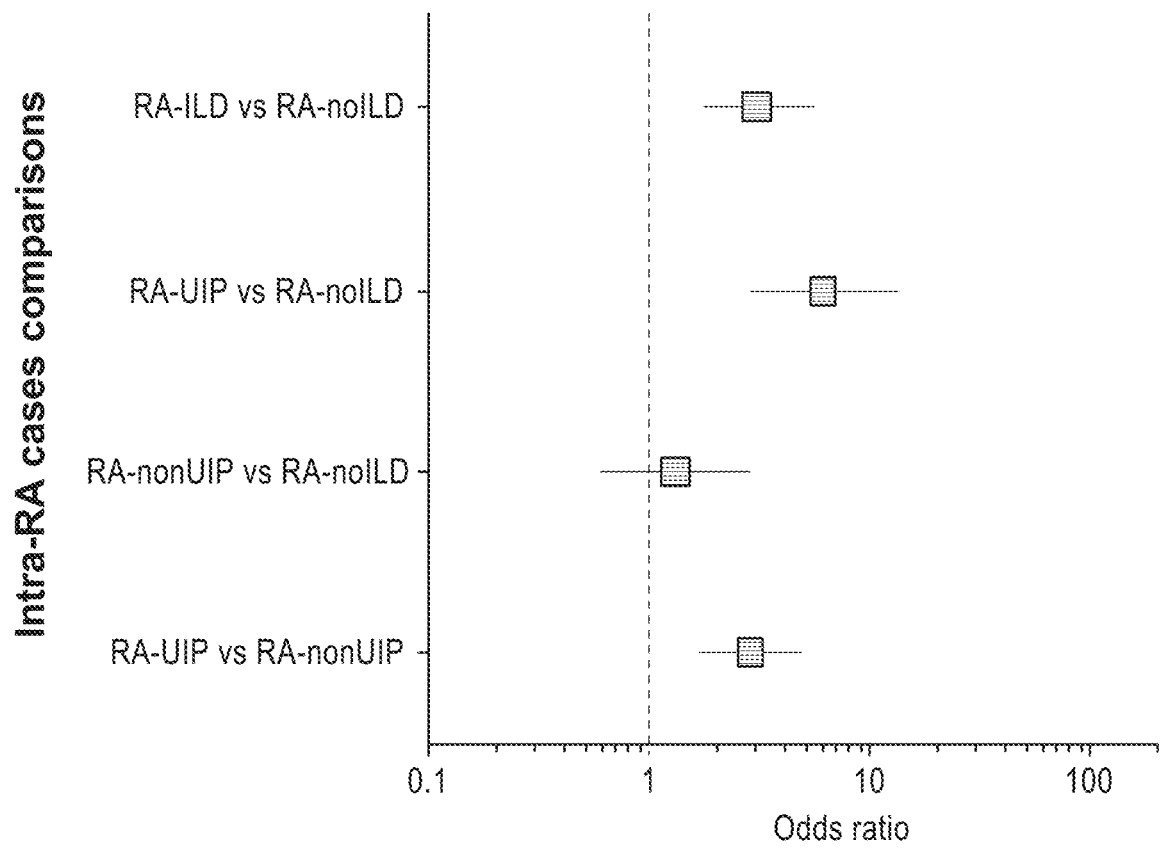
FIG. 16C is a forest plot of odds ratios {OR} and 95% confidence intervals {CI) depicting dominant genotypic association of the MUC5B re35705950 promoter variant with ILD among patients with RA and those with the usual interstitial pneumonia or possible usual interstitial pneumonia (UIP) pattern. The boxes indicate OR, and the horizontal lines indicate 95% CI for the best-fitting genetic model for each association test. The red dotted line represent the mean value of overall OR value. The black dotted line represents a mean OR value of 1. The red boxes and red lines indicate the overall OR and 95% CI, respectively. For comparisons between RA cases and controls, the associations were adjusted for the country of origin and sex. For intra-RA cases comparisons, the associations were adjusted for the country of origin, sex, age at inclusion and smoking.

MUC5B Promoter Variant and Risk of Rheumatoid Arthritis-Associated Interstitial Lung Disease Comparison of RA-noILD and controls revealed that none of the cohorts (discovery cohort and multi-ethnic cohorts) demonstrated a significant difference in the frequency of the MUC5B promoter variant (FIG. 14; FIG. 16A), suggesting a lack of association between the MUC5B promoter variant and RA. In the discovery cohort, the minor allele frequency (MAF) of the MUC5B promoter variant was 10.9% in unaffected controls and 32.6% in cases of RAILD; this variant was in Hardy-Weinberg equilibrium (HWE) in both study groups. I In the discovery population, after controlling for sex we detected a significant association between the MUC5B promoter variant and RA-ILD when compared to non-RA controls (ORadj=3.8; 95% CI, 2.8 to 5.2; P=9.7× 10-17) (FIG. 14). Similar to the discovery population, the MUC5B promoter variant was significantly over-represented among the cases of RA-ILD compared to unaffected non-RA controls in all of the multi-ethnic study case series, except in the two Asian case series (FIG. 14). Given that the MUC5B promoter variant is under-represented in Asian populations compared to non-Hispanic whites (FIG. 14; www.ncbi.nlm.nih.gov/projects/SNP/snp_ref.cgi?rs=35705950), a likely explanation, especially given the consistent point estimates, for the absence of a significant relationship between the MUC5B promoter variant and RA-ILD is that the analysis of the two Asian case series is likely underpowered. The relationship between the MUC5B promoter variant and RA-ILD in combined multi-ethnic study case series (ORadj=4.7; 95% CI, 3.9 to 5.8; P=1.3× 10-49) (FIG. 14) (FIG. 16B) validated the observed association between the MUC5B promoter variant and RA-ILD in the discovery study population.n addition, the cases of RA-ILD in the study populations from Greece and USA-1 were not in HWE, suggesting (as has been observed in cases of IPF 14), that the MUC5B promoter variant and/or common variants in high or complete linkage disequilibrium with the MUC5B promoter variant should be considered as causative in these cases of RA-ILD. For the comparison with non-RA controls, the best-fitting genetic model for the three study populations (discovery population, combined multi-ethnic case series, and combined analysis) for the association of the MUC5B MUC5B RS35705950 and Risk of Interstitial Lung Disease Among Patients with Rheumatoid Arthritis To further investigate whether the MUC5B promoter variant rs35705950 contributes to the risk of ILD among patients with RA, we compared RA-ILD and RA-noILD patients, adjusting for sex, age at inclusion and cigarette smoking. In the discovery cohort, the MUC5B variant was associated with RA-ILD (ORadj=3.1; 95% CI, 1.6 to 6.3; P=9.4×10$^{-4}$), and this finding was replicated in the aggregate multi-ethnic cohort (ORadj=2.9; 95% CI, 1.1 to 8.4; P=0.04) and the combined analysis (ORadj, 3.1; 95% CI, 1.8 to 5.4; P=7.4×10$^{-5}$) (FIG. 14; FIG. 16C). For the comparison of RA-ILD with RA-noILD, the best-fitting genetic model for the three study cohorts (discovery population, combined multi-ethnic case series, and combined analysis) was dominant. After adjusting for covariates, no association between tobacco smoking and the risk of ILD among patients with RA was found and no interaction of tobacco smoke exposure with the MUC5B promoter variant was observed (ORadj=0.7; 95% CI, 0.3 to 1.9; P=0.51).

MUC5B RS35705950 and UIP on HRCT Scan

Limiting the RA-ILD cases to those with radiographic evidence of definite or possible UIP on HRCT scan, the association observed in the discovery cohort (ORadj=5.0; 95% CI, 2.1 to 12.3; P=3.0×10$^{-4}$), was replicated in the combined multi-ethnic cohort (ORadj=9.2; 95% CI, 2.3 to 38.7; P=1.8×10$^{-3}$) (FIG. 16C), and was observed in the combined cohort analysis (ORadj=6.1; 95% CI, 2.9 to 13.1; P=2.5×10$^{-6}$) (FIG. 16C). In the combined analysis, the comparison of odds ratios for UIP RA-ILD vs RA-noILD (ORadj=6.1; 95% CI, 2.9 to 13.1; P=2.5×10$^{-6}$) to non-UIP RA-ILD vs RA-noILD (ORadj=1.3; 95% CI, 0.6 to 2.8; P=0.46) was statistically significant (P=0.02), suggesting that the effect of the MUC5B promoter variant was restricted to the UIP RA-ILD sub-phenotype (FIG. 16C). Finally, consistent with our previous findings, the MUC5B promoter variant was found to increase the risk of developing a UIP pattern among patients with RA-ILD through a dominant model in the discovery, replication and combined analysis; the odds of having a UIP and possible UIP pattern for patients with RA-ILD carrying at least one MUC5B rs35705950 T risk allele were 2.9 times greater than individuals having the GG genotype (ORadj=2.9; 95% CI, 1.7 to 4.8; P=5.1×10−5) (FIG. 15; FIG. 16C). After adjusting for covariates, tobacco smoking exposure did not contribute to a specific HRCT pattern for RA-ILD and no interaction with the MUC5B rs35705950 variant was detected.

Sites of MUC5B Expression in Ra-ILD

Figure 17:
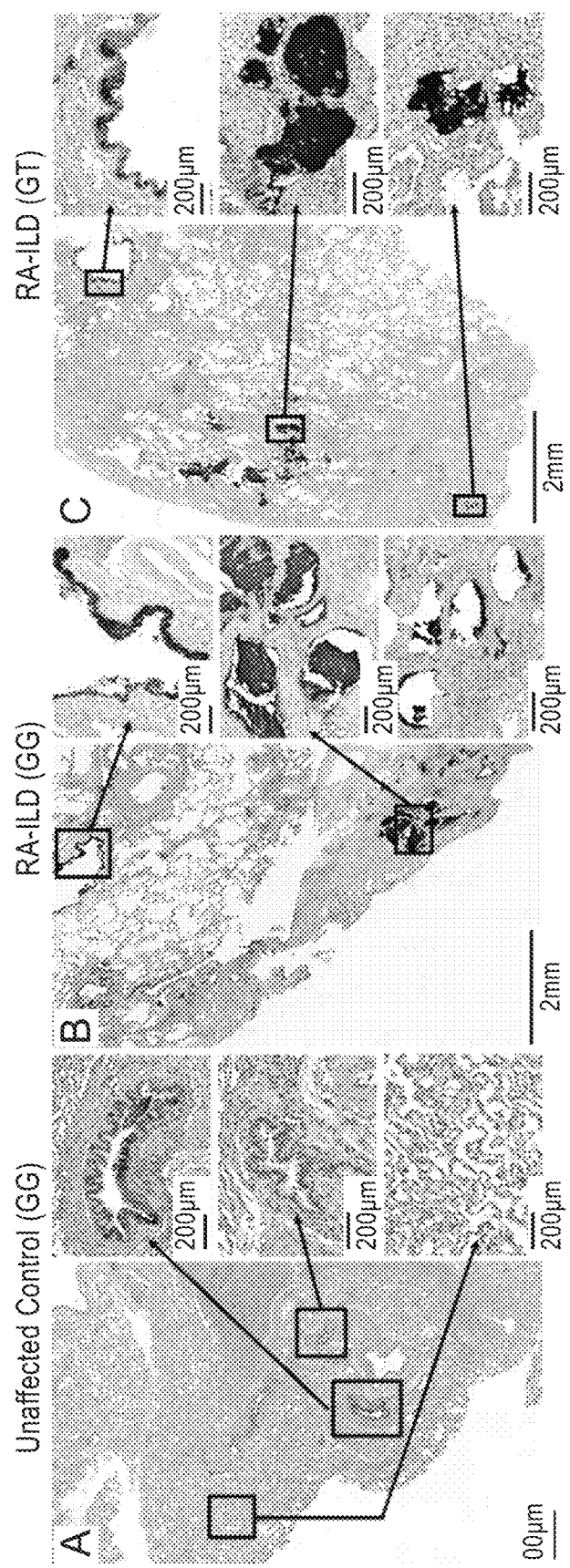
FIG. 17 is a series of photographs depicting MUC5B expression in explanted lung tissue from rheumatoid arthritis associates interstitial lung disease. Representative lung tissue images from unaffected control (GG genotype, Panel A), RA-ILD case #1 (GG genotype, Panel B), and RA-ILD case #2 (GT genotype, Panel C). Low power views with high power view insets identified. Panel A—low power view of normal lung; top and middle insets with high power view of bronchiole with MUC5B staining; bottom inset with high power view of alveolar epithelia. Panel B and C—low power view of the usual interstitial pneumonia pattern in explanted lung tissue of RA-ILD; top inset with high power view of bronchiole with MUC5B staining; middle and bottom insets with high power view of MUC5B staining in metaplastic epithelia lining honeycomb cysts and MUC5B staining of mucous in honeycomb cysts.

We performed immunohistochemical staining for MUC5B in nine RA-ILD lung tissue explants (5 GG and 4 GT) and 6 unaffected controls (3 GG and 3 GT). Similar to what has been reported in IPF, RA-ILD lung tissue demonstrated MUC5B in the cytoplasm of the bronchioles and in areas of microscopic honeycombing, including staining of the metaplastic epithelia lining the honeycomb cysts and the mucous within the cyst (FIG. 17). The controls demonstrated MUC5B expression in the bronchioles only. There were no obvious differences in MUC5B expression by genotype.

Exploratory Genetic Association Study of 12 Common IPF Risk Variants in Ra-ILD

Having provided evidence for the contribution of the dominant IPF genetic risk variant, i.e. the MUC5B promoter variant, to RA-ILD, we decided to test the association of 12 additional common IPF risk variants with RA-ILD (FIG. 29). This exploratory study included 272 RA-ILD and 242 RA-noILD patients from the France, USA-1 and Mexico case series. Taking into account the relatively small sample size and related low power of detection corresponding P-values, Odds Ratio and 95% CI for the 12 candidate variants were considered as descriptive and Bonferoni correction was therefore not applied (Table 4). Comparison between RA-ILD and RA-noILD revealed that 2 common IPF risk variants, TOLLIP rs5743890 and IVD rs2034650, were significantly associated with RA-ILD. The TOLLIP rs5743890 minor allele was associated with increased risk of RA-ILD and the IVD rs2034650 minor allele was associated with decreased risk of RA-ILD (ORadj=2.13; 95% CI, 1.13 to 4.10; P=0.02 and ORadj=0.59; 95% CI, 0.38 to 0.89; P=0.01, respectively) and the directionality of these relationships is consistent with what has been observed for IPF.16,17 No association with RA-ILD was detected for the 10 other IPF risk variants (FIG. 29).

Example 8: MUC5B Promoter Variant is Associated with Visually and Quantitatively Detected Preclinical Pulmonary Fibrosis Better understanding and recognition of early pulmonary fibrosis is critical because medical therapies have been shown to slow progression, not to reverse or even stabilize established fibrosis—therefore, intervention before irreversible fibrosis has become extensive has the potential to improve quality of life and decrease morbidity. While IPF affects approximately 5 million people worldwide, between 1.8 and 14% of the general population ≥50 years of age have radiologic findings of undiagnosed pulmonary fibrosis. Large cohort studies indicate that interstitial lung abnormalities, postulated to represent early pulmonary fibrosis, are associated with increased mortality, and that most of these abnormalities progress over time. Members of families with 2 or more cases of pulmonary fibrosis (FIP, Familial Interstitial Pneumonia) have been identified as an "at-risk" population. In a previous study of FIP relatives, 14% had interstitial lung abnormalities on high resolution computed tomography (HRCT), and 35% had an abnormal transbronchial biopsy indicating interstitial lung disease.

HRCT provides visualization of the lung parenchyma and plays a key role in the diagnosis of the Idiopathic Interstitial Pneumonias (TTPs), including IPF. Currently, visual diagnosis by thoracic radiologists, in conjunction with multidisciplinary clinical conference, is the gold standard for diagnosing IIPs. However, visual assessment is imprecise and hampered by inter-observer variation. Quantitative HRCT (qHRCT) evaluation provides measures of fibrosis extent that, in subjects diagnosed with IPF, correlate with degree of physiologic impairment at baseline, and may be more sensitive to subtle changes in disease status than routinely used physiological metrics. The design and utility of quantitative methods in the context of early forms of fibrotic ILD requires further study. Deep learning methods have been increasingly used in imaging to identify and classify CT patterns, and may be particularly valuable in detection of early lung fibrosis.

This study aims to: (1) examine risk factors, including two common fibrosis-associated genetic variants in MUC5B and TERT, for undiagnosed pulmonary fibrosis (PrePF) in FIP first-degree relatives; and (2) determine the utility of a deep learning, texture-based qHRCT method in the detection of early fibrosis in this cohort.

Materials and Methods

Figure 18:
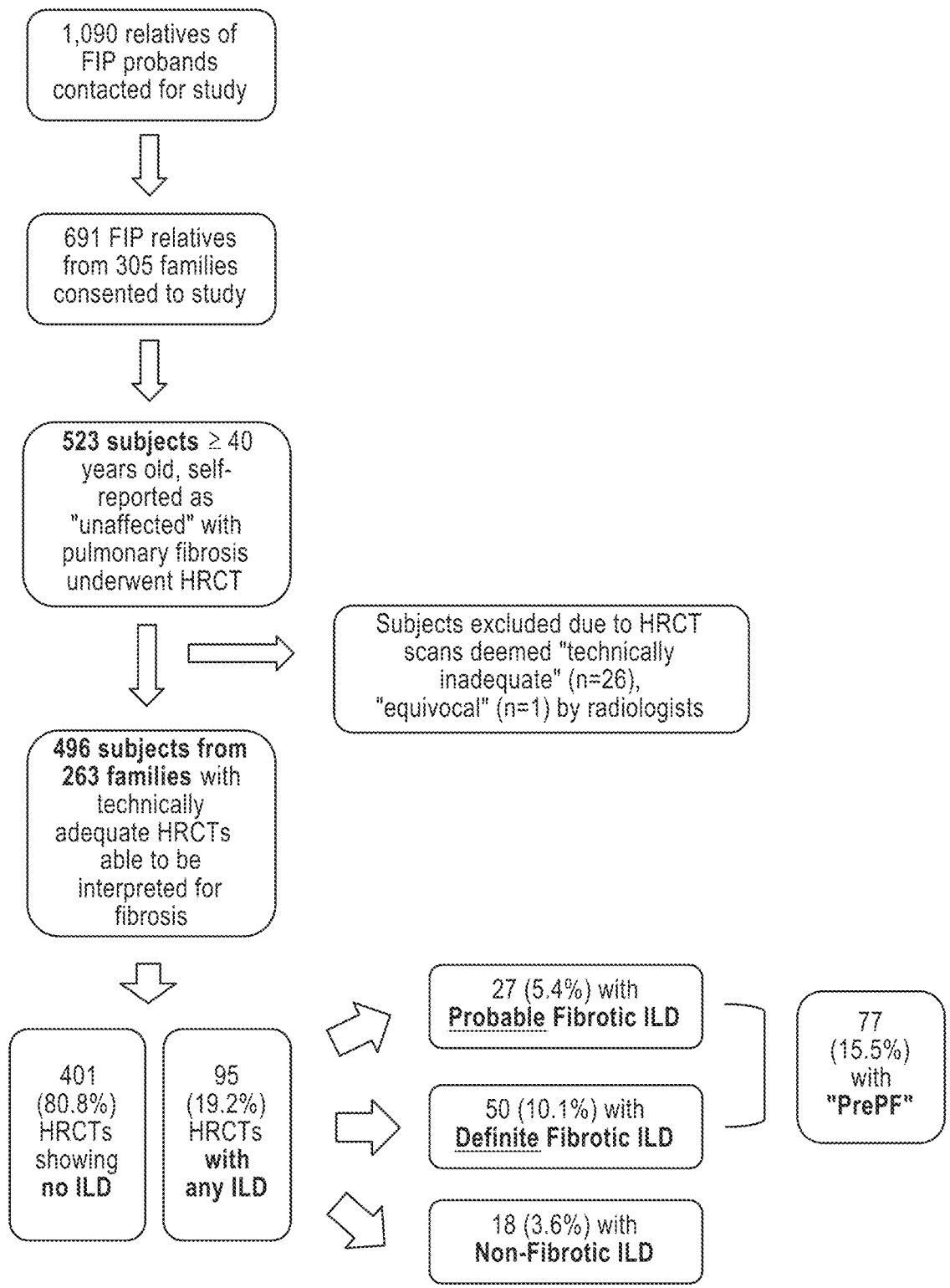
FIG. 18 is a flow chart depicting the screening and enrollment process for study subjects.

FIP Relatives Screening:

As part of a study of FIP conducted at the University of Colorado, National Jewish Health, and Vanderbilt University (COMIRB #15-1147; NJH IRB 1441a; Vanderbilt IRB #020343), non-Hispanic white (NHW) relatives of FIP patients, defined as those in families with two or more cases of pulmonary fibrosis, were contacted for enrollment. First-degree relatives without a known prior diagnosis of pulmonary fibrosis and greater than 40 years of age were offered HRCT scans of the chest and asked to undergo peripheral blood draw. Study subjects younger than 40 years of age or older than 40 years of age who reported on pre-study questionnaires to be personally affected by pulmonary fibrosis were excluded (FIG. 18).

Visual CT Review:

HRCT scans were interpreted by study radiologists and examined for the presence of fibrotic ILD. "PrePF" was defined as the presence of "probable" or "definite" fibrotic ILD on HRCT in FIP relatives who had no known diagnosis of pulmonary fibrosis at the time of study enrollment (FIGS. 18, 19).

Quantitative CT:

Inspiratory HRCT series with slice thickness ≤1·25 mm and spacing ≤20·0 mm were selected for quantitative analysis. This included 212 volumetric series with thin, contiguous sections (slice thickness and spacing both <=1·25 mm) and 191 non-volumetric scans (56 with slice spacing >1·25 mm and <10 mm, 65 with slice spacing of 10 mm and 70 with slice spacing=20 mm). Scans identified as technically inadequate were omitted. In addition, 100 inspiratory volumetric HRCT of never-smoking control subjects from the COPDGene cohort were analyzed (FIG. 20). The lungs were segmented in a semi-automatic fashion using open source software followed by manual editing, if necessary, performed by trained analysts. Examples of the categorization of different parts of CT scans are shown in FIG. 21. Some studies were acquired with contiguous thin axial sections while others used 1 or 2 cm intervals. Also, reconstruction kernel, a parameter that affects image sharpness and noise, was not standardized.

Fibrosis quantification on CT scans was performed using a deep learning technique, with a convolutional neural network (CNN) algorithm trained with image regions of normal and abnormal lung identified by expert radiologists. Training data and an earlier algorithm version were described previously. Here, a more complex CNN architecture was employed that classifies image regions using pixel and texture features extracted by multiple convolutional layers at different scales. Classification categories included normal lung, airways, reticular abnormality, honeycombing and ground glass. An additional category, "not normal", was also included for lung regions not classified into any of the named categories. Further, pixels in the "not normal" category were split into two subcategories: "not normal" low density and "not normal" high density using the threshold value of −650 Hounsfield Units (HU). Subject level scores were computed as the percentage of total lung volume classified in each category. HRCT fibrosis score was defined as the sum of CNN classification scores for reticular abnormality, honeycombing, ground glass, and "not normal high density" (FIG. 21).

A simpler previously described densitometric analysis of HRCTs was also performed for comparison. Percent high attenuation area (% HAA), the percentage of total lung volume with HRCT pixel intensity greater than −600 HU and less than −250 HU, has been used as a measure of interstitial lung disease on CT.

Statistical Analysis:

Analysis of the effect of specific alleles on PrePF risk was performed using minor allele frequency (MAF) for comparison of variant prevalence in the study groups; statistical significance was determined utilizing either a z-score test for proportions or a mixed effects logistic regression model when controlling for other clinical factors (age, sex, and history of smoking) and family [random effect]) in both dominant and log-additive models.

Distribution of qHRCT fibrosis scores was left skewed as was % HAA, and therefore these values were log transformed prior to analyses. Log of qHRCT fibrosis score (hereafter, "fibrosis score") and log (% HAA) were compared with visual scores using ANOVA and Tukey's honest significant difference (HSD) test. To determine the ability of qHRCT scores to predict visual diagnosis of PrePF, receiver-operating characteristic (ROC) analysis was performed. Optimal threshold for discriminating visual diagnosis of fibrotic ILD was determined with Youden's method. Five-fold cross-validation was performed to test detection accuracy, sensitivity and specificity, and consistency of optimal threshold. Linear regression was performed to test association between the MUC5B genotype and qHRCT fibrosis score and log (% HAA).

A p-value of <0.05 was considered statistically significant for differences between groups as well as for associations between individual variables and outcomes in linear and logistic regression modeling. Statistical analyses were performed using RStudio (Version 0.99.473).

Results

Study Cohort Characteristics

A total of 1,090 FIP relatives were contacted, and 523 eligible subjects were recruited and underwent HRCT screening (FIG. 18). Of the 523 subjects, 26 were excluded due to technical inadequacy of images and one for an equivocal consensus read by study radiologists. The remaining 496 subjects from 263 families were included in the final analyses. The mean age of study subjects was 57 years (95% CI: 56.5-58), 189 (38%) were male, and 148 (29%) were either current or former smokers. The minor allele (T) frequency of the MUC5B promoter polymorphism rs35705950 was 0.22 in this cohort; 45% of the subjects in this cohort had one or two copies of the minor allele (FIG. 22). The minor allele (C) frequency of the TERT variant rs2736100 was 0.47 in the entire cohort; 69% of the subjects in the cohort having one or two copies of the minor allele (FIG. 22).

Prevalence of Preclinical Pulmonary Fibrosis (PrePF) in FIP Relatives

Of the 496 HRCT scans, 401 showed no CT evidence of interstitial lung disease (ILD), and 95 showed evidence of ILD, either fibrotic (27 probable and 50 definite) or non-fibrotic (n=18). Therefore, among these 496 subjects who reported being personally unaffected by pulmonary fibrosis, the PrePF prevalence was 15.5% (n=77) (FIG. 18).

The CT patterns noted in PrePF subjects (FIG. 23) show that possible, probable, or definite UIP pattern was the most commonly considered (n=59, 77% of all PrePF cases). NSIP was considered in 45 subjects (58% of all PrePF cases). The fibrotic changes were most commonly lower-lobe predominant and subpleural in nature, consistent with a UIP pattern (FIG. 23). Non-fibrotic ILD scans, on the other hand, generally had more diffuse, upper-lobe predominant abnormalities.

Figure 24:
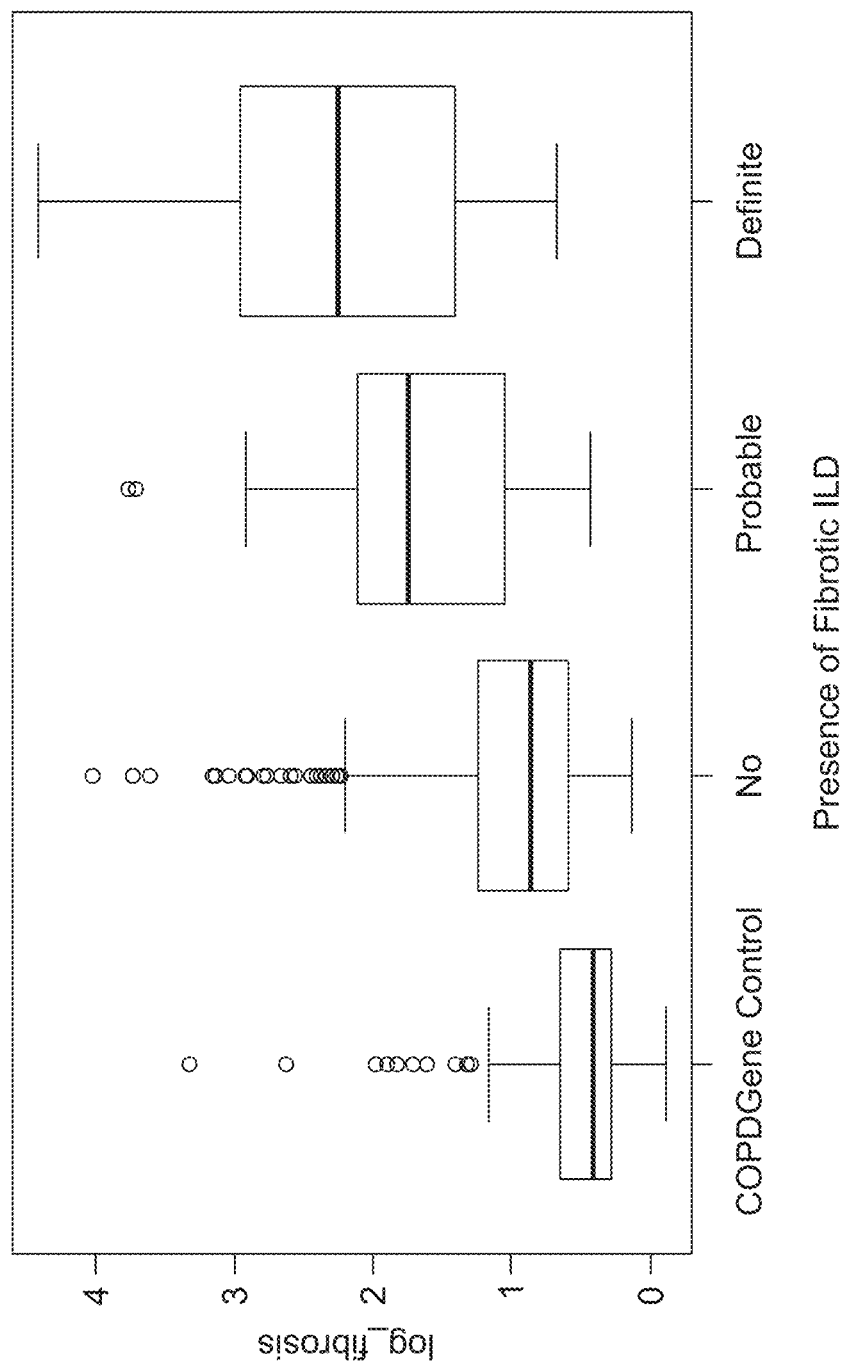
FIG. 24 is a box plot depicting fibrosis score by visual diagnosis. Boxplots of fibrosis scores based on quantitative HRCT assessment for each visual diagnosis category. Fibrosis score means were significantly different (ANOVA, p<0.0001) across groups defined by visual diagnosis. Comparison of fibrosis score between groups showed significant differences for all comparisons (p<0.01 for all).

There were 402 study subjects with HRCT scans that were technically adequate for quantitative assessment. 212 of the scans had both slice thickness and spacing <=1·25 mm (thin, contiguous); of the remaining 191 scans, 56 had slice spacing >1·25 mm and <10 mm, 65 had slice spacing=10 mm, and 70 had slice spacing=20 mm. Volumetric HRCT scans on an additional 100 COPDGene subjects were included as normal controls. Fibrosis score means were significantly different (p<0.0001) across groups defined by visual diagnosis (FIG. 24). Comparison of means showed fibrosis score were significantly different comparing each group (all between-group comparisons p<0.01). Means of log (% HAA) scores were also significantly different across visual scoring groups (p<0.0001), and individual between-group comparisons showed log (% HAA) was significantly different in most comparisons (p<0.0001), except between the "probable" and "definite" visual scores (p=0.35).

Figure 25A:
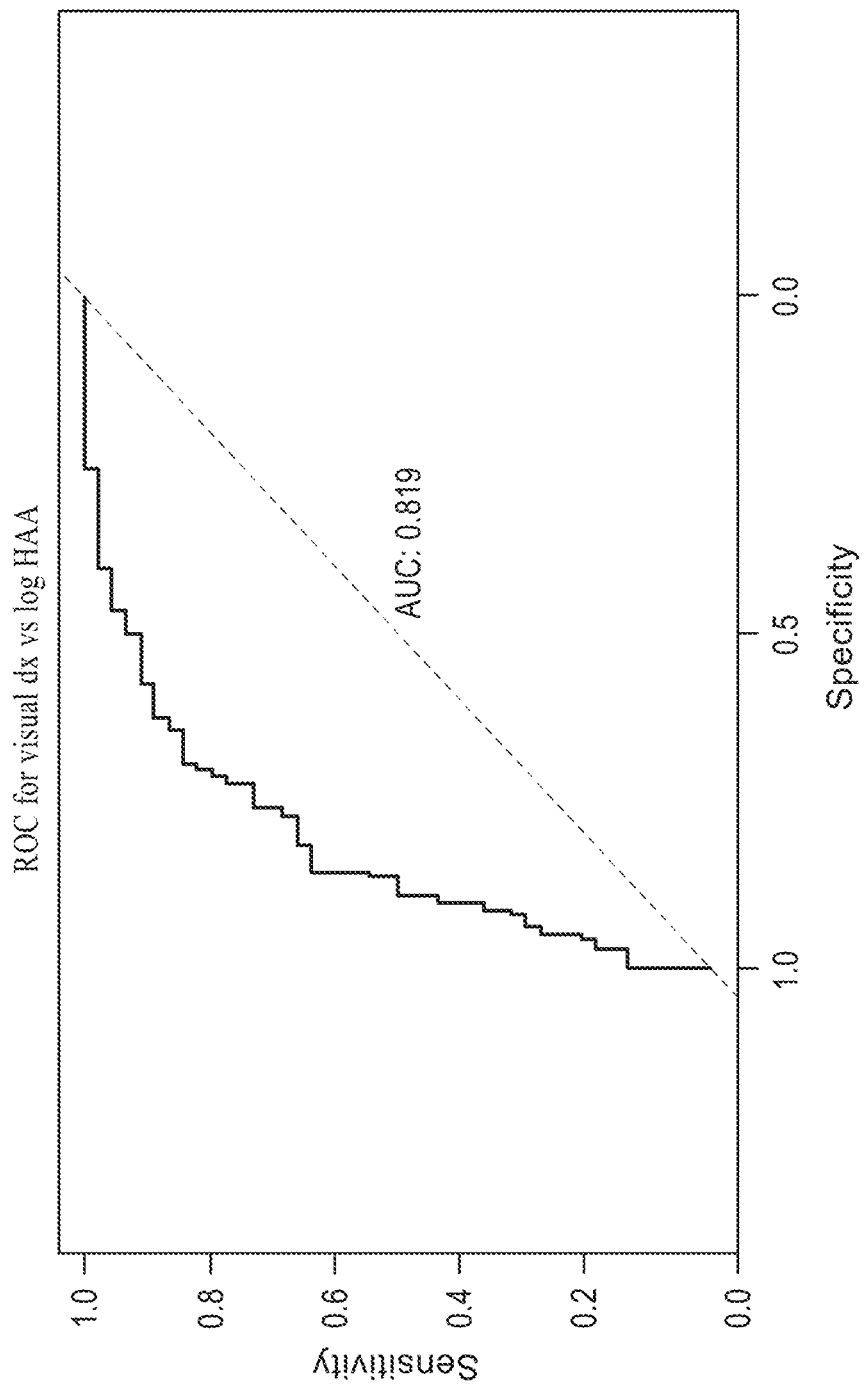
FIG. 25A-C is a series of graphs depicting Receiver Operating Characteristic (ROC) curves for quantitative imaging measures of Fibrosis and PrePF.
Figure 25B:
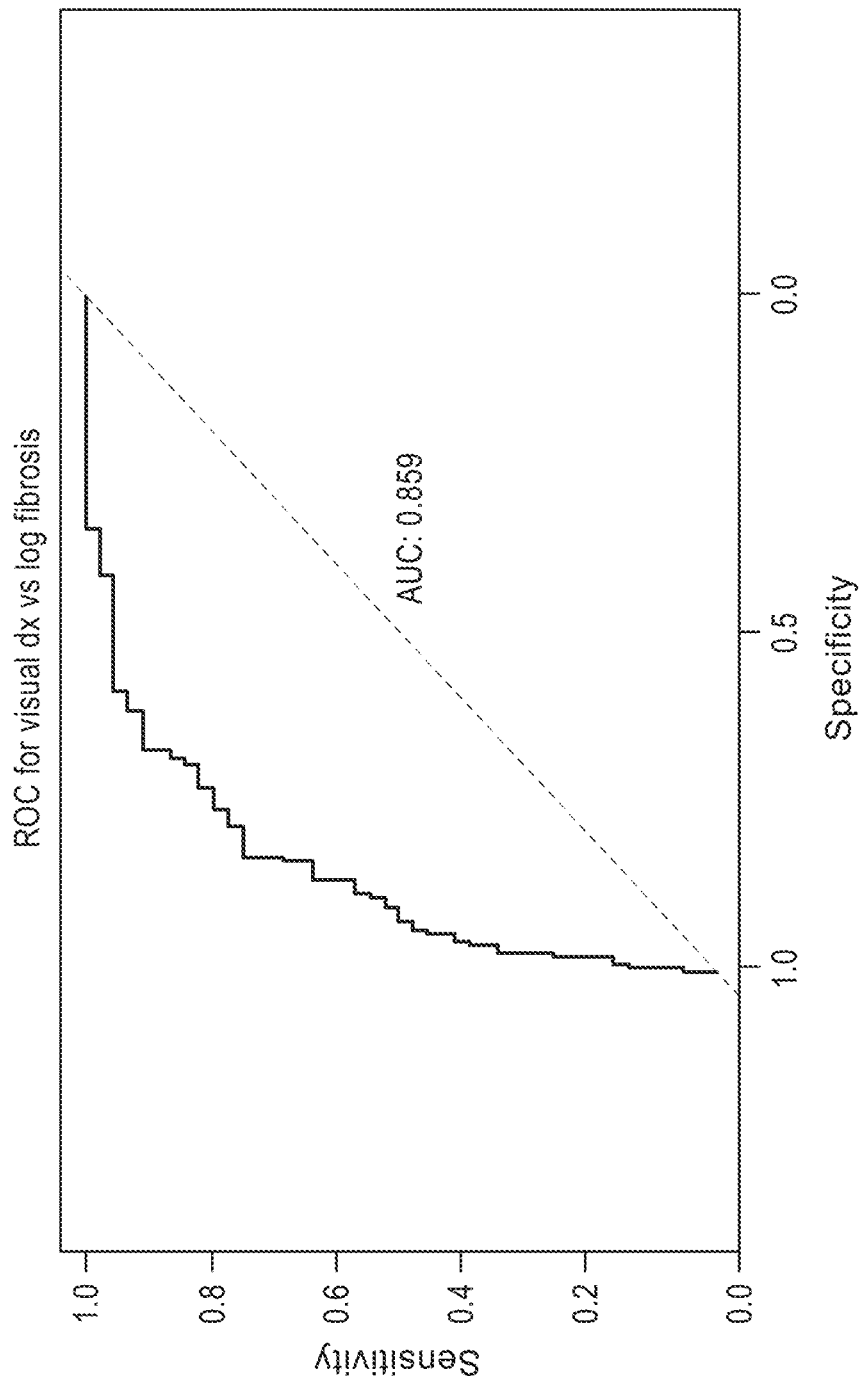
Figure 25C:
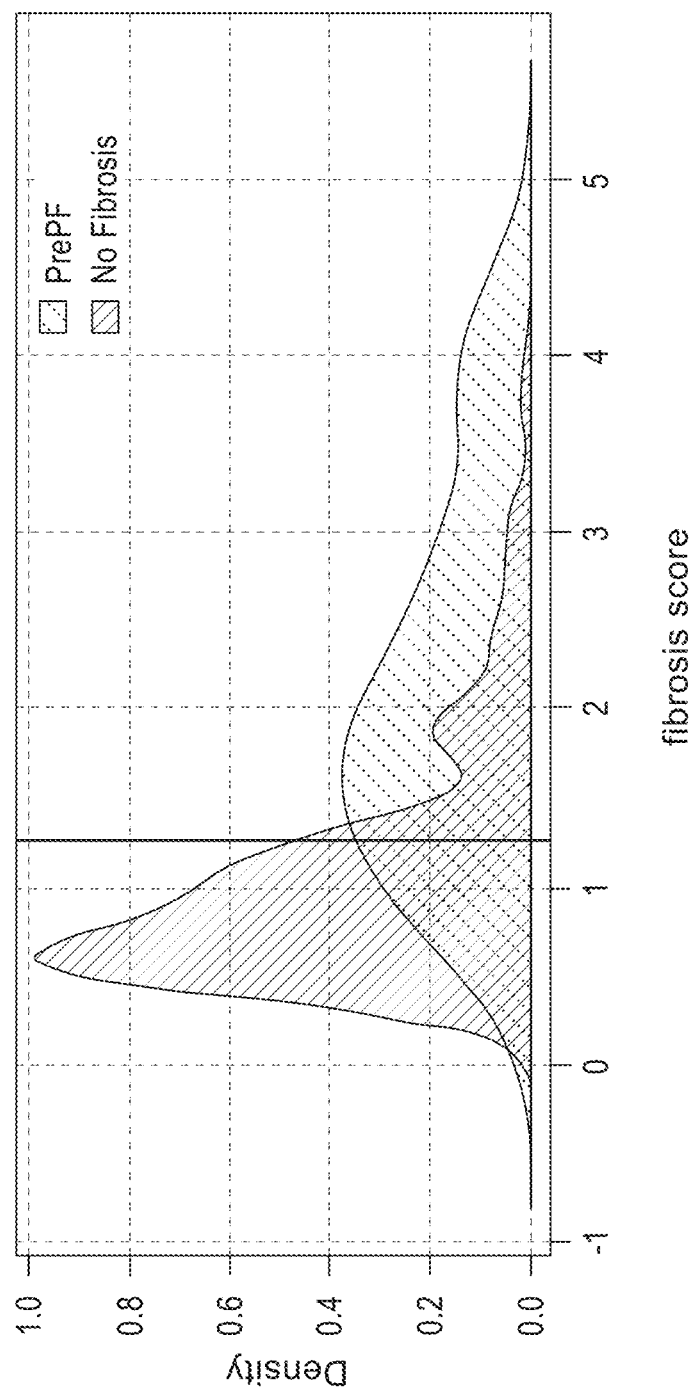

ROC analysis showed that fibrosis score discriminates subjects with visual diagnosis of PrePF (FIG. 25B). Average area under the curve (AUC) in five-fold cross validation was 0.85 (range 0.83-0.87) and average accuracy, sensitivity, and specificity in the test partitions were 0.83 (range 0.74-0.86), 0.74 (range 0.56-0.92), and 0.84 (range 0.76-0.89), respectively. Optimal threshold for fibrosis score ranged from 1.40-1.42, corresponding to 4.1% fibrotic area in examined lung. Utilizing a cutoff of 1.40 for fibrosis score on the entire dataset, the sensitivity was 74%, specificity was 82%, and accuracy was 81%; the negative predictive value of this test was 95%, exceeding its positive predictive value (42%) (FIG. 25C).

Compared to the classification achieved with the CNN as described above, ROC analysis of log % HAA had lower mean AUC 0.80 (range 0.79-0.81) and average accuracy, sensitivity, and specificity of 0.67 (range 0.63-0.70), 0.82 (range 0.75-0.91) and 0.64 (range 0.62-0.70) respectively (FIG. 25A). Optimal threshold for log % HAA ranged from 1.49-1.57. Utilizing a cutoff of 1.49 for log % HAA, the sensitivity was 88%, specificity was 55%, and accuracy was 60%; the negative predictive value of this test was 96%, exceeding its positive predictive value (26%).

Risk Factors for PrePF

Subjects with PrePF were older (mean age 65.8 years, 95% CI 63.5-68.1) than those without fibrosis (mean age 55.8, 95% CI 54.9-56.6, p=6.36×10$^{-13}$); they were also more likely to have ever smoked (43% versus 27%, p=0.007), and to be male (48% versus 36%, p=0.05). However, there was no difference in breathlessness between the PrePF and subjects without fibrosis (mean score 0.5 versus 0.6, p=0.24, FIG. 26). When fibrosis was defined by quantitative fibrosis score cutoff (1.4), there was a significant difference between groups in terms of mean breathlessness score (0.39 versus 0.78, p=0.003). Quantitative fibrosis score was positively associated with breathlessness score (p=0.001), even after controlling for age (p=1.9×10$^{-9}$), male sex (p=0.7), and smoking history (p=0.8).

Screening for autoantibodies in this cohort revealed that there were no differences between PrePF and No Fibrosis subjects in terms of overall seropositivity or individual antibodies' testing in this cohort. For quantitatively defined fibrosis, there was no significant difference between groups in terms of auto-antibody testing, with similar overall seropositivity rates (11% versus 16%, p=0.30).

Figure 27:
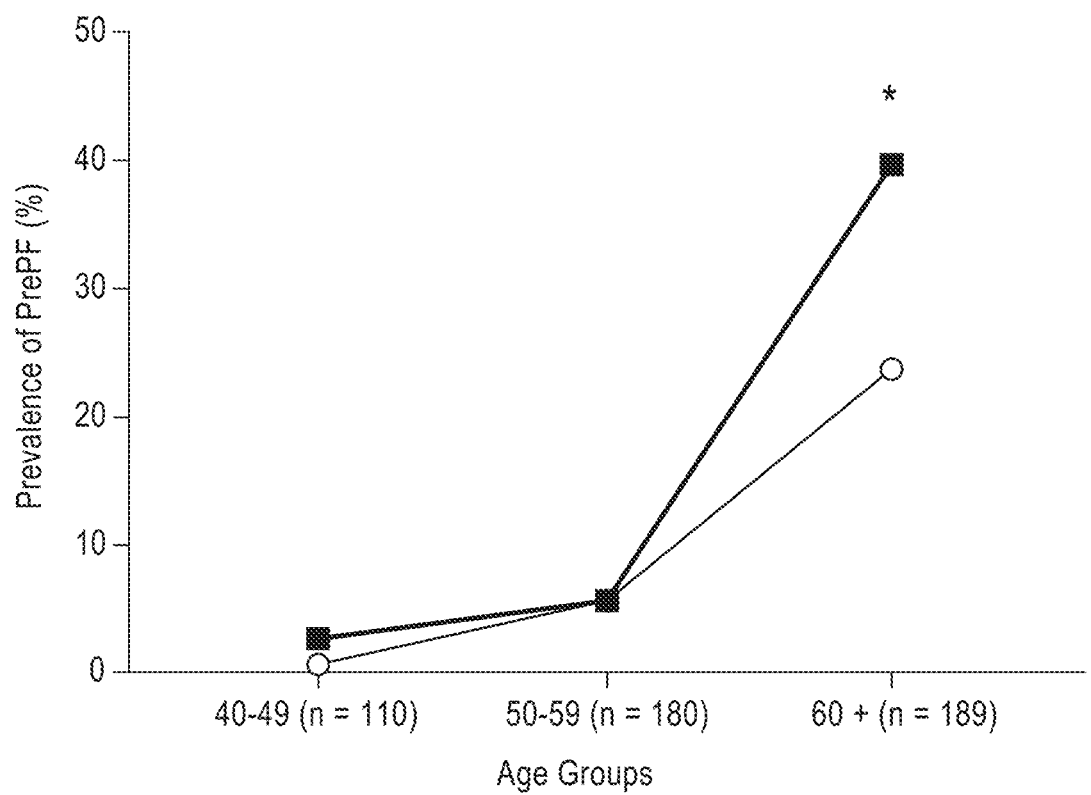
FIG. 27 is a graph that depicts the prevalence of PrePF in FIP Siblings Cohort by Age and MUC5B Genotype. PrePF prevalence in this FIP siblings cohort increases by age, as shown in this graph. By age >60 years, the prevalence of PrePF differed significantly based on MUC5B genotype (*p=0.02). Subjects with the variant are depicted by the red line, while those without it are depicted with the blue line.

The MUC5B promoter polymorphism rs35705950 was associated with the visual diagnosis of PrePF (present in 40% of those without fibrosis versus 53% with PrePF; MAF 0.29 versus 0.21, respectively, p=0.03, FIG. 22). After age 60, there was a statistically significant difference in the proportion of subjects with visually diagnosed PrePF when the cohort was stratified by MUC5B genotype (23.8% versus 39.8% prevalence, p=0.02) (FIG. 27).

MUC5B variant carriers, regardless of their visual CT diagnosis, had significantly higher qHRCT fibrosis scores (1.3 [95% CI 1.2-1.5] versus 1.1 [95% CI 1.0-1.2], p=0.02). The association between MUC5B genotype and fibrosis score was significant even when controlling for age and male sex in linear regression (p=0.03, FIG. 28). Age was significantly associated with fibrosis score (p=2.17×10$^{-9}$), but male sex (p=0.63) and smoking (p=0.94) were not. To determine whether individual textural components were driving the association of the composite fibrosis score with genotype, each score component was tested individually for association with the MUC5B variant, controlling for age and sex. Quantitative scores for reticulation, honeycombing, and ground glass were significantly associated with the MUC5B variant (p=0.02, p=0.02, p=0.04, respectively), while "not normal high density" was not (p=0.18). The simpler quantitative scoring method, log % HAA, was not significantly different in MUC5B variant carriers (p=0.4).

In contrast to the MUC5B variant, the common IPF-associated TERT polymorphism (r52736100) was not significantly associated with PrePF assessed either qualitatively (MAF 0.47 in PrePF versus 0.46 in unaffected, p=0.77) or quantitatively (MAF 0.50 fibrotic versus 0.47 not fibrotic, p=0.40).

When these factors were examined individually for their contributions to risk of PrePF in our study cohort, we used a mixed effects logistic regression model to test the independent effects of age sex, smoking, and MUC5B or TERT genotypes while controlling for family. Age and the MUC5B genotype remained statistically significantly associated with PrePF (OR 1.15, 95% CI 1.09-1.22, p=7.34×10$^{-7}$ and OR 2.18, 95% CI 1.00-4.73, p=0.05, respectively) (FIG. 22). The common TERT polymorphism (r52736100) associated with fibrotic idiopathic interstitial pneumonia (29) was not significantly associated with PrePF (MAF was 0.45 in PrePF versus 0.45 in unaffected, p=0.88) or in a log-additive model controlling for age, sex, and smoking history (p=0.57).

Given the presence of non-fibrotic ILD (n=18, FIG. 18) in the "No Fibrosis" cohort, secondary analyses were performed that (1) excluded non-fibrotic ILDs and (2) compared all ILD (inclusive of non-fibrotic ILD) to those without any ILD. When non-fibrotic ILDs were excluded from analyses, PrePF subjects were older (p=4.7×10$_{-13}$), more commonly male (p=0.04), more often had a smoking history (p=0.003), and had a higher prevalence of the MUC5B promoter variant (MAF 0.29 versus 0.20, p=0.02). However, when controlling for family relatedness and the other risk factors in a mixed effects logistic regression, only age and the MUC5B promoter variant were significantly associated with PrePF with odds ratios 1.15 (95% CI 1.09-1.22, p=9.5×10$^{-7}$) and 2.16 (95% CI 1.00-4.75, p=0.05), respectively. Another secondary analysis of the data was performed in which all subjects with CT findings of ILD (fibrotic or non-fibrotic) were compared to those without any evidence of ILD. Those with CT evidence of ILD were older (mean age 64.3 years, 95% CI 62.2-66.3) compared to those without any evidence of ILD (mean age 55.7 years, 95% CI 54.8-56.6, p=4.1×10$_{-12}$), more likely to be male (p=0.01), more likely to have smoked (p=0.0003), and more likely to carry the MUC5B promoter variant (MAF 0.21 versus 0.30, p=0.006). When controlling for family relatedness in a mixed effects logistic regression model, age (OR 1.10, 95% CI 1.07-1.14, p=1.21×10$^{-9}$), smoking history (OR 1.72, 95% CI 1.00-2.99, p=0.04), and the MUC5B promoter variant (OR 1.73, 95% CI 1.08-2.76, p=0·02) were significantly associated with risk of ILD.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method of treating a fibrotic lung disease in an asymptomatic human subject within an at-risk population, wherein the fibrotic lung disease is familial interstitial pneumonia (FIP), pulmonary fibrosis, idiopathic pulmonary fibrosis (IPF), interstitial lung disease (ILD), an interstitial lung abnormality (ILA), an asymptomatic ILA, fibrotic interstitial lung disease (FILD), or rheumatoid arthritis-associated interstitial lung disease (RA-ILD), and wherein the subject has a blood relative with a fibrotic lung disease selected from the group consisting of familial interstitial pneumonia (FIP), pre-clinical pulmonary disease, pulmonary fibrosis, idiopathic pulmonary fibrosis (IPF), an interstitial lung abnormality (ILA), an asymptomatic ILA, interstitial lung disease (ILD), fibrotic interstitial lung disease (FILD) and rheumatoid arthritis-associated interstitial lung disease (RA-ILD), the method comprising:

a) identifying pre-clinical pulmonary fibrosis (PrePF) in the subject by use of quantitative high resolution computed tomography (qHRCT) comprising the use of a convolutional neural network to quantify the extent of fibrosis in the subject and wherein the convolutional neural network architecture classifies image regions using pixel and texture features extracted by multiple convolutional layers at different scales;

b) determining that the subject has the T allele of the MUC5B rs35705950 polymorphism;

c) administering a therapeutic agent in an amount effective for the treatment of fibrotic lung disease to the subject, wherein the therapeutic agent:

(i) prevents the onset or development of a sign or symptom of the fibrotic lung disease;

(ii) delays the onset or development of a sign or symptom of the fibrotic lung disease when compared to the expected onset of the sign or symptom in the absence of treatment with the therapeutic agent; or (iii) agent reduces the severity of a sign or symptom of the fibrotic lung disease when compared to the expected severity of the sign or symptom in the absence of treatment with the therapeutic agent.

2. The method of claim 1, wherein the subject presents radiographic Usual Interstitial Pneumonia (UIP).

3. The method of claim 1, wherein the subject is greater than 40 years in age.

4. The method of claim 1, wherein the blood relative is a sibling.

5. The method of claim 1, wherein the MUC5B rs35705950 polymorphism is encoded by a sequence comprising SEQ ID NO: 7.

6. The method of claim 1, wherein the therapeutic agent comprises a N-acetylcysteine, pirfenidone, or nintedanib.

7. The method of claim 1, wherein PrePF is identified in the subject when a fibrosis score in the subject is above a predetermined cutoff value.

* * * * *